(12) United States Patent
Kamen et al.

(10) Patent No.: US 11,244,745 B2
(45) Date of Patent: Feb. 8, 2022

(54) COMPUTER-IMPLEMENTED METHOD, SYSTEM, AND APPARATUS FOR ELECTRONIC PATIENT CARE

(71) Applicant: DEKA Products Limited Partnership, Manchester, NH (US)

(72) Inventors: Dean Kamen, Bedford, NH (US); John J. Biasi, Groton, MA (US); Richard M. Newman, Stratham, NH (US); Eric L. Pribyl, Manchester, NH (US); John M. Kerwin, Manchester, NH (US); Rahul Gupta, Nashua, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 14/137,421

(22) Filed: Dec. 20, 2013

(65) Prior Publication Data

US 2014/0180711 A1 Jun. 26, 2014

Related U.S. Application Data

(63) Continuation-in-part of application No. 13/723,253, filed on Dec. 21, 2012, which is a (Continued)

(51) Int. Cl.
*G16H 10/60* (2018.01)
*G16H 10/65* (2018.01)
(Continued)

(52) U.S. Cl.
CPC ............ *G16H 10/60* (2018.01); *G06Q 10/06* (2013.01); *G06Q 10/10* (2013.01); *G16H 10/65* (2018.01);
(Continued)

(58) Field of Classification Search
USPC ........................................................ 705/2–4
See application file for complete search history.

(56) References Cited

U.S. PATENT DOCUMENTS 3,658,445 A  4/1972  Pulman
4,470,758 A  9/1984  Pazemenas et al.
(Continued)

FOREIGN PATENT DOCUMENTS

AU    659233 B2    5/1995
AU    738474 B2    9/2001
(Continued)

OTHER PUBLICATIONS

Prusch, Amanda E., et al. "Integrating technology to improve medication administration." American journal of health-system pharmacy 68.9 (2011): 835-842. (Year: 2011).*

(Continued)

*Primary Examiner* — Mark Holcomb
(74) *Attorney, Agent, or Firm* — James D. Wyninegar, Jr.

(57) ABSTRACT

A medical error reduction system may include a medical error reduction software for use in creating and revising at least one drug library. The software configured to provide one of a plurality of sets of privileges to each of a plurality of sets of users. Each of the plurality of sets of privileges arranged to allocate a degree of software functionality to one of the plurality of sets of users. The degree of software functionality configured to define the ability of a user to alter the at least one drug library. The medical error reduction system may include at least one server. The medical error reduction system may include at least one editor computer each of the at least one editor computer comprising a processor in communication with a display. The at least one editor computer and at least one server may be configured to communicate via a network in a client-server based model.

(Continued)

Each of the at least one drug library may be for use in at least one medical device.

36 Claims, 206 Drawing Sheets

Related U.S. Application Data continuation-in-part of application No. 13/333,574, filed on Dec. 21, 2011, now Pat. No. 10,453,157, and a continuation-in-part of application No. PCT/US2011/066588, filed on Dec. 21, 2011, said application No. 13/333,574 is a continuation-in-part of application No. 13/011,543, filed on Jan. 21, 2011, now abandoned, application No. 14/137,421, which is a continuation-in-part of application No. 13/723,239, filed on Dec. 21, 2012, now Pat. No. 10,108,785, which is a continuation-in-part of application No. 13/333,574, filed on Dec. 21, 2011, now Pat. No. 10,453,157, which is a continuation-in-part of application No. 13/011,543, filed on Jan. 21, 2011, now abandoned, said application No. 13/723,239 is a continuation-in-part of application No. PCT/US2011/066588, filed on Dec. 21, 2011, application No. 14/137,421, which is a continuation-in-part of application No. 13/723,242, filed on Dec. 21, 2012, now Pat. No. 10,911,515, and a continuation-in-part of application No. 13/900,655, filed on May 23, 2013, which is a continuation-in-part of application No. 13/480,444, filed on May 24, 2012, now Pat. No. 9,717,834, and a continuation-in-part of application No. PCT/US2012/000257, filed on May 24, 2012, application No. 14/137,421, which is a continuation-in-part of application No. PCT/US2013/042350, filed on May 23, 2013, which is a continuation of application No. 13/480,444, filed on May 24, 2012, now Pat. No. 9,717,834, and a continuation-in-part of application No. PCT/US2012/000257, filed on May 24, 2012.

(60) Provisional application No. 61/740,474, filed on Dec. 21, 2012, provisional application No. 61/578,649, filed on Dec. 21, 2011, provisional application No. 61/578,658, filed on Dec. 21, 2011, provisional application No. 61/578,674, filed on Dec. 21, 2011, provisional application No. 61/651,322, filed on May 24, 2012, provisional application No. 61/679,117, filed on Aug. 3, 2012, provisional application No. 61/297,544, filed on Jan. 22, 2010.

(51) Int. Cl.
  *G06Q 10/10* (2012.01)
  *G06Q 10/06* (2012.01)
  *G16H 20/10* (2018.01)
  *G16H 40/63* (2018.01)
  *G16H 70/40* (2018.01)
  *G16H 20/13* (2018.01)

(52) U.S. Cl.
  CPC ............ *G16H 20/10* (2018.01); *G16H 40/63* (2018.01); *G16H 70/40* (2018.01); *G06Q 10/103* (2013.01); *G06Q 10/107* (2013.01); *G06Q 10/109* (2013.01); *G16H 20/13* (2018.01)

(56) References Cited

U.S. PATENT DOCUMENTS

| | | |
|---|---|---|
| 4,696,671 A | 9/1987 | Epstein |
| 4,877,034 A | 10/1989 | Atkins |
| 4,939,689 A | 7/1990 | Davis |
| 5,041,086 A | 8/1991 | Koenig |
| 5,153,827 A | 10/1992 | Coutre et al. |
| 5,207,642 A | 5/1993 | Orkin |
| 5,317,506 A | 5/1994 | Coutre |
| D348,101 S | 6/1994 | Poli |
| 5,331,549 A | 7/1994 | Crawford, Jr. |
| 5,368,562 A | 11/1994 | Blomquist |
| 5,482,446 A | 1/1996 | Williamson |
| 5,485,408 A | 1/1996 | Blomquist |
| 5,527,289 A | 6/1996 | Foster |
| 5,537,618 A | 7/1996 | Boulton |
| 5,681,285 A * | 10/1997 | Ford .................... A61M 5/172 604/151 |
| 5,713,856 A | 2/1998 | Eggers |
| 5,719,761 A | 2/1998 | Gatti |
| 5,781,442 A | 7/1998 | Engleson |
| 5,836,910 A | 11/1998 | Duffy |
| 5,937,353 A | 8/1999 | Fapojuwo |
| 5,941,846 A | 8/1999 | Duffy |
| 5,961,487 A | 10/1999 | Davis |
| 6,021,392 A | 2/2000 | Lester |
| 6,024,539 A | 2/2000 | Blomquist |
| 6,139,495 A | 10/2000 | De La Huerga |
| 6,255,951 B1 | 7/2001 | De La Huerga |
| 6,267,559 B1 | 7/2001 | Mossman |
| 6,269,340 B1 | 7/2001 | Ford et al. |
| 6,308,171 B1 | 10/2001 | De La Huerga |
| 6,314,384 B1 | 11/2001 | Goetz |
| 6,315,720 B1 | 11/2001 | Williams |
| 6,317,719 B1 | 11/2001 | Schrier |
| 6,319,200 B1 | 11/2001 | Lai |
| 6,327,570 B1 | 12/2001 | Stevens |
| 6,346,886 B1 | 2/2002 | De La Huerga |
| 6,348,777 B1 | 2/2002 | Brown |
| 6,398,727 B1 | 6/2002 | Bui |
| 6,408,330 B1 | 6/2002 | DeLaHuerga |
| 6,421,650 B1 | 7/2002 | Goetz |
| 6,427,088 B1 | 7/2002 | Bowman, IV |
| 6,519,569 B1 | 2/2003 | White |
| 6,554,798 B1 | 4/2003 | Mann |
| 6,579,242 B2 | 6/2003 | Bui |
| 6,668,196 B1 | 12/2003 | Villegas |
| 6,671,563 B1 | 12/2003 | Engelson |
| 6,694,334 B2 | 2/2004 | DuLong |
| 6,745,764 B2 | 6/2004 | Hickle |
| 6,775,577 B2 | 8/2004 | Crnkovich |
| 6,776,152 B2 | 8/2004 | Gray et al. |
| 6,790,198 B1 | 9/2004 | White |
| 6,880,034 B2 | 4/2005 | Manke |
| 6,976,349 B2 | 12/2005 | Baldwin |
| 6,985,870 B2 | 1/2006 | Martucci |
| 6,993,402 B2 | 1/2006 | Klass |
| 7,039,878 B2 | 5/2006 | Auer |
| 7,096,072 B2 | 8/2006 | Engleson |
| 7,103,419 B2 | 9/2006 | Engleson |
| 7,107,106 B2 | 9/2006 | Engleson |
| 7,117,041 B2 | 10/2006 | Engleson |
| 7,161,484 B2 | 1/2007 | Tsoukalis |
| 7,165,221 B2 | 1/2007 | Monteleone |
| 7,171,277 B2 | 1/2007 | Engleson |
| 7,216,802 B1 | 5/2007 | De La Huerga |
| 7,236,936 B2 | 6/2007 | White |
| 7,300,418 B2 | 11/2007 | Zaleski |
| 7,302,266 B1 | 11/2007 | Sill et al. |
| 7,303,549 B2 | 12/2007 | Flaherty |
| 7,379,885 B2 | 5/2008 | Zakim |
| 7,384,410 B2 | 6/2008 | Eggers |
| 7,433,853 B2 | 10/2008 | Brockway |
| 7,452,190 B2 | 11/2008 | Bouton |
| 7,471,994 B2 | 12/2008 | Ford |
| 7,539,593 B2 | 5/2009 | Machacek |
| 7,565,301 B2 | 7/2009 | Moubayed |

(56) References Cited

U.S. PATENT DOCUMENTS

| | | | |
|---|---|---|---|
| 7,569,030 B2 | 8/2009 | Lebel | |
| 7,590,551 B2 | 9/2009 | Auer | |
| 7,612,679 B1 | 11/2009 | Fackler | |
| 7,636,718 B1 | 12/2009 | Steen | |
| 7,645,258 B2 | 1/2010 | White | |
| 7,647,237 B2 | 1/2010 | Malave | |
| 7,664,660 B2 | 2/2010 | Korpman | |
| 7,678,071 B2 | 3/2010 | Lebel | |
| 7,685,003 B2 | 3/2010 | Hasan | |
| 7,689,394 B2 | 3/2010 | Furem | |
| 7,693,730 B2 | 4/2010 | Hasan | |
| 7,699,806 B2 | 4/2010 | Ware | |
| 7,703,042 B2 | 4/2010 | Brummel | |
| 7,707,047 B2 | 4/2010 | Hasan | |
| 7,715,277 B2 | 5/2010 | de la Huerga | |
| 7,743,975 B2 | 6/2010 | Miller | |
| 7,771,385 B2 | 8/2010 | Eggers | |
| 7,771,386 B2 | 8/2010 | Eggers | |
| 7,788,369 B2 | 8/2010 | McAllen | |
| 7,813,879 B2 | 10/2010 | Bush | |
| 7,815,602 B2 | 10/2010 | Mann | |
| 7,818,184 B2 | 10/2010 | Penny | |
| 7,819,843 B2 | 10/2010 | Mann | |
| 7,831,446 B2 | 11/2010 | Korpman | |
| 7,835,927 B2 | 11/2010 | Schlotterbeck | |
| 7,839,266 B2 | 11/2010 | Hoglund | |
| 7,850,641 B2 | 12/2010 | Lebel | |
| 7,859,401 B2 | 12/2010 | Falck | |
| 7,860,583 B2 | 12/2010 | Condurso | |
| 7,871,394 B2 | 1/2011 | Halbert | |
| 7,873,489 B2 | 1/2011 | Dolgos | |
| 7,886,231 B2 | 2/2011 | Hopermann | |
| 7,893,876 B2 | 2/2011 | Brown | |
| 7,896,842 B2 | 3/2011 | Palmroos | |
| 7,901,394 B2 | 3/2011 | Ireland | |
| 7,911,353 B2 | 3/2011 | Bedingfield | |
| D636,779 S | 4/2011 | Boush | |
| D636,780 S | 4/2011 | Musleh | |
| 7,933,780 B2 | 4/2011 | De La Huerga | |
| 7,935,076 B2 | 5/2011 | Estes | |
| 7,938,796 B2 | 5/2011 | Moubayed | |
| 7,941,534 B2 | 5/2011 | de la Huerga | |
| 7,942,844 B2 | 5/2011 | Moberg | |
| 7,946,985 B2 | 5/2011 | Mastrototaro | |
| 7,955,289 B2 | 6/2011 | O'Mahony | |
| 7,976,508 B2 | 7/2011 | Hoag | |
| 7,978,564 B2 | 7/2011 | De La Huerga | |
| 8,025,634 B1 | 9/2011 | Moubayed | |
| 8,032,226 B2 | 10/2011 | Miller | |
| 8,038,593 B2 | 10/2011 | Friedman | |
| 8,041,542 B2 | 10/2011 | Pearson | |
| 8,060,381 B2 | 11/2011 | Dyer | |
| 8,065,161 B2 * | 11/2011 | Howard | A61M 5/142 |
| | | | 604/131 |
| 8,073,710 B2 | 12/2011 | Hasan | |
| 8,095,390 B2 | 1/2012 | Bluemler | |
| 8,099,301 B2 | 1/2012 | Keresman, III | |
| 8,126,728 B2 | 2/2012 | Dicks | |
| 8,126,729 B2 | 2/2012 | Dicks | |
| 8,131,565 B2 | 3/2012 | Dicks | |
| 8,131,566 B2 | 3/2012 | Dicks | |
| 8,134,459 B2 | 3/2012 | Smith | |
| 8,149,131 B2 | 4/2012 | Blomquist | |
| 8,152,486 B2 | 4/2012 | Fathallah | |
| 8,178,040 B2 | 5/2012 | Brauer | |
| 8,192,394 B2 | 6/2012 | Estes | |
| 8,214,227 B2 | 7/2012 | Patterson | |
| 8,214,234 B2 | 7/2012 | Hasan | |
| 8,217,946 B2 | 7/2012 | Halpern | |
| 8,219,413 B2 | 7/2012 | Martinez | |
| 8,219,982 B2 | 7/2012 | Harkanyi | |
| 8,222,768 B2 | 7/2012 | Cassidy | |
| 8,225,015 B2 | 7/2012 | Gao-Saari | |
| 8,229,760 B2 | 7/2012 | Hasan | |
| D665,401 S | 8/2012 | Rai | |
| 8,235,938 B2 | 8/2012 | Eggers | |
| 8,239,780 B2 | 8/2012 | Manetta | |
| 8,244,555 B2 | 8/2012 | Masson | |
| 8,255,585 B2 | 8/2012 | Levin | |
| 8,260,635 B2 | 9/2012 | Hasan | |
| 8,271,106 B2 | 9/2012 | Wehba | |
| 8,273,018 B1 | 9/2012 | Fackler | |
| 8,275,576 B2 | 9/2012 | Furem | |
| 8,275,633 B2 | 9/2012 | Baker | |
| 8,291,337 B2 | 10/2012 | Gannin | |
| 8,306,797 B2 | 11/2012 | Furem | |
| 8,308,680 B1 | 11/2012 | Chawla | |
| 8,312,877 B2 | 11/2012 | Elaz | |
| 8,317,752 B2 | 11/2012 | Cozmi | |
| D672,785 S | 12/2012 | Rai | |
| 8,340,792 B2 | 12/2012 | Condurso | |
| 8,352,290 B2 | 1/2013 | Bartz | |
| 8,359,338 B2 * | 1/2013 | Butterfield | G06F 19/3406 |
| | | | 707/803 |
| 8,373,557 B2 | 2/2013 | Smith | |
| 8,380,126 B1 | 2/2013 | Ma et al. | |
| 8,380,536 B2 | 2/2013 | Howard | |
| 8,414,523 B2 | 4/2013 | Blomquist | |
| D682,861 S | 5/2013 | Rounding | |
| 8,444,595 B2 | 5/2013 | Brukalo | |
| 8,451,230 B2 | 5/2013 | Celentano | |
| D694,774 S | 12/2013 | Schuller | |
| D701,526 S | 3/2014 | Poston | |
| D705,242 S | 5/2014 | Bohmfalk | |
| D709,905 S | 7/2014 | Bohmfalk et al. | |
| D714,339 S | 9/2014 | Hendrickson et al. | |
| 8,938,684 B2 | 1/2015 | Guertler | |
| 8,954,336 B2 | 2/2015 | Blomquist | |
| D726,752 S | 4/2015 | Angelides | |
| D728,601 S | 5/2015 | Angelides | |
| D728,779 S | 5/2015 | Sabin et al. | |
| D733,724 S | 7/2015 | Kim | |
| D735,319 S | 7/2015 | Sabin et al. | |
| D736,370 S | 8/2015 | Sabin et al. | |
| 9,151,646 B2 | 10/2015 | Kamen et al. | |
| D745,661 S | 12/2015 | Collins et al. | |
| D749,206 S | 2/2016 | Johnson et al. | |
| D751,689 S | 3/2016 | Peret et al. | |
| D751,690 S | 3/2016 | Peret et al. | |
| D752,209 S | 3/2016 | Peret et al. | |
| 9,295,778 B2 | 3/2016 | Kamen et al. | |
| D754,065 S | 4/2016 | Gray et al. | |
| D756,386 S | 5/2016 | Kendler et al. | |
| D758,399 S | 6/2016 | Kendler et al. | |
| D760,288 S | 6/2016 | Kendler et al. | |
| D760,289 S | 6/2016 | Kendler et al. | |
| 9,364,394 B2 | 6/2016 | Demers et al. | |
| 9,372,486 B2 | 6/2016 | Peret et al. | |
| D760,782 S | 7/2016 | Kendler et al. | |
| D760,888 S | 7/2016 | Gill et al. | |
| 9,400,873 B2 | 7/2016 | Kamen et al. | |
| 9,408,966 B2 | 8/2016 | Kamen | |
| D767,756 S | 9/2016 | Sabin | |
| 9,435,455 B2 | 9/2016 | Peret et al. | |
| D768,716 S | 10/2016 | Kendler et al. | |
| 9,465,919 B2 | 10/2016 | Kamen et al. | |
| 9,488,200 B2 | 11/2016 | Kamen et al. | |
| D774,645 S | 12/2016 | Gill et al. | |
| 9,518,958 B2 | 12/2016 | Wilt et al. | |
| 9,636,455 B2 | 5/2017 | Kamen et al. | |
| D789,516 S | 6/2017 | Gill et al. | |
| 9,675,756 B2 | 6/2017 | Kamen et al. | |
| 9,677,555 B2 | 6/2017 | Kamen et al. | |
| 9,687,417 B2 | 6/2017 | Demers et al. | |
| D792,963 S | 7/2017 | Gill | |
| D795,424 S | 8/2017 | Sloss | |
| D795,805 S | 8/2017 | Gray et al. | |
| 9,719,964 B2 | 8/2017 | Blumberg | |
| 9,724,465 B2 | 8/2017 | Peret et al. | |
| 9,724,466 B2 | 8/2017 | Peret et al. | |
| 9,724,467 B2 | 8/2017 | Peret et al. | |
| 9,730,731 B2 | 8/2017 | Langenfeld et al. | |
| 9,744,300 B2 | 8/2017 | Kamen et al. | |
| 9,746,093 B2 | 8/2017 | Peret et al. | |

(56) References Cited

U.S. PATENT DOCUMENTS

| | | |
|---|---|---|
| 9,746,094 B2 | 8/2017 | Peret et al. |
| 9,759,343 B2 | 9/2017 | Peret et al. |
| 9,759,369 B2 | 9/2017 | Gray et al. |
| 9,772,044 B2 | 9/2017 | Peret et al. |
| D799,025 S | 10/2017 | Johnson et al. |
| D801,519 S | 10/2017 | Sabin et al. |
| 9,789,247 B2 | 10/2017 | Kamen et al. |
| D802,118 S | 11/2017 | Peret et al. |
| D803,386 S | 11/2017 | Sabin et al. |
| D803,387 S | 11/2017 | Bodwell et al. |
| D804,017 S | 11/2017 | Sabin |
| 9,808,572 B2 | 11/2017 | Kamen et al. |
| D805,183 S | 12/2017 | Sabin et al. |
| 9,856,990 B2 | 1/2018 | Peret et al. |
| D813,376 S | 3/2018 | Peret et al. |
| D814,021 S | 3/2018 | Sabin |
| D815,730 S | 4/2018 | Collins et al. |
| D816,685 S | 5/2018 | Kendler et al. |
| D816,829 S | 5/2018 | Peret et al. |
| D817,479 S | 5/2018 | Sabin et al. |
| D817,480 S | 5/2018 | Sabin et al. |
| 9,968,730 B2 | 5/2018 | Blumberg, Jr. et al. |
| 9,976,665 B2 | 5/2018 | Peret et al. |
| 10,044,791 B2 | 8/2018 | Kamen et al. |
| 10,082,241 B2 | 9/2018 | Janway et al. |
| 10,088,346 B2 | 10/2018 | Kane et al. |
| 10,108,785 B2 | 10/2018 | Kamen et al. |
| 10,113,660 B2 | 10/2018 | Peret et al. |
| 10,126,267 B2 | 11/2018 | Blumberg, Jr. |
| 10,185,812 B2 | 1/2019 | Kamen et al. |
| 10,202,970 B2 | 2/2019 | Kamen et al. |
| 10,202,971 B2 | 2/2019 | Kamen et al. |
| 10,220,135 B2 | 3/2019 | Kamen et al. |
| 10,228,683 B2 | 3/2019 | Peret et al. |
| 10,242,159 B2 | 3/2019 | Kamen et al. |
| 10,245,374 B2 | 4/2019 | Kamen et al. |
| 10,265,463 B2 | 4/2019 | Biasi et al. |
| 10,288,057 B2 | 5/2019 | Kamen et al. |
| 10,316,834 B2 | 6/2019 | Kamen et al. |
| D854,145 S | 7/2019 | Collins |
| 10,380,321 B2 | 8/2019 | Kamen et al. |
| 10,391,241 B2 | 8/2019 | Desch et al. |
| D860,437 S | 9/2019 | Collins |
| 10,426,517 B2 | 10/2019 | Langenfeld et al. |
| 10,436,342 B2 | 10/2019 | Peret et al. |
| 10,453,157 B2 | 10/2019 | Kamen et al. |
| 10,468,132 B2 | 11/2019 | Kamen et al. |
| 10,471,402 B2 | 11/2019 | Demers et al. |
| 10,478,261 B2 | 11/2019 | Demers et al. |
| 10,488,848 B2 | 11/2019 | Peret et al. |
| 10,561,787 B2 | 2/2020 | Kamen et al. |
| 10,563,681 B2 | 2/2020 | Kamen et al. |
| 10,571,070 B2 | 2/2020 | Gray et al. |
| 10,655,779 B2 | 5/2020 | Janway et al. |
| 10,670,182 B2 | 6/2020 | Janway et al. |
| 10,718,445 B2 | 7/2020 | Yoo |
| 10,722,645 B2 | 7/2020 | Kamen et al. |
| 10,739,759 B2 | 8/2020 | Peret et al. |
| 10,753,353 B2 | 8/2020 | Kamen et al. |
| 10,761,061 B2 | 9/2020 | Wilt et al. |
| 10,839,953 B2 | 11/2020 | Kamen et al. |
| 10,844,970 B2 | 11/2020 | Peret et al. |
| D905,848 S | 12/2020 | Sloss et al. |
| 10,857,293 B2 | 12/2020 | Kamen et al. |
| 10,872,685 B2 | 12/2020 | Blumberg, Jr. et al. |
| 10,876,868 B2 | 12/2020 | Kane et al. |
| 10,894,638 B2 | 1/2021 | Peret et al. |
| 10,911,515 B2 | 2/2021 | Biasi et al. |
| 2001/0031944 A1 | 10/2001 | Peterson |
| 2001/0044731 A1 | 11/2001 | Coffman et al. |
| 2001/0051787 A1 | 12/2001 | Haller et al. |
| 2002/0013538 A1 | 1/2002 | Teller |
| 2002/0016568 A1 | 2/2002 | Lebel et al. |
| 2002/0032583 A1 | 3/2002 | Joao |
| 2002/0044059 A1 | 4/2002 | Reeder et al. |
| 2002/0072934 A1 | 6/2002 | Ross et al. |
| 2002/0077852 A1* | 6/2002 | Ford ............... G16H 40/40 705/2 |
| 2002/0084904 A1 | 7/2002 | De La Huerga |
| 2002/0169636 A1 | 11/2002 | Eggers et al. |
| 2002/0178126 A1 | 11/2002 | Beck |
| 2002/0184589 A1 | 12/2002 | Eatough |
| 2002/0188465 A1 | 12/2002 | Gogolak |
| 2003/0036683 A1 | 2/2003 | Kehr et al. |
| 2003/0036744 A1 | 2/2003 | Struys et al. |
| 2003/0046110 A1 | 3/2003 | Gogolak |
| 2003/0061073 A1 | 3/2003 | Seow |
| 2003/0106553 A1 | 6/2003 | Vanderveen |
| 2003/0114751 A1 | 6/2003 | Pedain |
| 2003/0135087 A1 | 7/2003 | Hickle et al. |
| 2003/0135388 A1 | 7/2003 | Martucci |
| 2003/0140928 A1 | 7/2003 | Bui et al. |
| 2003/0165128 A1 | 9/2003 | Sisodia et al. |
| 2003/0167030 A1 | 9/2003 | Weitzel et al. |
| 2003/0186199 A1* | 10/2003 | McCool ............... G09B 23/28 434/219 |
| 2004/0010425 A1 | 1/2004 | Wilkes |
| 2004/0015132 A1 | 1/2004 | Brown |
| 2004/0085186 A1 | 5/2004 | Eveland et al. |
| 2004/0147818 A1 | 7/2004 | Levy |
| 2004/0158193 A1* | 8/2004 | Bui ............... A61M 5/172 604/65 |
| 2004/0172283 A1 | 9/2004 | Vanderveen |
| 2004/0186357 A1* | 9/2004 | Soderberg ............... A61B 5/00 600/300 |
| 2004/0193325 A1 | 9/2004 | Bonderud |
| 2004/0193453 A1 | 9/2004 | Butterfield |
| 2005/0021622 A1 | 1/2005 | Cullen |
| 2005/0022184 A1 | 1/2005 | Birkestrand |
| 2005/0055242 A1 | 3/2005 | Bello |
| 2005/0060202 A1 | 3/2005 | Taylor et al. |
| 2005/0070227 A1 | 3/2005 | Shen et al. |
| 2005/0070767 A1 | 3/2005 | Maschke |
| 2005/0086288 A1 | 4/2005 | Data et al. |
| 2005/0099624 A1 | 5/2005 | Staehr |
| 2005/0133027 A1 | 6/2005 | Elaz et al. |
| 2005/0137653 A1* | 6/2005 | Friedman ............. A61B 5/0002 607/60 |
| 2005/0143632 A1 | 6/2005 | Elaz et al. |
| 2005/0144043 A1 | 6/2005 | Holland |
| 2005/0171815 A1 | 8/2005 | Vanderveen |
| 2005/0177096 A1 | 8/2005 | Bollish |
| 2005/0192844 A1 | 9/2005 | Esler et al. |
| 2005/0224083 A1 | 10/2005 | Crass |
| 2005/0288571 A1* | 12/2005 | Perkins ............... A61B 5/0002 600/407 |
| 2006/0047538 A1 | 3/2006 | Condurso |
| 2006/0080140 A1 | 4/2006 | Buttner |
| 2006/0089592 A1 | 4/2006 | Kadhiresan et al. |
| 2006/0095300 A1 | 5/2006 | Schrier |
| 2006/0149140 A1 | 7/2006 | Eldridge |
| 2006/0149591 A1 | 7/2006 | Hanf |
| 2006/0161214 A1 | 7/2006 | Patel |
| 2006/0168043 A1 | 7/2006 | Eisenberger et al. |
| 2006/0184123 A1 | 8/2006 | Gillespie |
| 2006/0229557 A1 | 10/2006 | Fathallah et al. |
| 2006/0253301 A1 | 11/2006 | Simms et al. |
| 2006/0258985 A1 | 11/2006 | Russell |
| 2006/0265246 A1 | 11/2006 | Hoag |
| 2006/0294230 A1 | 12/2006 | Takasu et al. |
| 2007/0061393 A1 | 3/2007 | Moore |
| 2007/0078445 A1 | 4/2007 | Malloy |
| 2007/0088574 A1 | 4/2007 | Byer |
| 2007/0109325 A1 | 5/2007 | Eveleigh |
| 2007/0136090 A1 | 6/2007 | Loutzenhiser |
| 2007/0191817 A1 | 8/2007 | Martin |
| 2007/0219823 A1 | 9/2007 | Warner |
| 2007/0249286 A1 | 10/2007 | Ma et al. |
| 2007/0250927 A1 | 10/2007 | Naik |
| 2007/0255114 A1 | 11/2007 | Ackermann et al. |
| 2007/0255250 A1 | 11/2007 | Moberg et al. |
| 2007/0255348 A1 | 11/2007 | Holtzclaw |
| 2008/0039744 A1 | 2/2008 | Hamilton |
| 2008/0086086 A1 | 4/2008 | Field et al. |

(56) References Cited

U.S. PATENT DOCUMENTS

| | | |
|---|---|---|
| 2008/0091175 A1 | 4/2008 | Frikart |
| 2008/0097913 A1 | 4/2008 | Dicks |
| 2008/0129496 A1 | 6/2008 | Koblasz |
| 2008/0133265 A1 | 6/2008 | Silkaitis |
| 2008/0140157 A1 | 6/2008 | Goetz |
| 2008/0160492 A1* | 7/2008 | Campbell ............. G09B 19/00 434/379 |
| 2008/0235765 A1 | 9/2008 | Shimizu |
| 2008/0243055 A1 | 10/2008 | Fathallah |
| 2008/0255438 A1 | 10/2008 | Saidara |
| 2008/0262441 A1 | 10/2008 | Walborn |
| 2008/0281259 A1 | 11/2008 | Owens et al. |
| 2008/0300572 A1 | 12/2008 | Rankers et al. |
| 2009/0006640 A1 | 1/2009 | Lambertus et al. |
| 2009/0063187 A1 | 3/2009 | Johnson et al. |
| 2009/0069642 A1 | 3/2009 | Gao et al. |
| 2009/0069743 A1 | 3/2009 | Krishnamoorthy |
| 2009/0099866 A1 | 4/2009 | Newman |
| 2009/0099867 A1 | 4/2009 | Newman |
| 2009/0119330 A1 | 5/2009 | Sampath et al. |
| 2009/0150818 A1 | 6/2009 | Bakhreiba |
| 2009/0153058 A1 | 6/2009 | Feng |
| 2009/0153463 A1 | 6/2009 | Arrizza |
| 2009/0153595 A1 | 6/2009 | Cozmi |
| 2009/0157432 A1 | 6/2009 | Palmroos |
| 2009/0163855 A1 | 6/2009 | Shin et al. |
| 2009/0183147 A1 | 7/2009 | Davis |
| 2009/0184842 A1 | 7/2009 | Baldus et al. |
| 2009/0203329 A1 | 8/2009 | White |
| 2009/0210152 A1 | 8/2009 | Kawa |
| 2009/0216562 A1 | 8/2009 | Faulkner |
| 2009/0217194 A1 | 8/2009 | Martin et al. |
| 2009/0234672 A1 | 9/2009 | Dicks |
| 2009/0240526 A1 | 9/2009 | Vesto |
| 2009/0270810 A1 | 10/2009 | DeBelser et al. |
| 2009/0270833 A1 | 10/2009 | DeBelser et al. |
| 2009/0275808 A1 | 11/2009 | DiMaio et al. |
| 2010/0019910 A1 | 1/2010 | Hassing et al. |
| 2010/0094653 A1 | 4/2010 | Tribble |
| 2010/0106224 A1 | 4/2010 | Von Arx et al. |
| 2010/0114027 A1 | 5/2010 | Jacobson |
| 2010/0130933 A1 | 5/2010 | Holland |
| 2010/0145506 A1 | 6/2010 | Waugh et al. |
| 2010/0150176 A1 | 6/2010 | Yakashiro |
| 2010/0160628 A1 | 6/2010 | Peglion et al. |
| 2010/0176166 A1 | 7/2010 | Siagri et al. |
| 2010/0229096 A1 | 9/2010 | Maiocco |
| 2010/0234718 A1 | 9/2010 | Sampath |
| 2010/0257189 A1 | 10/2010 | Campbell |
| 2010/0268157 A1 | 10/2010 | Wehba |
| 2010/0280486 A1 | 11/2010 | Khair |
| 2010/0287006 A1 | 11/2010 | Cannon |
| 2010/0292544 A1 | 11/2010 | Sherman et al. |
| 2010/0292556 A1 | 11/2010 | Golden |
| 2010/0298662 A1 | 11/2010 | Yu |
| 2011/0004186 A1 | 1/2011 | Butterfield |
| 2011/0006876 A1 | 1/2011 | Moberg et al. |
| 2011/0071420 A1 | 3/2011 | St. Pierre et al. |
| 2011/0074342 A1 | 3/2011 | MacLaughlin |
| 2011/0105979 A1 | 5/2011 | Schlaeper |
| 2011/0112418 A1 | 5/2011 | Feild et al. |
| 2011/0119612 A1 | 5/2011 | Gannon |
| 2011/0152629 A1 | 6/2011 | Eaton et al. |
| 2011/0153343 A1 | 6/2011 | Tremblay |
| 2011/0167250 A1 | 7/2011 | Dicks |
| 2011/0173704 A1 | 7/2011 | Hanov |
| 2011/0179083 A1 | 7/2011 | Galloway et al. |
| 2011/0179405 A1 | 7/2011 | Dicks |
| 2011/0184379 A1 | 7/2011 | Van Antwerp |
| 2011/0191767 A1 | 8/2011 | Pinsky et al. |
| 2011/0196306 A1 | 8/2011 | De La Huerga |
| 2011/0205965 A1 | 8/2011 | Sprigg |
| 2011/0218406 A1 | 9/2011 | Hussain |
| 2011/0224646 A1 | 9/2011 | Yodfat |
| 2011/0231203 A1 | 9/2011 | Rosow |
| 2011/0231204 A1 | 9/2011 | De La Huerga |
| 2011/0241878 A1 | 10/2011 | Hoag |
| 2011/0276605 A1 | 11/2011 | Masson |
| 2011/0282168 A1 | 11/2011 | Weiss |
| 2011/0282688 A1 | 11/2011 | Raggousis |
| 2011/0282691 A1 | 11/2011 | Coffman |
| 2011/0313789 A1 | 12/2011 | Kamen |
| 2011/0320049 A1 | 12/2011 | Chossat |
| 2012/0011253 A1 | 1/2012 | Friedman |
| 2012/0016215 A1 | 1/2012 | Condurso |
| 2012/0016295 A1 | 1/2012 | Tsoukalis |
| 2012/0016305 A1 | 1/2012 | Jollota et al. |
| 2012/0029300 A1 | 2/2012 | Paquet |
| 2012/0029307 A1 | 2/2012 | Paquet |
| 2012/0029308 A1 | 2/2012 | Paquet |
| 2012/0029309 A1 | 2/2012 | Paquet |
| 2012/0029310 A1 | 2/2012 | Paquet |
| 2012/0029311 A1 | 2/2012 | Raptis |
| 2012/0029312 A1 | 2/2012 | Beaudry |
| 2012/0029314 A1 | 2/2012 | Paquet |
| 2012/0029315 A1 | 2/2012 | Raptis |
| 2012/0029316 A1 | 2/2012 | Raptis |
| 2012/0029941 A1 | 2/2012 | Malave |
| 2012/0030547 A1 | 2/2012 | Raptis |
| 2012/0047289 A1 | 2/2012 | Krzystofczyk et al. |
| 2012/0053533 A1 | 3/2012 | Butterfield |
| 2012/0062387 A1 | 3/2012 | Vik |
| 2012/0065990 A1 | 3/2012 | Howard |
| 2012/0066609 A1 | 3/2012 | Howard |
| 2012/0075061 A1 | 3/2012 | Barnes |
| 2012/0078218 A1 | 3/2012 | Barnes |
| 2012/0084303 A1 | 4/2012 | Ledford |
| 2012/0092157 A1 | 4/2012 | Tran |
| 2012/0116796 A1 | 5/2012 | Bellon |
| 2012/0116800 A1 | 5/2012 | McCallie |
| 2012/0123229 A1 | 5/2012 | Butterfield |
| 2012/0124174 A1 | 5/2012 | Nudelman |
| 2012/0130308 A1 | 5/2012 | Silkaitis |
| 2012/0157920 A1 | 6/2012 | Flachbart |
| 2012/0172802 A1 | 7/2012 | Blomquist |
| 2012/0176394 A1 | 7/2012 | Vik |
| 2012/0179093 A1 | 7/2012 | Rinehart |
| 2012/0179136 A1 | 7/2012 | Rinehart |
| 2012/0185267 A1 | 7/2012 | Kamen |
| 2012/0239824 A1 | 9/2012 | Nguyen |
| 2012/0260012 A1 | 10/2012 | Gao-Saari |
| 2012/0302991 A1 | 11/2012 | Blomquist |
| 2012/0303388 A1 | 11/2012 | Venkata et al. |
| 2012/0310205 A1 | 12/2012 | Lee |
| 2012/0323212 A1 | 12/2012 | Murphy |
| 2013/0006651 A1 | 1/2013 | Saus |
| 2013/0006666 A1 | 1/2013 | Schneider |
| 2013/0012880 A1 | 1/2013 | Blomquist |
| 2013/0030830 A1 | 1/2013 | Schmoll |
| 2013/0041257 A1 | 2/2013 | Nemoto |
| 2013/0042194 A1 | 2/2013 | Gannon |
| 2013/0045764 A1 | 2/2013 | Vik |
| 2013/0046871 A1 | 2/2013 | Vik |
| 2013/0047113 A1* | 2/2013 | Hume .................... G06Q 50/22 715/771 |
| 2013/0091191 A1 | 4/2013 | Levin |
| 2013/0104120 A1 | 4/2013 | Arrizza |
| 2013/0132465 A1 | 5/2013 | Brown |
| 2013/0133036 A1 | 5/2013 | Wang |
| 2013/0141329 A1 | 6/2013 | Halbert |
| 2013/0177455 A1 | 7/2013 | Kamen |
| 2013/0182381 A1 | 7/2013 | Gray |
| 2013/0184676 A1 | 7/2013 | Kamen |
| 2013/0188040 A1 | 7/2013 | Kamen |
| 2013/0191513 A1 | 7/2013 | Kamen |
| 2013/0197693 A1 | 8/2013 | Kamen |
| 2013/0204188 A1 | 8/2013 | Kamen |
| 2013/0227462 A1 | 8/2013 | Hsu |
| 2013/0272773 A1 | 10/2013 | Kamen |
| 2013/0281965 A1 | 10/2013 | Kamen |
| 2013/0297330 A1 | 11/2013 | Kamen |
| 2013/0310990 A1 | 11/2013 | Peret et al. |
| 2013/0317753 A1 | 11/2013 | Kamen |
| 2013/0317837 A1 | 11/2013 | Ballantyne |

(56) References Cited

U.S. PATENT DOCUMENTS

| | | |
|---|---|---|
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0227021 A1 | 8/2014 | Kamen |
| 2014/0278458 A1 | 9/2014 | Borges et al. |
| 2014/0318639 A1 | 10/2014 | Peret |
| 2014/0343492 A1 | 11/2014 | Kamen |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0033823 A1 | 2/2015 | Blumberg, Jr. |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0314083 A1 | 11/2015 | Blumberg, Jr. et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |
| 2016/0346056 A1 | 12/2016 | Demers et al. |
| 2016/0362234 A1 | 12/2016 | Peret et al. |
| 2017/0011202 A1 | 1/2017 | Kamen et al. |
| 2017/0045478 A1 | 2/2017 | Wilt et al. |
| 2017/0216516 A1 | 8/2017 | Dale et al. |
| 2017/0224909 A1 | 8/2017 | Kamen et al. |
| 2017/0259230 A1 | 9/2017 | Demers et al. |
| 2017/0266378 A1 | 9/2017 | Kamen et al. |
| 2017/0268497 A1 | 9/2017 | Kamen et al. |
| 2017/0284968 A1 | 10/2017 | Blumberg, Jr. |
| 2017/0296745 A1 | 10/2017 | Kamen et al. |
| 2017/0303969 A1 | 10/2017 | Langenfeld et al. |
| 2017/0321841 A1 | 11/2017 | Gray et al. |
| 2017/0333623 A1 | 11/2017 | Kamen et al. |
| 2017/0335988 A1 | 11/2017 | Peret et al. |
| 2018/0038501 A1 | 2/2018 | Peret et al. |
| 2018/0066648 A1 | 3/2018 | Kamen et al. |
| 2018/0080605 A1 | 3/2018 | Janway et al. |
| 2018/0106246 A1 | 4/2018 | Kamen et al. |
| 2018/0128259 A1 | 5/2018 | Kamen et al. |
| 2018/0224012 A1 | 8/2018 | Peret et al. |
| 2018/0228964 A1 | 8/2018 | Blumberg, Jr. et al. |
| 2018/0252359 A1 | 9/2018 | Janway et al. |
| 2018/0278676 A1 | 9/2018 | Kamen et al. |
| 2019/0009018 A1 | 1/2019 | Kamen et al. |
| 2019/0033104 A1 | 1/2019 | Kane et al. |
| 2019/0041362 A1 | 2/2019 | Blumberg, Jr. |
| 2019/0049029 A1 | 2/2019 | Peret et al. |
| 2019/0134298 A1 | 5/2019 | Kamen et al. |
| 2019/0139640 A1 | 5/2019 | Kamen et al. |
| 2019/0154026 A1 | 5/2019 | Kamen et al. |
| 2019/0170134 A1 | 6/2019 | Kamen et al. |
| 2019/0175821 A1 | 6/2019 | Kamen et al. |
| 2019/0179289 A1 | 6/2019 | Peret et al. |
| 2019/0189272 A1 | 6/2019 | Kamen et al. |
| 2019/0219047 A1 | 7/2019 | Kamen et al. |
| 2019/0249657 A1 | 8/2019 | Kamen et al. |
| 2019/0298913 A1 | 10/2019 | Biasi et al. |
| 2019/0316948 A1 | 10/2019 | Karol et al. |
| 2019/0328964 A1 | 10/2019 | Desch et al. |
| 2019/0341146 A1 | 11/2019 | Kamen et al. |
| 2019/0365421 A1 | 12/2019 | Langenfeld et al. |
| 2020/0025305 A1 | 1/2020 | Peret et al. |
| 2020/0051190 A1 | 2/2020 | Kamen et al. |
| 2020/0054823 A1 | 2/2020 | Baier et al. |
| 2020/0066388 A1 | 2/2020 | Kamen et al. |
| 2020/0070113 A1 | 3/2020 | Demers et al. |
| 2020/0078127 A1 | 3/2020 | Demers et al. |
| 2020/0171241 A1 | 6/2020 | Kamen et al. |
| 2020/0173469 A1 | 6/2020 | Kamen et al. |
| 2020/0182400 A1 | 6/2020 | Gray et al. |
| 2020/0278078 A1 | 9/2020 | Janway et al. |
| 2020/0347949 A1 | 11/2020 | Yoo |
| 2020/0371497 A1 | 11/2020 | Peret et al. |
| 2020/0386220 A1 | 12/2020 | Kamen et al. |
| 2020/0393414 A1 | 12/2020 | Wilt et al. |
| 2021/0023296 A1 | 1/2021 | Langenfeld et al. |

FOREIGN PATENT DOCUMENTS

| | | |
|---|---|---|
| AU | 2003265858 B2 | 12/2008 |
| AU | 2003256732 B2 | 7/2009 |
| CN | 1386478 A | 12/2002 |
| CN | 1472681 A | 2/2004 |
| CN | 1610516 A | 4/2005 |
| CN | 2722826 Y | 9/2005 |
| CN | 1829956 A | 9/2006 |
| CN | 2868184 Y | 2/2007 |
| CN | 1936974 A | 3/2007 |
| CN | 101166321 A | 4/2008 |
| CN | 101258761 A | 9/2008 |
| CN | 101584178 A | 11/2009 |
| CN | 101821743 A | 9/2010 |
| CN | 101907630 A | 12/2010 |
| CN | 102046222 A | 5/2011 |
| CN | 102122364 A | 7/2011 |
| CN | 202168825 U | 3/2012 |
| CN | 102637291 A | 8/2012 |
| EP | 473240 B1 | 6/1994 |
| EP | 477551 B1 | 1/1995 |
| EP | 666699 A1 | 8/1995 |
| EP | 319268 B1 | 1/1997 |
| EP | 960627 A2 | 12/1999 |
| EP | 612004 B2 | 10/2000 |
| EP | 760244 B1 | 5/2003 |
| EP | 1640028 A2 | 3/2006 |
| EP | 1722310 A1 | 11/2006 |
| EP | 1744262 A2 | 1/2007 |
| EP | 1944709 A1 | 7/2008 |
| EP | 2278511 A2 | 1/2011 |
| EP | 2302884 A1 | 3/2011 |
| EP | 2330524 A2 | 6/2011 |
| EP | 2216913 B1 | 11/2011 |
| EP | 649316 B2 | 8/2013 |
| GB | 2020735 A | 11/1979 |
| JP | 04126159 A | 11/1990 |
| JP | 2002169891 A | 11/2000 |
| JP | 2002177225 A | 12/2000 |
| JP | 2002085556 A | 7/2001 |
| JP | 2003277155 A | 3/2002 |
| JP | 2004523305 A | 8/2004 |
| JP | 2007143834 A | 11/2005 |
| JP | 2007330424 A | 6/2006 |
| JP | 2008301110 A | 5/2007 |
| JP | 4814868 B2 | 12/2007 |
| JP | 2009152999 A | 12/2007 |
| JP | 2009192420 A | 2/2008 |
| JP | 2010160628 A | 1/2009 |
| JP | 2012181795 A | 3/2011 |
| JP | 2011124354 A | 6/2011 |
| JP | 2013038501 A | 8/2011 |
| JP | 2012187411 A | 5/2012 |
| JP | 6180089 B2 | 8/2012 |
| WO | WO9304285 A1 | 3/1993 |
| WO | WO9310835 A1 | 6/1993 |
| WO | WO9321978 A1 | 11/1993 |
| WO | WO9814234 A1 | 4/1998 |
| WO | WO9910829 A1 | 3/1999 |

(56) References Cited

FOREIGN PATENT DOCUMENTS

| WO | WO9952575 | A1 | 10/1999 |
| --- | --- | --- | --- |
| WO | WO00003344 | A1 | 1/2000 |
| WO | WO0072181 | A2 | 11/2000 |
| WO | WO0198876 | A2 | 12/2001 |
| WO | WO02068018 | A2 | 9/2002 |
| WO | WO02100262 | A1 | 12/2002 |
| WO | WO03094091 | A1 | 11/2003 |
| WO | WO03105931 | A1 | 12/2003 |
| WO | WO2004012043 | A2 | 2/2004 |
| WO | WO2004029853 | A2 | 4/2004 |
| WO | WO2004054429 | A2 | 7/2004 |
| WO | WO2004056301 | A2 | 7/2004 |
| WO | WO2004066834 | A1 | 8/2004 |
| WO | WO2004070546 | A2 | 8/2004 |
| WO | WO2004070548 | A2 | 8/2004 |
| WO | WO2004072828 | A2 | 8/2004 |
| WO | WO2004087241 | A1 | 10/2004 |
| WO | WO2005065750 | A1 | 7/2005 |
| WO | WO2005083619 | A2 | 9/2005 |
| WO | WO2005089263 | A2 | 9/2005 |
| WO | WO2006015330 | A2 | 2/2006 |
| WO | WO2006060291 | A2 | 6/2006 |
| WO | WO2006086723 | A2 | 8/2006 |
| WO | WO2006086735 | A2 | 8/2006 |
| WO | WO2006121510 | A2 | 11/2006 |
| WO | WO2006126105 | A1 | 11/2006 |
| WO | WO2007126948 | A2 | 3/2007 |
| WO | WO2007113709 | A1 | 10/2007 |
| WO | WO2008022880 | A1 | 2/2008 |
| WO | WO2008031821 | A1 | 3/2008 |
| WO | WO2008097316 | A1 | 8/2008 |
| WO | WO2008103991 | A2 | 8/2008 |
| WO | WO2009003196 | A1 | 12/2008 |
| WO | WO2009055635 | A1 | 4/2009 |
| WO | WO2009069642 | A1 | 6/2009 |
| WO | WO2009107011 | A2 | 9/2009 |
| WO | WO2010045119 | A2 | 4/2010 |
| WO | WO2010077851 | A2 | 7/2010 |
| WO | WO2010085867 | A1 | 8/2010 |
| WO | WO2010129720 | A2 | 11/2010 |
| WO | WO2010132860 | A2 | 11/2010 |
| WO | WO2010135518 | A1 | 11/2010 |
| WO | WO2011021098 | A1 | 2/2011 |
| WO | WO2011066556 | A1 | 6/2011 |
| WO | WO2011091998 | A1 | 8/2011 |
| WO | WO2011109500 | A1 | 9/2011 |
| WO | WO2011119810 | A1 | 9/2011 |
| WO | WO2013095459 | A1 | 6/2013 |
| WO | WO2013095459 | A9 | 6/2013 |
| WO | WO2013096713 | A2 | 6/2013 |
| WO | WO2013096718 | A2 | 6/2013 |
| WO | WO2013096722 | A2 | 6/2013 |
| WO | WO2013096909 | A2 | 6/2013 |
| WO | WO2013176770 | A2 | 11/2013 |
| WO | WO2013177357 | A1 | 11/2013 |
| WO | WO2014100557 | A2 | 6/2014 |
| WO | WO2014100571 | A2 | 6/2014 |
| WO | WO2014100658 | A1 | 6/2014 |
| WO | WO2014100687 | A2 | 6/2014 |
| WO | WO2014100736 | A2 | 6/2014 |
| WO | WO2014100744 | A2 | 6/2014 |
| WO | WO2014144557 | A2 | 9/2014 |
| WO | WO2015017275 | A1 | 2/2015 |

OTHER PUBLICATIONS

AAMI and FDA, Infusing Patients Safely: Priority Issues from the AAMI/FDA Infusion Device Summit, Symposium, Oct. 5-6, 2010, pp. 1-48, AAMI, Arlington, Va, USA.
Office Action and Formal Examination dated Aug. 24, 2015, received in Columbian U.S. Appl. No. 15/168,128 (L52CO),.
Office Action and Formal Examination dated Aug. 28, 2015, received in Columbian U.S. Appl. No. 15/167,289 (K22CO).
Office Action and Formal Examination dated Sep. 2, 2015, received in Columbian U.S. Appl. No. 15/168,109 (K50CO).
Bianco et al., Architecting Service-Oriented Systems, CMU/SEL2011-TN-008, Aug. 2011, 46 pages, Software Engineer Institute, Carnegie Mellon University, Hanscom AFB, Massachusetts.
B. Braun, B. Braun SpaceStation MRI, Automated Infusion System, brochure, 1 pg., B. Braun Meslungen AG.
B. Braun, Dialog+: Dialog with the future, brochure, Oct. 2008, 1-14, Edition Oct. 2008, B. Braun Avitum AG.
B. Braun, Integrated Glucose Control, brochure, 1-11, B. Braun Melsungen AG.
B. Braun, Outlook ES Safety Infusion System, 2008, 16 pgs., B. Braun Medical, Inc.
B. Braun, Perfusor Space PCA and Accessories: Instructions for Use, manual, Nov. 2010, 1-46, B. Braun Melsungen AG.
B. Braun, Space System Technical Data, brochure,, 7 pgs., B. Braun Meslungen AG.
B. Braun, SpaceControl for Automated Glucose Control: Instructions for use, manual, Dec. 2010, 1-43, B. Braun Melsungen AG.
B. Braun, SpaceStation and SpaceCom: Instructions for Use, manual, 1-39, B. Braun Melsungen AG.
B. Braun, The Whole Hospital in the Palm of Your Hand, Automated Infusion Systems, brochure, 1-24, B. Braun Melsungen AG.
Butterfield, Alaris SE Pump, Monitoring and Detection of IV Line Occlusions, 2010, 4 pgs., CareFusion Corporation.
Carayon et al., Observing Nurse Interaction with Infusion Pump Technologies, Advances in Patient Safety: vol. 2—Observing Medication Administration, 349-364.
Cardinal Health, Alaris DS Docking Station: Technical Service Manual, manual, 2007, 1-31, Issue 2, Cardinal Health, Inc.
Cardinal Health, Alaris Gateway Workstation: Technical Service Manual, manual, 2008, 1-67, Issue 4, Cardinal Health, Inc.
Cardinal Health, Alaris GP Volumetric Pump: Technical Service Manual, manual, 2008, 1-84, Issue 3, Cardinal Health, Inc.
Care Everywhere, Gateway User Manual: V1.0.13 W/Cqi 1.6: For use with the Sigma Spectrum Pump: Care Everywhere Document No. CE-100-003-IFU, manual, 1-55, CareEverywhere LLC, 9 Tech Circle, Natick, Ma, USA.
Carefusion, Alaris SE Pump: Models 7100/7130 and 7200/7230, Rev2.X - User Manual, manual, Apr. 2011, pgs. i-126, CareFusion Corporation, San Diego, CA, United States.
Carefusion, Alaris System Direction for Use—with Alaris PC unit, Model 8015, Dec. 2011, 1-360, CareFusion Corporation, San Diego, CA, United States.
Carefusion, Enhance your skills, methodology and safety performance: Guardrails CQI Reporter Software, 2010, 1-2.
Carefusion, Infusion Products, catalog, 2011, 1-16, CareFusion Corporation, San Diego, CA, United States.
Charter Kontron, Envoy: The Standard For Bedside Patient Monitoring, catalog, England.
Communication pursuant to Article 94(3) EPC dated May 27, 2015, from the European Patent Office for application 11 820 830.5 (I97EP), 1-4.
Communication of the Substantive Examination Result dated Oct. 29, 2015, from the Mexican Institute of Industrial Property for application MX/a/2014/014267 (K66MX), 1-3.
Corsaro et al., Quality of Service in Publish/Subscribe Middleware, Apr. 26, 2006, 1-22, SELEX-SI—Roma.
FDA, Medical Devices: SEDASYS Computer-Assisted Personalized Sedation System—P080009, Recently-Approved Devices, Mar. 24, 2013, 2 p. , U.S. Food and Drug Administration.
First Examination Report from The Intellectual Property Office of New Zealand for Application 626636 (I97NZ), dated Nov. 13, 2014, 2 pgs.
Food and Drug Administration, Envoy Patient Monitor - Device Modification: Special 510(k) for 12 Lead ECG/Resp. Module, Aug. 16, 2001, 1-12.
Further Examination Report from The Intellectual Property Office of New Zealand for Application 626636 (I97NZ), dated Sep. 24, 2015, 2 pgs.
Ge Fanuc, Controller Solutions: More Choices for Your Applications, GE Fanuc Controller Solutions catalog, 2004, 1-160, GE Fanuc Automation, Inc.

(56) References Cited

OTHER PUBLICATIONS

Ge Medical Systems Information Technologies, 510(k) Summary, Aug. 28, 2009, 1-6.
Gieras, Innovative Infusion Pump Technologies, Engineering in Medicine & Biology Society, Jun. 15, 2010, pp. 1-53, IEEE Long Island Chapter.
Goldman et al., Advancing the Adoption of Medical Device "Plug-and-Play" Interoperability to Improve Patient Safety and Healthcare Efficiency, a white paper from the MD PnP Program, Sep. 2009, 1-3,, MD PnP Program.
Goldman et al., Medical Device "Plug-and-Play" Interoperability Program, 2012, MD PnP Program.
Goldman, Astm final F-2761, Medical Devices and Medical Systems - Essential safety requirements for equipment comprising the patient-centric integrated clinical environment (ICE) -Part 1: General requirements and conceptual model, 2008, 1-34, ASTM.
Goldman, Gaps in the System: Medical Device Interoperability, NIST, Oct. 18, 2006, 1-46, MD PnP.
Hawk, Iii, The Role of Color Coding in Medication Error Reduction, Action of the AMA House of Delegates 2004 Annual Meeting: Report of the Council on Scientific Affairs, CSA Report 5-A-04, pp. 1-8.
Hewlett Packard, Hp Viridia Model 24/26 Series Anesthesia / Standard: Quick Guide, manual, 1998, 1-29, Hewlett Packard.
Hoenich et al., Research & Technology: The Current Status and Future Directions of Hemodialysis Machine Technology, Hemodialysis Horizons, 38-44, AAMI.
Hofmann, Modeling Medical Devices for Plug-and-Play Interoperability, Master of Engineering thesis, Massachusetts Institute of Technology, Jun. 2007, pp. 1-187, Robert Matthew Hofmann, MMVII.
Infusion Nurses Society, Infusion Nursing Standards of Practice, Journal of Infusion Nursing, Jan./Feb. 2011, pgs. S1-S110, vol. 34, No. 1S, Infusion Nurses Society.
INFUSION NURSES SOCIETY, Policies and Procedures for Infusion Nursing, 2011, 1-162, 4th edition, Infusion Nurses Society, Inc.
International Search Report & Written Opinion dated May 14, 2012, received in International patent application No. PCT/US2011/066588 (I97WO), 9 pgs.
International Search Report & Written Opinion dated Aug. 7, 2014, received in International patent application No. PCT/US2013/076851 (K22WO), 19 pgs.
International Search Report & Written Opinion dated Sep. 4, 2014, received in International patent application No. PCT/US2013/077258 (K50WO), 18 pgs.
International Search Report & Written Opinion dated Jul. 14, 2014, received in International patent application No. PCT/US2013/077135 (L52WO), 18 pgs.
International Preliminary Report on Patentability dated Jul. 3, 2014, received in International patent application PCT/US2011/066588 (I97WO), 6 pgs.
International Preliminary Report on Patentability dated Jul. 2, 2015, received in International patent application No. PCT/US2013/076851 (K22WO), 13 pgs.
International Preliminary Report on Patentability dated Jul. 2, 2015, received in International patent application No. PCT/US2013/077258 (K50WO), 13 pgs.
International Preliminary Report on Patentability dated Dec. 4, 2014, received in International patent application No. PCT/US2013/042350 (K66WO), 13 pgs.
International Preliminary Report on Patentability dated Jul. 2, 2015, received in International patent application No. PCT/US2013/077135 (L52WO), 13 pgs.
ISO/IEC, Information Technology - Open Systems Interconnection - Basic Reference Model: The Basic Model, Nov. 15, 1994, 1-59, Second edition (Corrected and reprinted Jun. 15, 1996), ISO/IEC, Geneva, Switzerland.
Israelski, The Symbiq (Next-Generation) IV Infusion Pump: A Feature-Filled "Intelligent" Pump Developed with and for the End-User, May 2007, 1-4, Hospira, Inc.
Invitation to Pay Additional Fees and, Where Applicable, Protest Fee dated May 6, 2014, received in International patent application No. PCT/US2013/077135 (L52WO), 6 pgs.
Jetley et al., Safety Requirements based Analysis of Infusion Pump Software, 1-4, US Food and Drug Administration, Silver Spring, MD, United States.
Joshi et al., OMG's Data Distribution Service Standard: The OMG Data Distribution Service (DDS) Standard specifies a mandatory API for data-centric publish-subscribe, Dr. Dobb's: The World of Software Development, Nov. 20, 2006, 1-9.
King et al., Prototyping Closed Loop Physiologic Control with the Medical Device Coordination Framework, 200X, 1-11.
Millard et al., XEP-0060: Publish-Subscribe, Jul. 12, 2010, 1-173, Version 1.13, XMPP Standards Foundation (XSF).
National Patient Safety Agency, Design for Patient Safety: A Guide to the Design of Electronic Infusion Devices, booklet, 2010, pp. 1-96, Edition 1, National Patient Safety Agency, London, USA.
Nemeth et al., Making Information Technology a Team Player in Safety: The Case of Infusion Devices, Advances in Patient Safety: Interface Design for Infusion Devices, pp. 319-330, vol. 1, Feb. 2005.
Notice for Reason for Rejection, mailing dated Oct. 6, 2015, received in Japanese patent application National Publication No. 2014-548986 (I97JP), 5 pgs.
Pfiedler Enterprises, A Comprehensive Surgical Checklist: Using Technology to Help Optimize Preparedness, Patient Safety and Performance (A Continuing Education Self-Study Activity), 2011, pp. 1-20, Pfiedler Enterprises.
Prusch et al., IV Interoperability: Smart Pump and BCMA Integration, brochure, Oct. 5, 2010, 1-13, Lancaster General Health.
Rafferty, Proposal for Wireless Transmission of Non-invasive Respiratory Data to the Servo Module of an Opioid Infusion-Pump for Real-Time Patient Safety Feedback Control, Yale School of Medicine (Publication date unknown but assumed to be prior to the filing date.).
Search Report and Written Opinion from The Intellectual Property Office of Singapore for Application 11201403511Y (I97SG), dated Feb. 9, 2015, 22 pgs.
Sprunk et al., System Design for Simultaneous Data Acquisition from Patient Monitor and Syringe Pumps in Intensive Care Unit, Dec. 17-19, 2010, 878-882, IEEE EMBS International Conference on Biomedical Engineering and Sciences, Langkawi.
Talbot et al., Making Stretchable Electronics, Technology Review, Aug. 21, 2012, 1-2, Sep./Oct. 2012, MIT.
The 2008 Annual Premier Breakthroughs Conference: Innovation Through Supply Chain, Technology, and Clinical Sessions, Christine Depietto, Supply Synergy, vol. 3, No. 2, Aug. 2008.
Turisco et al., Beyond E-Health Records, CSC World, Winter 2010, 26-29, CSC World.
Turisco et al., Equipped for Efficiency: Improved Nursing Care Through Technology, Dec. 2008, 1-29, California Healthcare Foundation.
Vanderveen, Technology Focus: Using Data to Improve Smart Intravenous Infusion Pumps, Human Factors Horizons, 2010, pp. 57-63, Human Factors Horizons.
Definition—wifi as downloaded on Jul. 23, 2015, 1 pg.
Wikipedia, Publish-Subscribe Pattern, Jul. 31, 2013, 1-5.
Wikipedia, Rss definition, as downloaded on Jul. 21, 2015, p. 1-9.
Written Opinion from The Intellectual Property Office of Singapore for Application 11201403511Y (I97SG), dated Jun. 19, 2015, 11 pgs.
Written Opinion from The Intellectual Property Office of Singapore for Application 11201403511Y (I97SG), dated Oct. 13, 2015, 11 pgs.
Invitation to Pay Additional Fees and, Where Applicable, Protest Fee dated Sep. 26, 2013, received in International patent application No. PCT/US2013/042350 (K66WO), 7 pgs.
International Search Report & Written Opinion dated Nov. 7, 2013, received in International patent application No. PCT/US2013/042350 (K66WO), 18 pgs.

(56) References Cited

OTHER PUBLICATIONS

Gregorczyk, David, et al., "A Proof of Concept for Medical Device Integration Using Web Services," 9th Annual International Multi-Conference on Systems, Signals and Devices, Mar. 20-23, 2012, 6pgs.

Mauro, Christina, et al., "Standardized Device Services - A Design Pattern for Services Oriented Integration of Medical Devices" Proceedings of the 43rd Hawaii International Conference on System Sciences, Jan. 5-8, 2010, 10 pgs.

Trinugroho, Yohanes Baptista Dafferianto, et al. "A SOA-Based eHealth Service Platform in Smart Home Enviroment" 13th International Conference on e-Health Networking, Applications and Services: Healthcom Jun. 13-15, 2011, 2011, Columbia, Missouri, USA, 4 pgs.

Invitation to Pay Additional Fees and, Where Applicable, Protest Fee dated May 19, 2014, received in International patent application No. PCT/US2013/077258 (K50WO), 7 pgs.

Invitation to Pay Additional Fees and, Where Applicable, Protest Fee dated May 23, 2014, received in International patent application No. PCT/US2013/076851 (K22WO), 8 pgs.

Invitation To Respond to Written Opinion from the Intellectual Property Office of Singapore for Application 11201504872Y (K50SG), dated Mar. 2, 2016.

Invitation To Respond to Written Opinion from the Intellectual Property Office of Singapore for Application 10201603585V (R93SG), mailed on Mar. 10, 2017.

Chapter 4.3 of Java, Distributed Computing, by Jim Farley, O'Reilly & Associated, Copyright 2001, accessed at https://docstore.mik.ua/orelly/java-ent/dist/ch04_03.htm on Jun. 28, 2021.

Hiroshi Tsuda et al.; Inter-Cloud Data Security for Secure Cloud-Based Business Collaborations, Fuji Tsu Sci. Tech. J., vol. 48, No. 2, Apr. 2012, pp. 169-176, retrieved from https://www.fujitsu.com/global/documents/about/resources/publications/fstj/archives/vol.48-2/paper10.pdf on Jun. 28, 2021.

Aronson, Medication errors resulting from the confusion of drug names, 2004, Expert Opinion on Drug Safety 3:3, pp. 167-172.

Body area network for wireless patient monitoring, IET Commun., 2008, 2, pp. 215-222, E. Monton, J .F. Hernandez, J.M. Blasco, T. Herve', J Micallef, I. Grech, A. Brincat and V. Traver (Year: 2008).

A Self-Managing Framework for Health Monitoring, Intel Technolog Journal, vol. 10, Issue 4, 2006, Amit Baxi, Nagaju Kodalapura (Year: 2006).

Trbovich, P. L et al. The impact of traditional and smart pump infusion technology on nurse medication administration performance in a simulated inpatient unit. BMJ Quality & Safety 19.5 (2010): 430-434. (Year: 2010).

Link, Richard E. Md, Sam B. Bhayani MD, and Louis R. Kavoussi Md. A prospective comparison of robotic and Laparoscopic Pyeloplasty. Annals of Surgery (2006), 243:486-491.

Greg, HOWTO: Port-Forwarding The NW Blog, Oct. 22, 2007 www.networkwebcams.eo.uk/blog.

\* cited by examiner

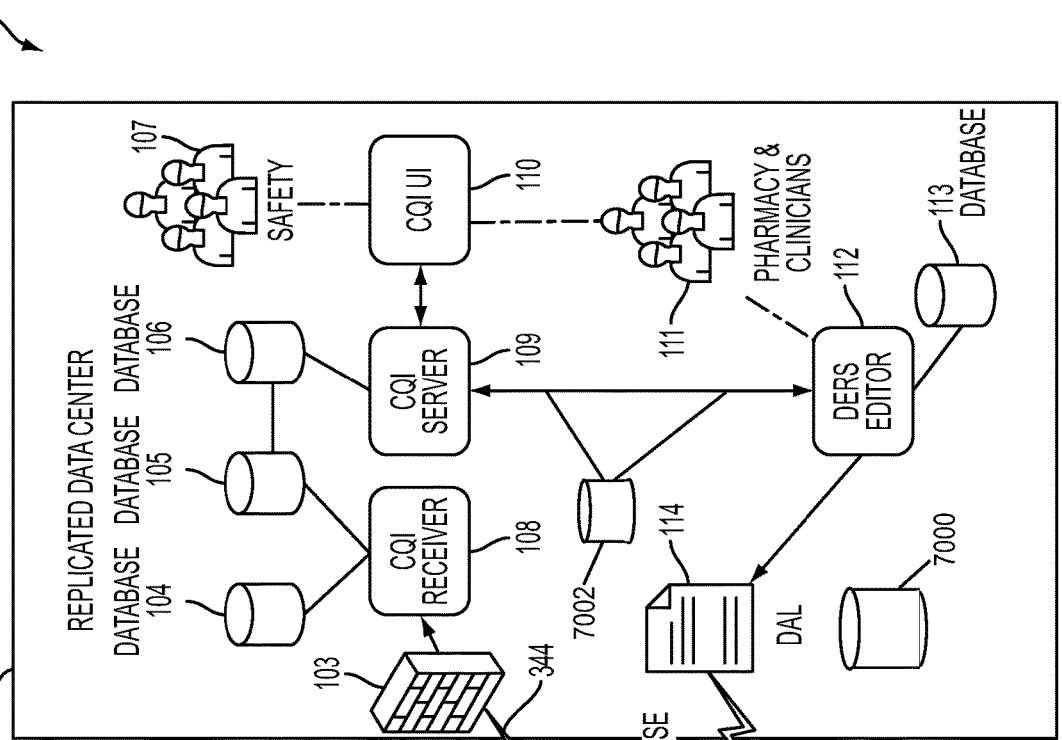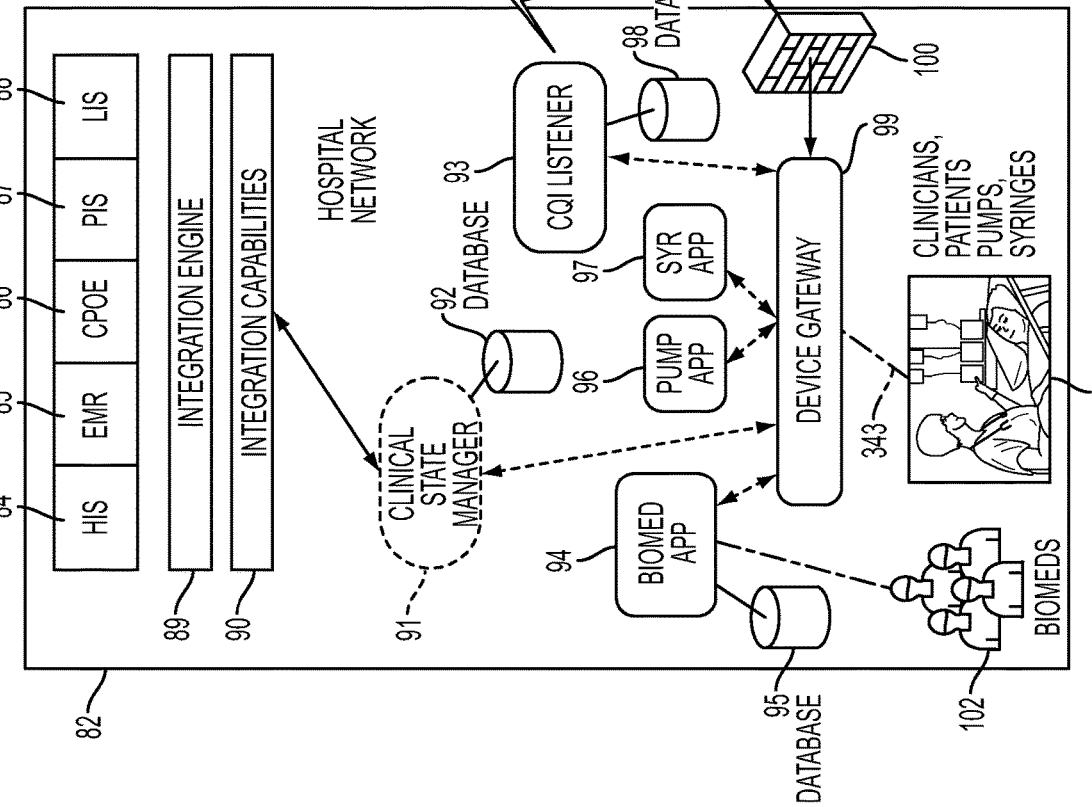
FIG. 4

FIG. 82

Add Care Group

| Add Care Group | Care Group Settings |

GROUP SETTINGS    1620    * = Required
- *Name    1622    4 West
- Care group type    1624    Adult ICU
- Sort order    1626    -1
- Require second review?    1628    No
- Screen Lock    1630    Enabled
- Default speaker volume    4
- Default screen brightness    4
- Automatically adjust brightness    Yes    1632
                                          1634

[1] 2 3 4 5        Next →    1616

FIG. 83

Add Care Group

| Add Care Group | Care Group Settings |    1640

PATIENT SETTINGS    * = Required

Second Entry of Weight and BSA    ○ Yes    ● No

Patient weight limits    1642
- High    Hard    1644    [ ] kg
- High    Soft    1646    [ ] kg
- Low    Soft    1648    [ ] kg
- Low    Hard    [ ] kg 1 [2] 3 4 5        Next →    1616

Add Care Group

| Add Care Group | Care Group Settings |

PATIENT SETTINGS (Continued)     * = Required

*BSA limits* 1650

| High | Hard | 1652 | [    ] m² |
|      | Soft | 1654 | [    ] m² |
| Low  | Soft | 1656 | [    ] m² |
|      | Hard |      | [    ] m² |

SYRINGE PUMP SETTINGS

*Syringe*  [                    ▼]
                                1658

1 2 3 4 5                Next ➪
                              1616

Add Care Group

| Add Care Group | Care Group Settings |

KVO SETTINGS 1660     * = Required

Default KVO Value  [    ] mL / hr

KVO can be changed by user  ○ Yes    ● No

RATE LIMITS 1664

| High | Hard | 1666 | [    ] mL / hr  1662 |
| High | Soft |      | [    ] mL / hr |

VBTI LIMITS 1668

| High | Hard | 1670 | [    ] mL |
| High | Soft |      | [    ] mL |

1 2 3 4 5                Next ➪
                              1616

FIG. 85

Add Care Group

| Add Care Group | Care Group Settings |

AIR INFUSION LIMIT 1680  \* = Required

| Default Air Infusion Limit | [      ] uL  1682 |
| User can change Air Infusion Limit | ○ Yes  ◉ No |
| Air Infusion Hard Limit | [      ] uL / 15 min |

1684

OCCLUSION SENSITIVITY  1686

| Default | Maximum ▼ |
| User can change | ○ Yes  ◉ No |
| Sensitivity hard limits | Maximum ▼   1688 |
| Back-pump relieve occlusion pressure | ○ Yes  ◉ No |

1690   1692

1 2 3 4 [5]    ✓ Finish

DERS Editor  SELECTED LIBRARY VERSION 1.0 (IN PROGRESS)  Welcome, Freddy Jones ▼

🔍 Search entire library

UNIVERSITY HOSPITAL

| Dashboard | Drugs | Care Groups | Review | Pump View |

🔍 Search drugs     5 Care Groups Available     ⇄ Copy     ➕ Add Care Group

| Care Group | DRUGS | CONC. | COMPLETED | 💬 | CQI |
|---|---|---|---|---|---|
| ▶ 4 West | 0 | 0 | 0% | - | 🕒 |
| ▶ Anesthesia | 47 | 5 | 95% | 1 | 🕒 |
| ▶ ER | 54 | 3 | 75% | - | 🕒 |
| ▶ OB/GYN | 63 | 12 | 65% | 1 | ⚠ |
| ▶ Medical Surgical | 122 | 10 | 65% | - | 🕒 |

FIG. 87

| DERS Editor | SELECTED LIBRARY VERSION 1.0 (IN PROGRESS) | | | | Welcome, Freddy Jones ▼ |
|---|---|---|---|---|---|

UNIVERSITY HOSPITAL

1598 · 1598 · 🔍 Search entire library

| Dashboard | Drugs | Care Groups | Review | Pump View | 1706 |

🔍 Search drugs · 767 Drugs Available · ⊞ Compare · ⇄ Copy · ➕ Add Drug — 1708

1704

| DRUG | CARE GROUPS | CLINICAL USES | TYPE | CONC. | 💬 | CQI |
|---|---|---|---|---|---|---|
| ▶ Abatacept | ER | 1 | 1 | 1 | 4 | ⚠ |
| ▶ Amikacin | ER | 1 | 2 | 1 | - | ⊙ |
| ▶ Bumetamide | Med./Surg. | 1 | 1 | 1 | - | ⊙ |
| ▶ Chlorothiazide | Surgery | 2 | 1 | 3 | 3 | ⚠ |
| ▶ Cyclophosphamide | Aneth. | 2 | 1 | 2 | - | ⊙ |
| ▶ DOBUTamine | Med./Surg. | 4 | 2 | 1 | - | ⊙ |
| ▶ Epirubicin | ER | 2 | 1 | 3 | - | ⊙ |
| ▶ HYDROmorphone | ER | 1 | 1 | 1 | 1 | ⊙ |
| ▶ Ibutilide | Aneth. | 1 | 1 | 2 | - | ⚠ |
| ▶ Streptozocin | OB/GYN. ER | 2 | 1 | 2 | - | ⊙ |

1702 — (pointing to table) · 1700 (top right)

Add Drug ⊗

| Enter Drug Name | Enter Drug Details | Add to Care Groups |

\* = Required

\* Drug name

| D | 1712

Dexmedetomidine
Dextrose
Diltiazem
DOBUTamine (in library) — 1714
DOPamine

Next ➔

FIG. 89

Add Drug  ⊗

| DOPamine | Enter Drug Details | Add to Care Groups |

\* = Required

\* Add drug to a care group:

Adult
- ■ 4 West  ⬅—1740
- ☐ Anesthesia
- ☐ Medical Surgical
- ☐ OB/GYN

Other
- ☐ Emergency Department

Next ➡

Drug Added  ⊗

You have successfully saved a new drug to 4 West in Library V1.0 —1752

DOPAMINE

Complete your new drug:
+ Add a Concentration
+ Add a Clinical use  ⟩—1754

⬅ Back                                              ✓ OK

Add Clinical Use                                1760

| Added to DOPamine - 4 West | Clinical Use Details |

GENERAL SETTINGS    1762                        * = Required

*Clinical Use Name    1764   Central Line
Display Order         1766   0
*Infusion Type        1768   Primary continuous
*Devices              1770   LVP
General notes         1772   [        ]
Clinical advisory summary  1774  [        ]
Detailed clinical advisory available on pump   [        ]

[1] 2 3 4                                    Next →

Add Clinical Use                                1760

| Added to DOPamine - 4 West | Clinical Use Details |

GENERAL SETTINGS (Continued)   1780         * = Required

*Can be Run with Secondary?      1782   No
*Second review required          1784   No
*VTBI Zero Handling for Primary Infusions   KVO

INFUSION SETTINGS   1786

*Alert near end of infusion      1788   ● Yes   ○ No
*Alert proximity to end of infusion       60 mins

PRIMARY CONTINUOUS INFUSION SETTINGS

*Dose Mode                               mcg/kg/min
                                  1790

1 [2] 3 4                                   Next →

FIG. 95                                   1716

Add Clinical Use                                    (×)

| Added to DOPamine - 4 West | Clinical Use Details |

PRIMARY CONTINUOUS INFUSION SETTINGS (Continued)     * = Required

| Default Dose Rate | 1800 → [    ] mcg/kg/min ▼ |
| Dose Rate Limits | 1802 |
| High | *Hard | 1804 → [ 50 ] mcg/kg/min |
|      | *Soft | 1806 → [ 25 ] mcg/kg/min |
| Low  | *Soft | 1808 → [ 1 ] mcg/kg/min |
|      | *Hard | 1810 → [ 1 ] mcg/kg/min |
| Dose titration increase hard limit | [ 101 ] % |

1 2 3 4                                    Next ➪

Add Clinical Use                                    (×)

| Added to DOPamine - 4 West | Clinical Use Details |

BOLUS SETTINGS                              ⟵ 1820    * = Required

*Is Bolus Allowed            ○ Yes    ⊙ No ⟵

LOADING DOSE PARAMETERS                     ⟵ 1822

*Loading Dose Allowed        ○ Yes    ⊙ No ⟵

*Loading Dose Settings       [ Not Specified    ▼ ]
                                              ⟵ 1824

1 2 3 4                                    Next ➪

FIG. 97

Add Concentration　　　　　　　　　　　　　　　　ⓧ

| Added to DOPamine - 4 West - Central Line | Concentration Details |

GENERAL
Allow operator change?　　　○ Yes　　　　⊙ No　—1832
Display format　　　　　　　○ Concentration　　⊙ Amount / Diluent　—1834

VOLUME　1836
Drug amount in container 1838　[ 400 ] [ mg ▼ ]
Container volume　1840　[ 250 ] [ mL ]
Default VTBI　1842　[ 250 ] [ mL ]
Concentration　　　　　　[ 1.6 ] [ mg / mL ]

✔ Finish　—1844

*DERS Editor*　　SELECTED LIBRARY VERSION 1.0 (IN PROGRESS)　　Welcome, Freddy Jones ▼

UNIVERSITY HOSPITAL　　　　　　　　　　　🔍 Search entire library

| Dashboard | Drugs | Care Groups | Review | Pump View |

🔍 Search drugs　　768 Drugs Available　　⊞ Compare　　⇆ Copy　　✚ Add Drug

| DRUG | CARE GROUPS | CLINICAL USES | TYPE | CONC. | 💬 | CQI |
|---|---|---|---|---|---|---|
| ▶ Abatacept | ER | 1 | 1 | 1 | 4 | ⚠ |
| ▶ Amikacin | ER | 1 | 2 | 1 | - | ⏲ |
| ▶ Bumetamide | Med./Surg. | 1 | 1 | 1 | - | ⏲ |
| ▶ Chlorothiazide | Surgery | 2 | 1 | 3 | 3 | ⚠ |
| ▶ Cyclophosphamide | Aneth. | 2 | 1 | 2 | - | ⏲ |
| ▶ DOBUTamine | Med./Surg. | 4 | 2 | 1 | - | ⏲ |
| ▼ DOPamine | 4 West | 1 | 1 | 1 | - | ⏲ |
| ☐ | 4 West ── Central Line ── 💧 400 mg / 250 mL | | | | - | ⏲ |
| | + Add care group　+ Add clinical use　+ Add concentration | | | | | |
| ▶ Epirubicin | ER | 2 | 1 | 3 | - | ⏲ |
| ▶ HYDROmorphone | ER | 1 | 1 | 1 | 1 | ⚠ |
| ▶ Ibutilide | Aneth. | 1 | 1 | 2 | - | ⏲ |
| ▶ Streptozocin | OB/GYN, ER | 2 | 1 | 2 | - | ⏲ |

FIG. 99

Add Clinical Use

| Intermittent | Abciximab - Critical Care | Clinical Use Details |

GENERAL SETTINGS

| *Display Order | 0 ▼ |
| *Infusion Type  1850 | Not Specified ▼ |
| *Medication Route  1852 | Not Specified ▼ |
| *Medication Site  1854 | Not Specified ▼ |
| *Delivery Method | Not Specified ▼ |
| General notes | |
| Clinical advisory summary | |
| Detailed clinical advisory available on pump | |

[1] 2 3 4 5    ✔ Finish Later    Next ➔

Add Clinical Use

| Intermittent | Abciximab - Critical Care | Clinical Use Details |

GENERAL SETTINGS (Continued)

| *Can be Run with Secondary? | Yes ▼ |
| *Second review required during programming? | Yes ▼ |
| *VTBI Zero Handling for Primary Infusions | Stop ▼ |
| *VTBI Zero Handling for Secondary Infusions | Notify and Revert to Primary ▼ |

1860

1 [2] 3 4 5    ✔ Finish Later    Next ➔

Add Clinical Use

| Intermittent | Abciximab - Critical Care | Clinical Use Details |

INFUSION SETTINGS

| *Alert near end of infusion | 0 ▼ |
|---|---|
| *Proximity to end of infusion | Not Specified ▼ |

PRIMARY CONTINUOUS INFUSION SETTINGS

| *Dose Mode | Not Specified ▼ |
|---|---|
| *Dose Rate | mg ▼ |

*Dose Rate Limits*

| High | *Hard | | mg / mL |
|---|---|---|---|
| | *Soft | | mg / mL |

1 2 3 4 5        ✔ Finish Later    Next ➔

Add Clinical Use

| Intermittent | Abciximab - Critical Care | Clinical Use Details |

PRIMARY CONTINUOUS INFUSION SETTINGS (Continued)

*Dose Rate Limits*

| Low | *Hard | | mg / mL |
|---|---|---|---|
| | *Soft | | mg / mL |
| *Dose Titration Increase Hard Limit | | 101% | mg / mL |
| *Dose Titration Increase Soft Limit | | 51% | mg / mL |

BOLUS SETTINGS    1870

| * Is Bolus Allowed | ○ Yes | ⦿ No |

1 2 3 4 5        ✔ Finish Later    Next ➔

| | | Acyclovir - Surgery<br>Non-Weight Based<br>25mg / mL | Acyclovir - Surgery<br>Weight Based<br>50mg / 250mL | Acyclovir - Surgery<br>Intermittent<br>75mg / 500mL |
|---|---|---|---|---|
| ▶ CLINICAL USE | | | | |
| ▶ CONCENTRATION | | | | |
| GENERAL | | | | |
| Allow operator change? | ≠ | Yes | No | Yes |
| Display format | | Concentration | Concentration | Concentration |
| VOLUME | | | | |
| Drug unit | | mg/mL | mg/mL | mg/mL |
| Drug amount in container | ≠ | 50mg | 500mg | 750mg |
| Container volume | | Not Specified | Not Specified | Not Specified |
| Default VTBI | ≠ | 250 mL | 500 mL | 500 mL |
| Concentration | | 25 mg / mL | 50 mg / mL | 75 mg / mL |
| LIMITS | | | | |
| High    Hard | ≠ | 10 mg | 50 mg / 250mL | 50 mg / 250mL |
|     Soft | ≠ | 5 mg / mL | 45 mg / 250mL | 45 mg / 250mL |
| Low     Soft | ≠ | 1 mg / mL | 15 mg / 250mL | 15 mg / 250mL |
|     Hard | ≠ | 0 mg / mL | 10 mg / 250mL | 10 mg / 250mL |

FIG. 111

| | | Acyclovir - Surgery<br>Non-Weight Based<br>25mg / mL | Acyclovir - Surgery<br>Weight Based<br>50mg / 250mL | Acyclovir - Surgery<br>Intermittent<br>75mg / 500mL |
|---|---|---|---|---|
| ▶ CLINICAL USE | | | | |
| ▶ CONCENTRATION | | | | |
| GENERAL | | | | |
| Allow operator change? | ≠ | Yes | No | Yes |
| VOLUME | | | | |
| Drug amount in container | ≠ | 50mg | 500mg | 750mg |
| Default VTBI | ≠ | 250 mL | 500 mL | 500 mL |
| LIMITS | | | | |
| High    Hard | ≠ | 10 mg | 50 mg / 250mL | 50 mg / 250mL |
|     Soft | ≠ | 5 mg / mL | 45 mg / 250mL | 45 mg / 250mL |
| Low     Soft | ≠ | 1 mg / mL | 15 mg / 250mL | 15 mg / 250mL |
|     Hard | ≠ | 0 mg / mL | 10 mg / 250mL | 10 mg / 250mL |

DERS Editor — Welcome, Freddy Jones ▼   ✔ New Tasks    1590

UNIVERSITY HOSPITAL

| Dashboard | Drugs | Care Groups | CQI | Review | Pump View |

Library Overview
Version
2.2
In progress ▼

768 Drugs
42 Care groups
68 Device groups

Review Progress
65%
Complete

6 New Changes
12 Reviewed changes
4 Care groups reviewed

REVIEW FEEDBACK — 2140
"This change is unneccessary. The soft high limit should stay the same." — 2142
Respond to comment — 2144
✖ Ignore    ✔ Revise — 2146

Quick Links
▶ Deploy Library   ▶ View history   ▶ Load prior library version
+ Add Task   + Add Drug   + Add Clinical Use

Review Feedback (4 new)

| DRUG | CARE GROUP | CHANGE | COMM... | | |
|---|---|---|---|---|---|
| Acyclovir | Surgery | Increased Soft High Limit to 45mg... | This change is un... | Terry Chang | Jan 24 |
| Ketamine | ICU | High Hard Limit to 60mg/mL... | This limit is to high... | Ruth Smith | Jan 22 |
| Lidocaine | ICU | Clinical Advisory to "Greater than..." | The clinical adviso... | Brendon Jones | Jan 15 |
| Abciximab | Pediatric | Soft High Limit from 35mg/ml... | Soft limit should be.. | Terry Chang | Jan 12 |

DERS Editor   SELECTED LIBRARY VERSION 2.2 (IN PROGRESS)   Welcome, Freddy Jones ▼   1590

UNIVERSITY HOSPITAL   🔍 Search entire drug library

| Dashboard | Drugs | Care Groups | CQI | Review | Pump View | — 1596a

Version 2.2   In progress ▼

1 Facility
8 Care groups
768 Drugs

▶ Deploy   ▶ View history   ▶ Open previous version — 1596b
Add a: [Drug ▼]   Go ▶

📊 LIBRARY - REVIEW PROGRESS

57% Changes approved
☐ 80 Changes awaiting review
☐ 12 Change requests
☐ 33 Feedback items
☑ 140 Changes approved
See all unapproved changes ⇨

(Bar chart: ICU, Interm. Care, Critical Care, Surgical, Medical-Surgical, Cont. Care, Adult Rehab, Ped. Rehab, Step-down) — 1596c

| 💬 REVIEW FEEDBACK | ✏ CHANGE REQUESTS |
|---|---|
| 33 Feedback Items | 12 Requests |
| 1 💬 Lidocaine ICU Weight-based 2mg/250mL | 1 ✏ Hydrocortisone Neonate Continuous 50mg/... |
| 1 💬 Abciximab ICU Non-weight-based 50mg/500... | 1 ✏ Ketorolac Medical Intermittent 2g/250mL |
| 3 💬 Lidocaine Medical Intermittent 2g/250mL | 3 ✏ Lidocaine ICU Weight-based 2mg/250mL |
| 1 💬 Acyclovir Surgery Non-Weight-based... | 2 ✏ DiphenhydrAMINE Obstetrics Non-Weight... |
| 1 💬 Lidocaine ICU Weight-based 2g/250mL | 1 ✏ Furosemide Medical Weight-based 2g/250mL |
| All feedback items ⇨ | All change requests ⇨ |

DERS Editor    SELECTED LIBRARY VERSION 2.1 (ACTIVE)    Welcome, Freddy Jones ▼    1590

UNIVERSITY HOSPITAL    🔍 Search entire drug library

| Dashboard | Drugs | Care Groups | CQI | Pump View |

1596a →

Version
2.1
Active ▼

1 Facility
8 Care groups
768 Drugs

LIBRARY IN PROGRESS
Version 57% Approved ▱▱▱▱
V2.2  12 Change requests  33 Feedback items
▶ View history  ▶ Open previous version ← 1596c
← 1596b 1596f →

⊙ CQI Snapshot    All Care Groups ▼ From: Jan 1, 2013  To: Feb 1, 2013

DERS Compliance

75% ☐ Compliant
9% ☐ Soft limit override
9% ☐ Hard limit pull back
7% ▨ Wild card infusion 8 Care groups   768 Drugs   13,800 Infusions

Trends

+12.5% ⇧ 600

+35% ⇧ 120 Wild card infusions
+2% ⇧ 200 Dose low soft limit overrides
-15% ⇩ 75 Dose high hard limits pull backs
-17% ⇩ 60 VTBI soft limit overrides
+8% ⇧ 145 Rate advisories ✏ Change Requests (22)

| DRUG | NAME | WHEN |
|---|---|---|
| 1 ✏ Lidocaine ICU Weight-based 2mg/250mL | Terry Chan, RN | Jan 24 |
| 1 ✏ Abciximab ICU Non-weight-based 50mg/500mL | Francis Scoffielf, RN | Jan 22 |
| 3 ✏ Hydrocortisone Neonate Continuous 50mg/250mL | Ruth Smith | Jan 15 |
| 1 ✏ Ketorolac Medical Intermittent 2g/250mL | Colin Dunkin, RN | Jan 12 |
| 1 ✏ Lidocaine ICU Weight-based 2g/250mL | William Stanford, RN | Jan 8 |
| 3 ✏ Furosemide Medical Weight-based 2g/250mL | Mansfield Brohanna, FNP | Jan 4 |

1 2 3 4 5 ➔     View All ➔

75% ☐ Compliant
9% ☐ Soft limit override
9% ☐ Hard limit pull back
7% ▨ Wild card infusion

+12.5% ⇧ 600

+35% ⇧ 120 Wild card infusions
+2% ⇧ 200 Dose low soft limit overrides
-15% ⇩ 75 Dose high hard limits pull backs
-17% ⇩ 60 VTBI soft limit overrides
+8% ⇧ 145 Rate advisories

1590

CHANGE REQUEST ✕

Ketorolac - Medical
Intermittent, 2g/250mL

REQUEST
"Please change Dose High Hard Limit to 10g.
We need extra dosage."
by: Colin Dunkin    on: Jan 12, 2013

[ ✕ Decline ]  [ View Record ➔ ]

← 2160

| | NAME | WHEN |
|---|---|---|
| | Terry Chan, RN | Jan 24 |
| | Francis Scoffielf, RN | Jan 22 |
| | Ruth Smith | Jan 15 |
| 1 ✏ Ketorolac Medical Intermittent 2g/250mL | Colin Dunkin, RN | Jan 12 |
| 1 ✏ Lidocaine ICU Weight-based 2g/250mL | William Stanford, RN | Jan 8 |
| 3 ✏ Furosemide Medical Weight-based 2g/250mL | Mansfield Brohanna, FNP | Jan 4 |

1 2 3 4 5 ➔     View All ➔

DERS Editor — Welcome, Dr. Terry Chang ▼  ✎ New Change — 1568, 1590

UNIVERSITY HOSPITAL

🔍 Acycl

| Dashboard | Drugs | Ca |

DRUGS (23)
Acyclovir   ICU, Weight-Based, 25mg/500mL
Acyclovir   ER, Non-Weight-Based, 50mg/500mL
Acyclomen Surgery, Non-Weight-Based, 50mg/500mL
Acyclomen Surgery, Intermittent, 25mg/500mL

DISPUTED CHANGES (12)
Add Dose Rate for 25mg/500mL of Acyclovir

COMMENTS (24)
"Hard limit to high on Acyclovir..."
"Acyclomen soft limit too low..."

View all results including "Acyclovir"

Library Overview

Version
2.2
[ In progress ▼ ]

768 Drugs
42 Care groups
68 Device groups

🗩 Recent Changes (2 new)

| DRUG | CARE GROUP | CHANGE | WHEN |
|---|---|---|---|
| Abcixim | ICU | Soft High Dose Limit increased from 35mg/mL to 40mg/mL | Jan 24 |
| Acyclovir | Surgery | Increased Soft High Dose Limit from 35mg/mL to 45mg/mL | Jan 22 |

✎ Changes In Progress (2)  View All

| DRUG | CARE GROUP | CHANGE | WHEN | STATUS |
|---|---|---|---|---|
| Abciximab | ICU | Soft High Dose Limit increased from 35mg/mL to 40mg/mL | Jan 24 | Open |
| Acyclovir | Surgery | Increased Soft High Dose Limit from 35mg/mL to 45mg/mL | Jan 22 | Not seen |

FIG. 147

DERS Editor — SELECTED LIBRARY VERSION 1.0 (IN PROGRESS) — Welcome, Freddy Jones ▼ — 2230

UNIVERSITY HOSPITAL

🔍 Search entire library

| Dashboard | Drugs | Care Groups | Review | Pump View |

58% Changes Reviewed — 2232

Anesthesia ▨▨▨ 12%
4 West ▨▨▨ 12%
ER ▨▨▨ 20%
— 2234

Feedback (33)   Show: 🗩 Feedback ✎ Requests [ Both ] — 2240

| TYPE | DRUG | CARE GROUP | CLINICAL USE | CONC. | NAME | WHEN |
|---|---|---|---|---|---|---|
| ▶ 1 🗩 | DOPamine | 4 West | Peripheral Line | 400mg/250mL | Jane Doe, RN | Mar 10 |
| ▶ 1 🗩 | Abciximab | ER | Peripheral Line | 400mg/250mL | Jane Doe, RN | Mar 7 |
| ▶ 3 🗩 | Hydrocortisone | OB/GYN | Continuous | 50mg/250mL | Francis Scoffi... | Mar 7 |
| ▶ 1 🗩 | Ketorolac | OB/GYN | Intermittent | 25mg/250mL | James Doe, R... | Mar 7 |
| ▶ 1 🗩 | Lidocaine | Anesthesia | Weight-based | 25mg/250mL | Colin Dunkin... | Mar 6 |
| ▶ 1 🗩 | Furosemide | ER | Weight-based | 2mg/250mL | William Stan... | Mar 6 |
| ▶ 1 🗩 | Lidocaine | Anesthesia | Weight-based | 2mg/250mL | James Doe, R... | Mar 6 |
| ▶ 🗩 | Abciximab | Med/Surg | Non-weight-based | 50mg/500mL | Colin Dunkin... | Mar 5 |
| ▶ ✎ | Hydrocortisone | ER | Continuous | 50mg/250mL | William Stan... | Mar 5 |
| ▶ 🗩 | Ketorolac | Anesthesia | Intermittent | 20mg/250mL | James Doe, R... | Mar 4 |
| ▶ ✎ | Hydrocortisone | ER | Continuous | 50mg/250mL | Colin Dunkin... | Mar 4 |
| ▶ ✎ | Ketorolac | OB/GYN | Intermittent | 5mg/250mL | William Stan... | Mar 3 |

DERS Editor — SELECTED LIBRARY VERSION 2.2 (IN PROGRESS) — Welcome, Freddy Jones ▼

UNIVERSITY HOSPITAL

| Dashboard | Drugs | Care Groups | CQI | Review | Pump View |

58% Changes approved

12 Change requests  33 Feedback items

Feedback & Changes Requests (45)  Show: 💬 Feedback  ✏ Requests  [Both]

| TYPE | MEDICATION RECORD | NAME | WHEN |
|---|---|---|---|
| ▶ 1 💬 | Lidocaine ICU Weight-based 2mg/250mL | Terry Chang, RN | Jan 24 |
| ▶ 1 💬 | Abciximab ICU Non-weight based 50mg/500mL | Francis Scoffield, RN | Jan 22 |

LIBRARY CHANGE  You increased Dose High Hard Limit from 5mg to 10mg on Jan 12

FEEDBACK  "Didn't we discuss changing the High Hard Limit to 15mg? Please come see me so I can explain." - *Terry Chang, RN*

COMMENT  Yes, but there can be adverse effects when delivering above 10mg

Cancel  ✔ Save  View Record ➤

| ▶ 3 ✏ | Hydrocortisone Neonate Continuous 50mg/250mL | Ruth Smith | Jan 15 |
| ▶ 1 💬 | Ketorolac Medical Intermittent 2g/250mL | Colin Dunkin, RN | Jan 12 |
| ▶ 1 ✏ | Lidocaine ICU Weight-based 2mg/250mL | William Stanford, RN | Jan 8 |

FIG. 151

DERS Editor — SELECTED LIBRARY VERSION 1.0 (IN PROGRESS) — Welcome, Jane Doe ▼

UNIVERSITY HOSPITAL

| Dashboard | Drugs | Care Groups | CQI | Review | Pump View |

58% Changes Reviewed

24 Changes to Review  7 Admin comments

Changes Needing Review  Show: [Changes to review]  Admin Comments  Both

| STATUS | CARE GROUP | DRUG | CLINICAL USE | CONC. | WHEN |
|---|---|---|---|---|---|
| ◆ Modified | 4 West | DOPamine | Peripheral Line | 400mg/250mL | Mar 5, 2013 |
| 💬 Comment | 4 West | Abciximab | Intermittent | 50mg/500mL | Mar 4, 2013 |
| ✦ New | 4 West | Epirubicin | Non-weight-based | 25mg/250mL | Mar 4, 2013 |
| ◆ Modified | 4 West | Ketamine | Non-weight-based | 50mg/mL | Mar 4, 2013 |
| ◆ Modified | 4 West | Lidocaine | Central Line | 25mg/250mL | Mar 3, 2013 |
| ✦ New | 4 West | Abciximab | Intermittent | 50mg/500mL | Mar 2, 2013 |
| ◆ Modified | 4 West | Abatacept | Non-weight-based | 25mg/250mL | Mar 2, 2013 |
| 💬 Comment | 4 West | Chlorothiazide | Non-weight-based | 50mg/mL | Mar 2, 2013 |
| ◆ Modified | 4 West | DOPamine | Central Line | 400mg/250mL | Mar 2, 2013 |
| ✦ New | 4 West | Lidocaine | Weight-based | 25mg/250mL | Mar 1, 2013 |

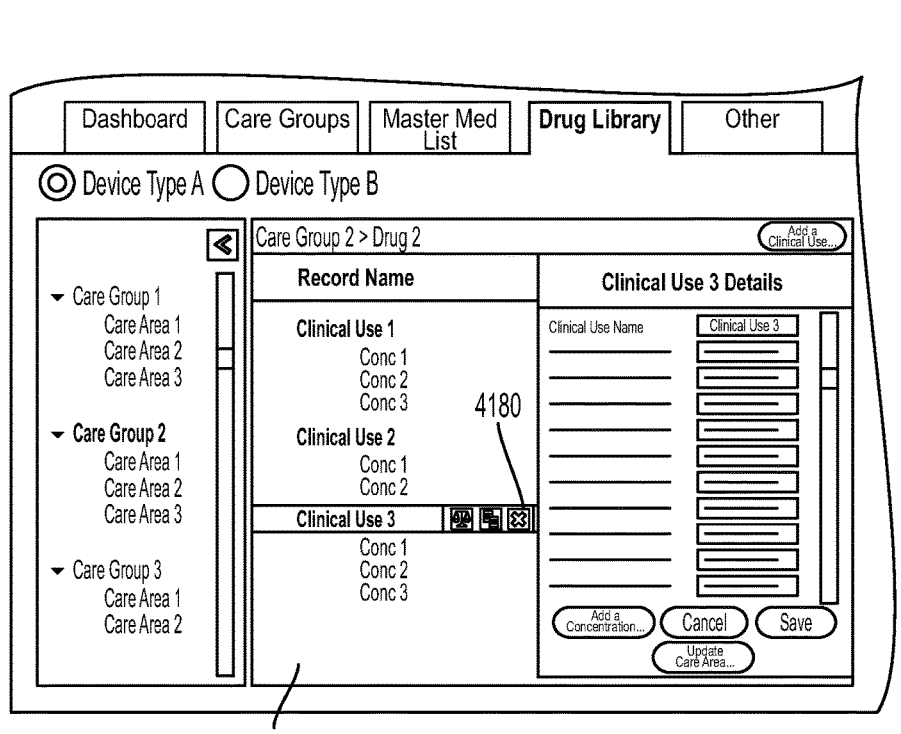
FIG. 178
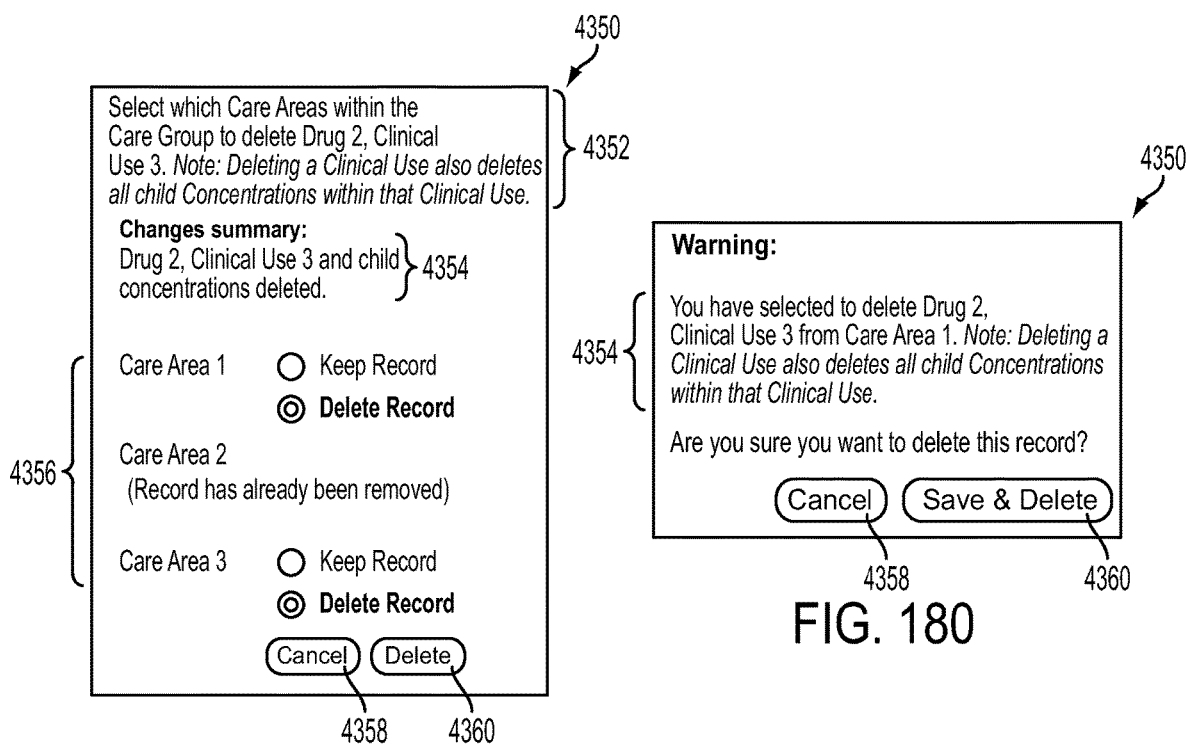
FIG. 179
FIG. 180

COMPUTER-IMPLEMENTED METHOD, SYSTEM, AND APPARATUS FOR ELECTRONIC PATIENT CARE

CROSS-REFERENCE TO RELATED APPLICATIONS

The present application is a Non-Provisional Application which claims the benefit of U.S. Provisional Patent Application Ser. No. 61/740,474, filed Dec. 21, 2012 and entitled System, Method, and Apparatus for Communicating Data, which is hereby incorporated herein by reference in its entirety.

The present application is also a Continuation-In-Part Application of U.S. patent application Ser. No. 13/723,253, filed Dec. 21, 2012 and entitled System, Method, and Apparatus for Electronic Patient Care, now U.S. Publication No. US-2013-0191413-A1, published Jul. 25, 2013, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care;

U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,253 is a Continuation-In-Part of U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/333,574 is a Continuation-In-Part Application of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application No. 61/297,544, filed Jan. 22, 2010 and entitled Electronic Order Intermediation System for a Medical Facility, both of which are hereby incorporated herein by reference in their entireties.

This application is also Continuation-In-Part Application of U.S. patent application Ser. No. 13/723,239, filed Dec. 21, 2012 and entitled System, Method, and Apparatus for Electronic Patient Care, now U.S. Publication No. US-2013-0297330-A1, published Nov. 7, 2013, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,239 claims priority to, benefit of, and is also a Continuation-In-Part Application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, which is a Continuation-In-Part Application of U.S. patent application Ser. No. 13/011,543, filed Jan. 21, 2011 and entitled Electronic Patient Monitoring System, now U.S. Publication No. US-2011-0313789-A1, published Dec. 22, 2011, which claims priority to U.S. Provisional Patent Application Ser. No. 61/297,544, filed Jan. 22, 2010 and entitled Electronic Order Intermediation System for a Medical Facility; and PCT Application Serial No. PCT/US11/66588, filed Dec. 21, 2011 and entitled System, Method, and Apparatus for Electronic Patient Care, now International Publication No. WO 2013/095459, published Sep. 12, 2013, each of which is hereby incorporated herein by reference in their entireties.

This application is also a Continuation-In-Part Application of U.S. patent application Ser. No. 13/723,242, filed Dec. 21, 2012 and entitled System, Method, and Apparatus for Electronic Patient Care, now U.S. Publication No. US-2013-0317753-A1, published Nov. 28, 2013, which claims priority to and the benefit of the following:

U.S. Provisional Patent Application Ser. No. 61/651,322, filed May 24, 2012 and entitled System, Method, and Apparatus for Electronic Patient Care, which is hereby incorporated herein by reference in its entirety.

This application is also a Continuation-In-Part Application of U.S. Ser. No. 13/900,655, filed May 23, 2013 and entitled System, Method, and Apparatus for Electronic Patient Care, now U.S. Publication No. US-2013-0317837-A1, published Nov. 28, 2013 which claims priority to and the benefit of U.S. Provisional Patent Application Ser. No. 61/651,322, filed May 24, 2012 and entitled System, Method, and Apparatus for Electronic Patient Care, both of which are hereby incorporated herein by reference in their entireties.

U.S. patent application Ser. No. 13/900,655 is also a Continuation-In-Part Application which claims priority to and the benefit of the following:

U.S. patent application Ser. No. 13/480,444, filed May 24, 2012 and entitled Blood Treatment Systems and Methods, now U.S. Publication No. US-2013-0037485-A1, published Feb. 14, 2013; and PCT Application Serial No. PCT/US12/00257, filed May 24, 2012 and entitled Blood Treatment Systems and Methods, now International Publication No. WO/2012/161744, published Nov. 29, 2012.

This application is also a Continuation-In-Part Application of PCT Application Serial No. PCT/US13/42350, filed May 23, 2013 and entitled System, Method, and Apparatus for Electronic Patient Care, which claims priority to and the benefit of U.S. Provisional Patent Application Ser. No. 61/651,322, filed May 24, 2012 and entitled System, Method, and Apparatus for Electronic Patient Care, both of which are hereby incorporated herein by reference in their entireties.

PCT Application Serial No. PCT/US13/42350 is also a Continuation-In-Part Application which claims priority to and the benefit of the following:

U.S. patent application Ser. No. 13/480,444, filed May 24, 2012 and entitled Blood Treatment Systems and Methods, now U.S. Publication No. US-2013-0037485-A1, published Feb. 14, 2013; and PCT Application Serial No. PCT/US12/00257, filed May 24, 2012 and entitled Blood Treatment Systems and Methods, now International Publication No. WO/2012/161744, published Nov. 29, 2012.

The present application may also be related to one or more of the following patent applications filed on Dec. 21, 2012, all of which are hereby incorporated herein by reference in their entireties:

Nonprovisional application for System, Method, and Apparatus for Clamping, Ser. No. 13/723,238;

Nonprovisional application for System, Method, and Apparatus for Dispensing Oral Medications, Ser. No. 13/723,235;

PCT application for System, Method, and Apparatus for Dispensing Oral Medications, Serial No. PCT/US12/71131;

Nonprovisional application for System, Method, and Apparatus for Estimating Liquid Delivery, Ser. No. 13/724,568;

Nonprovisional application for System, Method, and Apparatus for Infusing Fluid, Ser. No. 13/725,790;

PCT application for System, Method, and Apparatus for Infusing Fluid, Serial No. PCT/US12/71490;

Nonprovisional application for System, Method, and Apparatus for Monitoring, Regulating, or Controlling Fluid Flow, Ser. No. 13/723,244;

PCT application for System, Method, and Apparatus for Monitoring, Regulating, or Controlling Fluid Flow, Serial No. PCT/US12/71142;

Nonprovisional application for System, Method, and Apparatus for Estimating Liquid Delivery, Ser. No. 13/723,251; and PCT application for System, Method, and Apparatus for Estimating Liquid Delivery, Serial No. PCT/US12/71112.

The present application may also be related to one or more of the following patent applications, all of which are hereby incorporated herein by reference in their entireties:

U.S. Provisional Patent Application Ser. No. 61/738,447, filed Dec. 18, 2012 and entitled System, Method, and Apparatus for Detecting Air in a Fluid Line Using Active Rectification;

U.S. patent application Ser. No. 13/840,339, filed Mar. 15, 2013 and entitled Apparatus for Infusing Fluid;

PCT Application Serial No. PCT/US13/32445, filed Mar. 15, 2013 and entitled Apparatus for Infusing Fluid;

U.S. patent application Ser. No. 13/833,432, filed Mar. 15, 2013 and entitled Syringe Pump and Related Method;

U.S. patent application Ser. No. 13/836,497, filed Mar. 15, 2013 and entitled System and Apparatus for Electronic Patient Care;

U.S. patent application Ser. No. 13/833,712, filed Mar. 15, 2013 and entitled System, Method, and Apparatus for Clamping;

U.S. patent application Ser. No. 13/834,030, filed Mar. 15, 2013 and entitled System, Method, and Apparatus for Monitoring, Regulating, or Controlling Fluid Flow;

U.S. Provisional Patent Application Ser. No. 61/860,398, filed Jul. 31, 2013 and entitled System, Method, and Apparatus for Bubble Detection in a Fluid Line Using a Split-Ring Resonator;

U.S. Provisional Patent Application Ser. No. 61/900,431, filed Nov. 6, 2013 and entitled System, Method, and Apparatus for Monitoring, Regulating, or Controlling Fluid Flow;

U.S. Provisional Patent Application Ser. No. 61/894,801, filed Oct. 23, 2013 and entitled Syringe Pump and Related Method;

U.S. Provisional Patent Application Ser. No. 61/843,574, filed Jul. 8, 2013 and entitled System, Method, and Apparatus for Clamping;

U.S. patent application Ser. No. 13/971,258, filed Aug. 20, 2013 and entitled Electronic Patient Monitoring System;

U.S. Provisional Patent Application Ser. No. 61/904,123, filed Nov. 14, 2013 and entitled Syringe Pump and Related Method;

U.S. patent application Ser. No. 14/101,848, filed Dec. 10, 2013 and entitled System, Method, and Apparatus for Detecting Air in a Fluid Line Using Active Rectification;

U.S. patent application Ser. No. 14/135,809, filed Dec. 20, 2013 and entitled System, Method, and Apparatus for Communicating Data;

PCT Application Serial No. PCT/US13/76886, filed Dec. 20, 2013 and entitled System, Method, and Apparatus for Communicating Data;

PCT Application Serial No. PCT/US13/77258, filed Dec. 20, 2013 and entitled Computer-Implemented Method, System, and Apparatus for Electronic Patient Care;

U.S. patent application Ser. No. 14/136,243, filed Dec. 20, 2013 and entitled System, Method, and Apparatus for Electronic Patient Care; and PCT Application Serial No. PCT/US13/77135, filed Dec. 20, 2013 and entitled System, Method, and Apparatus for Electronic Patient Care.

BACKGROUND

Field of Disclosure

The present disclosure relates to patient care. More particularly, the present disclosure relates to a system and apparatus for electronic patient care.

Description of Related Art

Patient care often involves administering fluids such as medications directly into the patient. This can be accomplished by way of gravity-fed tubing connected to a reservoir (e.g., an IV bag). Fluids or medication can also be administered by way of forced infusion. Administering fluids or medication to a patient often requires the interaction of many parties (e.g., doctors, nurses, pharmacists). These interactions can be subject to miscommunication, mistakes, or other events that result in an inaccurate amount of fluid being administered to the patient.

SUMMARY

In accordance with an exemplary embodiment of the disclosure involving electronic patient care, a medical error reduction system comprises medical error reduction software for use in creating and revising at least one drug library that is configured for use in at least one medical device. The software is configured to provide sets of privileges to sets of users. The sets of privileges allocate a degree of software functionality to the sets of users, the degree of software functionality configured to define the ability of a user to alter the at least one drug library. The medical error reduction system also comprises at least one server and at least one editor computer. The editor computer is in communication with the server via a network, and includes a processor in communication with a display.

In accordance with an embodiment of the disclosure, a medical error reduction system may include a medical error reduction software for use in creating and revising at least one drug library. The software may be configured to provide one of a plurality of sets of privileges to each of a plurality of sets of users. Each of the plurality of sets of privileges may be arranged to allocate a degree of software functionality to one of the plurality of sets of users. The degree of software functionality may be configured to define the ability of a user to alter the at least one drug library. The medical error reduction system may include at least one server. The medical error reduction system may include at least one editor computer. Each of the at least one editor computer may comprise a processor in communication with a display. The at least one editor computer and at least one server may be configured to communicate via a network in a client-server based model. Each of the at least one drug library may be for use in at least one medical device.

In some embodiments of the system each of the at least one drug library may be organized in a hierarchy. In some embodiments, the hierarchy may include a plurality of care areas which are subordinate to at least one care group. In some embodiments, each level of the hierarchy may include a number of delivery parameters for the at least one medical device. In some embodiments, each of the at least one drug library includes a plurality of entries each corresponding to a specific medicament. In some embodiments, the at least one drug library may include a number of parameters to inform operation of the at least one medical device In some embodiments, the drug library may include a plurality of programming limits for the at least one medical device. In some embodiments, the medical error reduction software may further be configured to provide quality improvement information to a user. In some embodiment, at least one of the plurality of sets of privileges may allocate a drug library review privilege to one of the plurality of sets of users. In some embodiments, at least one of the plurality of sets of privileges may allocate a drug library editing privilege to one of the plurality of sets of users. In some embodiments, at least one of the plurality of sets of privileges may allocate a privilege set editing or creation privilege to one of the plurality of sets of users. In some embodiments, at least one of the plurality of sets of privileges may allocate an add user privilege to one of the plurality of sets of users. In some embodiments, the plurality of sets of privileges allocated to each of the plurality of sets of users may force a collaborative process between the plurality of sets of users for the creating and revising of the at least one drug library.

In accordance with an embodiment of the present disclosure, a medical error reduction system may include at least one server. The medical error reduction system may include at least one editor computer. Each of the at least one editor computer may include a processor in communication with a display. The at least one editor computer and at least one server may be configured to communicate via a network in a client-server based model. The medical error reduction system may include a medical error reduction software configured to be executed by the at least one server. The medical error reduction software may be accessible via the at least one editor computer for use in creating and revising at least one drug library. Each of the at least one drug library may be for use in at least one medical device. Each of the at least one medical device may include a medical device processor and a medical device graphical user interface configured to display a user interface. The user interface may convey information and may be used to program its respective medical device. Each of the at least one drug library may contain a plurality of entries which guide user programming of the at least one medical device. The medical error reduction software may be configured to display a simulated medical device graphical user interface. The simulated medical device graphical user interface may mimic behavior of the medical device graphical user interface for a medical device using a selected drug library of the at least one drug library.

In some embodiments, the simulated medical device graphical user interface is context sensitive. In some embodiments, the medical error reduction software may include a number of privilege sets. Each of the privilege sets may be assigned to one of a plurality of sets of users. The number of privilege sets may each allocate a degree of software functionality to each of the plurality of sets of users. In some embodiments, the simulated medical device graphical user interface may be a software functionality which may be toggled on or off the number of sets of privileges. In some embodiments, each of the at least one drug library may be organized in a hierarchy. In some embodiments, the hierarchy may include a plurality of care areas which are subordinate to at least one care group. In some embodiments each level of the hierarchy may include a number of delivery parameters for the at least one medical device. In some embodiments, each of the at least one drug library may include a plurality of entries each corresponding to a specific medicament. In some embodiments, the at least one drug library may include a number of parameters to inform operation of the at least one medical device. In some embodiments, the drug library may include a plurality of programming limits for the at least one medical device. In some embodiments, the medical error reduction software may be further configured to provide quality improvement information to a user.

In accordance with another embodiment of the present disclosure, a medical device for delivering a medicament to a patient may include a controller configured to control operation of a pumping mechanism which causes the medicament to be delivered. The medical device may include a display. The medical device may include a computer readable memory configured to store program code for a drug library. The drug library may contain a plurality of entries. The plurality of entries may comprise at least one entry corresponding to a portion of a facility. For each such entry there may be at least one drug entry. Each of the at least one drug entry may have parameters associated therewith. At least one drug entry in the drug library may not be associated with a specific drug, but rather a broad drug category. The medical device may include a processor configured to display a graphical user interface on the display of the medical device. The graphical user interface may be for use by a user to program the controller using the drug library.

In some embodiments, a user may select one of the at least one drug entry in the drug library not associated with a specific drug, but rather a broad drug category to program delivery of the medicament to the patient. In some embodiments, at least one drug entry in the drug library not associated with a specific drug, but rather a broad drug category may be associated with at least one parameter governing medicament delivery. In some embodiments, the drug library may be created or modified with a medical error reduction software. In some embodiments, the display may be a touch screen display. In some embodiments, at least one of the at least one drug entry in the drug library not associated with a specific drug, but rather a broad drug category may allow the user to program the medical device to deliver the medicament in a volume per hour mode. In some embodiments, each of the plurality of entries may be associated with at least one parameter. In some embodiments, at least one of the at least one parameters may be a medicament delivery parameter.

In accordance with an embodiment of the present disclosure a medical error reduction system may include a drug library editing software for use in creating and revising at least one drug library. The at least one drug library may contain a plurality of entries. Each of the at least one drug library may be for use with at least one medical device. The software may be configured to provide one of a plurality of sets of privileges to each of a plurality of sets of users. Each of the plurality of sets of privileges may be arranged to allocate a degree of software functionality to one of the plurality of sets of users. The medical error reduction system may include at least one server. The medical error reduction system may include at least one editor computer. Each of the at least one editor computer may include a processor in communication with a user interface. The at least one editor computer and at least one server may be configured to communicate via a network in a client-server based model. At least one of the plurality of sets of users may use the software to request a change to at least a portion of the at least one drug library.

In some embodiments, at least one of the plurality of sets of privileges may be configured to allow a user to decline implementation of the change. In some embodiments, at least one of the plurality of sets of privileges may be configured to allow a user to accept implementation of the change. In some embodiments, at least one of the plurality of sets of privileges may be configured to allow a user to submit a question to the change. In some embodiments, at least one of the plurality of sets of privileges may be configured to allow a user to propose a revision to the change. In some embodiments, the server may be configured to execute the medical error reduction software. In some embodiments, the degree of software functionality may be configured to define the ability of a user to alter the at least one drug library. In some embodiments, the at least one medical device may be an infusion pump.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The medical error reduction system may include at least one server configured to execute the medical error reduction software. The medical error reduction system may include at least one editor computer. Each of the at least one editor computer may include a processor in communication with a user interface. The user interface may be for use by one or more user to edit the at least one drug library. The at least one editor computer and at least one server may be configured to communicate via a network. At least one of the one or more user may request a change to the at least one drug library by tendering an electronic change request.

In some embodiments, the at least one medical device may be an infusion pump. In some embodiments, the electronic change request may be linkable to medical data.

In some embodiments, the medical data may be stored in an electronic database to provide contextual information. In some embodiments, the electronic database may be in a hosted environment. In some embodiments, the medical data may be generated from the at least one medical device. In some embodiments, the medical data may be stored in an electronic database In some embodiments, the medical data may be associated with the one of the at least one drug library used in the at least one medical device which generated the medical data. In some embodiments, the medical data may be displayed in the form of a table. In some embodiments, the medical data may be displayed in the form of a chart. In some embodiments, the medical data may be displayed in the form of a graph. In some embodiments, the medical data may be displayed in the form of a diagram. In some embodiments, the medical data may be displayed in the form of an infusion story. In some embodiments, a user may use the drug library editing software to search the medical data. In some embodiments, a user may use the drug library editing software to filter the medical data. In some embodiments the medical data may be displayed in a user selectable format. In some embodiments, the user may only access medical data for versions of the one of the at least one library currently being edited. In some embodiments, the plurality of entries may be each associated with one or more delivery parameters. In some embodiments, at least one of the one or more user may accept the electronic change request. In some embodiments, at least one of the one or more user may respond to the electronic change request. In some embodiments, at least one of the one or more user may propose an alteration to the electronic change request. In some embodiments, at least one of the one or more user may deny the electronic change request.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The drug library editing software may be executed by a server. The medical error reduction system may include at least one drug library database. The medical error reduction system may include at least one medical data database. The medical error reduction system may include at least one editor computer. Each of the at least one editor computer may comprise a processor in communication with a user interface. The user interface may be for use by a user to edit the at least one drug library. The at least editor computer, at least one drug library database, and at least one medical data database may be configured to communicate via a network. While editing the at least one drug library, the user may use the drug library editing software to access medical data.

In some embodiments, the medical data may be stored in the at least one medical data database. In some embodiments, the at least one medical data database may be stored in a hosted environment. In some embodiments, the medical data may be displayed in the form of a chart. In some embodiments, the medical data may be displayed in the form of a graph. In some embodiments, the medical data may be displayed in the form of a table. In some embodiments, the medical data may be displayed in the form of a diagram. In some embodiments, the medical data may be displayed in the form of an infusion story. In some embodiments, the medical data may be displayed in a user selectable format. In some embodiments, the accessed medical data is searchable. In some embodiments, the accessed medical data may be filterable by applying a filter. In some embodiments, the filter may be a device type filter. In some embodiments, the filter may be a data category. In some embodiments, the filter may be a therapy based criteria. In some embodiments, the filter may be a medical device identifier. In some embodiments, the filter may be a care giver identifier. In some embodiments, the filter may be an area based criteria. In some embodiments, the filter may be a drug criteria. In some embodiments, the drug criteria may be a drug identifier. In some embodiments, the drug criteria may be a drug type. In some embodiments, the at least one drug library database may be in a hosted environment. In some embodiments, the medical device may be an infusion pump.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The drug library editor software may be executed by a server. The medical error reduction system may include at least one drug library database. The medical error reduction system may include at least one medical data database. The medical error reduction system may include at least one editor computer. Each of the at least one editor computer may include a processor in communication with a user interface. The user interface may be for use by a user to edit the at least one drug library. The at least one editor computer, at least one drug library database, and at least one medical data database may be configured to communicate via a network. While creating or revising the at least one drug library, the drug library editing software may be configured to display medical data from the at least one medical data database on the user interface and filter the medical data with a filter criteria.

In some embodiments, the at least one medical device may be an infusion pump. In some embodiments, the at least one drug library database may be in a hosted environment. In some embodiments, the at least one medical data database may be in a hosted environment. In some embodiments, the filter criteria may be user selectable. In some embodiments, the filter criteria may be a medical device type. In some embodiments, filter criteria may be a data category. In some embodiments, the filter criteria may be a therapy based criteria. In some embodiments, the filter criteria may be a medical device identifier. In some embodiments the filter criteria may be a care giver identifier. In some embodiments, the filter criteria may be a care area based criteria. In some embodiments the filter criteria may be a drug criteria. In some embodiments, the drug criteria may be a drug identifier. In some embodiments, the drug criteria may be a drug type. In some embodiments, the filter criteria may be applied by interaction with the medical data displayed on the user interface to display a subset of the medical data. In some embodiments, the filter criteria may be applied by interaction with the medical data displayed on the user interface to drill down on the medical data. In some embodiments, the medical data may be display on the user interface in one or more of a number of user specified formats.

In accordance with an embodiment of the present disclosure, a medical device may include a processor. The medical device may include a graphical user interface. The processor may be configured to generate at least one screen for display on the graphical user interface. At least one of the at least one screen may include one or more parameter value. The processor may be further configured to visibly alter the font of at least one of the one or more parameter value in response to a change in the one or more parameter value.

In some embodiments, the change may be an order of magnitude change in the one or more parameter value. In some embodiments, the processor may be configured to visibly alter the font by changing the size of the font. In some embodiments, the processor may be configured to visibly alter the font by changing the color of the font. In some embodiments, at least one of the one or more parameter value must be specified by a user. In some embodiments, one of the one or more parameter value may be a patient weight. In some embodiments, one of the one or more parameter value may be a patient body surface area. In some embodiments, one of the one or more parameter value may be a dose value. In some embodiments, one of the one or more parameter value may be a time value. In some embodiments, one of the one or more parameter value may be a volume to be infused volume. In some embodiments, one of the one or more parameter value may be an infusion rate value. In some embodiments, one of the one or more parameter value may be a medicament concentration value. In some embodiments, at least one or more parameter value may be pre-programmed. In some embodiments, the processor may be configured to visibly alter the font by decreasing the size of the parameter value.

In accordance with an embodiment of the present disclosure, a medical device may include a graphical user interface. The medical device may include a processor. The processor may be configured to generate at least one screen for display on the graphical user interface. At least one of the at least one screen may be a therapy in progress screen. The therapy in progress screen may include a pressure indicator which indicates the pressure of a fluid in an infusion line.

In some embodiments, the pressure indicator may be a pressure trend indicator. In some embodiments, the pressure trend indicator may depict a pressure trend over the last four hours. In some embodiments, the pressure indicator may be a bar. In some embodiments, the bar may include a number of segments. In some embodiments, the pressure indicator may be configured to indicate different pressures by filling a different number of segments. In some embodiments, the pressure indicator may be configured to indicate different pressures by filling different amounts of the bar. In some embodiments, the graphical user interface may be a touch screen.

In accordance with an embodiment of the present disclosure, a medical device may include a graphical user interface. The medical device may include a processor. The processor may be configured to generate at least one screen for display on the graphical user interface. At least one of the at least one screen may be a therapy in progress screen displayed when the medical device is delivering a therapy. The therapy in progress screen may include a medicament indicator indicating a medicament which is being delivered by the medical device. The processor may color code at least a portion of the medicament indicator displayed on the user interface in one of a plurality of colors depending on a classification of a plurality of classification assigned to the medicament.

In some embodiments, the graphical user interface may be a touch screen. In some embodiments, the processor may be in communication with a memory storing a drug library for use with the medical device. In some embodiments, the drug library may contain color coding information for the portion of the medicament indicator. In some embodiments, at least one of the at least one screen may be a programming screen where the medicament to be delivered by the medical device is specified. In some embodiments, at least one of the plurality of classifications may be a high risk classification.

In some embodiments, at least one of the plurality of classifications may be a drug type. In some embodiments, at least one of the plurality of classifications may be an anesthetic classification. In some embodiments, the medicament indicator may include a name for the medicament. In some embodiments, the medicament indicator may include a non text indicia. In some embodiments, the non text indicia may be the only portion of the medicament indicator which is color coded.

In accordance with an embodiment of the present disclosure, a medical device may include a graphical user interface. The medical device may include a processor. The processor may be configured to generate at least one screen for display on the graphical user interface. The medical device may include a computer readable memory. The computer readable memory may store a plurality of parameter values related to therapies which may be programmed into the medical device. At least one of said parameter values may be a value for a user overrideable limit for a therapy parameter value. The user overrideable limit for a therapy parameter value may be overrideable by one or more user via the graphical user interface. The processor may cause an indicia to be displayed next to the therapy parameter value in response to override of the user overrideable limit.

In some embodiments, the graphical user interface may be a touch screen. In some embodiments, at least one of the at least one screen may display a limit violation notification. In some embodiments, the limit violation notification may not display the value of the overrideable limit. In some embodiments, the limit violation notification may include an override option. In some embodiments, the user overrideable limit for a therapy parameter value may require both a first user and a second user to override the limit via the graphic user interface. In some embodiments, the plurality of parameter values related to therapies which may be programmed into the medical device may be part of a drug library file stored in the computer readable memory. In some embodiments, the indicia may be a non text indicia.

In accordance with an embodiment of the present disclosure, a medical device may include a graphical user interface. The medical device may include a processor. The processor may be configured to generate at least one screen for display on the graphical user interface. The medical device may include a computer readable memory. The computer readable memory may store a plurality of medicaments which may be delivered by the medical device. The medicaments may be organized by one or more medicament category. Each of the medicaments may further be associated with one or more parameter values related to therapies which may be programmed into the medical device. A user may program the medical device to deliver a therapy using the graphical user interface. At least one step in programming the medical device may include selecting a medicament category from which a medicament to be delivered by the medical device is included.

In some embodiments, the graphical user interface may be a touch screen. In some embodiments, the plurality of medicaments and one or more medicament categories are a part of a drug library file. In some embodiments, the medicament categories may be searchable via the graphical user interface. In some embodiments, the medicament categories may be filterable via the graphical user interface. In some embodiments, at least one of the one or more parameter values may be a user overrideable parameter limit.

In accordance with an embodiment of the present disclosure, a medical error reduction system may include a medical error reduction software for use in creating and revising at least one drug library that is configured for use in at least one medical device. The software may be configured to provide one of a plurality of sets of privileges to each of a plurality of sets of users. Each of the plurality of sets of privileges may be arranged to allocate a degree of software functionality to one of the plurality of sets of users. The degree of software functionality may be configured to define the ability of a user to alter the at least one drug library. The medical error reduction system may include at least one server. The medical error reduction system may include at least one editor computer including a processor in communication with a display. The at least one editor computer may be configured to communicate to the at least one server via a network in a client-server based model.

In accordance with an embodiment of the present disclosure, a medical error reduction system may include a medical device. The medical device may include a medical device processor. The medical device may include a medical device graphical user interface configured to allow a user to program the medical device. The medical device may include at least one server. The medical error reduction system may include at least one editor computer including a processor in communication with a display. The at least one editor computer may be configured to communicate to the at least one server via a network in a client-server based model. The medical error reduction system may include a medical error reduction software configured to be executed by the at least one server and accessible via the at least one editor computer for use in creating and revising at least one drug library. The at least one drug library may be for use in the at least one medical device and include a plurality of entries that guide user programming of the at least one medical device. The medical error reduction software may further be configured to display a simulated medical device graphical user interface. The simulated medical device graphical user interface may mimic behavior of the medical device graphical user interface for a medical device using one of the at least one drug library.

In accordance with an embodiment of the present disclosure, a medical device for delivering a medicament to a patient may include a controller configured to control operation of a pumping mechanism which causes the medicament to be delivered. The medical device may include a display. The medical device may include a computer readable memory configured to store program code for a drug library. The drug library may have a plurality of entries. The plurality of entries may include at least one entry corresponding to a portion of a facility. For each such entry, the plurality of entries may further comprise at least one drug entry corresponding to the portion of the facility. The medical device may include a processor configured to display a graphical user interface on the display of the medical device. The graphical user interface for use by a user to program the controller using the drug library. A user may select one of the at least one drug entry corresponding to the portion of the facility to program delivery of the medicament to the patient.

In some embodiments, the at least one drug entry may comprise parameters associated therewith. In some embodiments, the drug library may further comprise at least one drug entry not associated with a specific drug, but rather a broad drug category. In some embodiments, the user may select one of the at least one drug entry in the drug library not associated with a specific drug, but rather a broad drug category to program delivery of the medicament to the patient.

In accordance with an embodiment of the present disclosure, a medical error reduction system may include a drug library editing software for use in creating and revising at least one drug library for use with at least one medical device. The at least one drug library may contain a plurality of entries. The software may be configured to provide at least one of a plurality of sets of privileges to each of a plurality of sets of users. Each of the plurality of sets of privileges may be configured to allocate a degree of software functionality to one of the plurality of sets of users. The degree of software functionality may be configured to define the ability of a user to alter the at least one drug library. The medical error reduction system may include at least one server configured to execute the drug library editing software. The medical error reduction system may include at least one editor computer including a processor in communication with a user interface. The at least one editor computer may be configured to communicate with the at least one server via a network in a client-server based model. At least one of the plurality of set of users may use the at least one editor computer to access the drug library editing software to request a change to the at least one drug library.

In some embodiments, at least one of the plurality of sets of privileges may be further configured to allow a user to decline implementation of the requested change to the at least one drug library or to accept implementation of the requested change to the at least one drug library.

In accordance with an embodiment of the present disclosure, a medical error reduction system may include a drug library editing software for use in creating and revising at least one drug library. the at least one drug library may include a plurality of entries. The at least one drug library may be for use with at least one medical device. The medical error reduction system may include at least one server configured to execute the drug library editing software. The medical error reduction system may include at least one editor computer comprising a processor in communication with a user interface. The user interface may be for use by a user to edit the at least one drug library. The at least one editor computer may be configured to communicate with the at least one server via a network in a client-server based model such that the at least one editor computer is able to access the drug library editing software. A user may request a change to the at least one drug library by tendering an electronic change request via the user interface.

In some embodiments, the electronic change request may be linkable to medical data in an electronic database to provide contextual information.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The drug library editing software to may be executed by a server. The medical error reduction system may include at least one drug library database. The medical error reduction system may include at least one medical data database. The medical error reduction system may include at least one editor computer configured to communicate with the server at least one drug library database, and the at least one medical data database via a network. The at least one editor computer may include a processor in communication with a user interface. The user interface may be for use by a user to edit the at least one drug library using the at least one drug library editing software. While editing the at least one drug library, the user may use the drug library editing software to access medical data from the at least one medical data database.

In some embodiments, while editing the at least one drug library, the user may use the drug library editing software to access medical data from the at least one medical data database. In some embodiments, the medical data may be in the form of at least one of a chart, graph, plot, and diagram displayed on the user interface. In some embodiments, while editing the at least one drug library, a user may use the drug library editing software to display medical data from the at least one medical data database on the user interface and filter the medical data such that only medical data of interest to the user is displayed on the user interface.

In accordance with an embodiment of the present disclosure a medical device may include a graphical user interface. The medical device may include a processor. The processor may be configured to generate at least one screen for display on the graphical user interface. The at least one screen may include at least one parameter value. The processor may be further configured to visibly alter the font of the at least one parameter value in response to a change in the order of magnitude of the at least one parameter value.

In some embodiments, the at least one screen may include a therapy in progress screen, the therapy in progress screen including a pressure indicator which indicates the pressure of a fluid in an infusion line. In some embodiments, the at least one screen may be a therapy in progress screen. The therapy in progress screen may include a medicament indicator indicating a medicament which is being delivered by the medical device. The processor may be further configured to color code the medicament indicator displayed on the user interface in one of a plurality of colors. Each of the plurality of colors may correspond to a classification of the medicament. In some embodiments, the medical device may include a computer readable memory. The computer readable memory may store a plurality of parameter values related to therapies that may be programmed into the medical device. At least one of the parameter values may be a user overrideable limit for a therapy parameter value. The user overrideable limit for a therapy parameter value may be overrideable by a user via the graphical user interface. The processor may be further configured to display an indicia next to the therapy parameter value in response to the user overriding the user overrideable limit. In some embodiments, the computer readable memory may be configured to store a plurality of medicaments that may be delivered by the medical device. Each medicament may be organized into one or more medicament category. Each of the medicaments may further be associated with one or more parameter values related to therapies that may be programmed into the medical device. A user may program the medical device, using the graphical user interface, to at least select a medicament category within which a medicament to be delivered by the medical device is included.

In accordance with an embodiment of the present disclosure, a medical error reduction system may include a medical error reduction software for use in creating and revising at least one drug library. The software may be configured to provide a set of privileges to each of a plurality of users. The set of privileges may be arranged to allocate a degree of software functionality to each of the plurality of users. The degree of software functionality may be configured to define the ability of users to alter the at least one drug library. The medical error reduction system may include at least one server. The medical error reduction system may include at least one editor computer. Each of the at least one editor computer may include a processor in communication with a display. The at least one editor computer and at least one server may be configured to communicate via a network in a client-server based model. Each of the at least one drug library may be for use in at least one medical device.

In some embodiments, each of the at least one drug library may be organized in a hierarchy. In some embodiments, the hierarchy may include a plurality of care areas which are subordinate to at least one care group. In some embodiments, each level of the hierarchy may include a number of delivery parameters for the at least one medical device. In some embodiments, each of the at least one drug library may include a plurality of entries each corresponding to a specific medicament. In some embodiments, the at least one drug library may include a number of parameters to inform operation of the at least one medical device. In some embodiments, the drug library may include a plurality of programming limits for the at least one medical device. In some embodiments, the medical error reduction software may be further configured to provide quality improvement information to the plurality of users. In some embodiments, the set of privileges may be configurable to allocate a drug library review privilege. In some embodiments, the set of privilege may be configurable to allocate a drug library editing privilege. In some embodiments, the set of privileges may be configurable to allocate and editing or creation privilege. In some embodiments, the set of privileges may be configurable to allocate an add user privilege. In some embodiments, the set of privileges allocated to each of the plurality of users may force a collaborative process between the plurality of users for the creating and revising of the at least one drug library.

In accordance with an embodiment of the present disclosure, a medical error reduction system may include a drug library editing software for use in creating and revising a number of drug libraries. The number of drug libraries may each contain a plurality of entries. Each of the a number of drug libraries may be for use with at least one medical device. The medical error reduction system may include at least one editor computer. Each of the at least one editor computer may comprise a processor in communication with a user interface. The user interface may be for use by one or more user to edit the at least one drug library. The drug library editing software may be configured to import entries of the plurality of entries in a first drug library in the number of drug libraries to a second drug library in the number of drug libraries.

In some embodiments, the system may further comprise at least one server configured to execute the medical error reduction software. In some embodiments, the number of drug libraries are stored on a drug library database. In some embodiments, the drug library database is in a hosted environment. In some embodiments, the one or more user may specify the entries of the plurality of entries they would like to import to the first drug library in the number of drug libraries to the second drug library in the number of drug libraries. In some embodiments, the first drug library in the number of drug libraries and the second drug library in the number of drug libraries may both belong to a sub-set of drug libraries in the number of drug libraries. In some embodiments, the sub-set of drug libraries, may be associated with a set of permissions allowing access to the sub-set of drug libraries by the one or more user. In some embodiments, the set of permissions disallows access to the sub-set of drug libraries by another one or more user.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The drug library editor software may be executed by a server. The medical error reduction system may include at least one drug library database storing the at least one drug library. The medical error reduction system may include at least one editor computer. Each of the at least one editor computer may comprise a processor in communication with a user interface. The user interface may be for use by a user to edit the at least one drug library. The at least one editor computer and at least one drug library database may be configured to communicate via a network. The plurality of entries may include one or more clinical advisory.

In some embodiments, the drug library database is in a hosted environment. In some embodiments, the one or more clinical advisory may be a free text entry. In some embodiments, the one or more clinical advisory may include an image. In some embodiments, the one or more clinical advisory may include a document. In some embodiments, the one or more clinical advisory may be limited to be between 0 and 100 characters in length. In some embodiments, each of the one or more clinical advisory may be associated with a short text clinical advisory. In some embodiments, the short text clinical advisory may be limited to be between 0 and 100 characters in length. In some embodiments, the short text clinical advisory may be displayed on at least one screen of a graphic user interface of the at least one medical device. In some embodiments, each of the one or more clinical advisory may be displayed on at least one screen of a graphic user interface of the at least one medical device. In some embodiment, each of the at least one clinical advisory may be associated with a drug entry in the at least one drug library.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The drug library editor software may be executed by a server. The medical error reduction system may include at least one drug library database storing the at least one drug library. The medical error reduction system may include at least one editor computer. Each of the at least one editor computer may comprise a processor in communication with a user interface. The user interface may be for use by a user to edit the at least one drug library. The at least one editor computer and at least one drug library database may be configured to communicate via a network. The drug library editing software may be configure to allow a user to enter a note for one or more of the plurality of entries.

In some embodiments, the drug library database may be in a hosted environment. In some embodiments, the note may be a free text entry. In some embodiments, the note may include an image. In some embodiments, the note may include a document. In some embodiments, the drug library editing software may be configured to allow a user to enter a note for one or more sub-set of the plurality of entries. In some embodiments, the drug library editing software may be configured to allow a user to enter a note for each of the plurality of entries. In some embodiments, each of the plurality of entries associated with a note may be depicted on the user interface with a note indicator. In some embodiments, user interaction with the note indicator may cause the note to be displayed on the user interface.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The drug library editor software may be executed by a server. The medical error reduction system may include at least one drug library database storing the at least one drug library. The medical error reduction system may include at least one editor computer. Each of the at least one editor computer may include a processor in communication with a user interface. The user interface may be for use by a user to edit the at least one drug library. The at least one editor computer and at least one drug library database may be configured to communicate via a network. The plurality of entries may include a flush parameter.

In some embodiments, the flush parameter may govern flushing of a fluid line associated with the at least one medical device. In some embodiments, the flush parameter may include default delivery parameter values to be used by the at least one medical device when the medical device flushes a fluid line associated therewith. In some embodiments, the flush parameter may include a volume to be delivered. In some embodiments, the flush parameter may include a delivery rate. In some embodiments, the flush parameter may include a time.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The drug library editor software may be executed by a server. The medical error reduction system may include at least one drug library database storing the at least one drug library. The medical error reduction system may include at least one editor computer. Each of the at least one editor computer may comprise a processor in communication with a user interface. The user interface may be for use by a user to edit the at least one drug library. The at least one editor computer and at least one drug library database may be configured to communicate via a network. The drug library editing software may be configured to display a user customizable screen which provides desired at a glance information to the user.

In some embodiments, the user customizable screen may include one or more widget. In some embodiments, the user may choose the one or more widget which is included on the user customizable screen. In some embodiments, one of the one or more widget may be a progress widget. In some embodiments, one of the one or more widget may be a trend widget. In some embodiments, one of the one or more widget may be an overview widget. In some embodiments, one of the one or more widget may be a quick links widget. In some embodiments, one of the one or more widget may be a change request widget. In some embodiments, one of the one or more widget may be a feedback widget. In some embodiment one of the one or more widget may be a medical data widget. In some embodiments, one of the one or more widget may be a changes to review widget. In some embodiments, one of the one or more widget may be an administrator comments widget. In some embodiments, the user may choose the one or more widget from a list of permitted widgets. In some embodiments, the user may be assigned a specific role in the medical error reduction software, the list of permitted widgets associated the specific role. In some embodiments, the system further may comprise a user database. In some embodiments, the user customizable screen, once customized, may be stored on a user database and associated with the user. In some embodiments, the user customizable screen may be selected from a number of loadable, customized screen configurations.

In accordance with an embodiment of the present disclosure, a medical error reduction system may include a drug library editing software for use in creating and revising at least one drug library. The at least one drug library may contain a plurality of entries. Each of the at least one drug library may be for use with at least one medical device. The drug library editor software may be executed by a server. The medical error reduction system may include at least one drug library database storing the at least one drug library. The medical error reduction system may include at least one editor computer. Each of the at least one editor computer may comprise a processor in communication with a user interface. The user interface may be for use by a user to edit the at least one drug library. The at least one editor computer and at least one drug library database may be configured to communicate via a network. The user may compare two or more entries of the plurality of entries using the drug library editing software. The comparison may be displayed on the user interface.

In some embodiments, the comparison may be display on the user interface in a table. In some embodiments, the comparison may be a side by side comparison. In some embodiments, differences between the two or more entries in the comparison may be visually indicated on the user interface. In some embodiments, the comparison may include a difference only option. In some embodiments, interaction with the difference only option may toggle the comparison between a state in which only differences between the two or more of the plurality of entries are shown and a state in which all information associated with the two or more of the plurality of entries is shown. In some embodiments, the comparison may include an edit option which may be used to open one of the two or more of the plurality of entries for editing.

In accordance with an embodiment of the present disclosure, a method for producing a drug library file may comprise, assigning one of a plurality of sets of privileges to each of a plurality of sets of users. The plurality of sets of privileges may be arranged to allocate a degree of software functionality in a drug library editing software. The degree of software functionality may be configured to define the ability of a user to alter the at least one drug library. The method for producing a drug library file may comprise creating a drug library using at least one editor computer. Each of the at least one editor computer may comprise a processor in communication with a user interface. The user interface may be for use by a user to edit the at least one drug library using the drug library editing software. Creating the drug library may comprise appropriate users of the plurality of sets of users, the appropriate users defined by the plurality of sets of privileges, specifying a master medication list for an institution, defining medication records for one or more portion of the institution, and verifying the defined medication records. The method may include approving the drug library for release to at least one medical device in the institution.

In some embodiments, one of the plurality of sets of privileges may allocate an editing privilege. In some embodiments, one of the plurality of sets of privileges may allocate a review privilege. In some embodiments, specifying the master medication list may comprise selecting a number of medications from a formulary database. In some embodiments, defining medication records for one or more portion of the institution may comprise selecting desired medications from the master medication list for each of the one or more portions of the institution. In some embodiments, defining medication records for one or more portion of the institution may comprise defining a number of parameters for each of the desired medications. In some embodiments verifying the defined medication records may comprise reviewing the defined medication records. In some embodiments, verifying the defined medication records may comprise editing and revising the defined medication records. In some embodiments, producing a drug library file further may comprise conducting a pilot phase for the drug library file in which the drug library file is tested on a test medical device. In some embodiments, producing a drug library file further may comprise conducting a pilot phase for the drug library file in which the drug library file is tested on a simulated medical device user interface. In some embodiments, verifying the defined medication records may comprise reviewing the defined medication records using a simulated medical device user interface.

In accordance with an embodiment of the present disclosure, a method for deploying a drug library file to at least one medical device may include creating the drug library file. The method may include approving the drug library file for release to the at least one medical device. The method may include sending a notification to a user via a drug error reduction system editor service. The method may include downloading the drug library file to a device gateway. The method may include disseminating the drug library file to the at least one medical device over a network which allows the device gateway to communicate with the at least one medical device.

In some embodiments, the method may further comprise the user commanding downloading of the drug library file to device gateway. In some embodiments, the method may further comprises selecting the at least one medical device from a list of medical devices. In some embodiments, the method may further comprise the device gateway periodically checking for updates to the drug library file. In some embodiments, the method further may comprise the at least one medical device validating the drug library file. In some embodiments, the method further may comprise sending a confirmation message to the device gateway from each of the at least one medical device in the event that the drug library file is successfully validated and updated.

BRIEF DESCRIPTION OF THE DRAWINGS

These and other aspects will become more apparent from the following detailed description of the various embodiments of the present disclosure with reference to the drawings wherein:

FIG. 4 shows a diagram illustrating a system for electronic patient care in accordance with an embodiment of the present disclosure;

Figure 19:
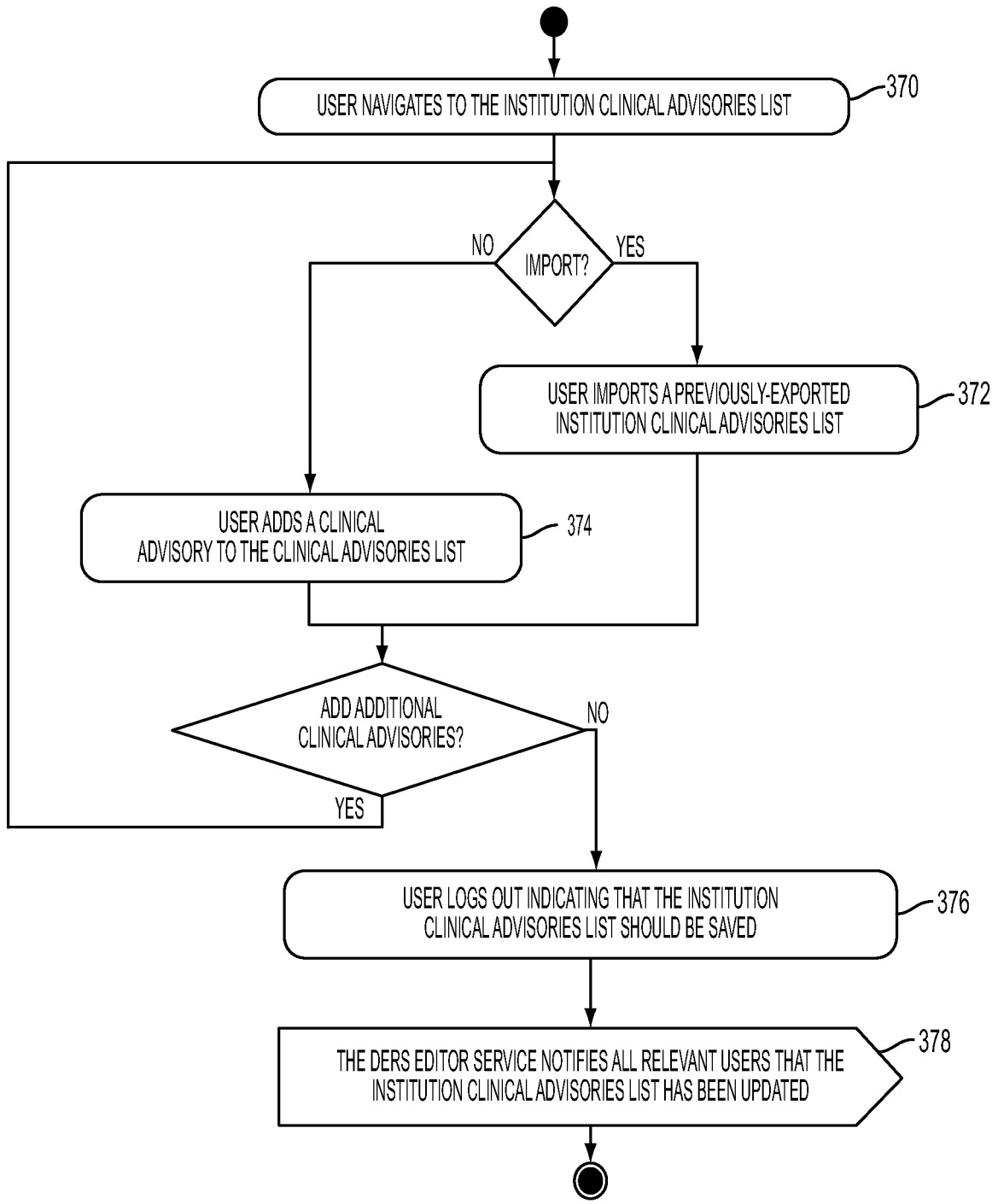
Figure 20:
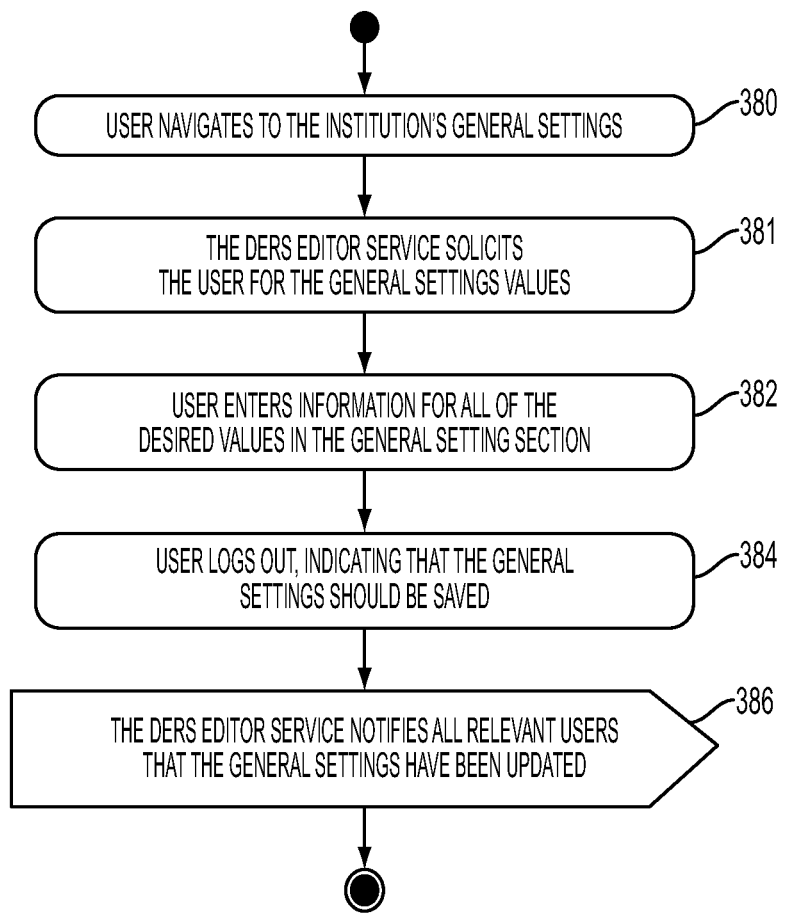
Figure 21:
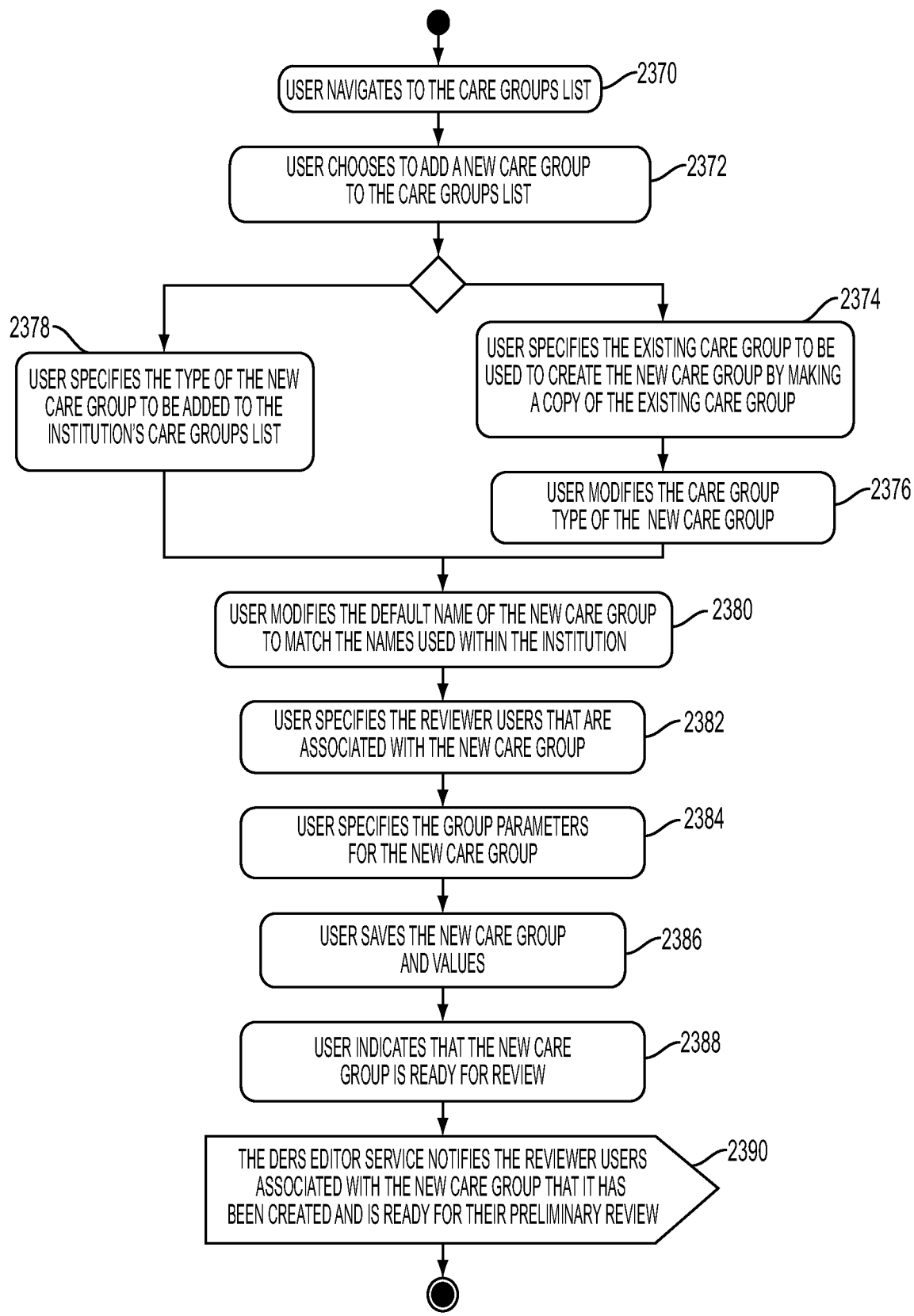
Figure 22:
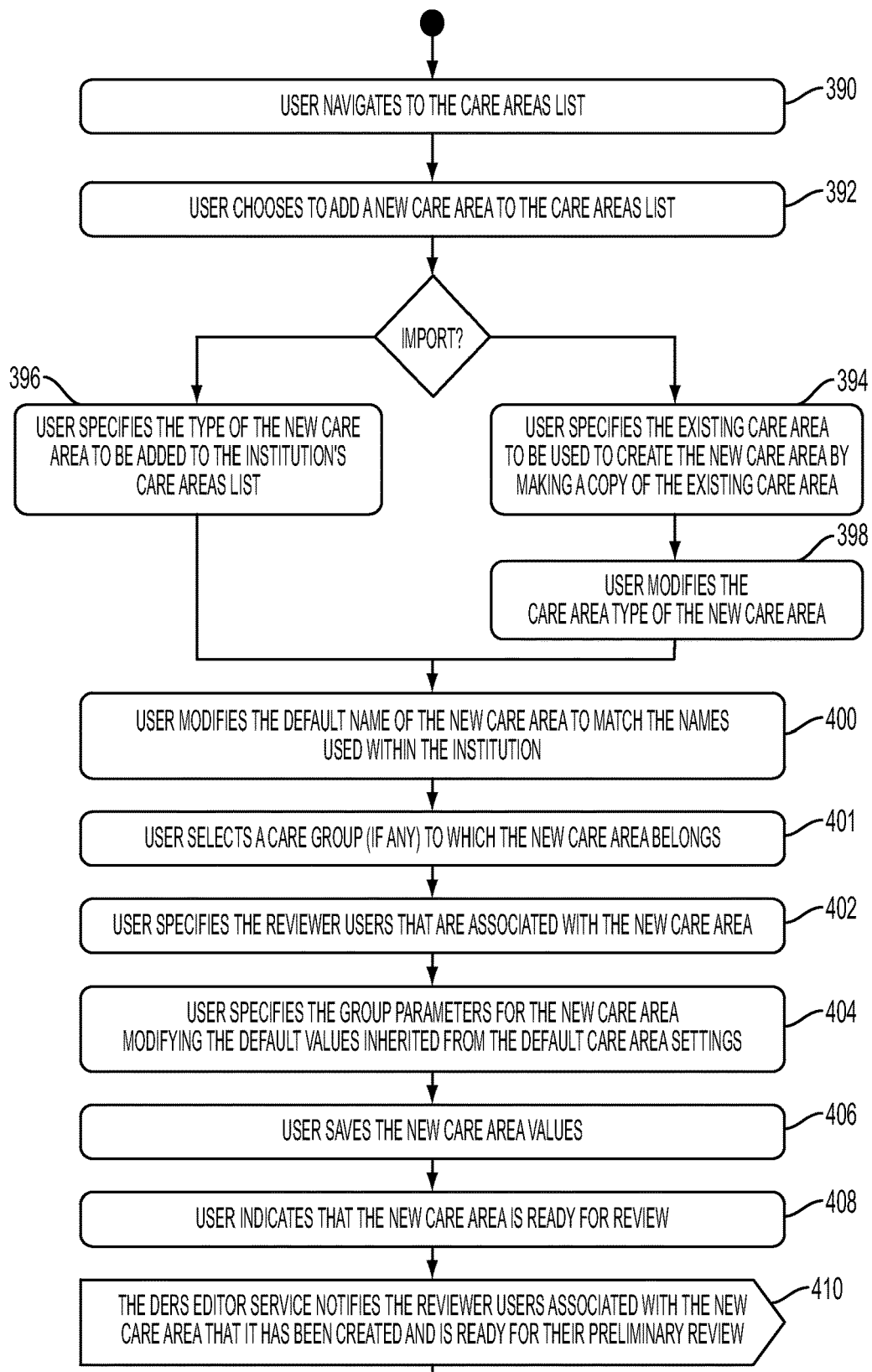
Figure 23:
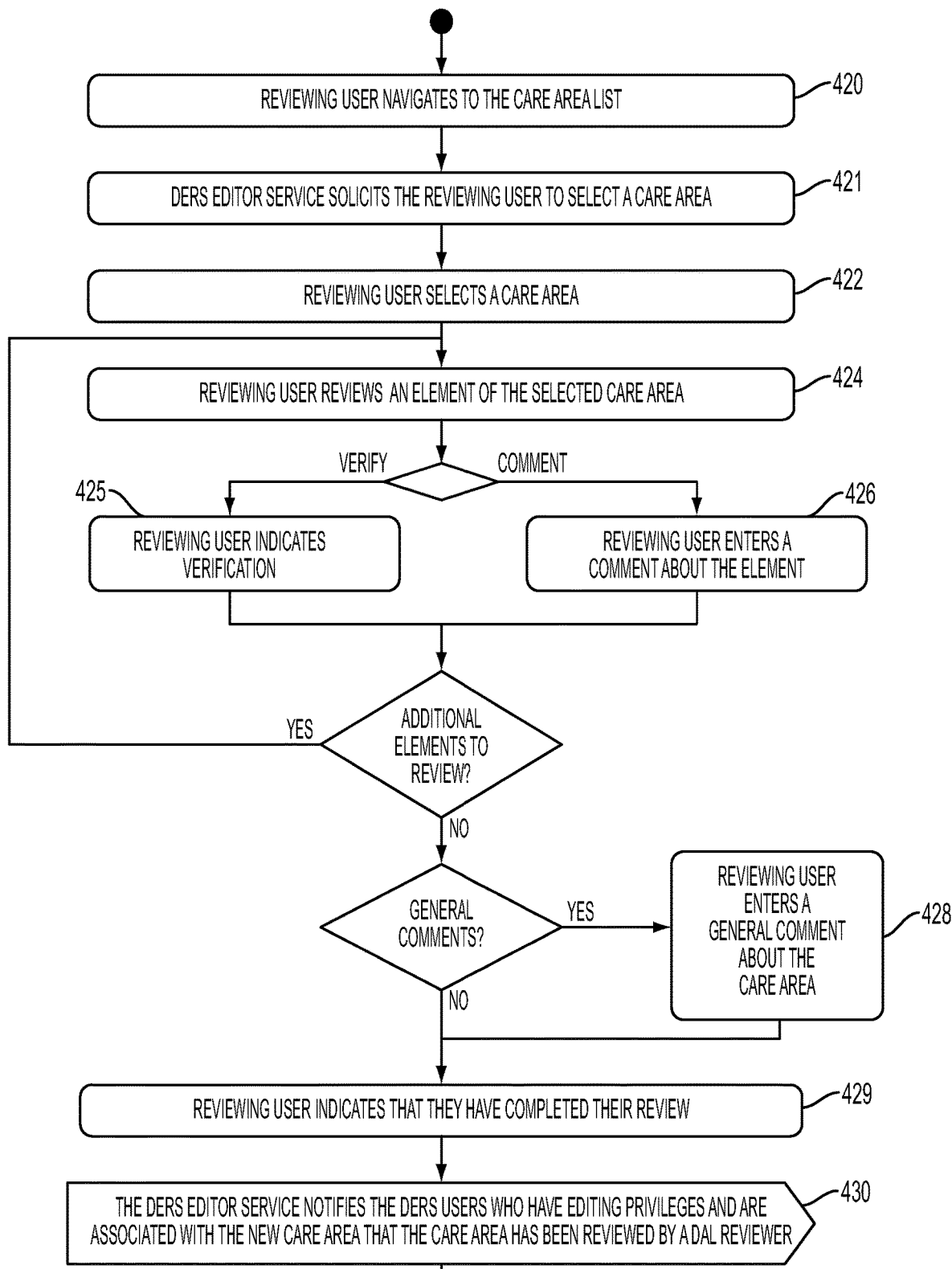
Figure 24:
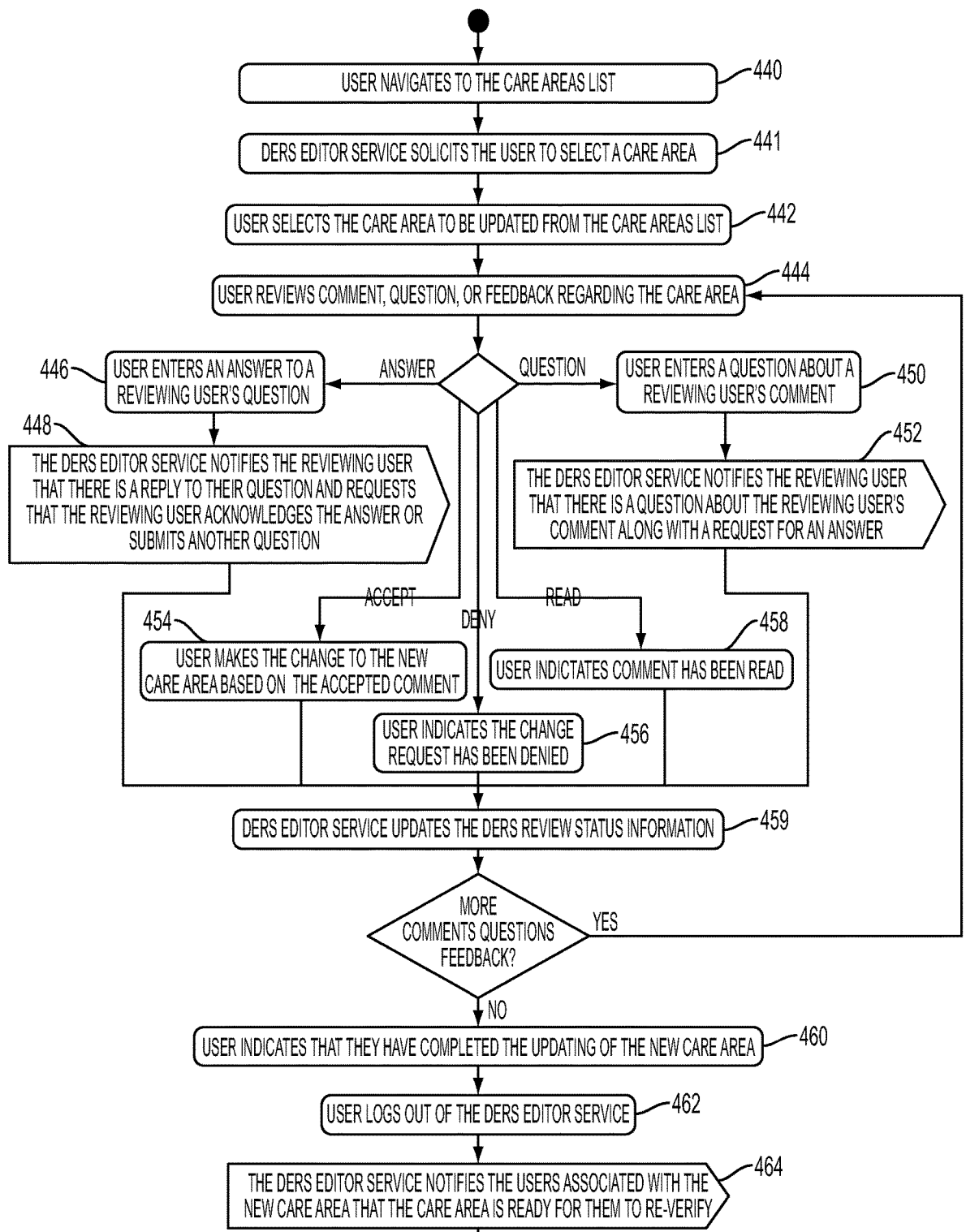
Figure 25:
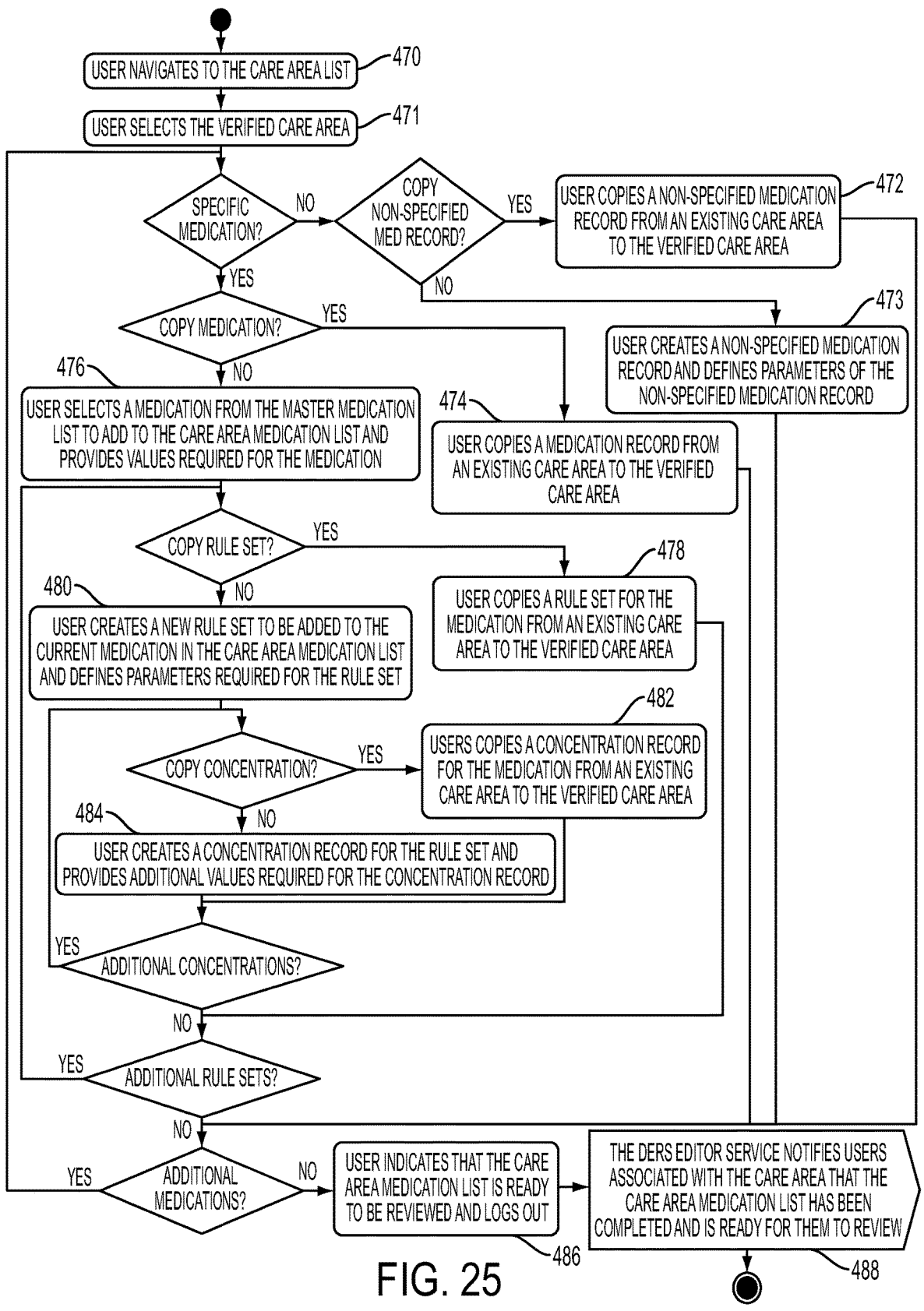
Figure 26:
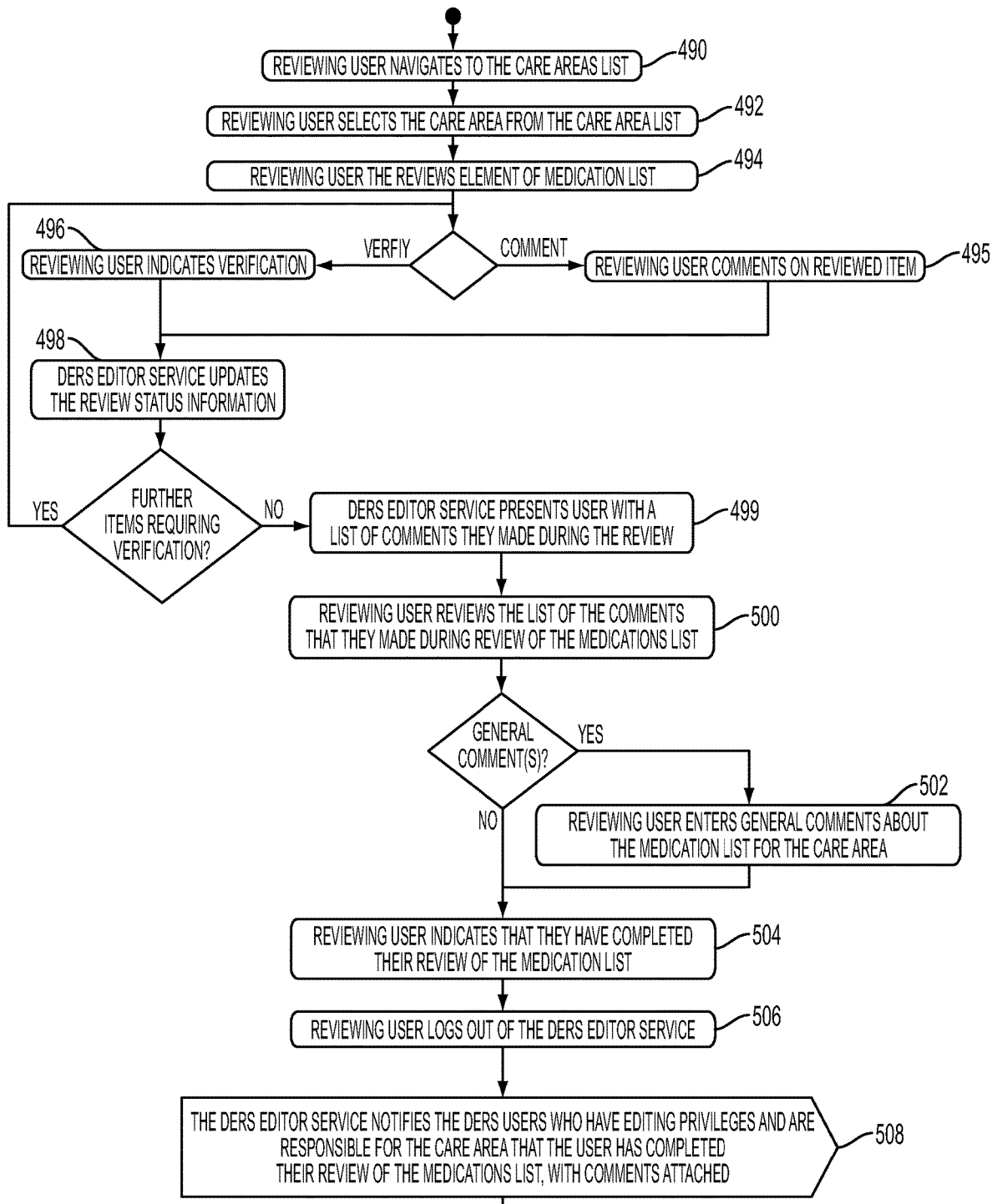
Figure 27:
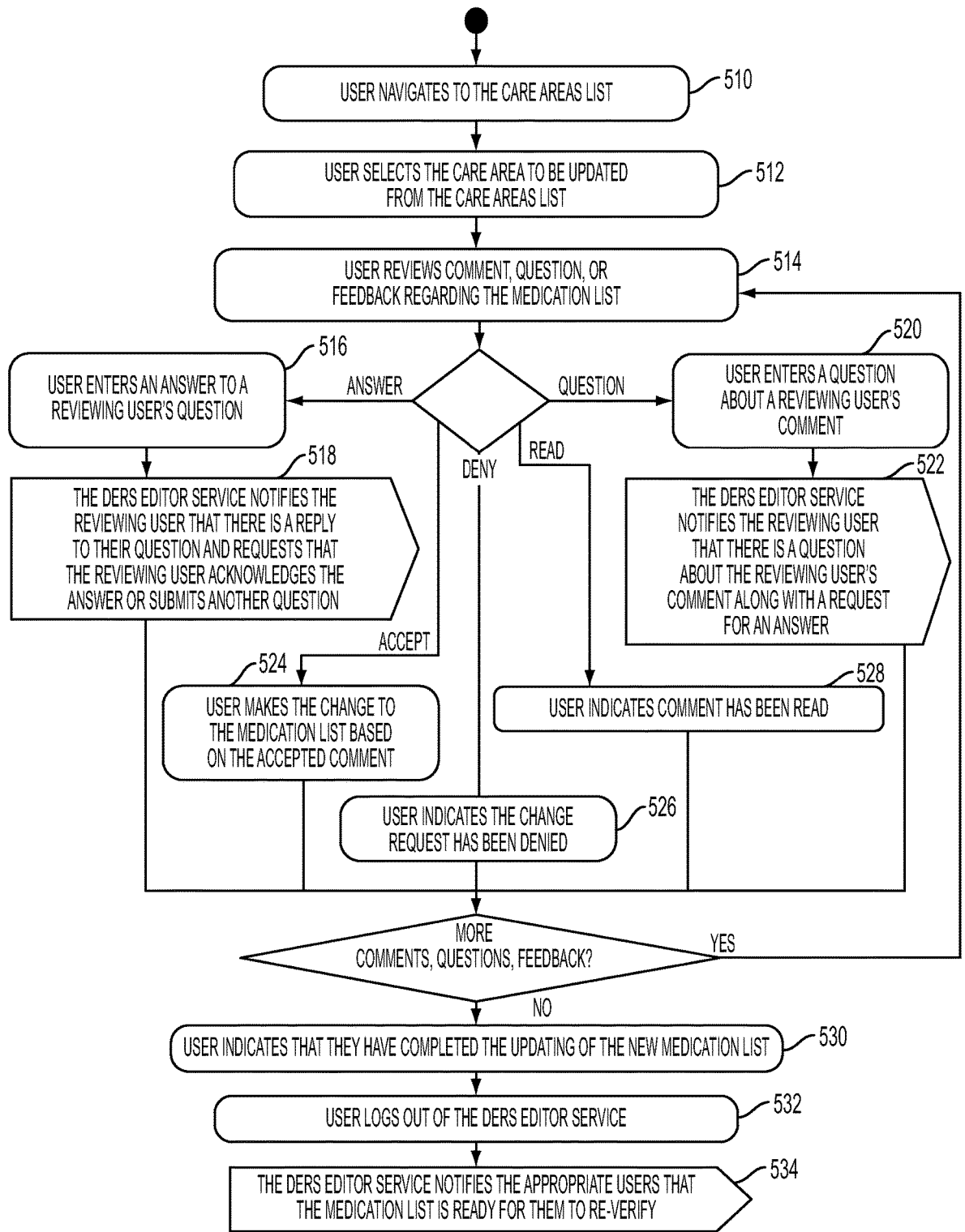
Figure 28:
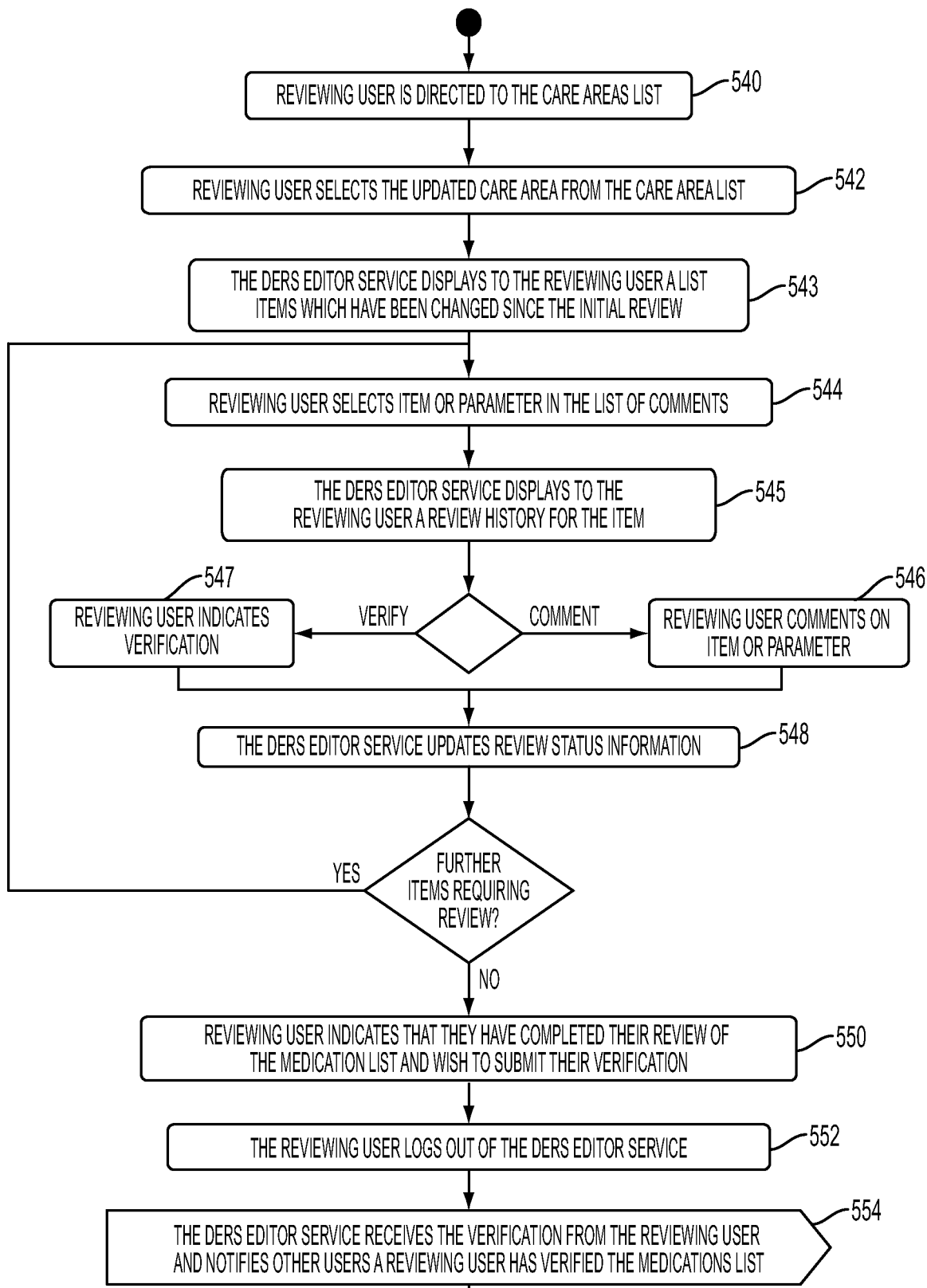
Figure 29:
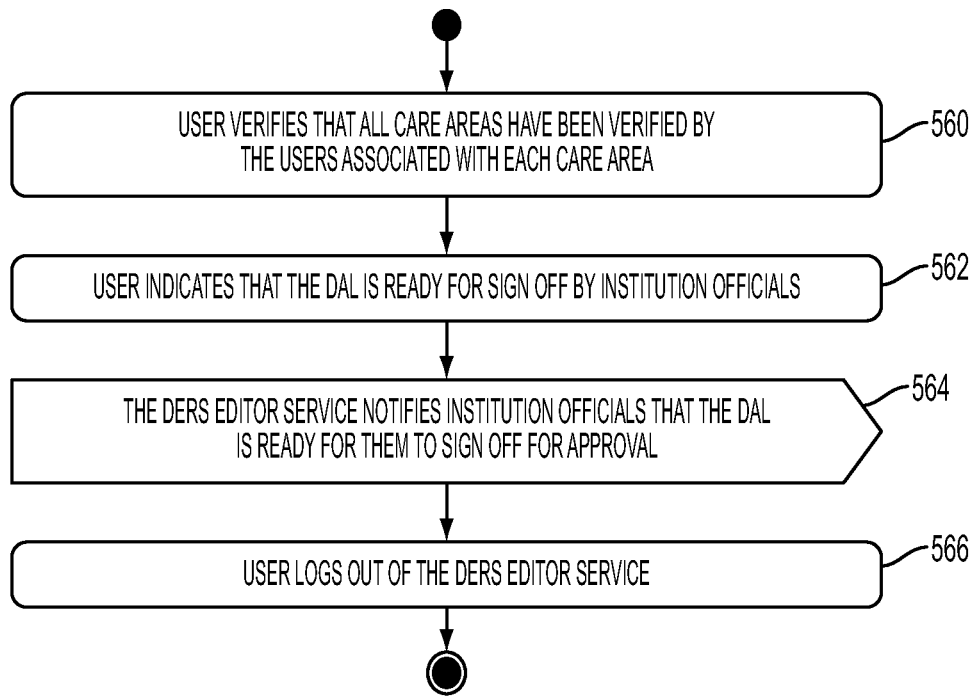
Figure 30:
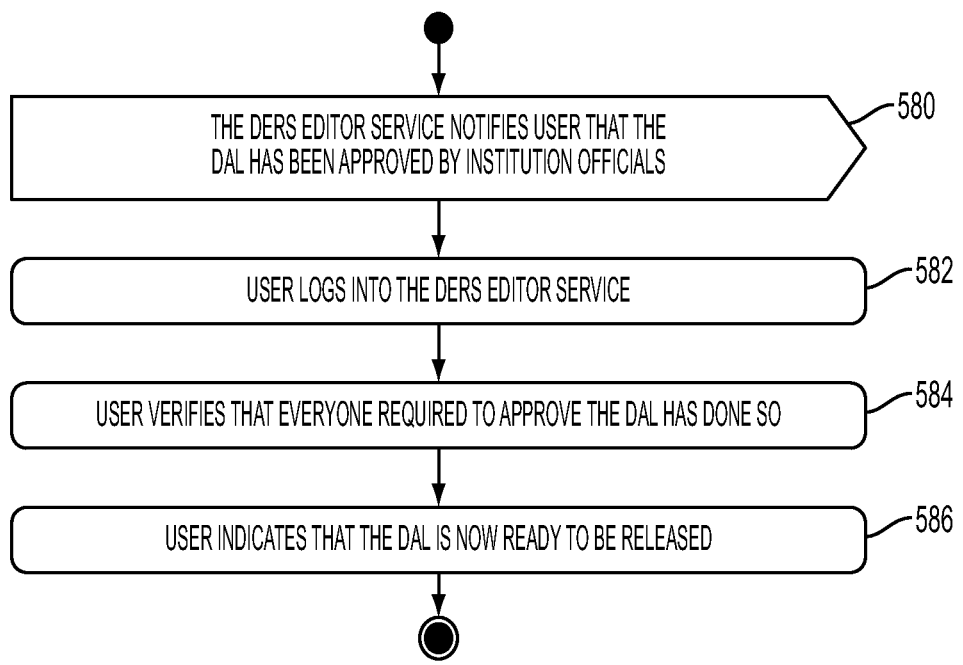
Figure 31A:
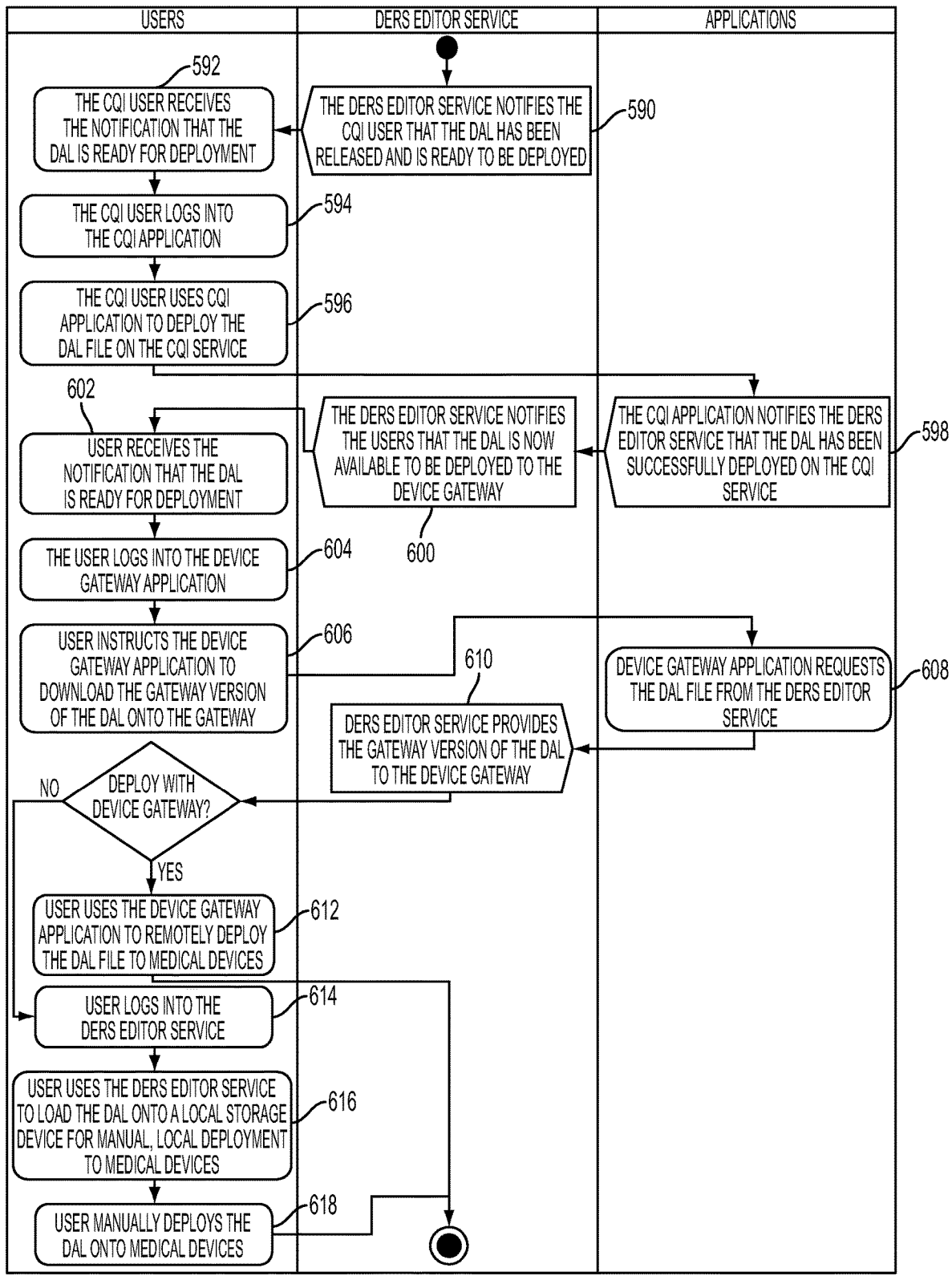
Figure 31B:
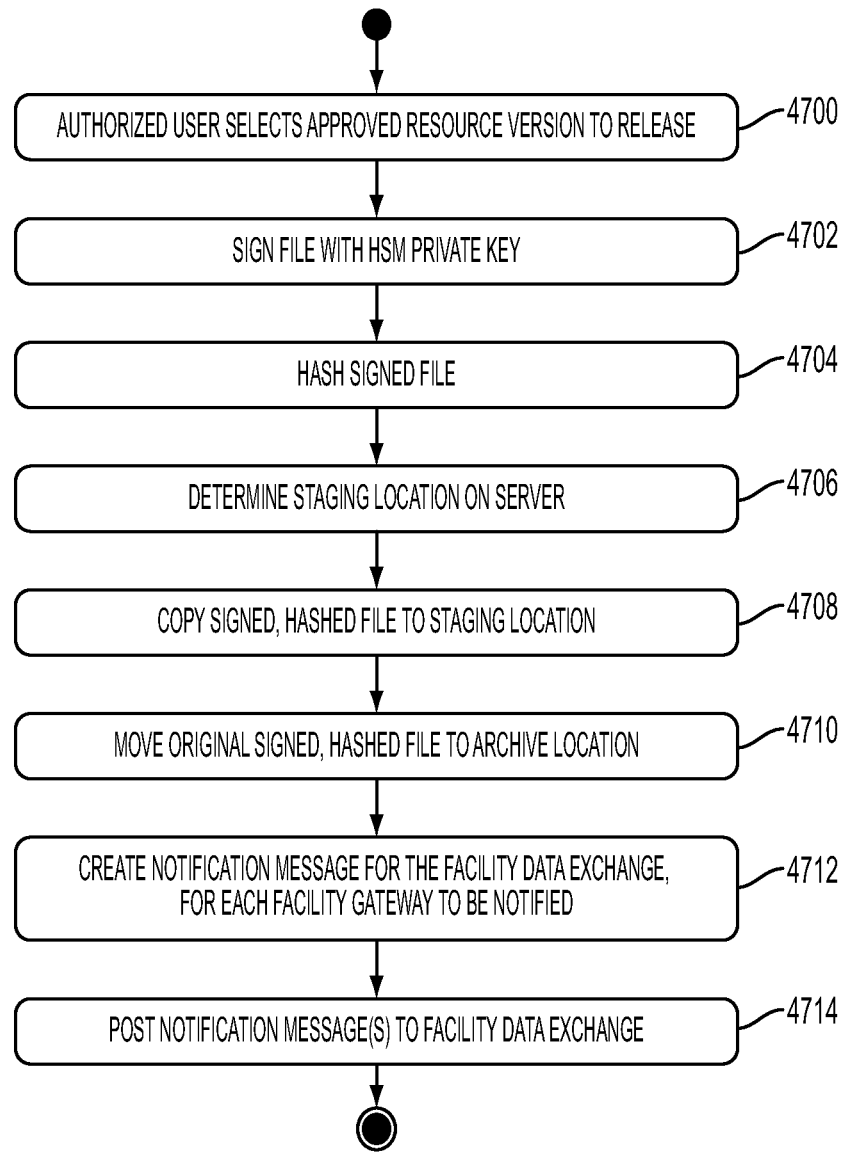
Figure 31C:
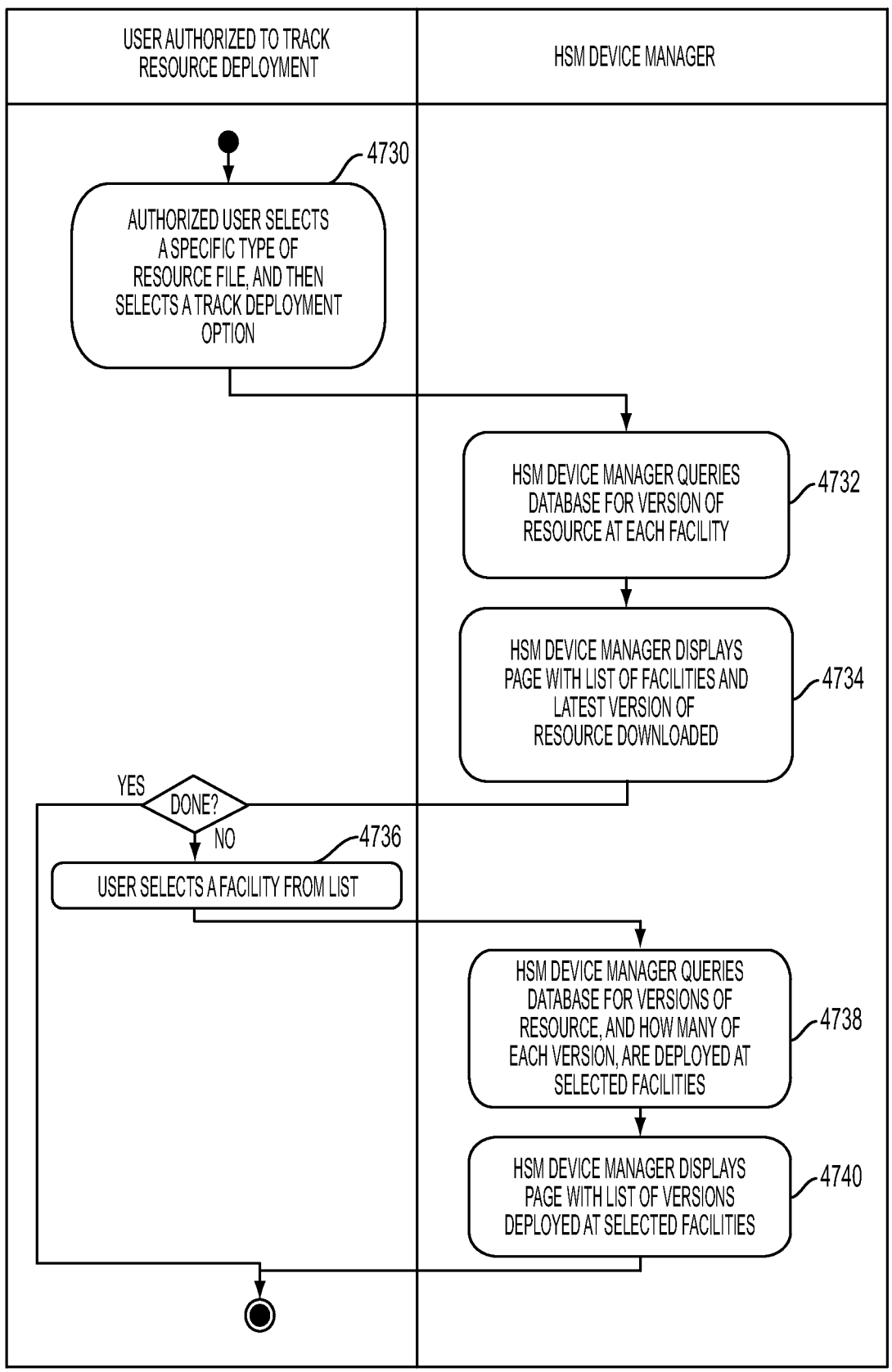
Figure 32:
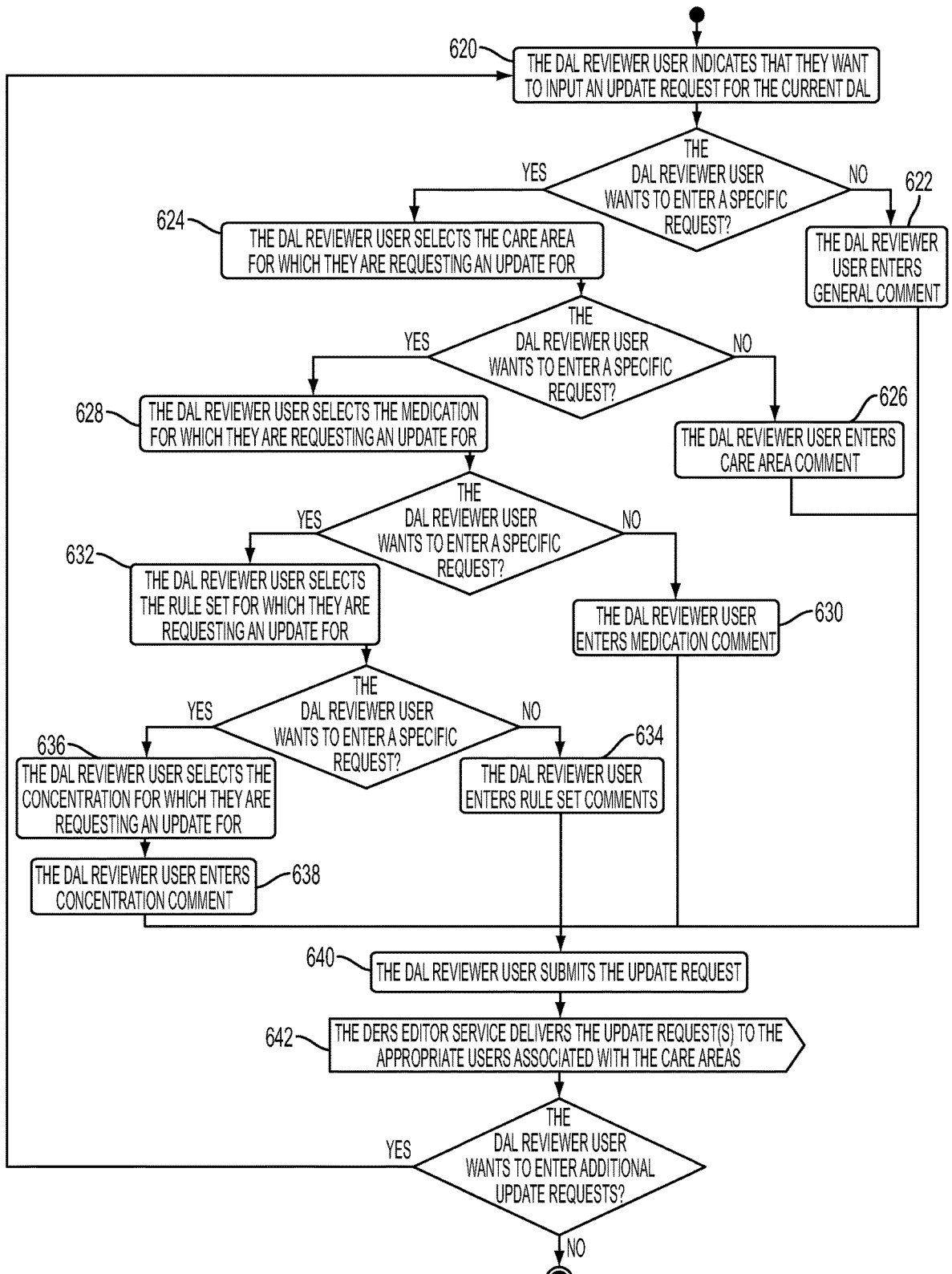
Figure 33:
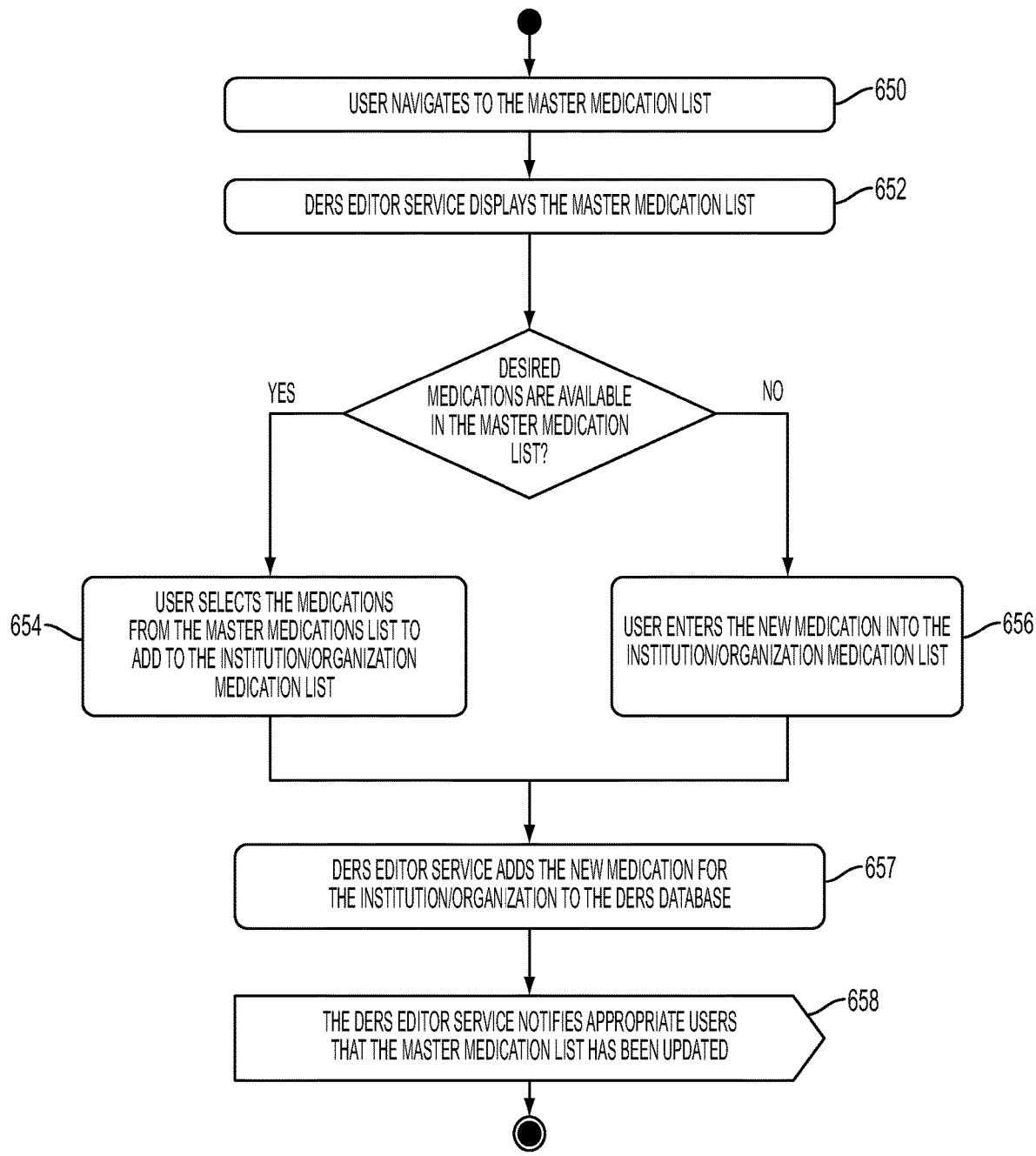
Figure 34:
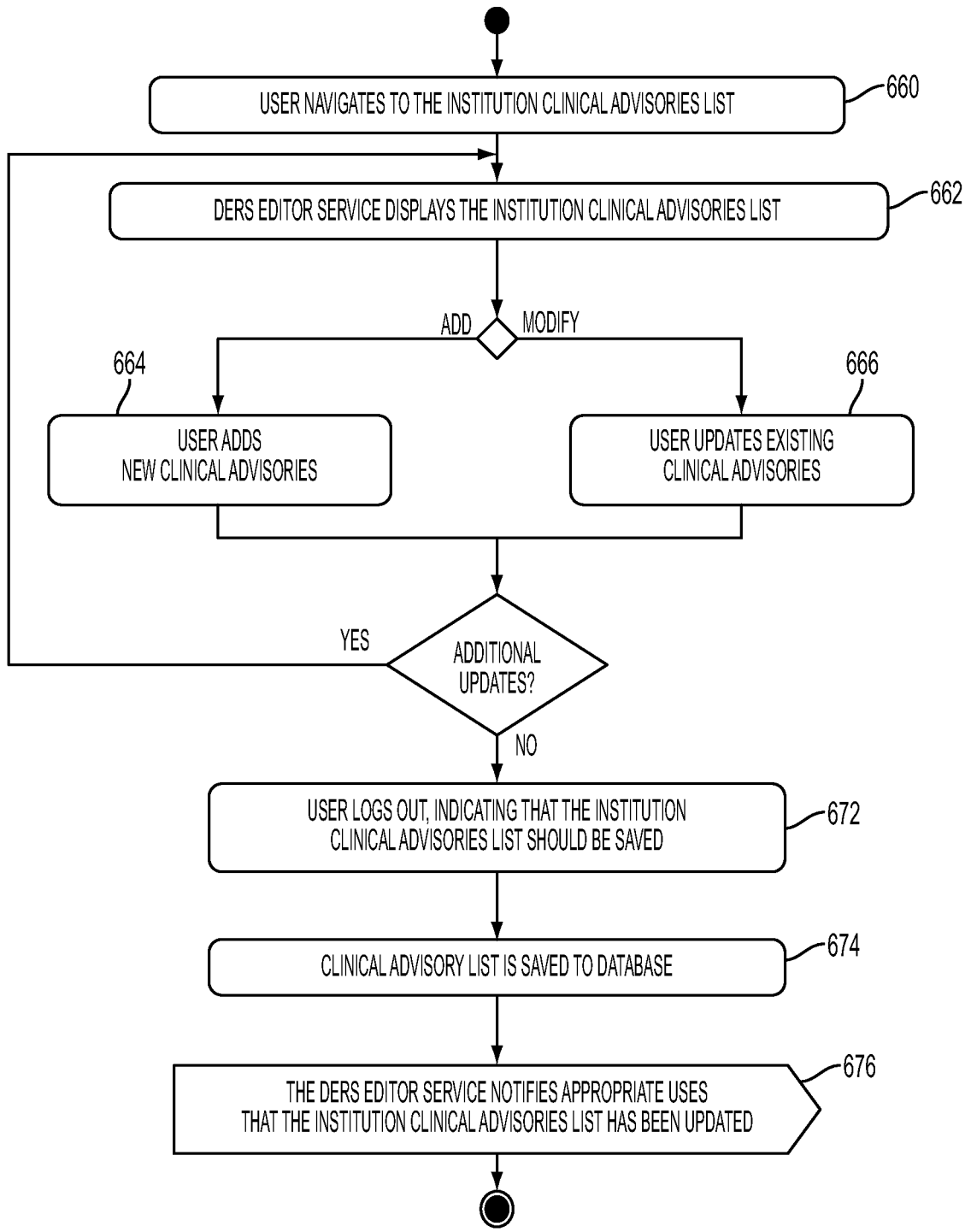
Figure 35:
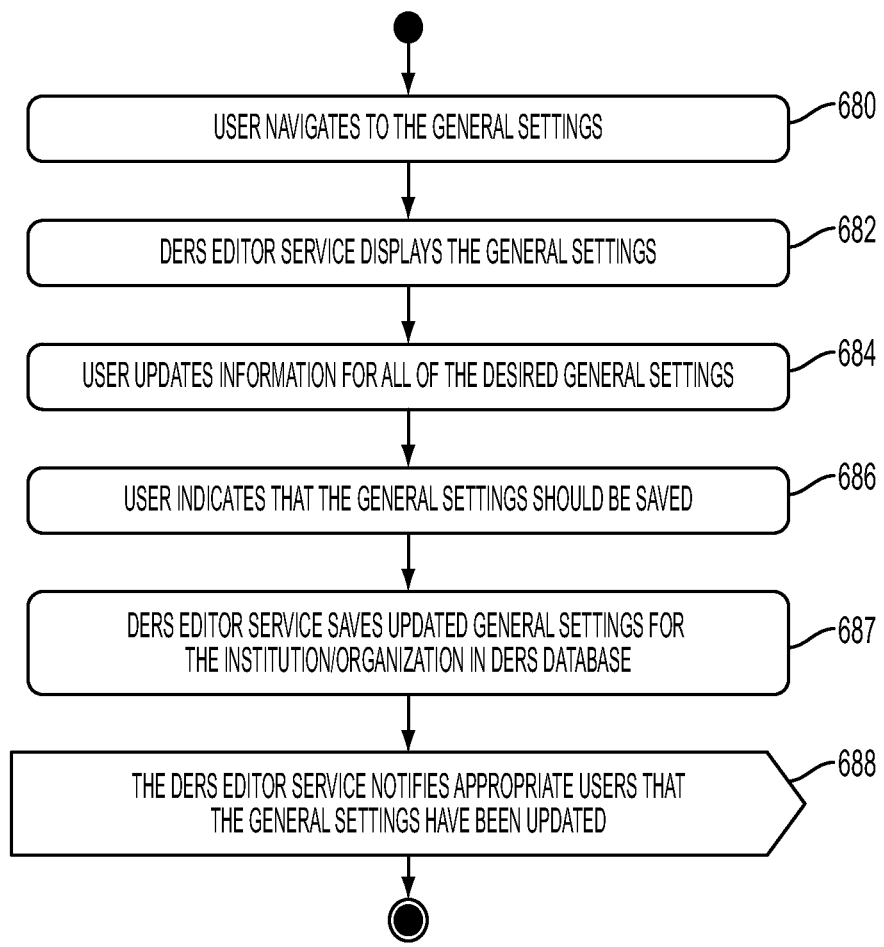
Figure 36:
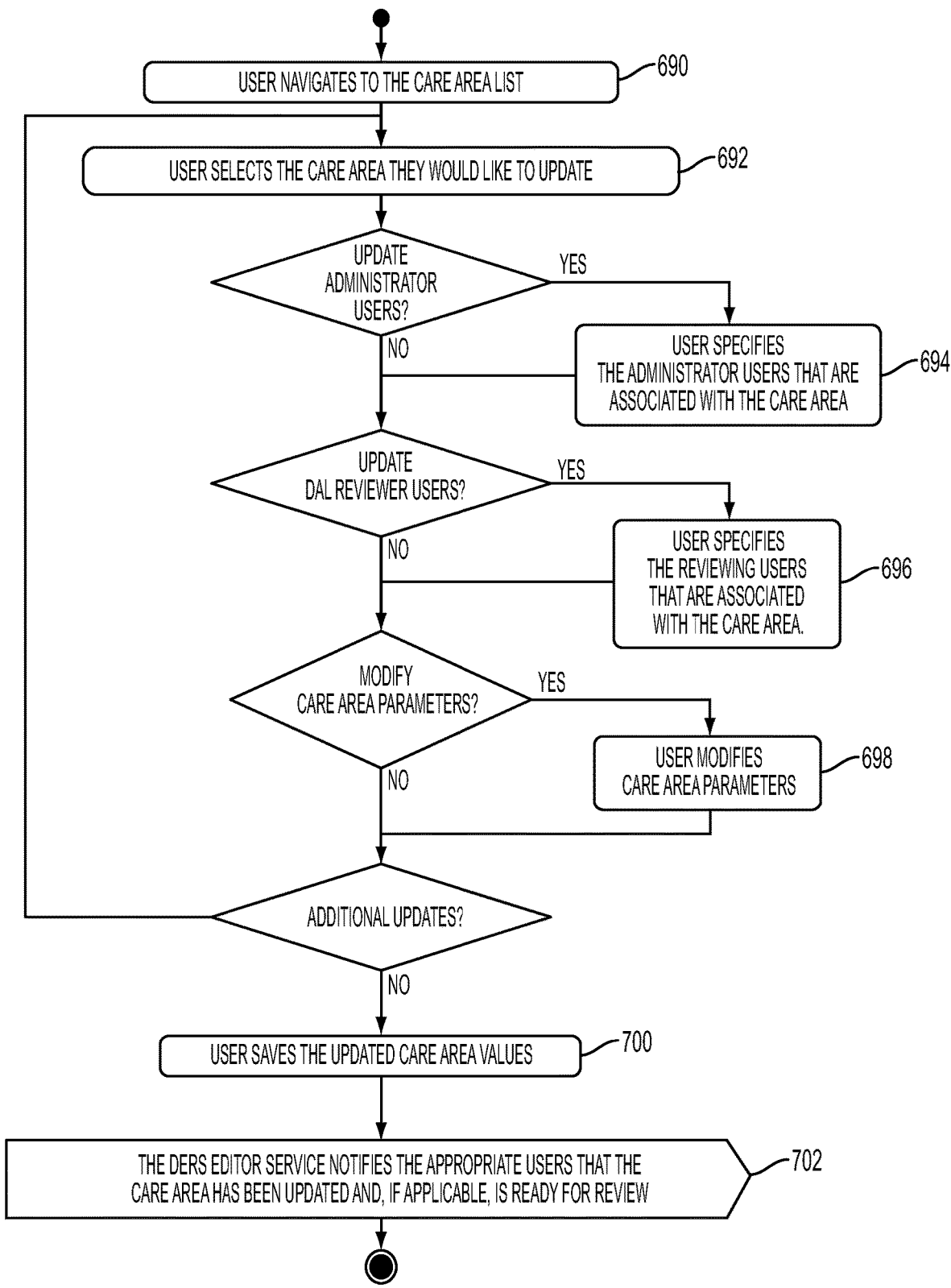
Figure 37:
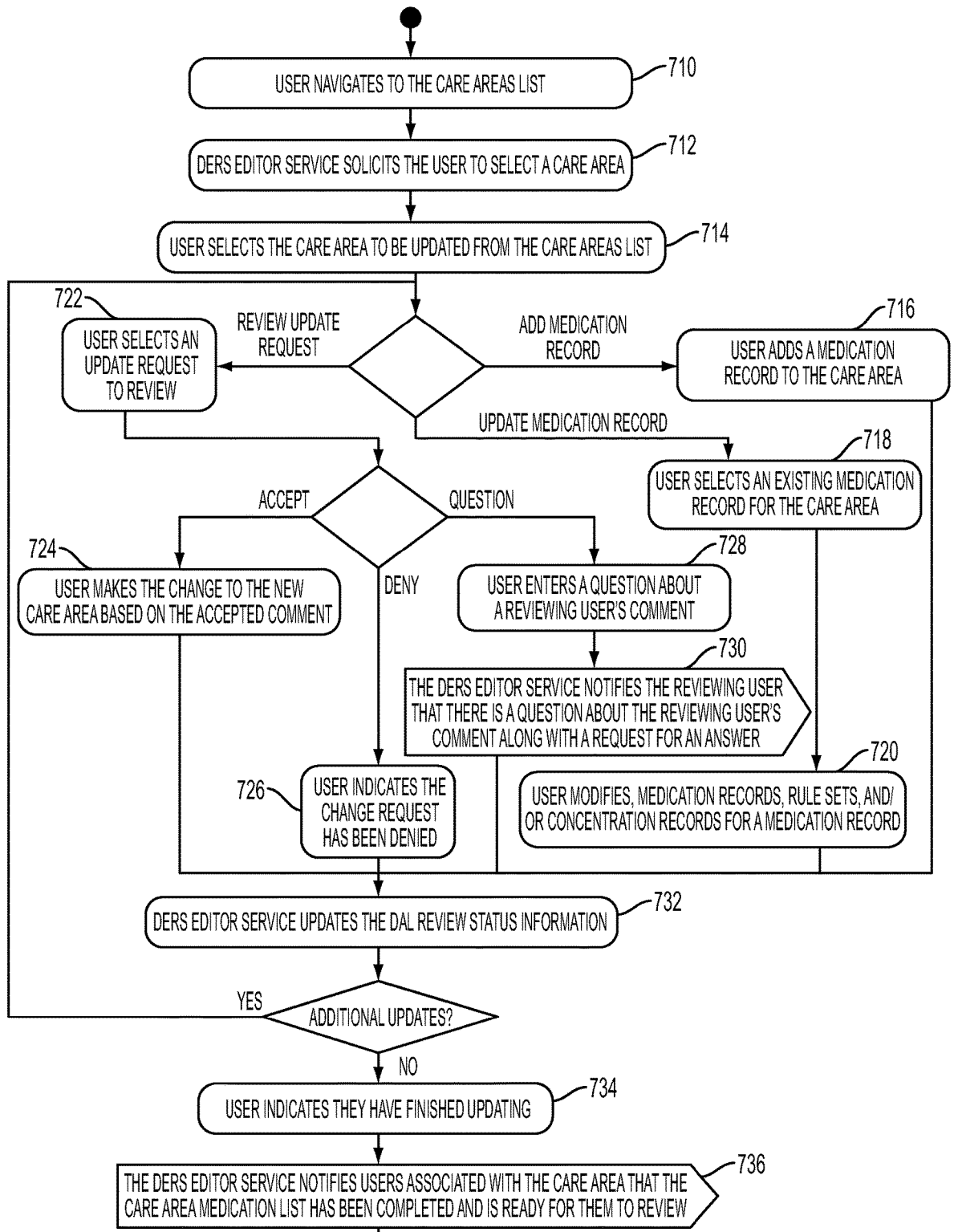
Figure 38:
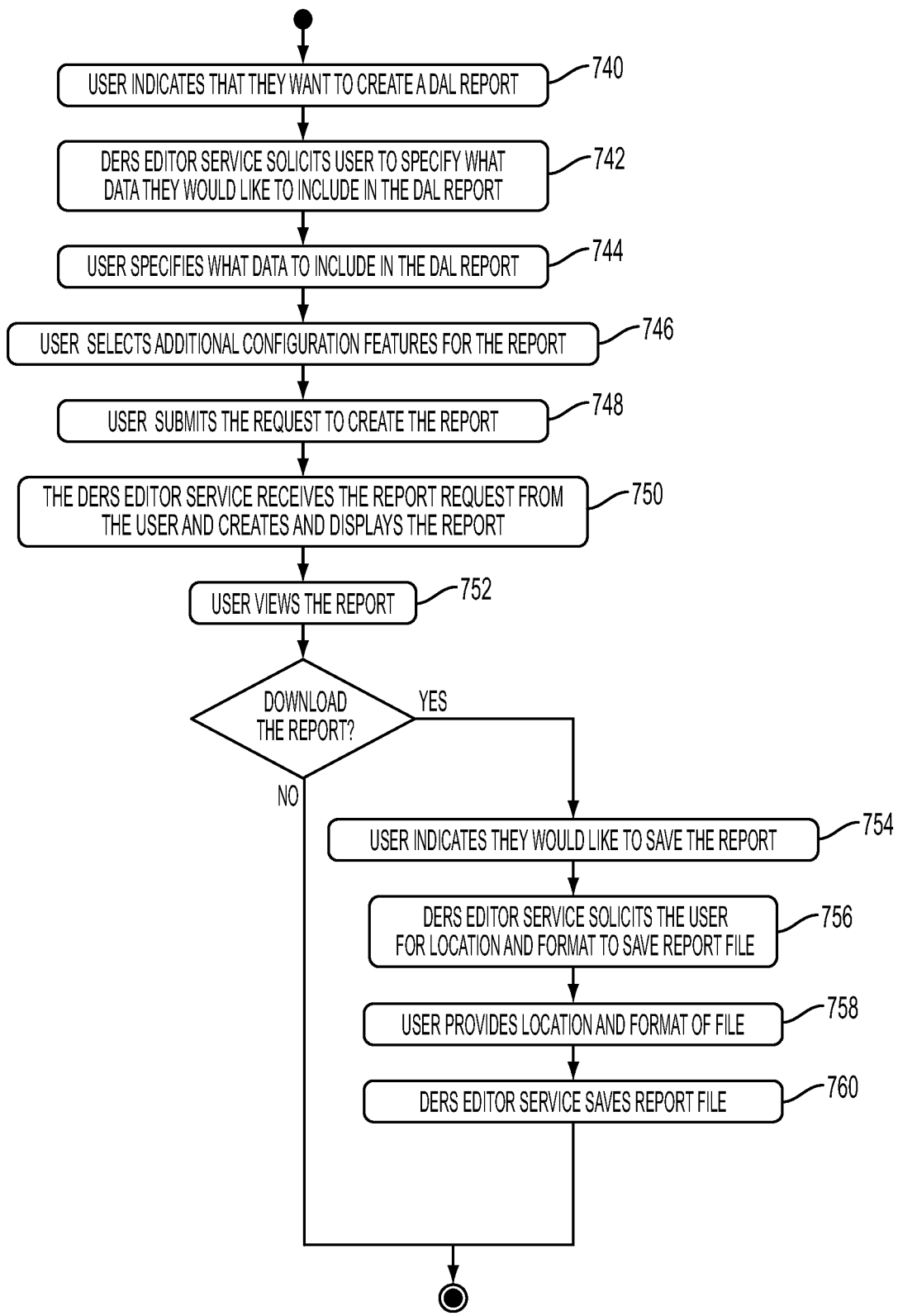
Figure 39:
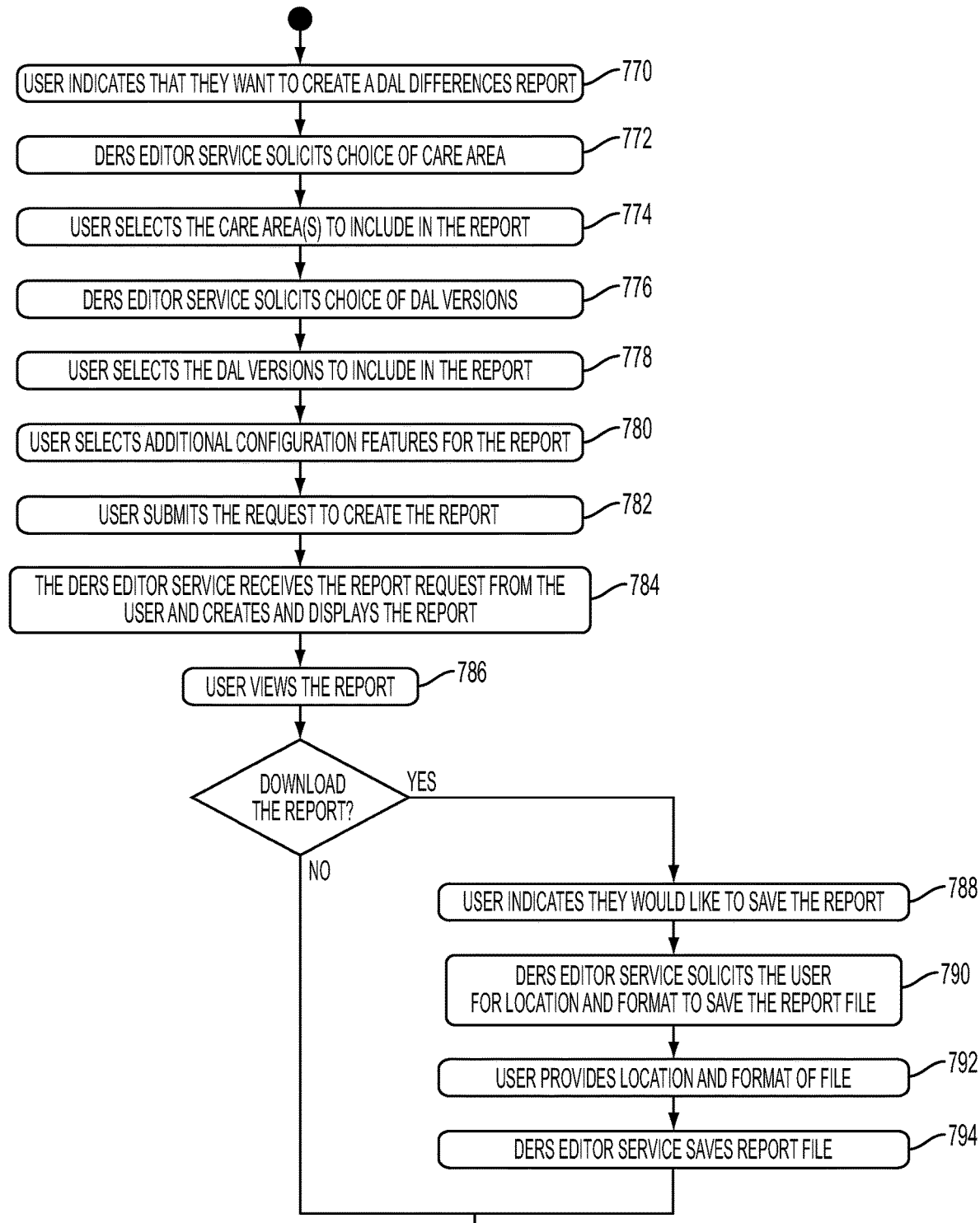
Figure 40:
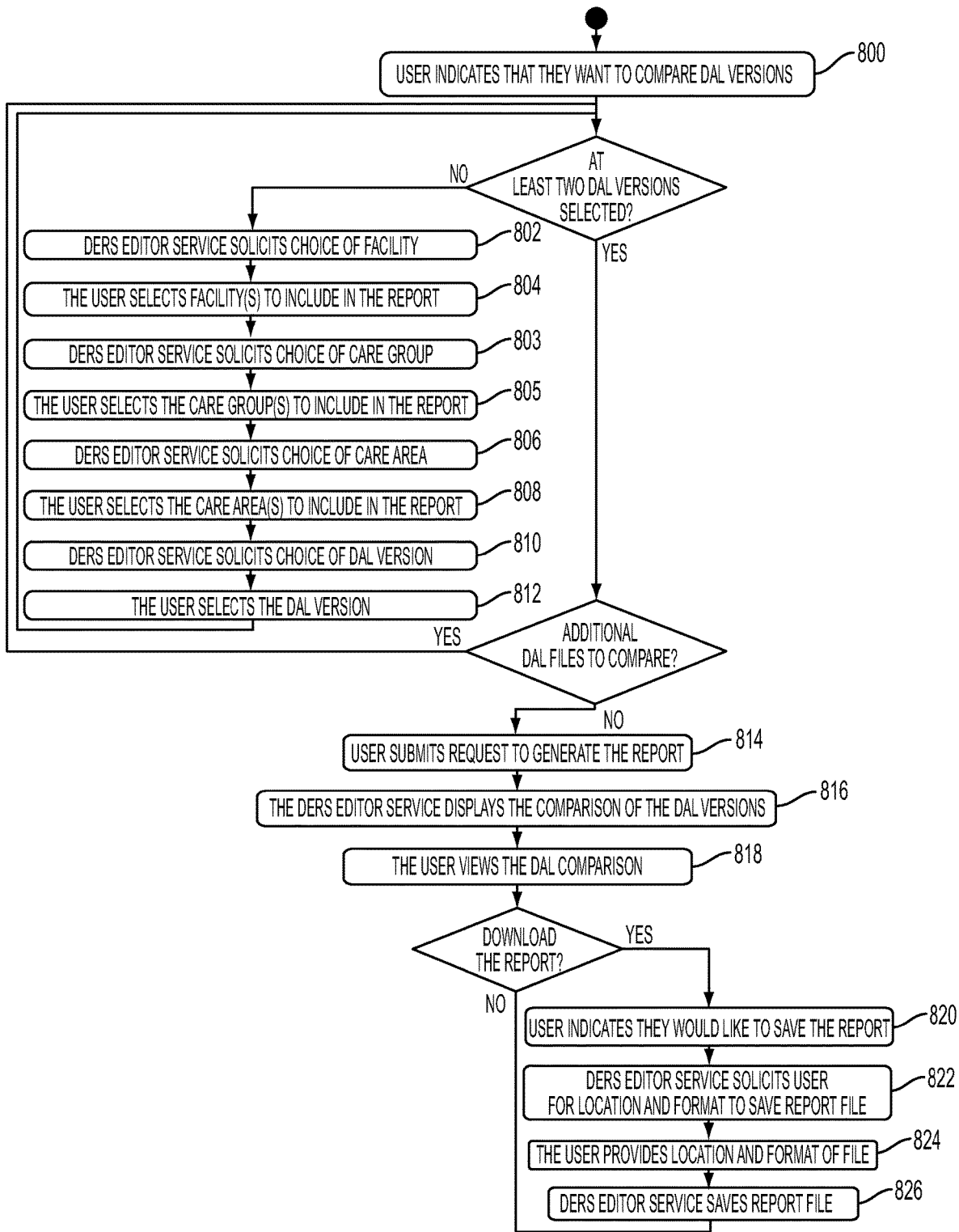
Figure 41:
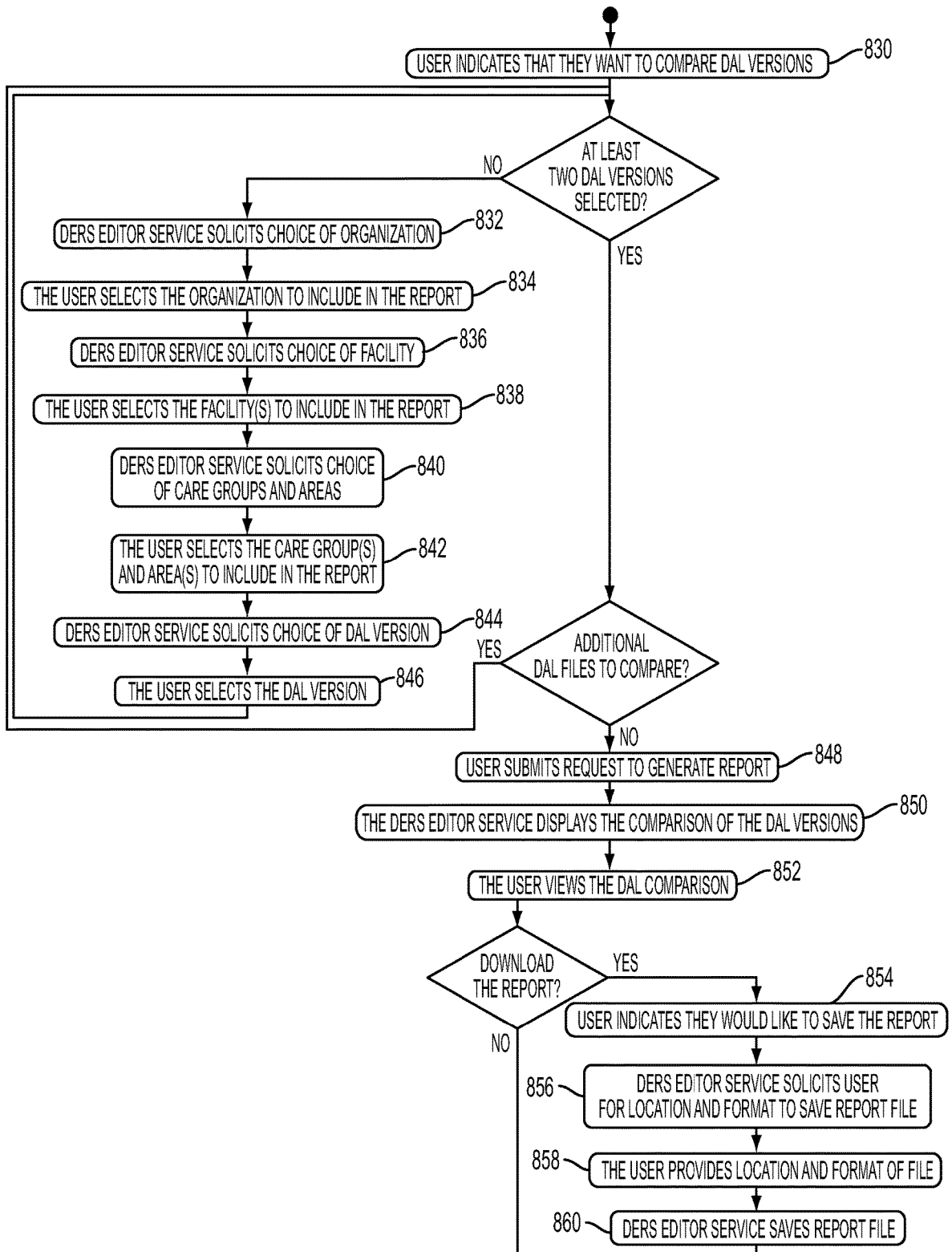
Figure 42:
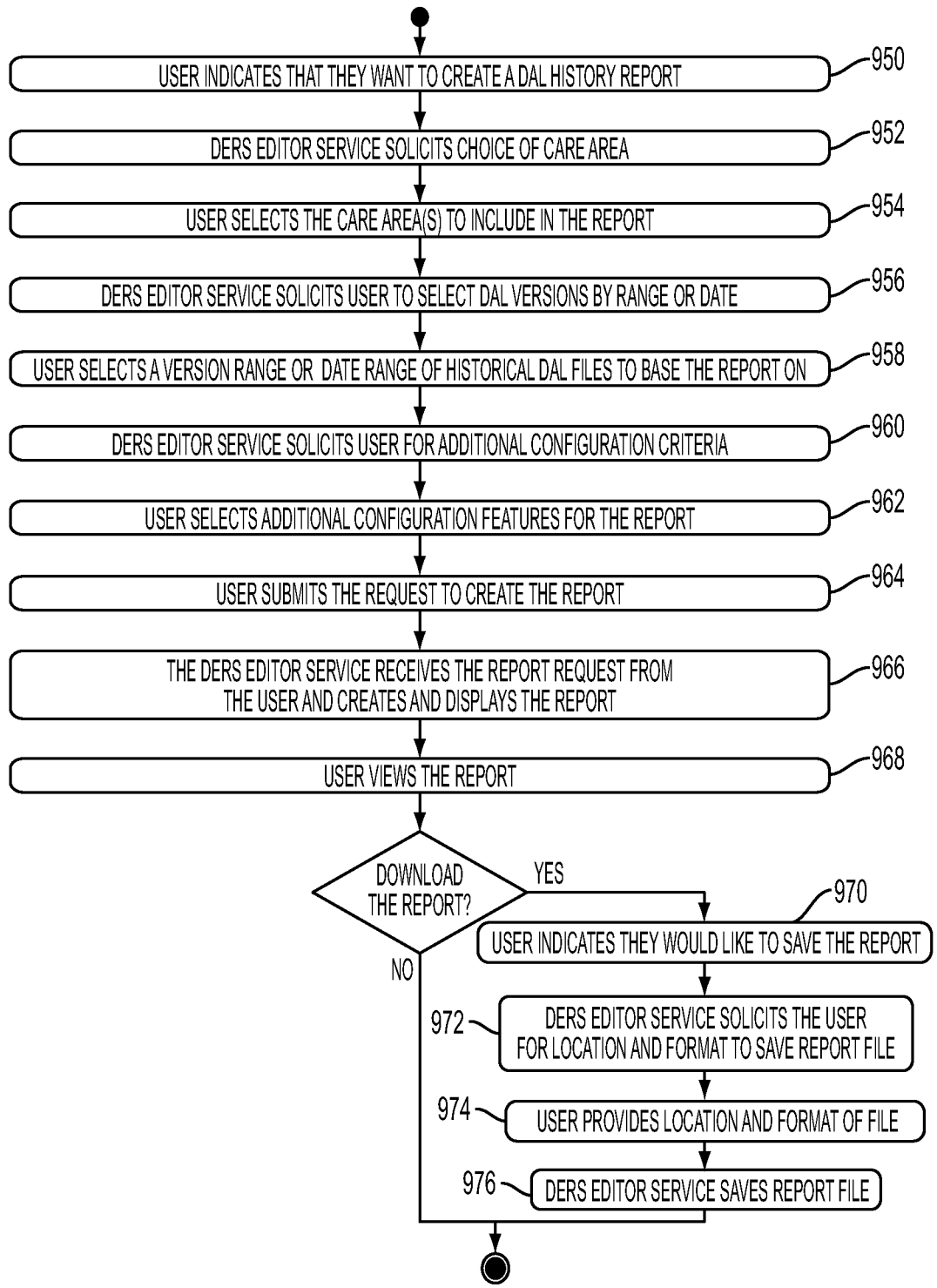
Figure 43:
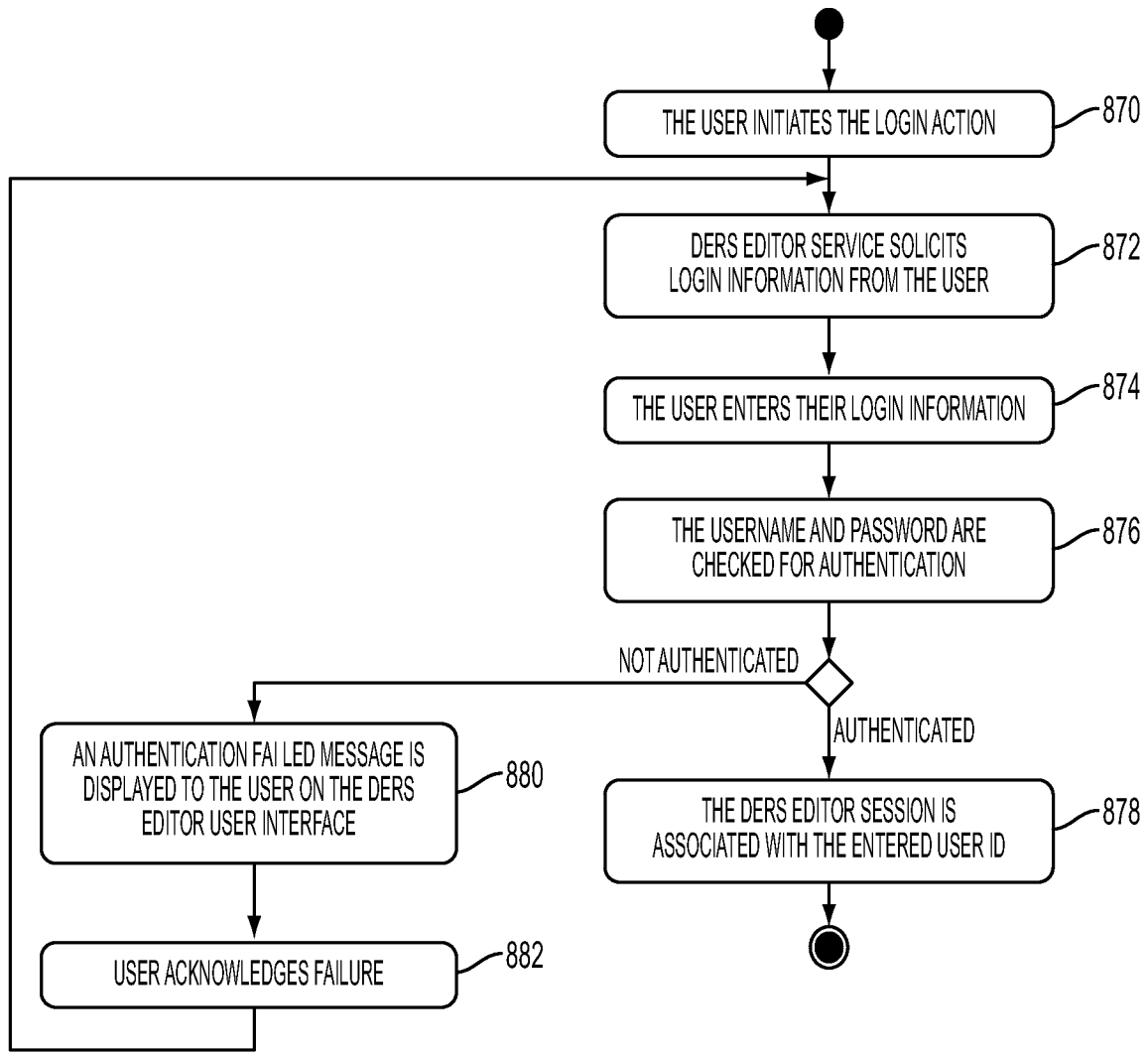
Figure 44:
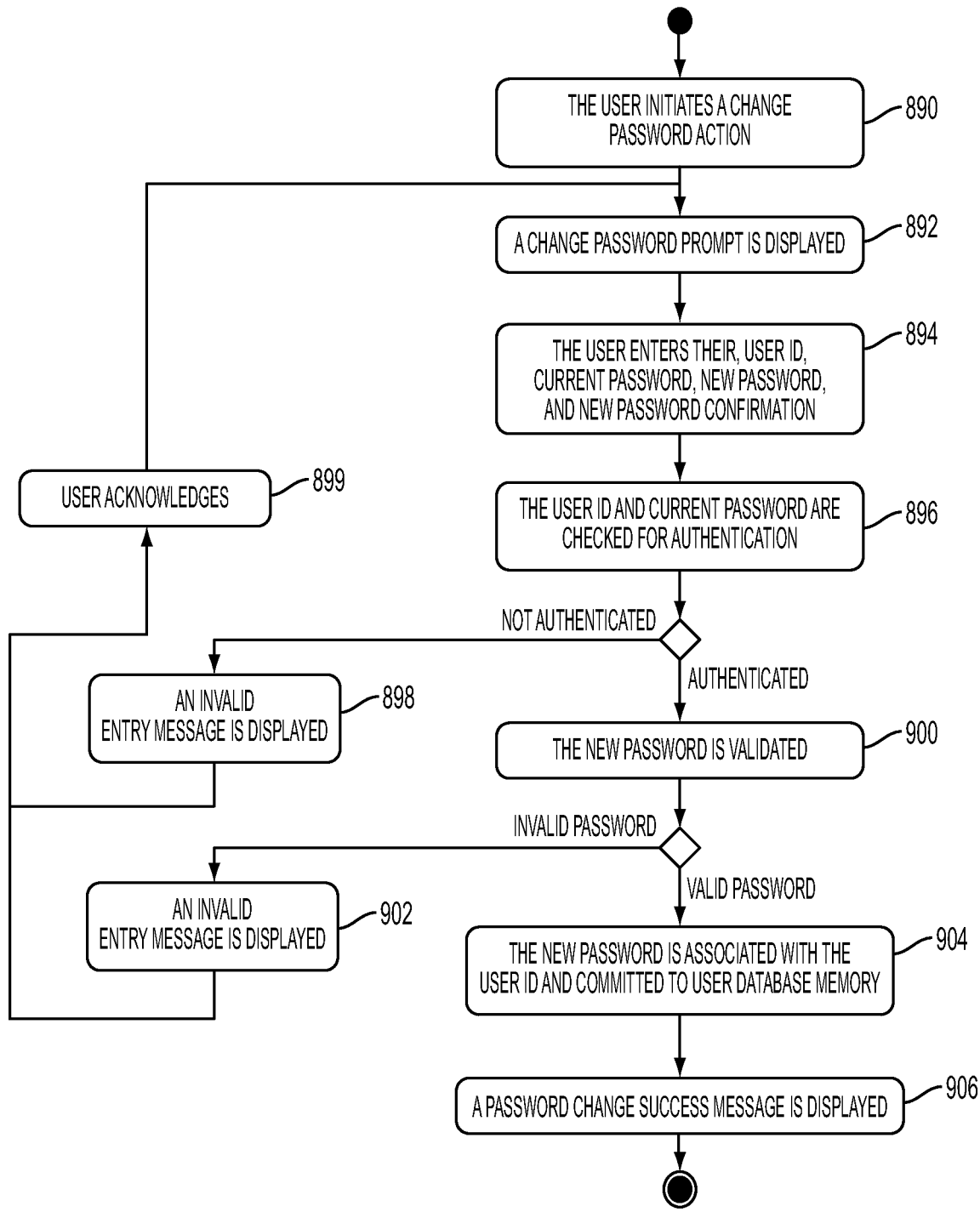
Figure 45:
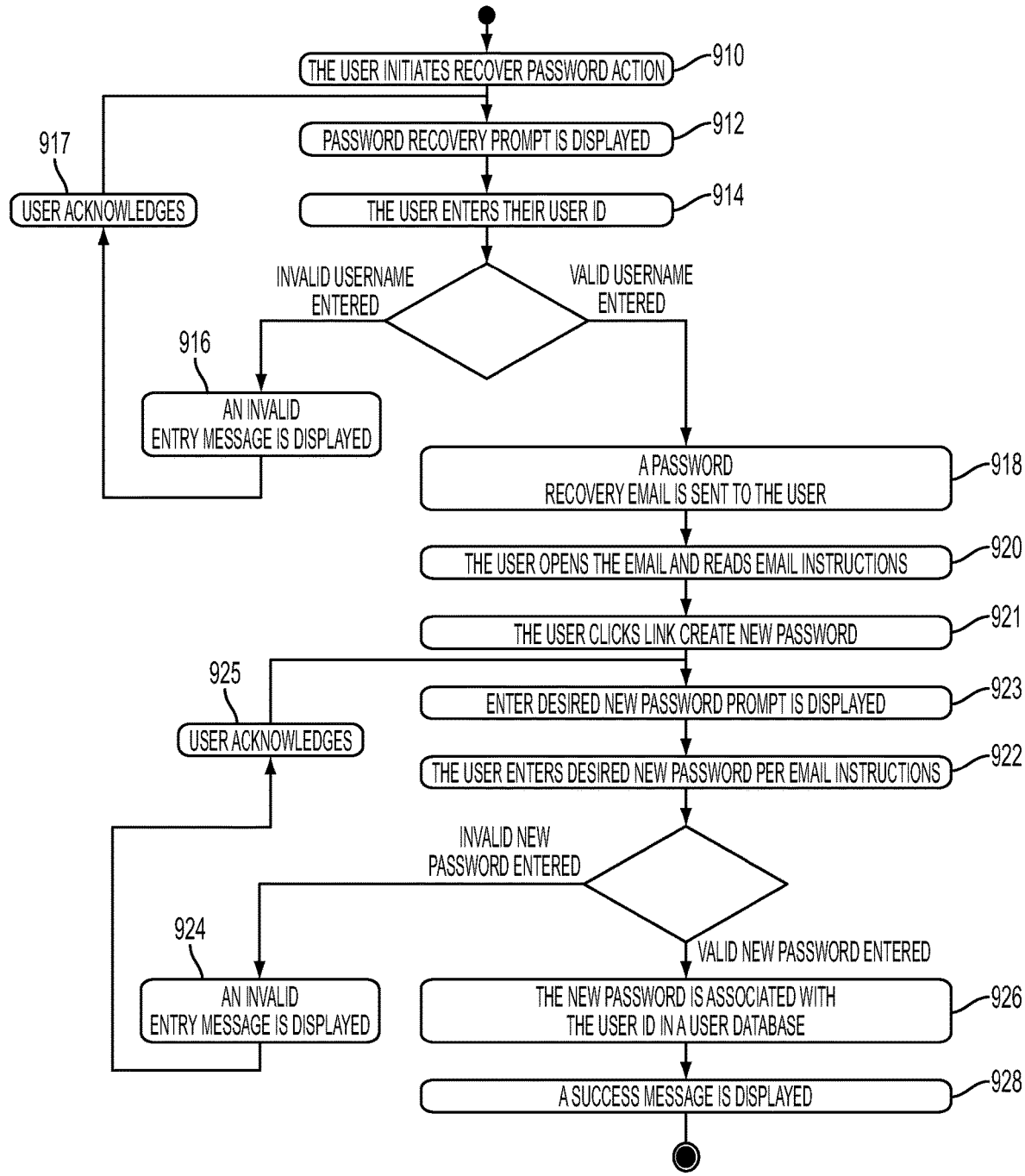
Figure 46:
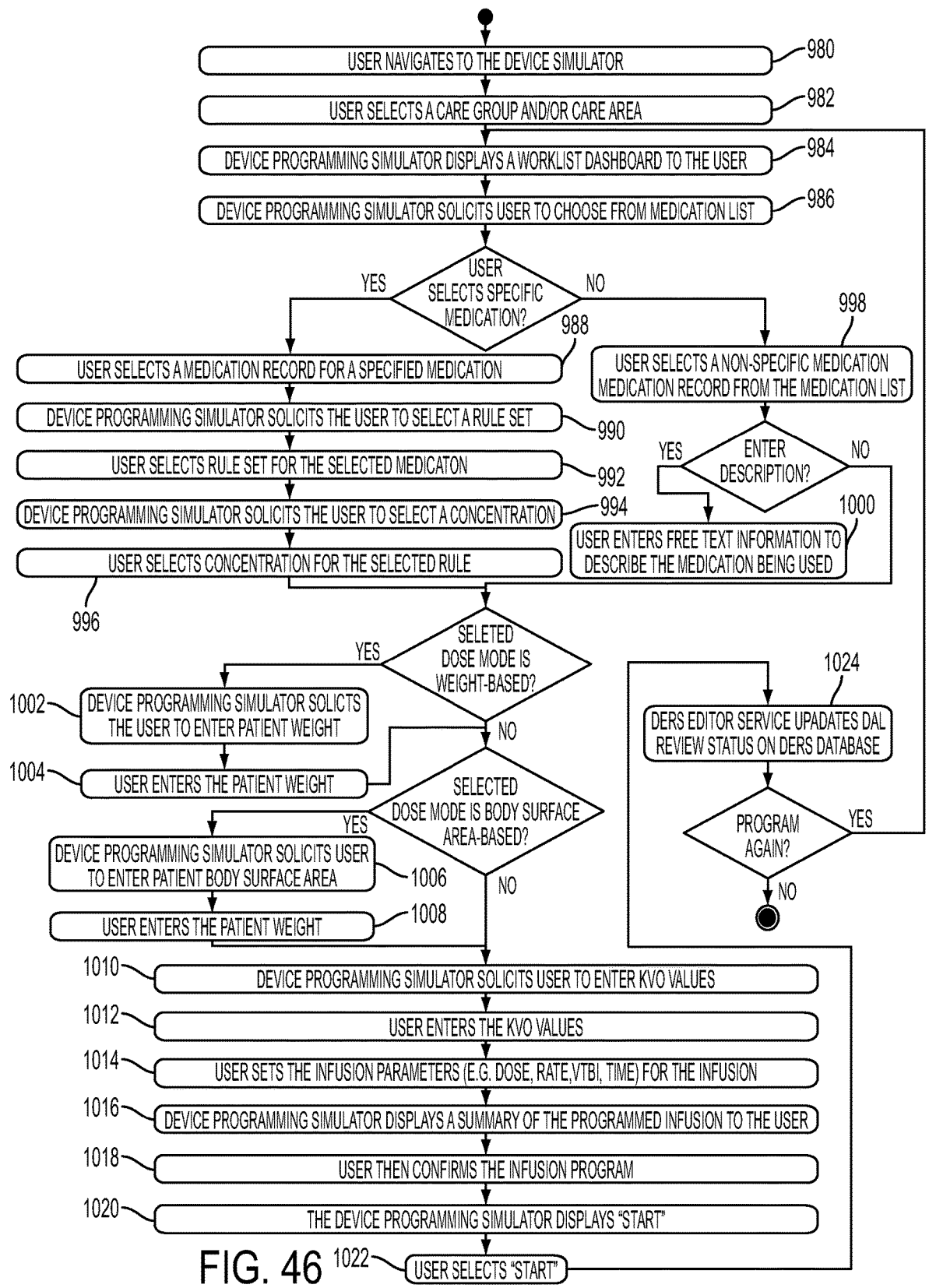
Figure 47:
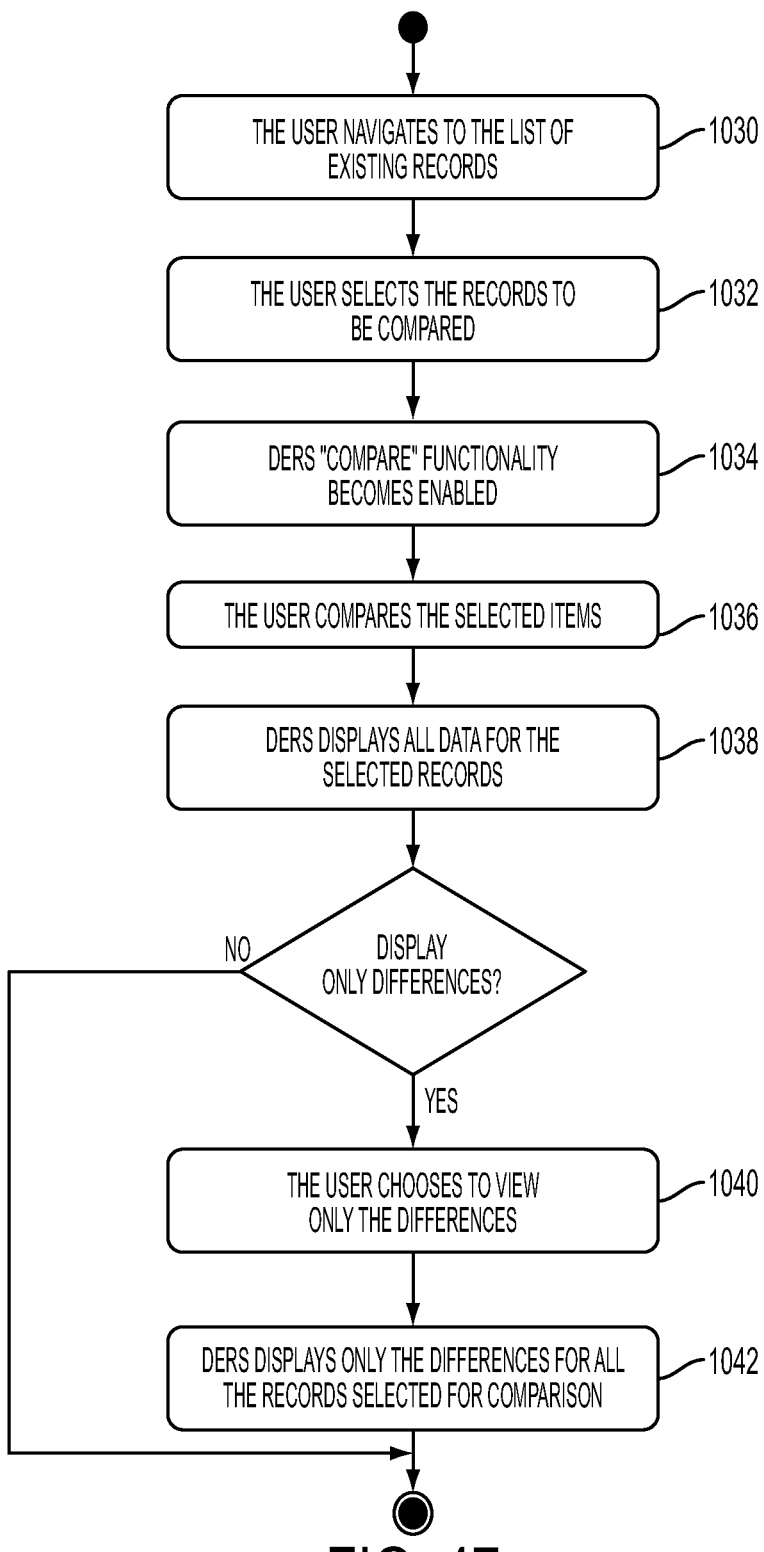
Figure 48:
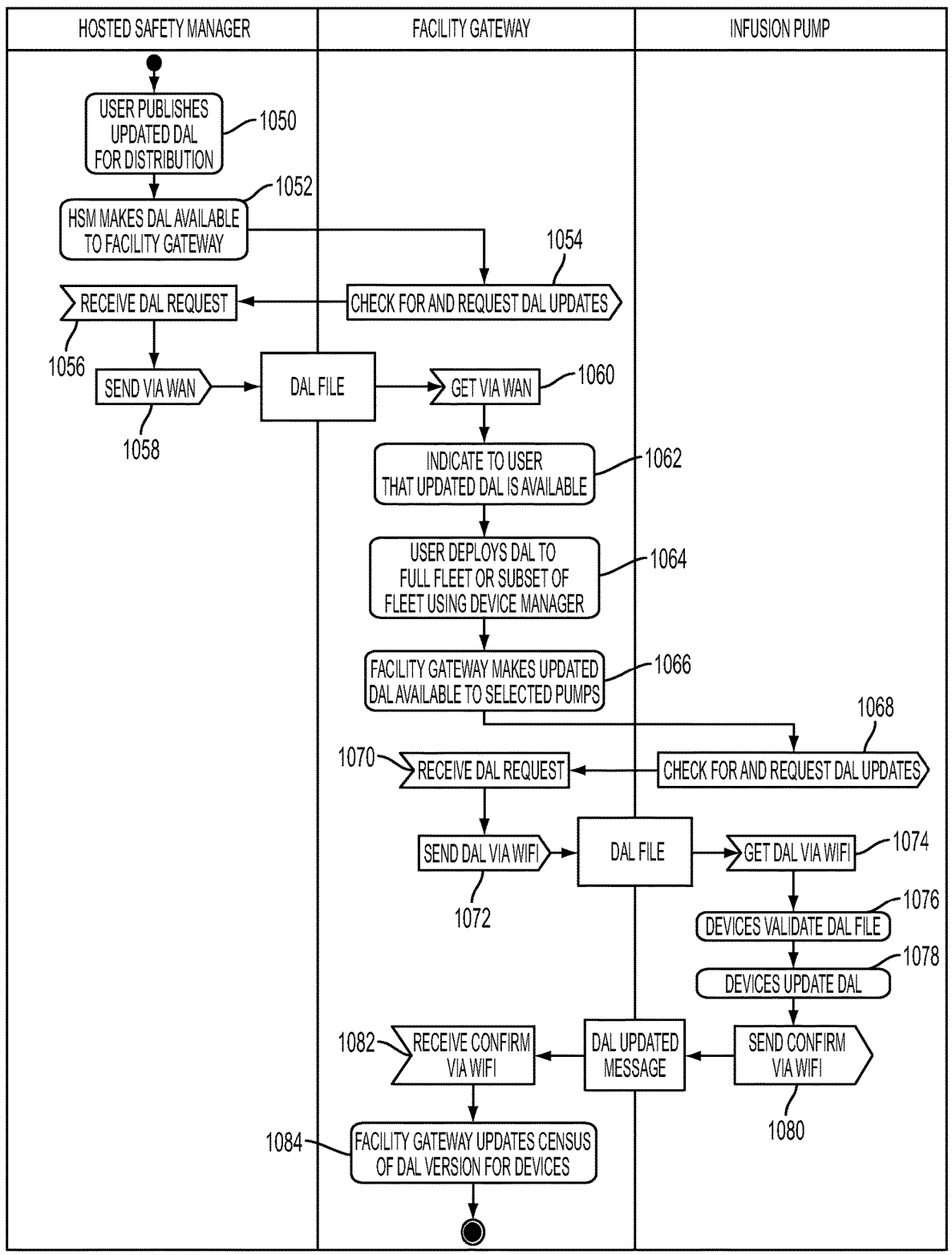
Figure 49:
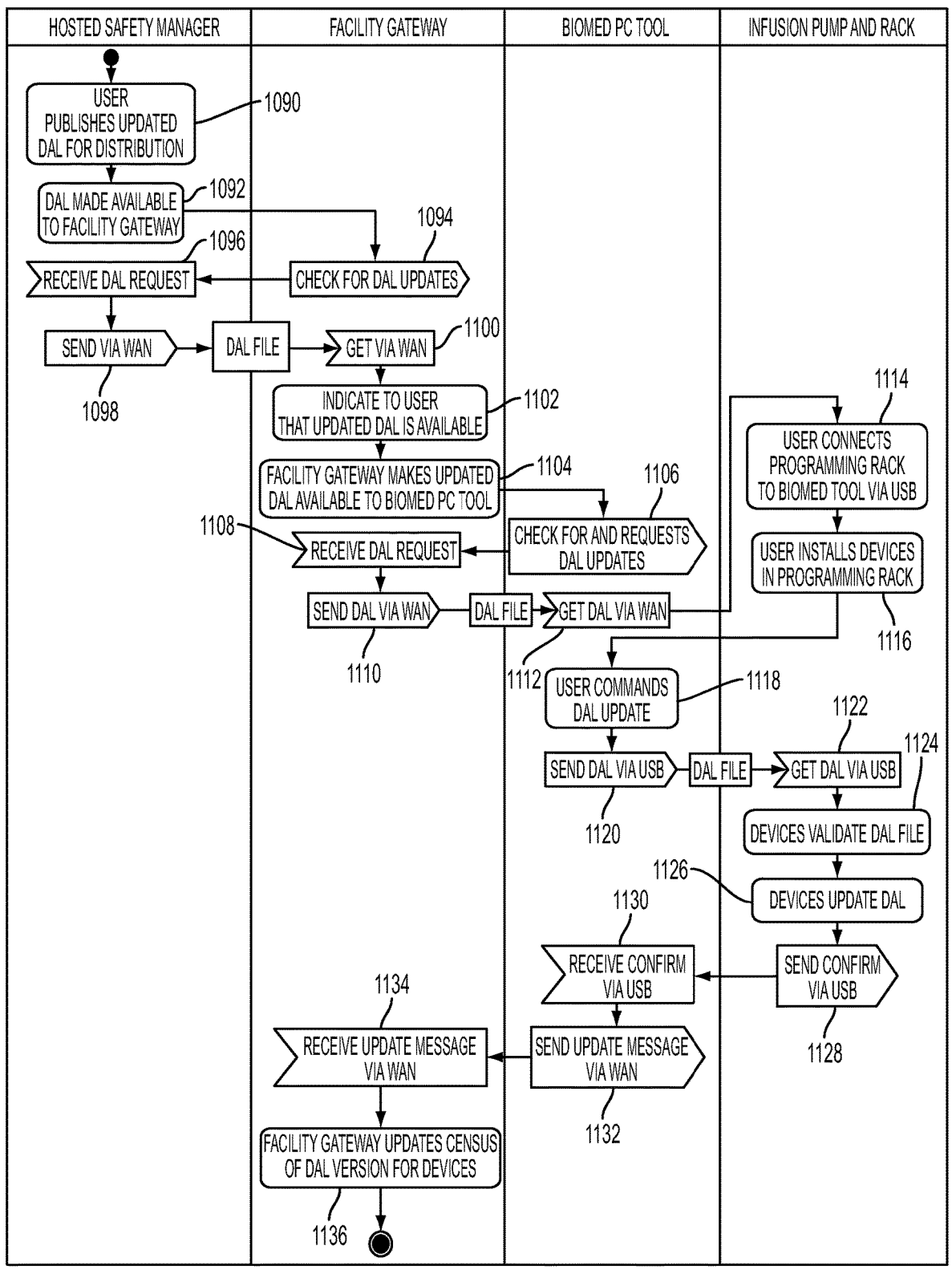
Figure 50:
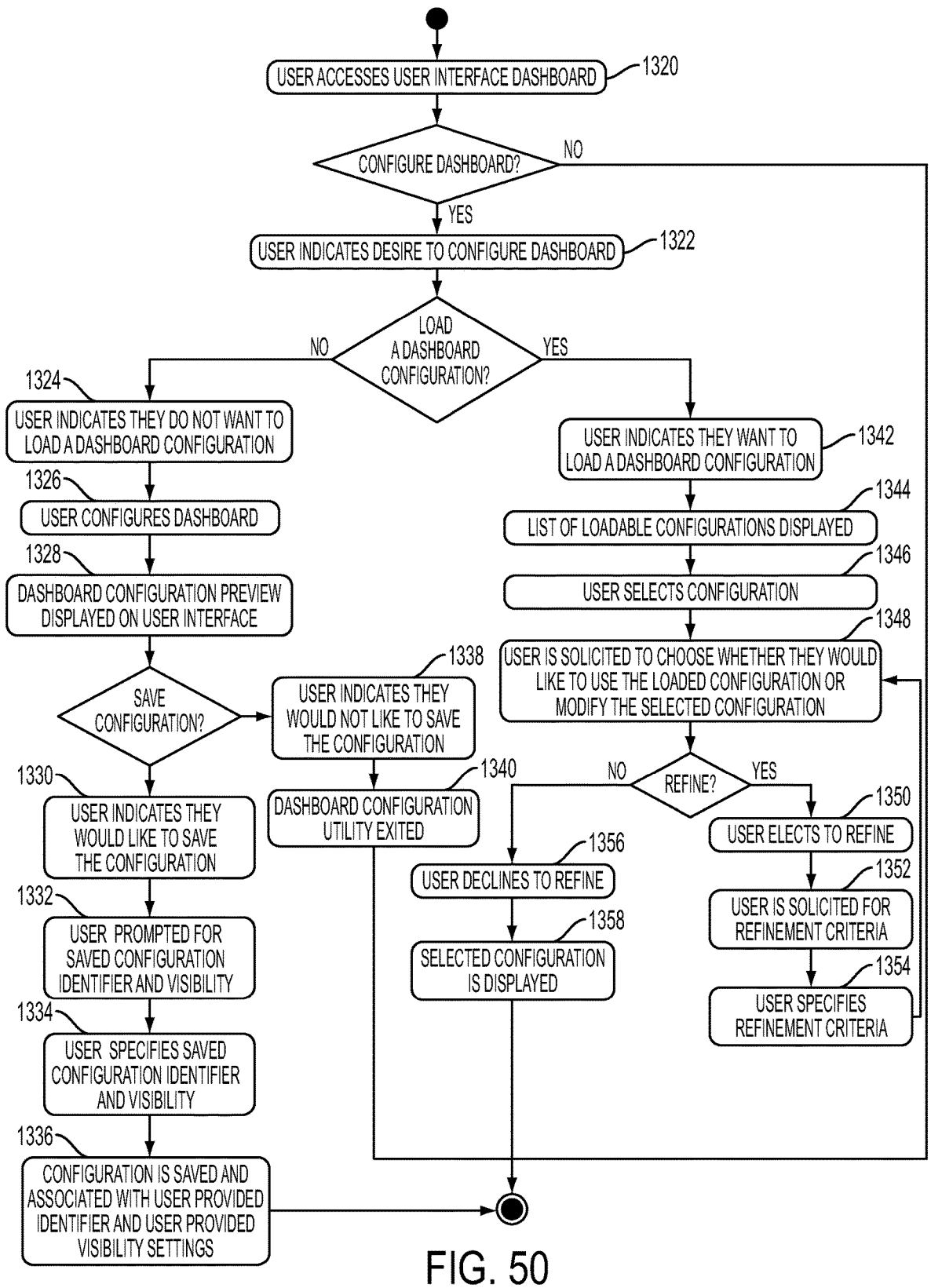
Figure 51:
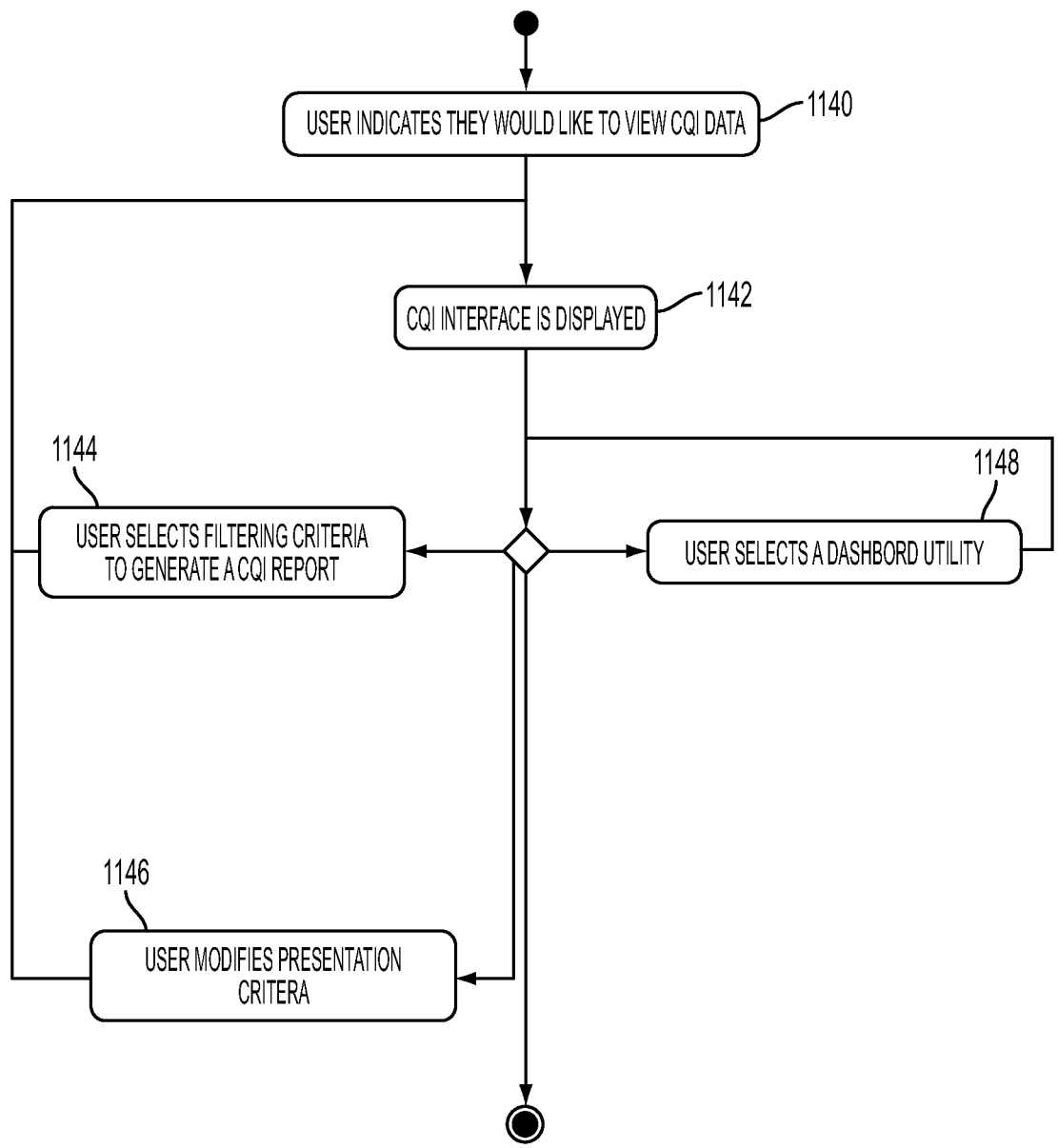
Figure 52:
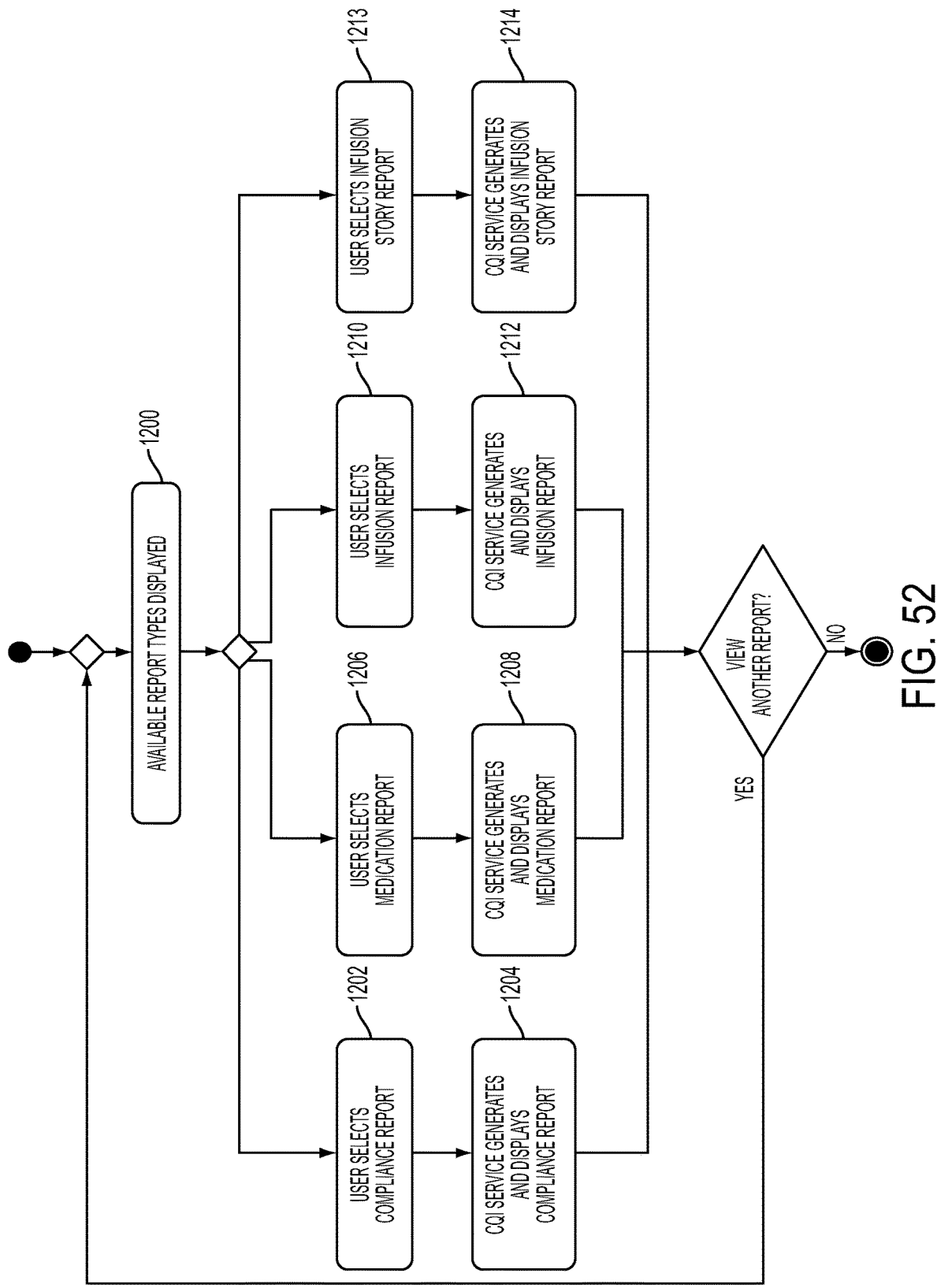
Figure 53:
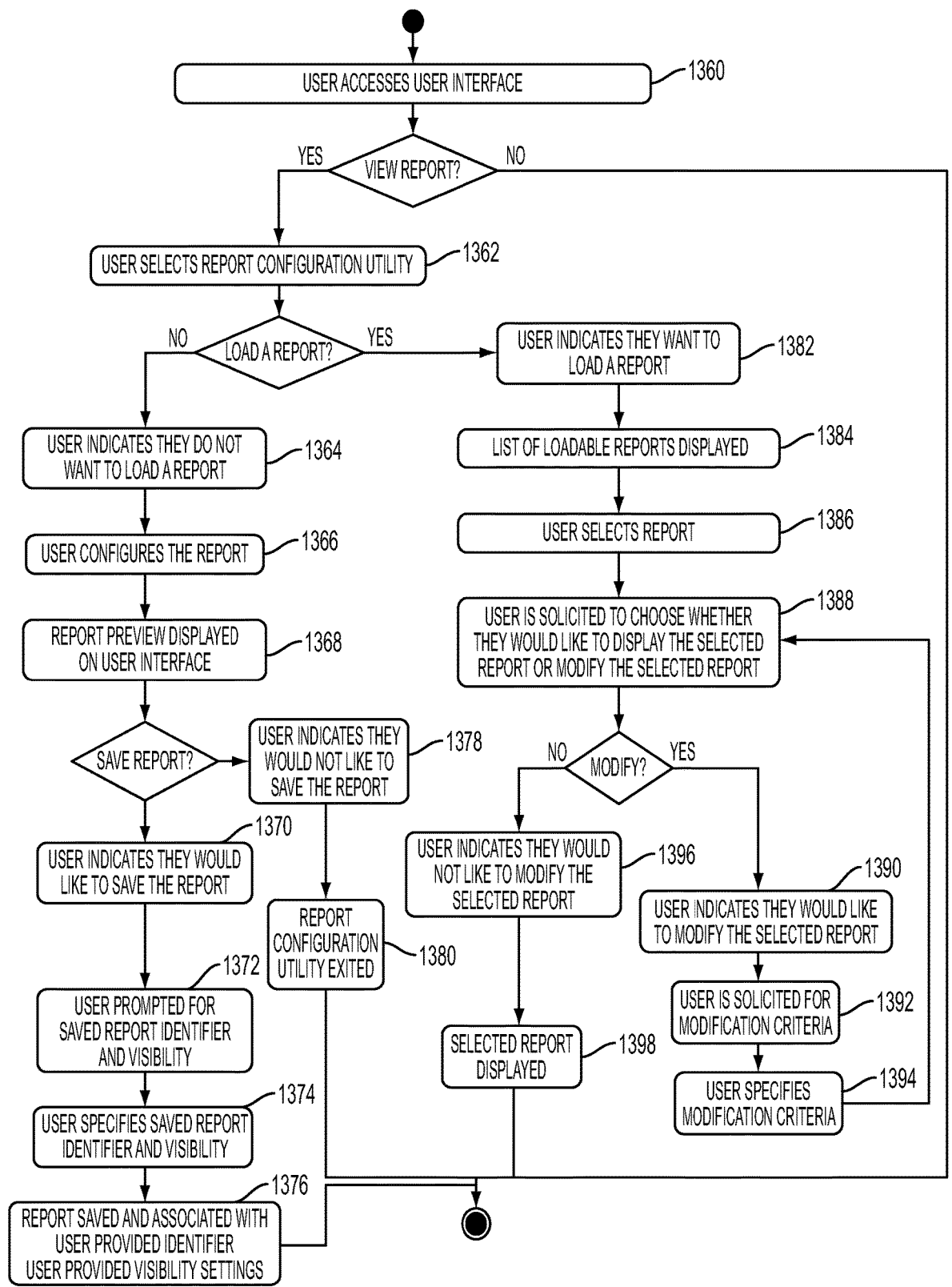
Figure 54:
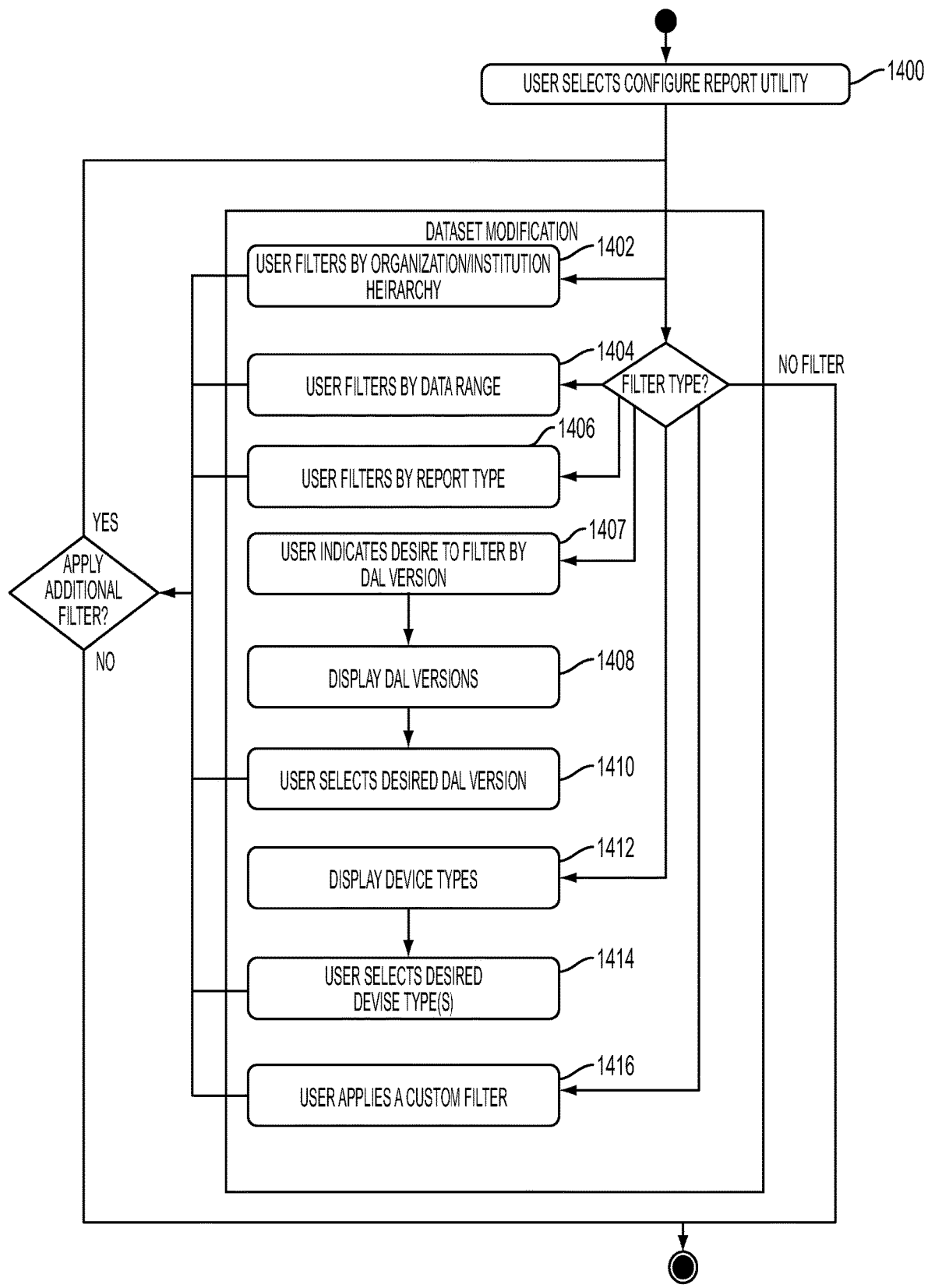
Figure 55:
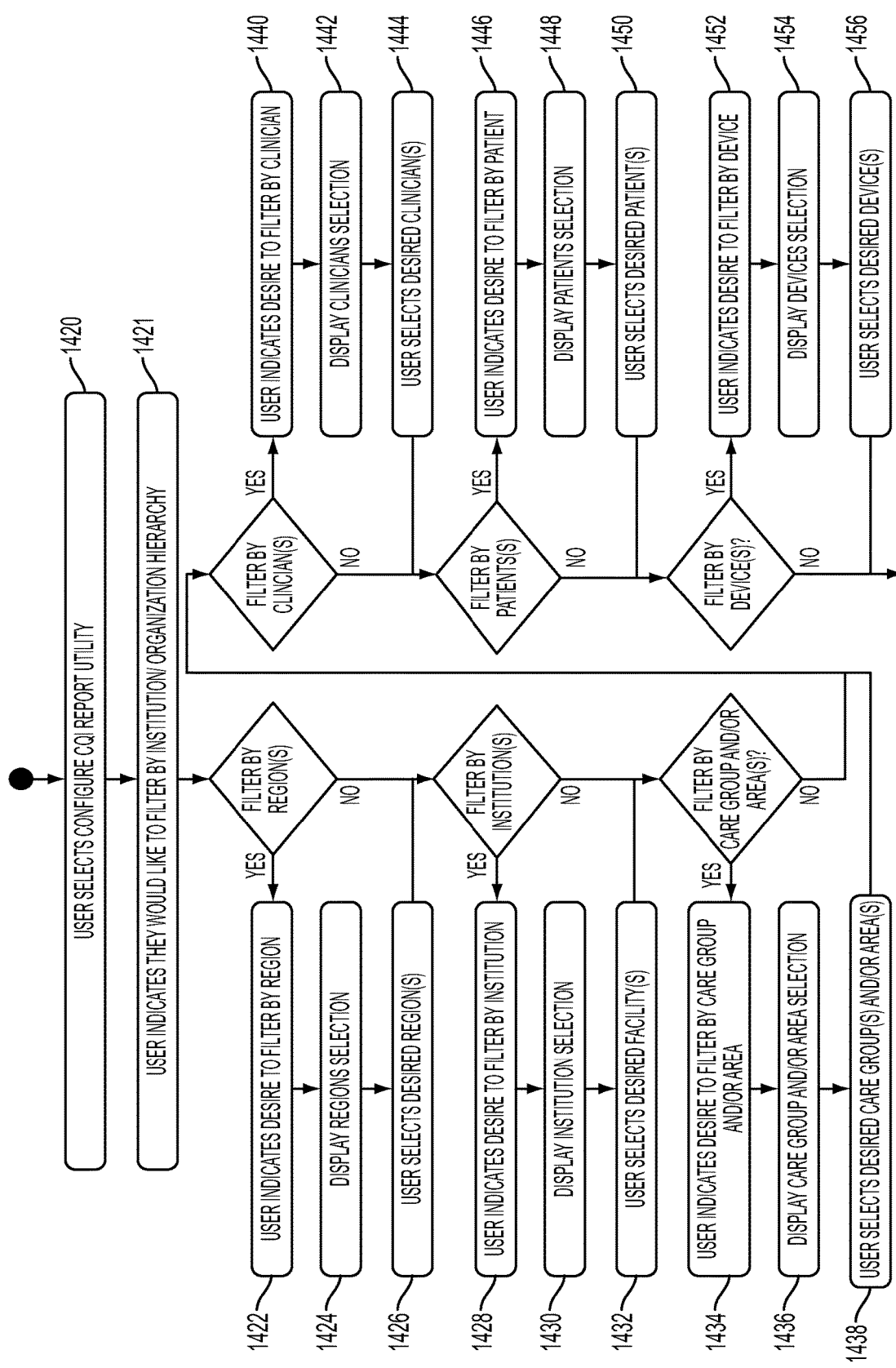
Figure 56:
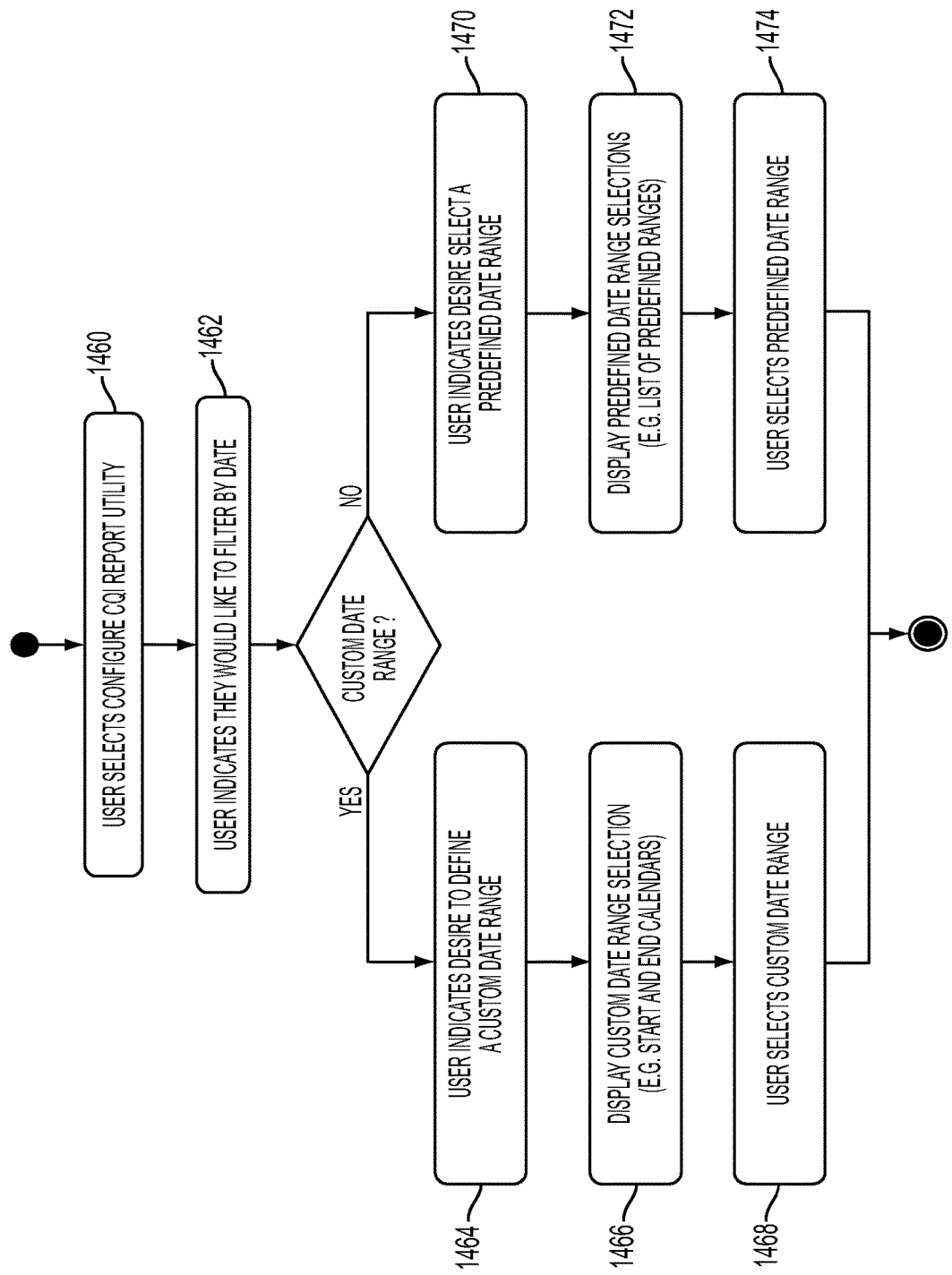
Figure 57:
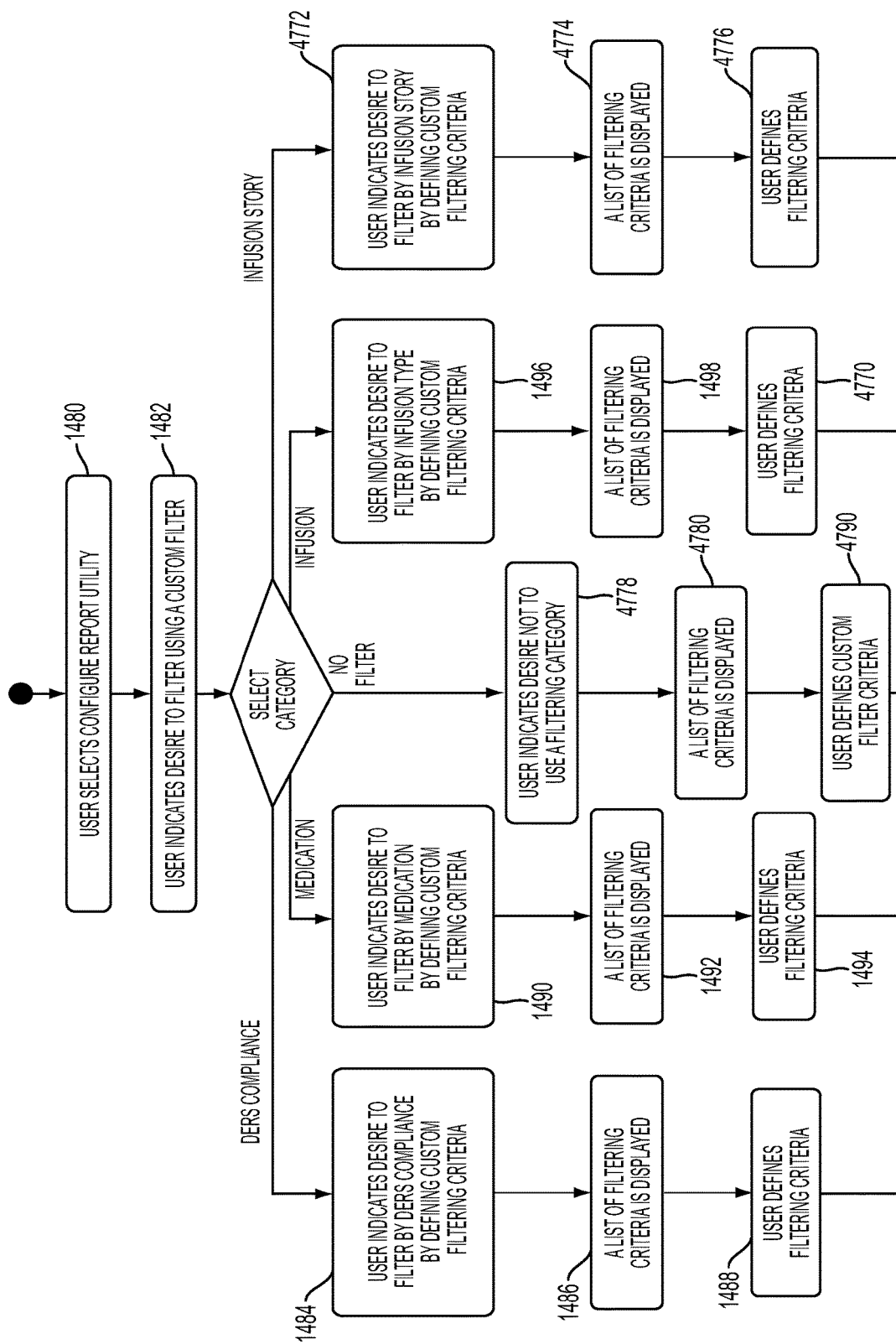
Figure 58:
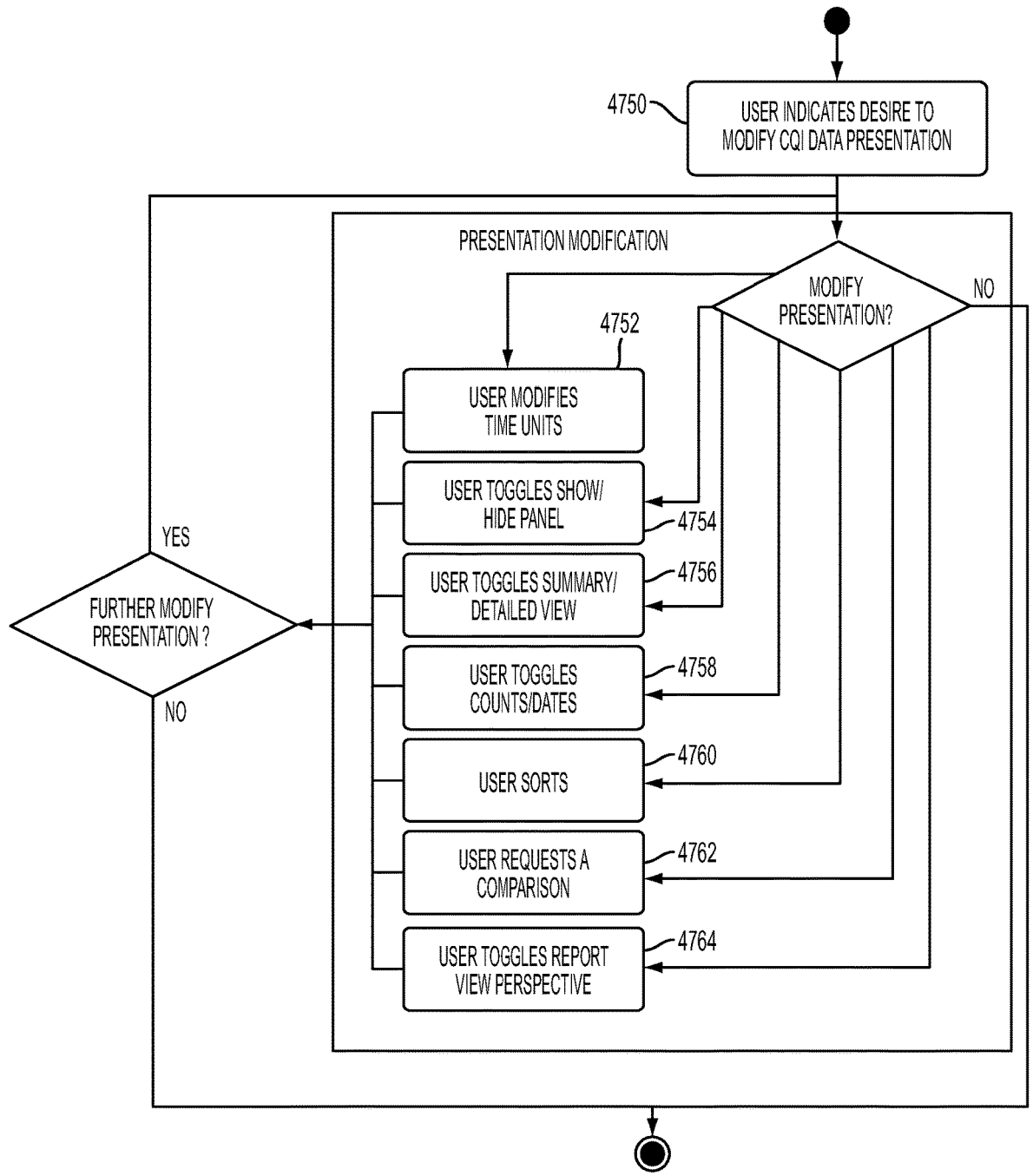
Figure 59:
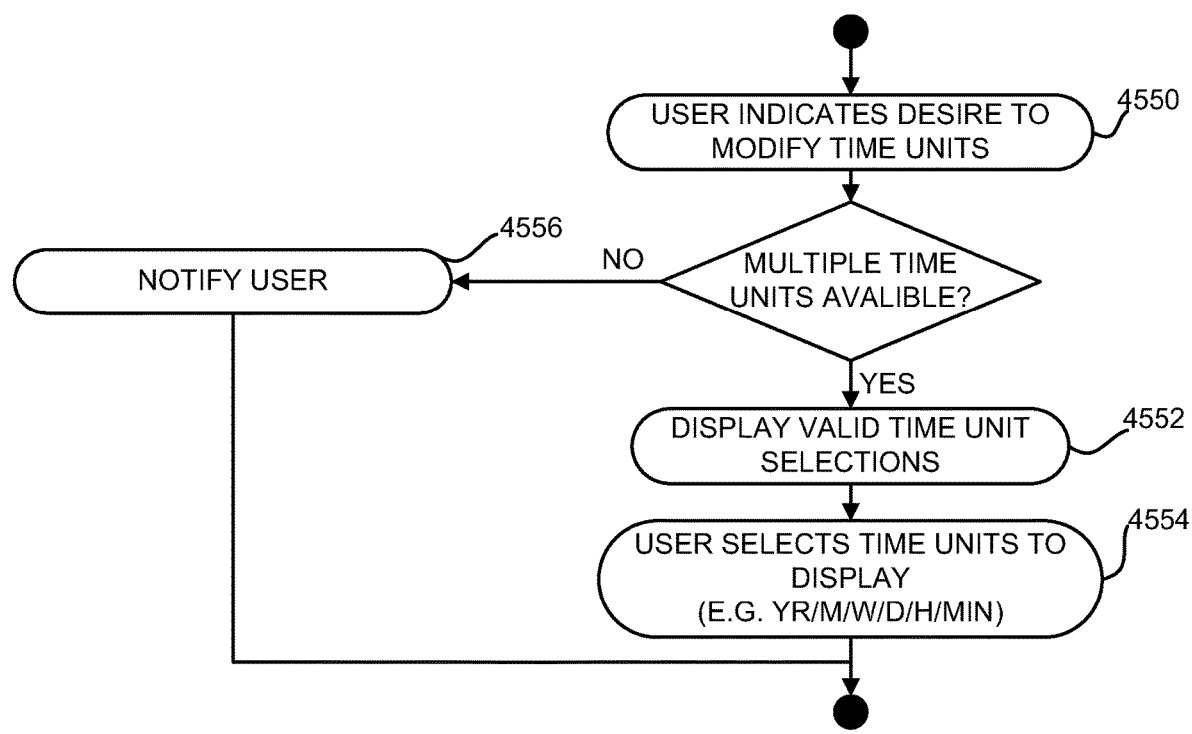

FIG. 19 depicts a flowchart detailing a number of example steps which may be used to add clinical advisory entries to a database in accordance with an embodiment of the present disclosure;

FIG. 20 depicts a flowchart detailing a number of example steps which may be used to modify the general settings for an institution or organization in accordance with an embodiment of the present disclosure;

FIG. 21 depicts a flowchart detailing a number of example steps which may be used to add a care group to a drug administration library file in accordance with an embodiment of the present disclosure;

FIG. 22 depicts a flowchart detailing a number of example steps which may be used to add a care area to a drug administration library file in accordance with an embodiment of the present disclosure;

FIG. 23 depicts a flowchart detailing a number of example steps which may be used in the verification of a care area in accordance with an embodiment of the present disclosure;

FIG. 24 depicts a flowchart detailing a number of example steps which may be used to update a care area in accordance with an embodiment of the present disclosure;

FIG. 25 depicts a flowchart detailing a number of exemplary steps which may be used to add drug records or medication records to a specified care area in accordance with an embodiment of the present disclosure;

FIG. 26 depicts a flowchart detailing a number of example steps which may be used to review a medication list for a particular care area in accordance with an embodiment of the present disclosure;

FIG. 27 depicts a flowchart detailing a number of example steps which may be used to update a medication list in accordance with an embodiment of the present disclosure;

FIG. 28 depicts a flowchart detailing a number of example steps which may be used to re-verify a medication list in accordance with an embodiment of the present disclosure;

FIG. 29 depicts a flowchart which details a number of example steps which may be used to submit a drug administration library file for approval in accordance with an embodiment of the present disclosure;

FIG. 30 depicts a flowchart detailing a number of example steps which may be used to place a drug administration library file into condition for release in accordance with an embodiment of the present disclosure;

FIG. 31a depicts a flowchart detailing a number of exemplary steps which may be used to deploy a drug administration library file onto various system components in accordance with an embodiment of the present disclosure;

FIG. 31b depicts an example flowchart detailing a number of steps which may be used to package and stage a resource for release to a facility gateway in accordance with an embodiment of the present disclosure;

FIG. 31c depicts an flowchart detailing a number of example steps which may be used to track the deployment of various resources in accordance with an embodiment of the present disclosure;

FIG. 32 depicts a flowchart which details a number of example steps which may be used to update an existing drug administration library file in accordance with an embodiment of the present disclosure;

FIG. 33 depicts a flowchart detailing a number of example steps which may be used to update an institution/organization's master medication list in accordance with an embodiment of the present disclosure;

FIG. 34 depicts a flowchart detailing a number of example steps which may be used to update the clinical advisories list in accordance with an embodiment of the present disclosure;

FIG. 35 depicts a flowchart detailing a number of example steps which may be used to update the general settings for an institution/organization in accordance with an embodiment of the present disclosure;

FIG. 36 depicts a flowchart detailing a number of example steps which may be used to update a care area in accordance with an embodiment of the present disclosure;

FIG. 37 depicts a flowchart detailing a number of example steps which may be used to update Medication Records for a care area in accordance with an embodiment of the present disclosure;

FIG. 38 depicts a flowchart detailing a number of example steps which may be used to create and save a drug administration library report in accordance with an embodiment of the present disclosure;

FIG. 39 depicts a flowchart detailing a number of example steps which may be used to create a drug administration library difference report in accordance with an embodiment of the present disclosure;

FIG. 40 depicts flowchart detailing a number of example steps which may be used to create an intra-organization drug administration library Comparison Report in accordance with an embodiment of the present disclosure;

FIG. 41 depicts a flowchart detailing a number of example steps which may be used to create an inter-organization drug administration library Comparison Report in accordance with an embodiment of the present disclosure;

FIG. 42 depicts a flowchart detailing a number of example steps which may be followed to create a drug administration library History Report in accordance with an embodiment of the present disclosure;

FIG. 43 depicts a flowchart detailing a number of example steps which may be used to log into a drug error reduction system editor in accordance with an embodiment of the present disclosure;

FIG. 44 depicts an example flowchart detailing a number of steps which may be used to change a password for a drug error reduction system editor service in accordance with an embodiment of the present disclosure;

FIG. 45 depicts a flowchart detailing a number of example steps which may be used to recover a password for a drug error reduction system editor service in accordance with an embodiment of the present disclosure;

FIG. 46 depicts a flowchart detailing a number of example steps which may be used to review drug library entry using a medical device programming simulator in accordance with an embodiment of the present disclosure;

FIG. 47 depicts a flowchart detailing a number of exemplary steps which may be used to compare records in a drug administration library file in accordance with an embodiment of the present disclosure;

FIG. 48 depicts a flowchart detailing a number of example steps which may be used to update a drug administration library file on a medical device in accordance with an embodiment of the present disclosure;

FIG. 49 depicts a flowchart detailing a number of example steps which may be used to update a DAL file on a medical device in accordance with an embodiment of the present disclosure;

FIG. 50 depicts a flowchart detailing a number of example steps which may be used to configure a user interface for a drug error reduction system editor service or Continuous Quality Improvement ("CQI") service in accordance with an embodiment of the present disclosure;

FIG. 51 depicts a flowchart detailing a number of example steps which may be used to view and make use of Continuous Quality Improvement data in accordance with an embodiment of the present disclosure;

FIG. 52 depicts a flowchart detailing a number of exemplary steps which may be used to display a desired continuous quality improvement report on a user interface in accordance with an embodiment of the present disclosure;

FIG. 53 depicts a flowchart detailing a number of example steps which may be used to configure a Continuous Quality Improvement report in accordance with an embodiment of the present disclosure;

FIG. 54 depicts a flowchart detailing a number of example steps which may be used to configure a Continuous Quality Improvement report in accordance with an embodiment of the present disclosure;

FIG. 55 depicts a flowchart detailing a number of example steps which may be used to apply a filter to Continuous Quality Improvement data using organization/institutional hierarchy in accordance with an embodiment of the present disclosure;

FIG. 56 depicts a flowchart detailing a number of example steps which may be used to apply a filter to Continuous Quality Improvement data using a date range or time frame in accordance with an embodiment of the present disclosure;

FIG. 57 depicts a flowchart detailing a number of example steps which may be used to apply a filter to Continuous Quality Improvement data based on user defined, custom filtering criteria in accordance with an embodiment of the present disclosure;

FIG. 58 depicts a flowchart detailing a number of example steps which may be used to modify the appearance of Continuous Quality Improvement data such as a Continuous Quality Improvement report on a user interface in accordance with an embodiment of the present disclosure;

FIG. 59 depicts a flowchart detailing a number of example steps which may be used to modify the time units in a Continuous Quality Improvement report based on a user input in accordance with an embodiment of the present invention.

Figure 60:
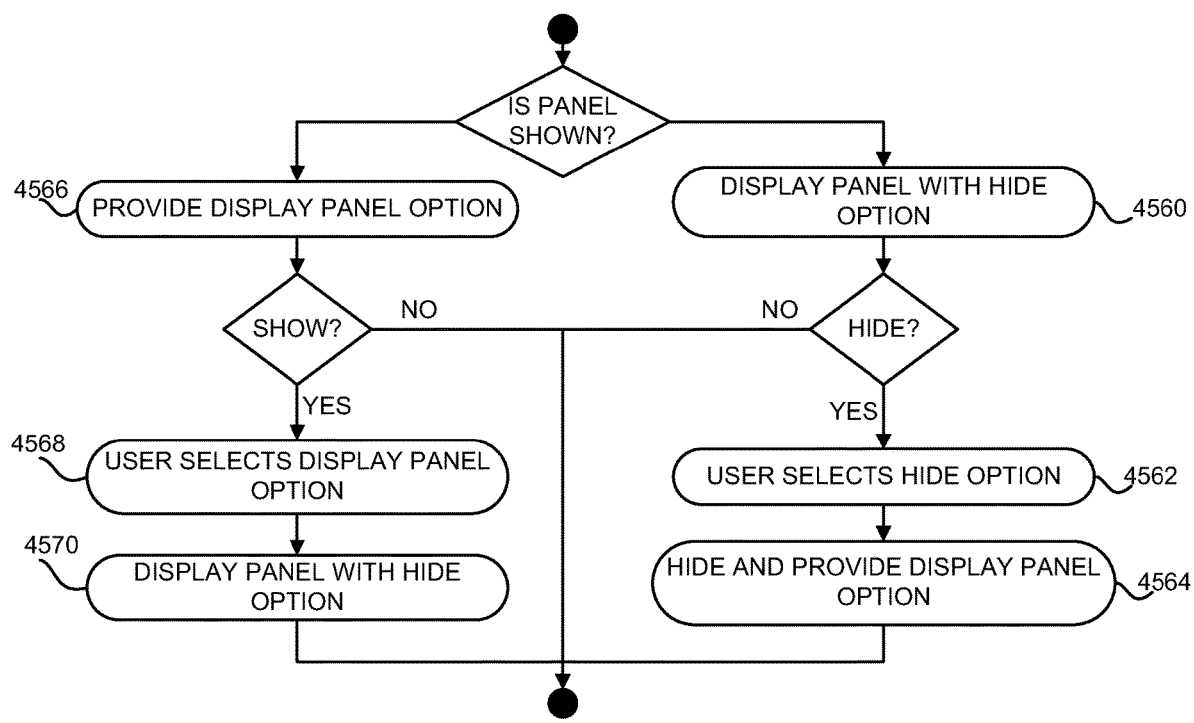

FIG. 60 depicts a flowchart detailing a number of example steps which may be used to hide a shown panel or show a hidden panel in a Continuous Quality Improvement report in accordance with an embodiment of the present invention.

Figure 61:
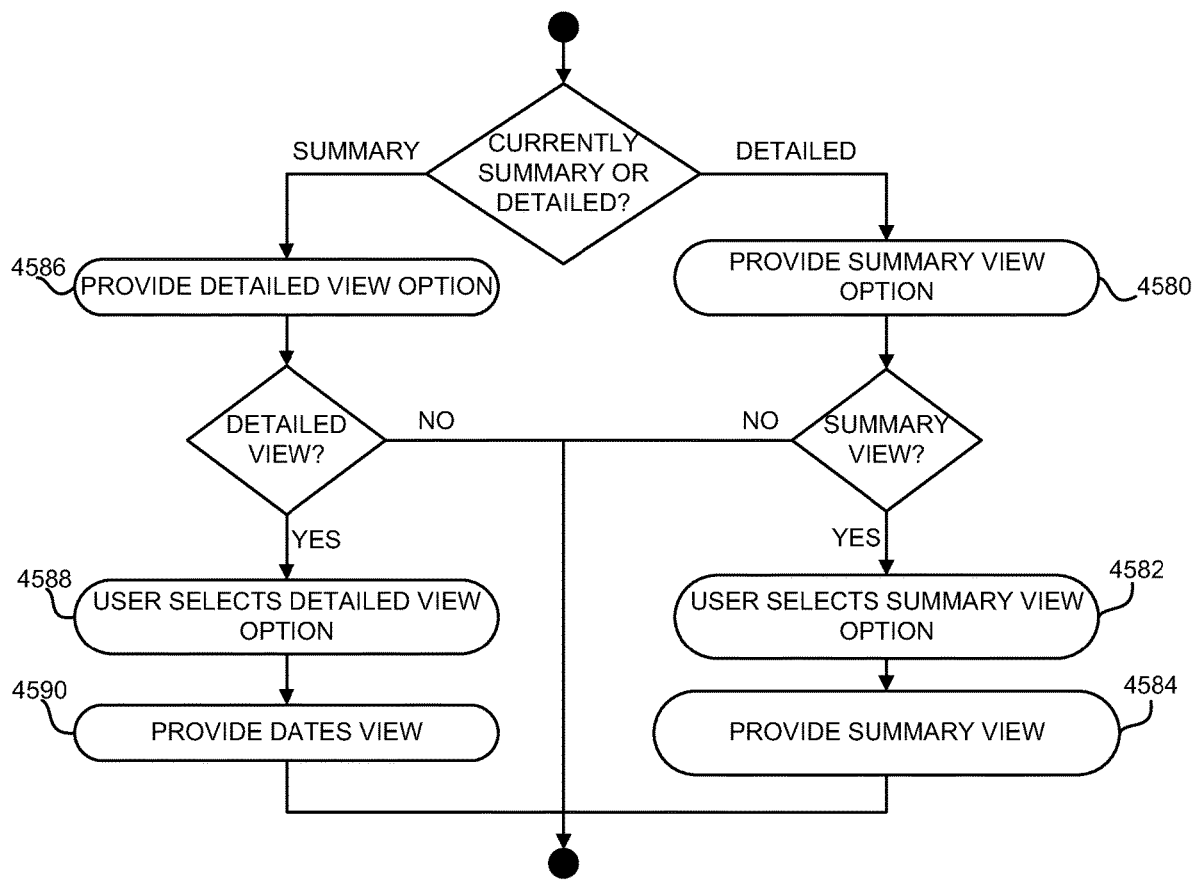

FIG. 61 depicts a flowchart detailing a number of example steps which may be used to toggle between a summary view and a detailed view in a Continuous Quality Improvement report in accordance with an embodiment of the present invention.

Figure 62:
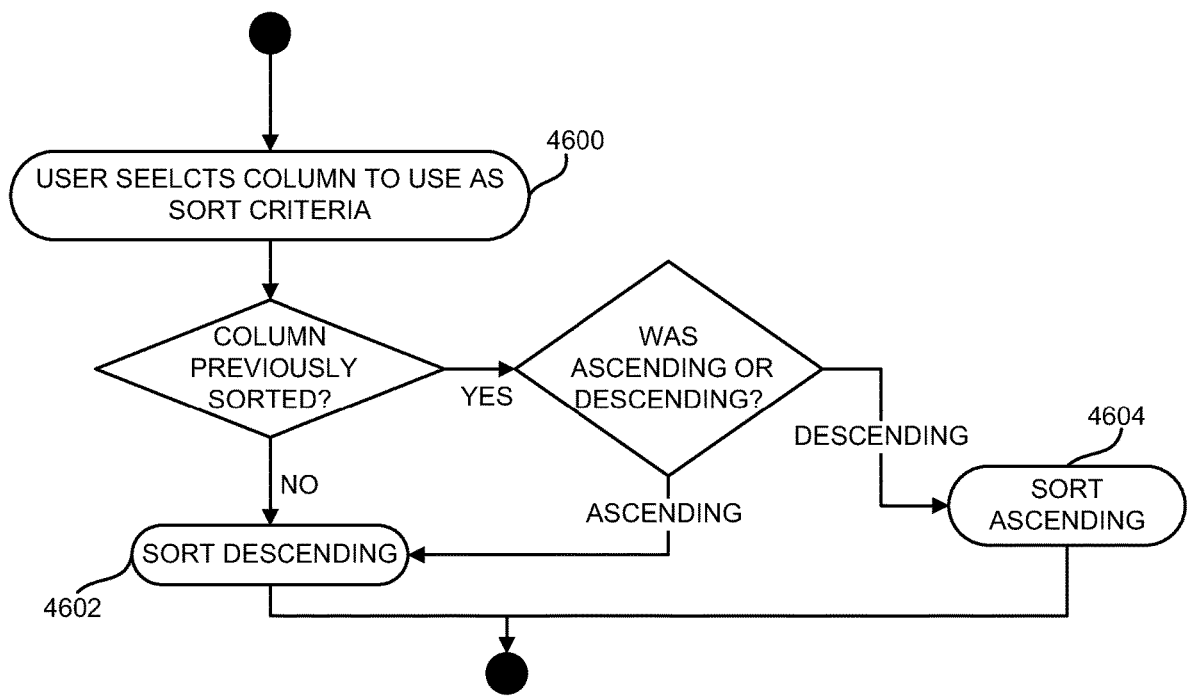

FIG. 62 depicts a flowchart detailing a number of example steps which may be used to sort CQI data in a CQI report in accordance with an embodiment of the present invention.

Figure 63:
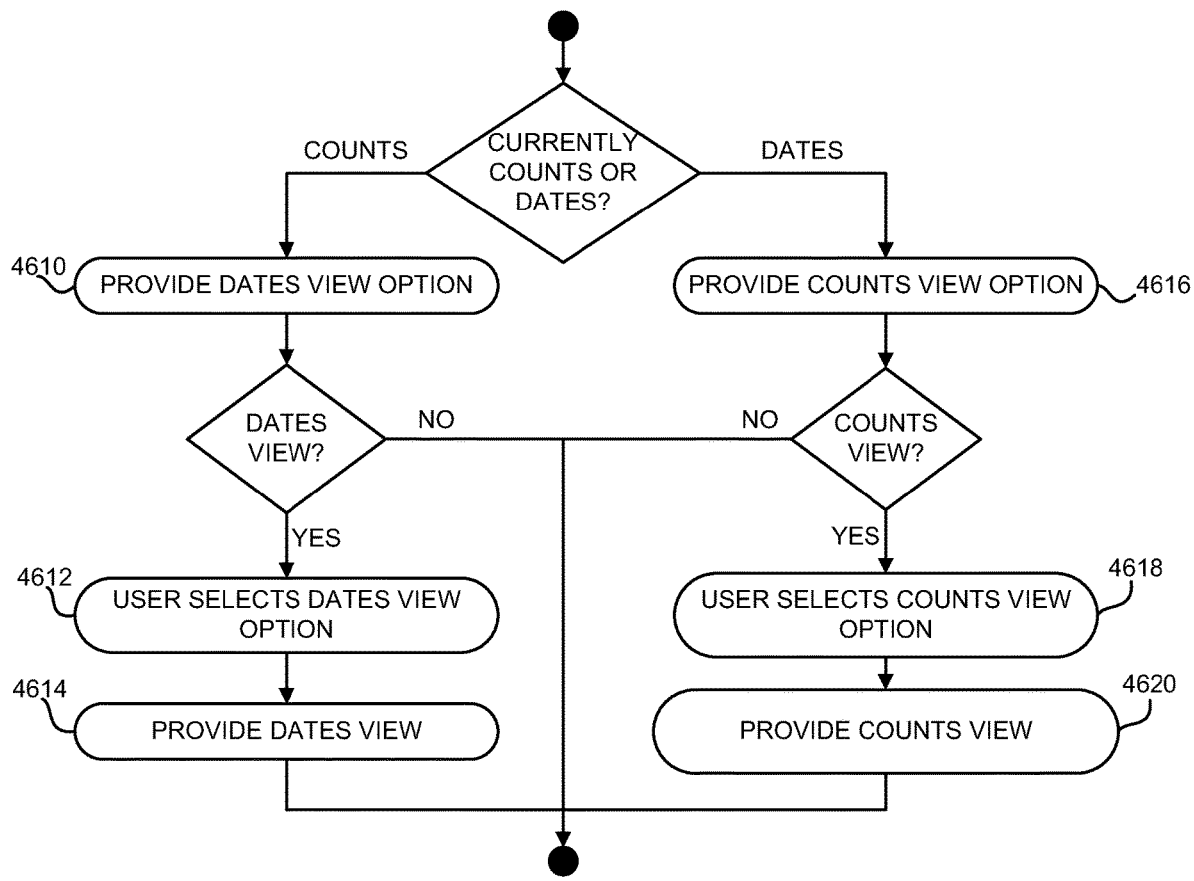

FIG. 63 depicts a flowchart detailing a number of example steps which may be used to toggle between a counts view and a dates view in a CQI report in accordance with an embodiment of the present invention.

Figure 64:
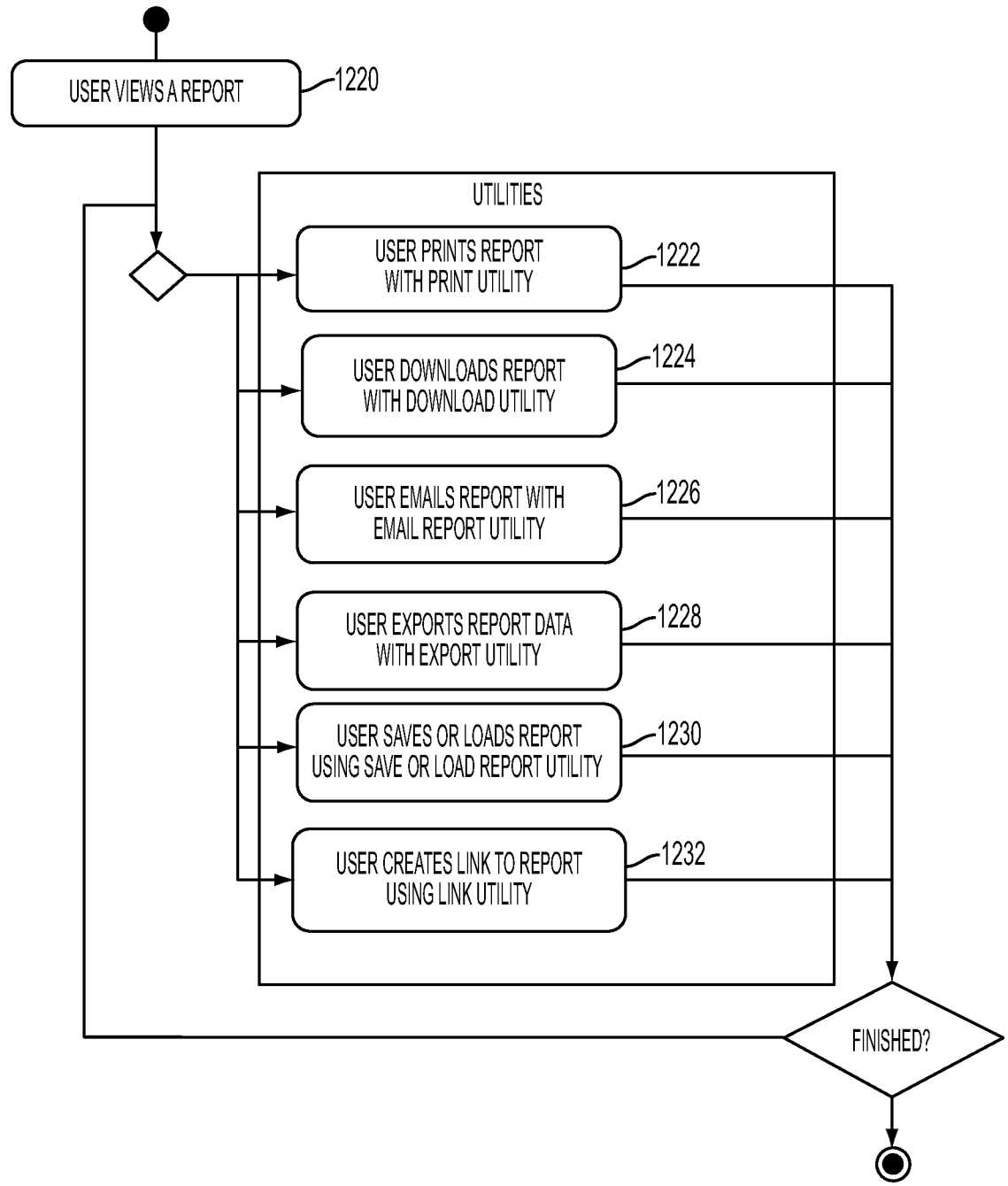
Figure 65:
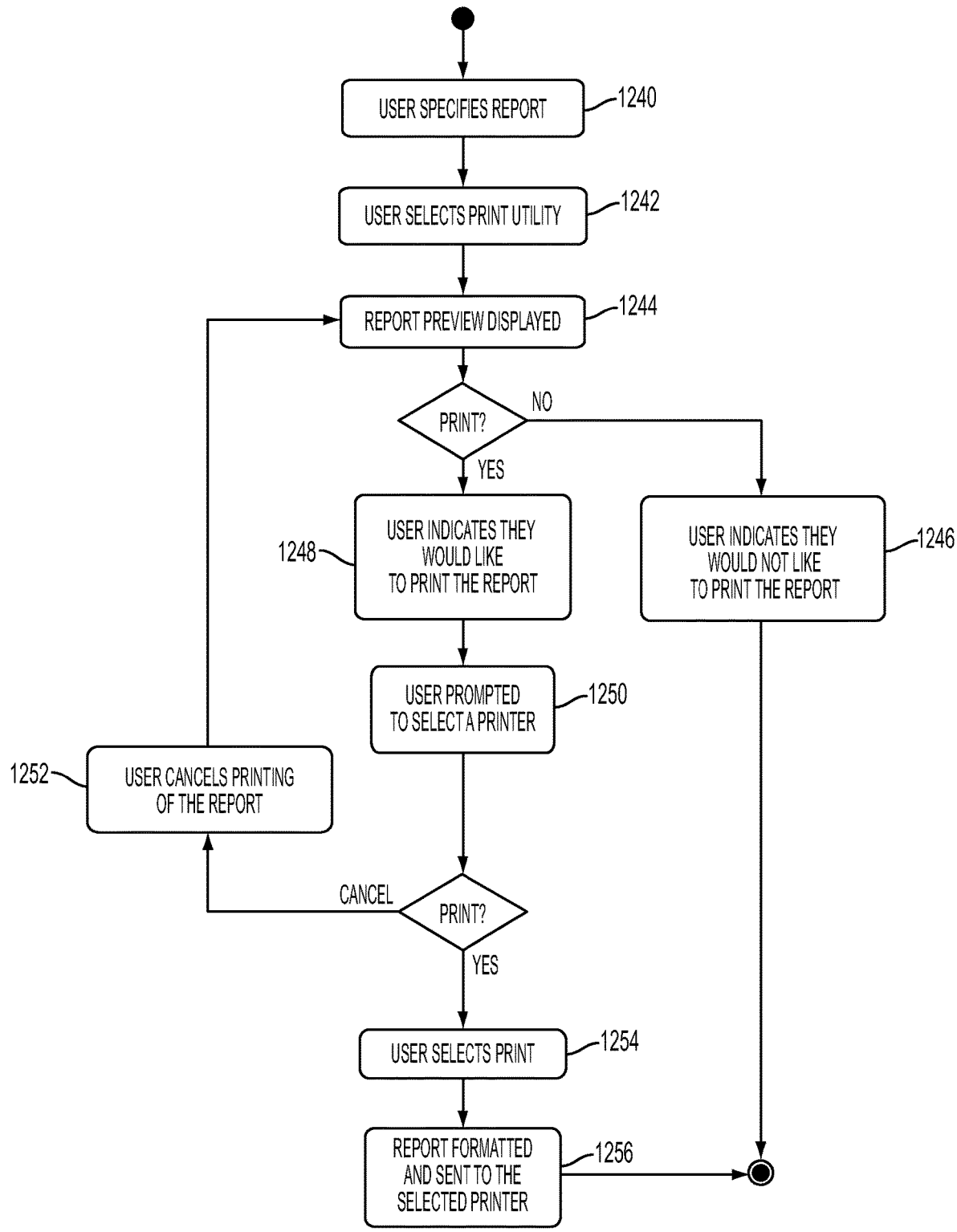
Figure 66:
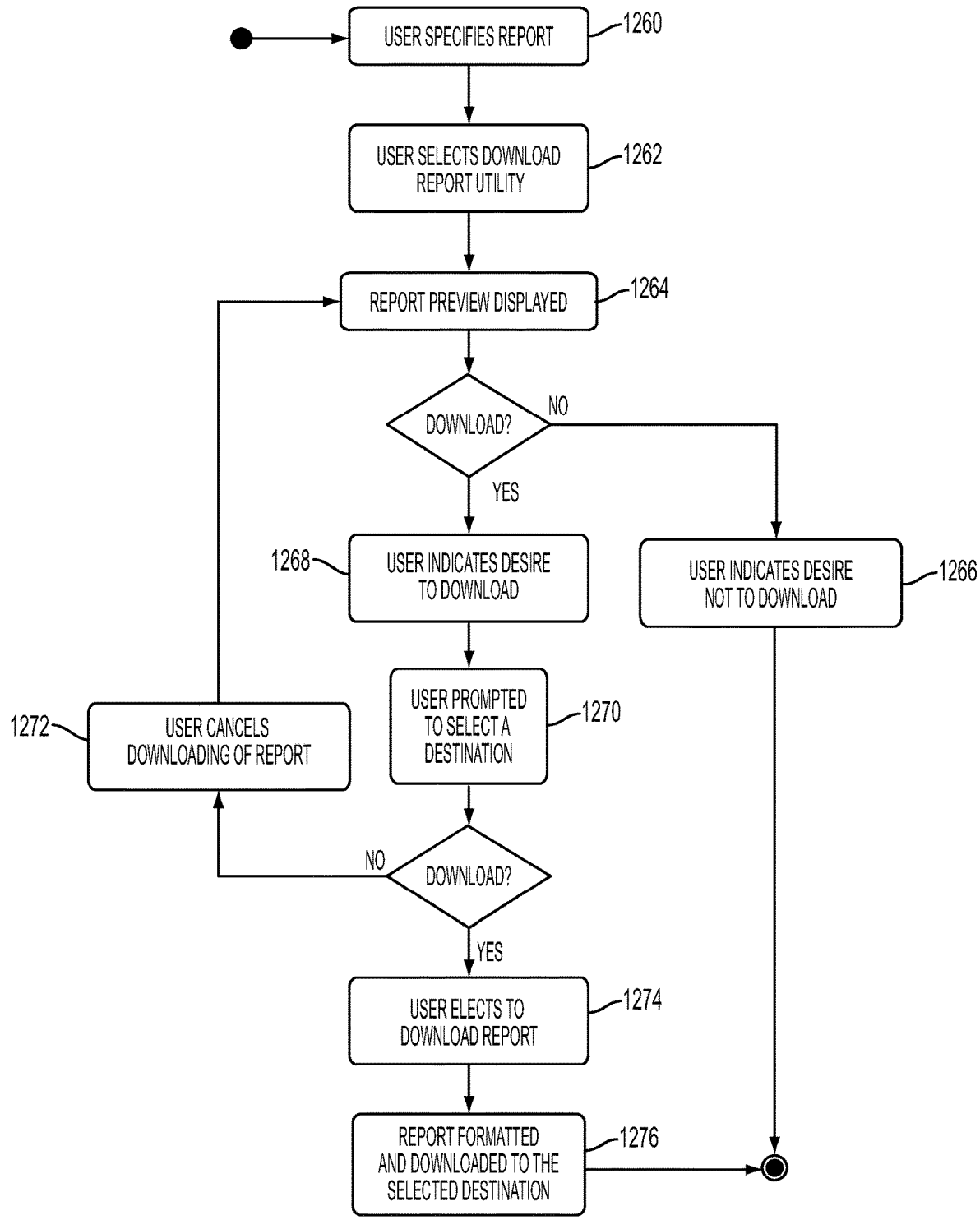
Figure 67:
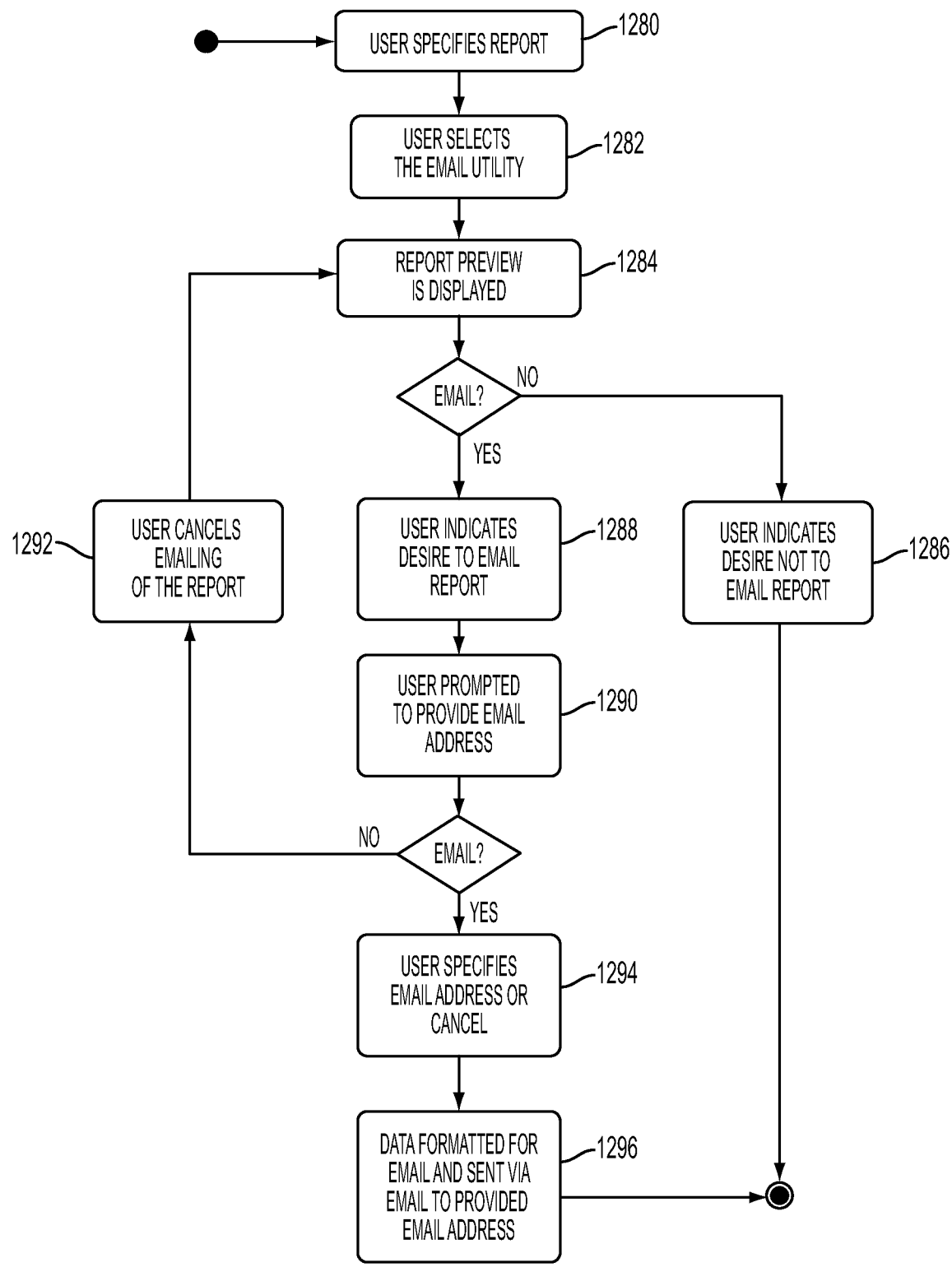
Figure 68:
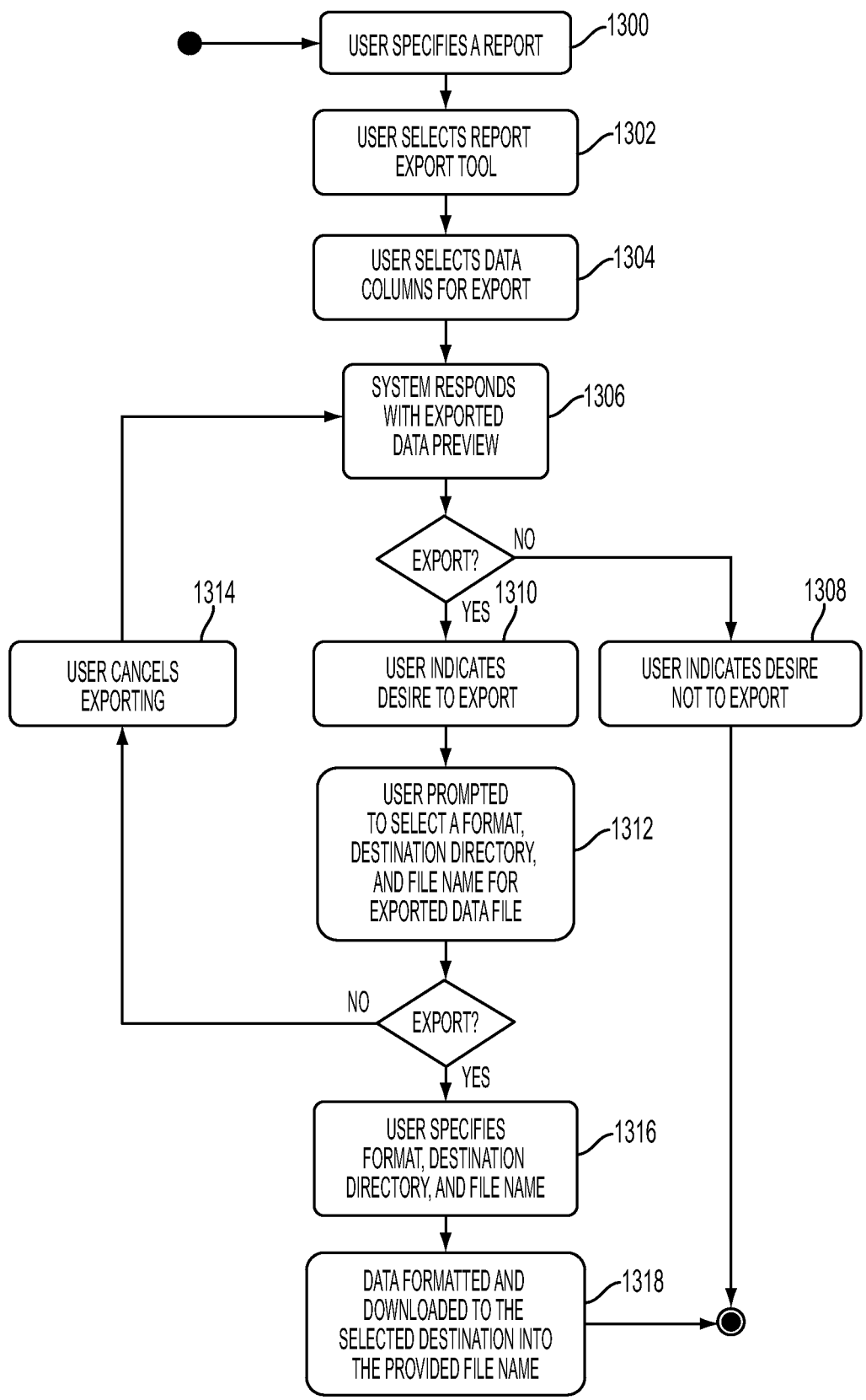
Figure 69:
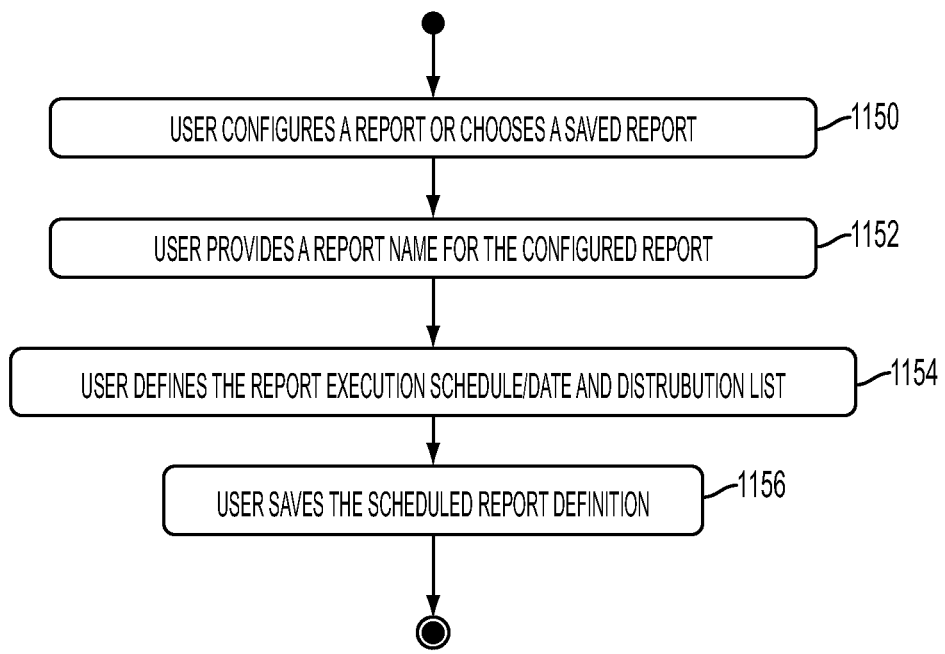
Figure 70:
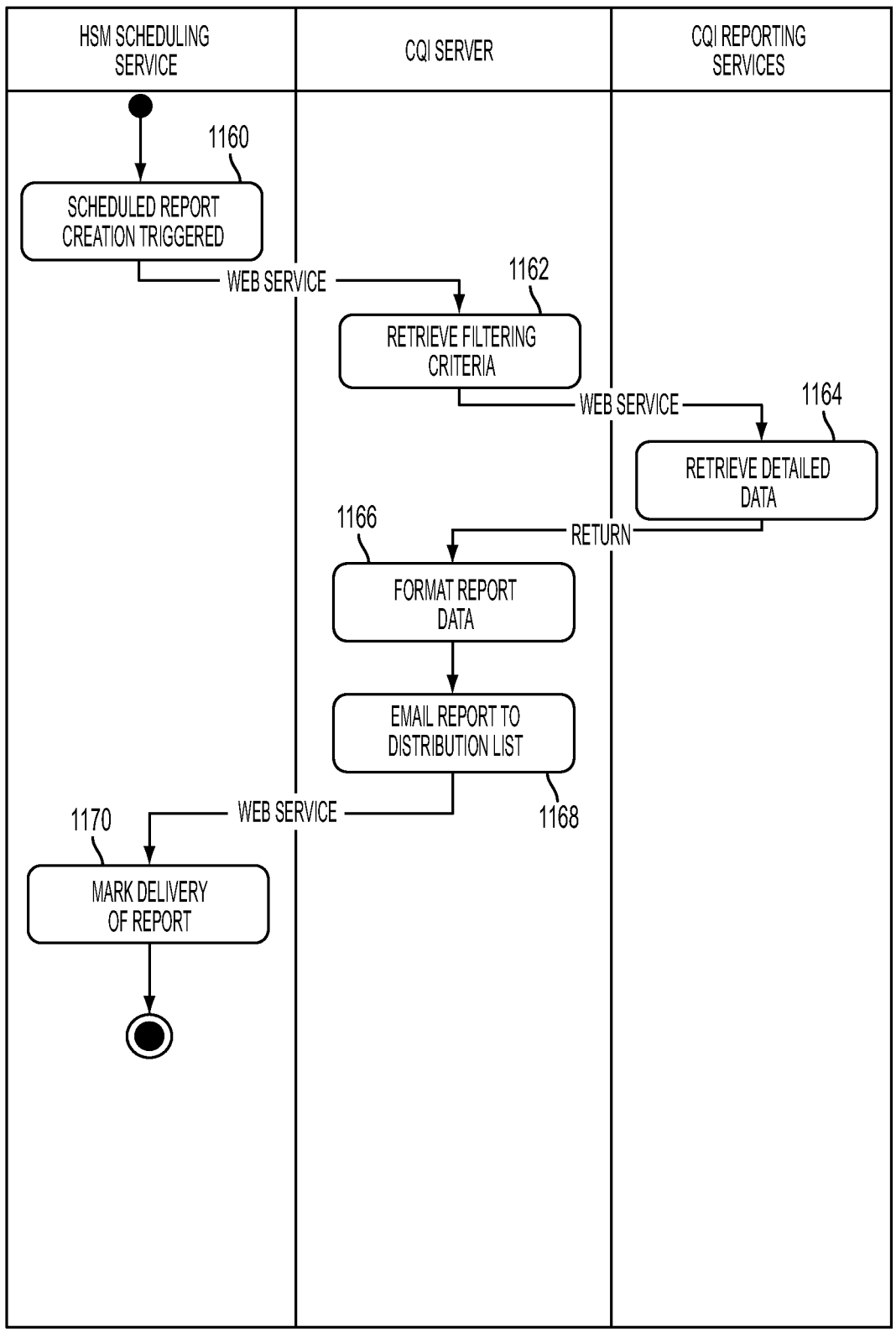
Figure 71:
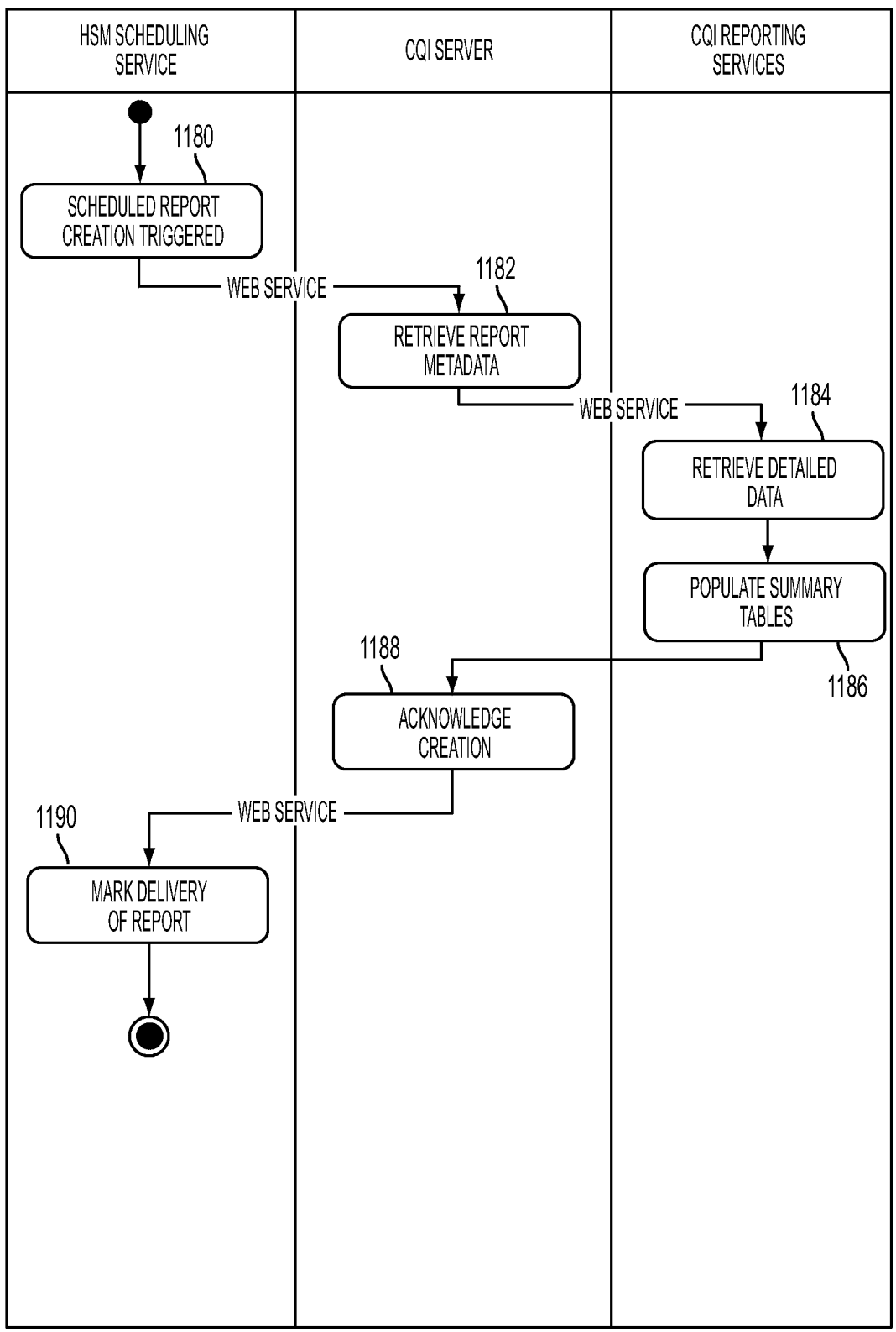
Figure 72:
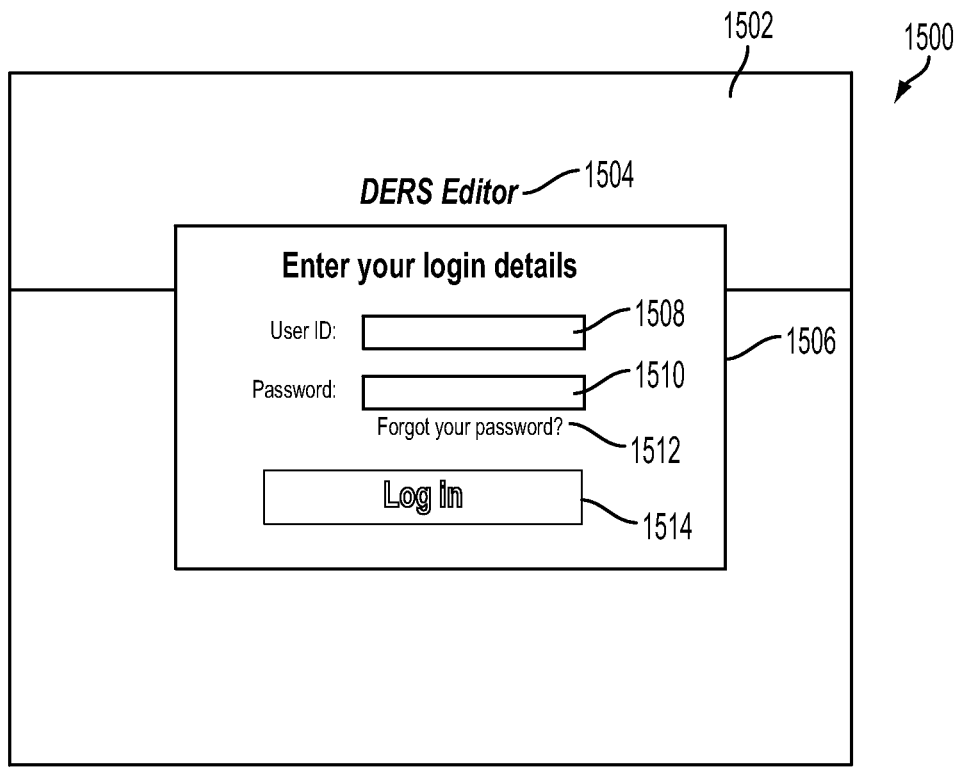
Figure 73:
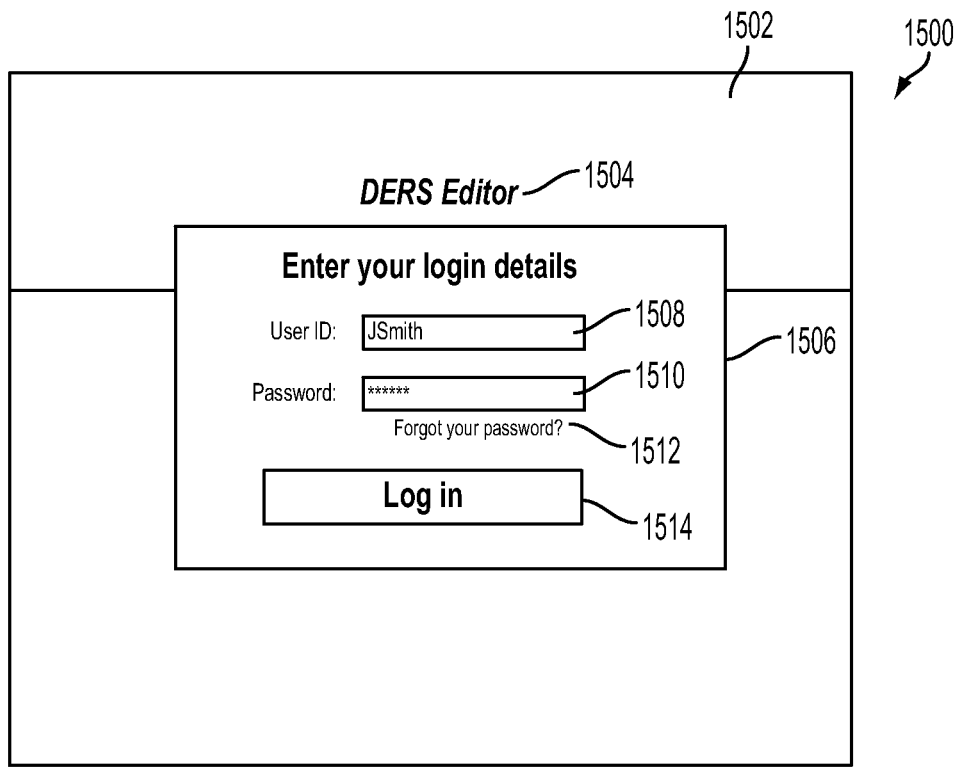
Figure 74:
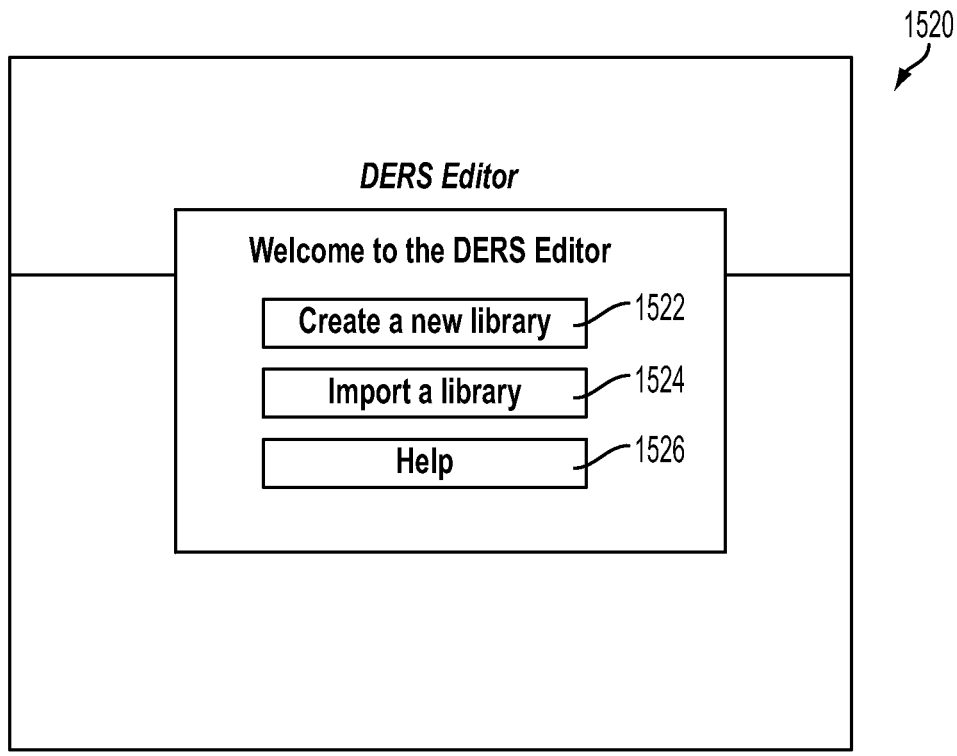
Figure 75:
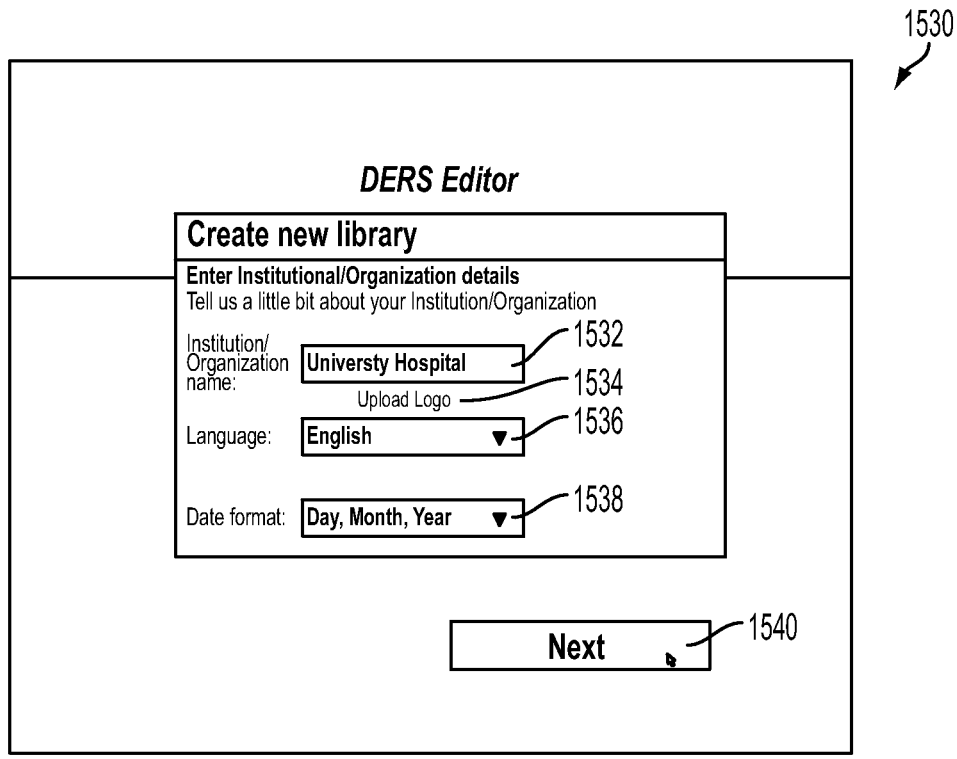
Figure 76:
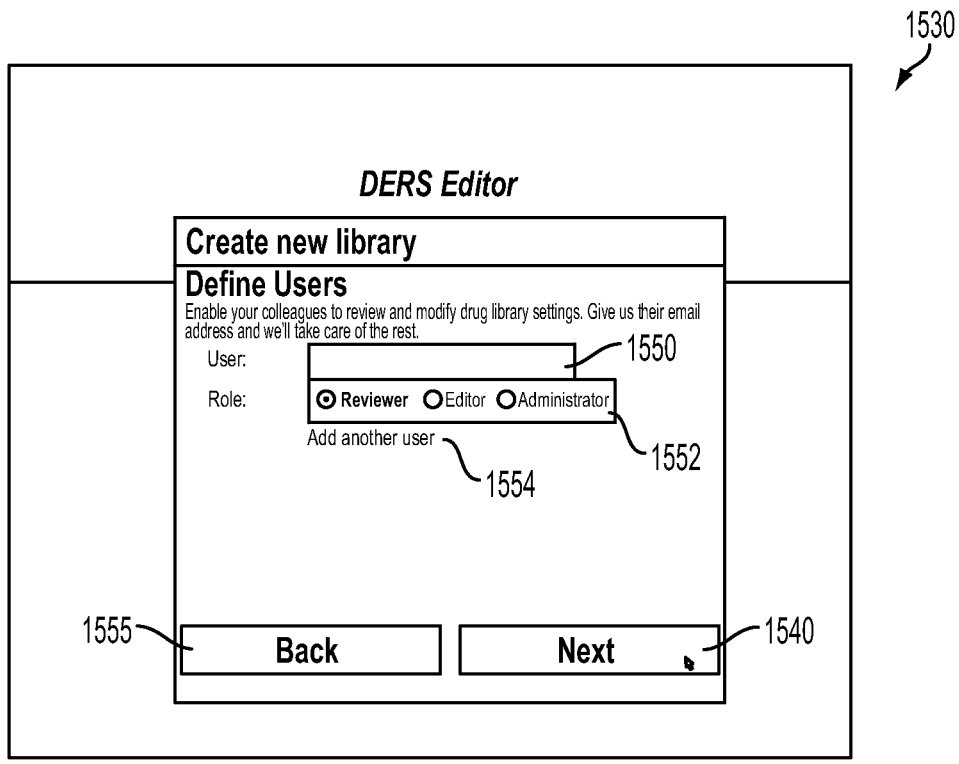
Figure 77:
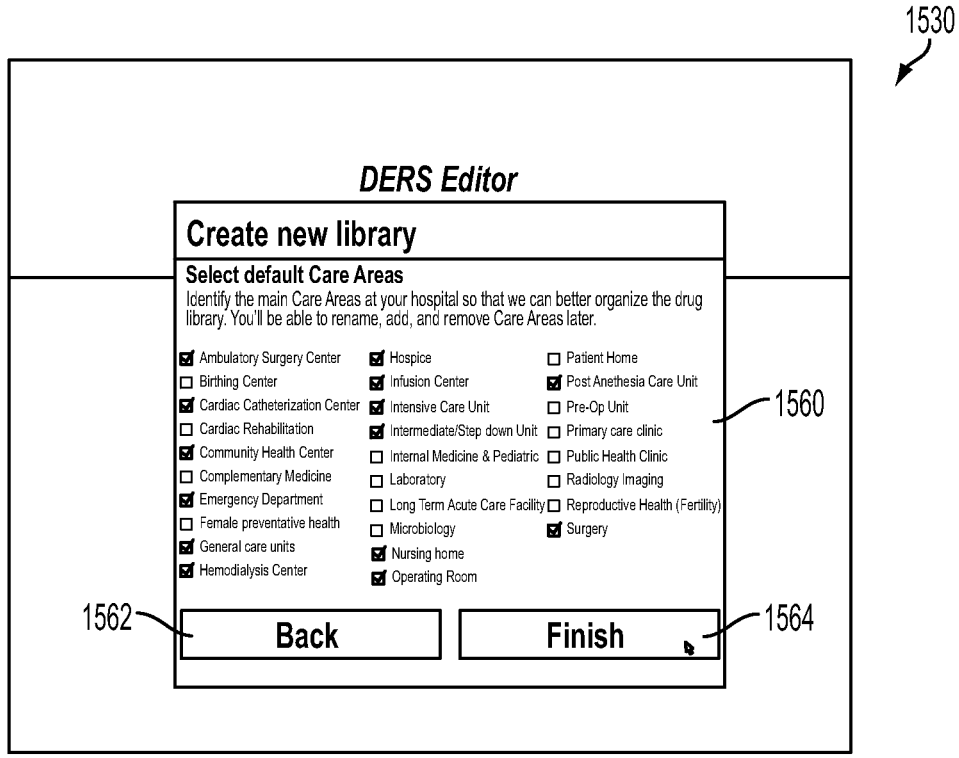
Figure 78:
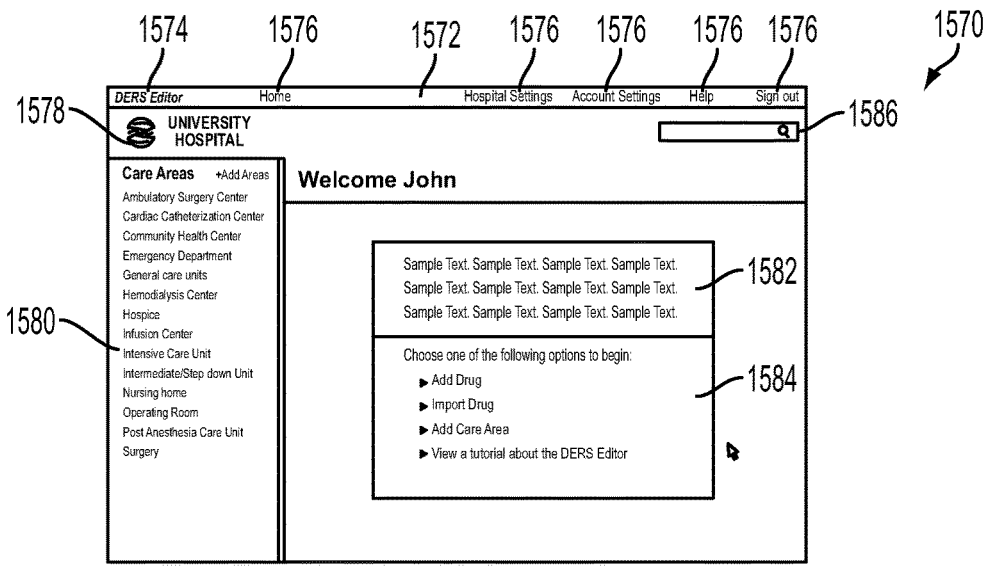
Figure 79:
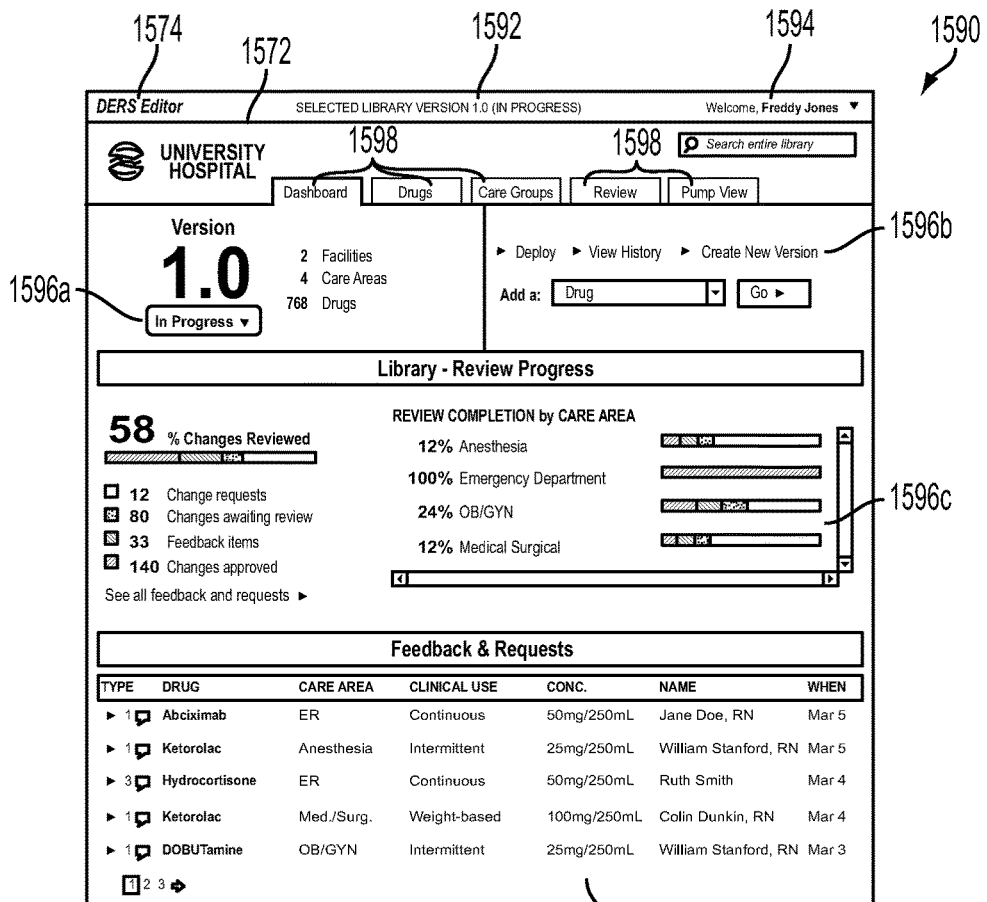
Figures 80, 81:
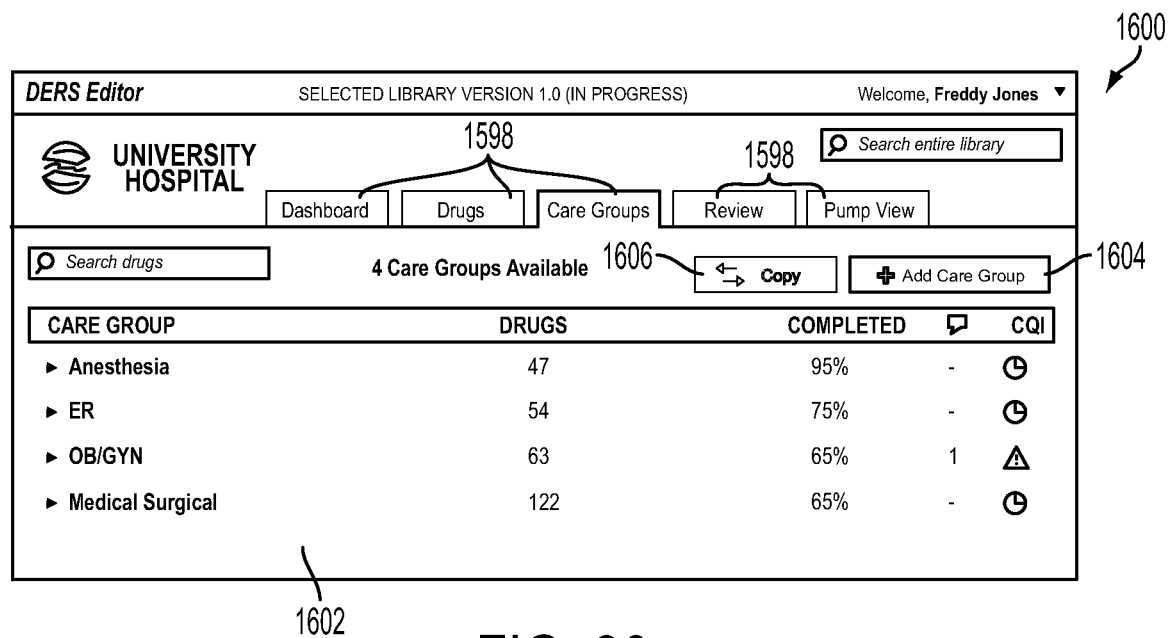
Figure 90:
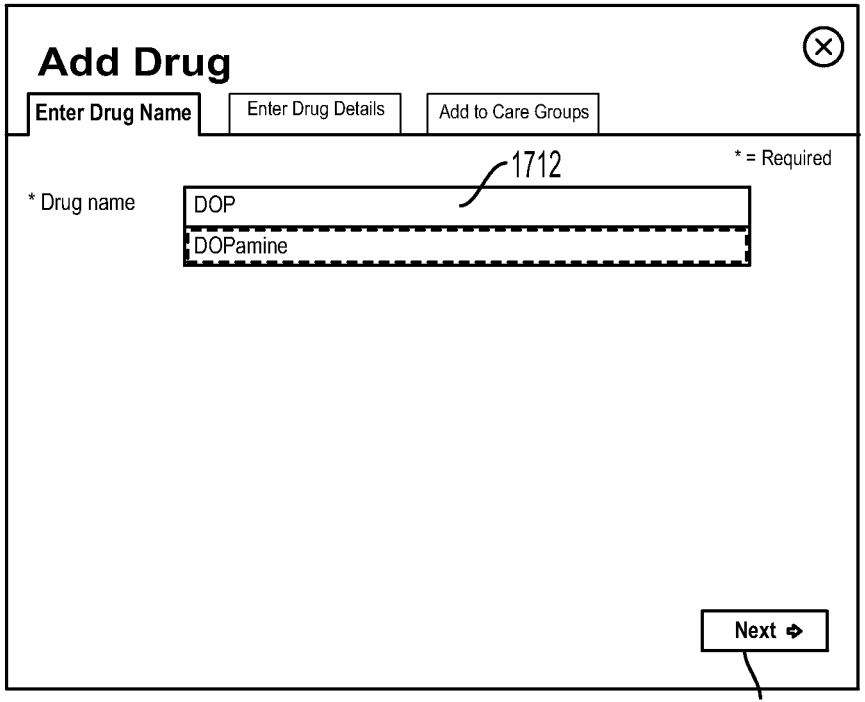
Figure 91:
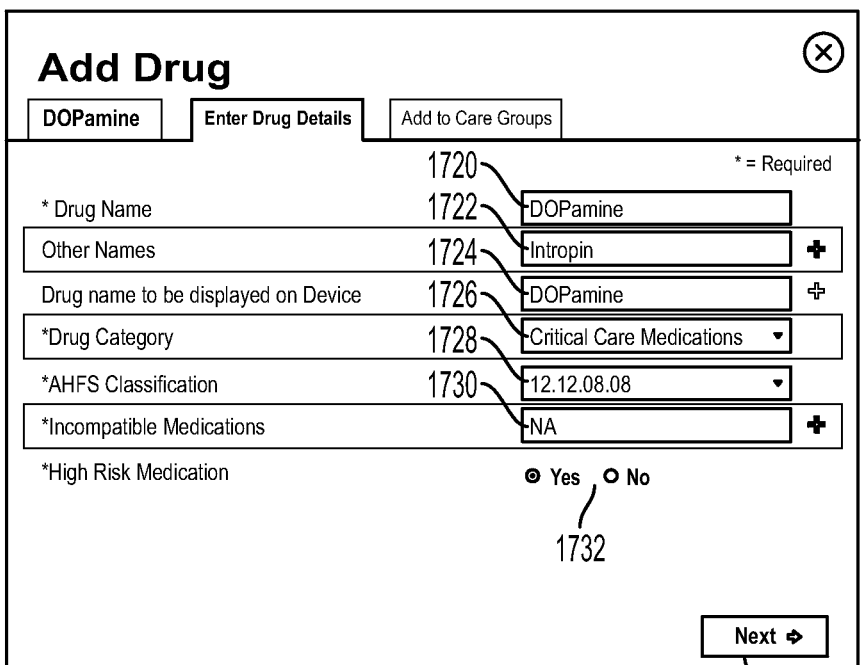
Figures 106, 107:
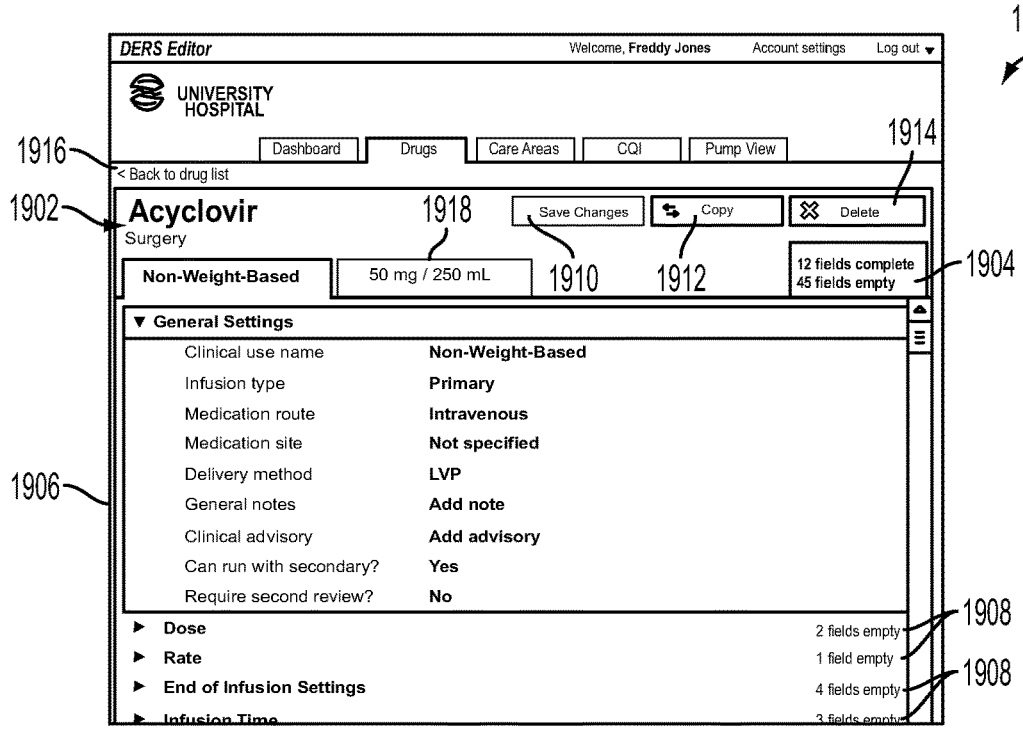
Figure 112:
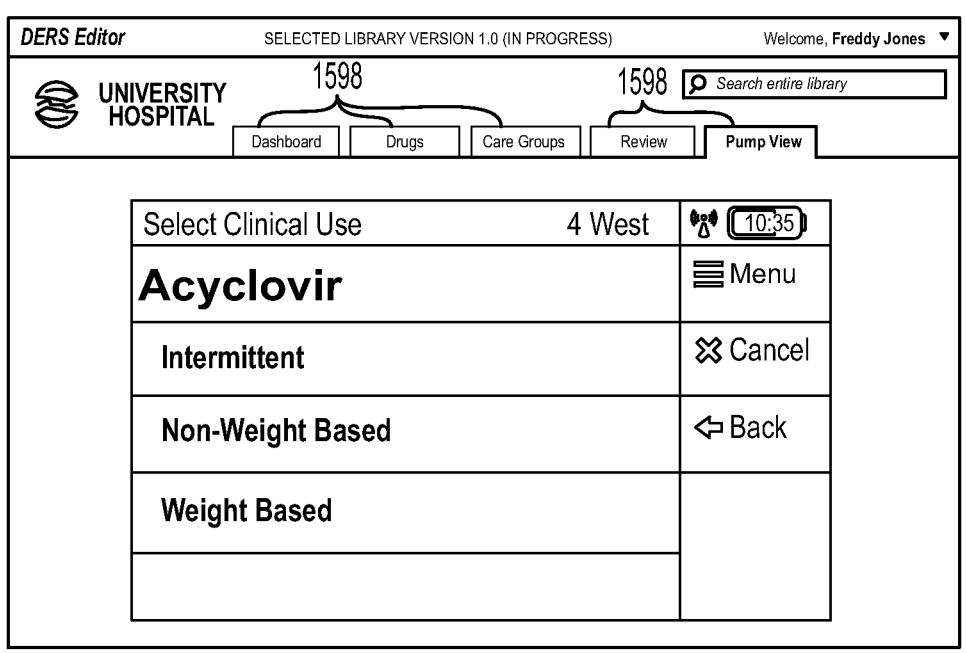
Figure 113:
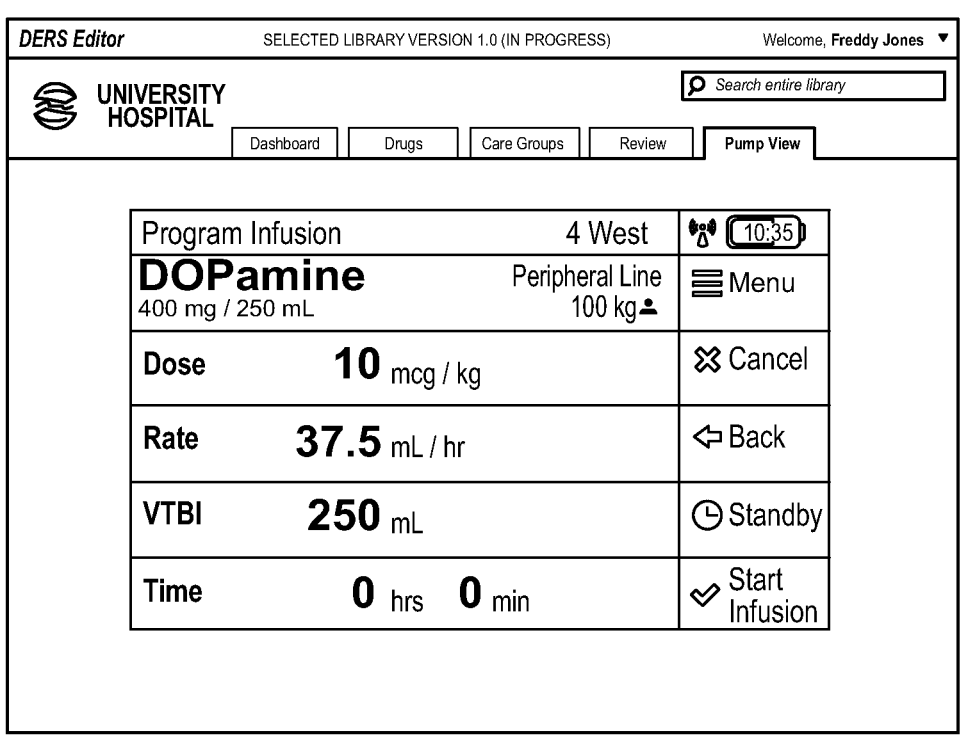
Figure 114:
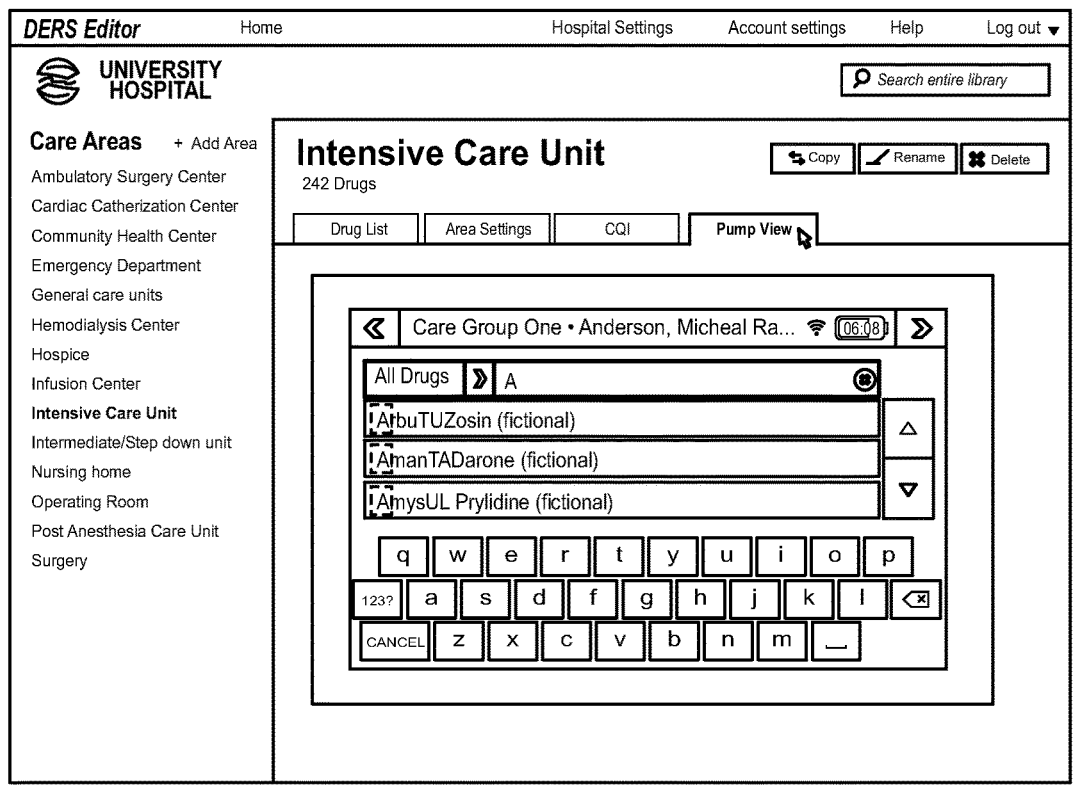
Figure 115:
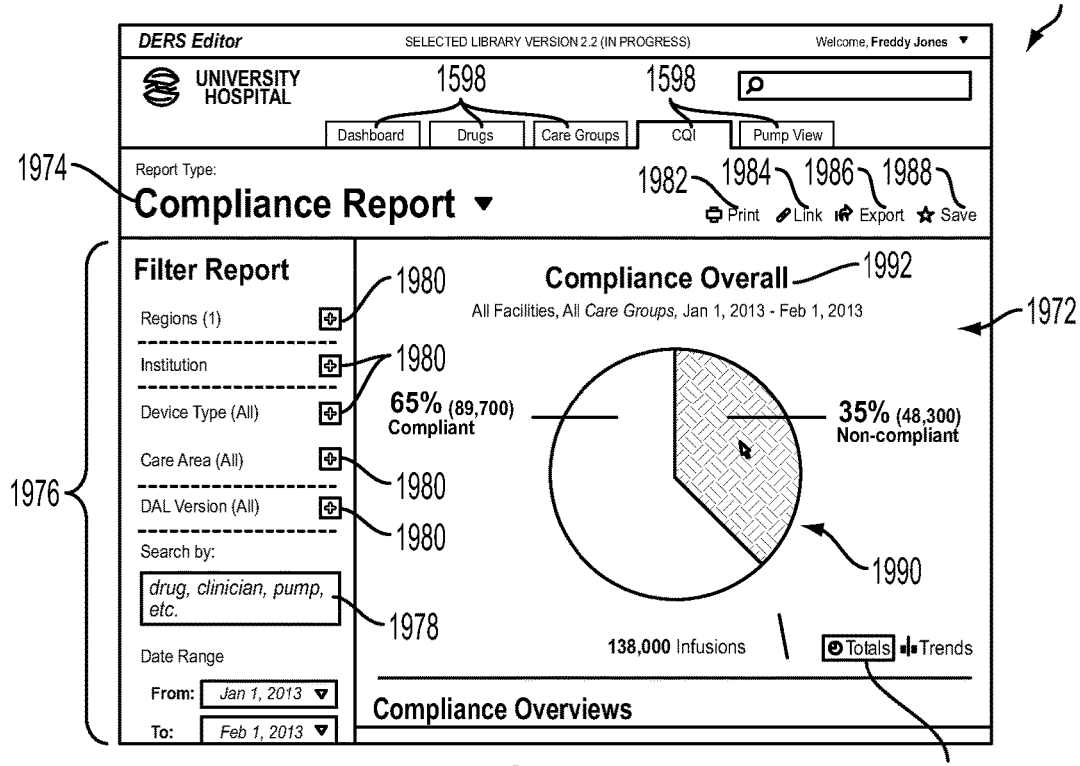
Figure 116:
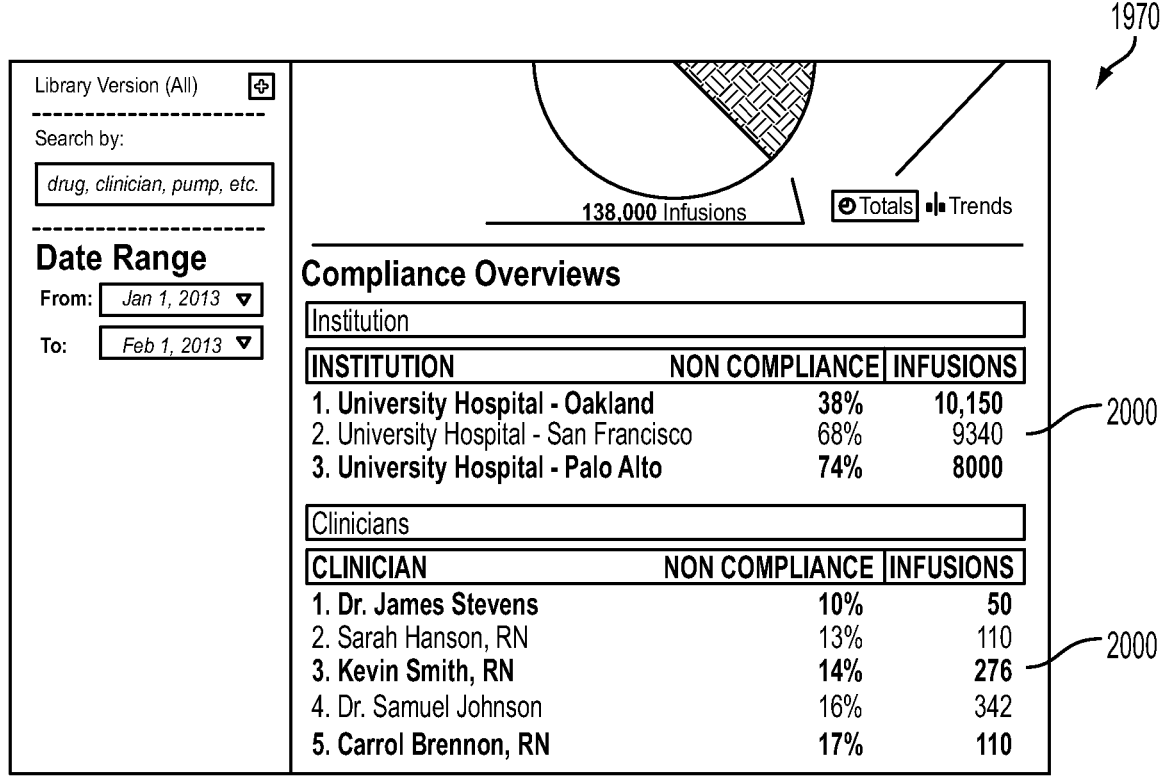
Figure 117:
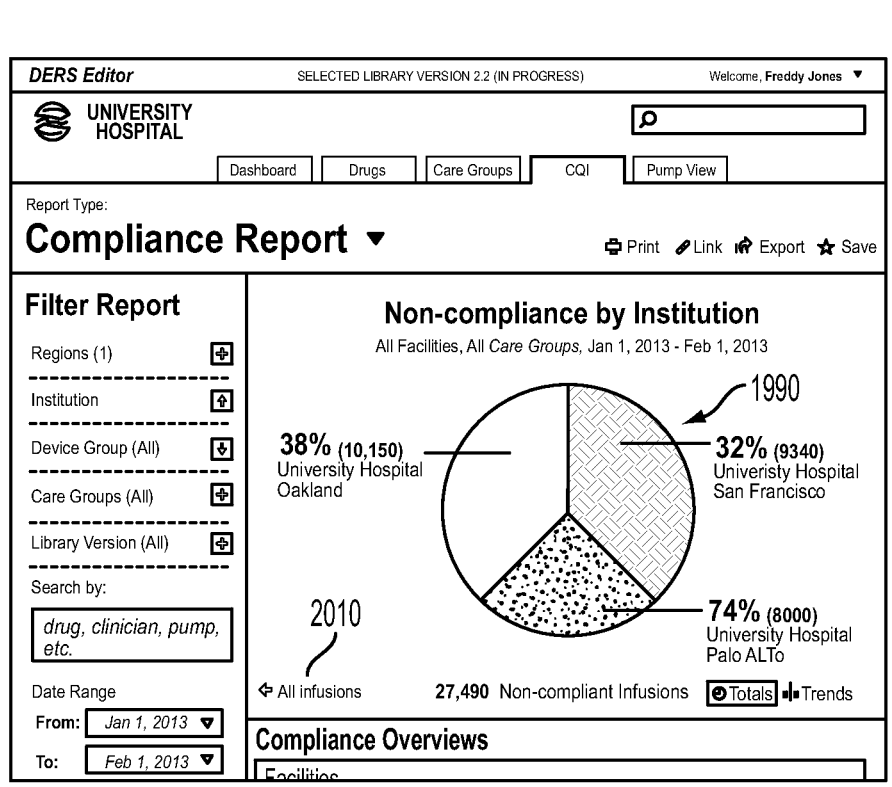
Figure 118:
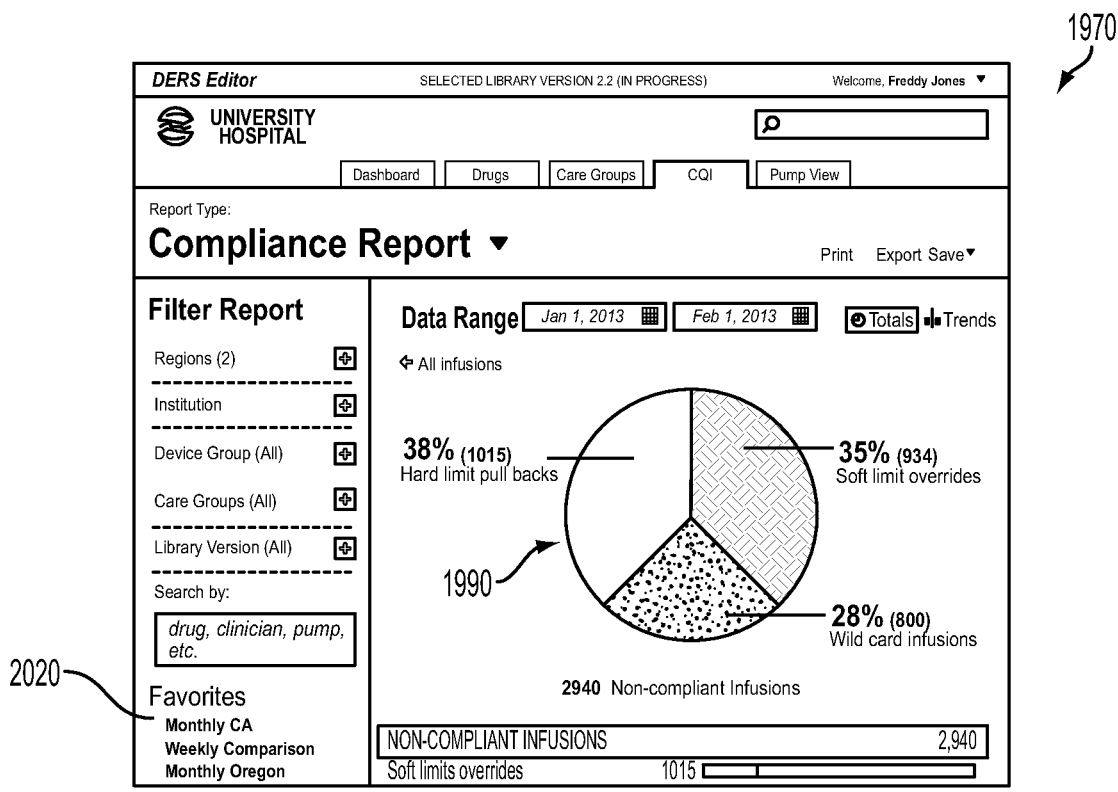
Figure 119:
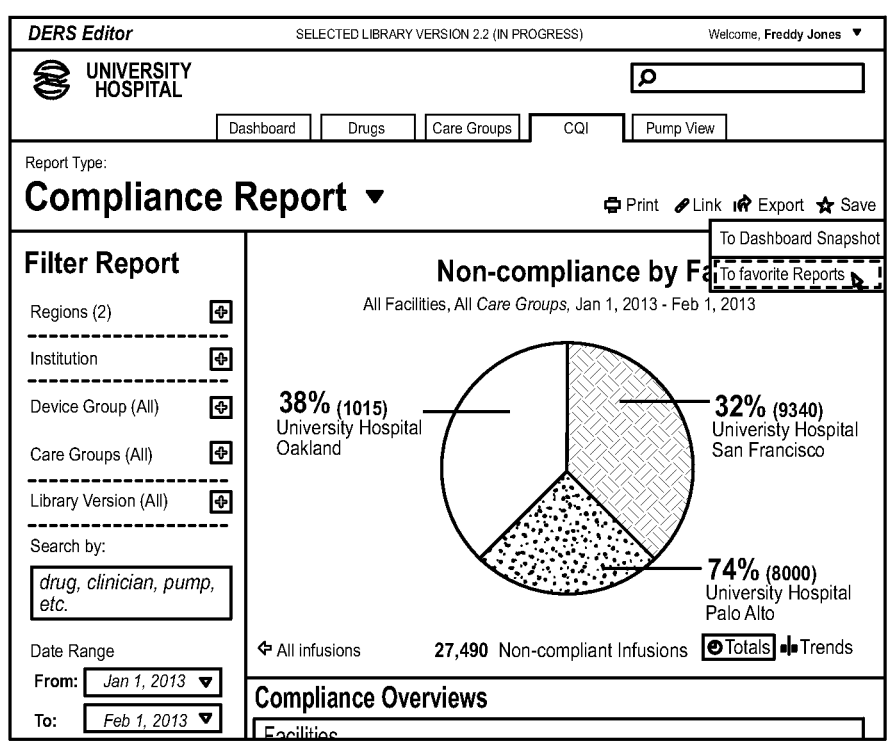
Figure 120:
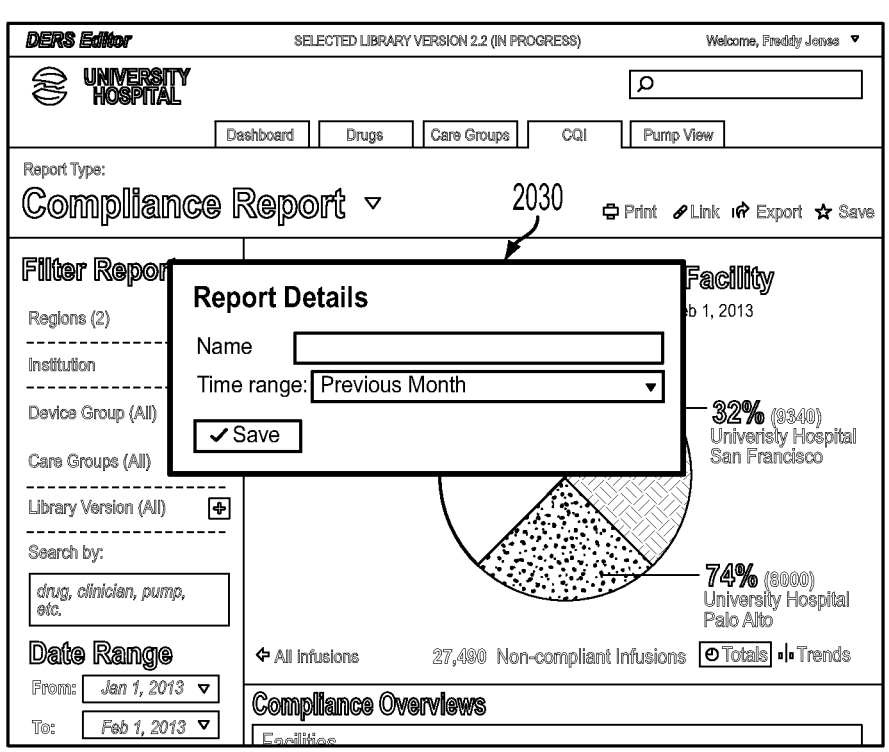
Figure 121:
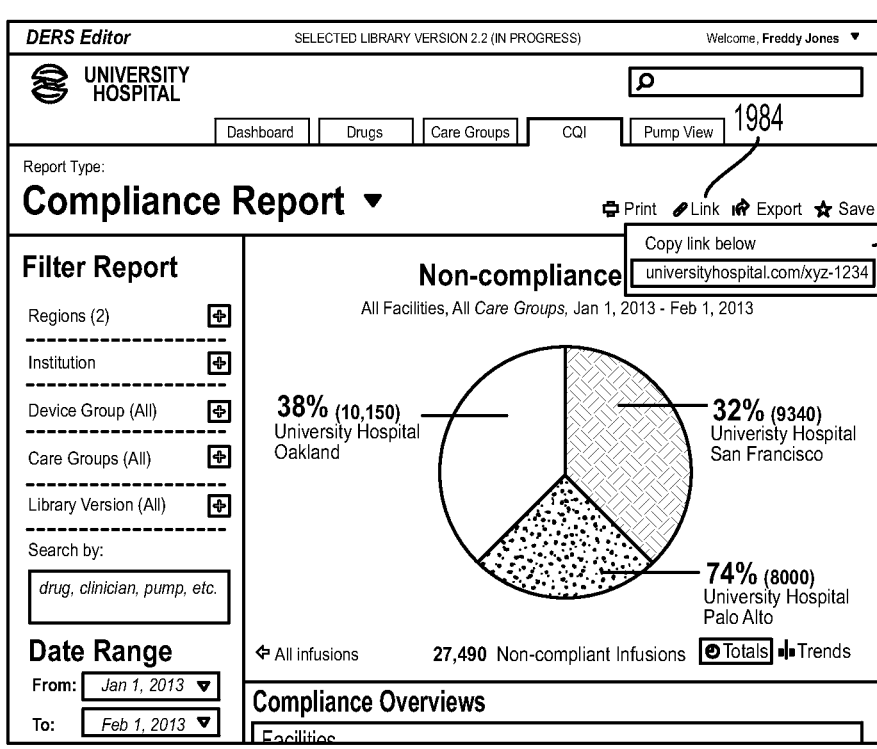
Figure 122:
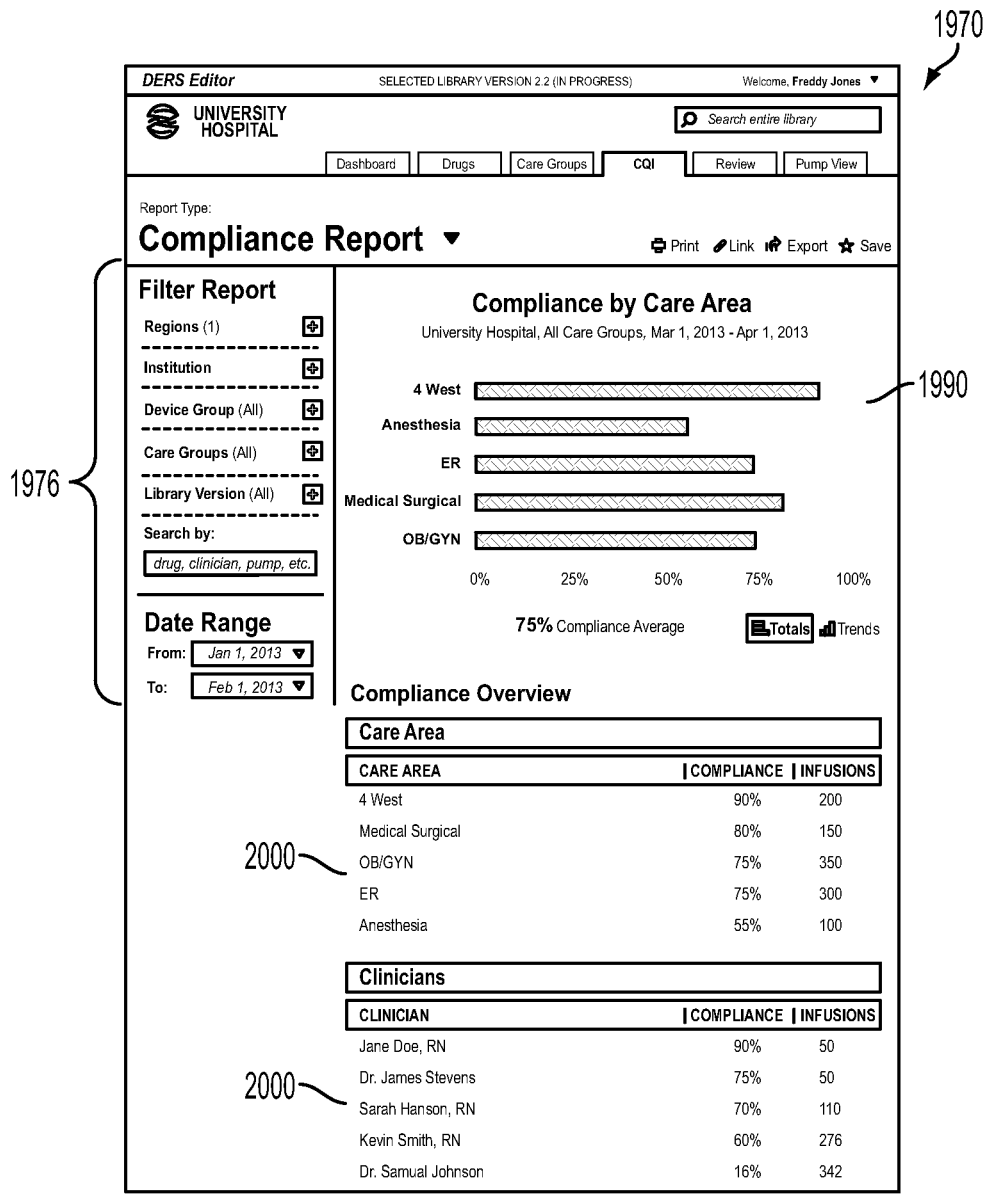
Figures 123, 124:
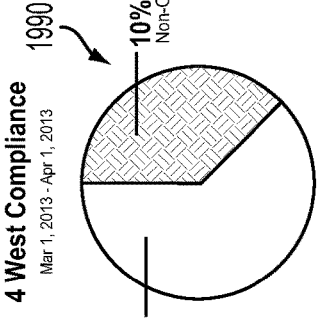
Figure 125:
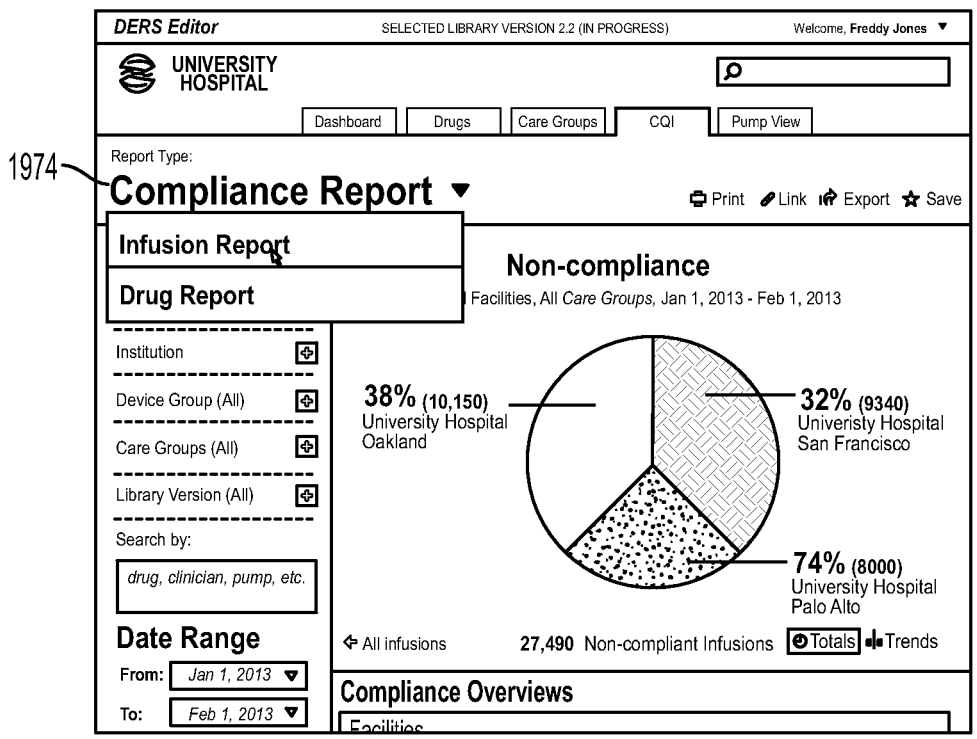
Figure 126:
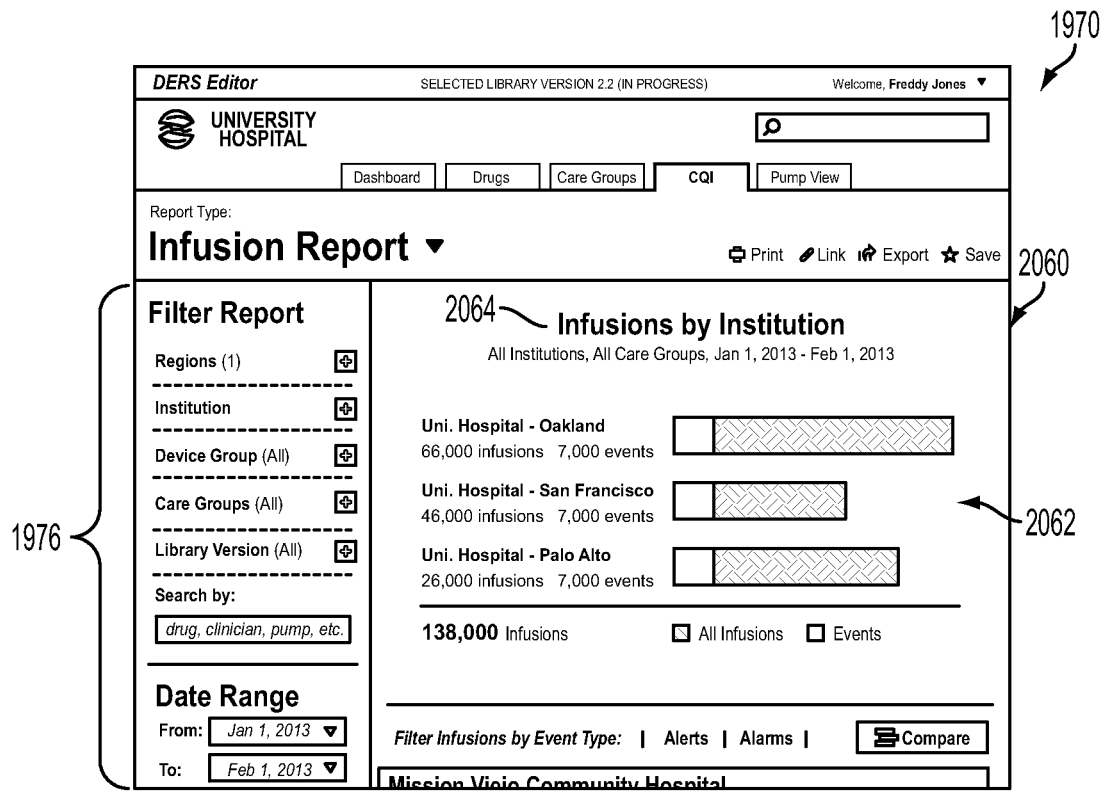
Figure 129:
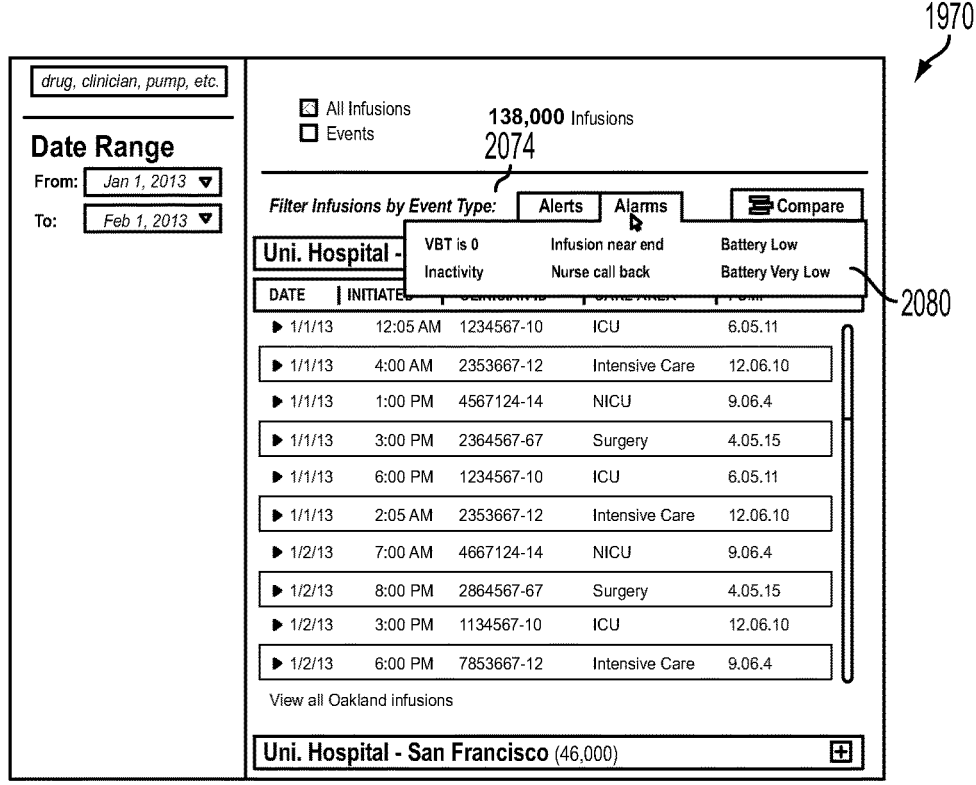
Figure 130:
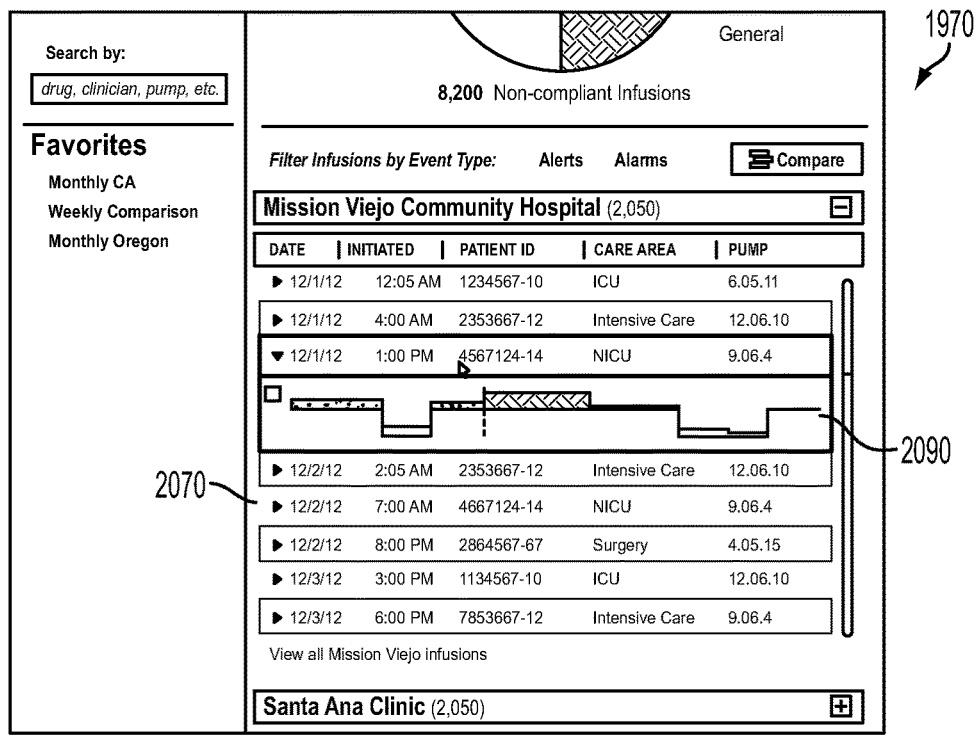
Figure 131:
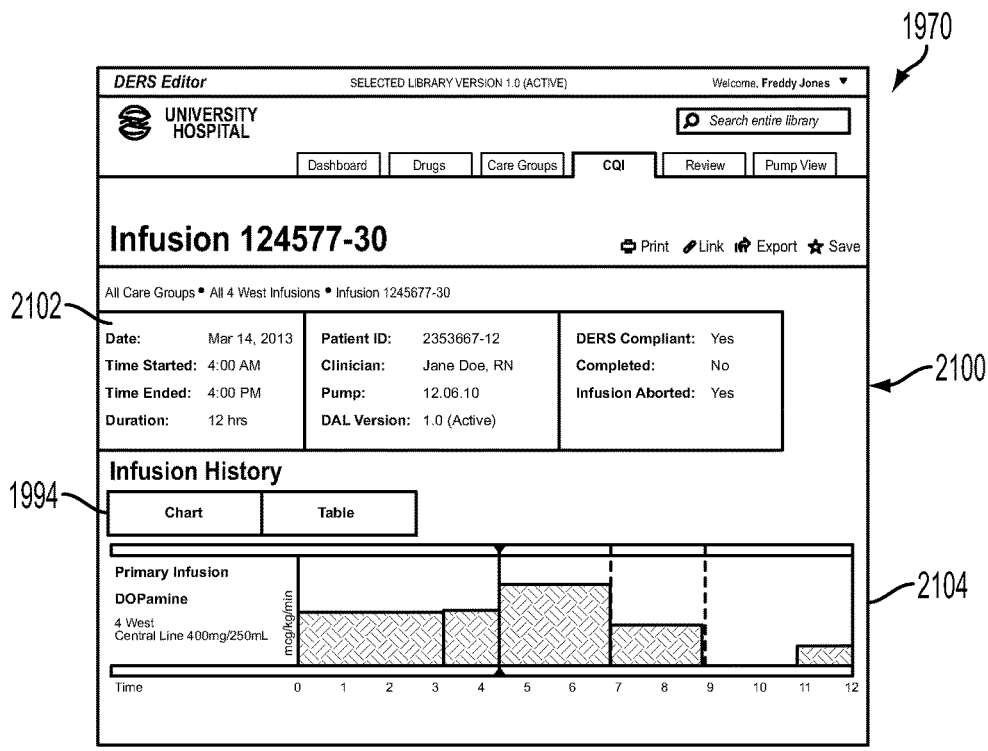
Figure 132:
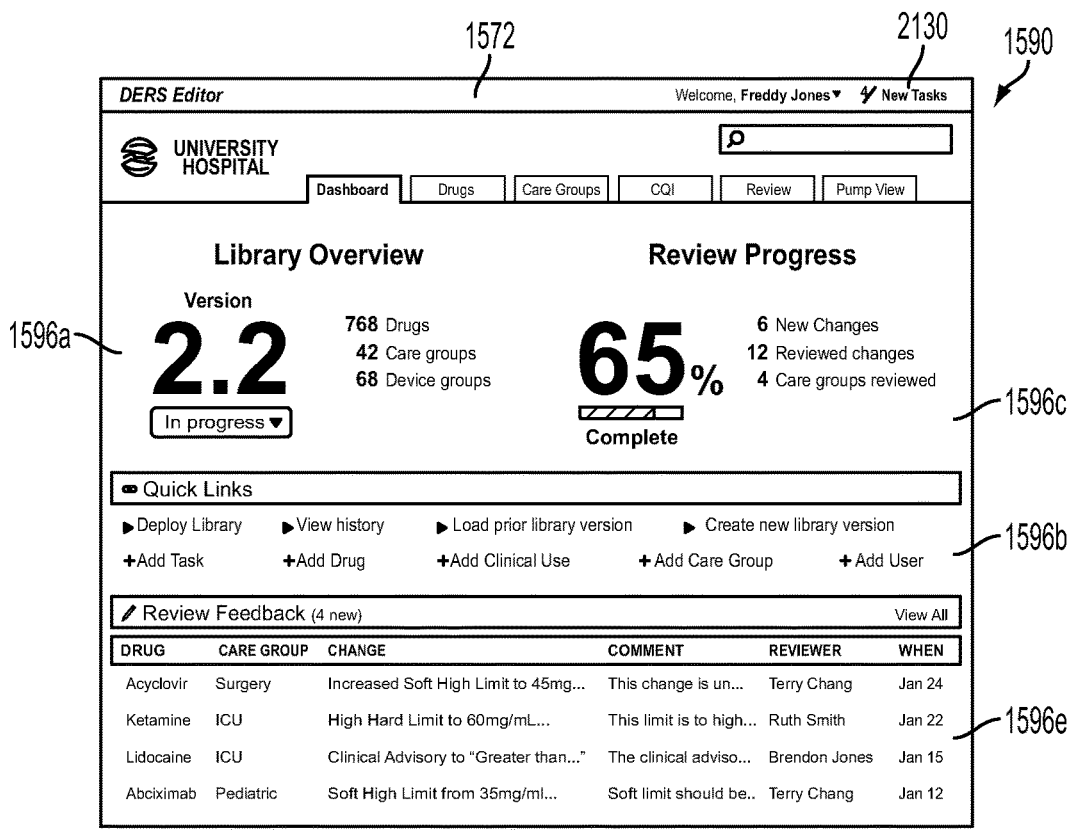
Figure 135:
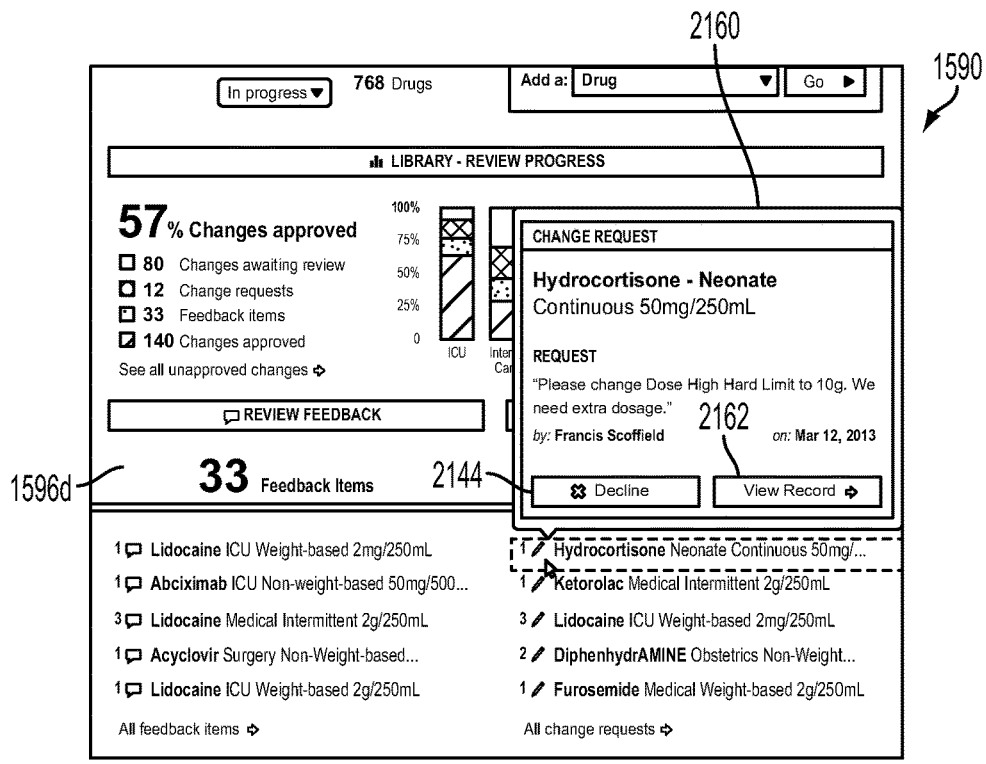
Figure 136:
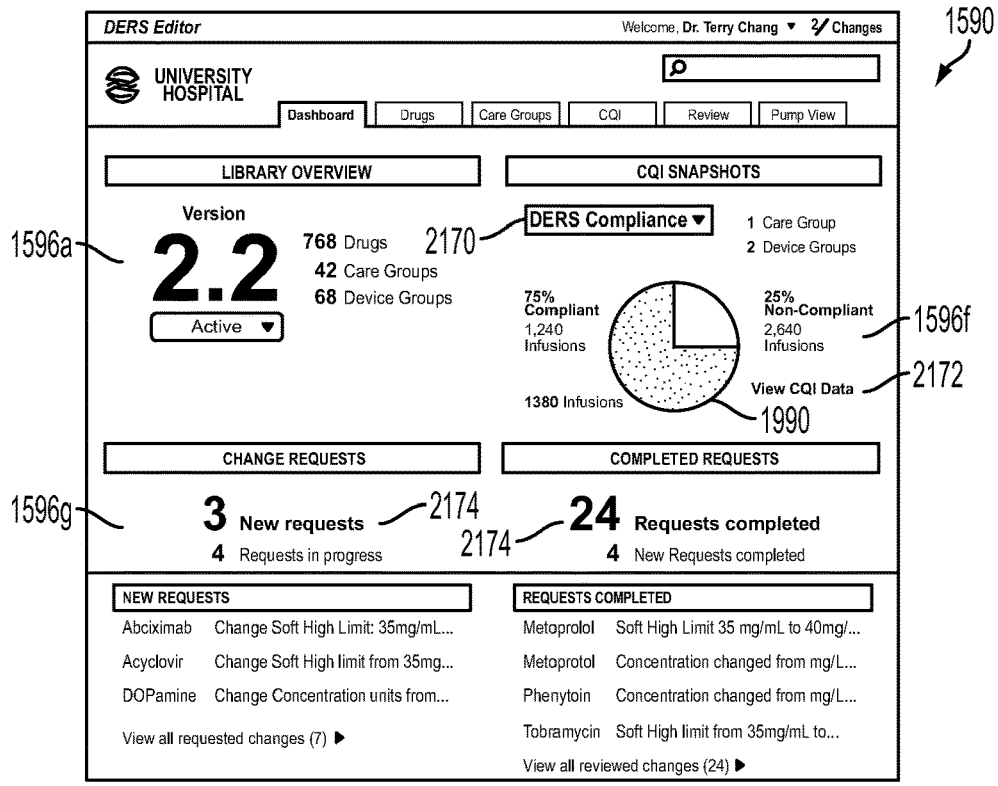
Figure 137:
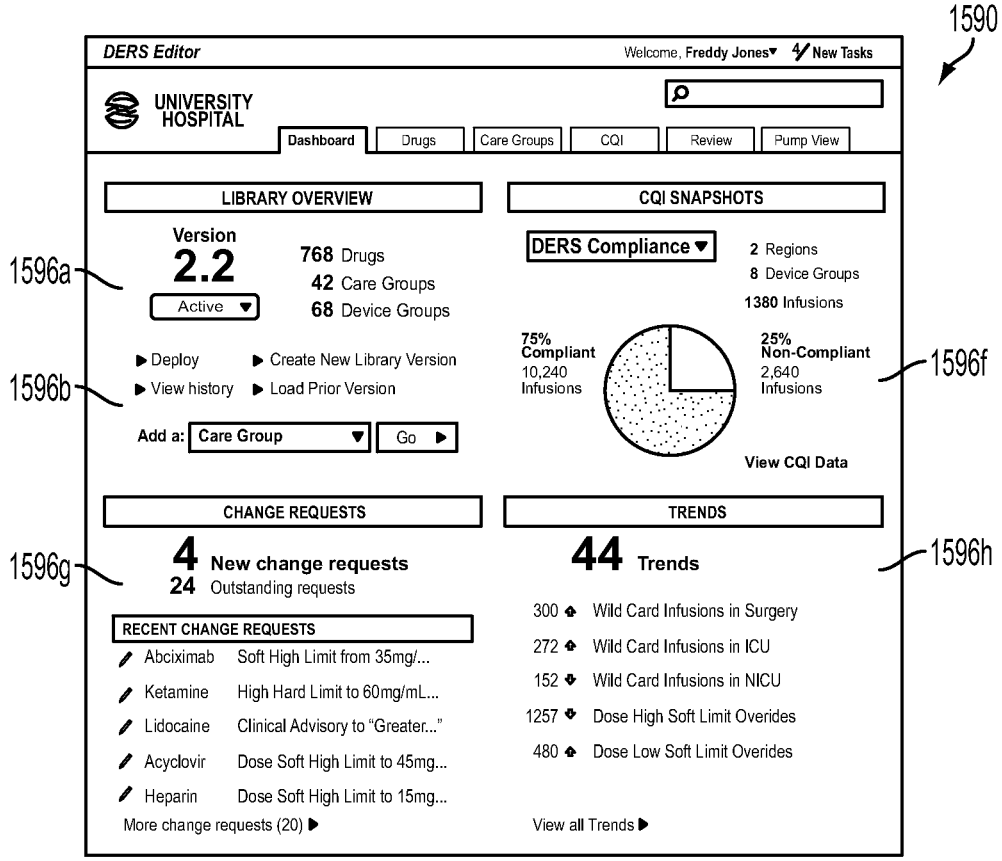
Figure 140:
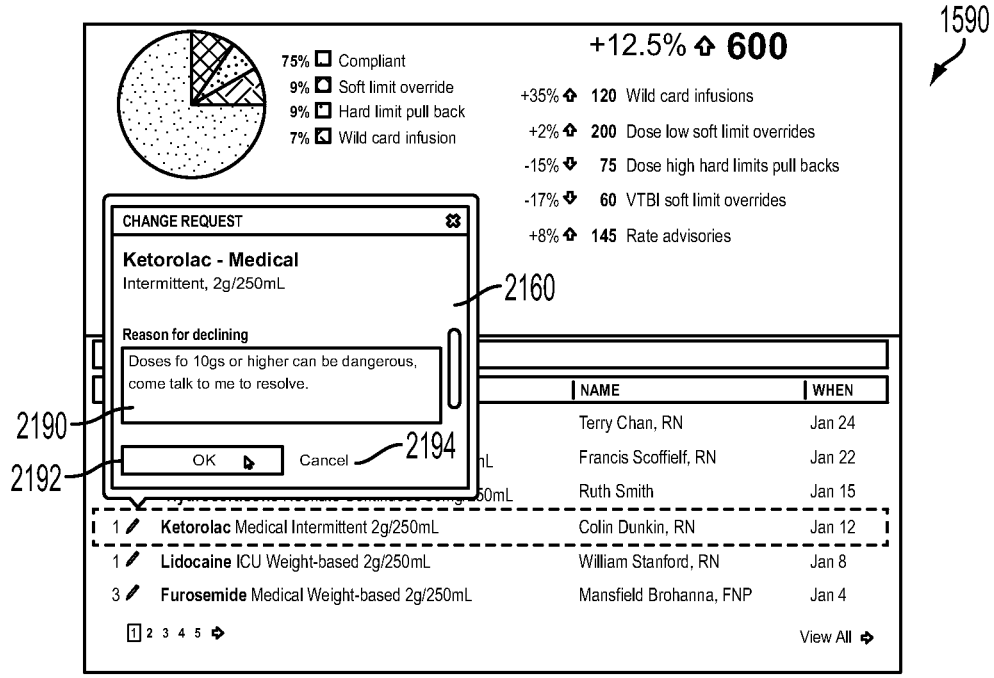
Figure 141:
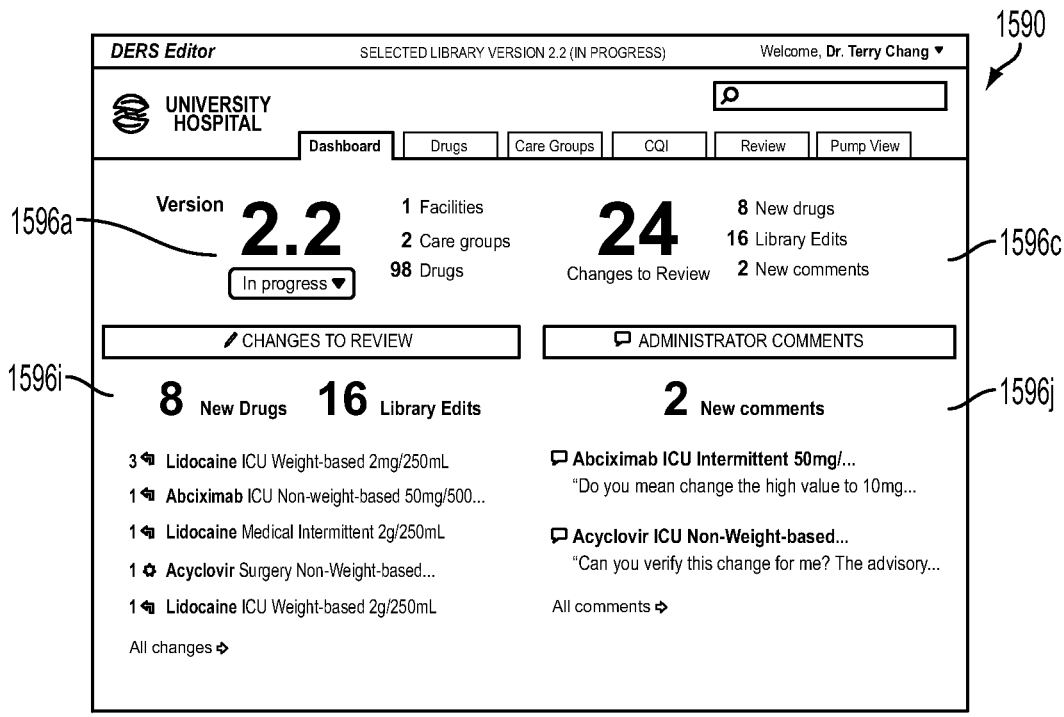
Figure 142:
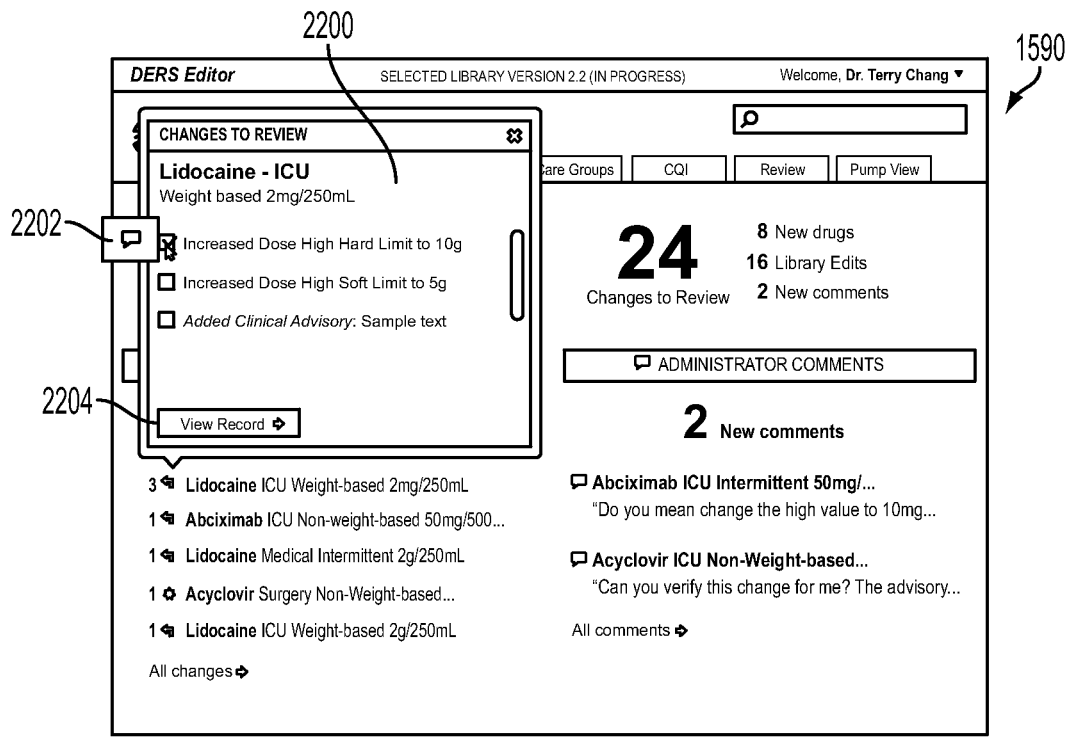
Figure 143:
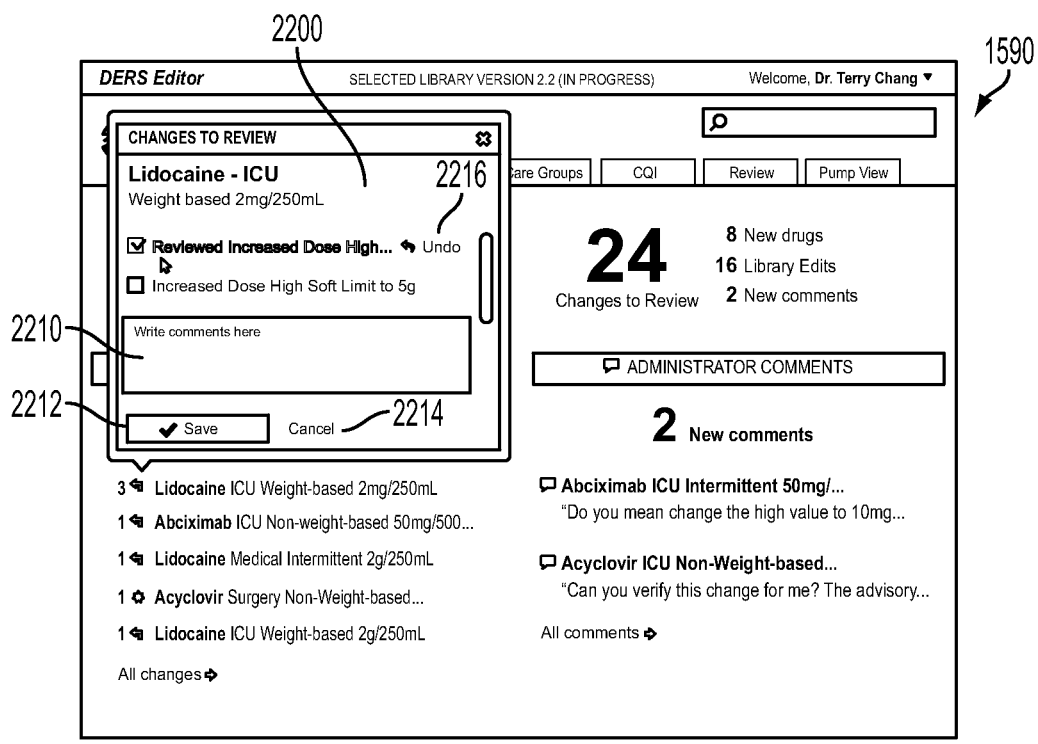
Figure 148:
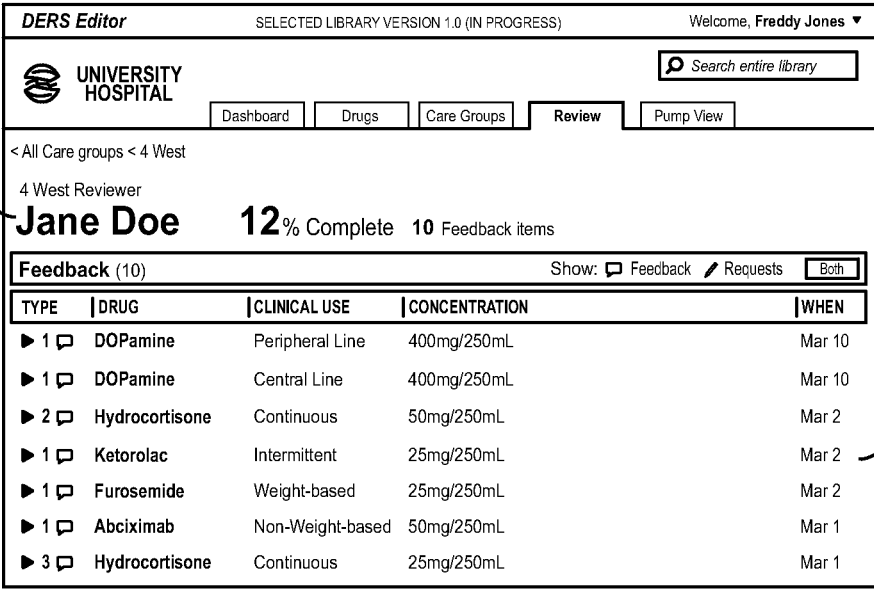
Figure 149:
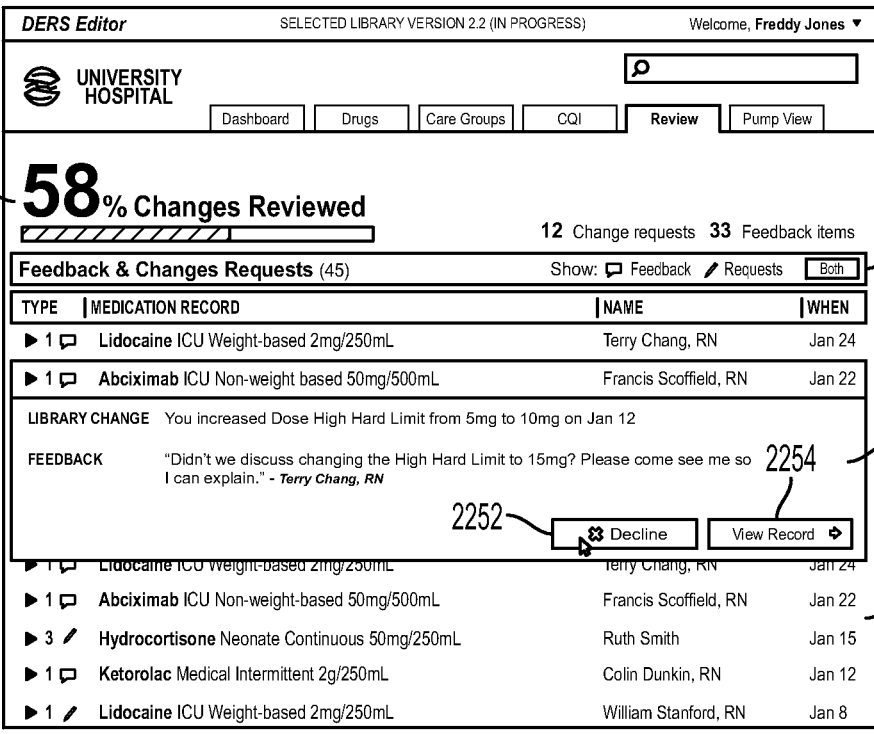
Figure 160:
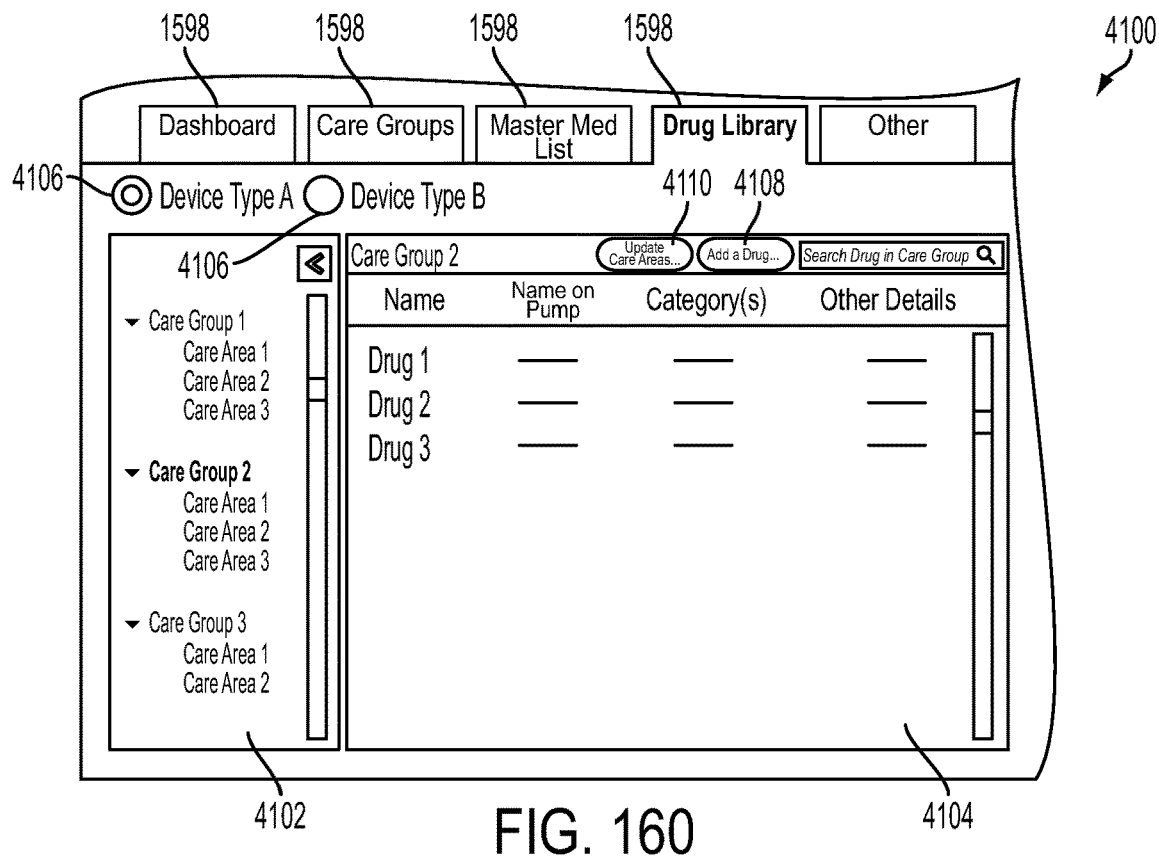
Figure 161:
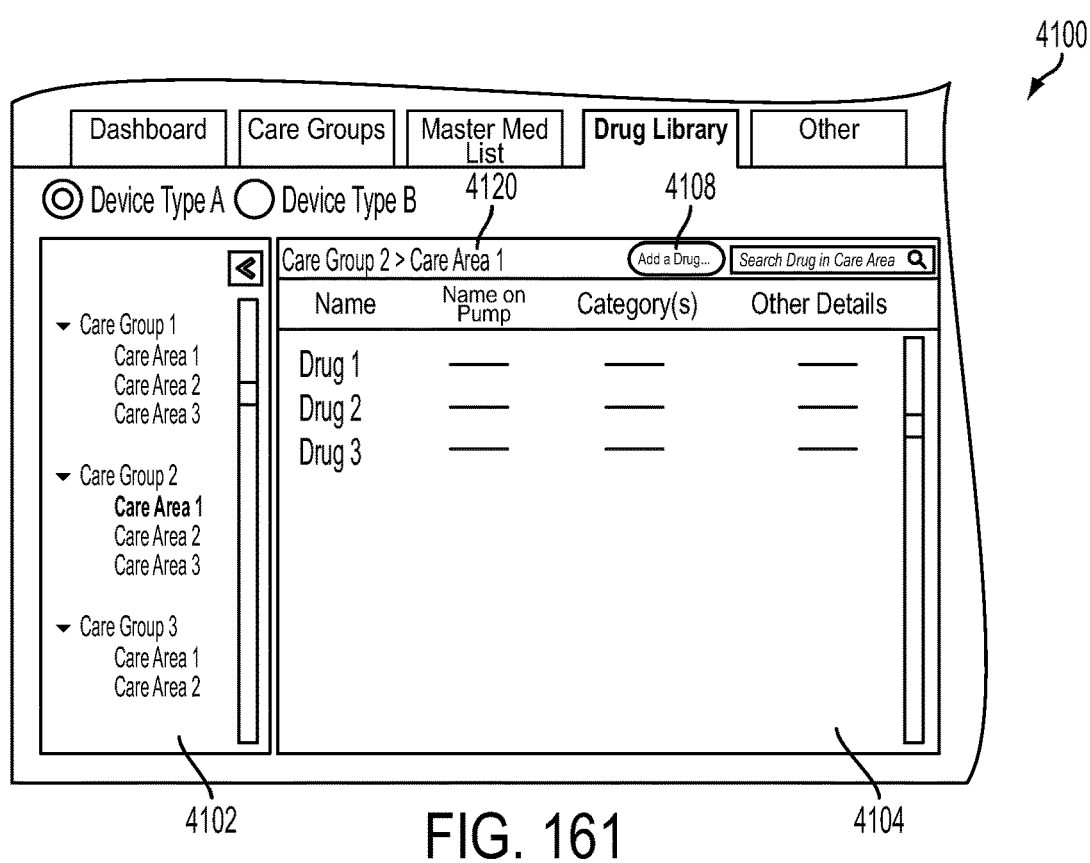
Figure 162:
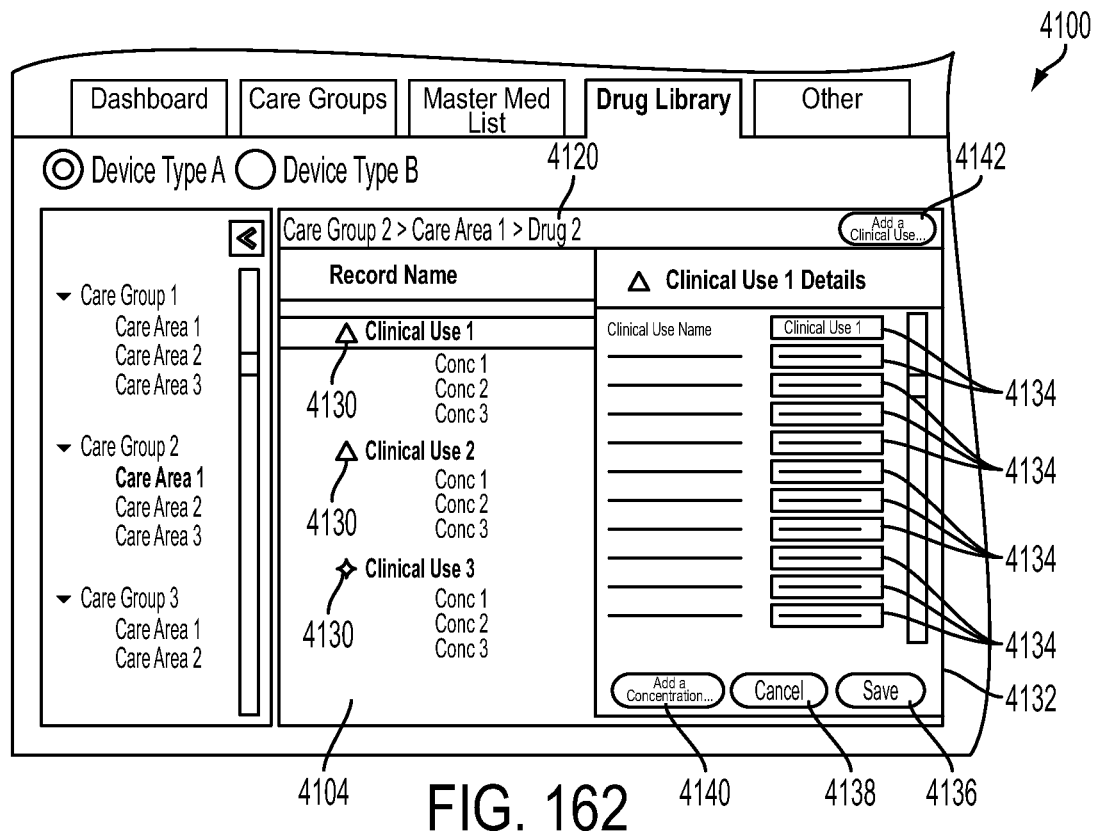
Figure 163:
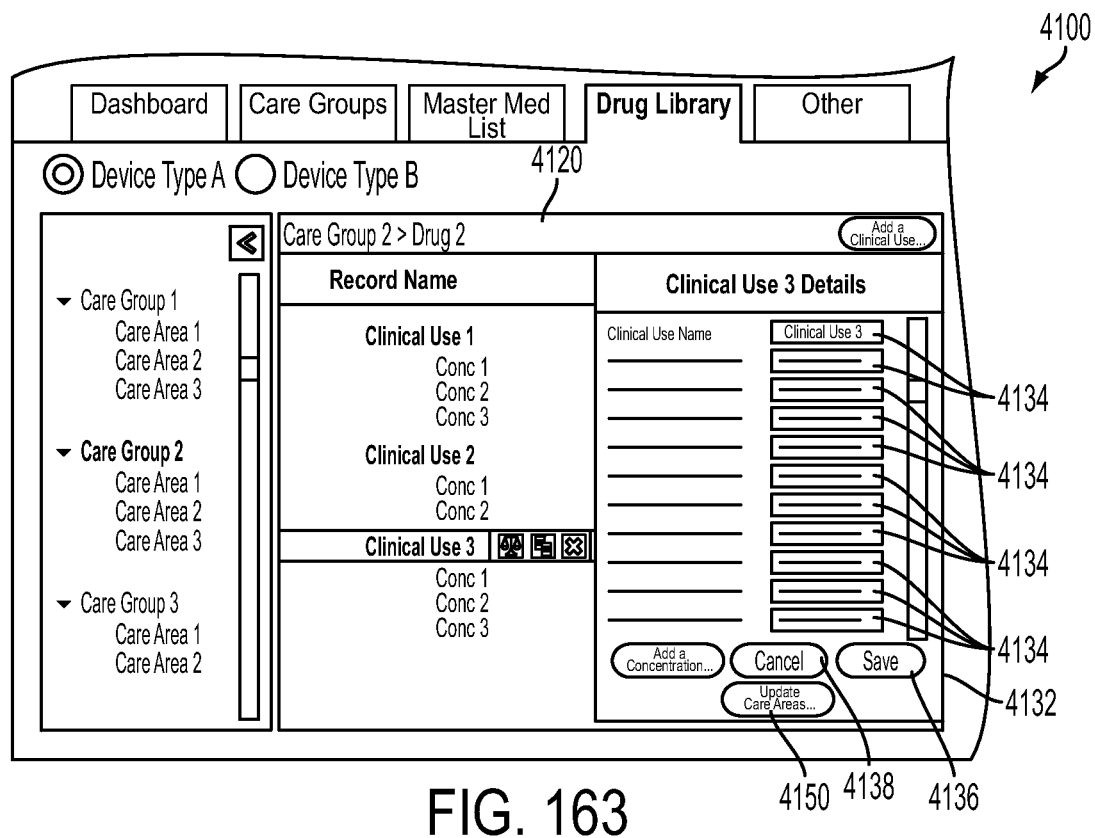
Figure 164:
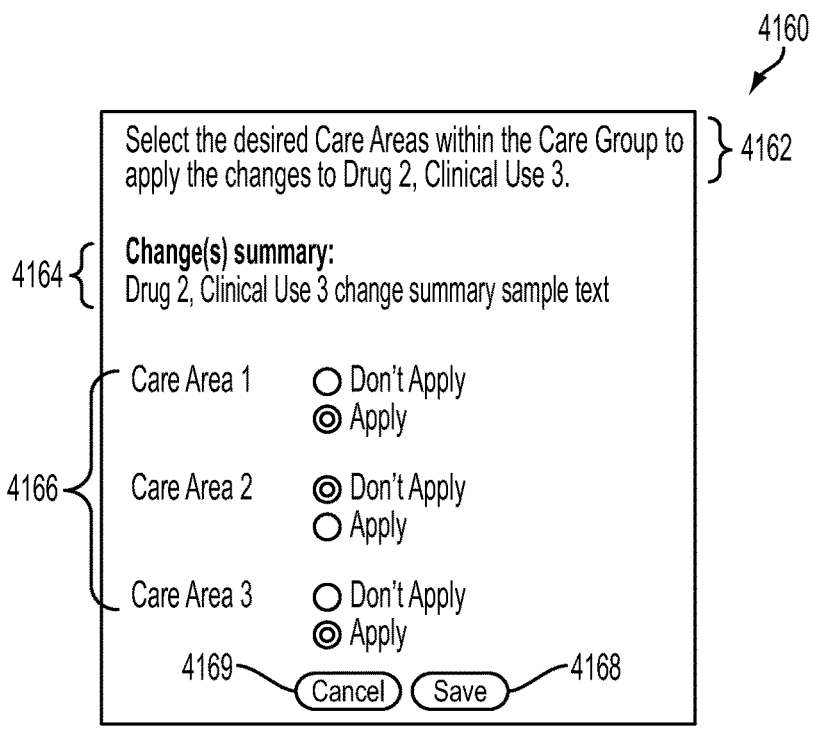
Figure 165:
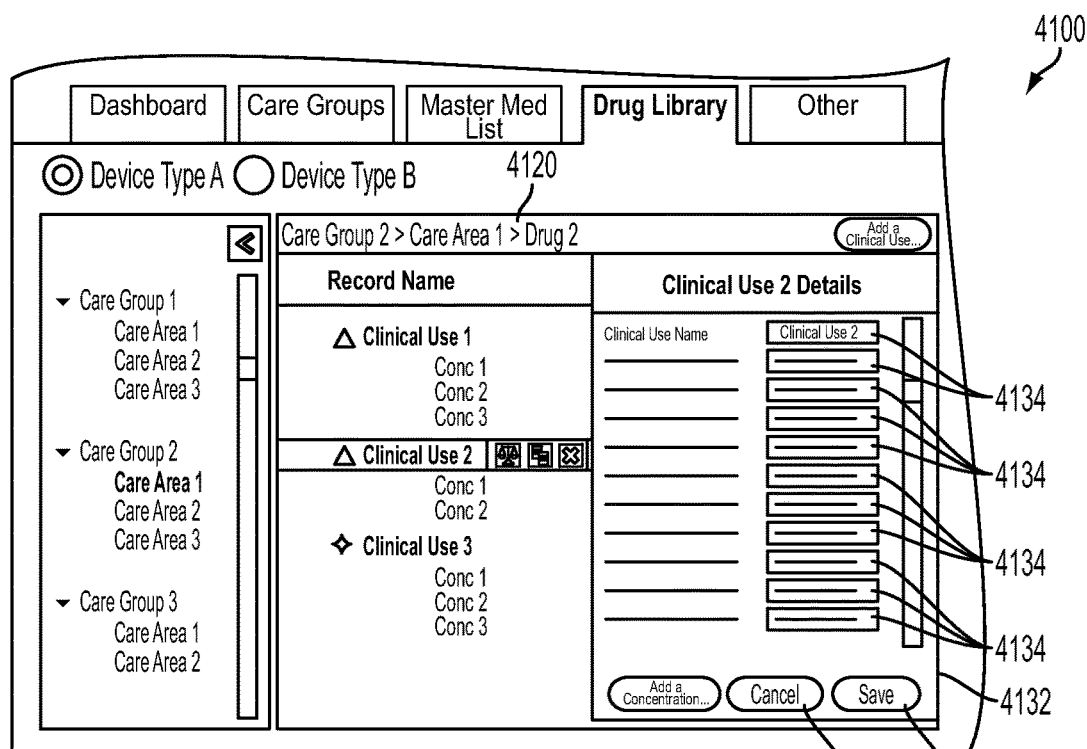
Figure 166:
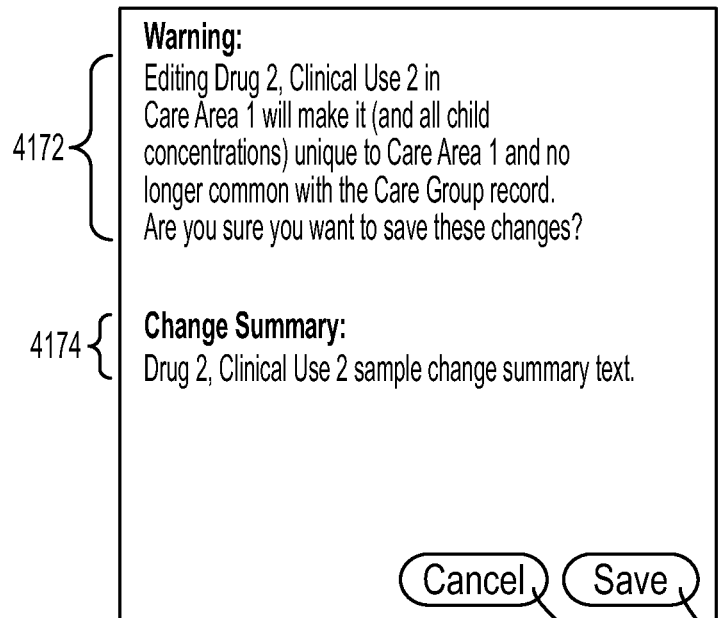
Figure 167:
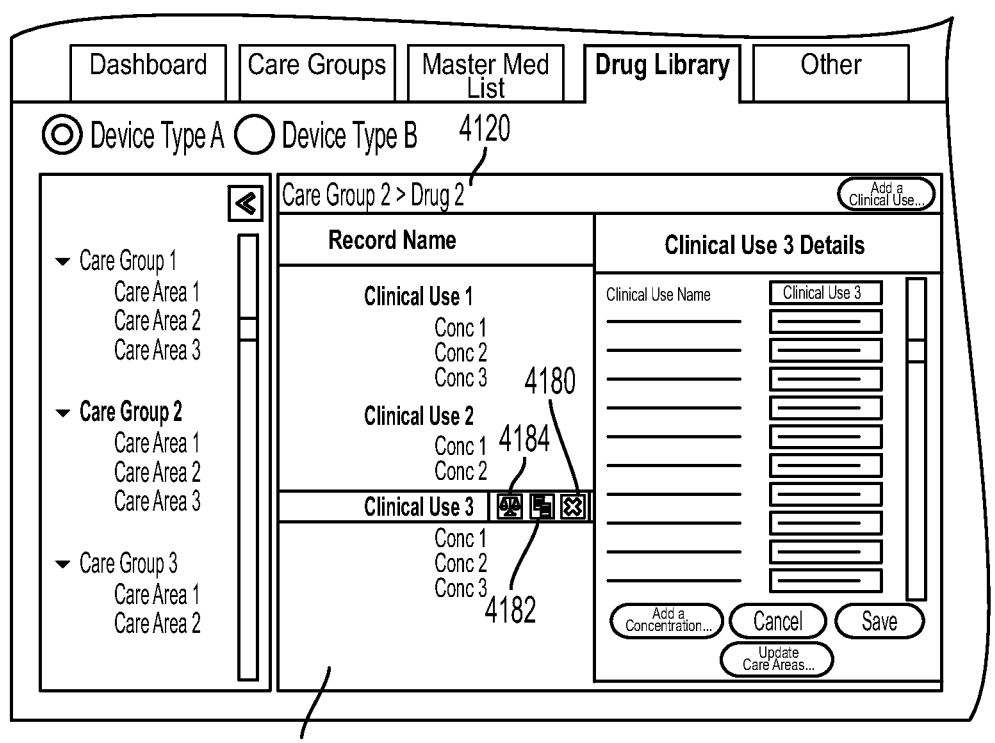
Figure 168:
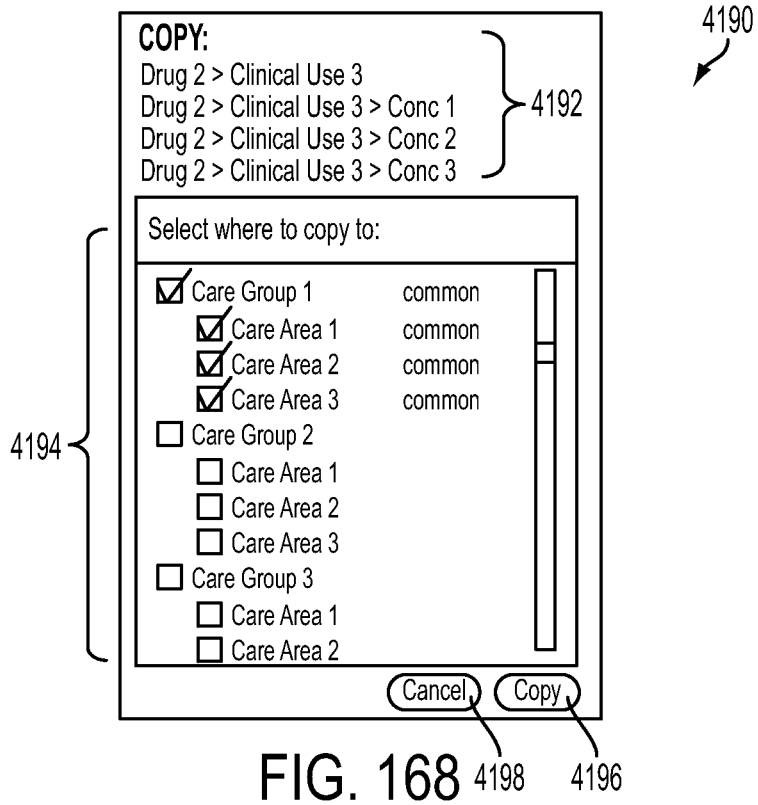
Figure 169:
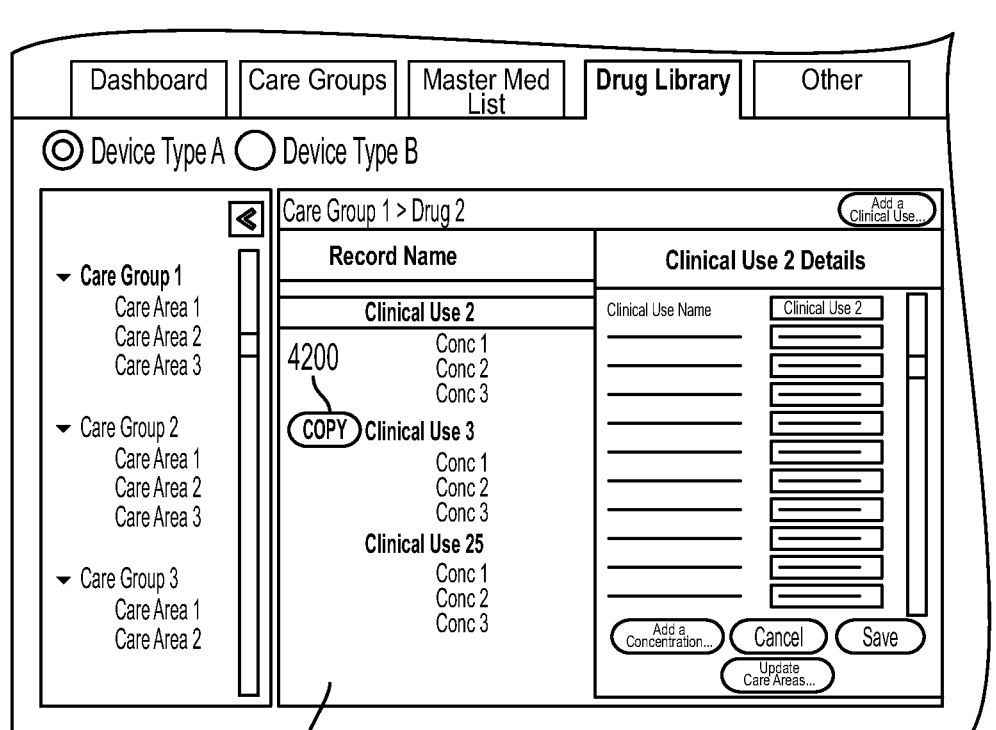
Figure 170:
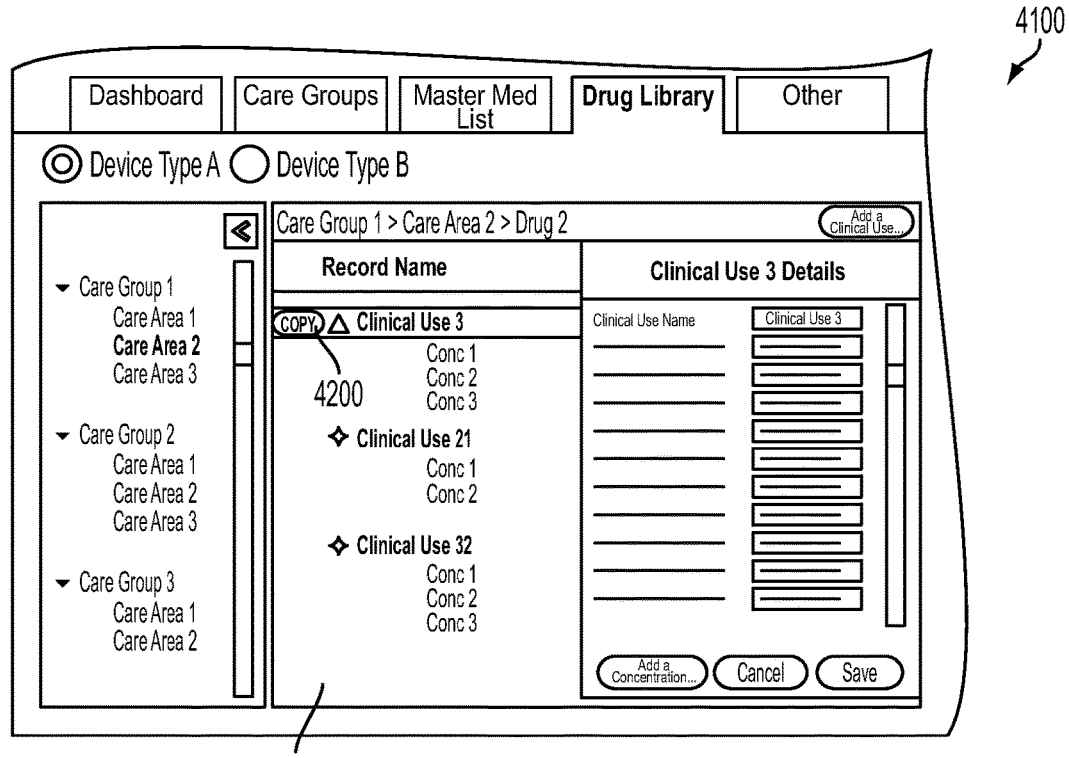
Figure 171:
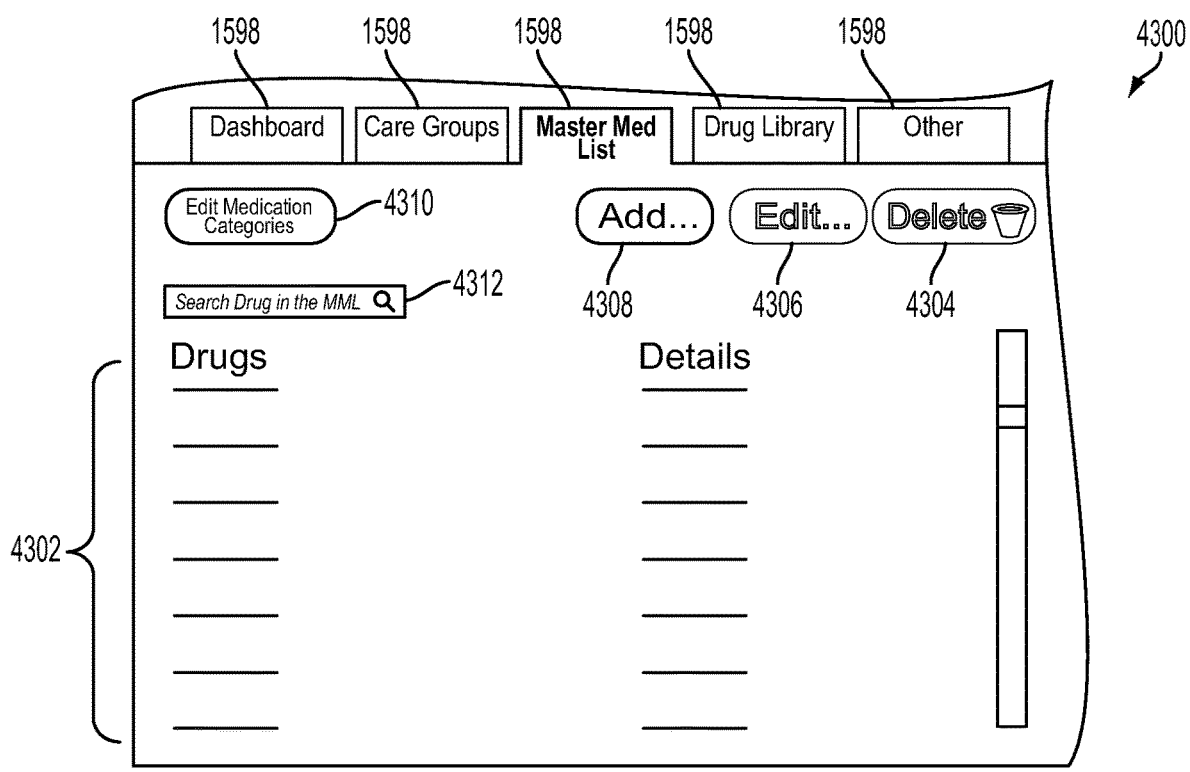
Figure 172:
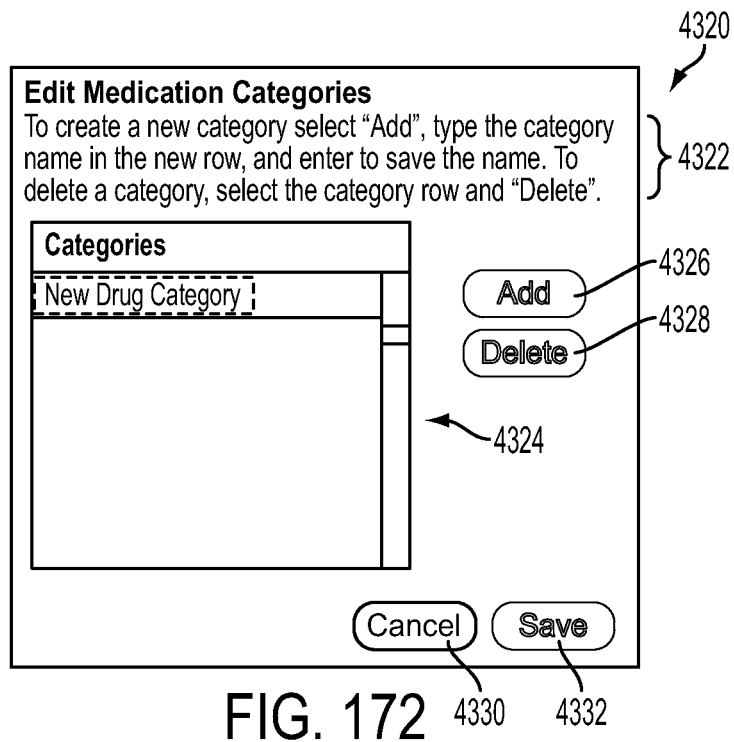
Figure 173:
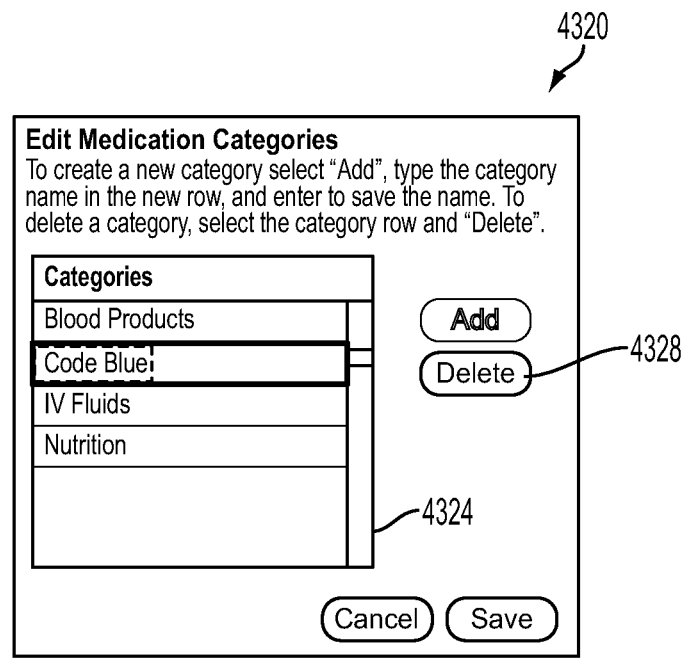
Figure 174:
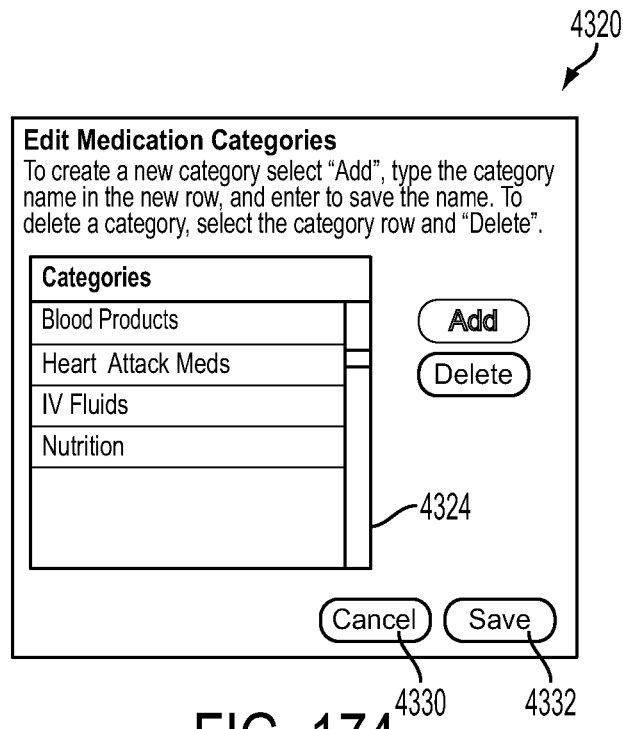
Figure 175:
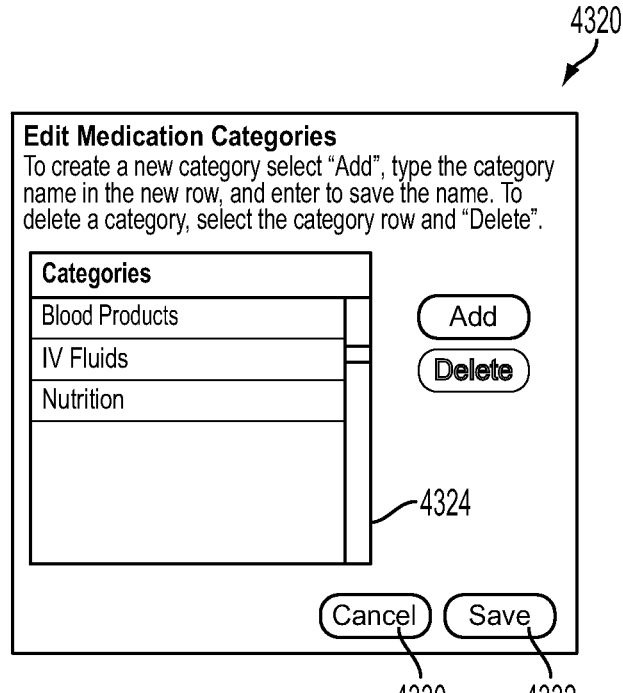
Figure 176:
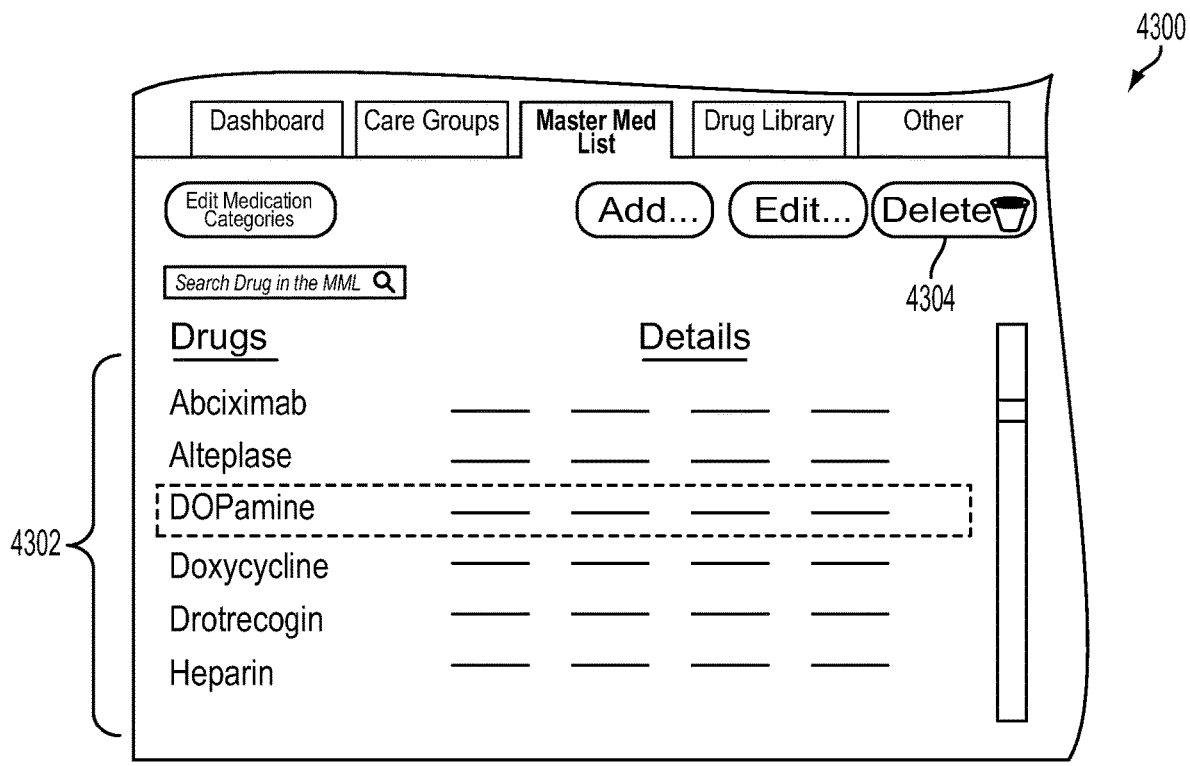
Figure 177:
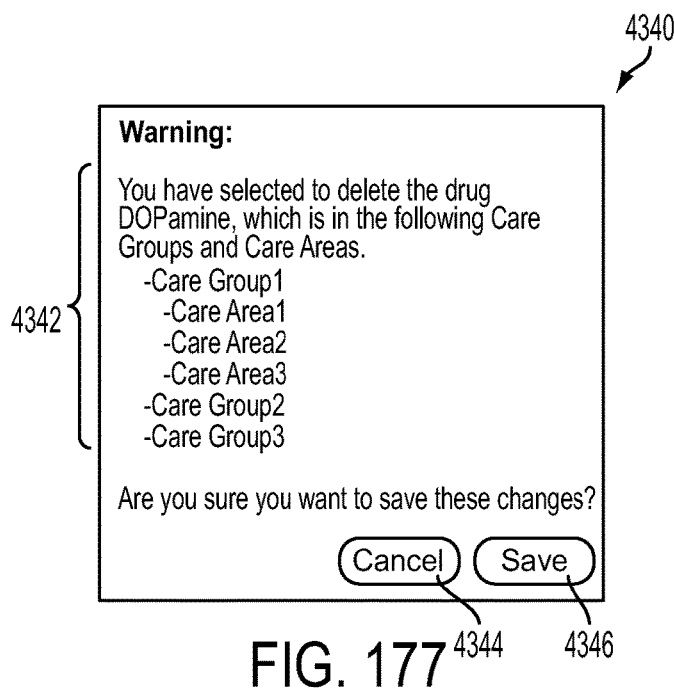
Figure 181:
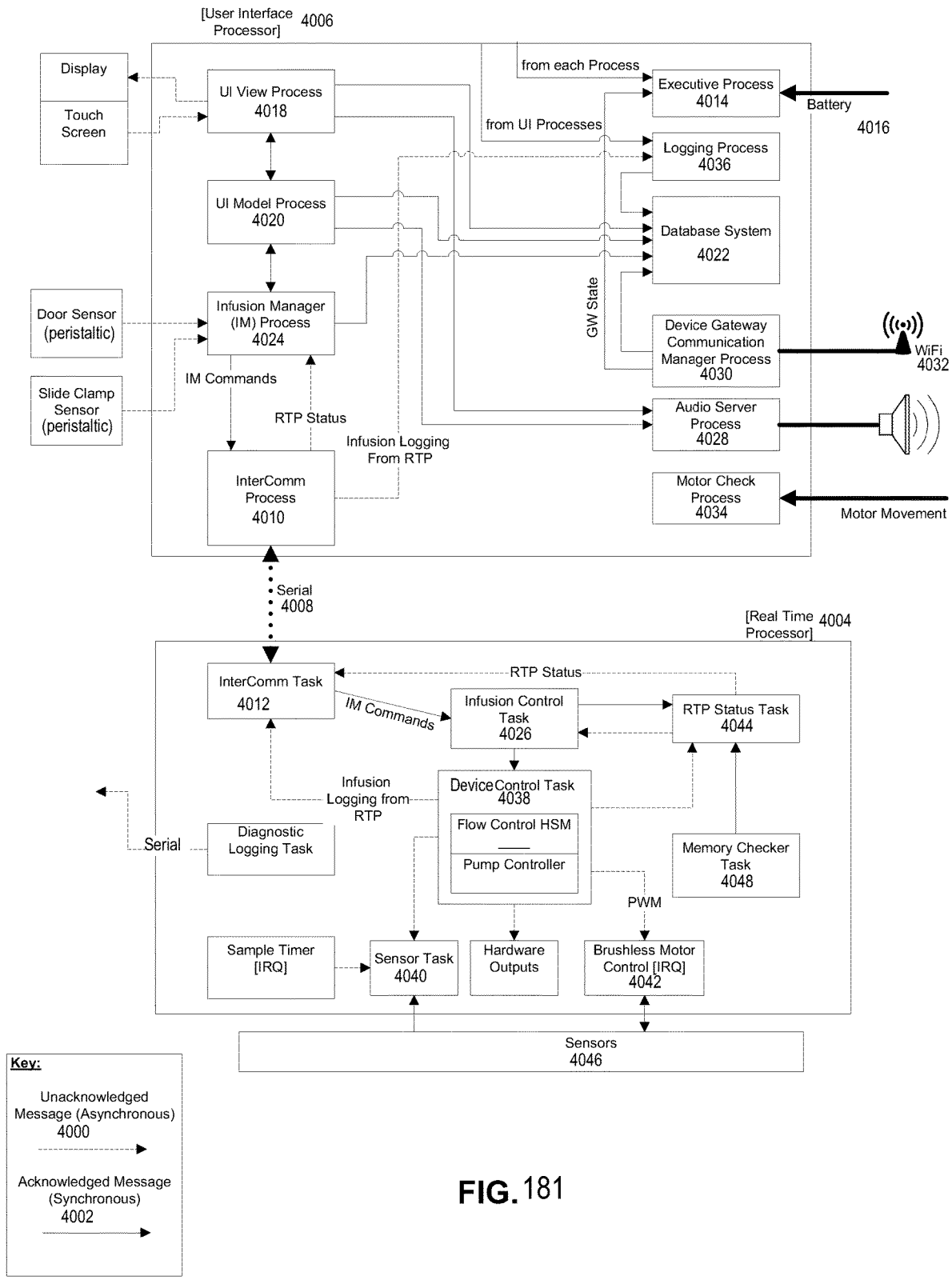
Figure 182:
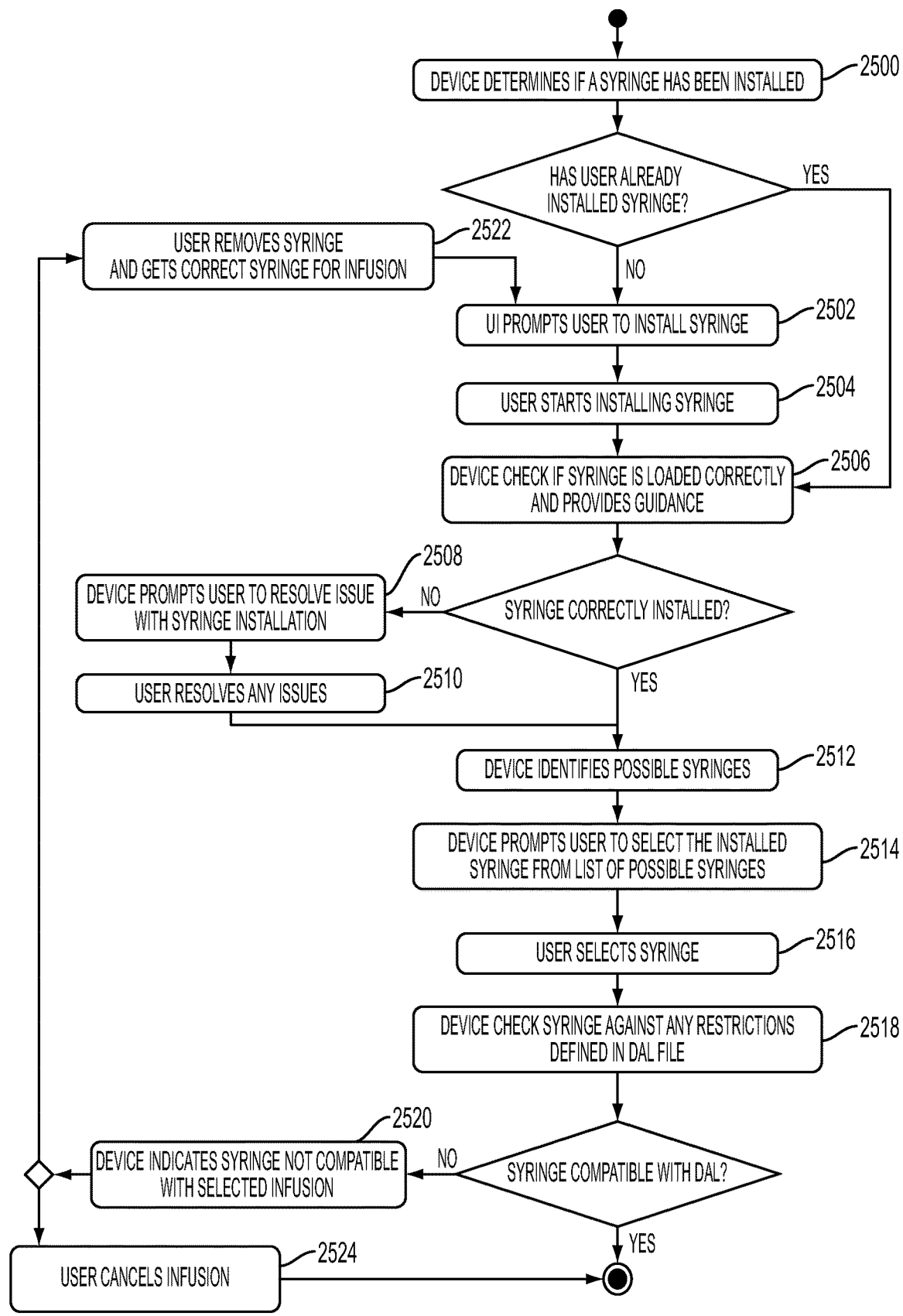
Figure 183:
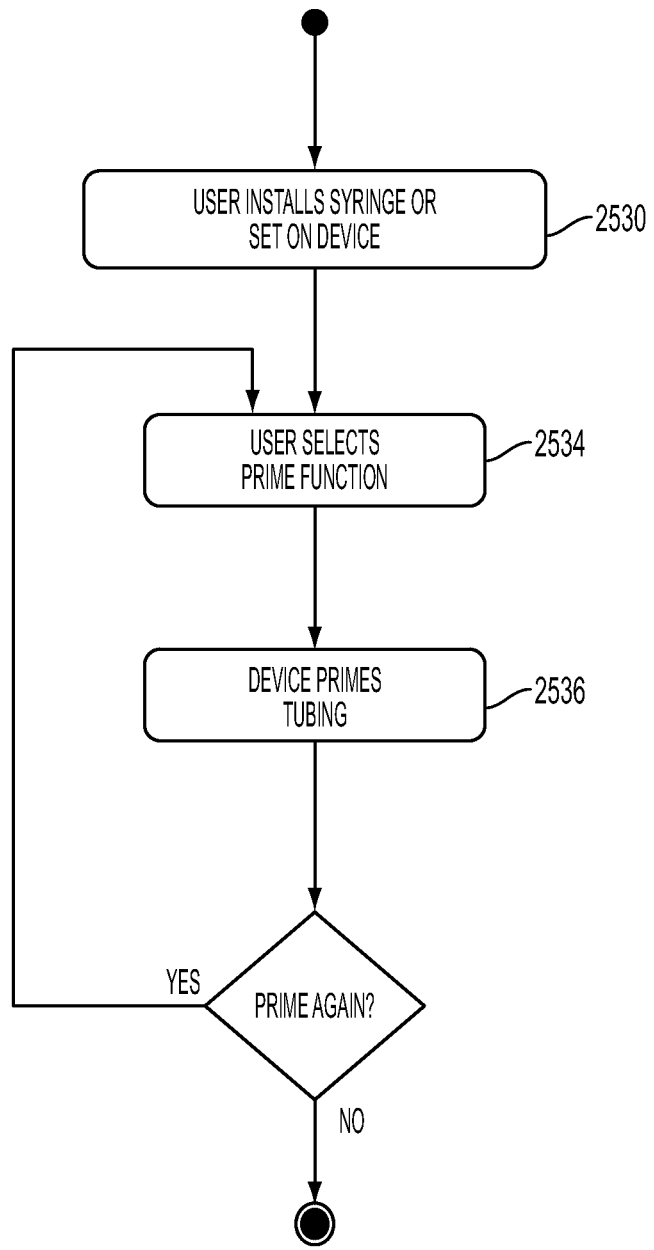
Figure 184:
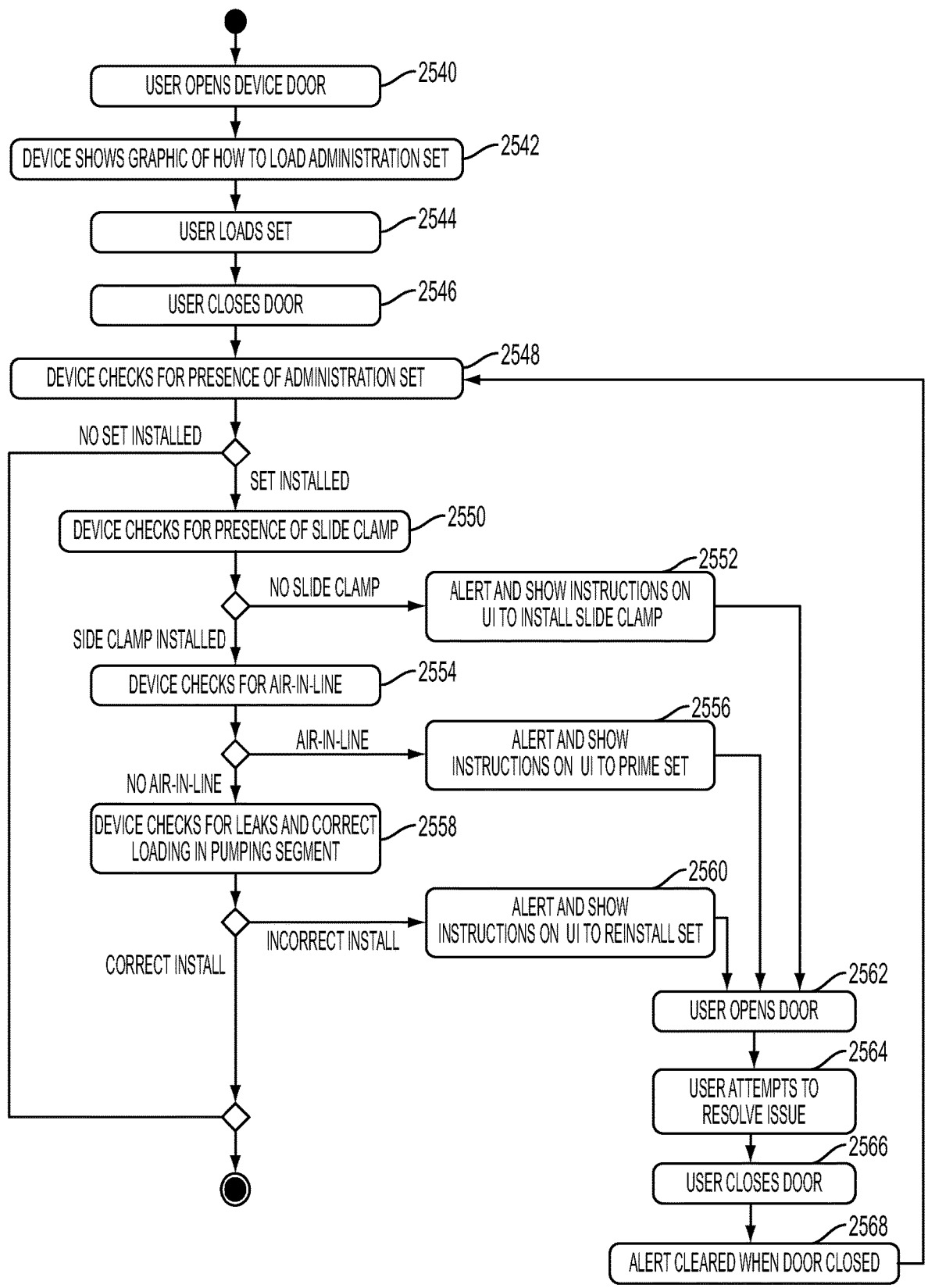
Figure 185:
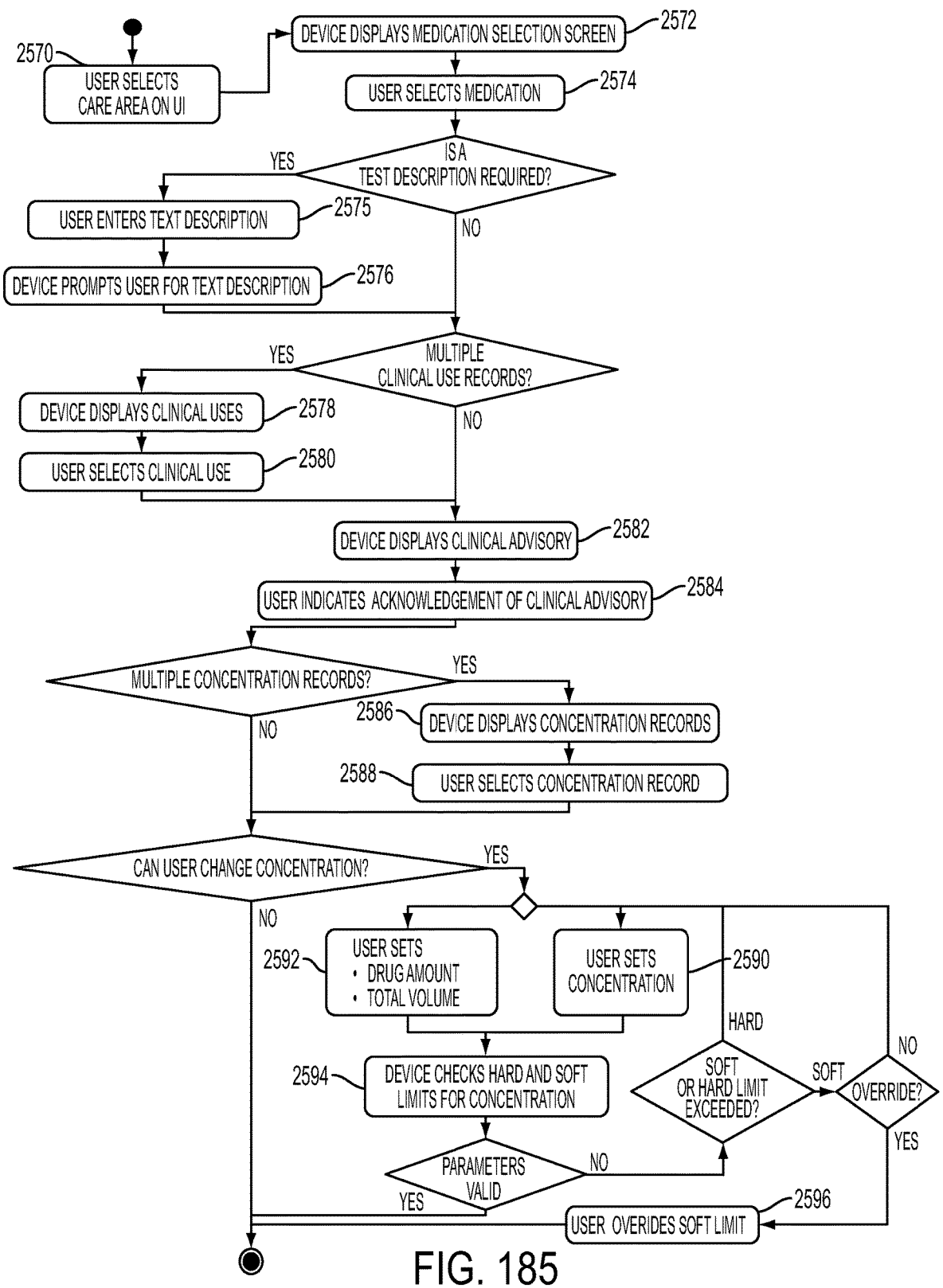
Figure 186:
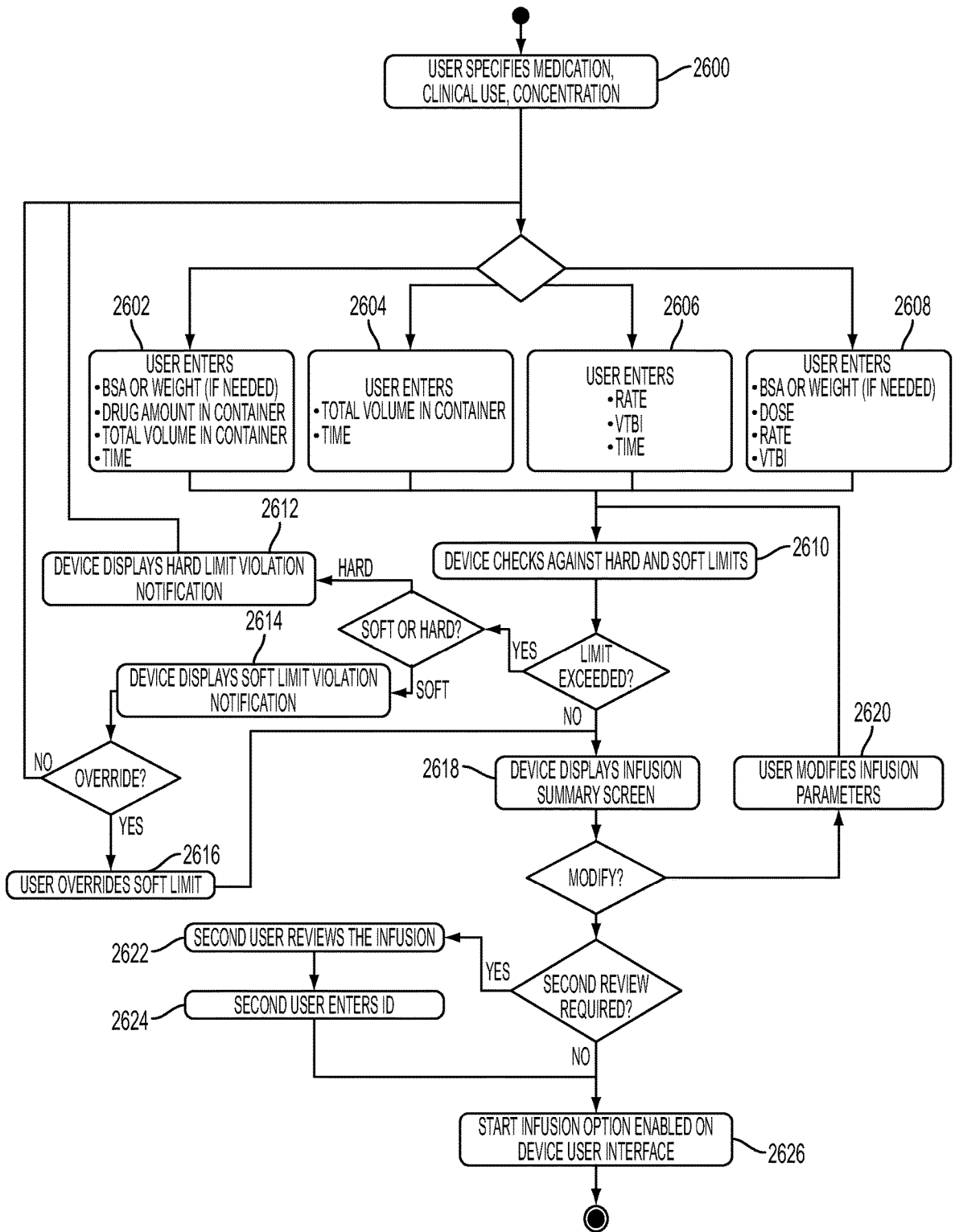
Figure 187:
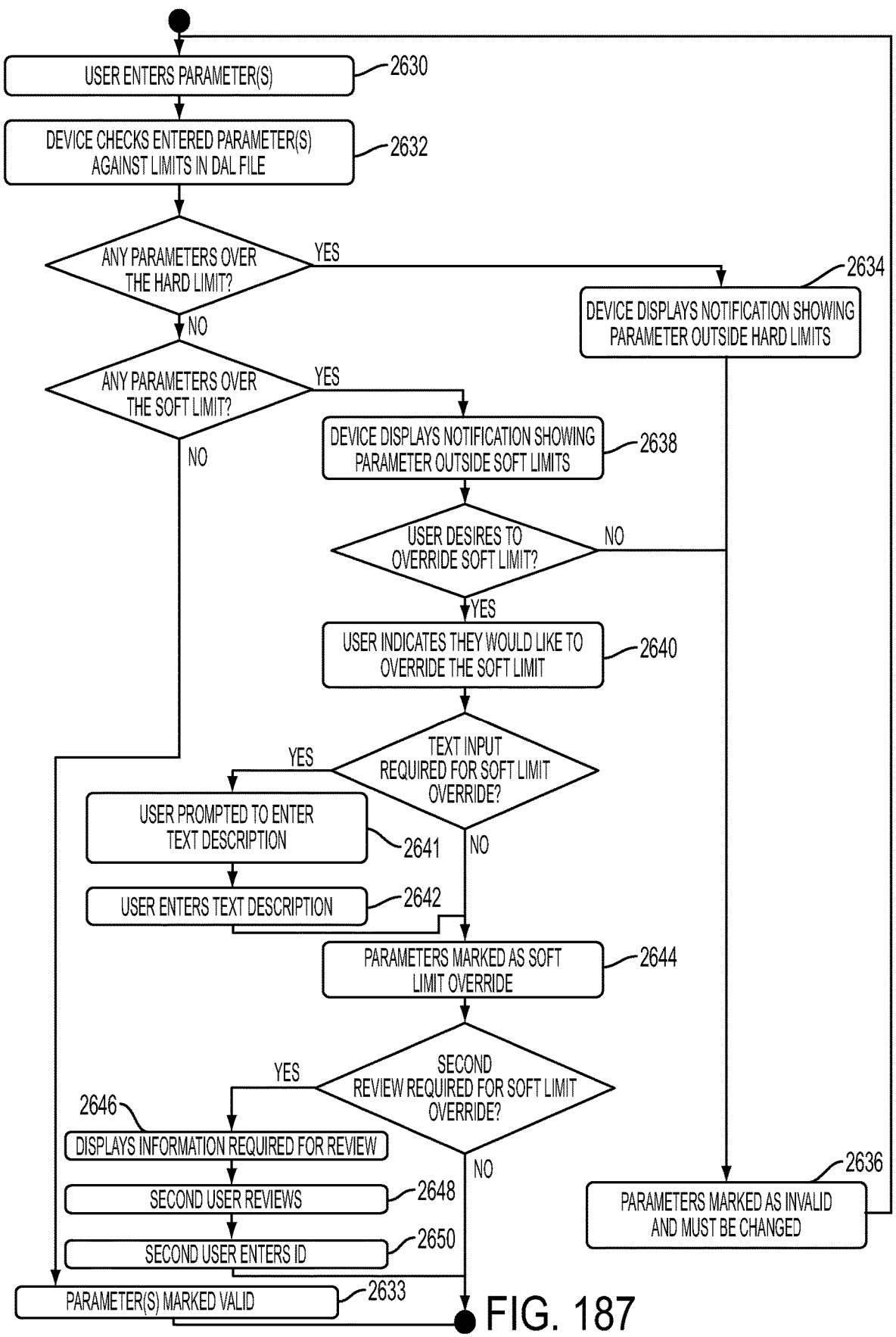
Figure 188:
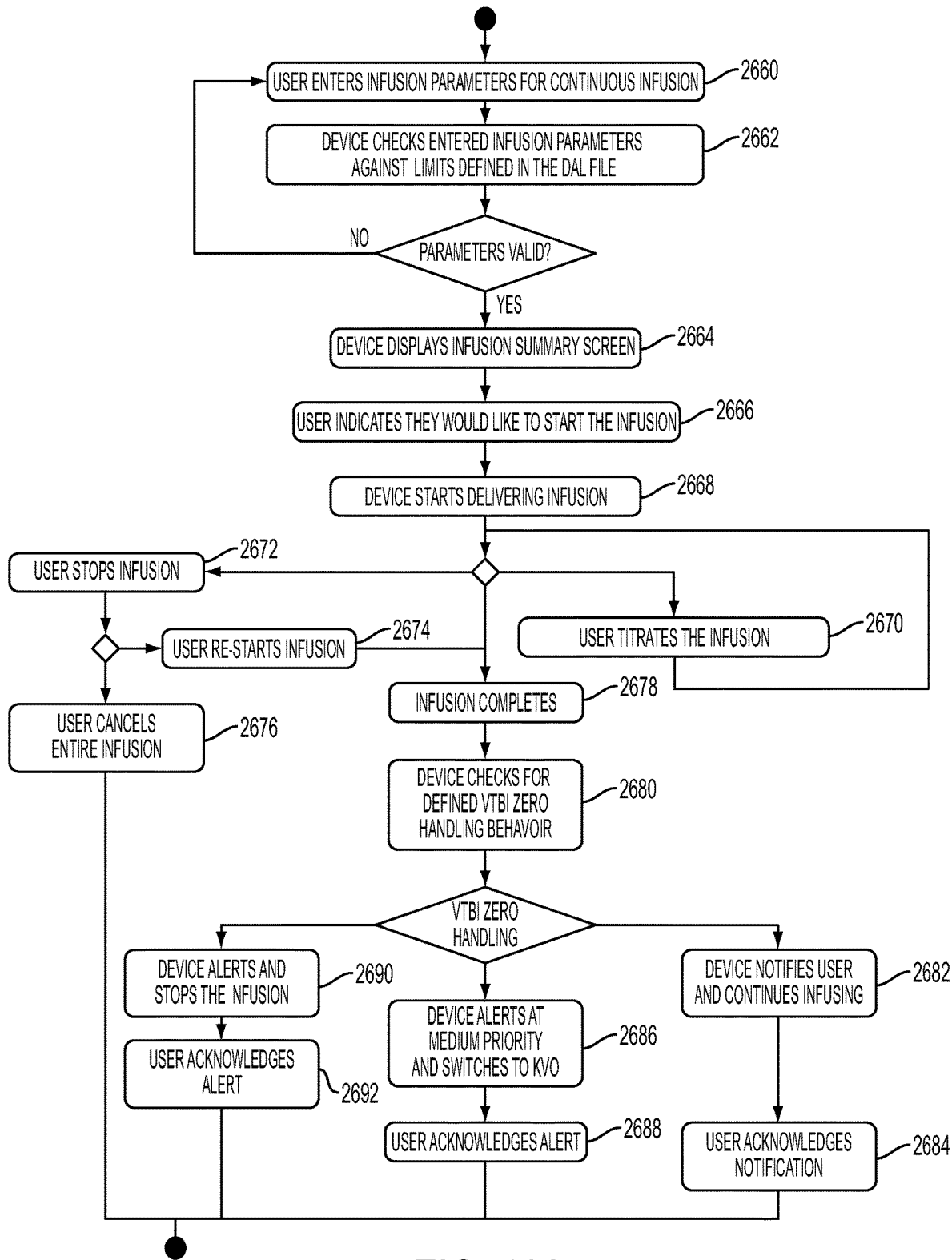
Figure 189:
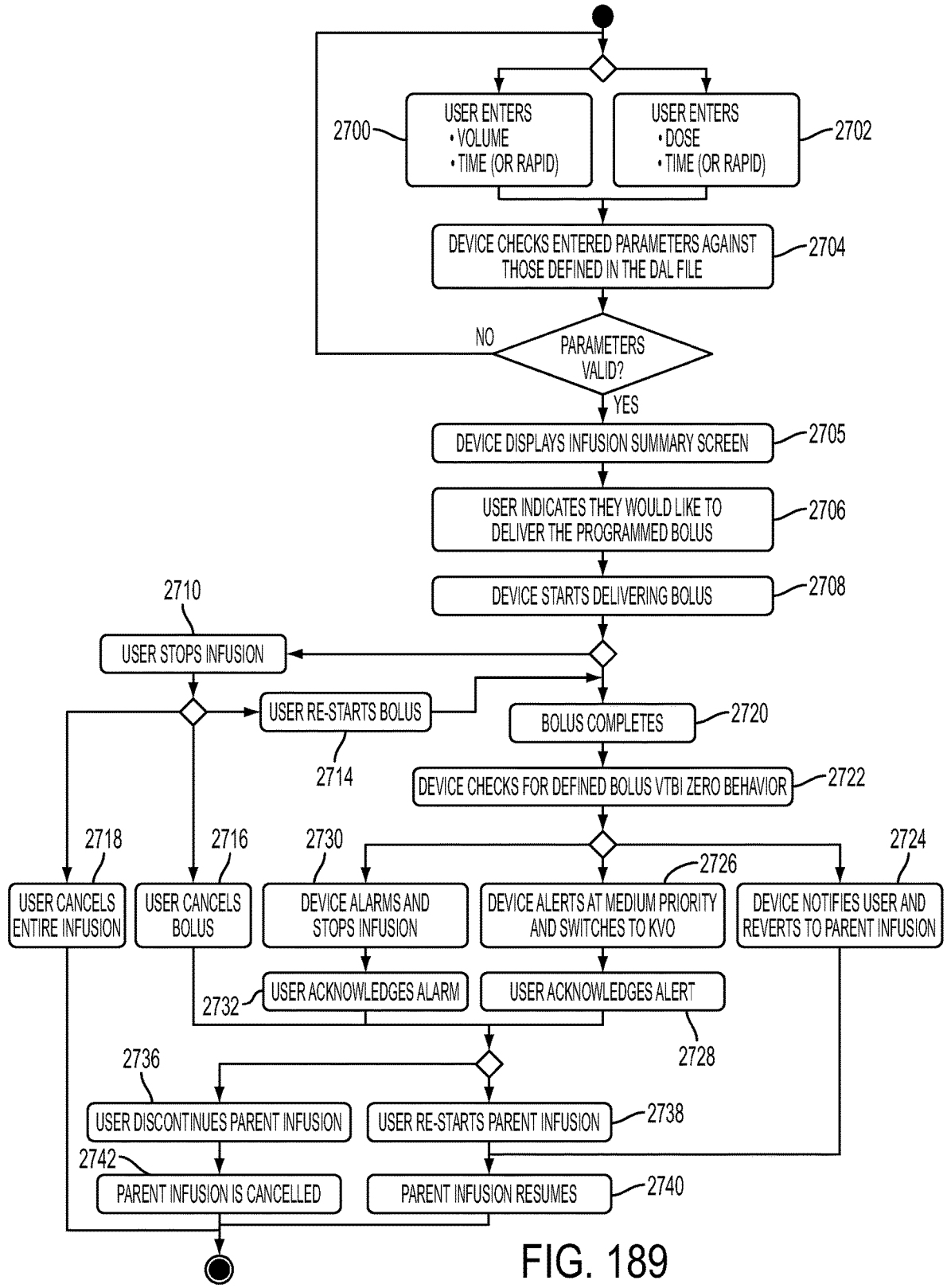
Figure 190:
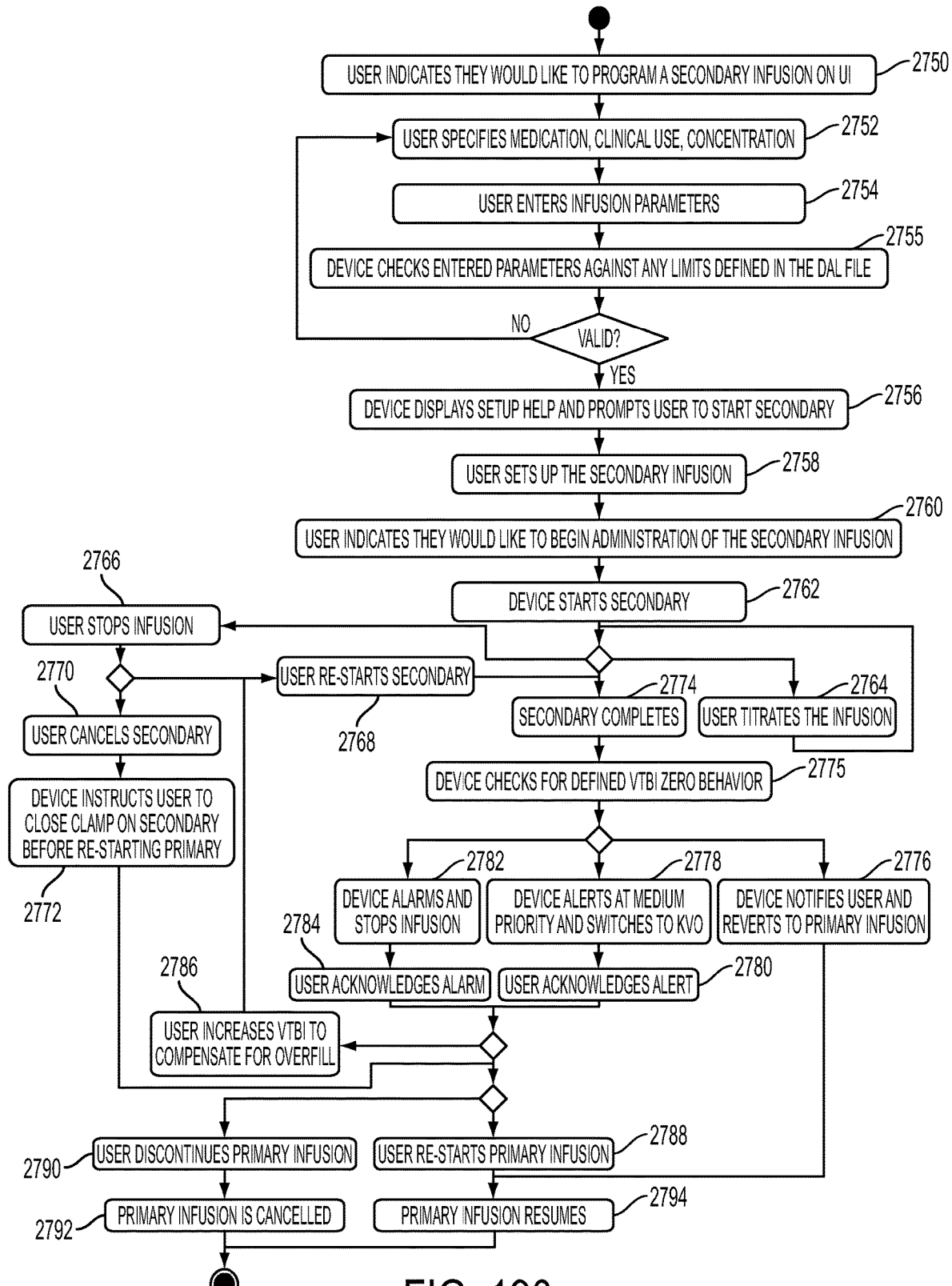
Figure 191:
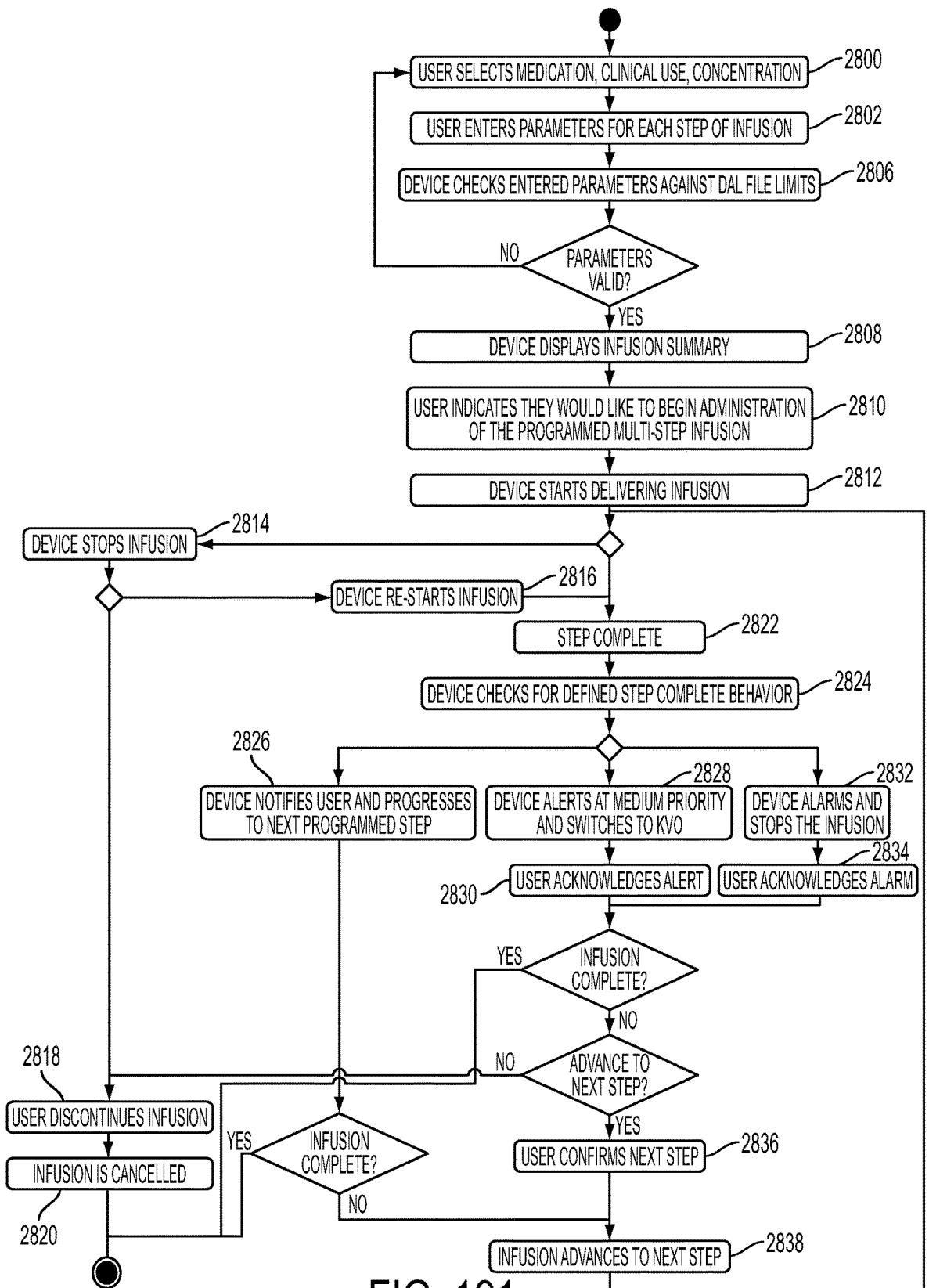
Figure 192:
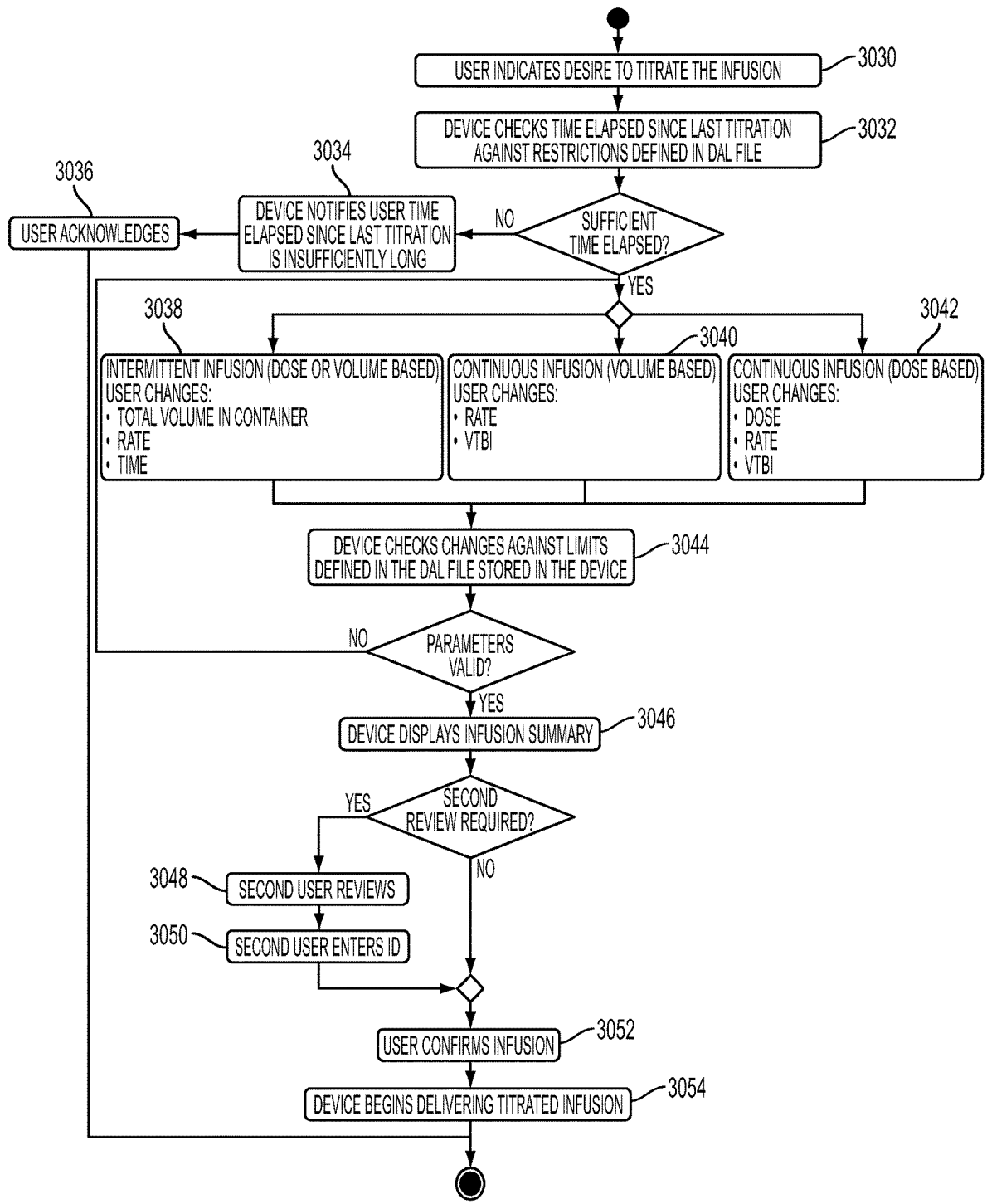
Figure 193:
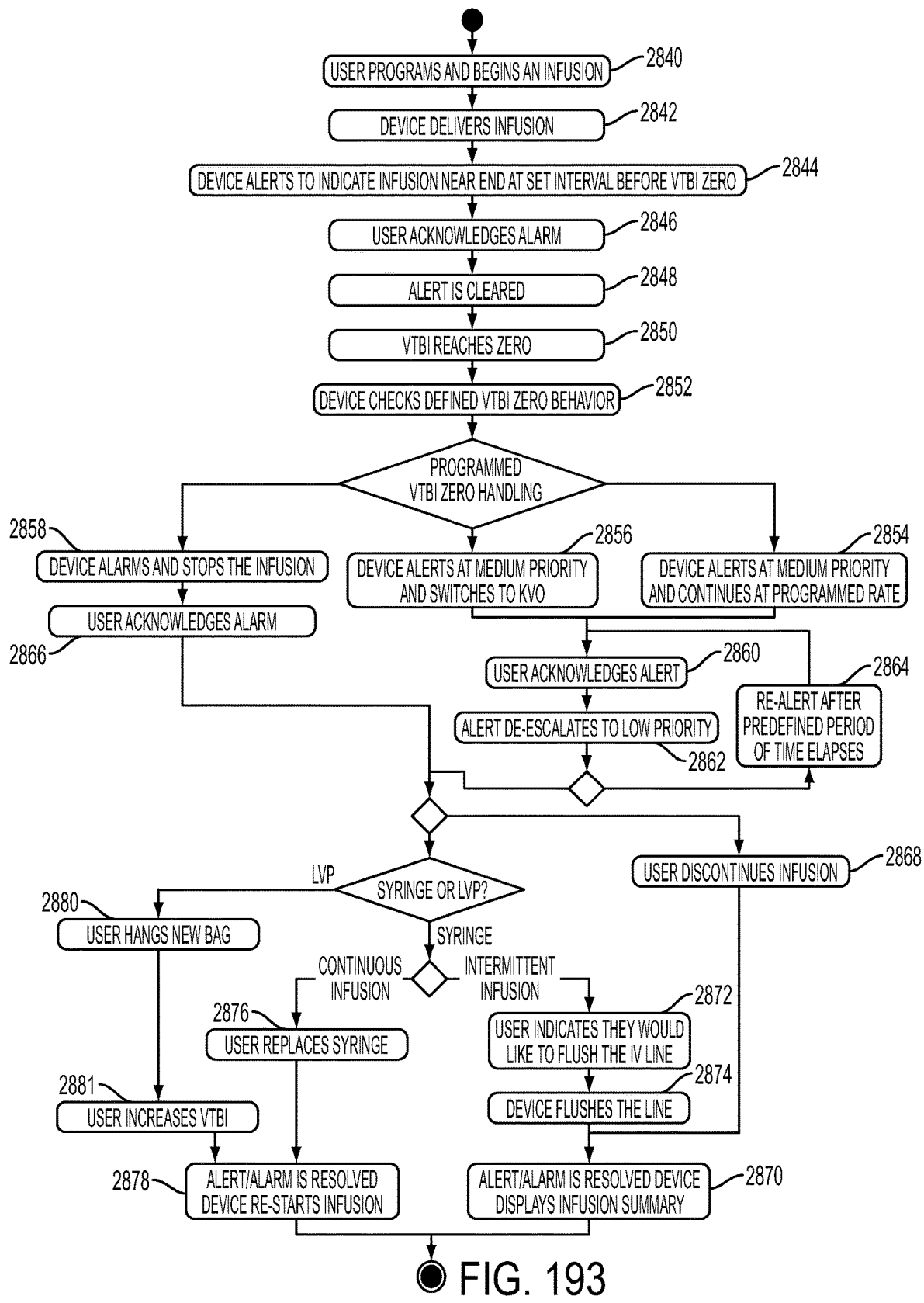
Figure 194:
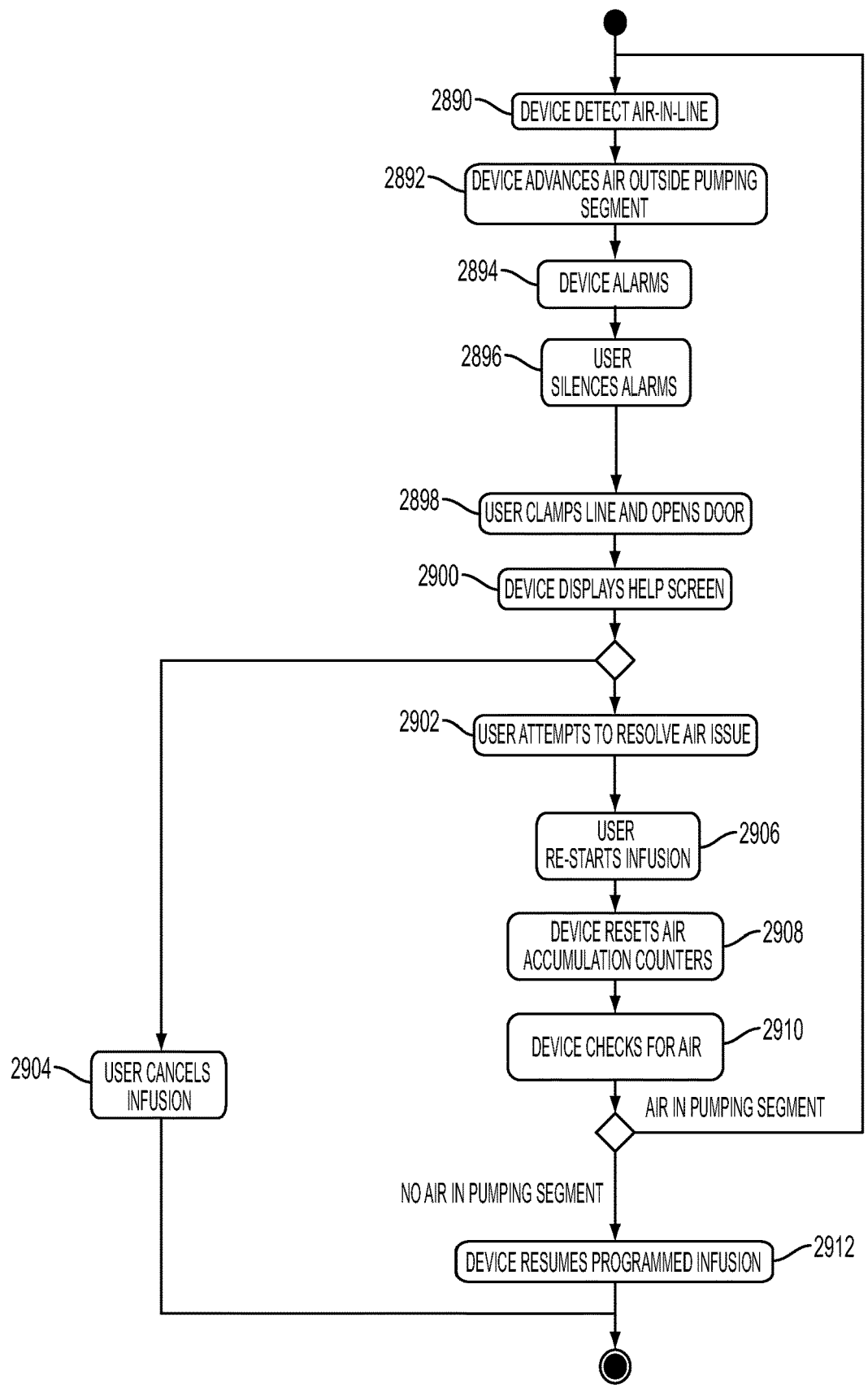
Figure 195:
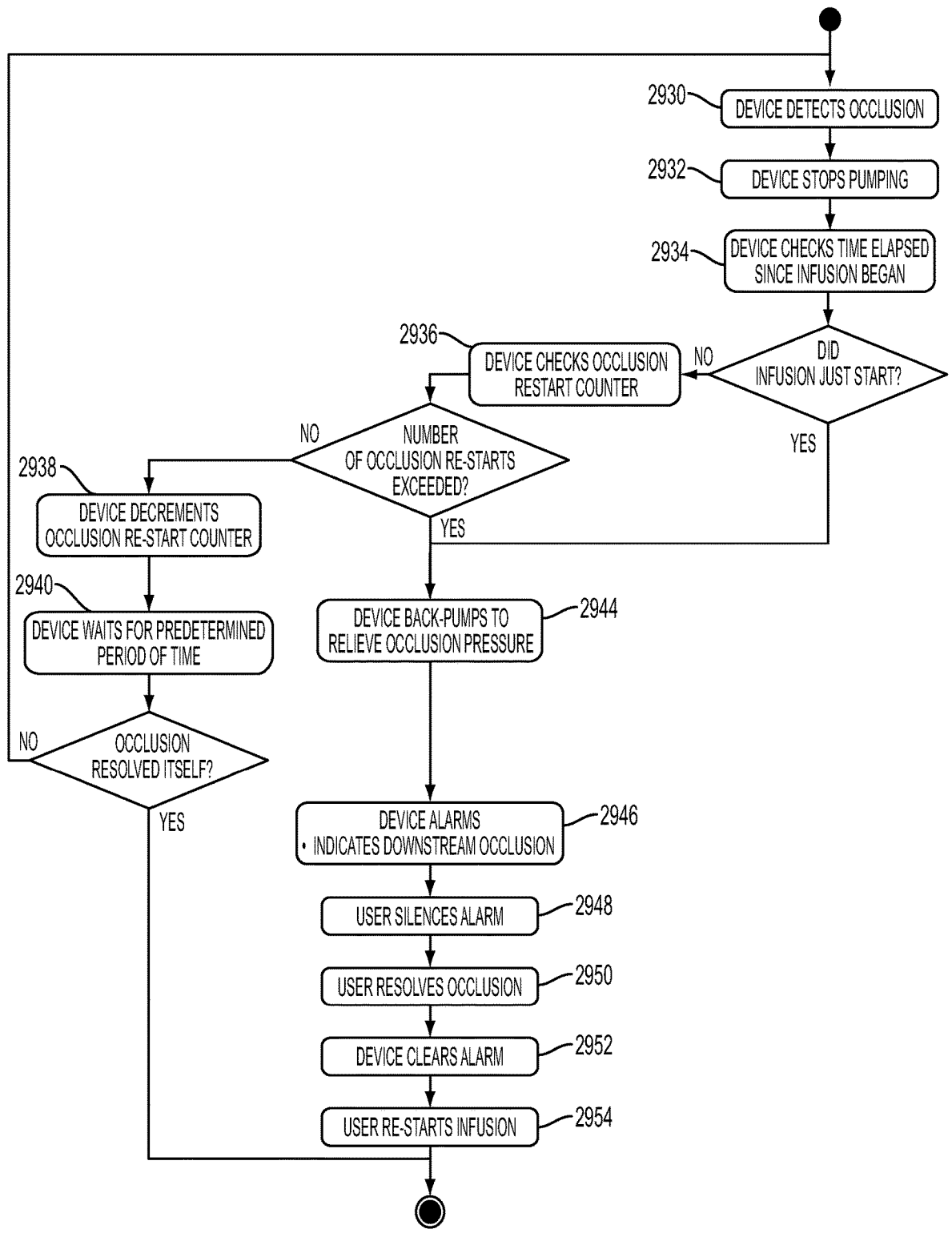
Figure 196:
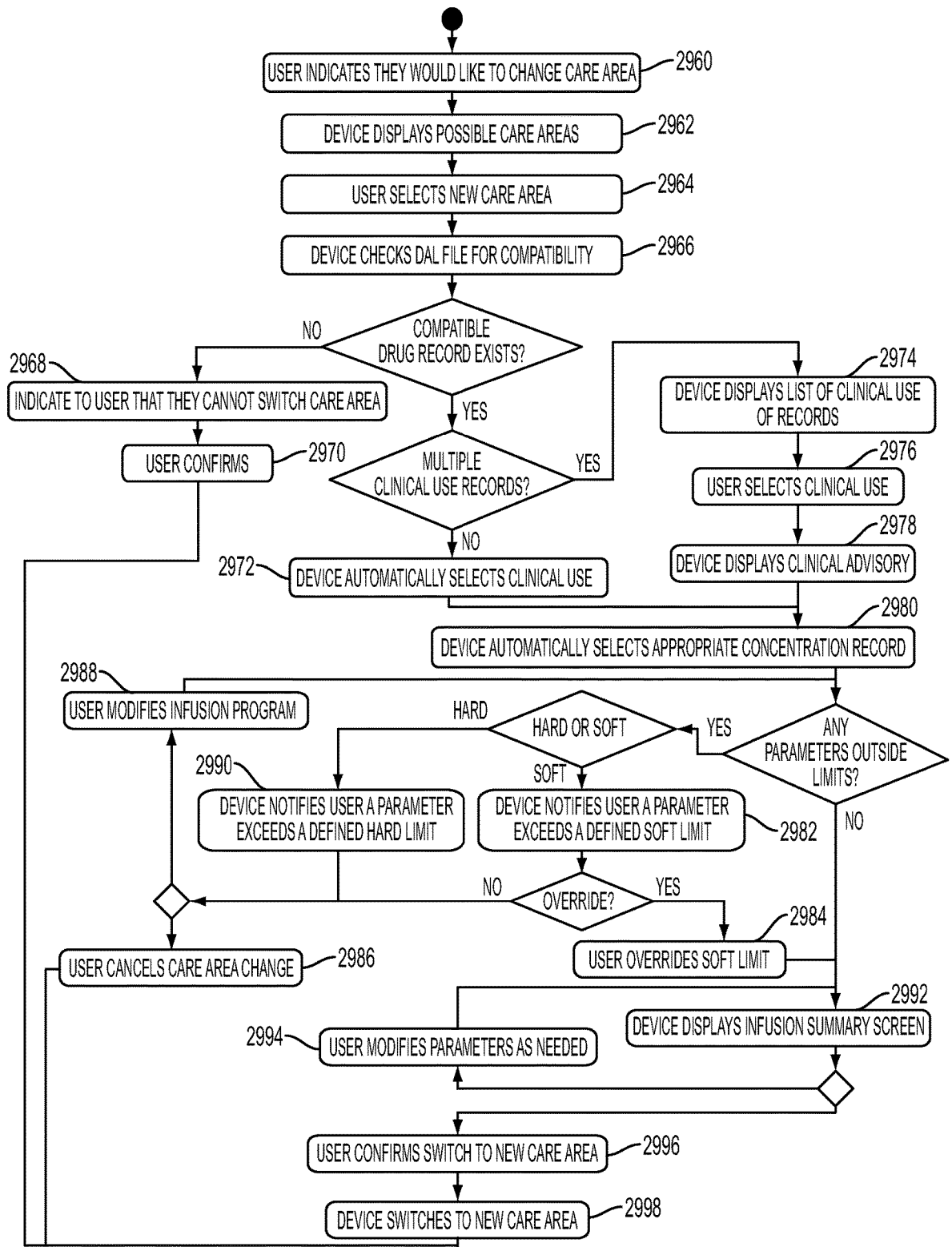
Figure 197:
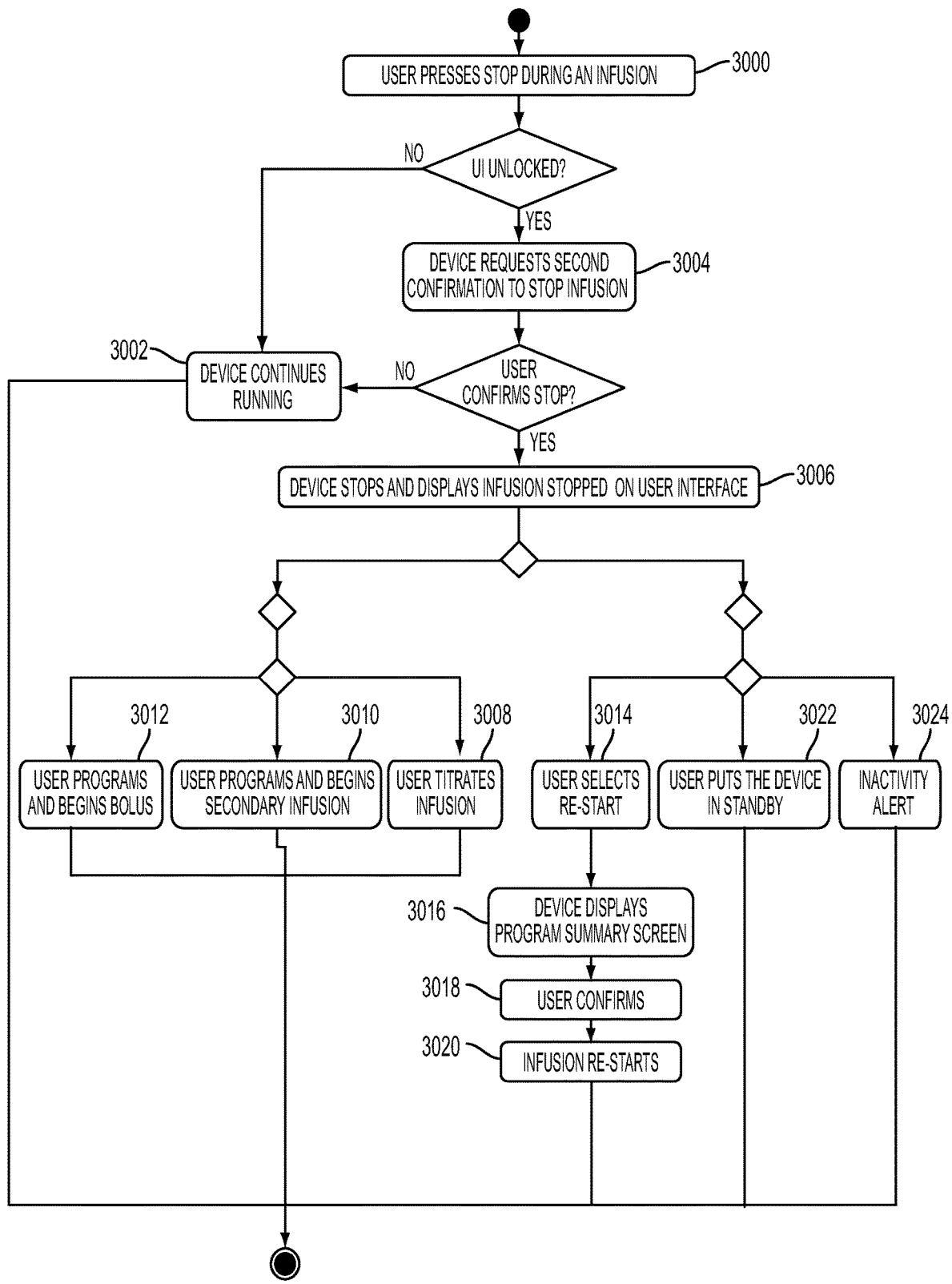
Figure 198:
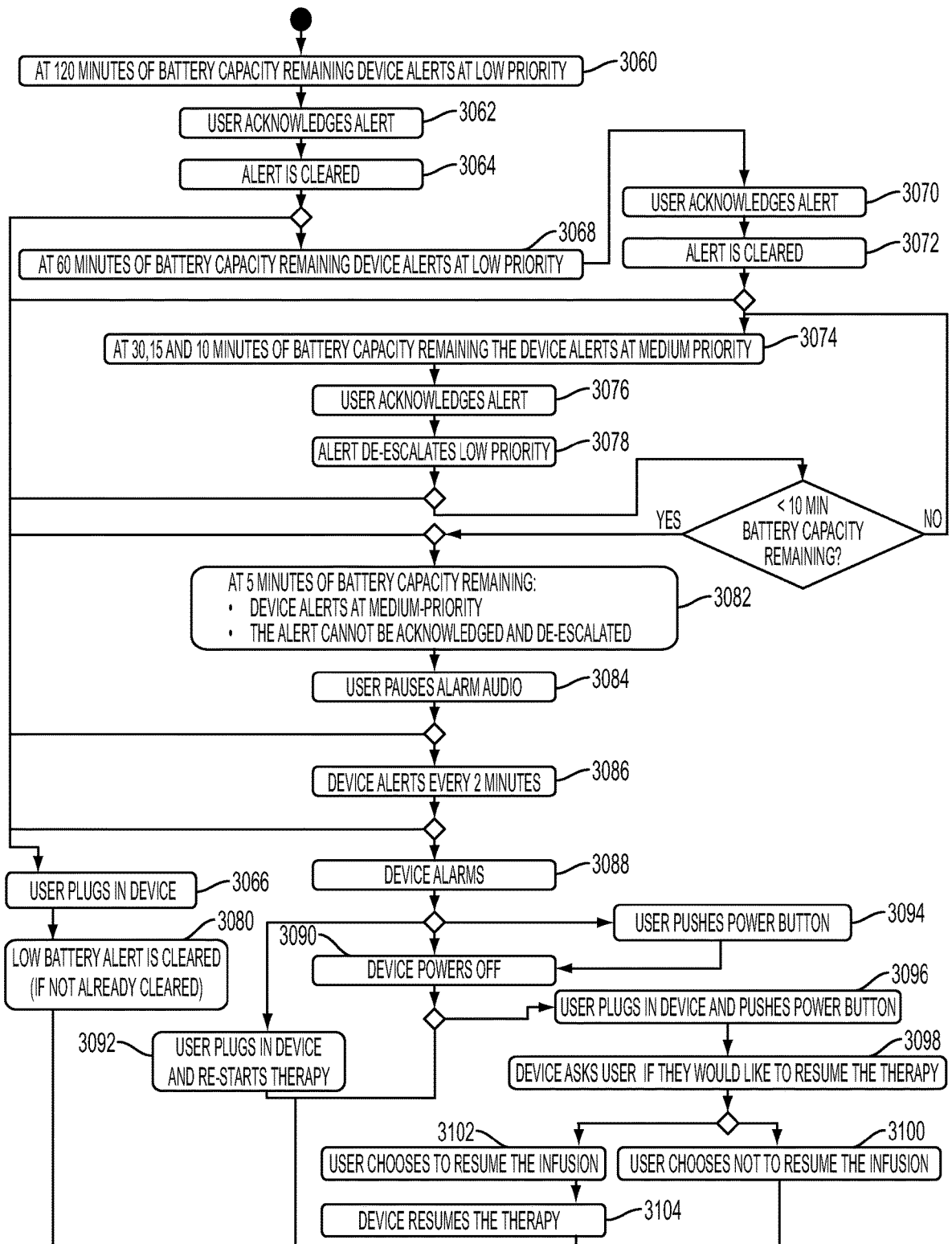
Figure 199:
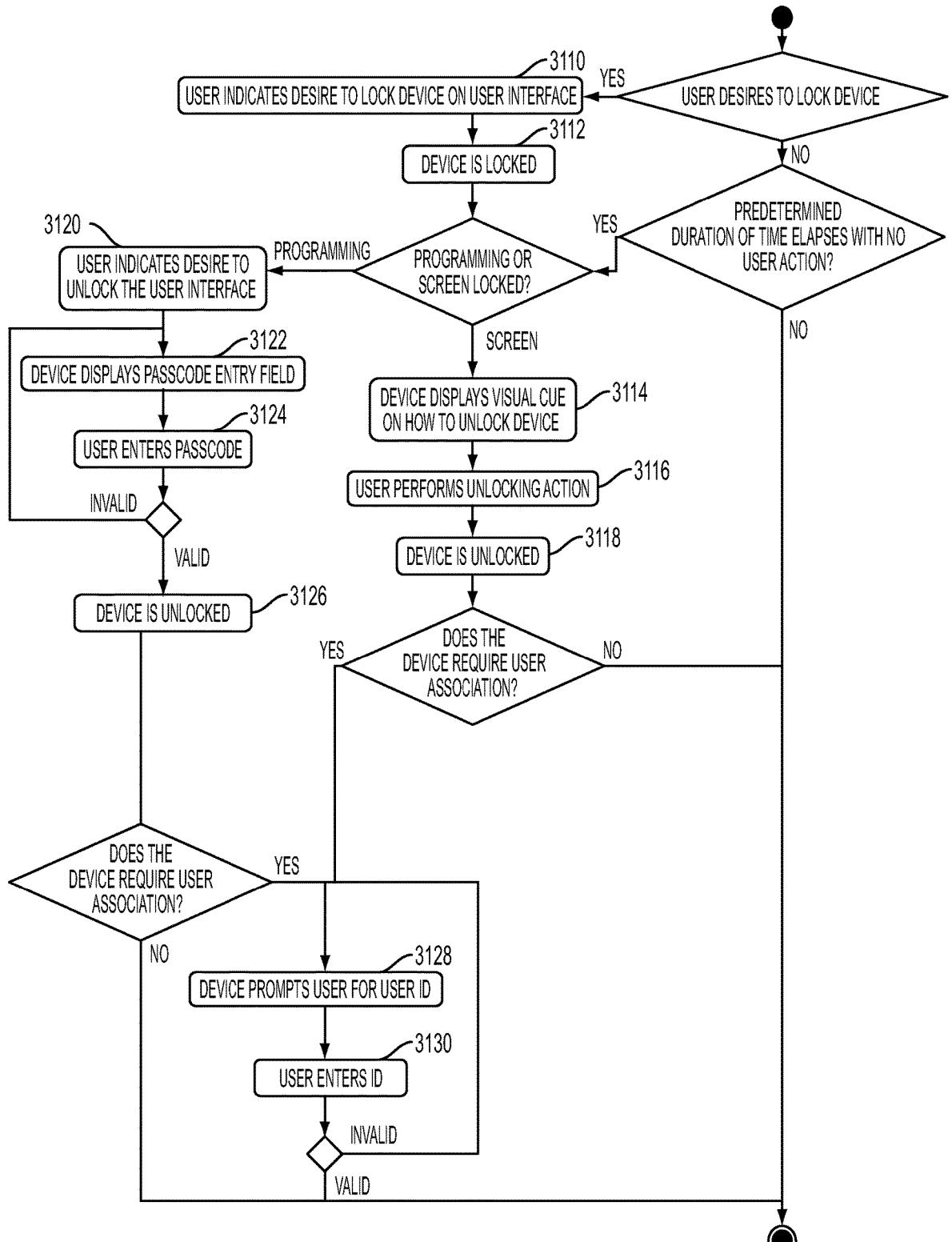
Figure 200:
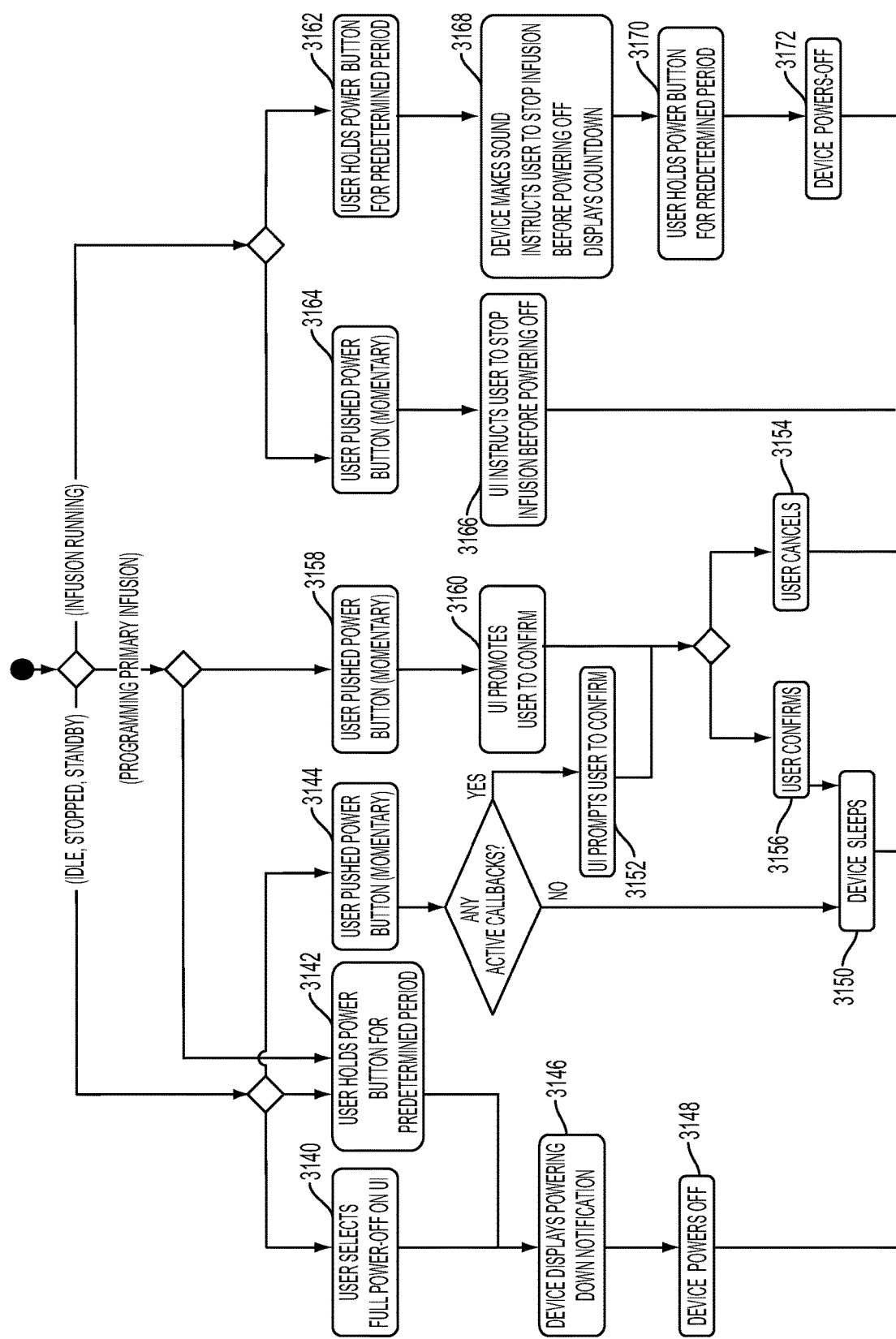
Figure 201:
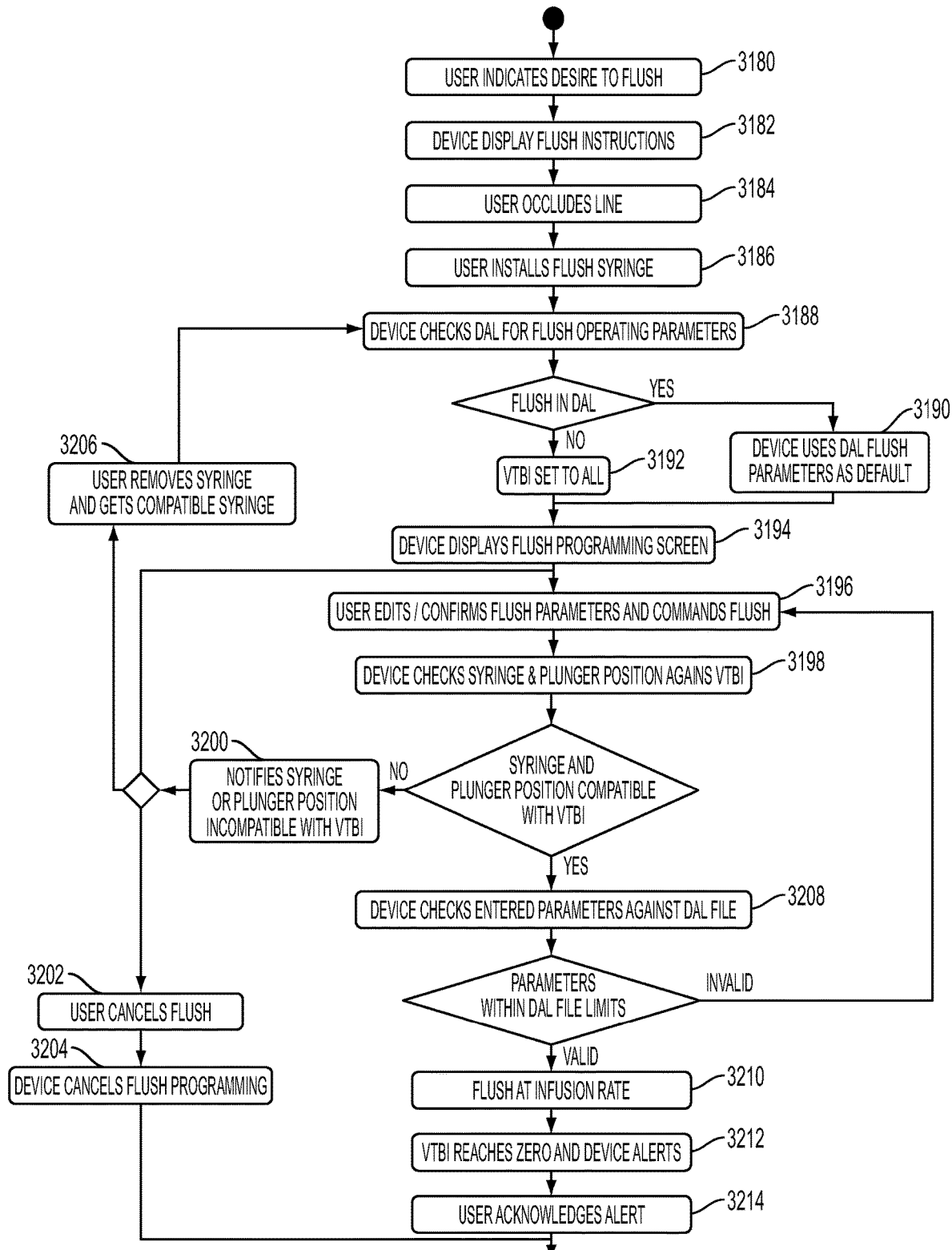
Figure 202:
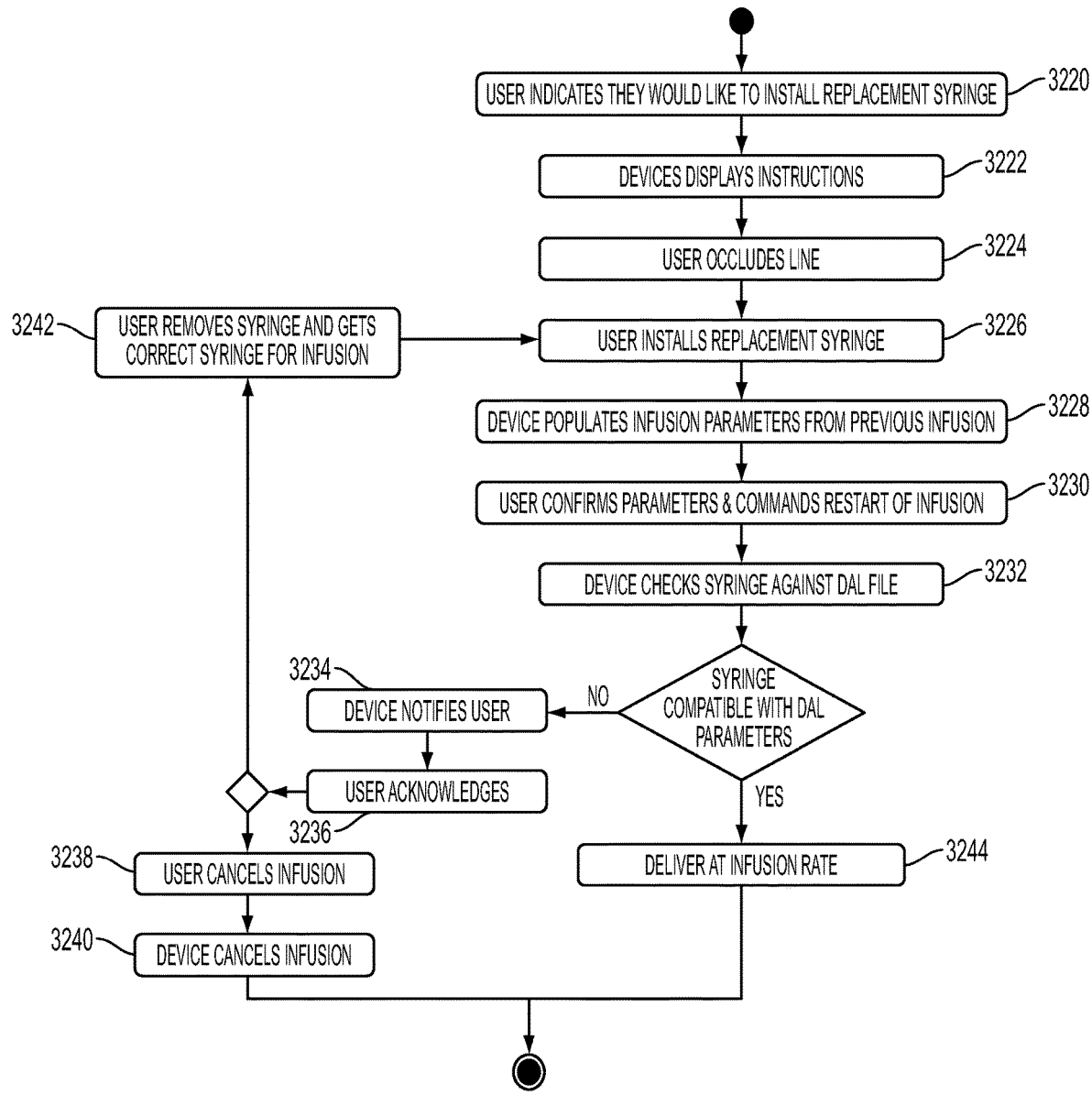
Figure 203:
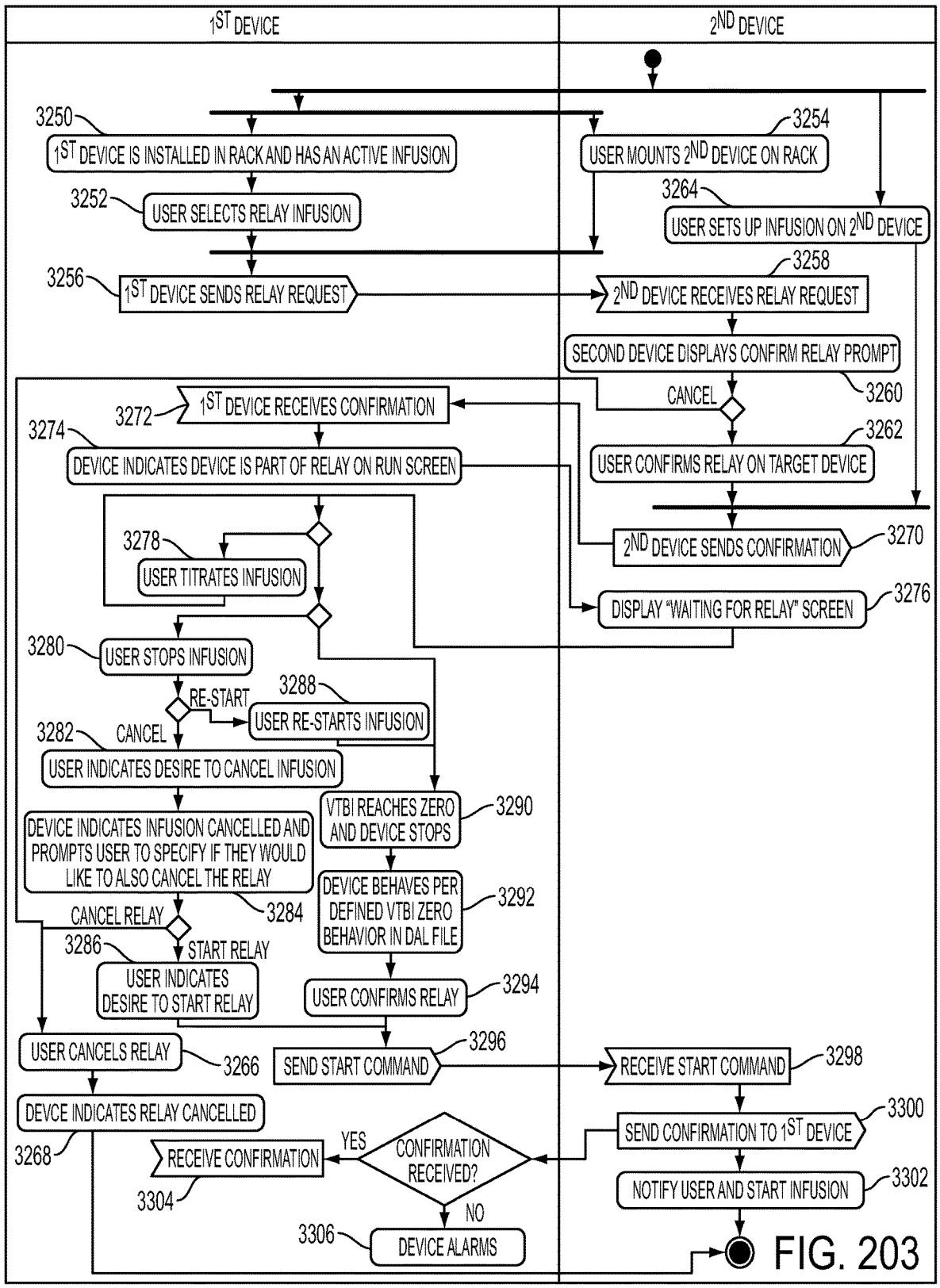
Figure 204:
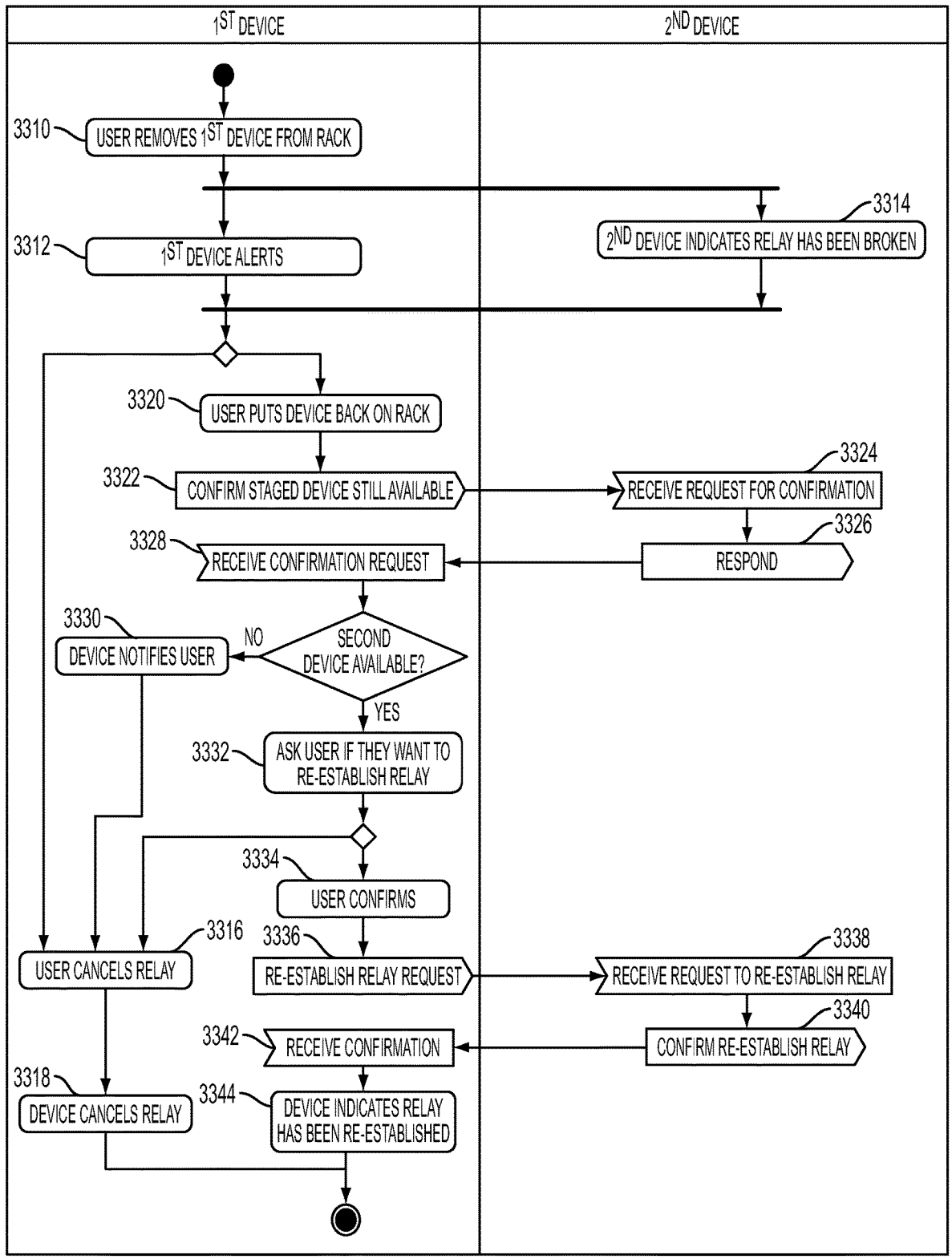
Figure 205:
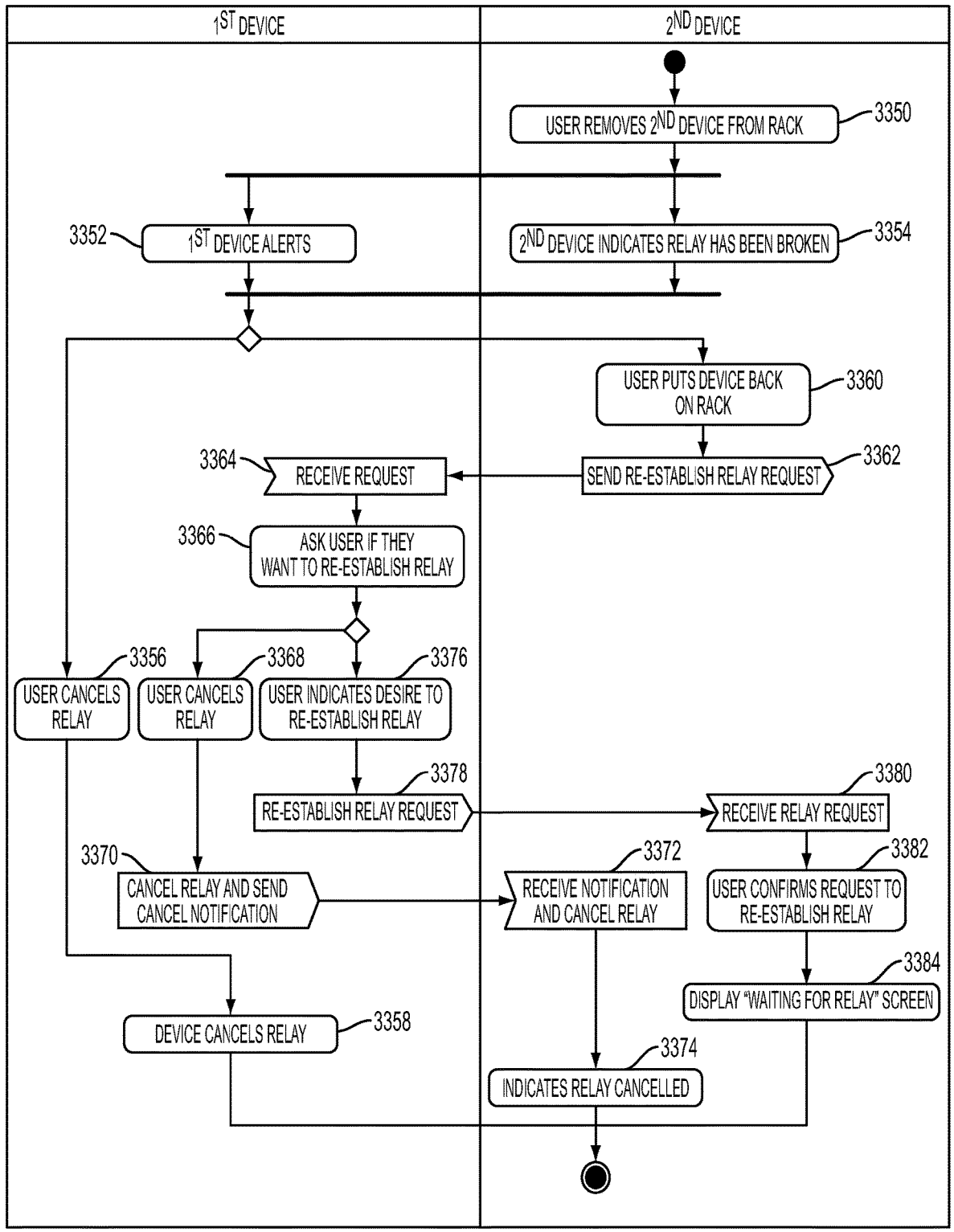
Figure 206:
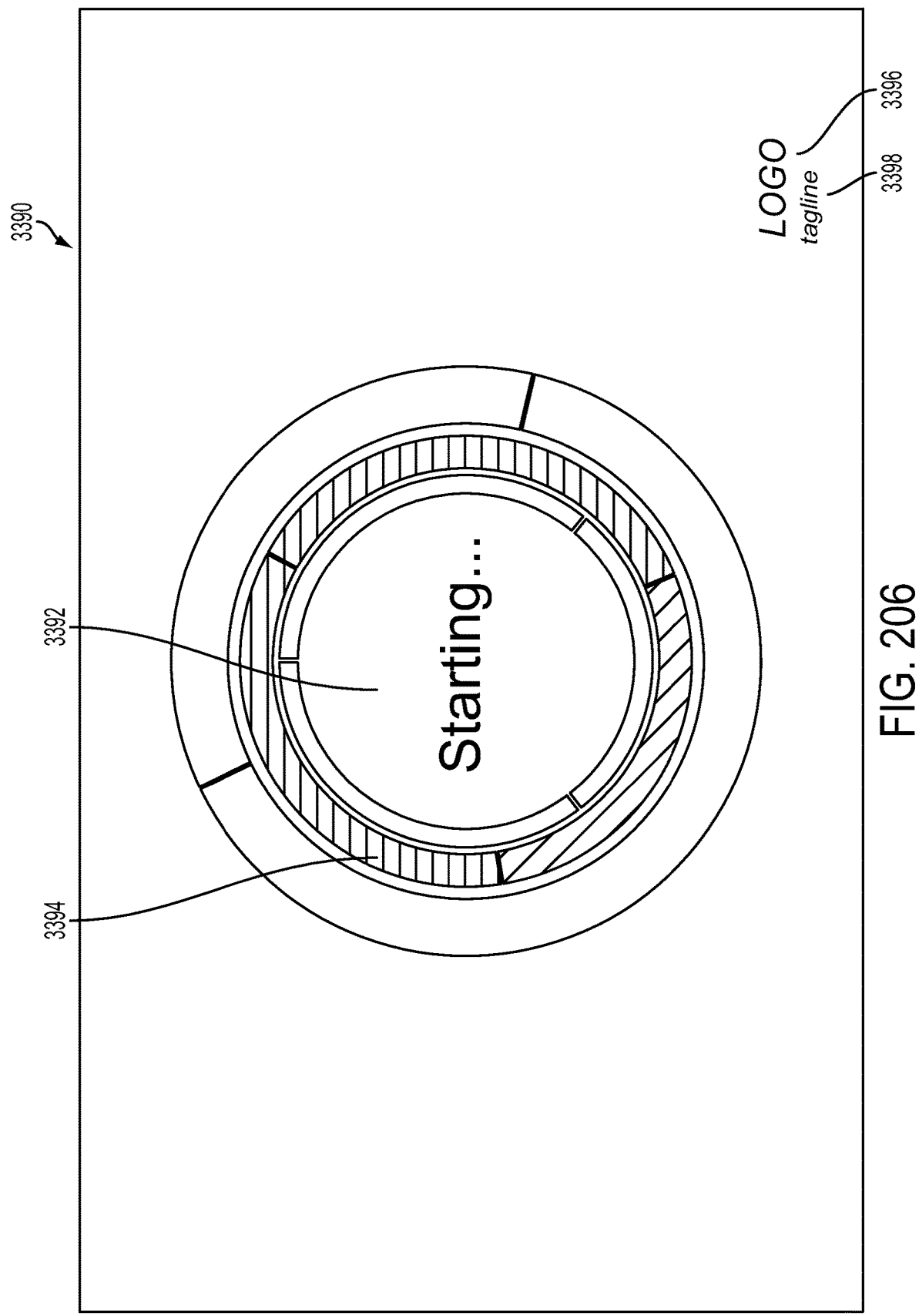
Figure 207:
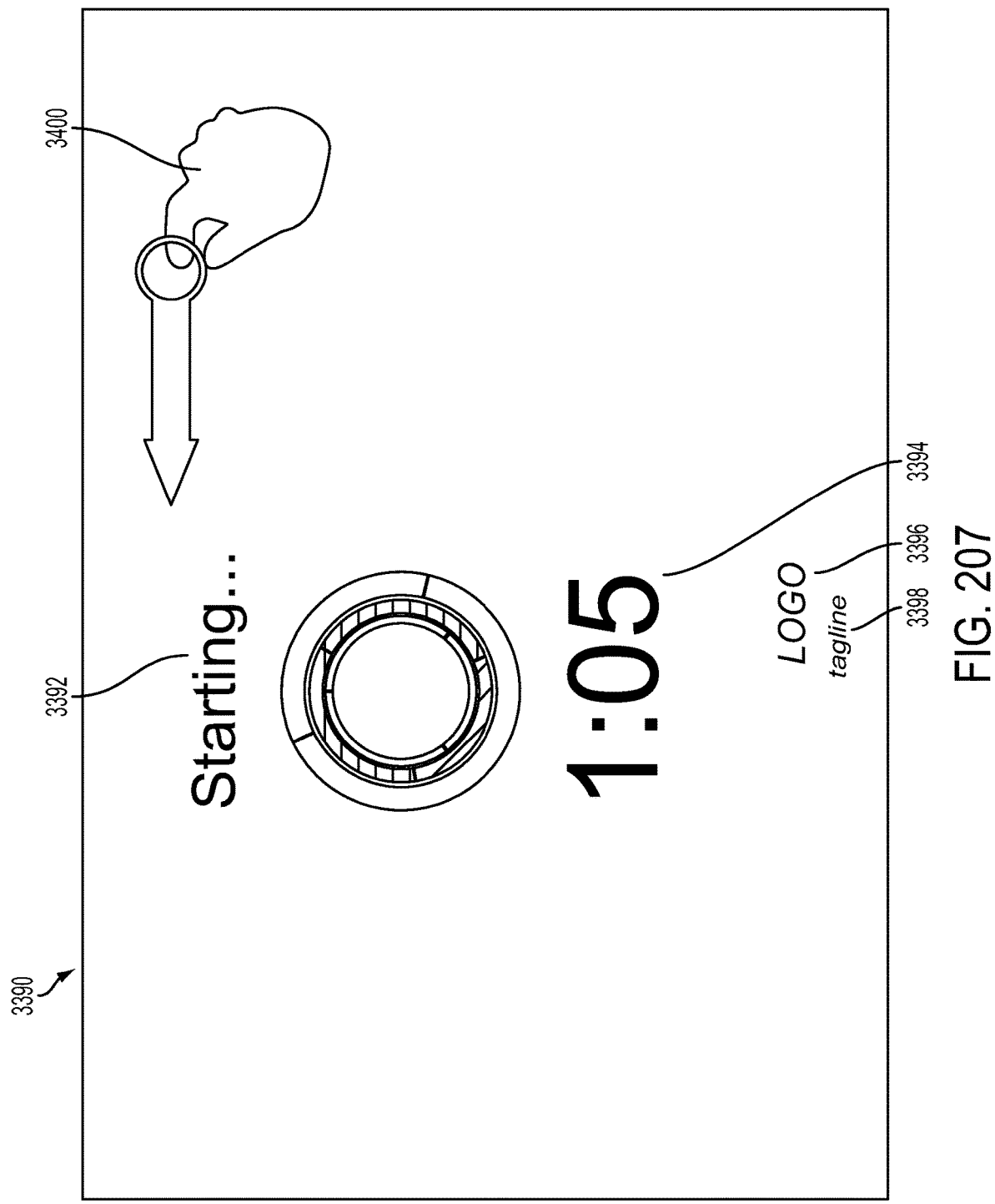
Figure 208:
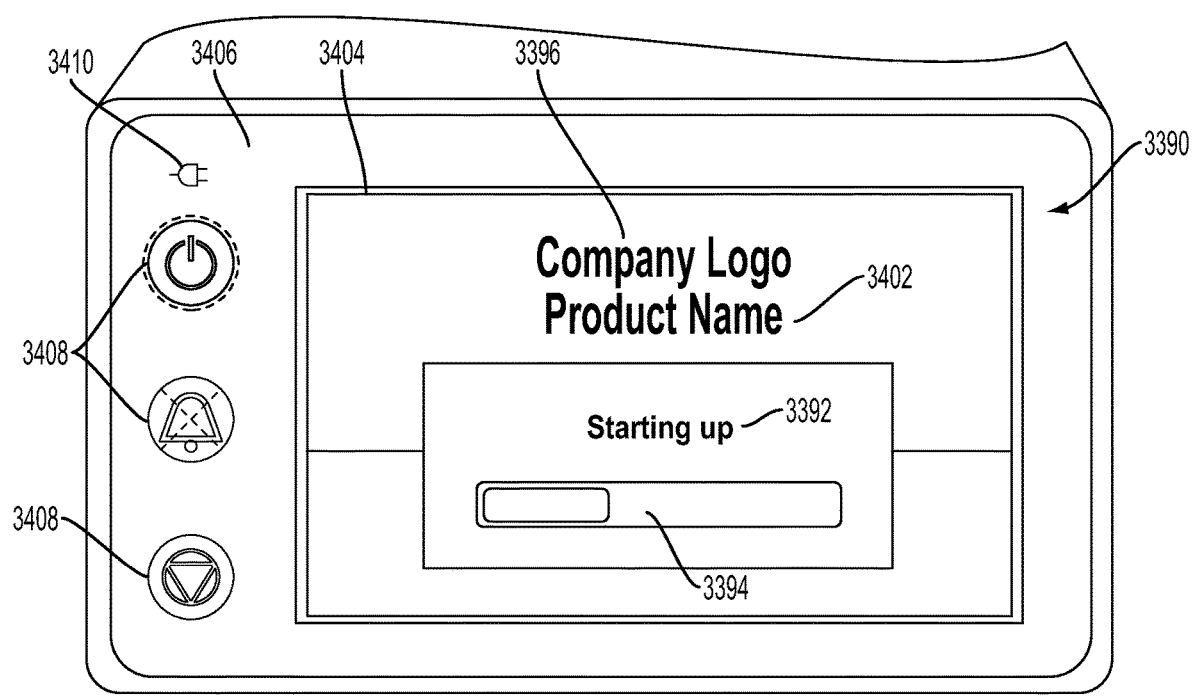
Figure 209:
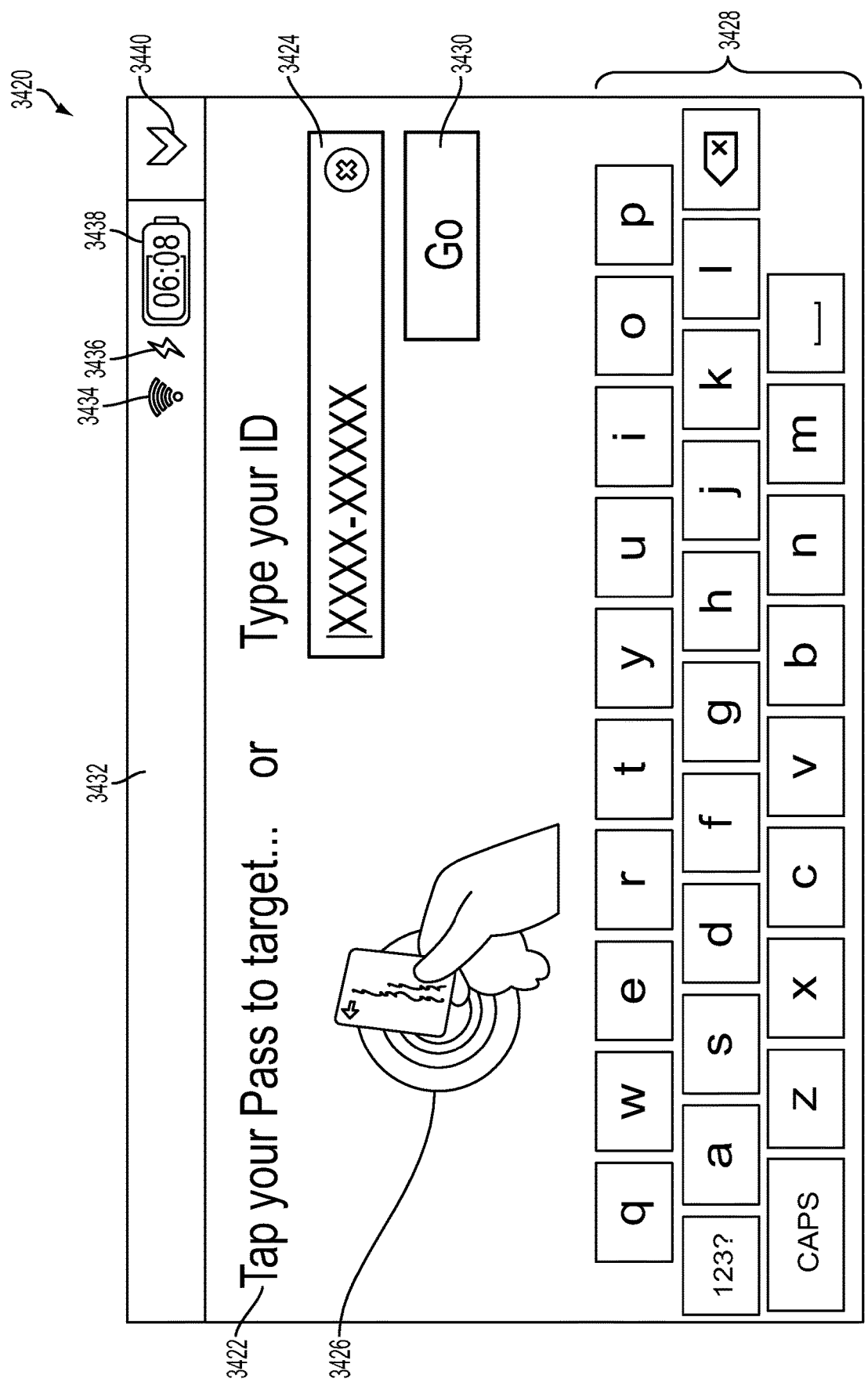
Figure 210:
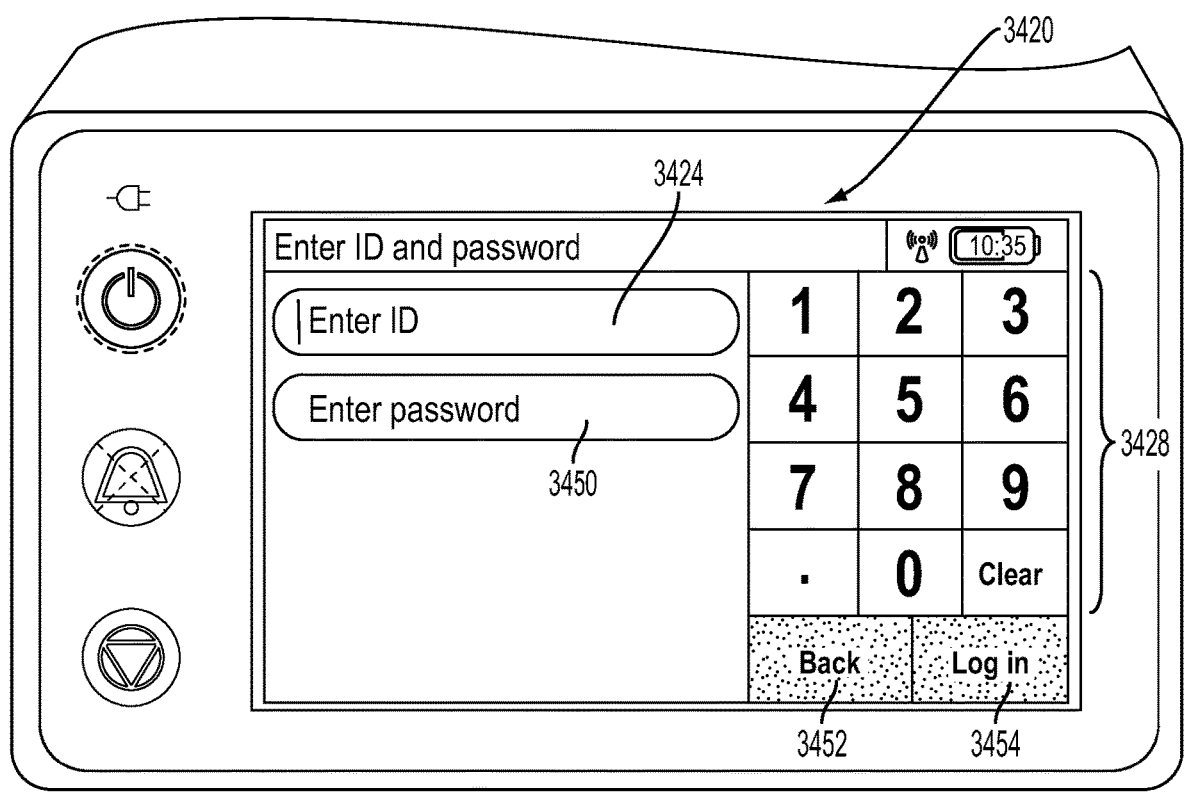
Figure 211:
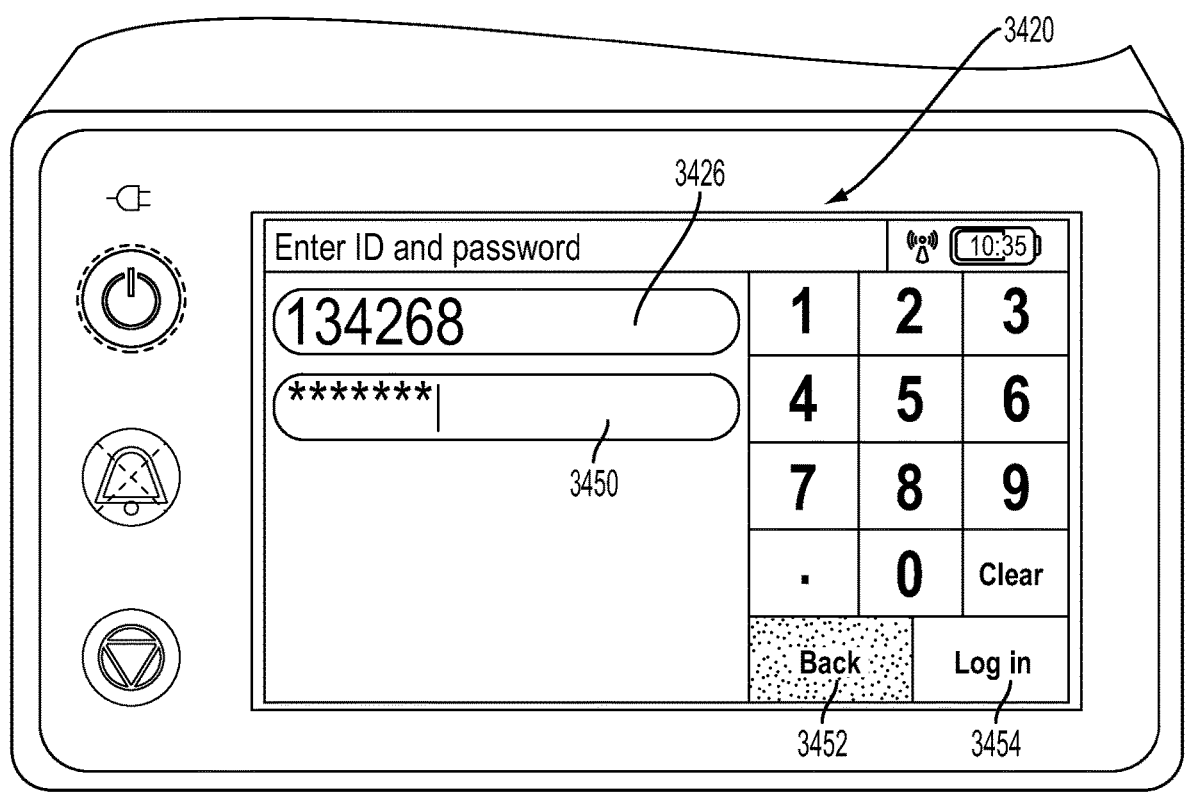
Figure 212:
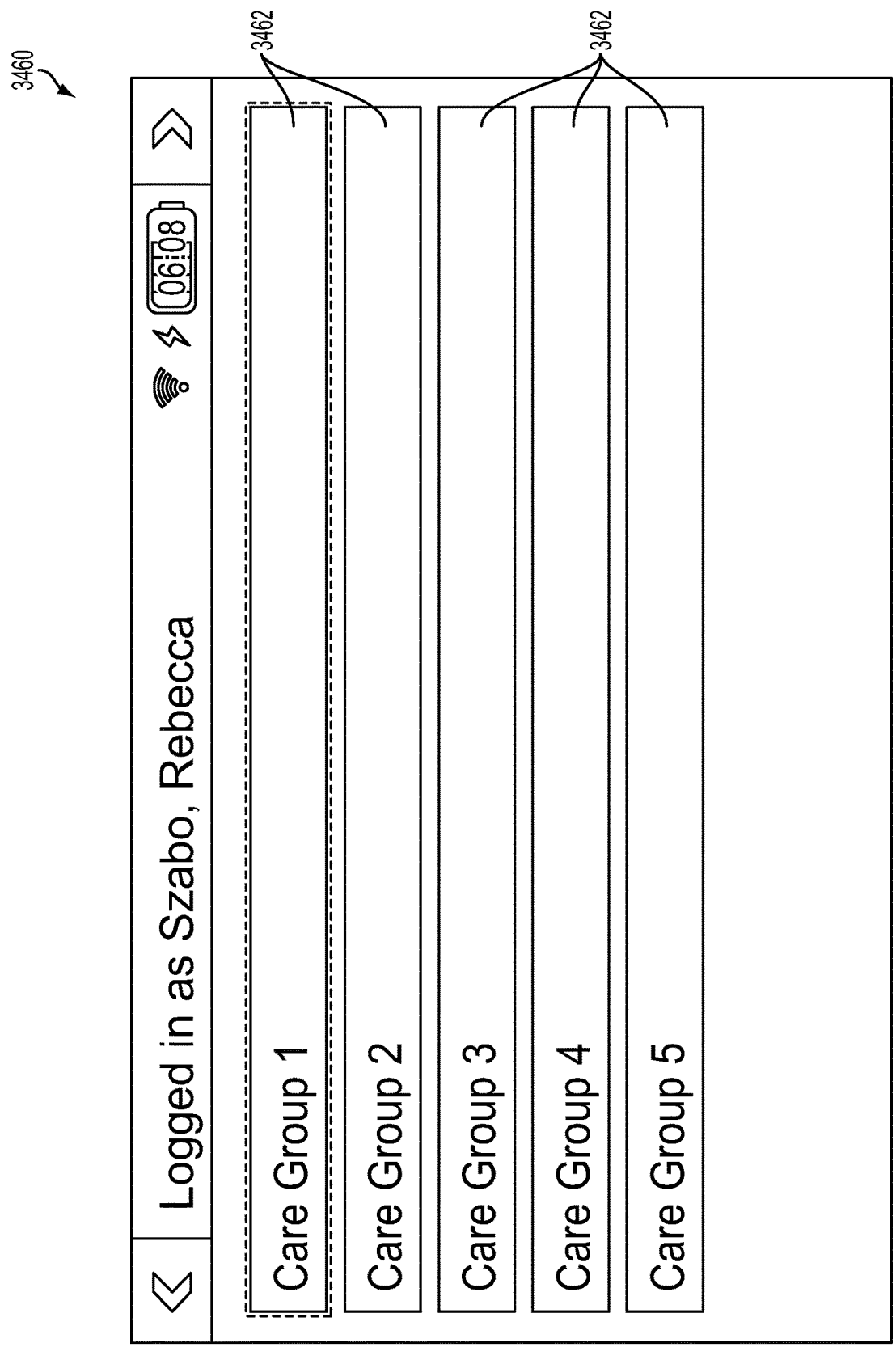
Figure 213:
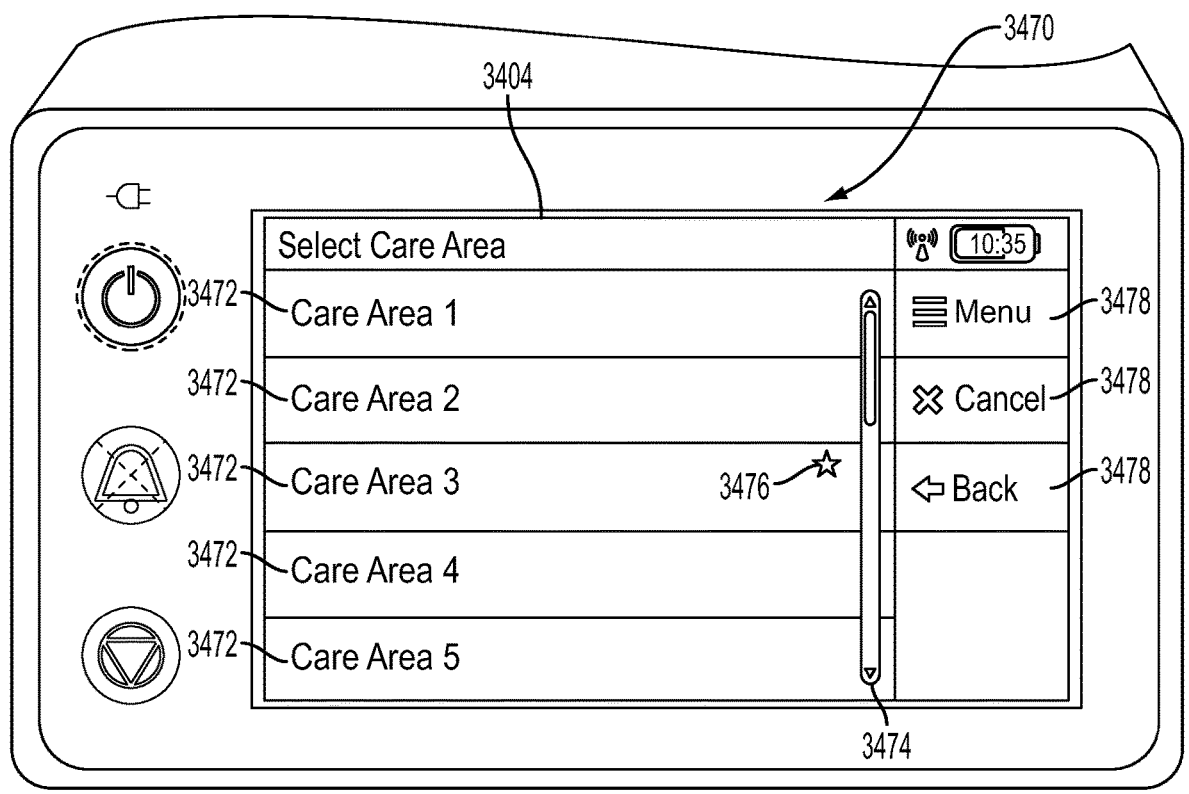
Figure 214:
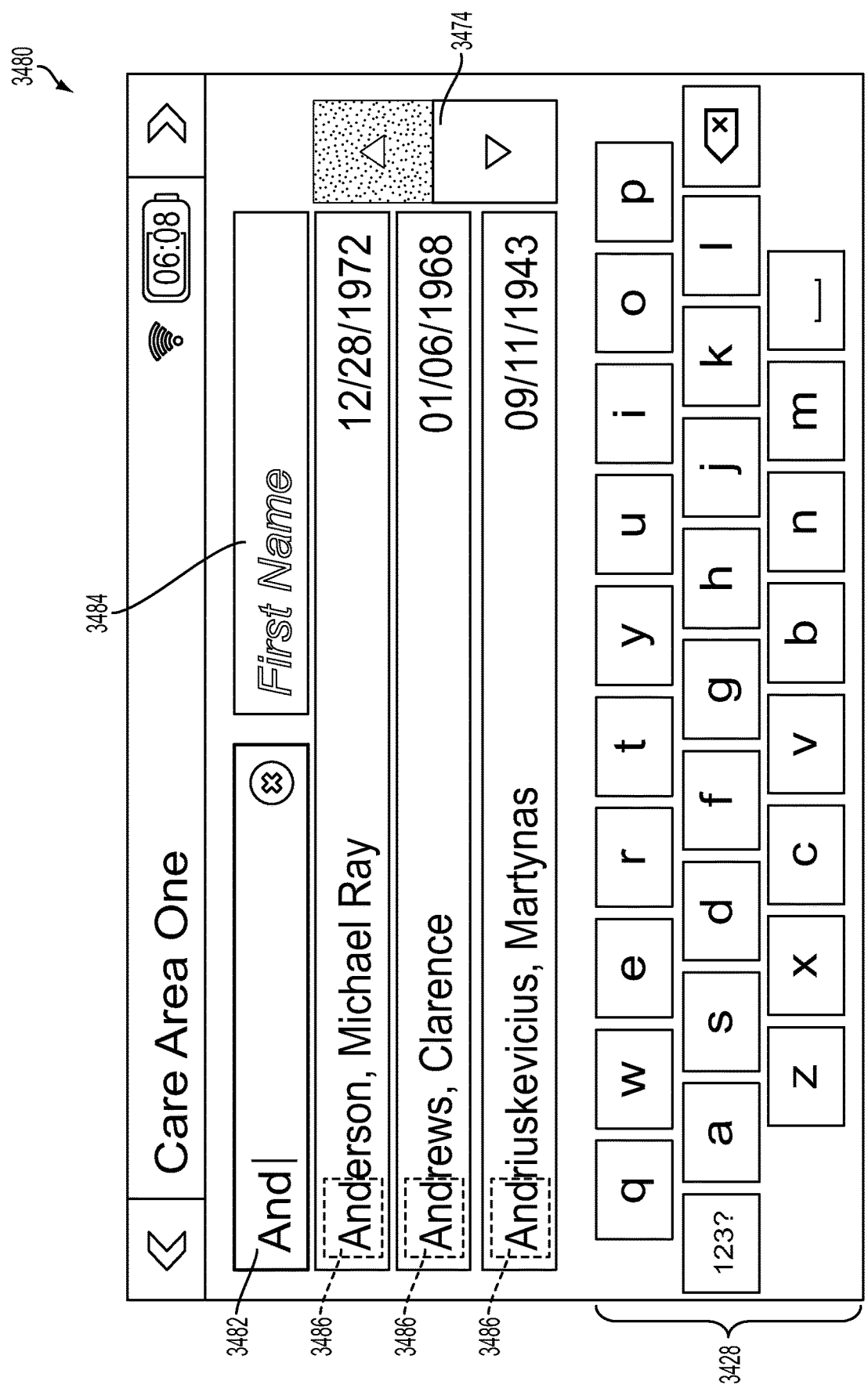
Figure 215:
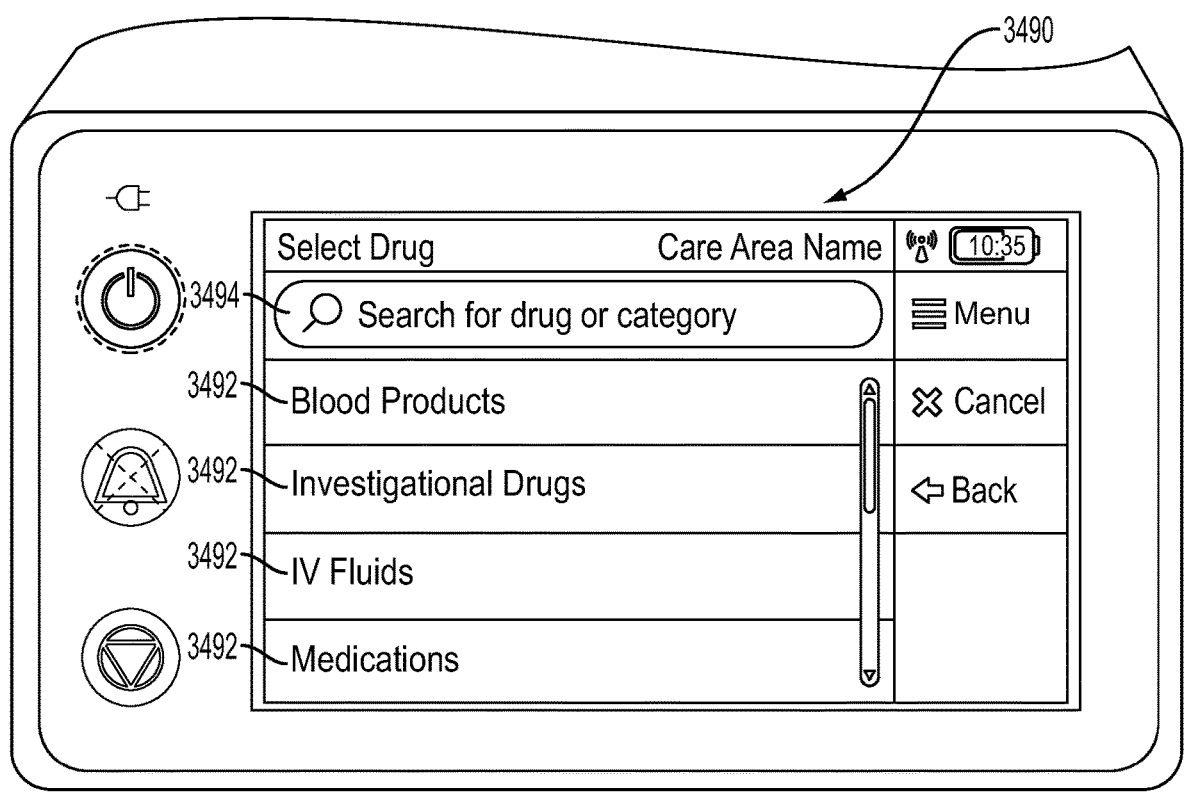
Figure 216:
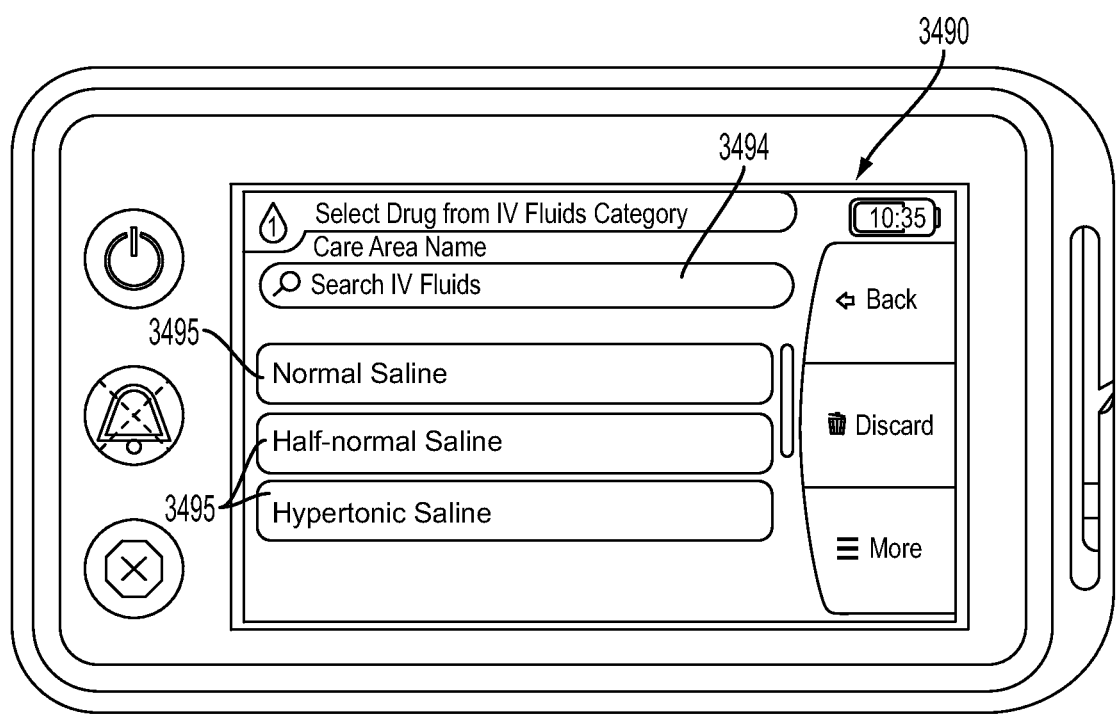
Figure 217:
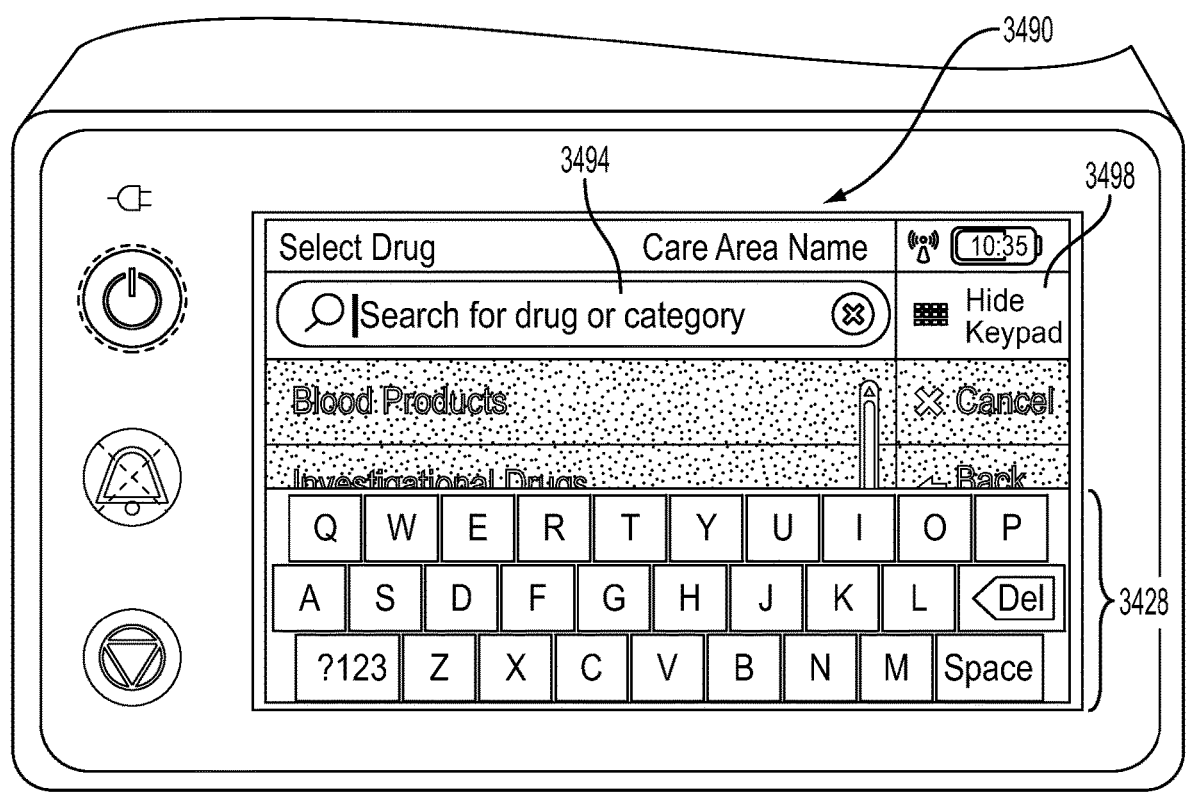
Figure 218:
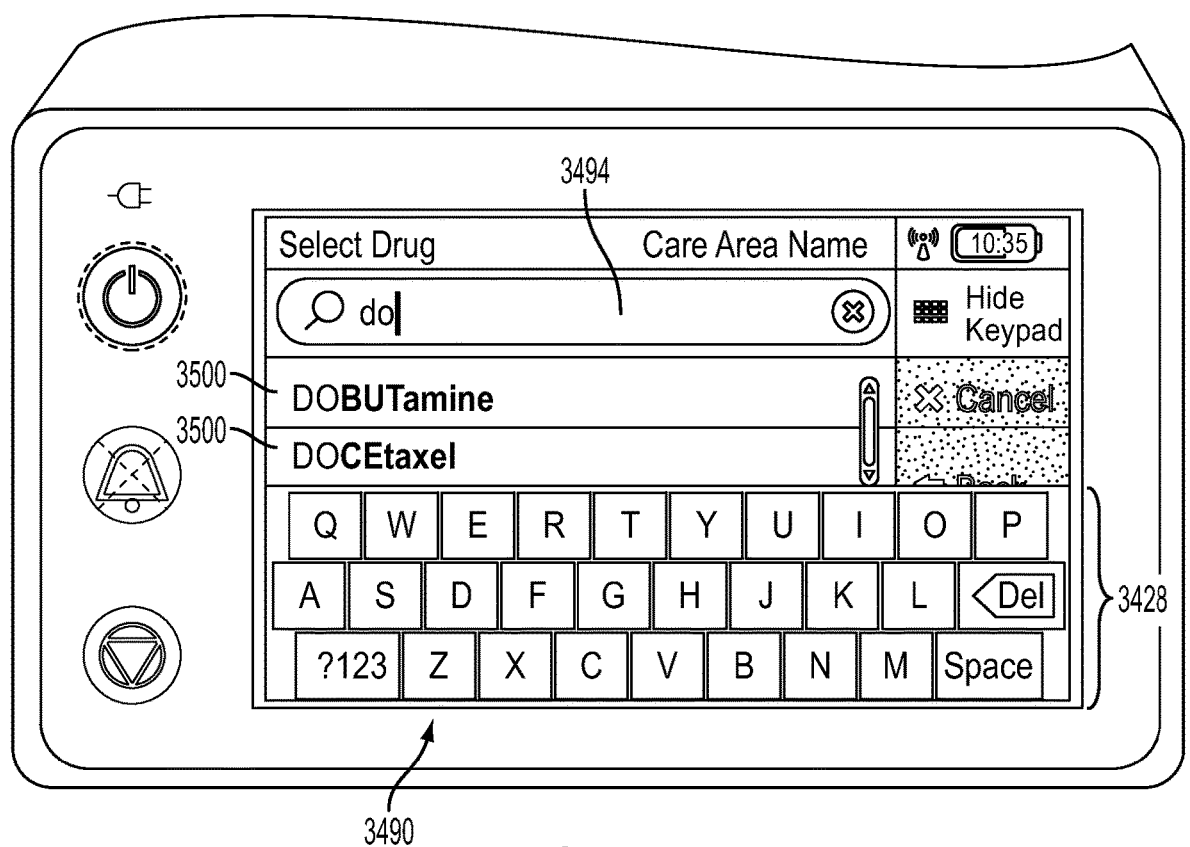
Figure 219:
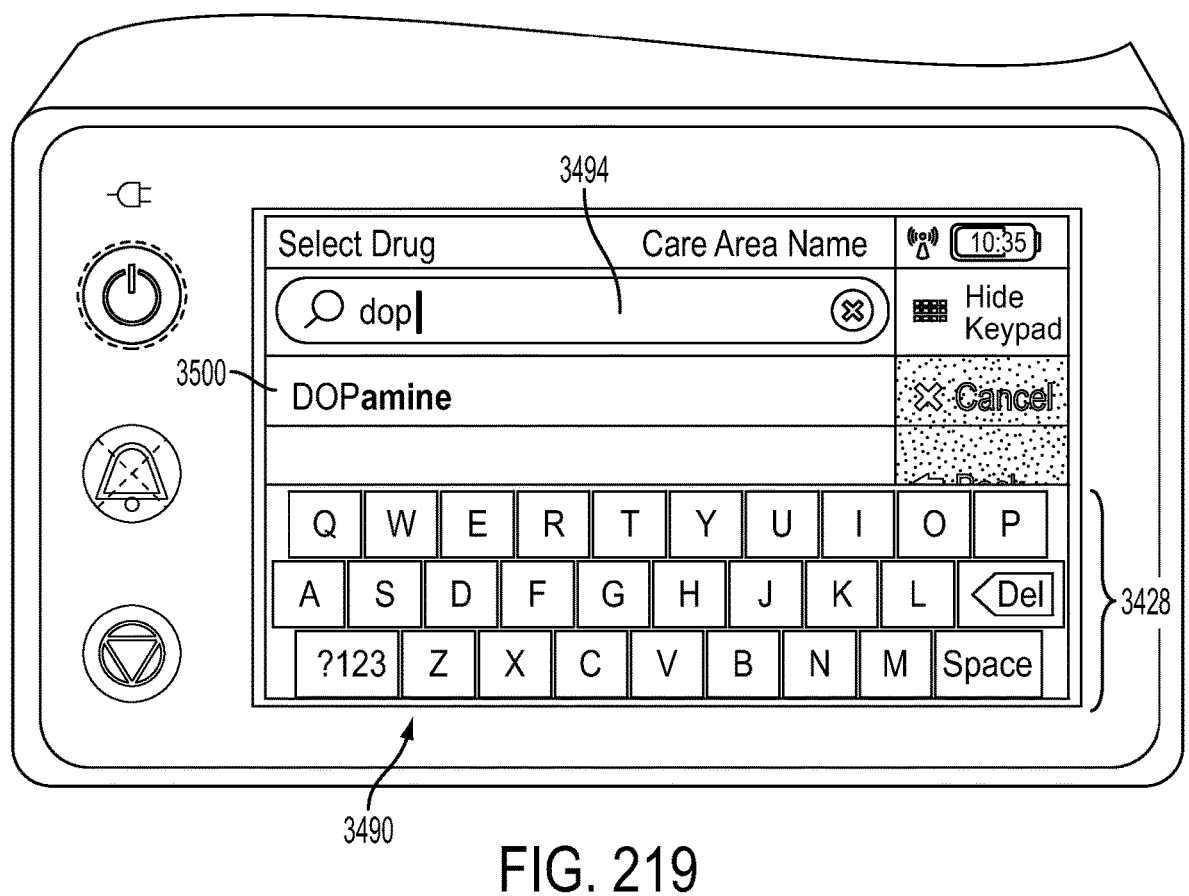
Figure 220:
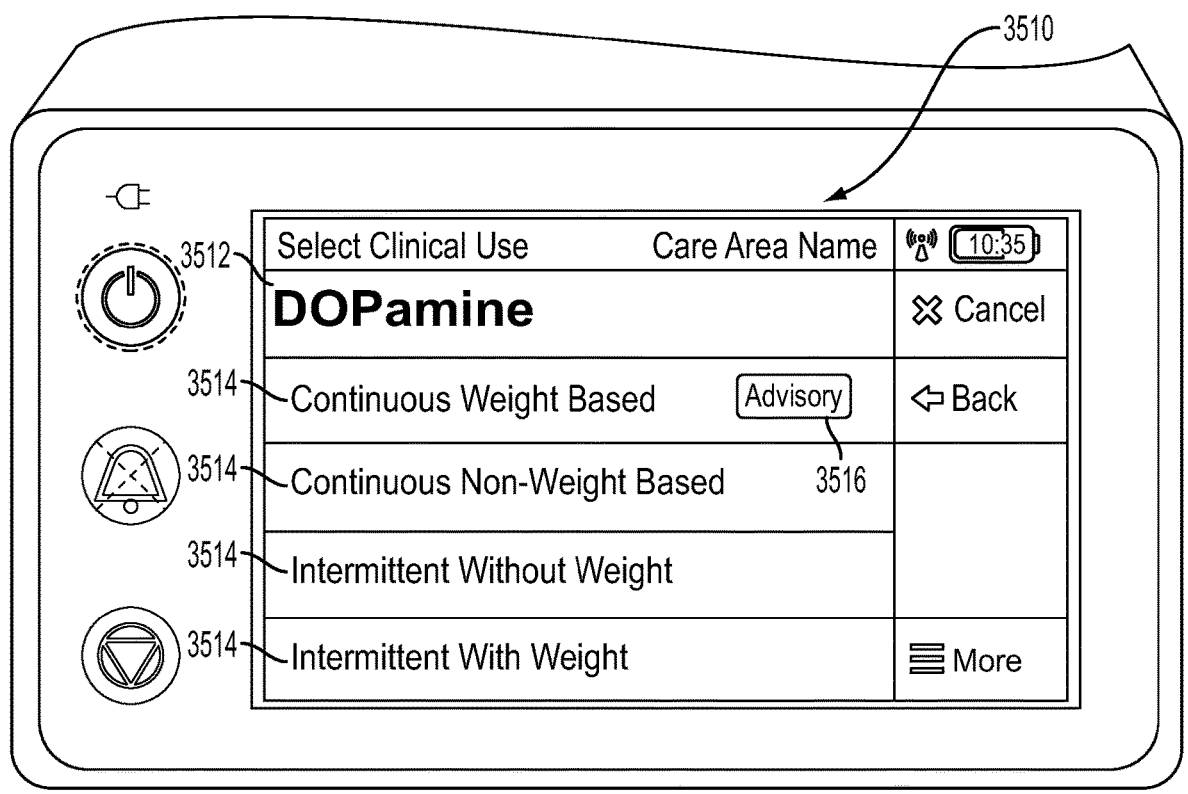
Figure 221:
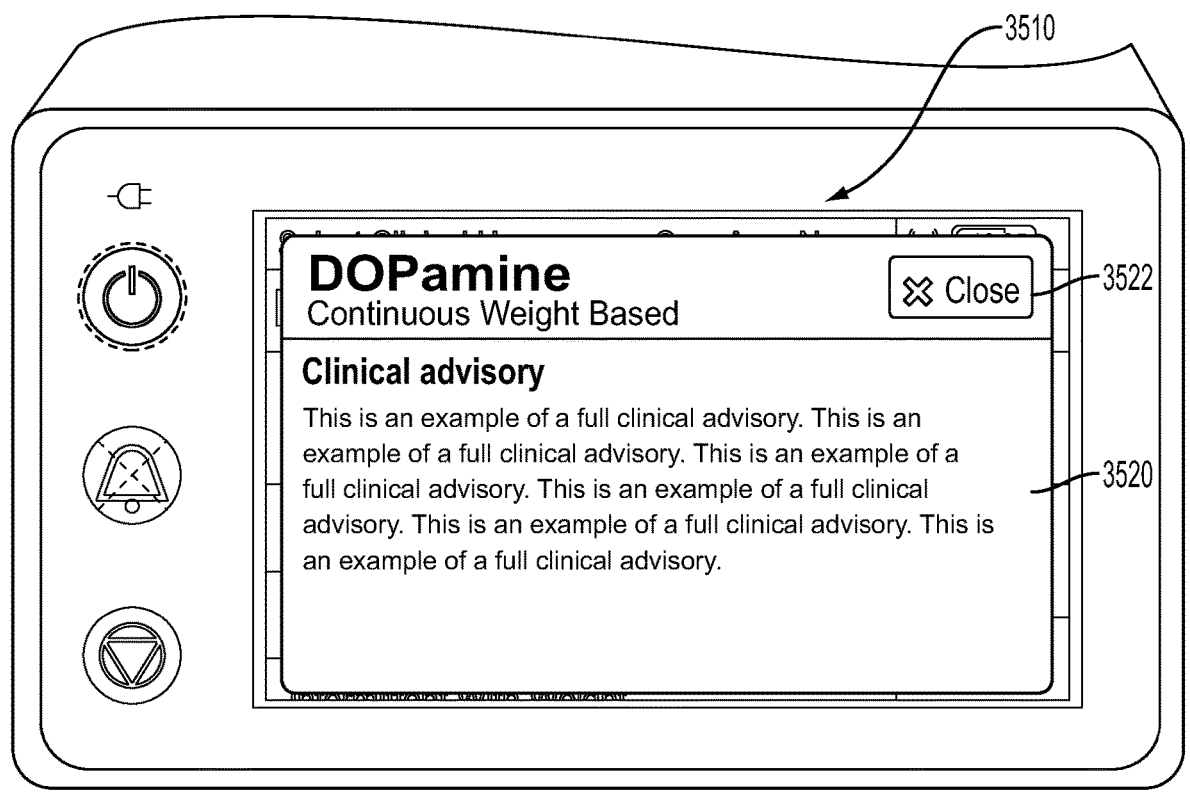
Figure 222:
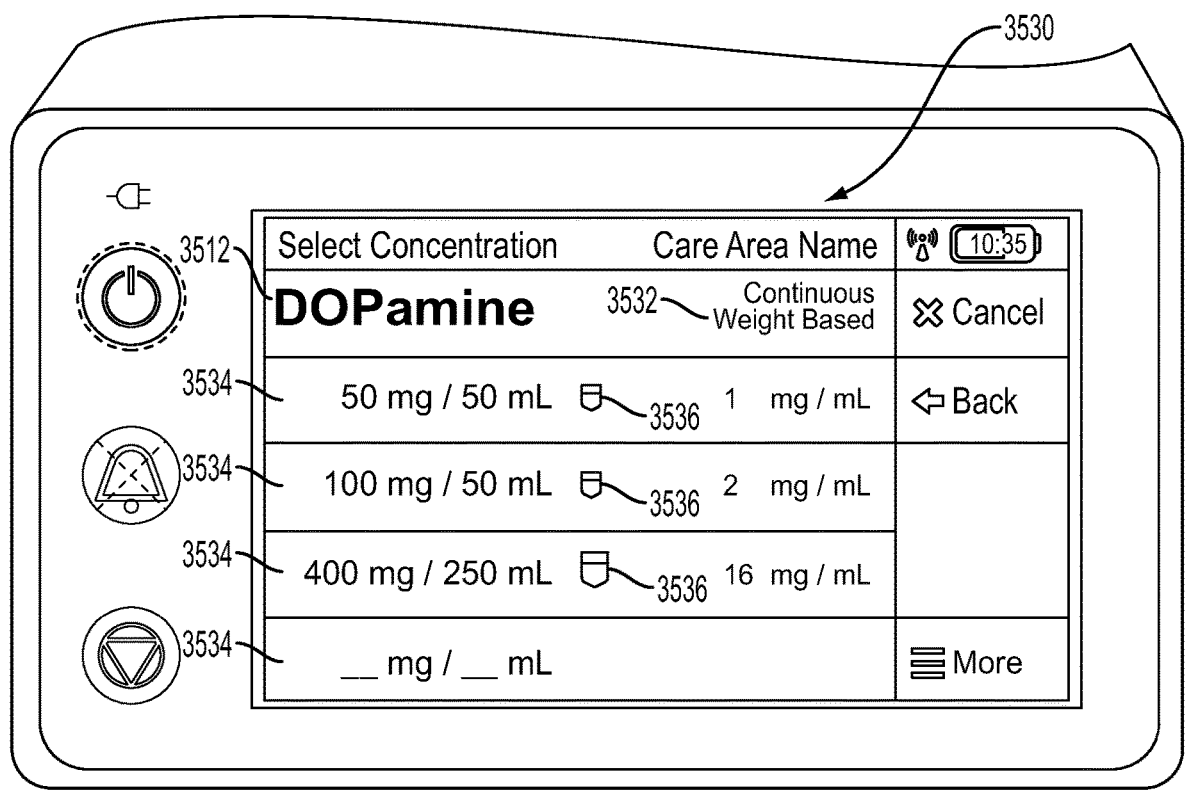
Figure 223:
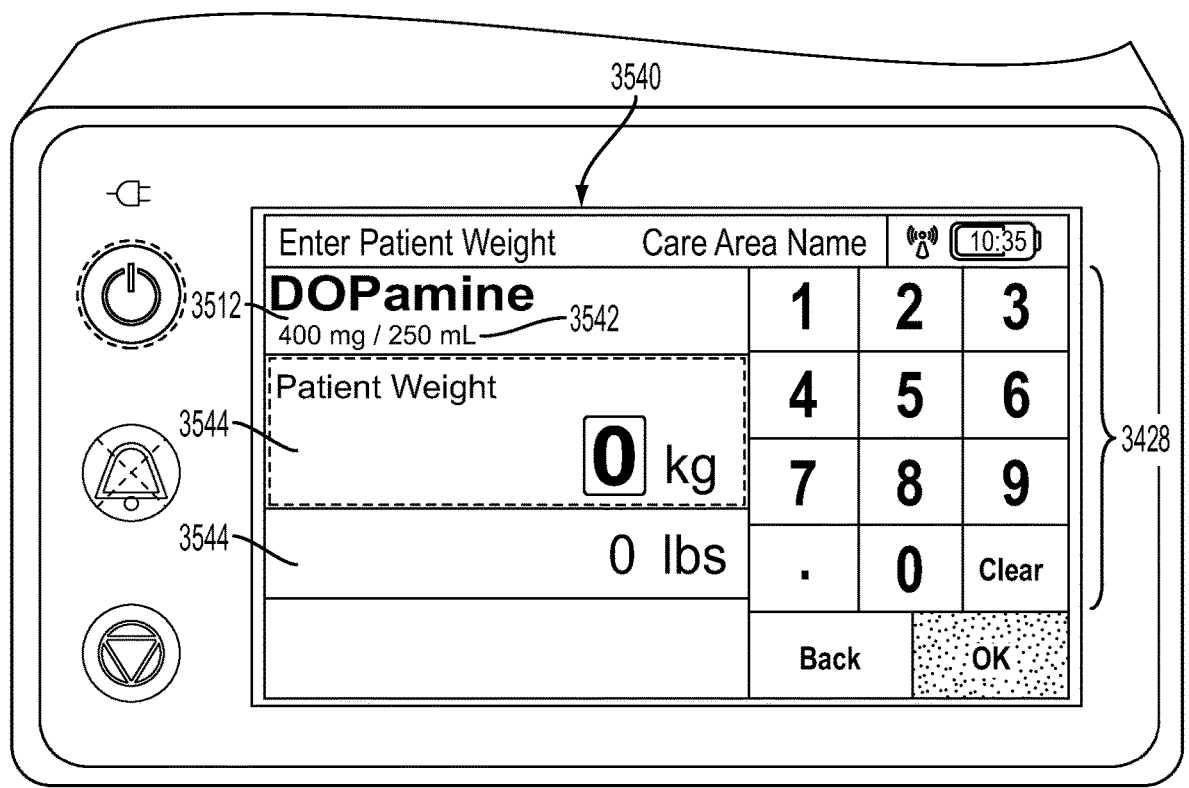
Figure 224:
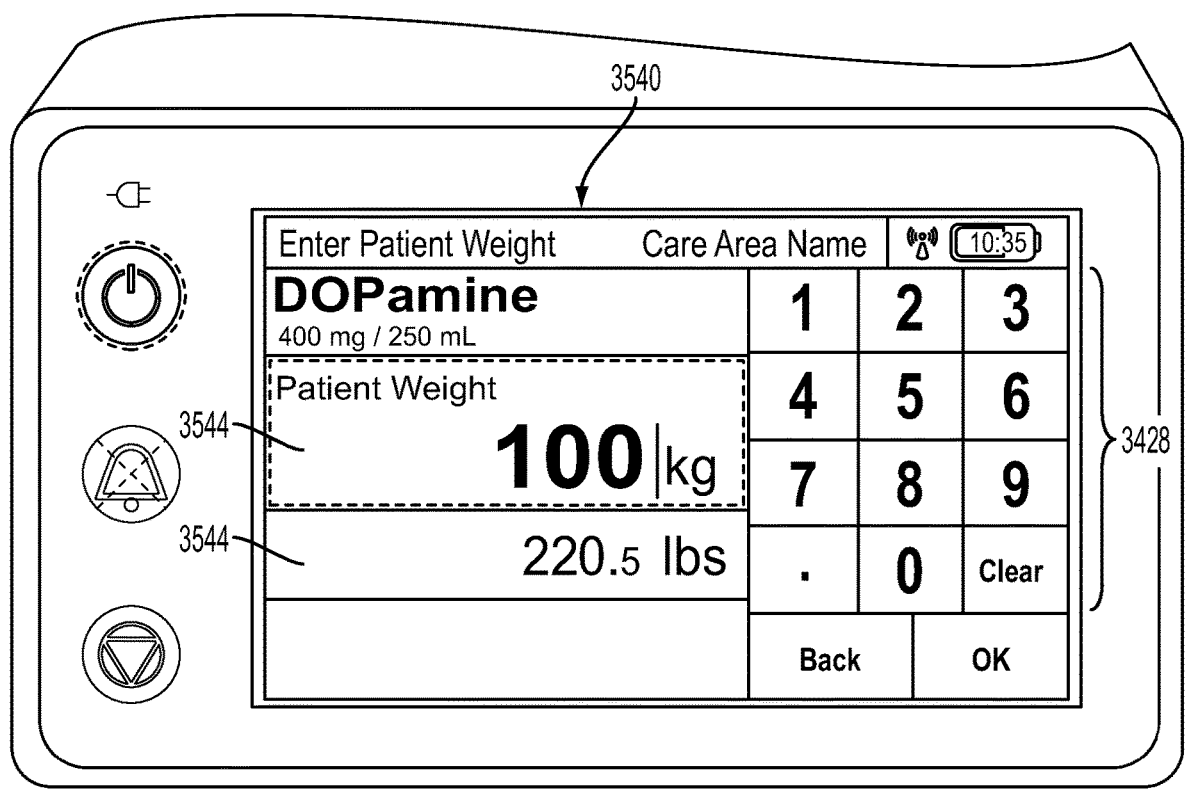
Figure 225:
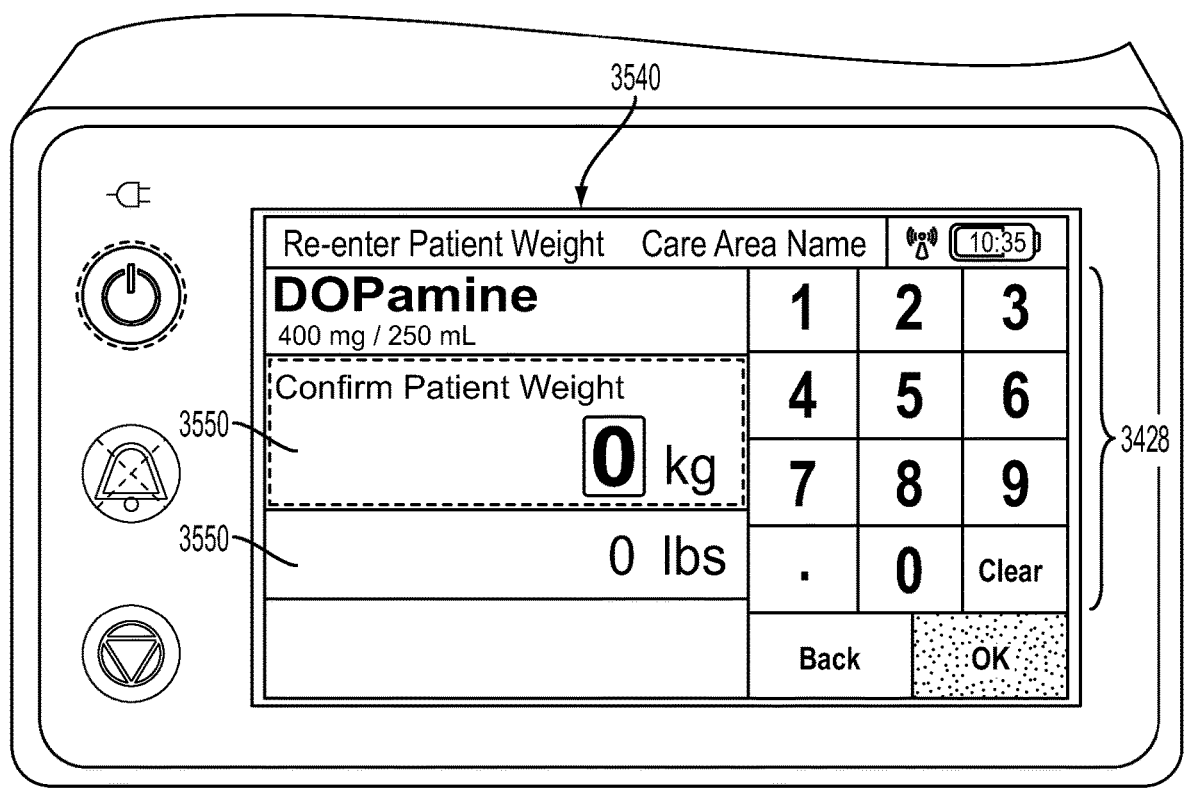
Figure 226:
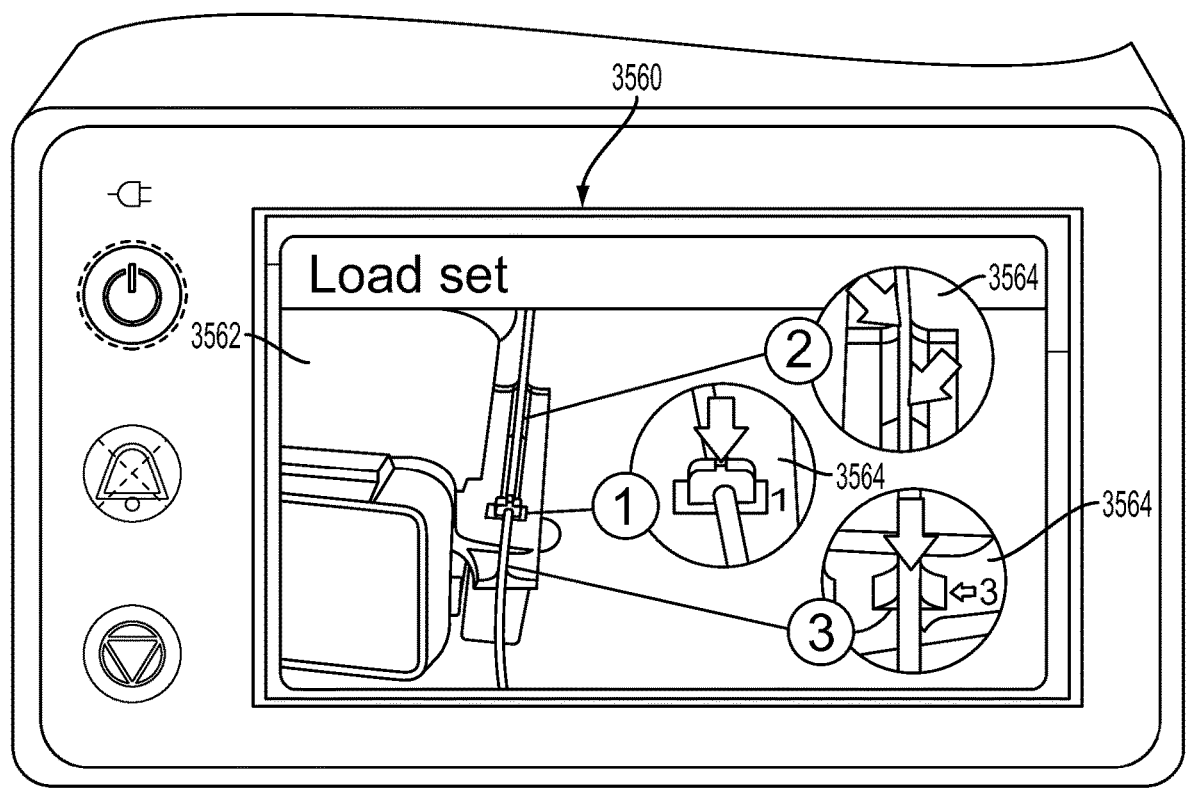
Figure 227:
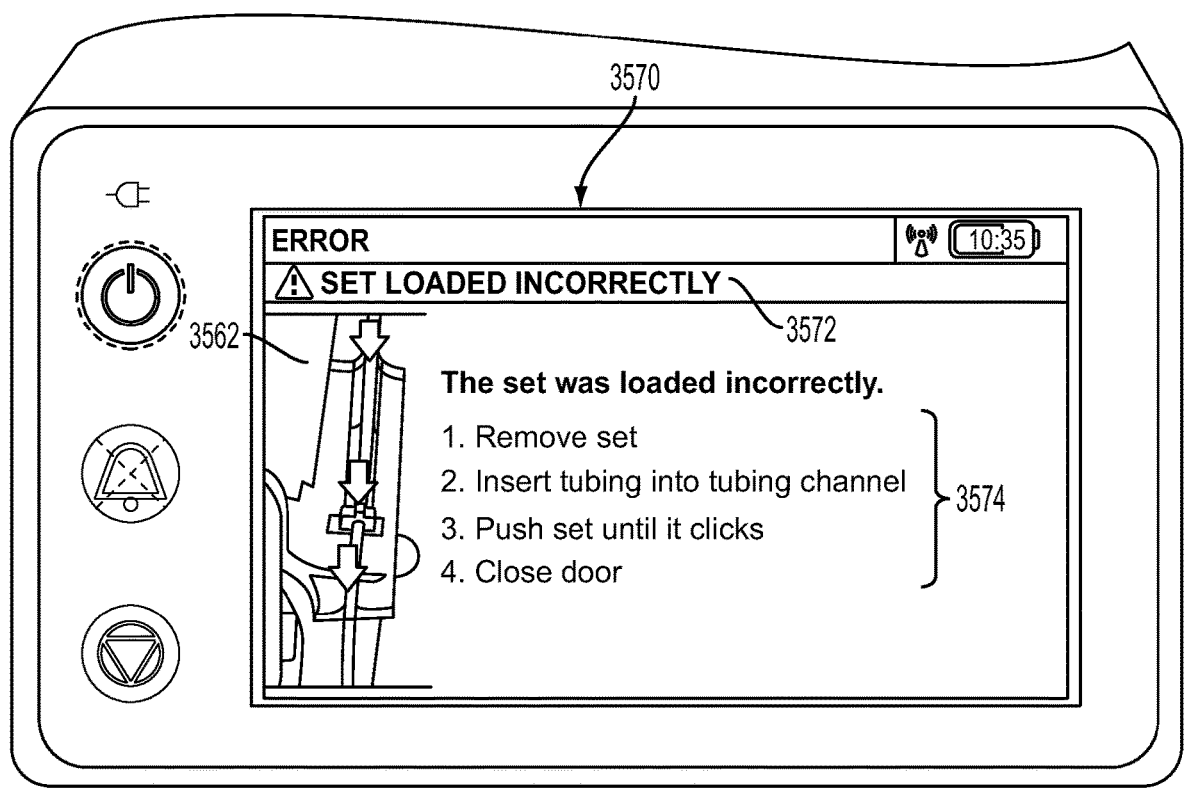
Figure 228:
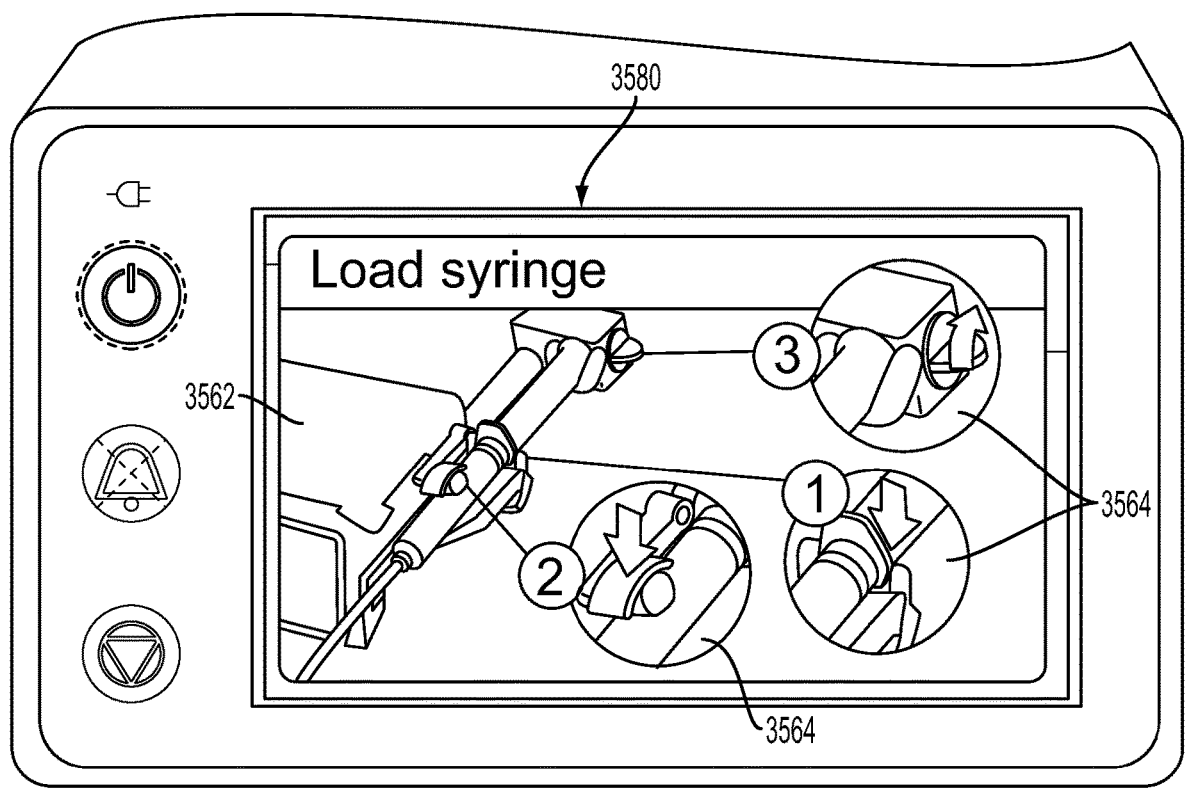
Figure 229:
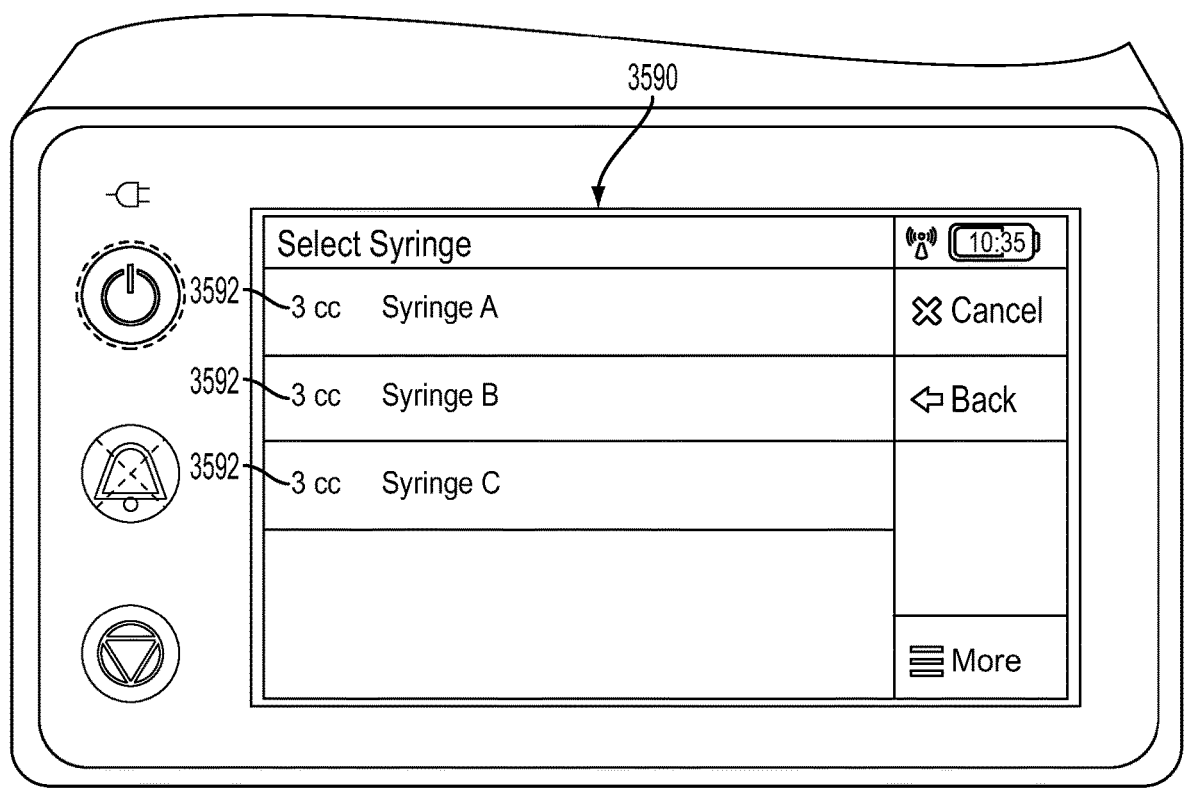
Figure 230:
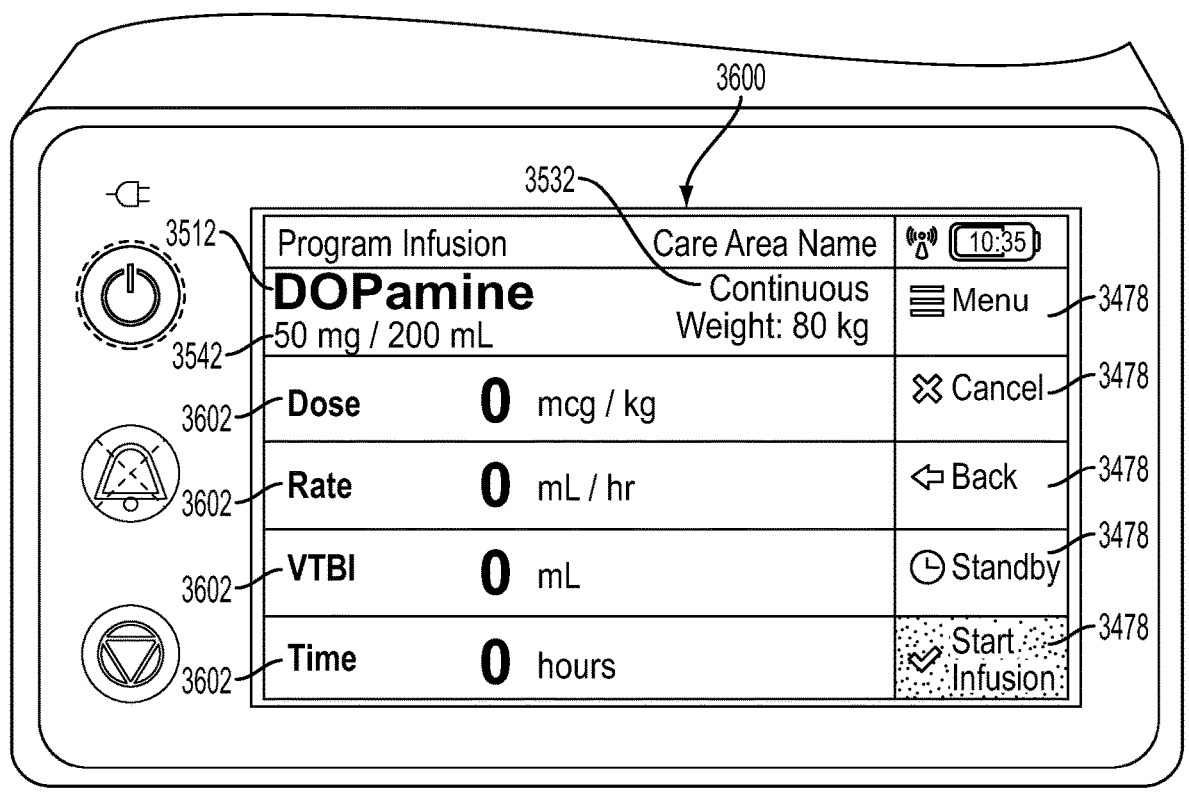
Figure 231:
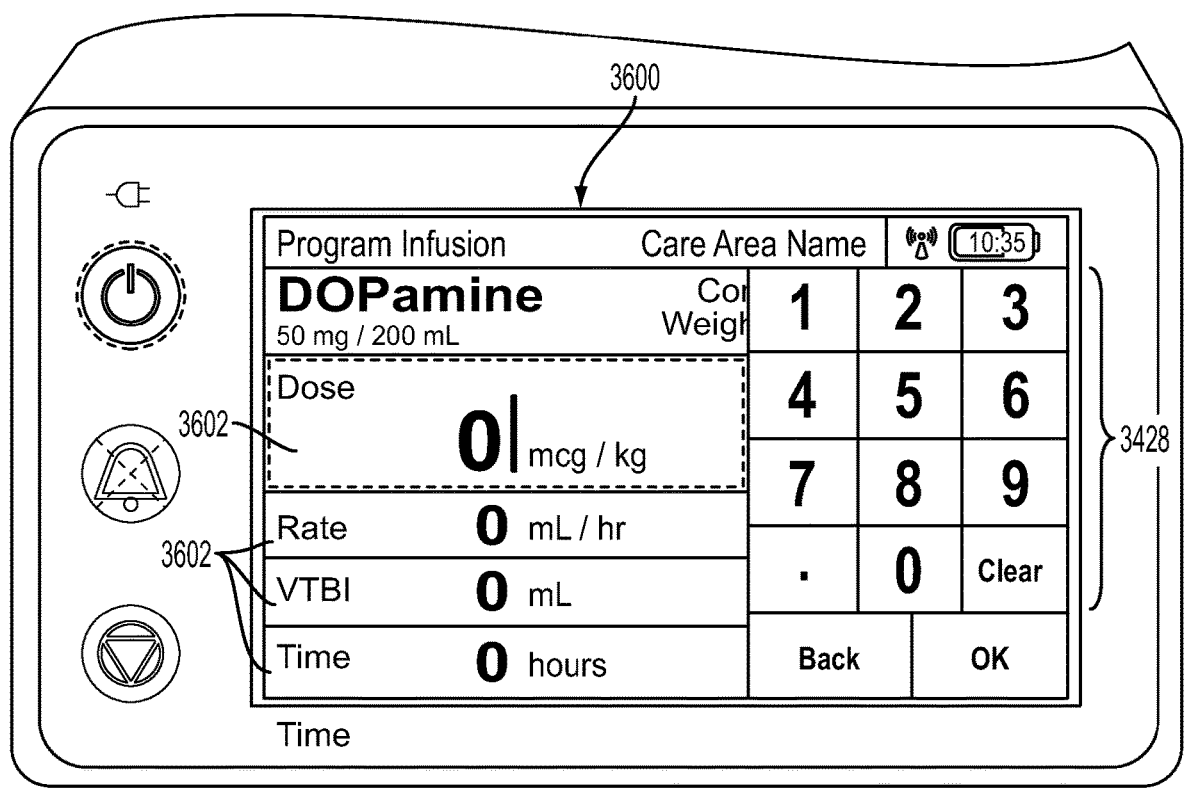
Figure 232:
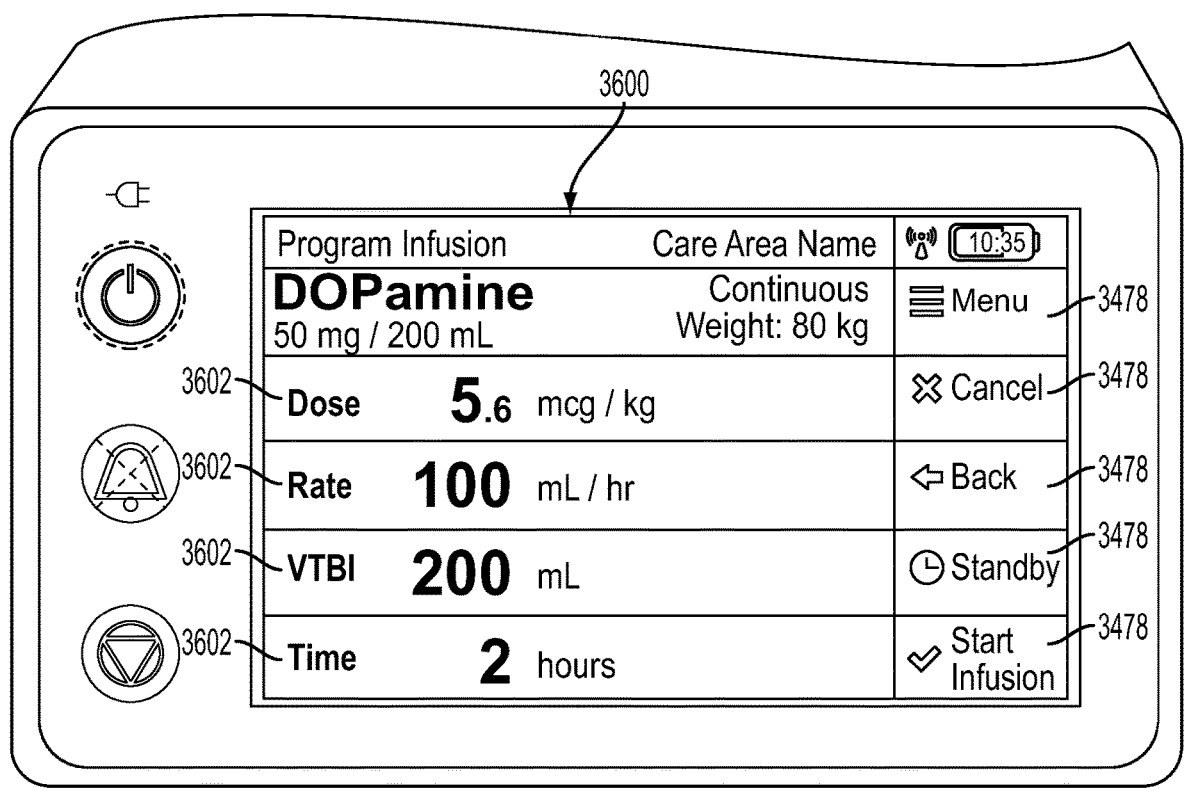
Figure 233:
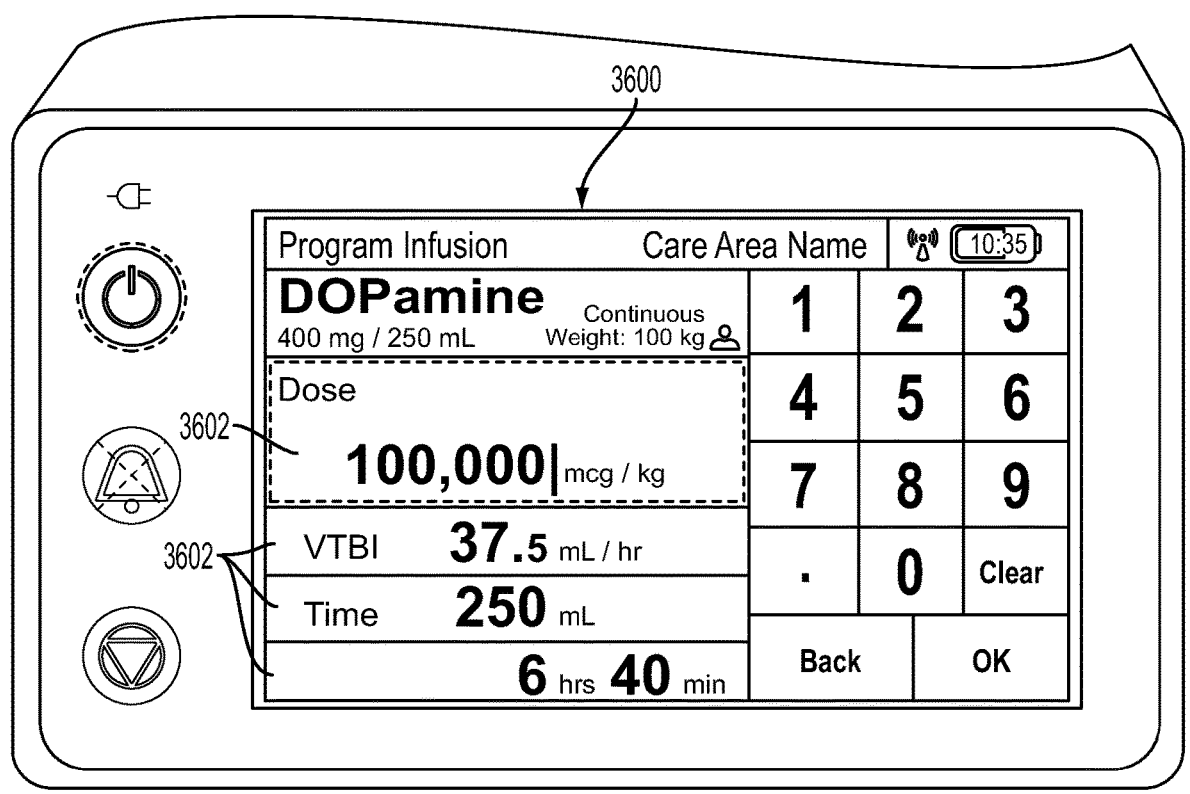
Figure 234:
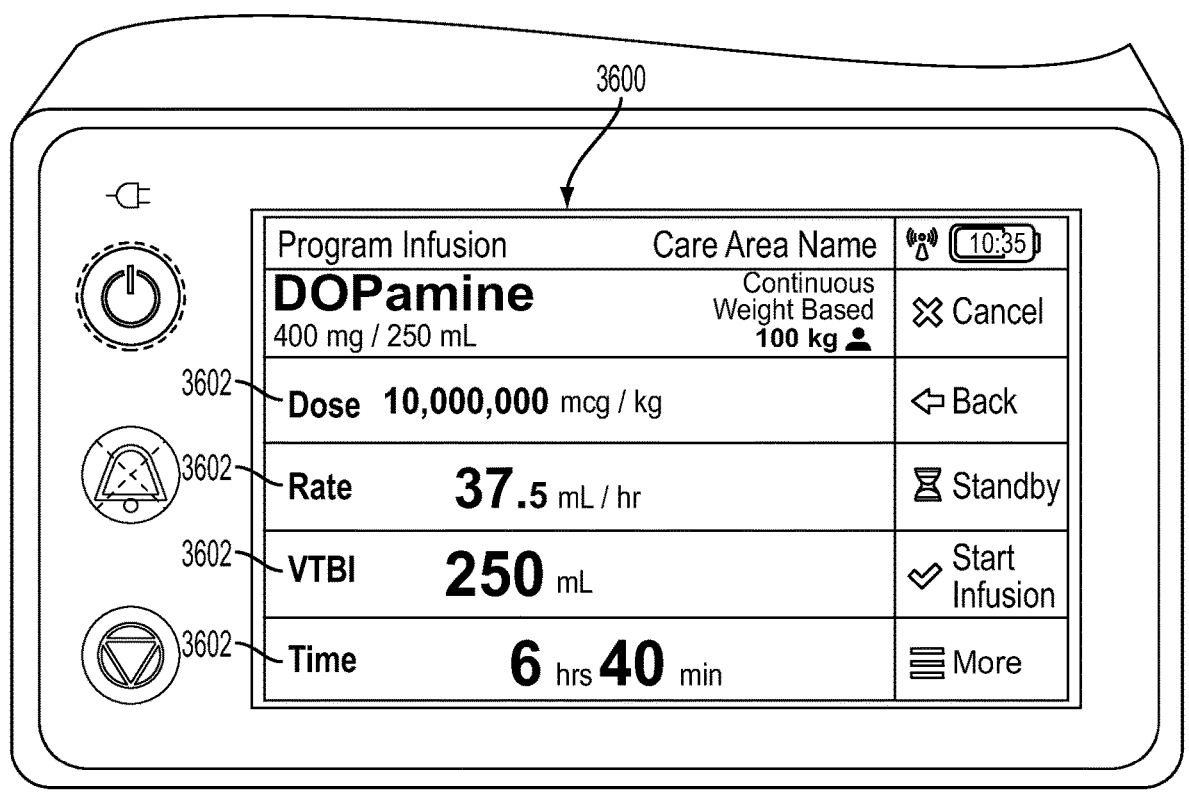
Figure 235:
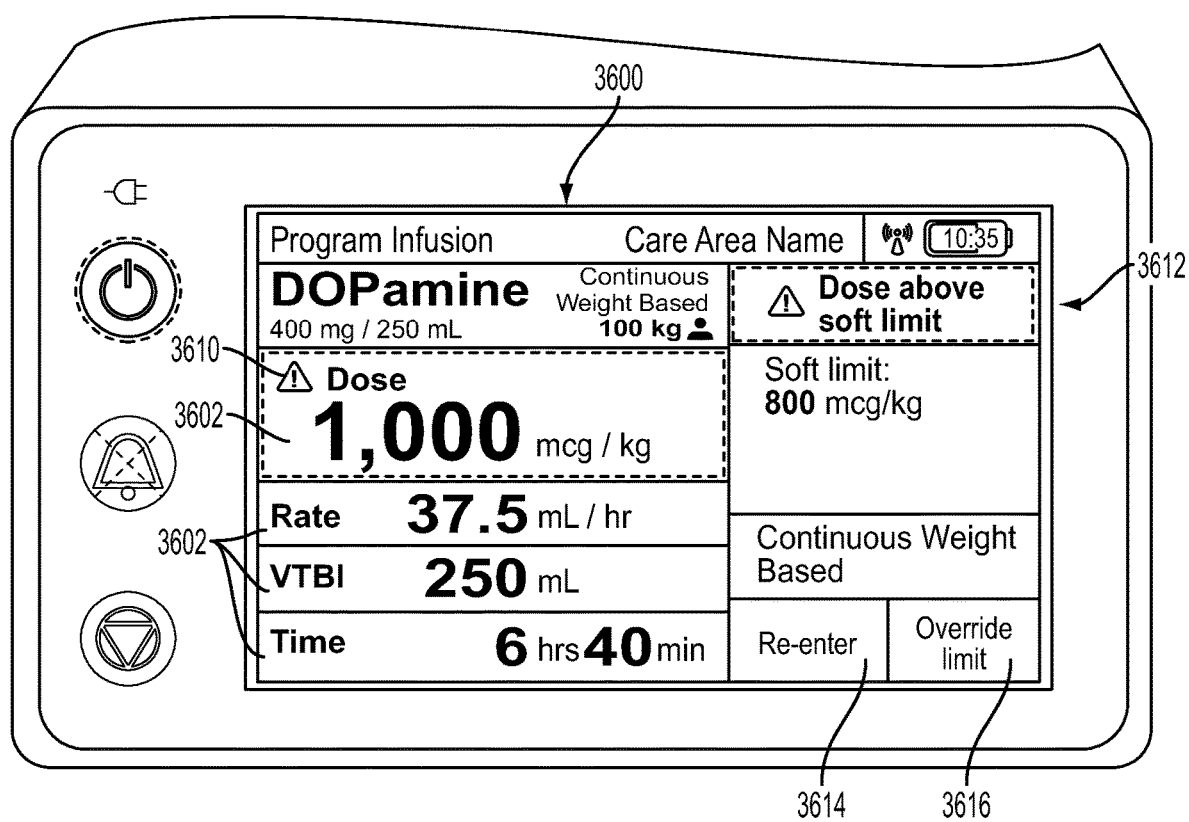
Figure 236:
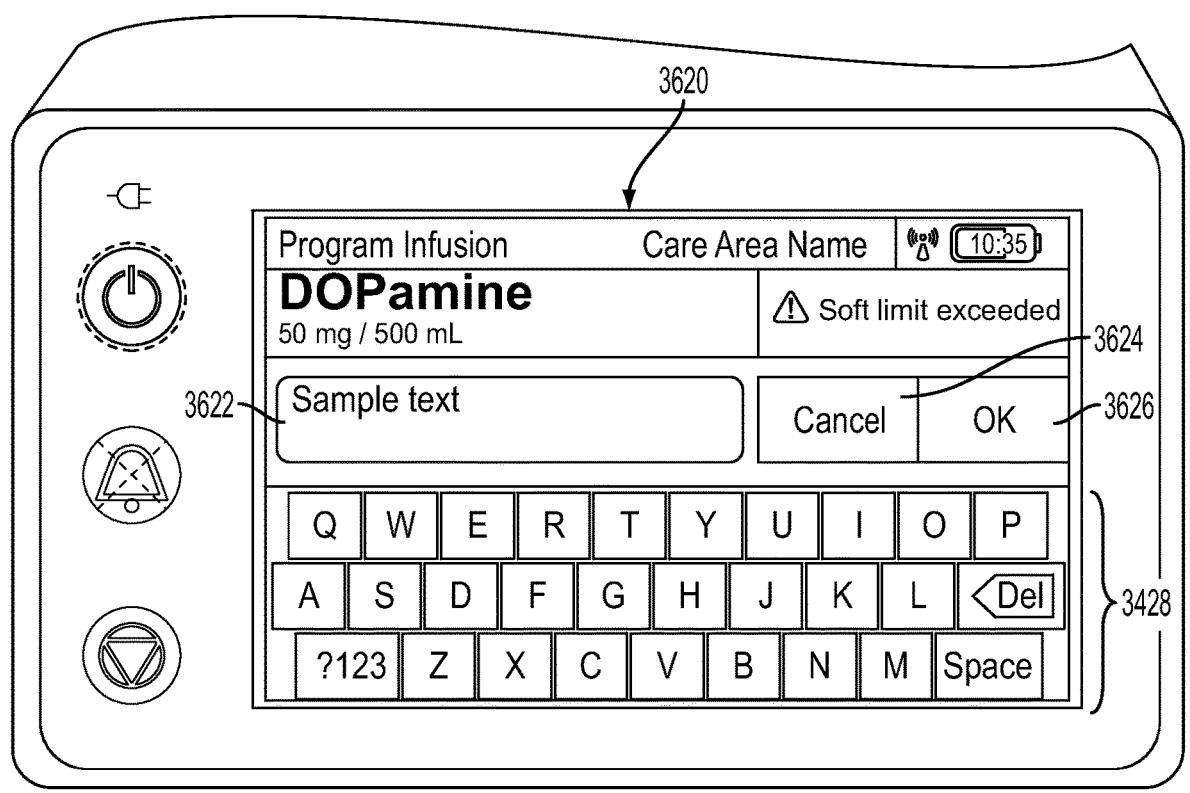
Figure 237:
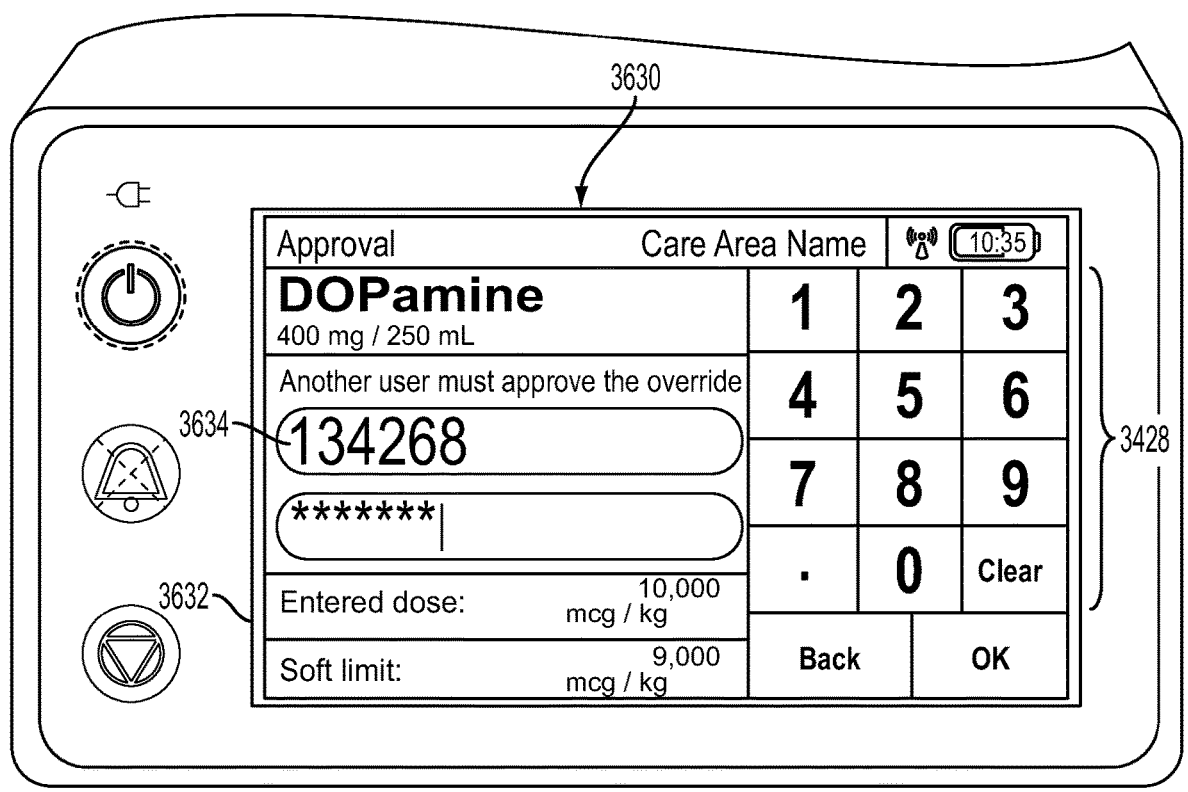
Figure 238:
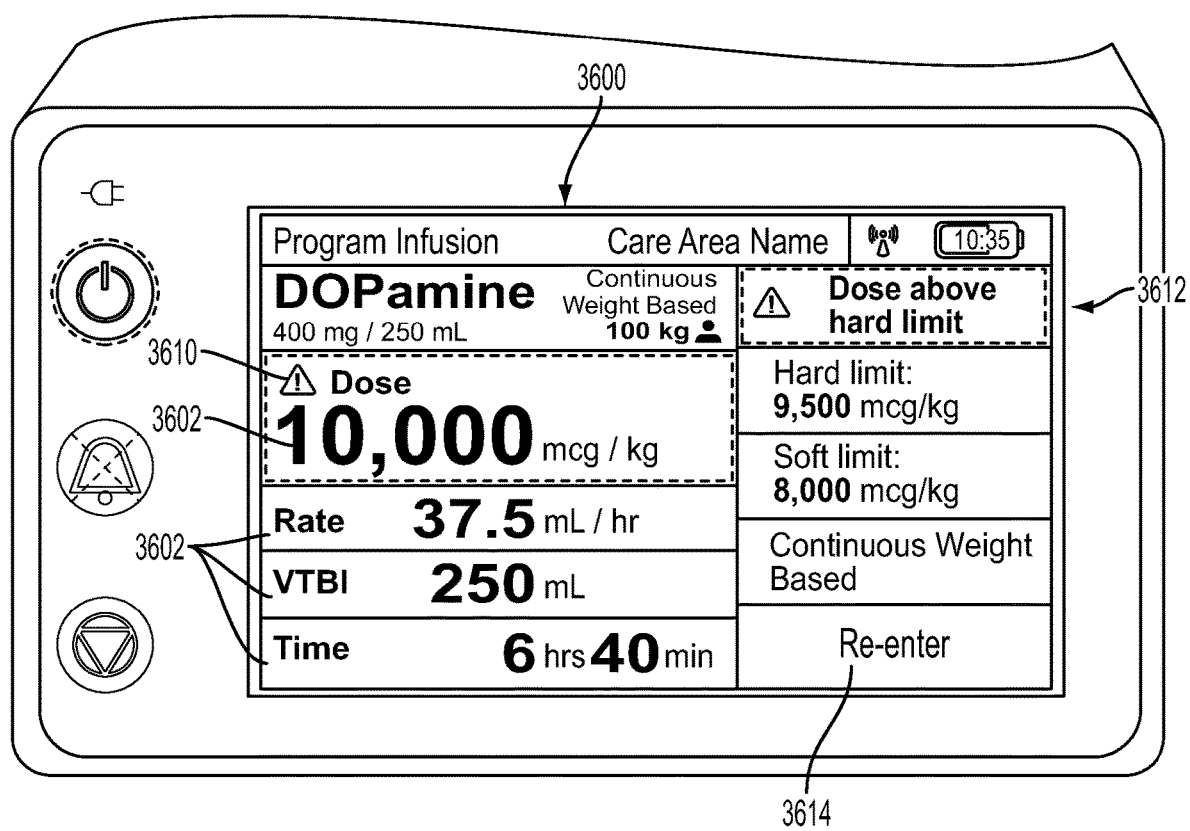
Figure 239:
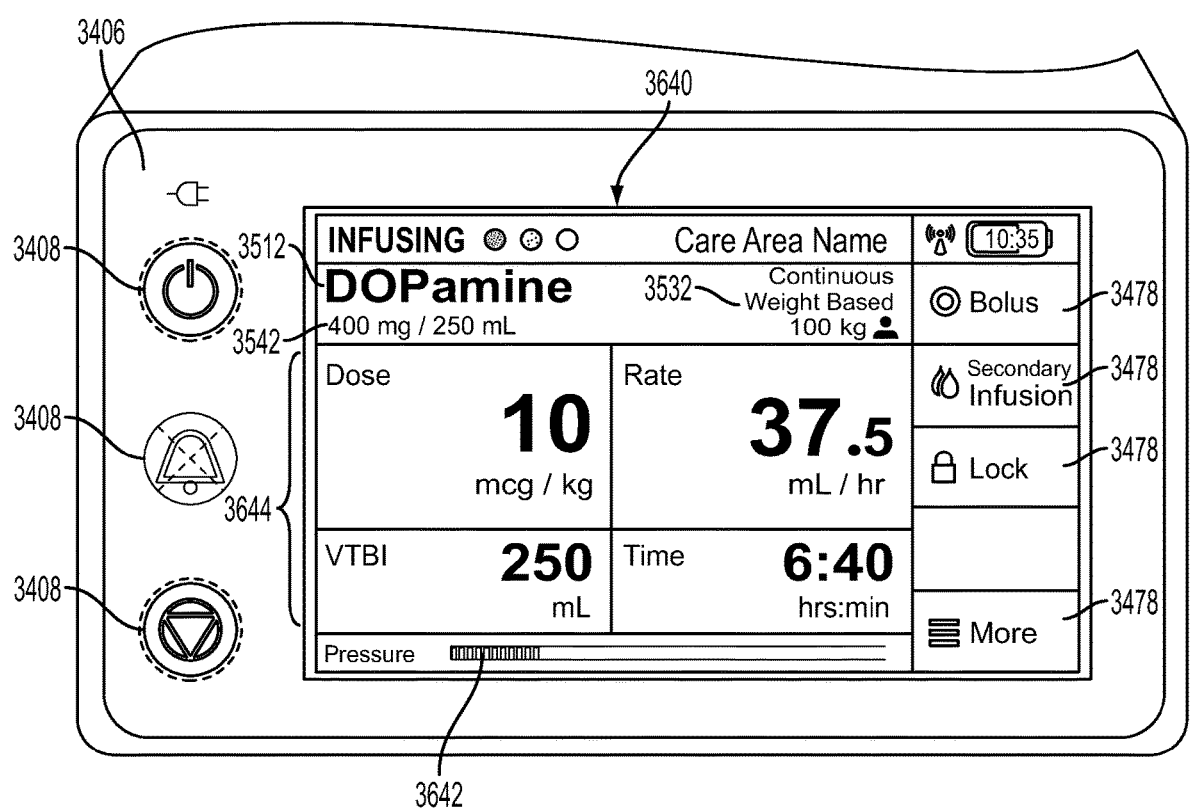
Figure 240:
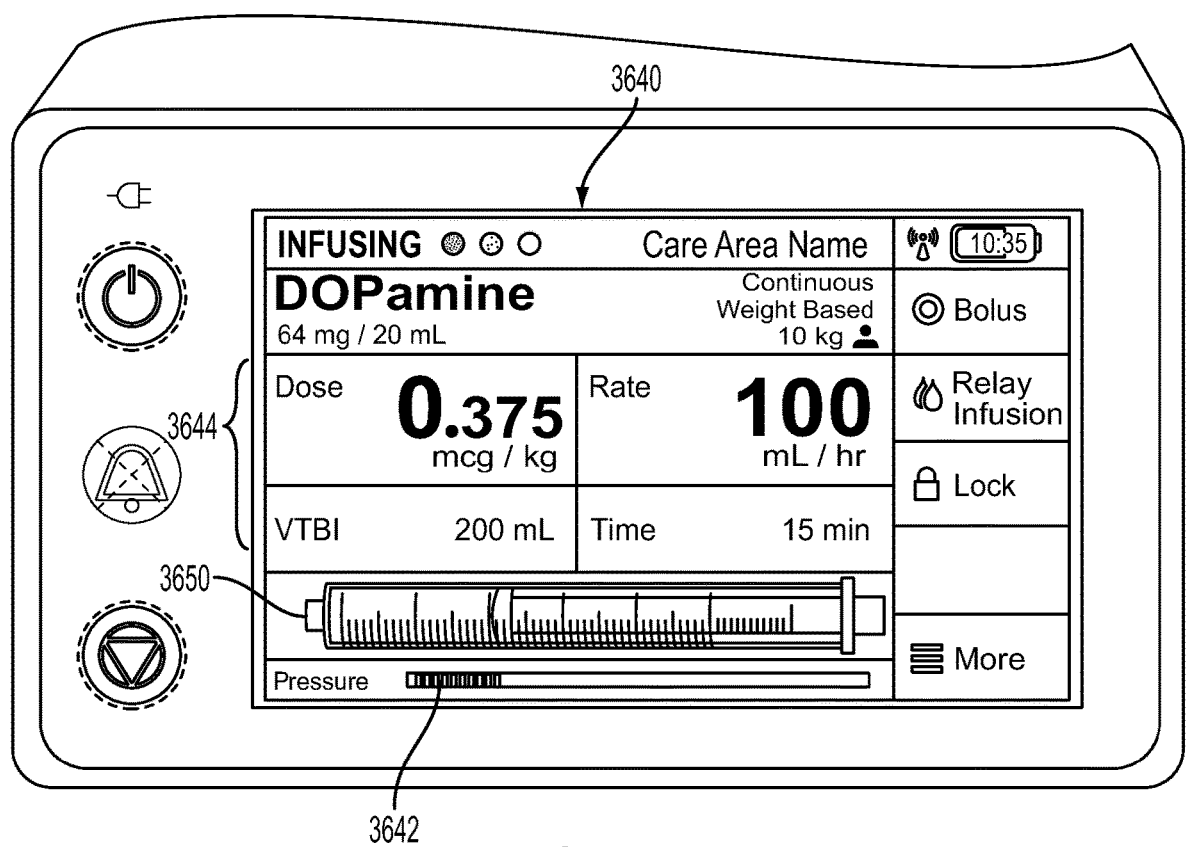
Figure 241:
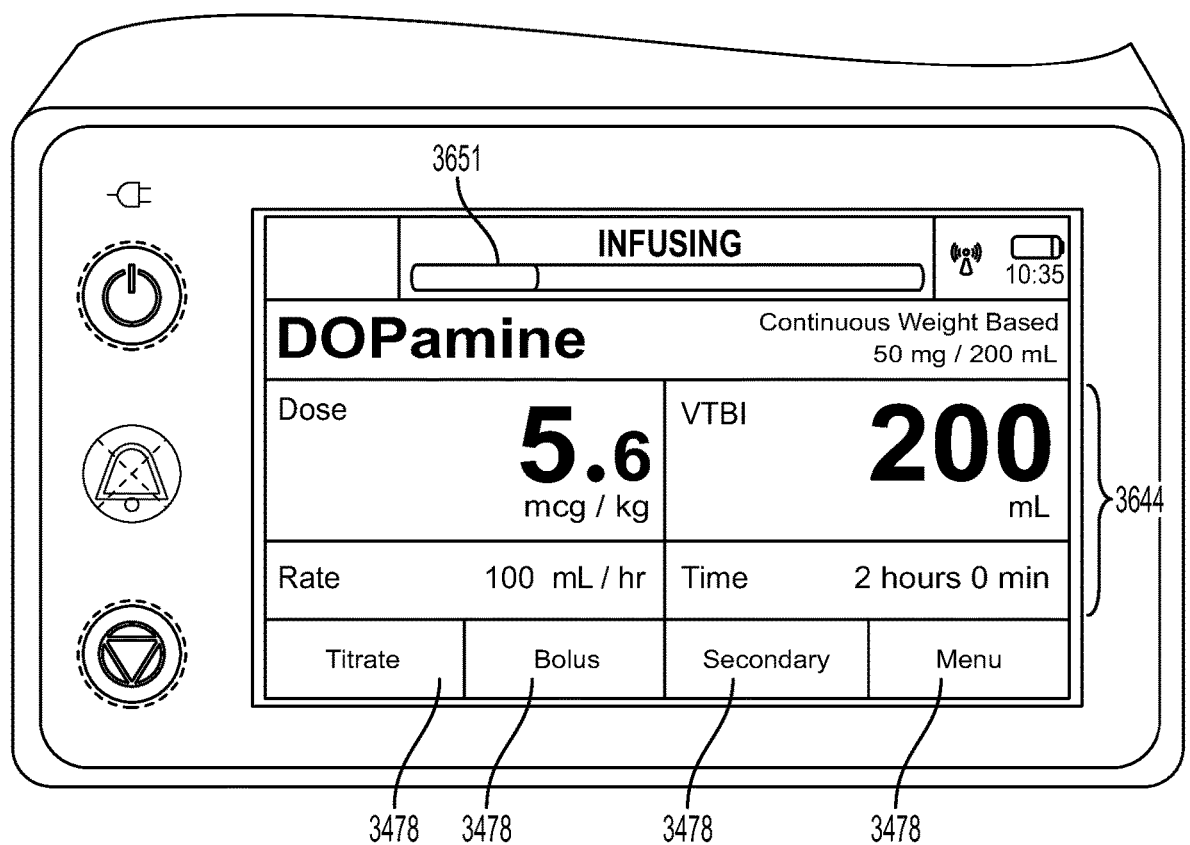
Figure 242:
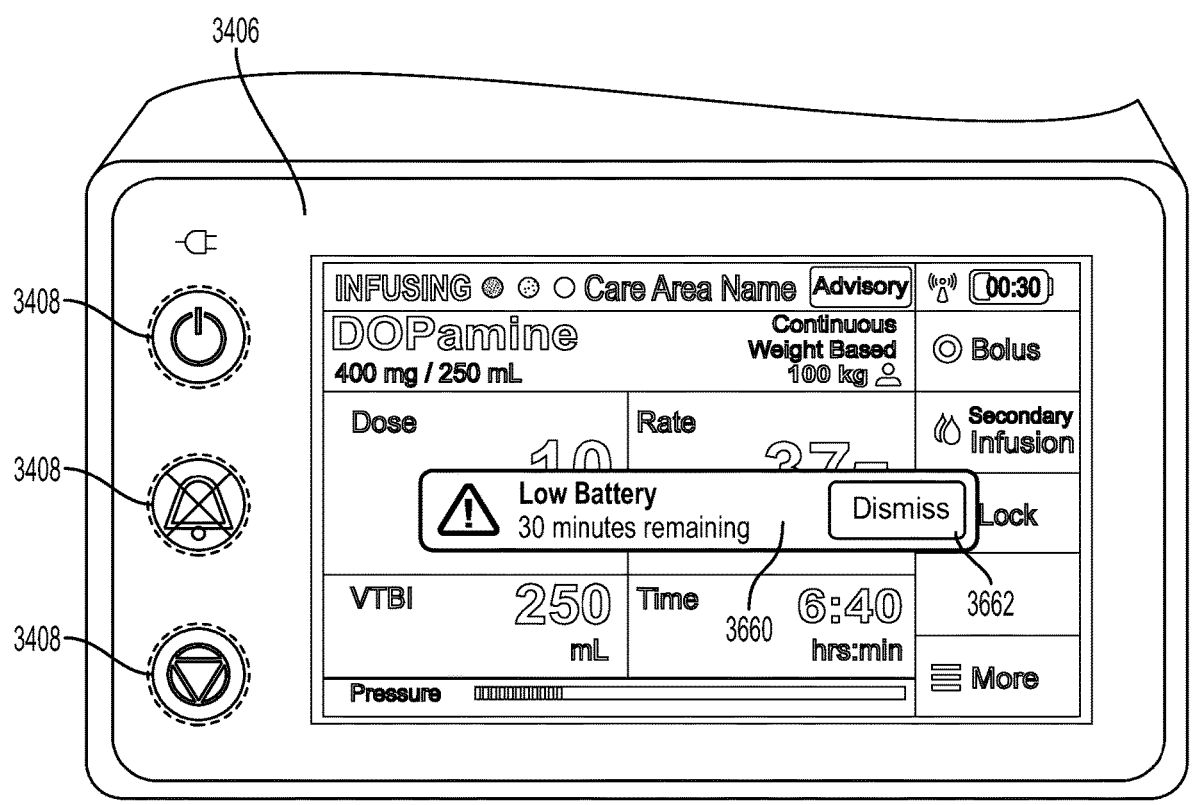
Figure 243:
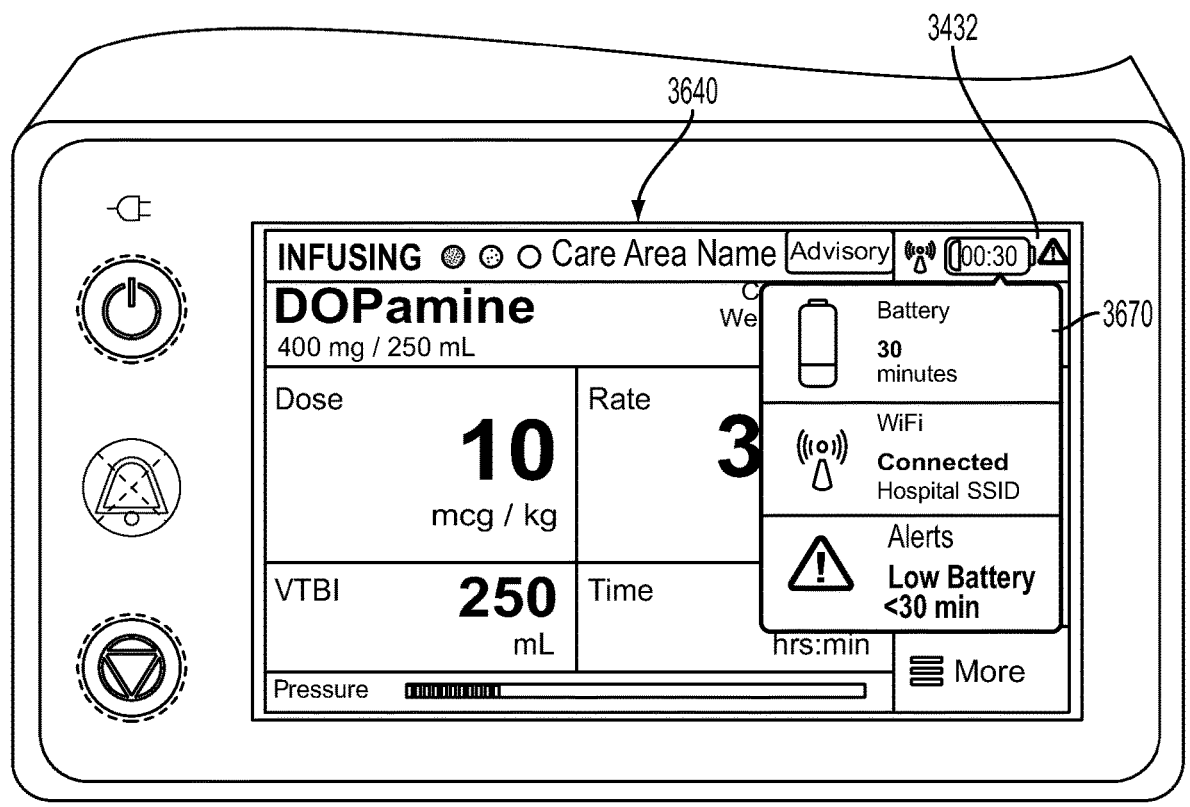
Figure 244:
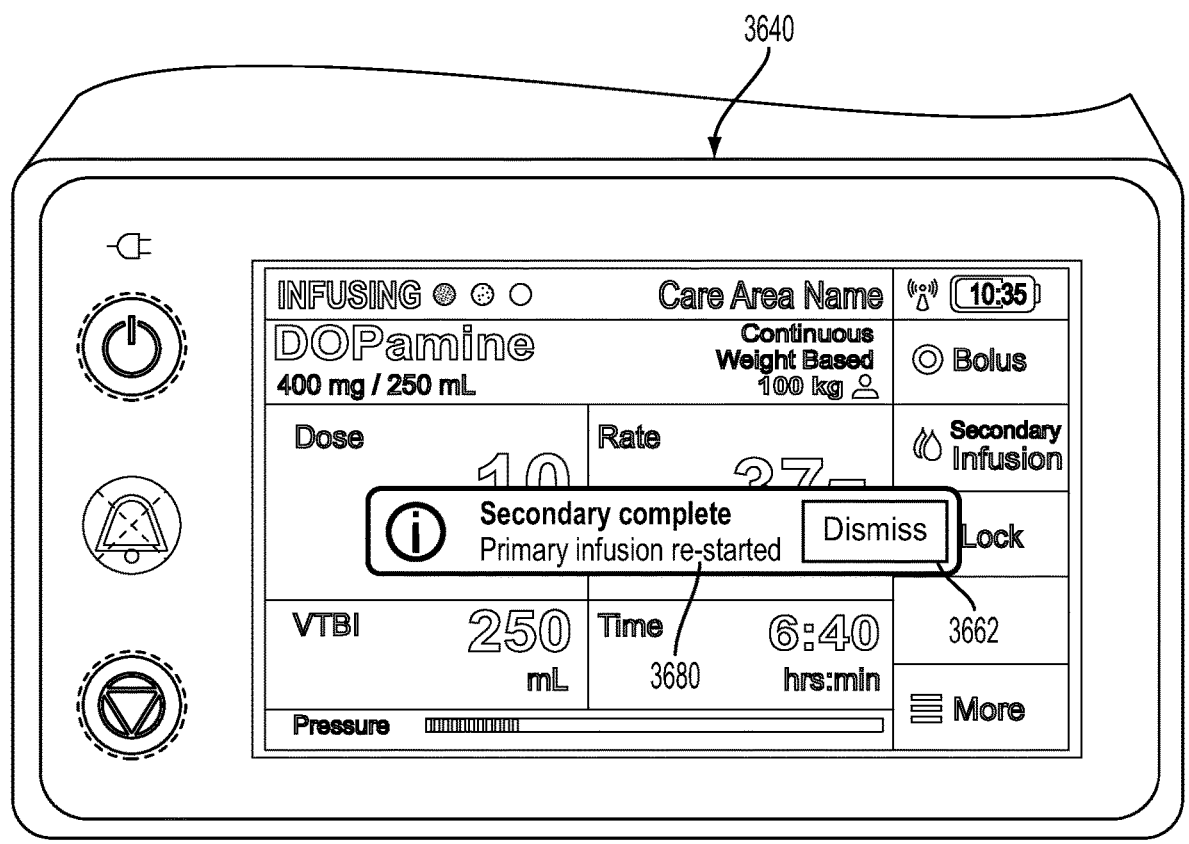
Figure 245:
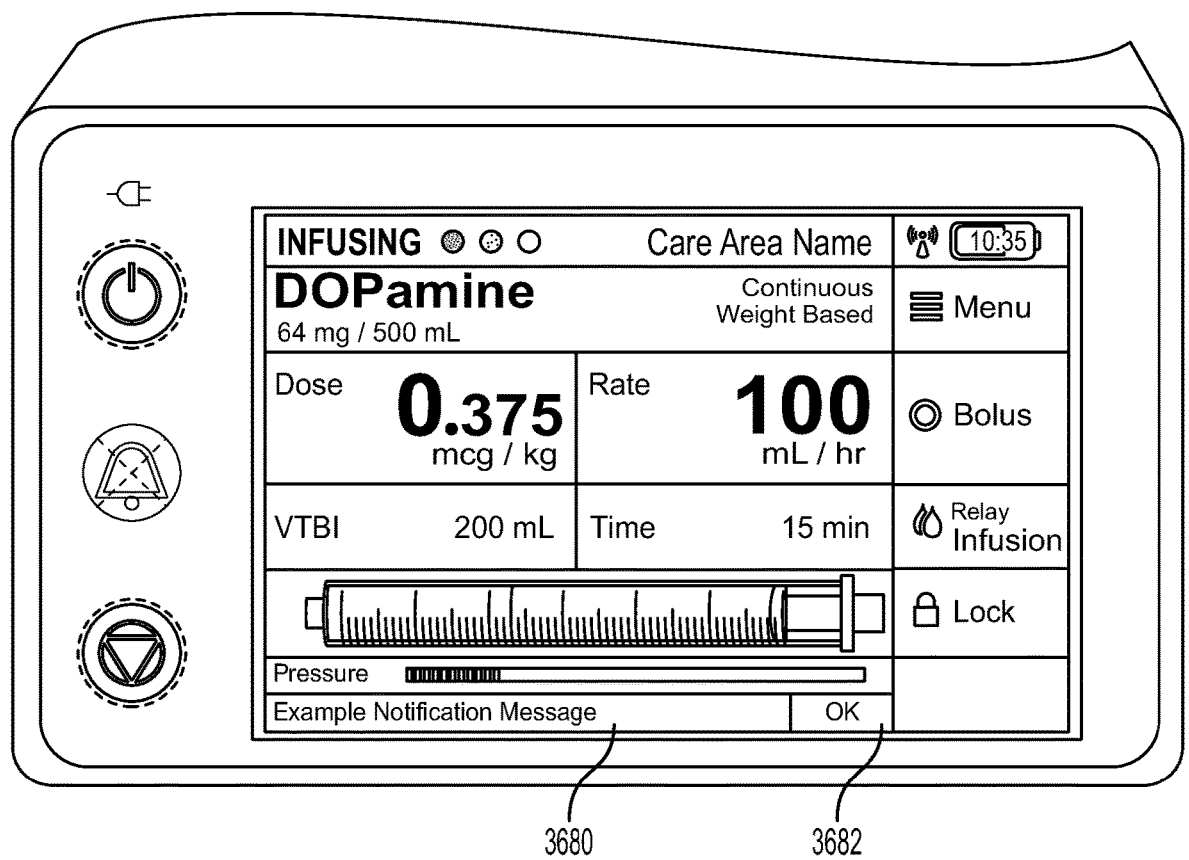
Figure 246:
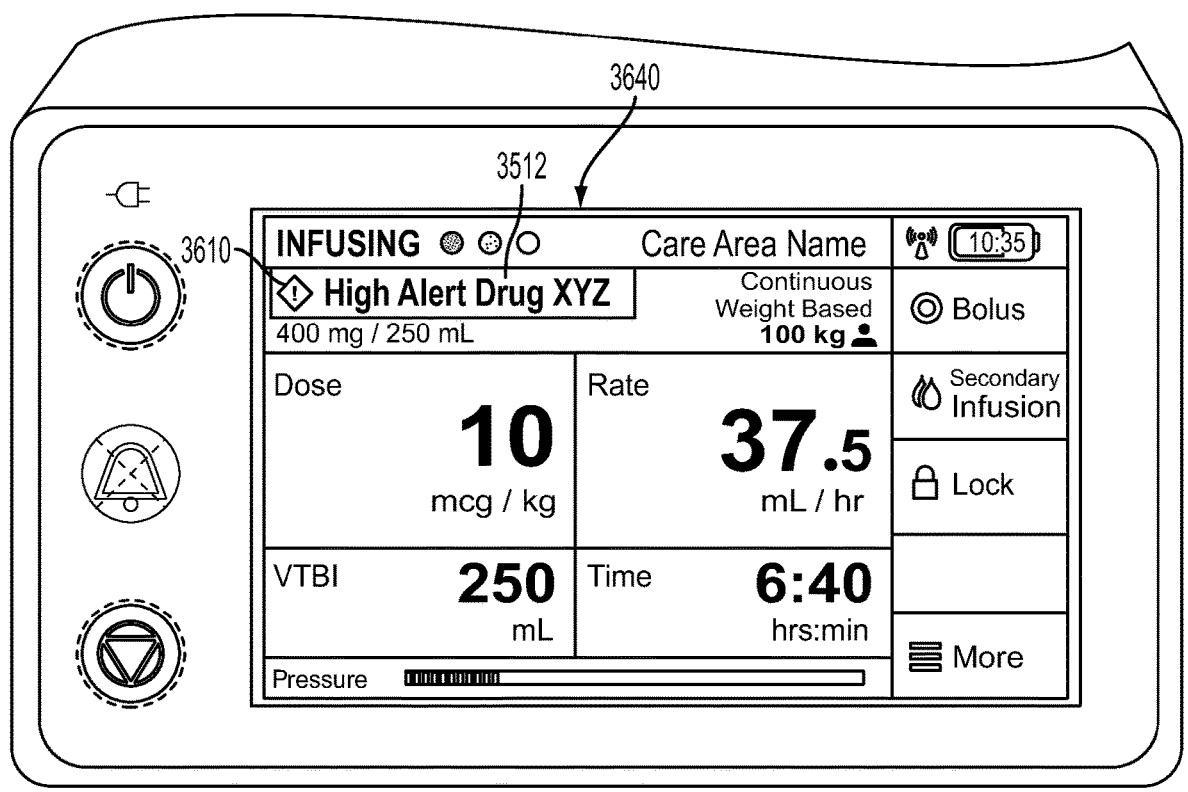
Figure 247:
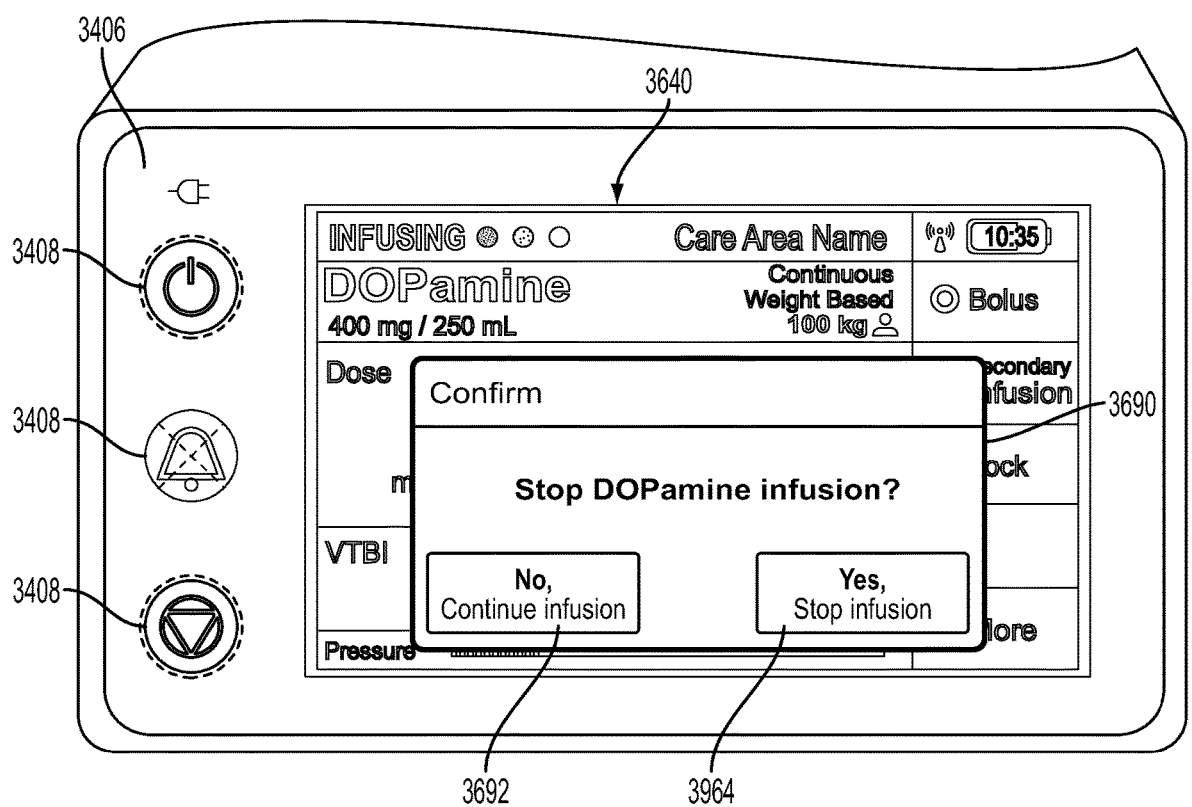
Figure 248:
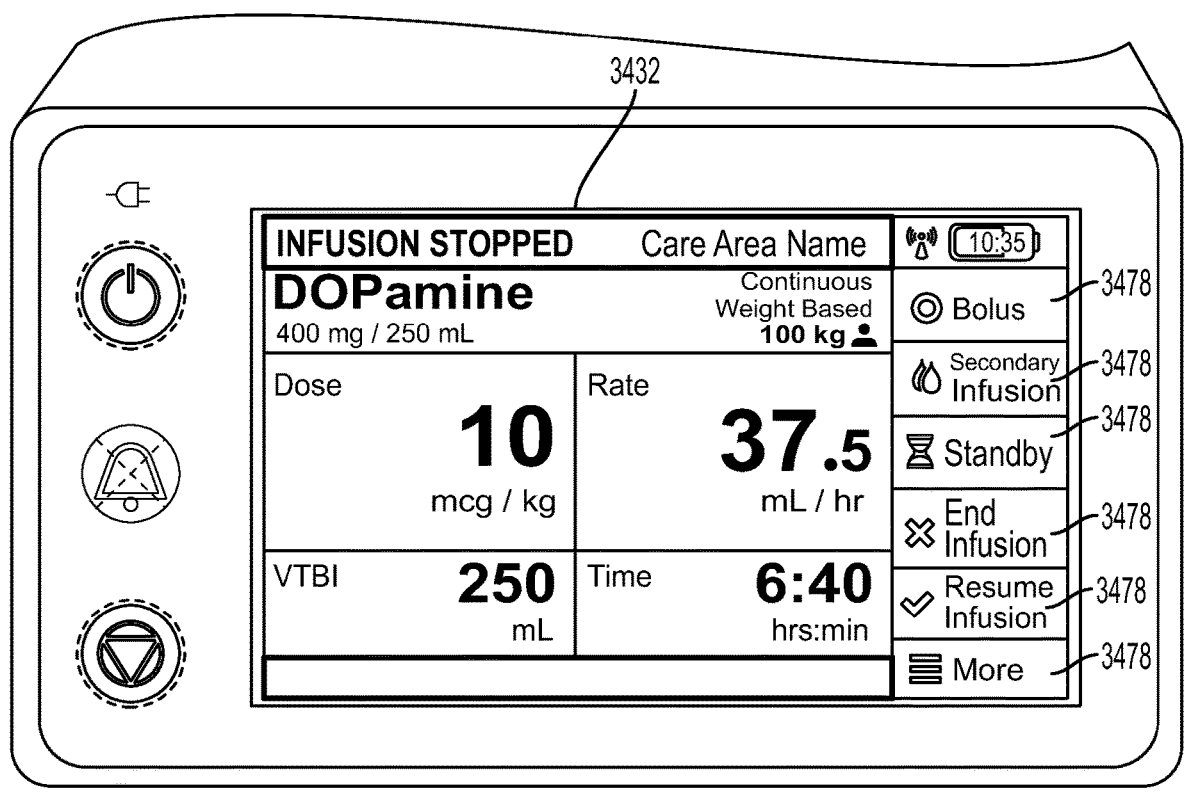
Figure 249:
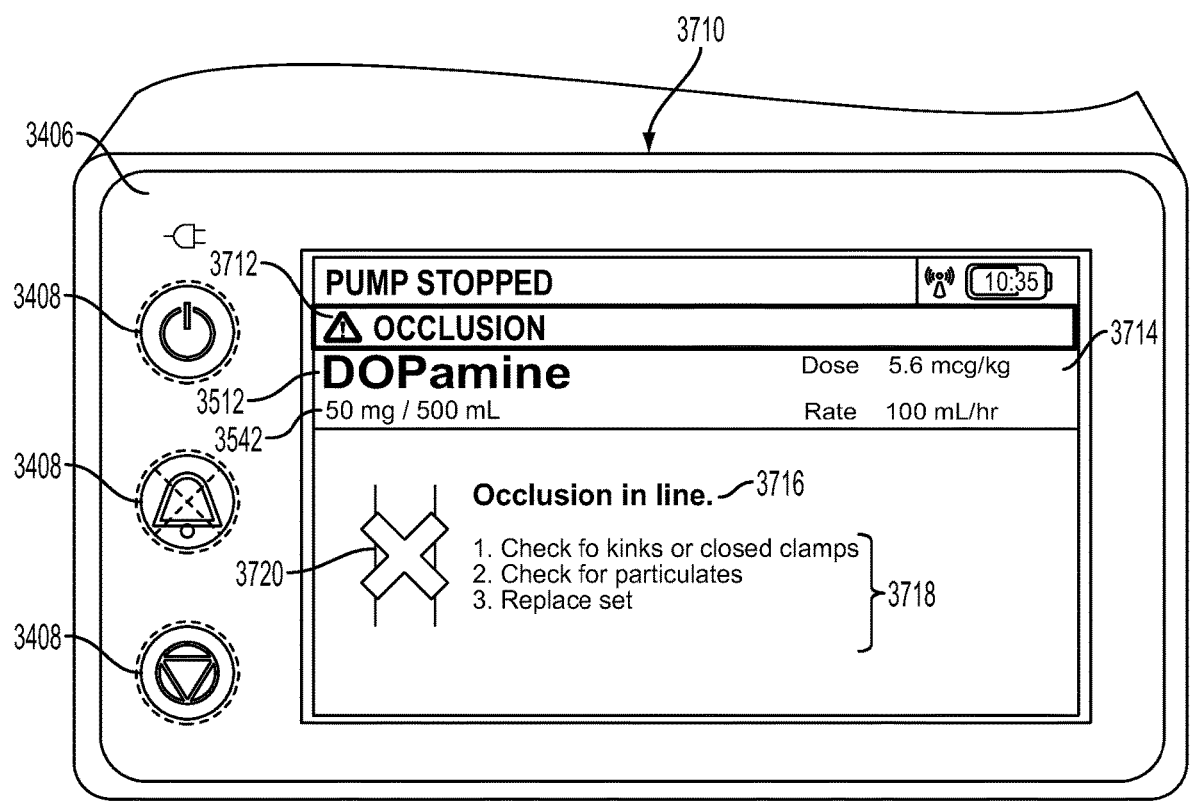
Figure 250:
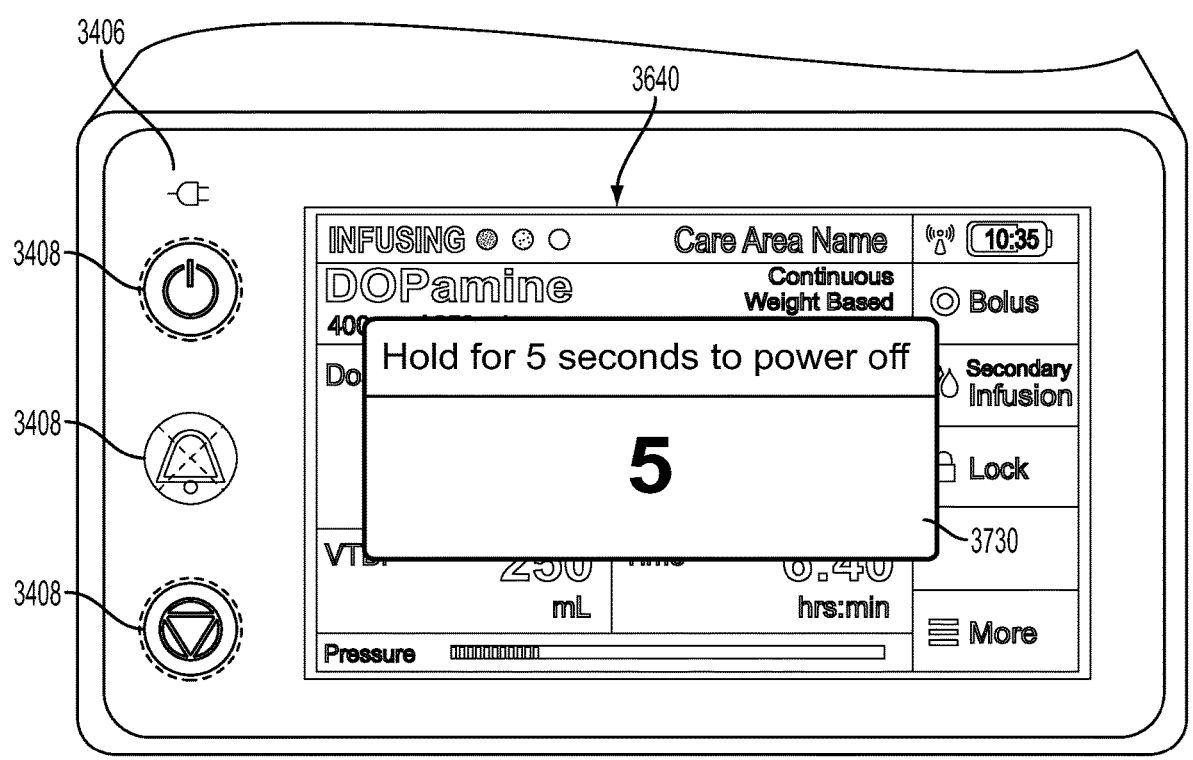
Figure 251:
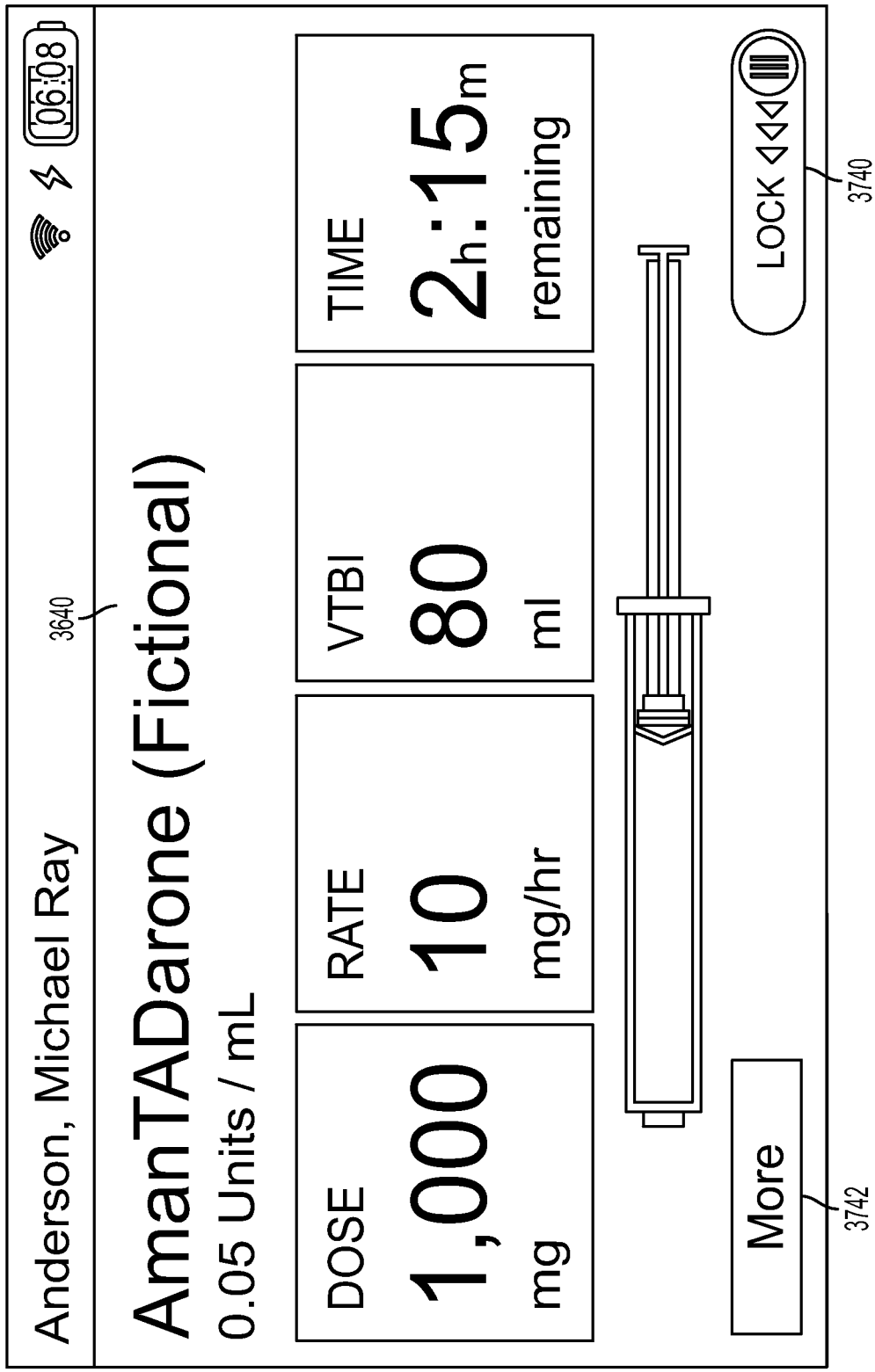
Figure 252:
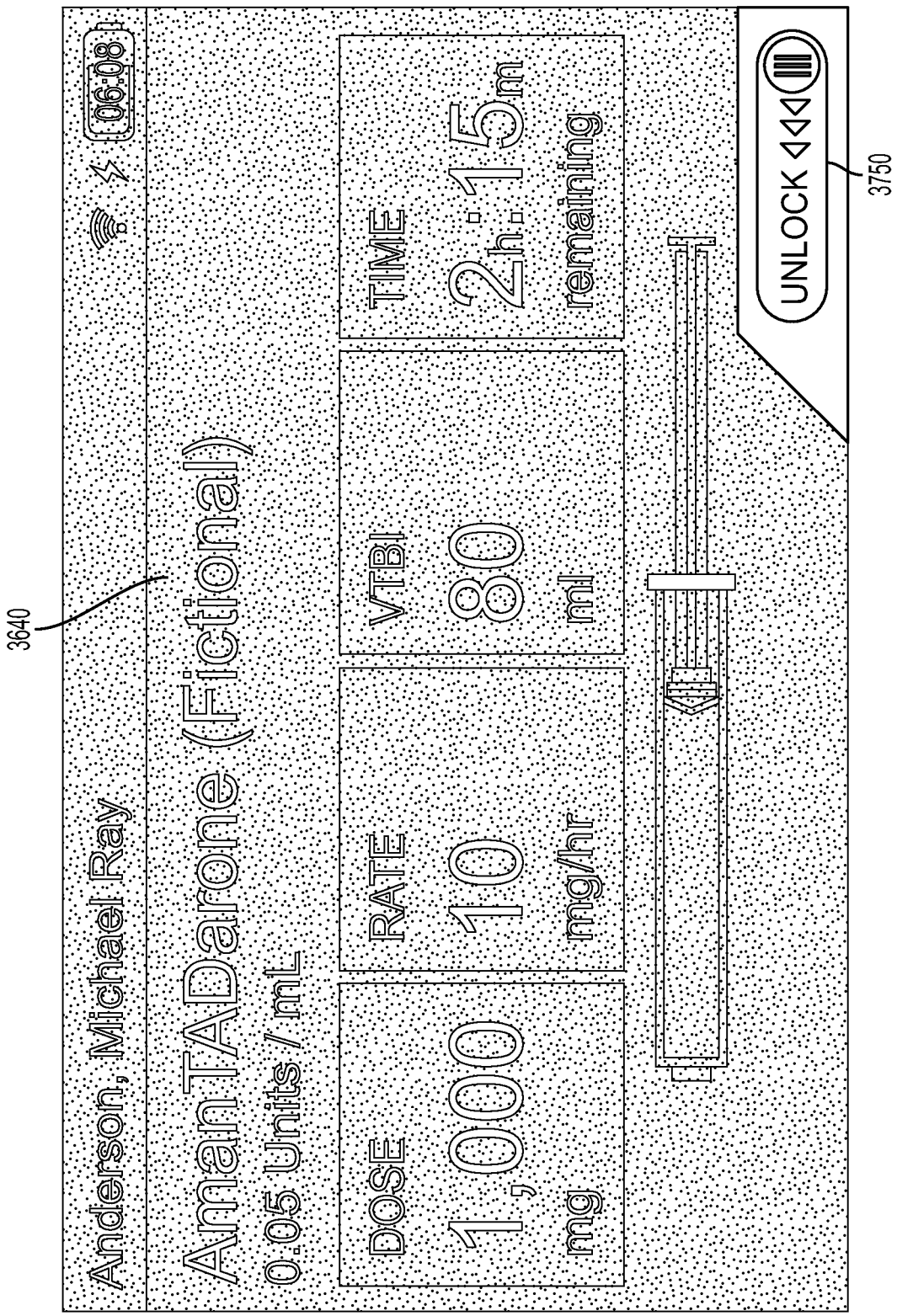
Figure 253:
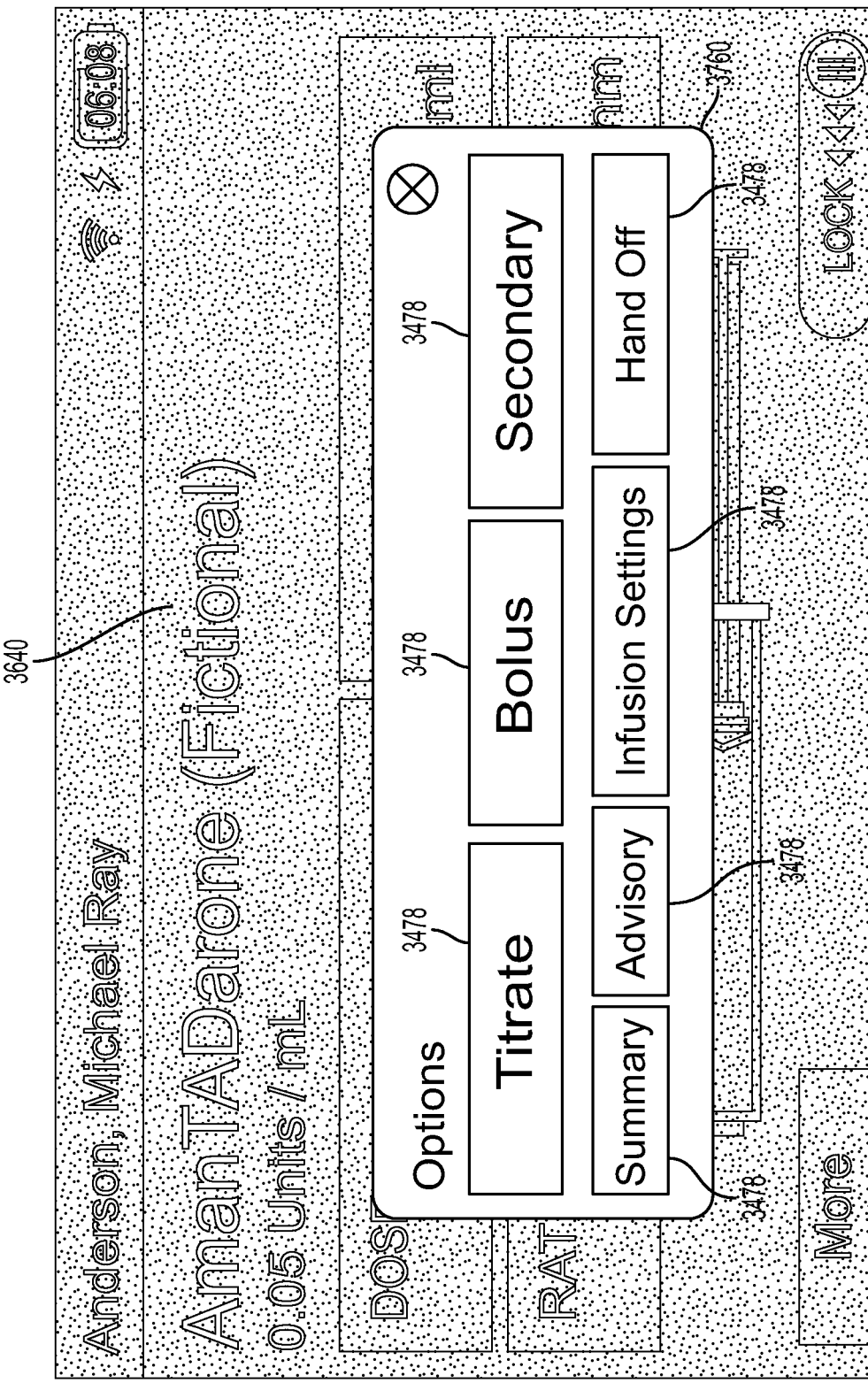
Figure 254:
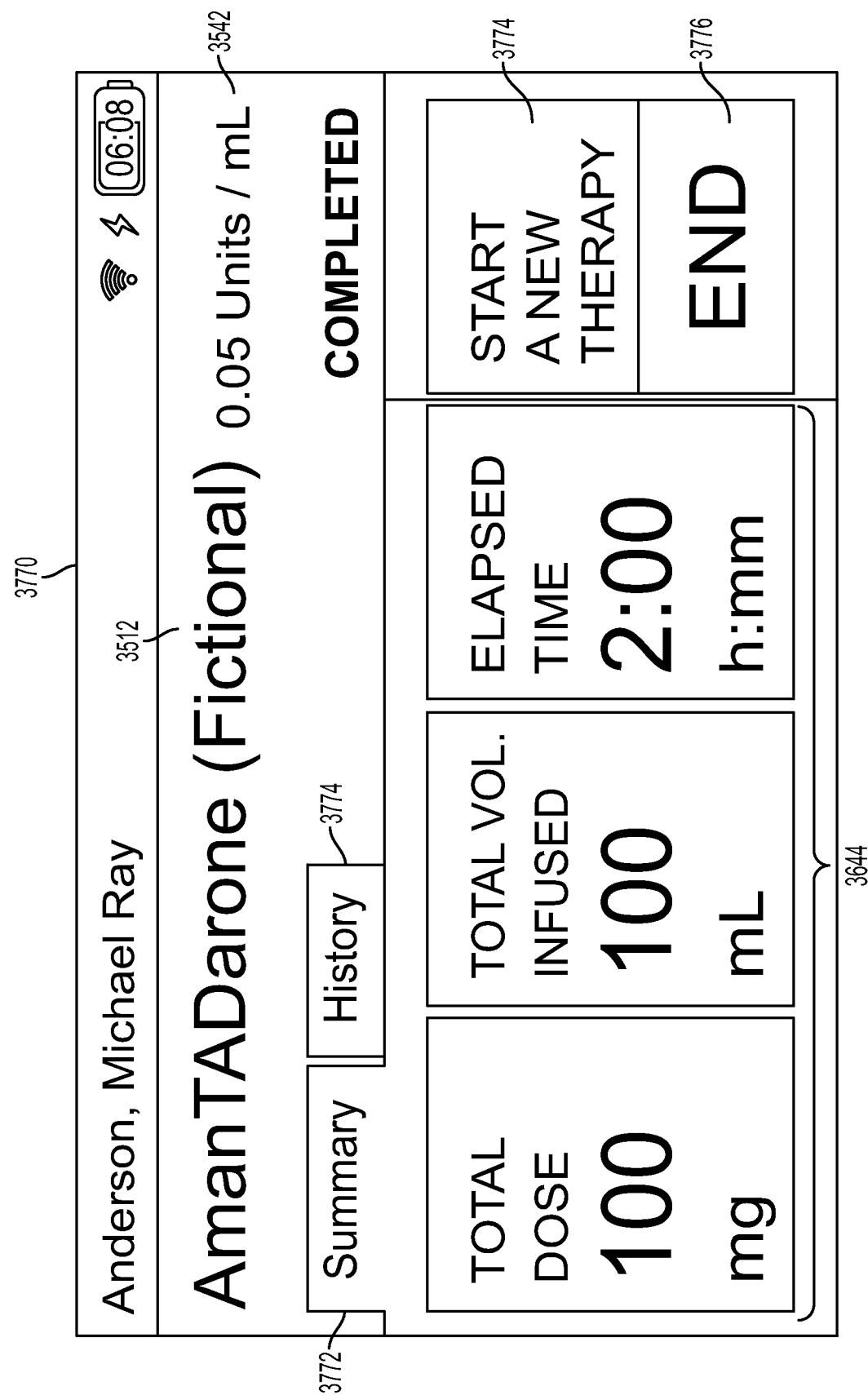
Figure 255:
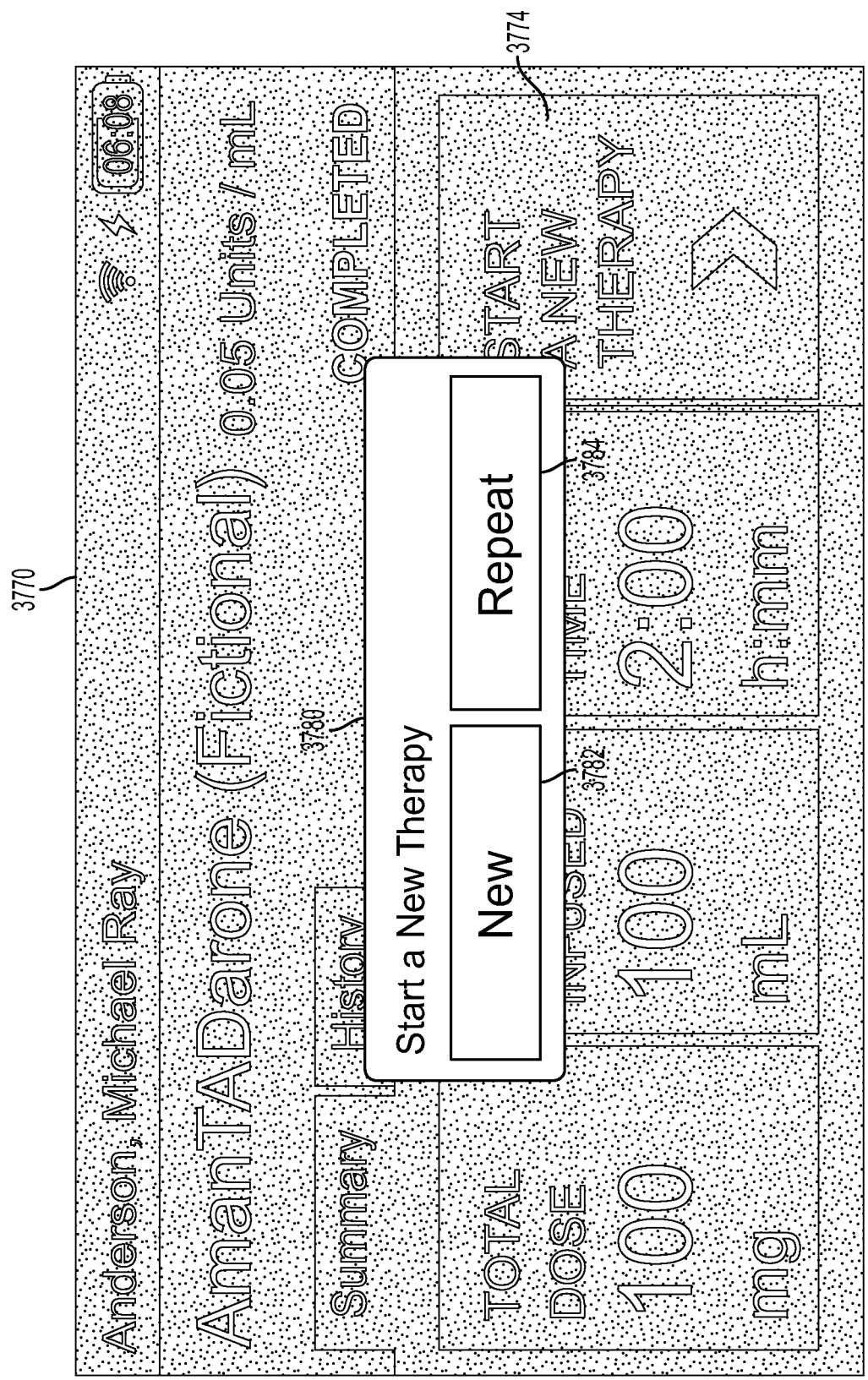
Figure 256:
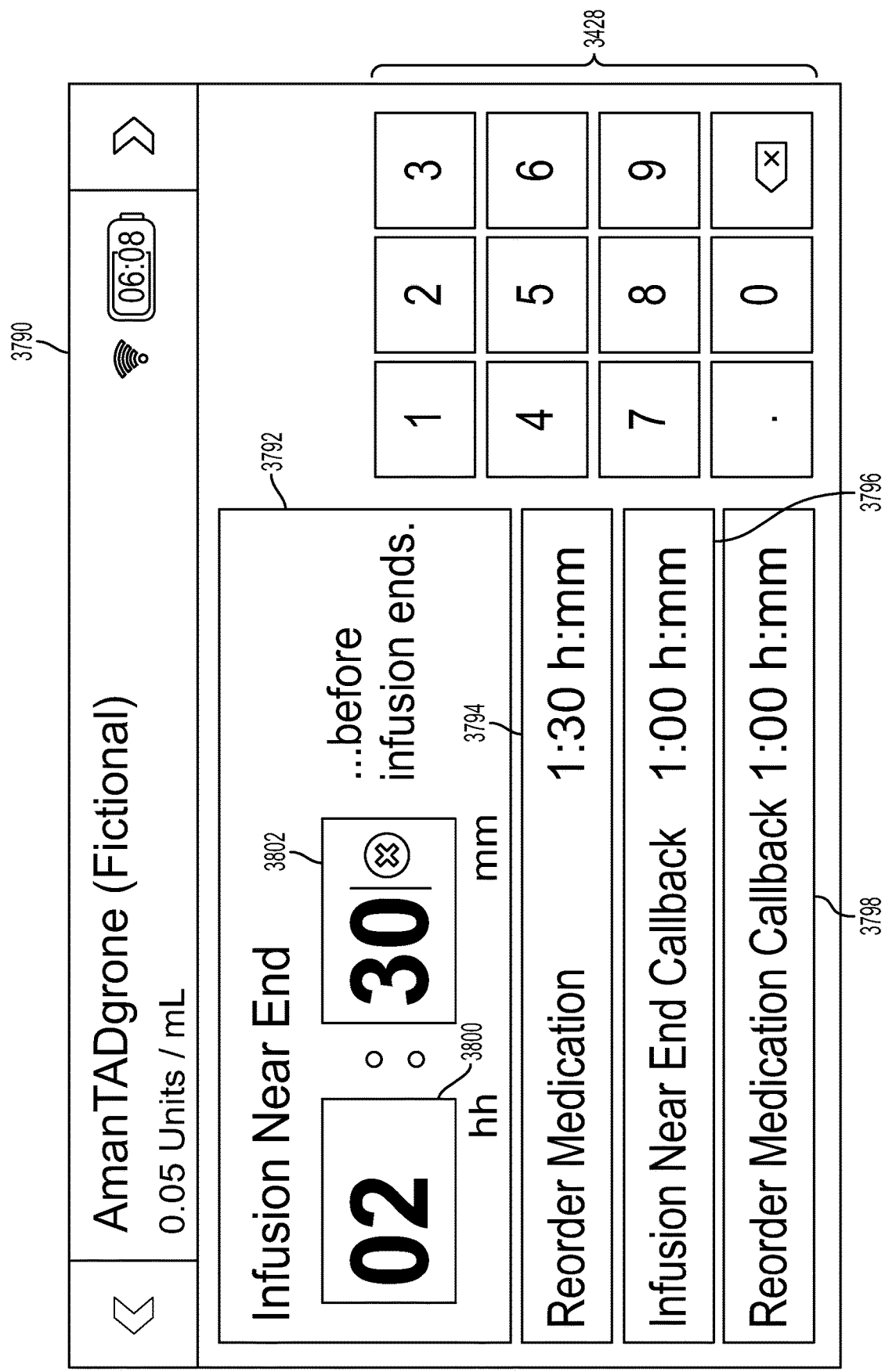
Figure 257:
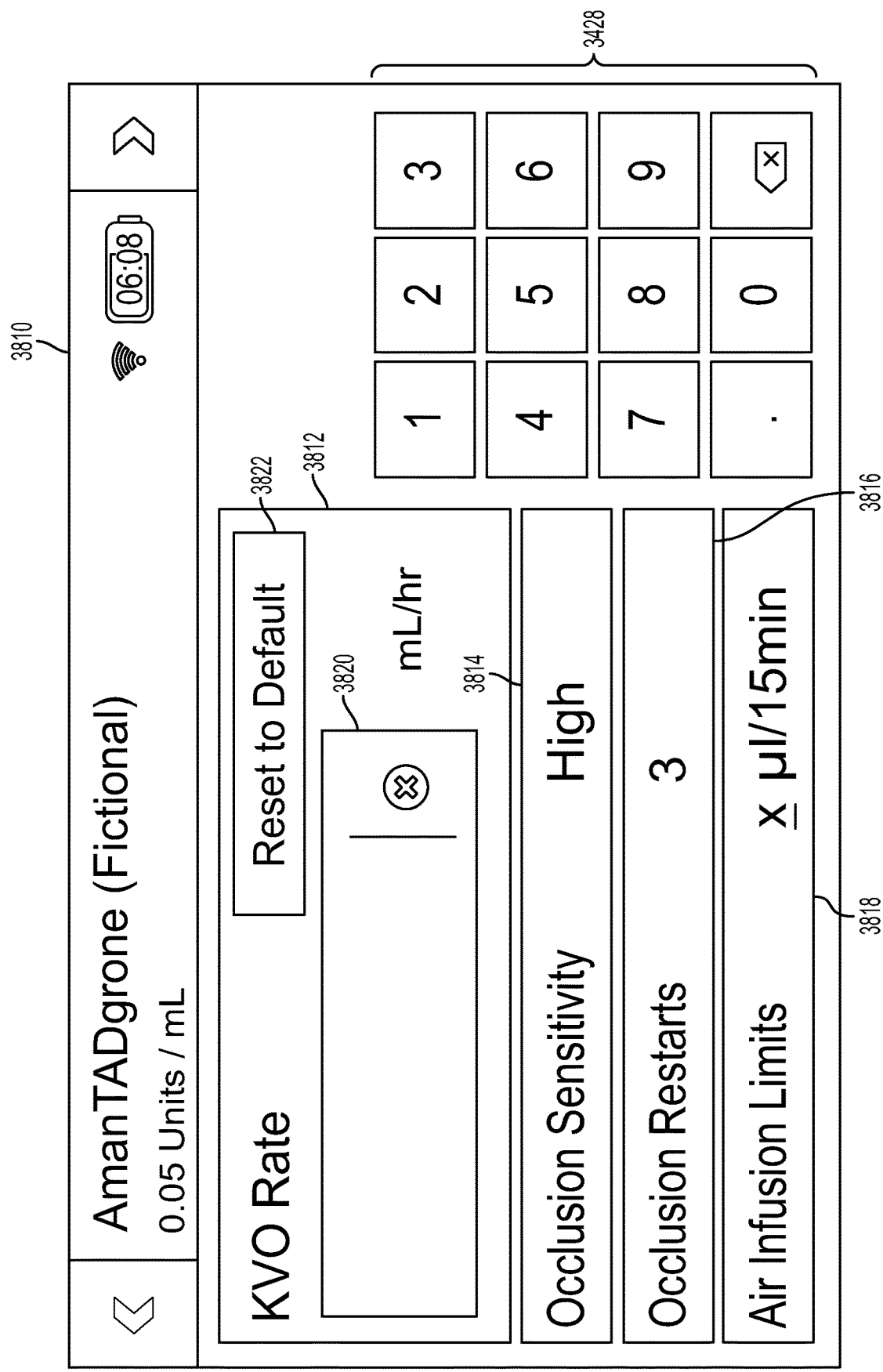

FIG. 64 depicts a flowchart detailing a number of example steps which may be used to select a utility on a user interface which may allow a user to perform a function or functions in accordance with an embodiment of the present disclosure;

FIG. 65 depicts a flowchart detailing a number of example steps which may be used to print a continuous quality improvement report in accordance with an embodiment of the present disclosure;

FIG. 66 depicts a flowchart detailing a number of example steps which may be used to download a continuous quality improvement report in accordance with an embodiment of the present disclosure;

FIG. 67 depicts a flowchart detailing a number of exemplary steps which may be used to email a continuous quality improvement report in accordance with an embodiment of the present disclosure;

FIG. 68 depicts a flowchart detailing a number of example steps which may be used to export data from a continuous quality improvement report in accordance with an embodiment of the present disclosure;

FIG. 69 depicts a flowchart detailing a number of example steps which may be used to schedule a continuous quality improvement report for automatic generation and distribution in accordance with an embodiment of the present disclosure;

FIG. 70 depicts a flowchart showing a number of example steps which may be used to generate and distribute a scheduled continuous quality improvement report in accordance with an embodiment of the present disclosure;

FIG. 71 depicts a flowchart showing a number of example steps which may be used to generate an automated continuous quality improvement summary report in accordance with an embodiment of the present disclosure;

FIG. 72 depicts an example graphical user interface login screen which may be presented to a user when a user attempts to access a drug error reduction system editor service or continuous quality improvement service in accordance with an embodiment of the present disclosure;

FIG. 73 depicts an example graphical user interface login screen which may be presented to a user when a user attempts to access a drug error reduction system editor service or continuous quality improvement service in accordance with an embodiment of the present disclosure;

FIG. 74 depicts an example initialization screen which may be displayed on a user interface in accordance with an embodiment of the present disclosure;

FIG. 75 depicts an example initialization wizard screen in accordance with an embodiment of the present disclosure;

FIG. 76 depicts an example initialization wizard screen in accordance with an embodiment of the present disclosure;

FIG. 77 depicts an example initialization wizard screen in accordance with an embodiment of the present disclosure;

FIG. 78 depicts an example embodiment of a "welcome" screen which may be displayed on a user interface such as a drug error reduction system editor service user interface in accordance with an embodiment of the present disclosure;

FIG. 79 depicts an example of a drug error reduction system editor dashboard screen in accordance with an embodiment of the present disclosure;

FIG. 80 depicts an example care area screen which may be displayed on a user interface such as the user interface of a drug error reduction system in accordance with an embodiment of the present disclosure;

FIG. 81 depicts an example add care area screen which may be displayed on a user interface such as the user interface of a drug error reduction system in accordance with an embodiment of the present disclosure;

FIG. 82 depicts an example add care area screen which may be displayed on a user interface such as the user interface of a drug error reduction system in accordance with an embodiment of the present disclosure;

FIG. 83 depicts an example add care area screen which may be displayed on a user interface such as the user interface of a drug error reduction system in accordance with an embodiment of the present disclosure;

FIG. 84 depicts an example add care area screen which may be displayed on a user interface such as the user interface of a drug error reduction system in accordance with an embodiment of the present disclosure;

FIG. 85 depicts an example add care area screen which may be displayed on a user interface such as the user interface of a drug error reduction system in accordance with an embodiment of the present disclosure;

FIG. 86 depicts an example add care area screen which may be displayed on a user interface such as the user interface of a drug error reduction system in accordance with an embodiment of the present disclosure;

FIG. 87 depicts an example care area screen which may be displayed on a user interface such as the user interface of a drug error reduction system in accordance with an embodiment of the present disclosure;

FIG. 88 depicts an example medication screen which may be displayed on a user interface such as the user interface of a drug error reduction system in accordance with an embodiment of the present disclosure;

FIG. 89 depicts an example add medication record screen which may be displayed on a user interface such as the user interface of a drug error reduction system in accordance with an embodiment of the present disclosure;

FIG. 90 depicts an example add medication record screen which may be displayed on a user interface such as the user interface of a drug error reduction system in accordance with an embodiment of the present disclosure;

FIG. 91 depicts an example add medication record screen which may be displayed on a user interface such as the user interface of a drug error reduction system in accordance with an embodiment of the present disclosure;

FIG. 92 depicts an example add medication record screen which may be displayed on a user interface such as the user interface of a drug error reduction system in accordance with an embodiment of the present disclosure;

FIG. 93 depicts an example add medication record screen which may be displayed on a user interface such as the user interface of a drug error reduction system in accordance with an embodiment of the present disclosure;

FIG. 94 depicts an example add medication record screen which may be displayed on a user interface such as the user interface of a drug error reduction system in accordance with an embodiment of the present disclosure;

FIG. 95 depicts an example add medication record screen which may be displayed on a user interface such as the user interface of a drug error reduction system in accordance with an embodiment of the present disclosure;

FIG. 96 depicts an example add medication record screen which may be displayed on a user interface such as the user interface of a drug error reduction system in accordance with an embodiment of the present disclosure;

FIG. 97 depicts an example add medication record screen which may be displayed on a user interface such as the user interface of a drug error reduction system in accordance with an embodiment of the present disclosure;

FIG. 98 depicts an example add medication record screen which may be displayed on a user interface such as the user interface of a drug error reduction system in accordance with an embodiment of the present disclosure;

FIG. 99 depicts an example medication screen which may be displayed on a user interface such as the user interface of a drug error reduction system in accordance with an embodiment of the present disclosure;

FIG. 100 depicts an example add medication record screen which may be displayed on a user interface such as the user interface of a drug error reduction system in accordance with an embodiment of the present disclosure;

FIG. 101 depicts an example add medication record screen which may be displayed on a user interface such as the user interface of a drug error reduction system in accordance with an embodiment of the present disclosure;

FIG. 102 depicts an example add medication record screen which may be displayed on a user interface such as the user interface of a drug error reduction system in accordance with an embodiment of the present disclosure;

FIG. 103 depicts an example add medication record screen which may be displayed on a user interface such as the user interface of a drug error reduction system in accordance with an embodiment of the present disclosure;

Figures 104, 105:
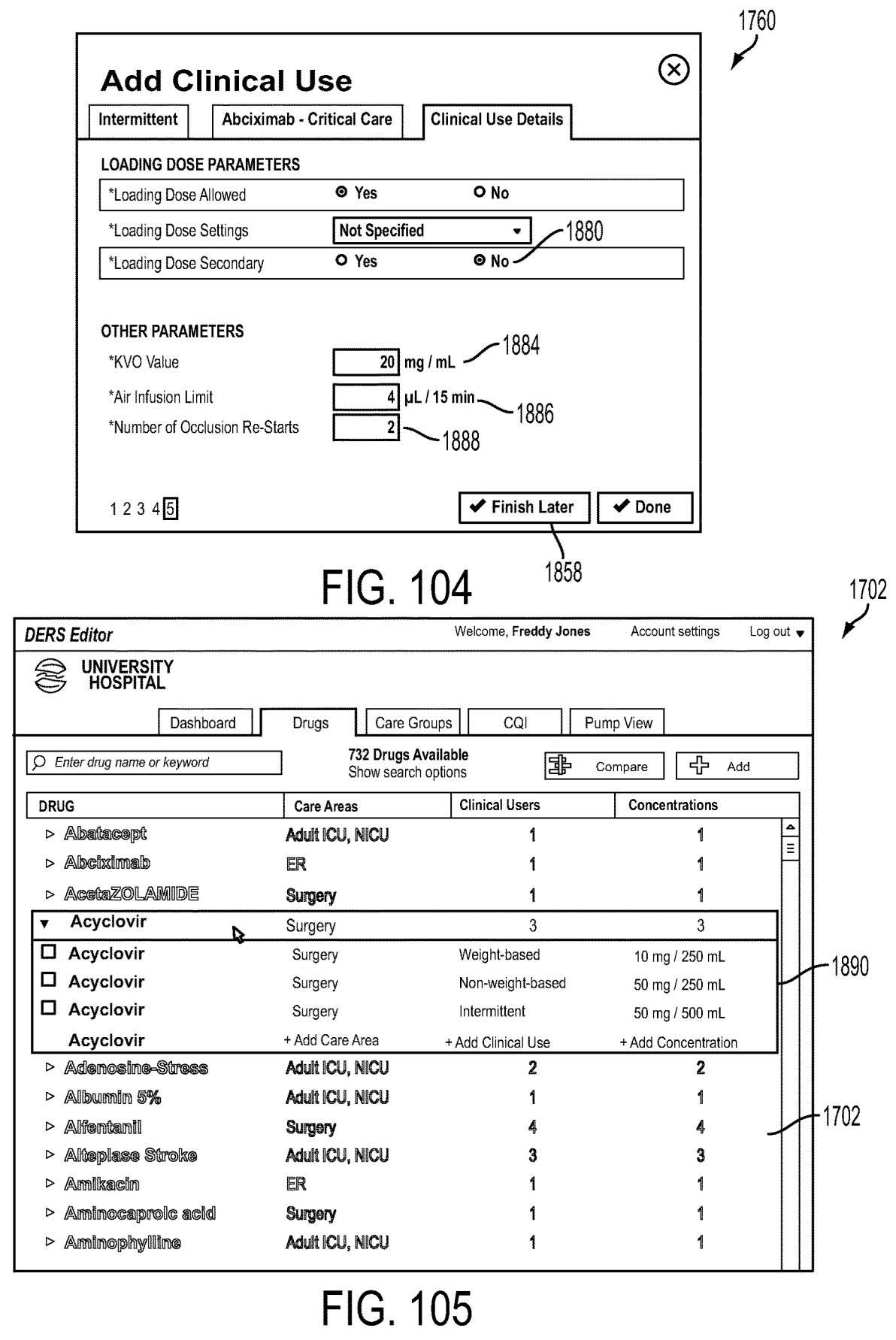

FIG. 104 depicts an example add medication record screen which may be displayed on a user interface such as the user interface of a drug error reduction system in accordance with an embodiment of the present disclosure;

FIG. 105 depicts an example medication screen which may be displayed on a user interface such as the user interface of a drug error reduction system in accordance with an embodiment of the present disclosure;

FIG. 106 depicts an example drug library entry screen which may be displayed on a user interface such as the user interface of a drug error reduction system in accordance with an embodiment of the present disclosure;

FIG. 107 depicts an example medication screen which may be displayed on a user interface such as the user interface of a drug error reduction system in accordance with an embodiment of the present disclosure;

Figures 108, 109:
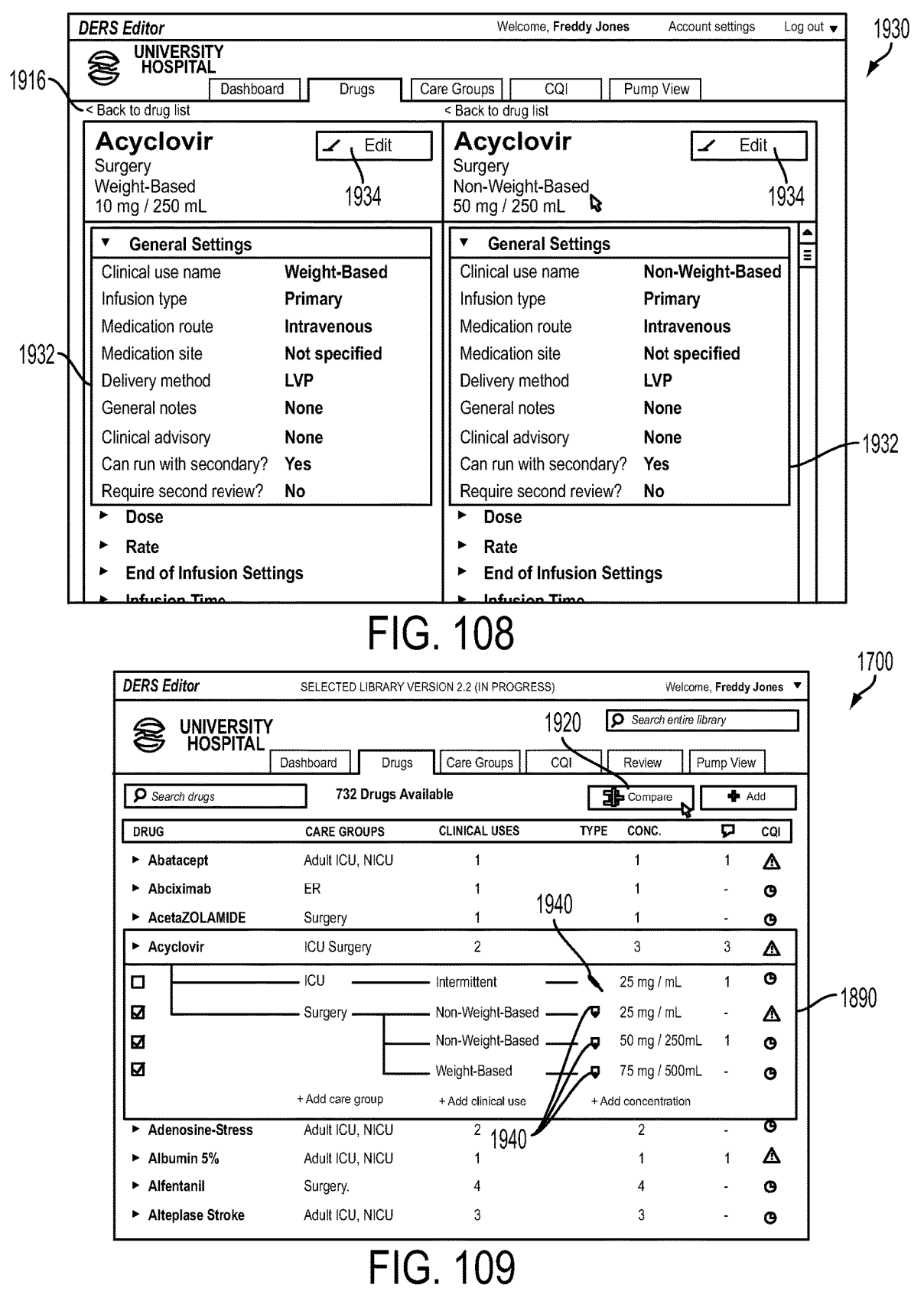

FIG. 108 depicts an example medication record comparison screen which may be displayed on a user interface such as the user interface of a drug error reduction system in accordance with an embodiment of the present disclosure;

FIG. 109 depicts an example medication screen which may be displayed on a user interface such as the user interface of a drug error reduction system in accordance with an embodiment of the present disclosure;

FIG. 110 depicts an example medication record comparison screen which may be displayed on a user interface such as the user interface of a drug error reduction system in accordance with an embodiment of the present disclosure;

FIG. 111 depicts an example medication record comparison screen which may be displayed on a user interface such as the user interface of a drug error reduction system in accordance with an embodiment of the present disclosure;

FIG. 112 depicts an example medical device simulator screen which may be displayed on a user interface such as the user interface of a drug error reduction system in accordance with an embodiment of the present disclosure;

FIG. 113 depicts an example medical device simulator screen which may be displayed on a user interface such as the user interface of a drug error reduction system in accordance with an embodiment of the present disclosure;

FIG. 114 depicts an example medical device simulator screen which may be displayed on a user interface such as the user interface of a drug error reduction system in accordance with an embodiment of the present disclosure;

FIG. 115 depicts an example continuous quality improvement screen which may be displayed on a user interface such as the user interface of a drug error reduction system in accordance with an embodiment of the present disclosure;

FIG. 116 depicts an example continuous quality improvement screen which may be displayed on a user interface such as the user interface of a drug error reduction system in accordance with an embodiment of the present disclosure;

FIG. 117 depicts an example continuous quality improvement screen which may be displayed on a user interface such as the user interface of a drug error reduction system in accordance with an embodiment of the present disclosure;

FIG. 118 depicts an example continuous quality improvement screen which may be displayed on a user interface such as the user interface of a drug error reduction system in accordance with an embodiment of the present disclosure;

FIG. 119 depicts an example continuous quality improvement screen which may be displayed on a user interface such as the user interface of a drug error reduction system in accordance with an embodiment of the present disclosure;

FIG. 120 depicts an example continuous quality improvement screen which may be displayed on a user interface such as the user interface of a drug error reduction system in accordance with an embodiment of the present disclosure;

FIG. 121 depicts an example continuous quality improvement screen which may be displayed on a user interface such as the user interface of a drug error reduction system in accordance with an embodiment of the present disclosure;

FIG. 122 depicts an example continuous quality improvement screen which may be displayed on a user interface such as the user interface of a drug error reduction system in accordance with an embodiment of the present disclosure;

FIG. 123 depicts an example continuous quality improvement screen which may be displayed on a user interface such as the user interface of a drug error reduction system in accordance with an embodiment of the present disclosure;

FIG. 124 depicts an example continuous quality improvement screen which may be displayed on a user interface such as the user interface of a drug error reduction system in accordance with an embodiment of the present disclosure;

FIG. 125 depicts an example continuous quality improvement screen which may be displayed on a user interface such as the user interface of a drug error reduction system in accordance with an embodiment of the present disclosure;

FIG. 126 depicts an example continuous quality improvement screen which may be displayed on a user interface such as the user interface of a drug error reduction system in accordance with an embodiment of the present disclosure;

Figures 127, 128:
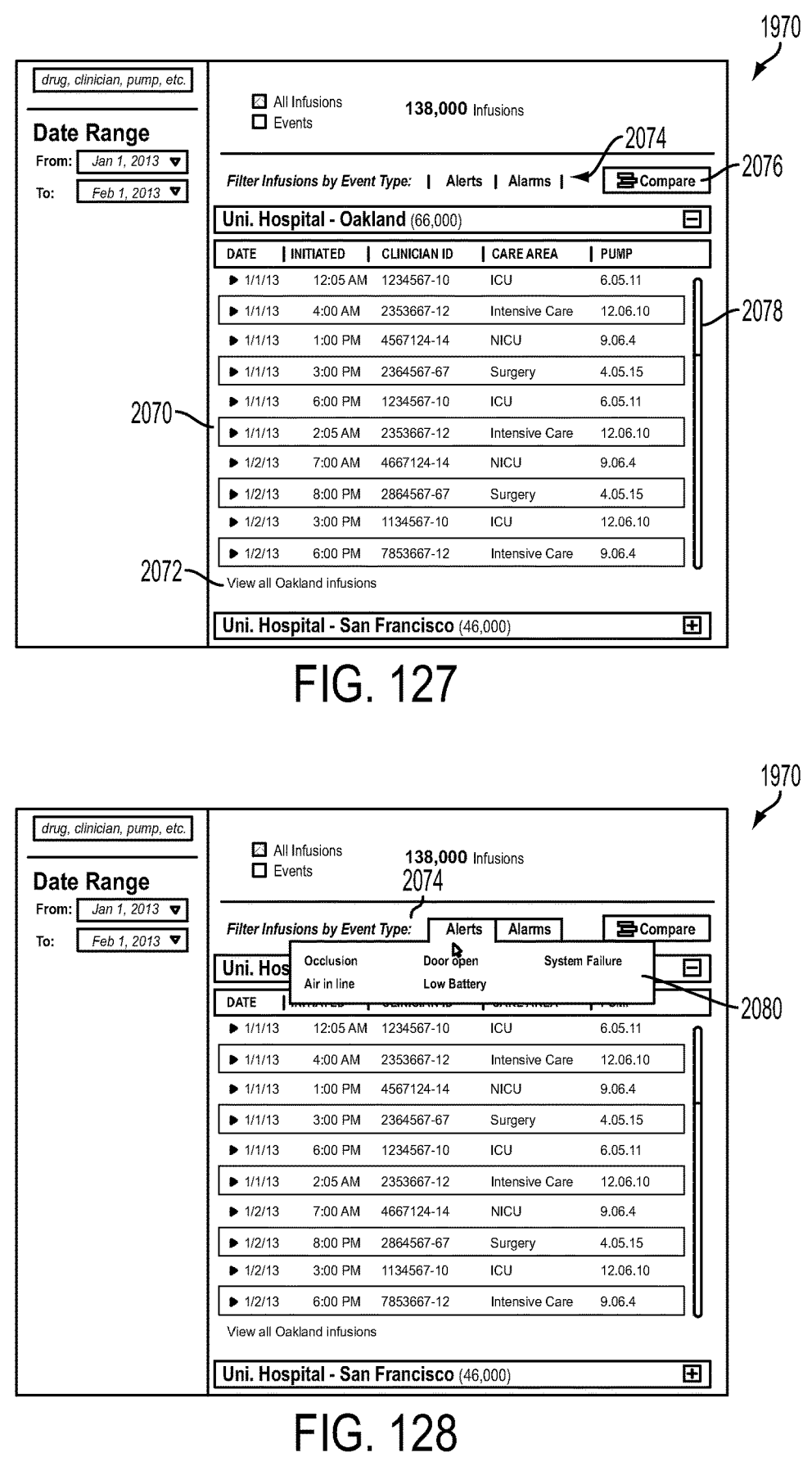

FIG. 127 depicts an example continuous quality improvement screen which may be displayed on a user interface such as the user interface of a drug error reduction system in accordance with an embodiment of the present disclosure;

FIG. 128 depicts an example continuous quality improvement screen which may be displayed on a user interface such as the user interface of a drug error reduction system in accordance with an embodiment of the present disclosure;

FIG. 129 depicts an example continuous quality improvement screen which may be displayed on a user interface such as the user interface of a drug error reduction system in accordance with an embodiment of the present disclosure;

FIG. 130 depicts an example continuous quality improvement screen which may be displayed on a user interface such as the user interface of a drug error reduction system in accordance with an embodiment of the present disclosure;

FIG. 131 depicts an example continuous quality improvement screen which may be displayed on a user interface such as the user interface of a drug error reduction system in accordance with an embodiment of the present disclosure;

FIG. 132 depicts an example of a drug error reduction system editor dashboard screen in accordance with an embodiment of the present disclosure;

FIG. 133 depicts an example of a drug error reduction system editor dashboard screen in which a feedback item has been accessed in accordance with an embodiment of the present disclosure;

FIG. 134 depicts an example of a drug error reduction system editor dashboard screen in accordance with an embodiment of the present disclosure;

FIG. 135 depicts an example of a drug error reduction system editor dashboard screen in which a change request has been accessed in accordance with an embodiment of the present disclosure;

FIG. 136 depicts an example of a drug error reduction system editor dashboard screen in accordance with an embodiment of the present disclosure;

FIG. 137 depicts an example of a drug error reduction system editor dashboard screen in accordance with an embodiment of the present disclosure;

FIG. 138 depicts an example of a drug error reduction system editor dashboard screen in accordance with an embodiment of the present disclosure;

FIG. 139 depicts an example of a drug error reduction system editor dashboard screen in which a change request has been accessed in accordance with an embodiment of the present disclosure;

FIG. 140 depicts an example of a drug error reduction system editor dashboard screen in which a change request has been accessed in accordance with an embodiment of the present disclosure;

FIG. 141 depicts an example of a drug error reduction system editor dashboard screen in accordance with an embodiment of the present disclosure;

FIG. 142 depicts an example of a drug error reduction system editor dashboard screen in which a proposed change has been accessed for review in accordance with an embodiment of the present disclosure;

FIG. 143 depicts an example of a drug error reduction system editor dashboard screen in which a proposed change has been accessed for review in accordance with an embodiment of the present disclosure;

Figures 144, 145:
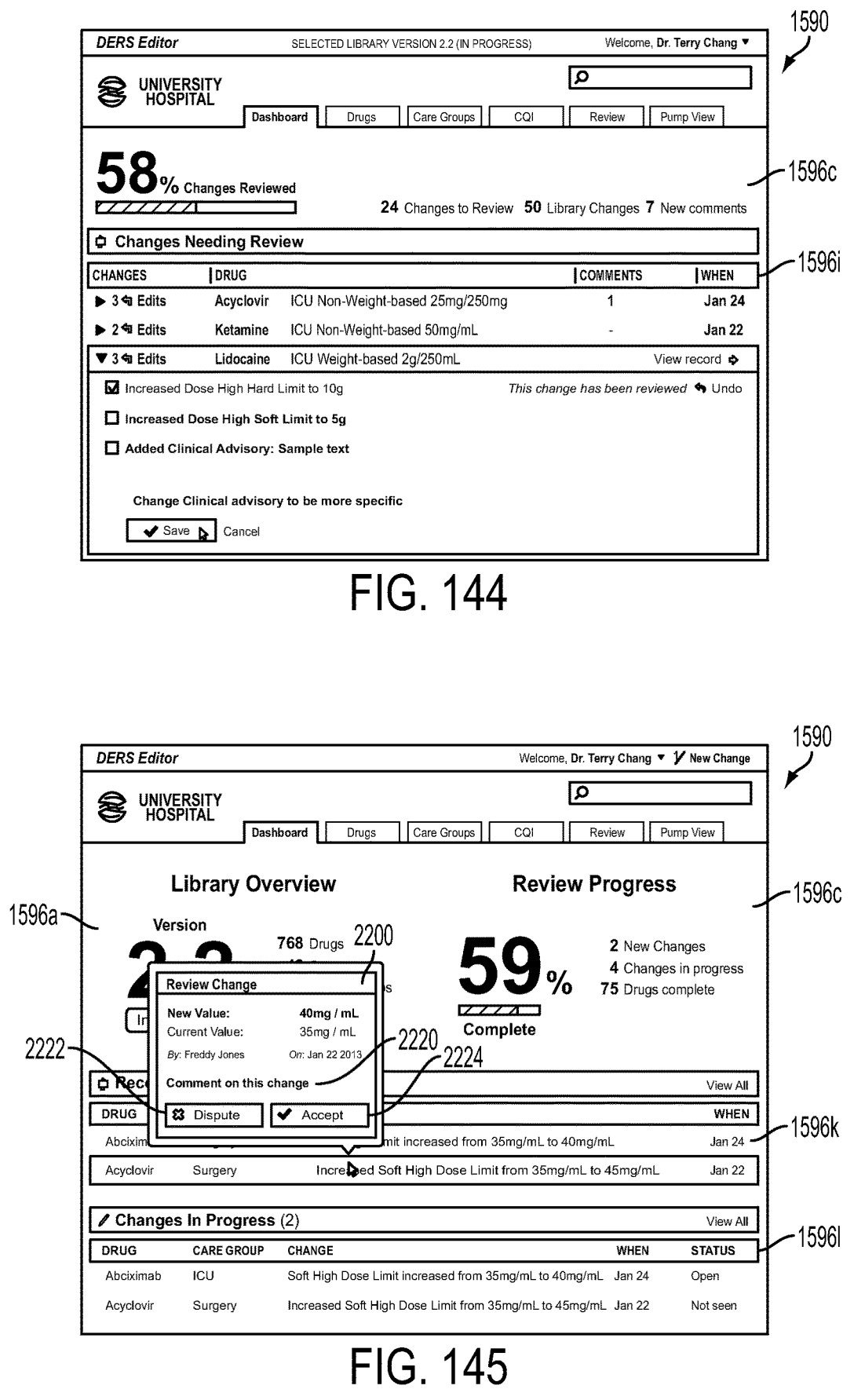

FIG. 144 depicts an example of a drug error reduction system editor dashboard screen in accordance with an embodiment of the present disclosure;

FIG. 145 depicts an example of a drug error reduction system editor dashboard screen in which a proposed change has been accessed for review in accordance with an embodiment of the present disclosure;

FIG. 146 depicts an example of a drug error reduction system editor dashboard screen in which a user is using a search utility in accordance with an embodiment of the present disclosure;

FIG. 147 depicts an example of a review screen which may be displayed on a user interface such as a drug error reduction system user interface in accordance with an embodiment of the present disclosure;

FIG. 148 depicts an example of a review screen which may be displayed on a user interface such as a drug error reduction system user interface in accordance with an embodiment of the present disclosure;

FIG. 149 depicts an example of a review screen which may be displayed on a user interface such as a drug error reduction system user interface in accordance with an embodiment of the present disclosure;

FIG. 150 depicts an example of a review screen which may be displayed on a user interface such as a drug error reduction system user interface in accordance with an embodiment of the present disclosure;

FIG. 151 depicts an example of a review screen which may be displayed on a user interface such as a drug error reduction system user interface in accordance with an embodiment of the present disclosure;

Figures 152, 153:
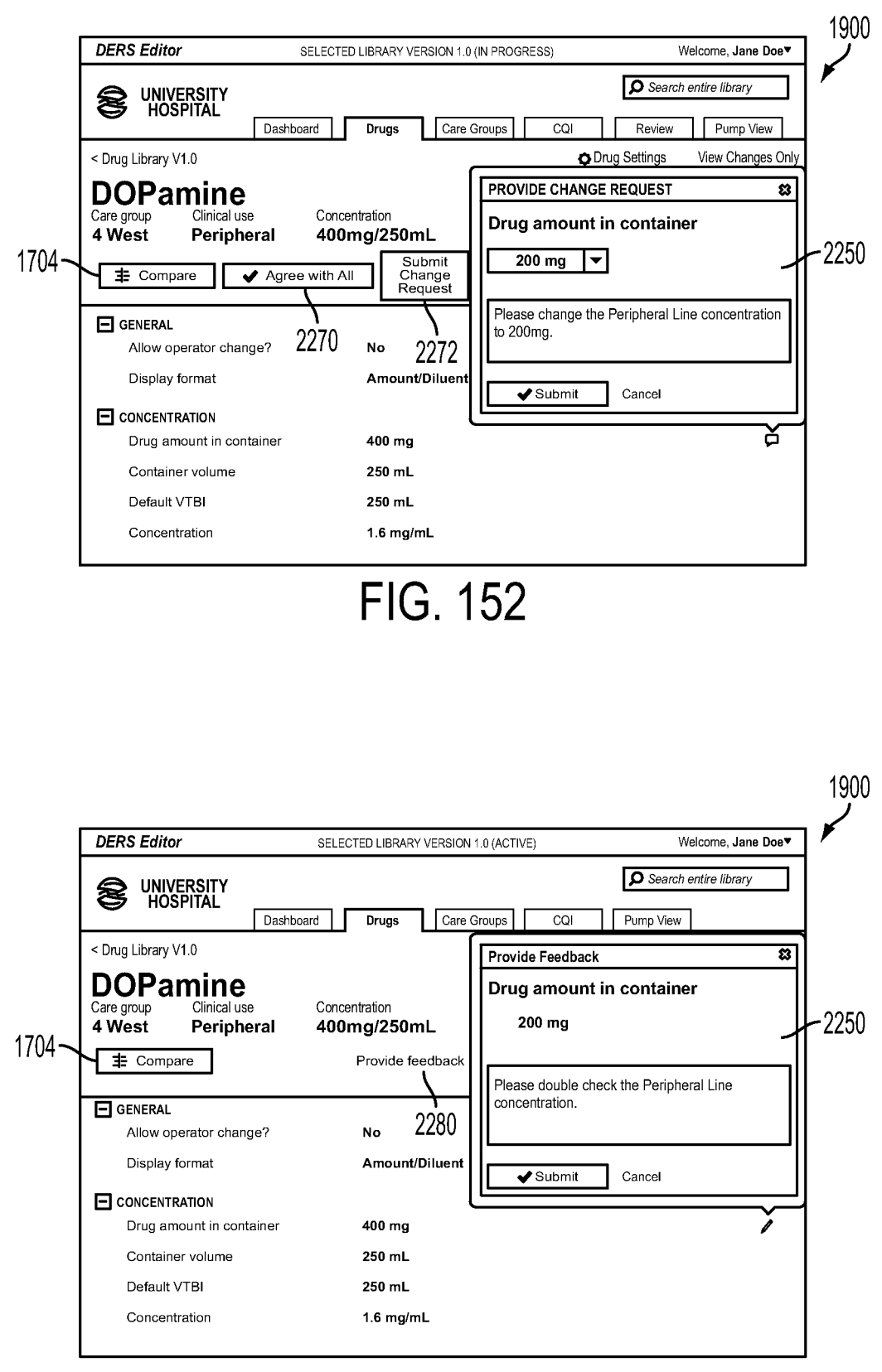

FIG. 152 depicts an example drug library entry screen which may be displayed on a user interface such as the user interface of a drug error reduction system in accordance with an embodiment of the present disclosure;

FIG. 153 depicts an example drug library entry screen which may be displayed on a user interface such as the user interface of a drug error reduction system in accordance with an embodiment of the present disclosure;

Figures 154, 155:
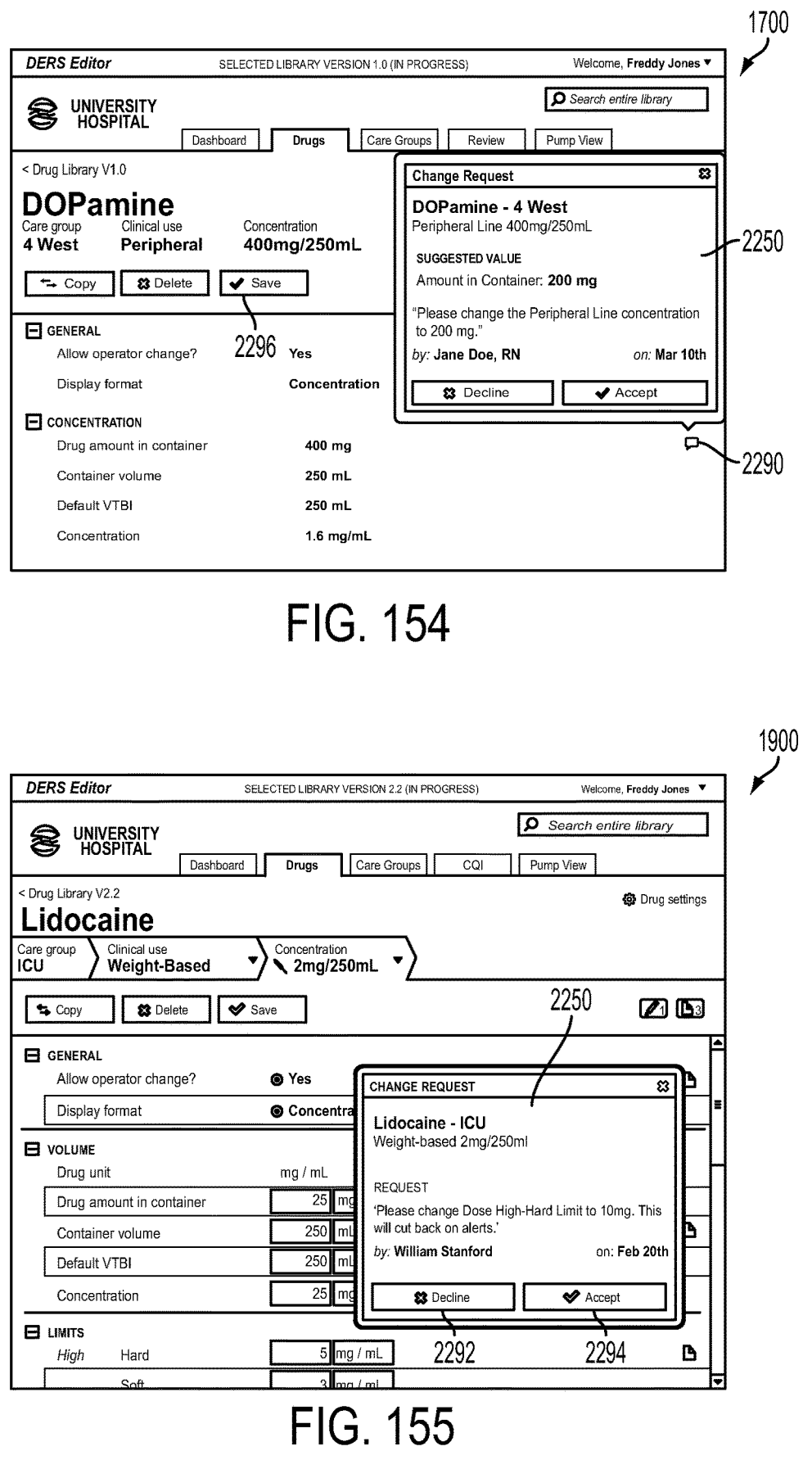

FIG. 154 depicts an example drug library entry screen which may be displayed on a user interface such as the user interface of a drug error reduction system in accordance with an embodiment of the present disclosure;

FIG. 155 depicts an example drug library entry screen which may be displayed on a user interface such as the user interface of a drug error reduction system in accordance with an embodiment of the present disclosure;

Figures 156, 157:
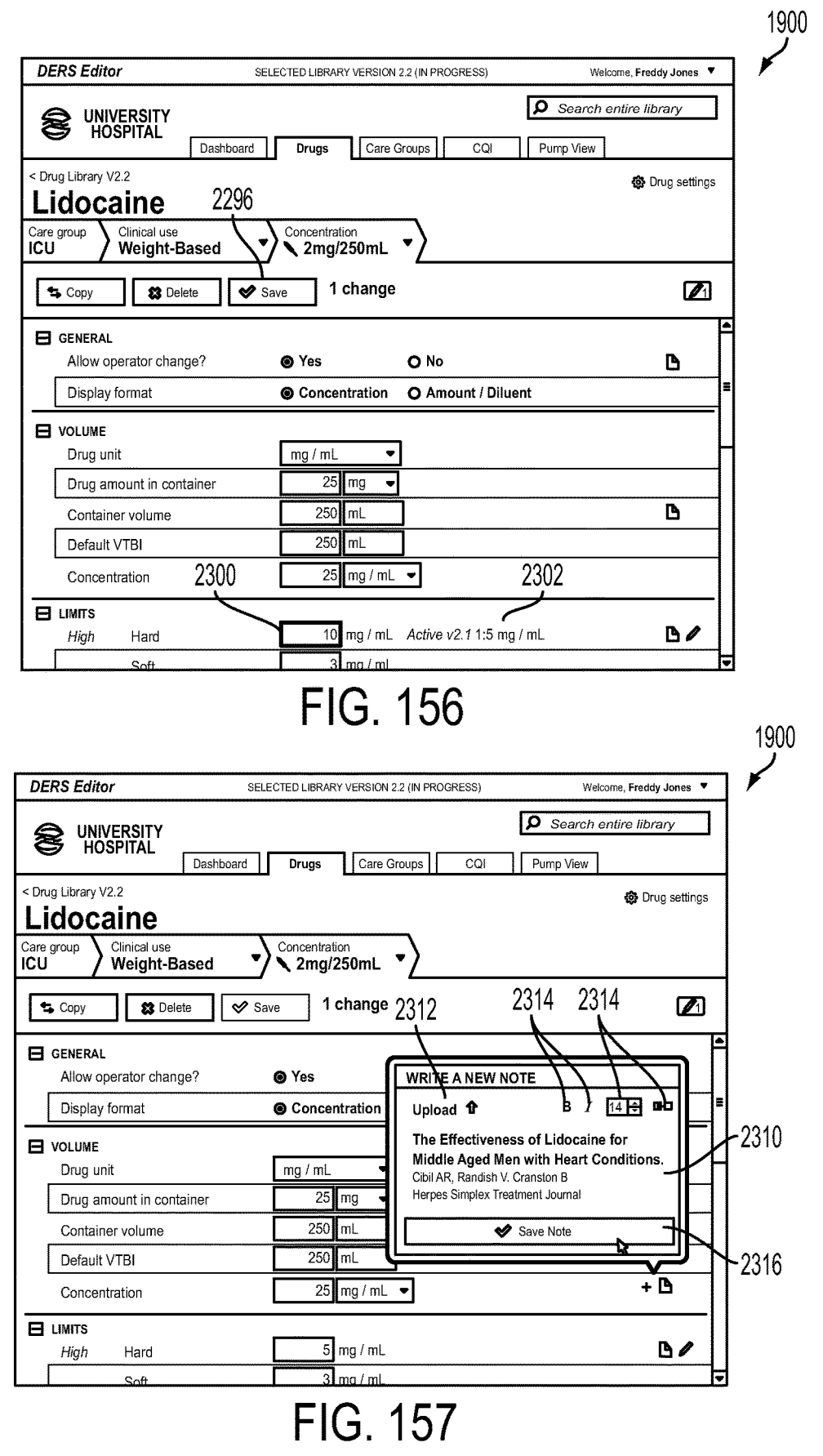

FIG. 156 depicts an example drug library entry screen which may be displayed on a user interface such as the user interface of a drug error reduction system in accordance with an embodiment of the present disclosure;

FIG. 157 depicts an example drug library entry screen which may be displayed on a user interface such as the user interface of a drug error reduction system in accordance with an embodiment of the present disclosure;

Figures 158, 159:
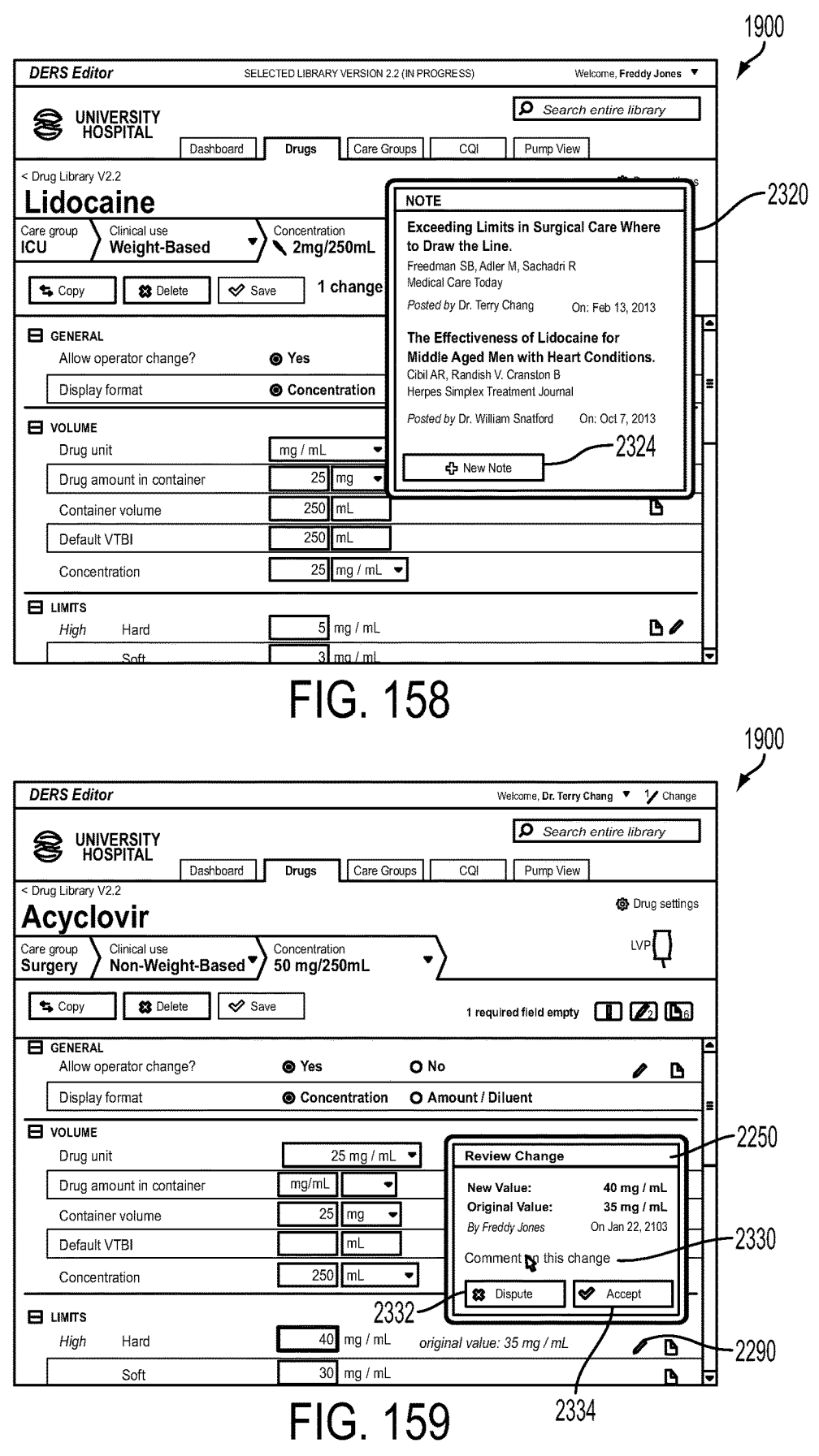

FIG. 158 depicts an example drug library entry screen which may be displayed on a user interface such as the user interface of a drug error reduction system in accordance with an embodiment of the present disclosure;

FIG. 159 depicts an example drug library entry screen which may be displayed on a user interface such as the user interface of a drug error reduction system in accordance with an embodiment of the present disclosure;

FIG. 160 depicts an example drug library screen which may be displayed on a user interface such as the user interface of a drug error reduction system in accordance with an embodiment of the present disclosure;

FIG. 161 depicts an example drug library screen which may be displayed on a user interface such as a drug error reduction system user interface in accordance with an embodiment of the present disclosure;

FIG. 162 depicts an example drug library screen which may be displayed on a user interface such as a drug error reduction system user interface in accordance with an embodiment of the present disclosure;

FIG. 163 depicts an example drug library screen which may be displayed on a user interface such as a drug error reduction system user interface in accordance with an embodiment of the present disclosure;

FIG. 164 depicts an example prompt which may be displayed on a user interface such as a drug error reduction system user interface in accordance with an embodiment of the present disclosure;

FIG. 165 depicts an example drug library screen which may be displayed on a user interface such as a drug error reduction system user interface in accordance with an embodiment of the present disclosure;

FIG. 166 depicts an example prompt which may be displayed on a user interface such as a drug error reduction system user interface in accordance with an embodiment of the present disclosure;

FIG. 167 depicts an example drug library screen which may be displayed on a user interface such as a drug error reduction system user interface in accordance with an embodiment of the present disclosure;

FIG. 168 depicts an example prompt which may be displayed on a user interface such as a drug error reduction system user interface in accordance with an embodiment of the present disclosure;

FIG. 169 depicts an example drug library screen which may be displayed on a user interface such as a drug error reduction system user interface in accordance with an embodiment of the present disclosure;

FIG. 170 depicts an example drug library screen which may be displayed on a user interface such as a drug error reduction system user interface in accordance with an embodiment of the present disclosure;

FIG. 171 depicts an example master medication list screen which may be displayed on a user interface such as a drug error reduction system user interface in accordance with an embodiment of the present disclosure;

FIG. 172 depicts an example prompt which may be displayed on a user interface such as a drug error reduction system user interface in accordance with an embodiment of the present disclosure;

FIG. 173 depicts an example prompt which may be displayed on a user interface such as a drug error reduction system user interface in accordance with an embodiment of the present disclosure;

FIG. 174 depicts an example prompt which may be displayed on a user interface such as a drug error reduction system user interface in accordance with an embodiment of the present disclosure;

FIG. 175 depicts an example prompt which may be displayed on a user interface such as a drug error reduction system user interface in accordance with an embodiment of the present disclosure;

FIG. 176 depicts an example master medication list screen which may be displayed on a user interface such as a drug error reduction system user interface in accordance with an embodiment of the present disclosure;

FIG. 177 depicts an example prompt which may be displayed on a user interface such as a drug error reduction system user interface in accordance with an embodiment of the present disclosure;

FIG. 178 depicts an example drug library screen which may be displayed on a user interface such as a drug error reduction system user interface in accordance with an embodiment of the present disclosure;

FIG. 179 depicts an example prompt which may be displayed on a user interface such as a drug error reduction system user interface in accordance with an embodiment of the present disclosure;

FIG. 180 depicts an example prompt which may be displayed on a user interface such as a drug error reduction system user interface in accordance with an embodiment of the present disclosure;

FIG. 181 depicts an example software architecture block diagram for an example medical device in accordance with an embodiment of the present disclosure;

FIG. 182 depicts a flowchart detailing a number of example steps which may be used to install a syringe on a medical device when preparing to administer an infusion with the medical device in accordance with an embodiment of the present disclosure;

FIG. 183 depicts a flowchart detailing a number of example steps which may be used to prime an IV line of a medical device in accordance with an embodiment of the present disclosure;

FIG. 184 depicts a flowchart detailing a number of example steps which may be used to load an administration set into a medical device such as a large volume pump in accordance with an embodiment of the present disclosure;

FIG. 185 depicts a flowchart detailing a number of example steps which may be used to select a care area, medication, clinical use, and a concentration for a medication when programming an infusion on a medical device in accordance with an embodiment of the present disclosure;

FIG. 186 depicts a flowchart detailing a number of example steps which may be used to program an infusion on a medical device in accordance with an embodiment of the present disclosure;

FIG. 187 depicts a flowchart detailing a number of example steps which may be used to determine if a parameter entered on a medical device falls outside the limits defined for that parameter in accordance with an embodiment of the present disclosure;

FIG. 188 depicts a flowchart which details a number of example steps which may be used to deliver a primary continuous infusion in accordance with an embodiment of the present disclosure;

FIG. 189 depicts a flowchart detailing a number of example steps which may be used to deliver a bolus of a medication with a medical device in accordance with an embodiment of the present disclosure;

FIG. 190 depicts a flowchart detailing a number of example steps which may be used to deliver a secondary infusion in accordance with an embodiment of the present disclosure;

FIG. 191 depicts an example flowchart which details a number of steps which may be used to deliver a multi-step infusion with a medical device in accordance with an embodiment of the present disclosure;

FIG. 192 depicts a flowchart detailing a number of example steps which may be used to titrate an infusion being administered by a medical device in accordance with an embodiment of the present disclosure;

FIG. 193 depicts a flowchart detailing a number of exemplary steps which may be used at and near the end of an infusion administered by a medical device in accordance with an embodiment of the present disclosure;

FIG. 194 depicts a flowchart detailing a number of steps which may be used to detect and resolve an air-in-line condition on a medical device in accordance with an embodiment of the present disclosure;

FIG. 195 depicts a flowchart detailing a number of example steps which may be used to detect and resolve an occlusion in an infusion line associated with a medical device in accordance with an embodiment of the present disclosure;

FIG. 196 depicts a flowchart detailing a number of steps which may be used to change the care area for a medical device during an on-going therapy in accordance with an embodiment of the present disclosure;

FIG. 197 depicts a flowchart detailing a number of example steps which may be used to stop an on-going infusion on a medical device in accordance with an embodiment of the present disclosure;

FIG. 198 depicts a flowchart detailing a number of exemplary steps which may be used in the event that the batteries of a medical device become drawn down to a predetermined level in accordance with an embodiment of the present disclosure;

FIG. 199 depicts a flowchart detailing a number of steps which may be used to lock and unlock the user interface of a medical device in accordance with an embodiment of the present disclosure;

FIG. 200 depicts a flowchart detailing a number of exemplary steps which may be used to power down a medical device or put a medical device into a sleep state in accordance with an embodiment of the present disclosure;

FIG. 201 depicts a flowchart detailing a number of steps which may be used to flush an IV line associated with a medical device in accordance with an embodiment of the present disclosure;

FIG. 202 depicts a flowchart detailing a number of example steps which may be used to install a replacement syringe on a medical device during the course of an infusion in accordance with an embodiment of the present disclosure;

FIG. 203 depicts a flowchart detailing a number of example steps which may be used to set up a relay infusion with a number of medical devices in accordance with an embodiment of the present disclosure;

FIG. 204 depicts a flowchart detailing a number of example steps which may be used if a medical device which is part of an established relay infusion is removed from a medical device rack in accordance with an embodiment of the present disclosure;

FIG. 205 depicts a flowchart detailing a number of exemplary steps which may be used in the event that a medical device which is part of an established relay infusion is removed from a medical device rack in accordance with an embodiment of the present disclosure;

FIG. 206 depicts an example start up screen which may be displayed on a user interface such as the user interface of a medical device in accordance with an embodiment of the present disclosure;

FIG. 207 depicts an example start up screen which may be displayed on a user interface such as the user interface of a medical device in accordance with an embodiment of the present disclosure;

FIG. 208 depicts an example start up screen which may be displayed on a user interface such as the user interface of a medical device in accordance with an embodiment of the present disclosure;

FIG. 209 depicts an example login screen which may be displayed on a user interface such as the user interface of a medical device in accordance with an embodiment of the present disclosure;

FIG. 210 depicts an example login screen which may be displayed on a user interface such as the user interface of a medical device in accordance with an embodiment of the present disclosure;

FIG. 211 depicts an example login screen which may be displayed on a user interface such as the user interface of a medical device in accordance with an embodiment of the present disclosure;

FIG. 212 depicts an example select care group screen which may be displayed on a user interface such as the user interface of a medical device in accordance with an embodiment of the present disclosure;

FIG. 213 depicts an example select care area screen which may be displayed on a user interface such as the user interface of a medical device in accordance with an embodiment of the present disclosure;

FIG. 214 depicts an example select patient screen which may be displayed on a user interface such as the user interface of a medical device in accordance with an embodiment of the present disclosure;

FIG. 215 depicts an example select medication screen which may be displayed on a user interface such as the user interface of a medical device in accordance with an embodiment of the present disclosure;

FIG. 216 depicts an example select medication screen which may be displayed on a user interface such as the user interface of a medical device in accordance with an embodiment of the present disclosure;

FIG. 217 depicts an example select medication screen which may be displayed on a user interface such as the user interface of a medical device in accordance with an embodiment of the present disclosure;

FIG. 218 depicts an example select medication screen which may be displayed on a user interface such as the user interface of a medical device in accordance with an embodiment of the present disclosure;

FIG. 219 depicts an example select medication screen which may be displayed on a user interface such as the user interface of a medical device in accordance with an embodiment of the present disclosure;

FIG. 220 depicts an example select clinical use screen which may be displayed on a user interface such as the user interface of a medical device in accordance with an embodiment of the present disclosure;

FIG. 221 depicts an example select clinical use screen which may be displayed on a user interface such as the user interface of a medical device in accordance with an embodiment of the present disclosure;

FIG. 222 depicts an example select concentration screen which may be displayed on a user interface such as the user interface of a medical device in accordance with an embodiment of the present disclosure;

FIG. 223 depicts an example enter patient weight screen which may be displayed on a user interface such as the user interface of a medical device in accordance with an embodiment of the present disclosure;

FIG. 224 depicts an example enter patient weight screen which may be displayed on a user interface such as the user interface of a medical device in accordance with an embodiment of the present disclosure;

FIG. 225 depicts an example enter patient weight screen which may be displayed on a user interface such as the user interface of a medical device in accordance with an embodiment of the present disclosure;

FIG. 226 depicts an example load administration set screen which may be displayed on a user interface such as the user interface of a medical device in accordance with an embodiment of the present disclosure;

FIG. 227 depicts an example troubleshooting screen which may be displayed on a user interface such as the user interface of a medical device in accordance with an embodiment of the present disclosure;

FIG. 228 depicts an example load syringe screen which may be displayed on a user interface such as the user interface of a medical device in accordance with an embodiment of the present disclosure;

FIG. 229 depicts an example select syringe screen which may be displayed on a user interface such as the user interface of a medical device in accordance with an embodiment of the present disclosure;

FIG. 230 depicts an example therapy programming screen which may be displayed on a user interface such as the user interface of a medical device in accordance with an embodiment of the present disclosure;

FIG. 231 depicts an example therapy programming screen which may be displayed on a user interface such as the user interface of a medical device in accordance with an embodiment of the present disclosure;

FIG. 232 depicts an example therapy programming screen which may be displayed on a user interface such as the user interface of a medical device in accordance with an embodiment of the present disclosure;

FIG. 232 depicts an example therapy programming screen which may be displayed on a user interface such as the user interface of a medical device in accordance with an embodiment of the present disclosure;

FIG. 233 depicts an example therapy programming screen which may be displayed on a user interface such as the user interface of a medical device in accordance with an embodiment of the present disclosure;

FIG. 234 depicts an example therapy programming screen which may be displayed on a user interface such as the user interface of a medical device in accordance with an embodiment of the present disclosure;

FIG. 235 depicts an example therapy programming screen which may be displayed on a user interface such as the user interface of a medical device in accordance with an embodiment of the present disclosure;

FIG. 236 depicts an example limit override screen which may be displayed on a user interface such as the user interface of a medical device in accordance with an embodiment of the present disclosure;

FIG. 237 depicts an example second user approval screen which may be displayed on a user interface such as the user interface of a medical device in accordance with an embodiment of the present disclosure;

FIG. 238 depicts an example therapy programming screen which may be displayed on a user interface such as the user interface of a medical device in accordance with an embodiment of the present disclosure;

FIG. 239 depicts an example therapy in progress screen which may be displayed on a user interface such as the user interface of a medical device in accordance with an embodiment of the present disclosure;

FIG. 240 depicts an example therapy in progress screen which may be displayed on a user interface such as the user interface of a medical device in accordance with an embodiment of the present disclosure;

FIG. 241 depicts an example therapy in progress screen which may be displayed on a user interface such as the user interface of a medical device in accordance with an embodiment of the present disclosure;

FIG. 242 depicts an example therapy in progress screen which may be displayed on a user interface such as the user interface of a medical device in accordance with an embodiment of the present disclosure;

FIG. 243 depicts an example therapy in progress screen which may be displayed on a user interface such as the user interface of a medical device in accordance with an embodiment of the present disclosure;

FIG. 244 depicts an example therapy in progress screen which may be displayed on a user interface such as the user interface of a medical device in accordance with an embodiment of the present disclosure;

FIG. 245 depicts an example therapy in progress screen which may be displayed on a user interface such as the user interface of a medical device in accordance with an embodiment of the present disclosure;

FIG. 246 depicts an example therapy in progress screen which may be displayed on a user interface such as the user interface of a medical device in accordance with an embodiment of the present disclosure;

FIG. 247 depicts an example therapy in progress screen which may be displayed on a user interface such as the user interface of a medical device in accordance with an embodiment of the present disclosure;

FIG. 248 depicts an example therapy stopped screen which may be displayed on a user interface such as the user interface of a medical device in accordance with an embodiment of the present disclosure;

FIG. 249 depicts an example alarm screen which may be displayed on a user interface such as the user interface of a medical device in accordance with an embodiment of the present disclosure;

FIG. 250 depicts an example therapy in progress screen which may be displayed on a user interface such as the user interface of a medical device in accordance with an embodiment of the present disclosure;

FIG. 251 depicts an example therapy in progress screen which may be displayed on a user interface such as the user interface of a medical device in accordance with an embodiment of the present disclosure;

FIG. 252 depicts an example locked therapy in progress screen which may be displayed on a user interface such as the user interface of a medical device in accordance with an embodiment of the present disclosure;

FIG. 253 depicts an example therapy in progress screen which may be displayed on a user interface such as the user interface of a medical device in accordance with an embodiment of the present disclosure;

FIG. 254 depicts an example therapy complete screen which may be displayed on a user interface such as the user interface of a medical device in accordance with an embodiment of the present disclosure;

FIG. 255 depicts an example therapy complete screen which may be displayed on a user interface such as the user interface of a medical device in accordance with an embodiment of the present disclosure;

FIG. 256 depicts an example notification settings screen which may be displayed on a user interface such as the user interface of a medical device in accordance with an embodiment of the present disclosure;

FIG. 257 depicts an example therapy parameters screen which may be displayed on a user interface such as the user interface of a medical device in accordance with an embodiment of the present disclosure;

DETAILED DESCRIPTION

Figure 1:
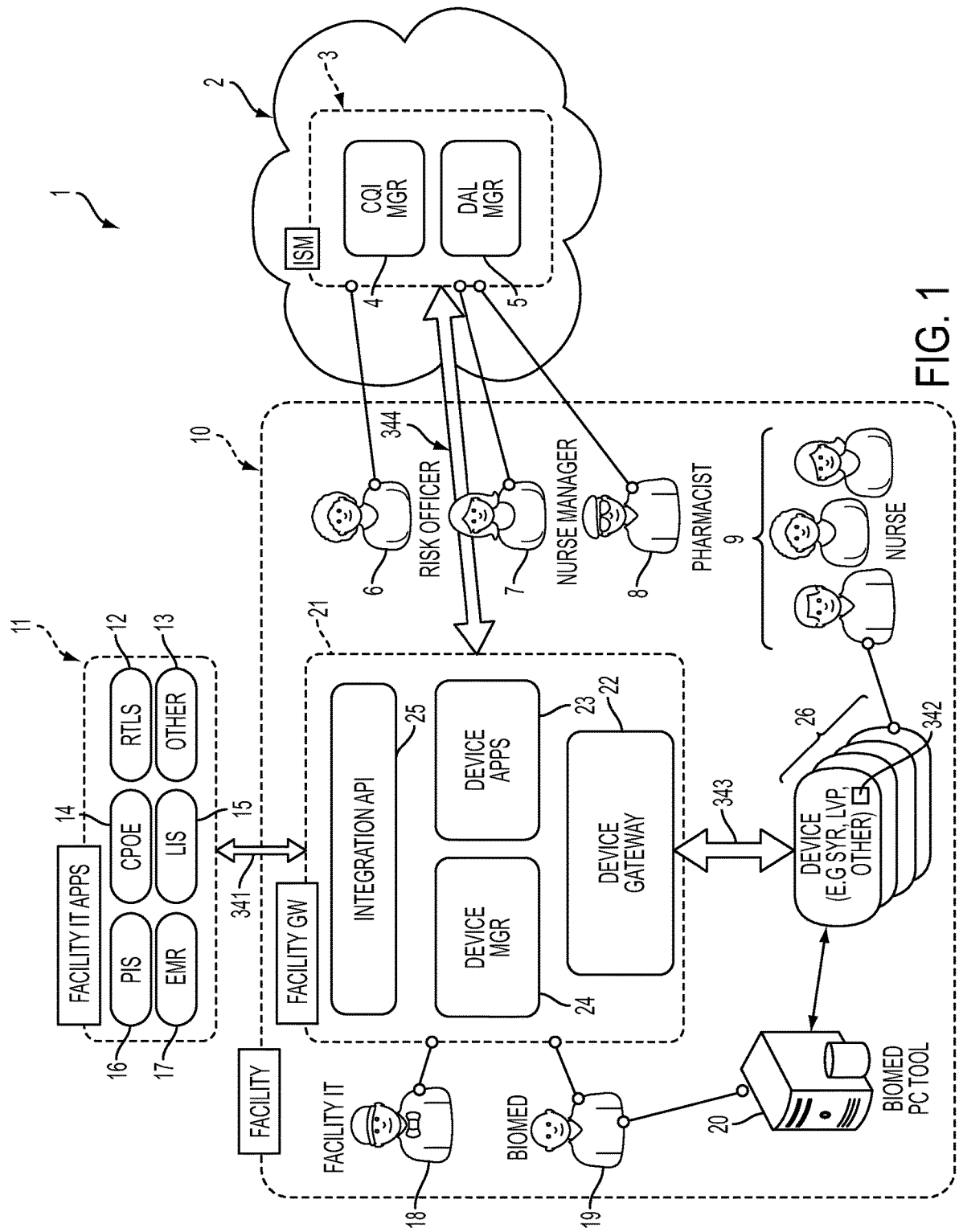
FIG. 1 shows a block diagram of a system for electronic patient care in accordance with an embodiment of the present disclosure.

FIG. 1 shows a block diagram of a system 1 for electronic patient care in accordance with an embodiment of the present disclosure. System 1 includes facility IT applications/services 11, a facility 10, and a cloud services 2.

The facility 10 may be a hospital, a clinic, a medical facility, an outpatient care center, an urgent care center, or a combination or grouping thereof. The facility 10 may include a facility gateway 21 such that various medical devices 26 can communicate with the facility IT applications/services 11 and/or with the cloud services 2. The facility 10 includes various medical devices 26 operated and used by nurses 9 on patients that are in the care of the facility 10. The medical devices 26 may be infusion pumps, peristaltic pumps, syringe pumps, nephrology devices, physiological parameter monitoring devices, other patient-care devices, or some combination thereof.

The facility gateway 21 may be hosted, may be in the cloud, may be maintained for the facility 10 by a service provider, may be controlled, maintained or serviced by a combination of service providers and/or facility IT 18 personnel, and/or may be implemented in a virtual or physical environment. In some embodiments, the facility gateway 21 may be implemented in an appliance in a patient's home. The facility gateway 21 may be used by a hospital, a nursing group, an integrated delivery network ("IDN"), an integrated services group or clinic, a group of clinics, a central clinic, or other healthcare facility or infrastructure.

A biomed PC tool 20 may be used by a biomed technician 19 to update the software of the devices 26. The biomed PC tool 20 may be a browser-based tool for Biomed users 19 to monitor the health of their medical devices 26, view log files, track maintenance activities, and manage the installation of software/firmware. The biomed technician 19 may be a hospital employee (or contract service) who installs, upgrades, and services medical devices 26 (including infusion pumps) to ensure they are in proper working order. The biomed PC tool 20 may interface into the devices 26 via a physical data connection, such as a USB connection or serial cable connection so that the biomed technician 19 may perform these services. The biomed technician 19 may also use the device manager 24 to update the devices 26 wirelessly.

The devices 26 communicate with the facility IT applications/services 11 (via a communications link 343) and/or with the cloud services 2 (via the communications link 344) via the facility gateway 21. The communications links 343 and 344 may use WiFi, Ethernet, TCP/IP, WiMax, fiber optic cables, or any other known communication technology.

The devices 26 communicate with the facility gateway 21 by establishing communications (e.g., via registering) with the device gateway 22. The facility gateway 21 may be a computer, a virtual machine, a hardware device, a software device, a hosted device, software in execution, the like, or some combination thereof. The device gateway 22 may be software executable by the facility gateway 21. The devices 26 may communicate with the device gateway 22 using web services. In some specific embodiments, only the medical devices 26 initiate communication with the device gateway 22 (and thus the facility gateway 21). The device gateway 22 may include a message routing engine that supports both publish/subscribe and point-to-point routing mechanisms. The device gateway 22 may also provide name resolution and capability registry capabilities. Object-Relational Mapping may be used by the device gateway 22 for small-scale object persistence (e.g., using an object-relational mapping (ORM) engine). Additionally or alternatively, the device manager 24 can provide name resolution and/or registry capabilities.

In some embodiments of the present disclosure, a device of the devices 26 is a monitoring client, such as a tablet computer, a tablet device, a PDA, a smart phone, a laptop computer, or a touchscreen-based computer. A monitoring client of the devices 26 may have a monitoring client app within the device apps 23 which allows a caregiver to communicate with other devices of the devices 26. The monitoring client may be used to receive status information from a medical device of the devices 26, receive CQI-messages from a medical device of the devices 26, receive reportable biomed events (RBEs) or reportable clinical events (RCEs) from a medical device of the devices 26, to program a medical device of the devices 26, or otherwise communicate with a medical device of the devices 26.

The communication links 343 between the devices 26 and the facility gateway 21 may use WiFi, Ethernet, TCP/IP, WiMax, fiber optic cables, or any other known communication technology. In some embodiments of the present disclosure, the devices 26 communicate with the facility gateway 21 through a cellular connection (e.g., the communications link 343 includes a cellular connection). For example, one or more of the devices 26 may be a located within a patient's home, within a clinic, within a field facility (e.g., a tent facility), emergency location, other location, or some combination thereof.

The device gateway 22 may provide: (1) component registry and license management (e.g., using the device manager 24); (2) an installation repository for receiving, maintaining and tracking new versions of installable components, such as device firmware/software, drug administration libraries, enterprise application software, and infrastructure software (e.g. operating system releases, application servers, database management system ("DBMS")); and/or (3) message routing capabilities, such as distributing messages, both among applications within the facility gateway 21 and with external subsystems (e.g. the cloud services 2).

Deployment environments where medical devices 26 maintain active network connections to the device gateway 22 are called connected environments and may, as previously mentioned, be achieved using wireless networks (IEEE 802.11 b/g/n). Also as previously mentioned, in other embodiments, network connectivity may be achieved through other technologies, like cellular technology.

Environments where devices 26 do not maintain wireless connections are called standard environments, despite the fact that enterprise application components and external subsystems may still be connected. In this specific embodiment, the device gateway 22 still performs all three roles for enterprise application components and external subsystems, while, message exchange involving the devices 26 may use the biomed technician 19 (e.g., using the biomed PC tool 26) to store the messages into an external media device (e.g. memory sticks).

Event subscribers, such as the device applications 23, may refine the event stream and republish higher-level events back to the device gateway 22. Reportable biomed events ("RBE"), described below, will be among the events republished by these applications. The RBEs may be reported as CQI messages to the cloud services 2. In some embodiments, an application running on the facility gateway 21 is a Biomed Server that subscribes to RBEs and stores them in a local database within the facility gateway 21.

Biomed technicians 19 may use their browser to access the device manager 19 and request device status reports of a device of the devices 26. The UI of the device manager 24 may command the biomed server to access the database and generate HTML/JS pages for browser display to the biomed technician 19.

In some embodiments, before a new device of the medical devices 26 is authorized for use with the device gateway 22, the biomed technician 19 must register the new device using its serial number. This may be validated using asymmetric key (public/private key pairs) encryption, and may be performed as part of the manufacturing process. Once a device of the medical devices 26 is registered with the device gateway 22, the biomed technician 19 configures its wireless protocol and encryption settings. Once a medical device of the medical devices 26 is registered with the device gateway 22, it reports its initial configuration, including model, options, and hardware, firmware and device control software version for storage within the device gateway 22 and/or within the device manager 24. Similarly, when a device is removed from the list of authorized devices of the device gateway 22, the biomed technician 19 can unregister it.

Each of the medical devices 26 may run a self-test on startup, and publish an event to the device gateway 22 containing the results. In addition, because the medical devices 26 may routinely run for a long time interval between restarts, the medical devices 26 may automatically schedule and run certain self-tests at times which do not interfere with patient safety and/or treatment.

The facility gateway 21 includes device apps 23 which may communicate data using publish-subscribe data connections (described below). Each device app of the devices apps 23 may be for a particular type and/or model of device of the devices 26. These applications may provide software intelligence to medical devices 26, by receiving, filtering and analyzing raw events, and retransmitting higher-level interpretations. Each type of medical device (of the medical devices 26) may have a corresponding device application (of the device applications 23).

The facility gateway 21 also includes a device manager 24 for controlling, managing, or monitoring the devices 26. For example, the device manager 24 may be used to update and/or download configuration files (e.g. DAL files) into a device of the devices 26. As previously mentioned, the biomed technician 19 may control the updating of software, firmware, or configuration files of the devices 26. The device manager 24 may provide a browser-based tool for IT managers and/or technicians 18 to monitor the health of the hardware, software and network resources used to support delivery of patient care. That is, the facility gateway 21 may be managed by a facility IT employee/contractor 18.

When a new drug administration library ("DAL") version is released, a secure messaging link may send the DAL file from the DAL manager 5 to the device gateway 22 to notify the Biomed technician 19 of its availability. This notification specifies the device type, location of the DAL, documentation, release notes URL, installer URL, checksum, and installation dependencies. In some embodiments of the present disclosure, the device manager 24 has access to the new DAL file, receives the DAL file from the device gateway 22, receives the DAL file directly from the DAL manager 5, and/or controls the updating of the medical devices 26 using the DAL file.

In a specific embodiment, the Biomed technician 19 uses the release notes URL (e.g., via a webpage of the device manager 24 and/or via the biomed PC tool 20) to access information about the upgrade, and uses the installer URL and checksum to download and validate the DAL file and save it in the device gateway's 22 repository. Next, the biomed technician 19 selects one or more of the medical devices 26 to copy the new DAL file to. The selected one or more of the medical devices 26 may then be notified (e.g., via the device gateway 22) that a new DAL file is available for them. On the next medical device restart (of the medical devices 26 that were selected to be updated), the selected group of the medical devices 26 installs the new DAL version (backing it out on error) and notifies the device gateway 22 and/or the device manager 24 of the outcome. Any of the procedures described herein to update the DAL file may be used to update firmware, software, an OS, or other configuration files of a medical device of the medical devices 26.

The facility gateway 21 may also include an integration API 25 that allows the devices 26, the device apps 23, and/or the device manager 24 to communicate with various databases of the facility IT apps 11, such as the Patient Information System 16, the Electronic Medical Records 17, the Computerized Physician Order Entry 14, the Laboratory Information System 15, the Real-Time Location Services 12, and/or other databases or services 13. The integration API 25 enables the components within the facility gateway 21 to interoperate with the facility IT applications/services 11. The facility gateway 21 may communicate with the facility IT apps 11 via a communications link 341 that may include a wireless link, a hardwired link, a TCP/IP link, an internet link, a software communications link, a hardware communications link, or other communications technique or technology.

The facility IT apps/services 11 support the administrative functions of the hospital (e.g. admission, discharge, transfer, coding, billing, collections, etc.). The integration API 25 isolates differences in the applications 12-17 of the facility IT apps 11 from the applications 23-24, the device gateway 22, and/or the devices 26. For example, a device of the devices 26 may request from the device gateway 22 programming information (or the programming information may be pushed to the device of the devices 26). The patient ID, the pump ID, the drug, and the rate of flow, may reside in one or more of the facility IT apps 11; the integration API 25 provides a common format for communicating this information to the devices 26 regardless of the needs or requirements of the facility IT apps 11. This information may be gathered by the integration API 25 querying various ones of the facility IT apps 11 to obtain the data and provide the data to the devices 26 in a standardized format. The integration API 25 may be capable of being used with a variety of facility IT apps 12-17 having different formats, data standards, communication standards, encryption standards, etc., but provides a standard interface with the apps 22-24 and/or the devices 26.

The integration API 25 facilitates auto-programming of one or more of the devices 26. The prescription may be sent from one of the servers of the facility IT applications 14. The integration API 25 may receive the prescription to reformat it and send it to the device gateway 22. The facility gateway 21 may include a clinical server which writes the prescription event to a persistent cache. The clinical server may start an auto-programming workflow. This workflow may identify a medical device of the medical devices 26 corresponding to the target patient and send a command message to the respective device of the medical devices 26 to load the prescription. The respective medical device of the medical devices 26 will acknowledge receipt of the prescription and display a notification on the display. The clinician may locate the medication bag and may use a barcode reader, for example, on the respective medical device of the medical devices 26 to validate the medication and patient. The respective medical device of the medical devices 26 may then confirm that the medication matches the prescription, and the clinician starts administration. The respective medical device of the medical devices 26 completes the auto-programming workflow by sending a message to the clinical server via the device gateway.

The caregiver may use a UI to verify the programming of a medical device of the devices 26. The clinician locates the medication, and uses the user interface of the respective medical device of the medical devices 26 to either verify the auto-programming parameters of the medical device of the devices 26 and/or manually program the medical device of the medical devices 26.

The PIS 16 is a departmental system used by the pharmacists 8 to receive, review, track and fill orders for prescription medications. The EMR 17 system keeps track of patient medical history in the health care institution (encounters, exams, diagnoses, procedures, etc.). The CPOE 14 is a system used by doctors or nurses 9 to order lab tests, prescription drugs, medical images and other clinical procedures. The LIS 15 is a departmental system used by lab technicians to receive and process orders for clinical samples (e.g. tissue, blood, urine, etc.) The RTLS 12 tracks the location and status of the devices 26. The other 13 may be any other database used for patient care.

The cloud services 2 include a cloud-hosted infusion safety manager 3 ("ISM"). Infusion safety manager may be used interchangeably herein with the term hosted safety manager ("HSM"). The HSM 3 includes a Continuous Quality Improvement ("CQI") manager 4 and a DAL manager 5. The risk officers 6, the nurse managers 7, and the pharmacists 8 may all review the CQI messages retrieved by the CQI manager 4 to facilitate the development and improvement of a DAL file via the DAL manager 5. The DAL file may thereafter be downloaded into one or more of the devices 26. The DAL manager 5 may include or is associated with a Drug Error Reduction System ("DERS") editor (e.g., the DERS editor 112 of FIG. 4, described below).

Figure 2:
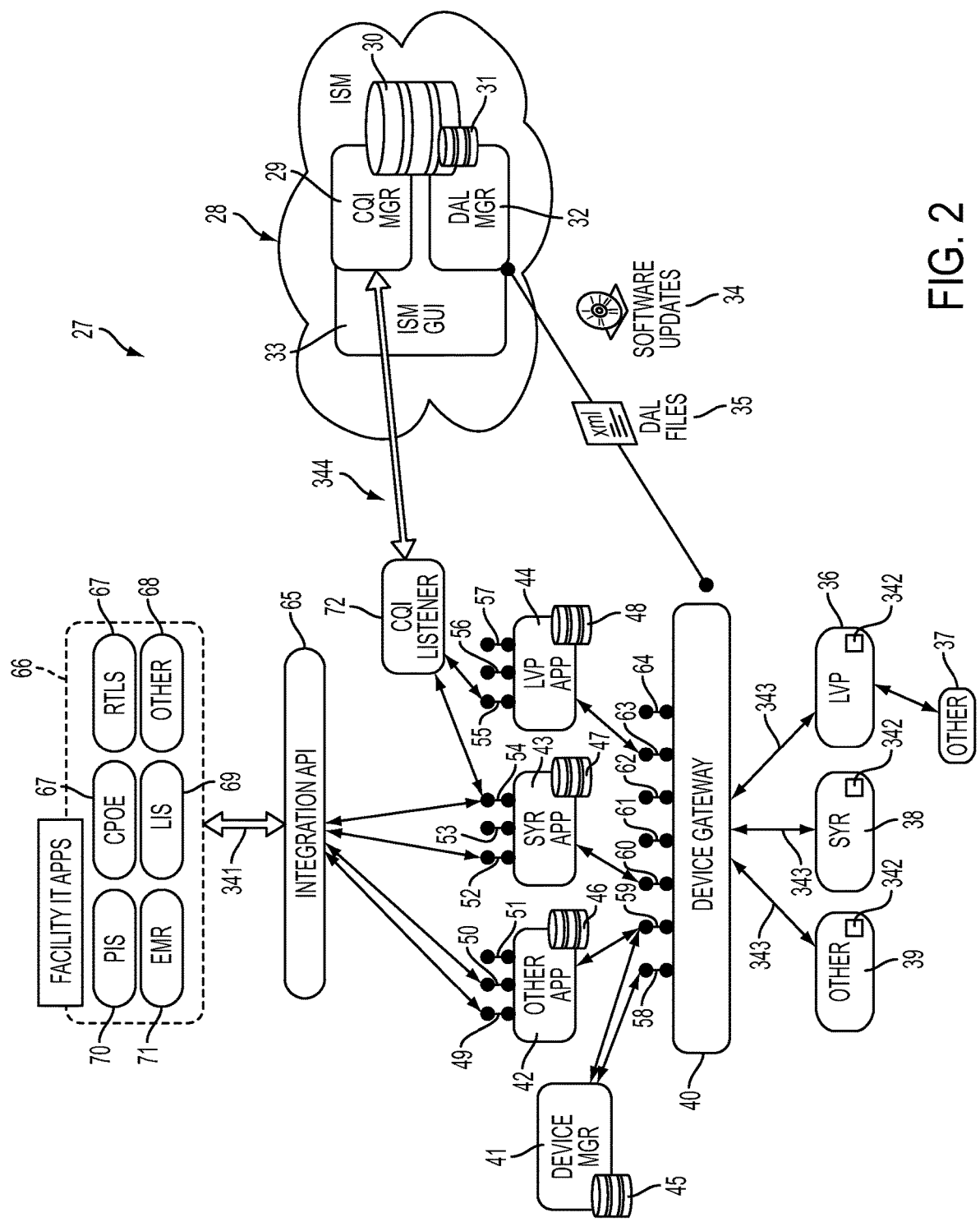
FIG. 2 shows a block diagram of some aspects of the system of FIG. 1 in accordance with an embodiment of the present disclosure.

FIG. 2 shows a block diagram of some aspects of the system of FIG. 1 in accordance with an embodiment of the present disclosure. That is, FIG. 2 shows more details of some aspects of FIG. 1.

The device gateway 40, the device manager 41 and the integration API 65 are all part of the facility gateway 21 of FIG. 1. The large volume app 44, the syringe pump app 43, and the other app 42 are all applications that are part of the device apps 23 of FIG. 1. The device manager 41 including its associated database 45 may be the device manager 24 of FIG. 1.

The Large Volume Pump ("LVP") app 44 is an application for the LVP 36. The syringe app 43 is an application for the syringe pump 38, and the other application 42 is an application for another device 39. The other application 42 and the another device 39 may correspond to any medical device.

The device gateway 40 provides publish-subscribe data connections 58-64. The applications 42, 43, 44 also provide publish-subscribe data connections 49-57. The publish-subscribe messaging pattern provides for the communication between the device gateway 40 and/or the applications 41, 42, 43, 44, 65, 72. However, in additional embodiments, another messaging pattern may be utilized for communications.

The CQI listener 72 may subscribe to various data feeds from the applications 42, 43, 44 to report CQI messages to the CQI manager 29 which may store them in the database 30. The CQI listener 72 may report the raw results of the published connections 49-57 and/or 58-64, and/or may format them.

In some embodiments, the applications 42, 43, 44 reformat the raw events from a respective device of the devices 36-39 (that are received via subscriptions to topics registered by the device gateway 40) into CQI-messages. The applications 42, 43, 44 may register CQI-topics which are subscribed to by the CQI-listener 72. The applications 42, 43, 44 publish the CQI-messages into these CQI-topics which causes the CQI-listener 72 to receive the CQI messages. The CQI-listener 72 transmits the CQI messages to the cloud services 28.

In a specific embodiment, a single GUI interface 33 may be used to view the CQI messages within the database 30 while creating a DAL file 35 for use by the devices 36, 37, 38, and 39. Software updates 34 may also be sent to the device gateway 40 to update the medical devices 36, 37, 38, and 39.

Figure 3:
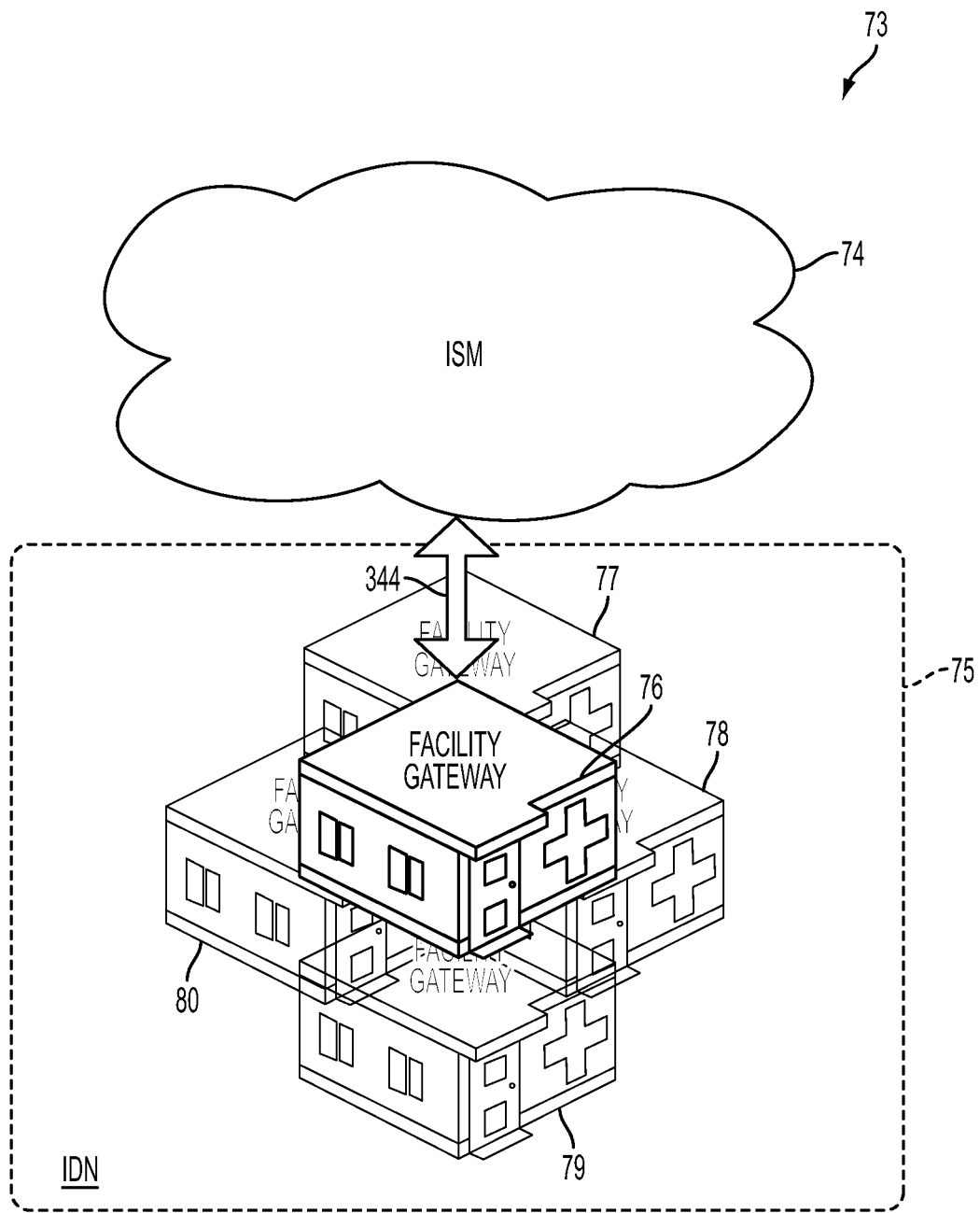
FIG. 3 shows a diagram illustrating the aggregation of several facilities for communication in accordance with an embodiment of the present disclosure.

FIG. 3 shows a diagram 73 illustrating the aggregation of several facilities 76-80 for communication in accordance with an embodiment of the present disclosure. The several facilities 76-80 may each include a facility gateway 21 (see FIG. 2) for communication with cloud services, such as the infusion safety manager 74. In some embodiments, the several facilities 76-80 are part of a group of facilitates that share a common infusion safety manager 74 that is not accessible by other facilities not within the group of facilities 76-80. The group of facilities 76-80 in FIG. 3 communicates with the infusion safety manager via the communications link 344. Such an arrangement may be used in the event that a group of facilities 76-80 is grouped into a larger organization such as an Integrated Delivery Network (IDN) 75.

FIG. 4 shows a diagram illustrating a system 81 for electronic patient care in accordance with an embodiment of the present disclosure. The system 81 includes a facility, e.g., a hospital network 82, and cloud services 83.

The hospital network 82 includes a hospital information network 84, an EMR 85, a CPOE 86, a PIS 87, a LIS 88, an integration engine 89, a integration capabilities component 90, a clinical state manager 91, databases 92, 95 and 98, a biomed application 94, a CQI listener 93, a pump application 96, a syringe application 97, a device gateway 99, a firewall 100, and medical devices 101. In some embodiments, systems 84-88 may be external to the hospital network 82. A team of biomed technicians 102 may be available to use the biomed application 94.

The cloud services 83 includes databases 104, 105, 106 and 113, a firewall 103, a CQI receiver 108, a CQI server 109, a CQI UI 110, and a DERS editor 112. Pharmacists and clinicians 111 may interface into the DERS editor 112 and/or the CQI UI 110. Safety staff 107 may interface into the CQI UI 110 and/or the DERS editor 112. The DERS editor 112 and/or the CQI UI 110 may be a browser-based interface. In some embodiments, the DERS editor 112 and CQI UI 110 may be accessed by the same browser-based interface.

The HIS 84 supports the administrative functions of the hospital (e.g. admission, discharge, transfer, coding, billing, collections). The EMR 85 keeps track of patient medical history in the health care institution (encounters, exams, diagnoses, procedures, etc.). The CPOE 86 is a system used by doctors to order lab tests, prescription drugs, medical images and other clinical procedures. The PIS 97 is a departmental system used by pharmacists to receive, review, track and fill orders for prescription medications. The LIS 88 is a departmental system used by lab technicians to receive and process orders for clinical samples (e.g. tissue, blood, urine, etc.). The hospital integration engine 89 provides message translation capabilities to enable the information system 84-88 to interoperate with each other and with external systems. Most of these engines may map between different dialects of HL7. An Integration Engine may be located on the device gateway 99 to interoperate with the HIS, EMR and PIS, through the hospital integration engine 89. The device gateway 99 provides message routing engine, supporting both publish/subscribe and point-to-point routing mechanisms. The device gateway 99 also provides name resolution and capability registry capabilities.

Various devices 101 are used to treat patients, such as infusion devices that deliver medication, nutrition and hydration in liquid form to patients via intravenous (IV), subcutaneous, or other routes. A pump application 96 and a syringe application 97 are applications that provide software intelligence to medical devices 101, by receiving, filtering and analyzing raw events, and retransmitting higher-level interpretations. Each type of medical device of the devices 101 may have a corresponding device application, e.g., one of the applications 96-97.

Each infusion device of the devices 101 may be used to control delivery of a specific infusate (e.g. hydration, nutrition, blood or medication in liquid form) to a specific patient. Dose adjustments, in the form of loading or bolus doses, or dose titrations may be considered to be separate infusion phases within a parent infusion. A collection of infusions or infusion events for the same patient as part of the same therapy are considered to be an "Infusion Story" which may be recorded by a CQI server 109.

An infusion may be organized into a setup phase, a programming phase, and a delivery phase. During the setup phase, a clinician verifies the infusate, patient and pump, and connects the tubing from the infusate to the pump and the pump to patient, which may be recorded by the CQI server 109. During the programming phase, the clinician enters the dose parameters into the pump and the pump verifies them using the installed DAL version (which may also be recorded by the CQI server 109). During the delivery phase, the pump delivers the specified volume of infusate at the programmed rate.

Each of the medical devices 101 may detect alarm conditions (i.e. situations where the pump is not infusing), as well as alert and advisory conditions, which may or may not be safety-critical. Each of the medical devices 101 may attempt to establish a secure network connection to the device gateway 99. Each of the medical devices 101 may collect programming, delivery status and exception events for each infusion and provide them to the device gateway 99 so that they may be reported as CQI messages to the CQI receiver 108. Each of the medical devices 101 may communicate these events to the device gateway 99, which routes the data to the CQI receiver 108 (directly or indirectly). If or when, in some embodiments, a medical device of the medical devices 101 cannot establish or maintain a working connection to the device gateway 99, the medical device may save these events in an internal buffer, and permit the biomed technician 102 to copy them to portable media (e.g., a memory stick) with or without the use of the biomed application 94. In some embodiments, these events may be downloaded via the biomed application 94 running on a personal computer that has a USB cable coupled to the medical device.

The biomed app 94 provides a browser-based tool for biomed users 102 to monitor the health of their medical devices 101, view log files, track maintenance activities, and manage the installation of software/firmware. The log files, maintenance logs, and software/firmware installation and upgrade tracking data may be stored in the database 95.

The device gateway 99 may be a bed-side device that couples to all of the devices 101 associated with a particular patient. In another embodiment, the device gateway 99 is a software application executable on a facility gateway. In yet another embodiment, the device gateway 99 is software executable on a bed-side appliance (e.g., a compact computer). The device gateway 99 may be a message router, a service registry, and/or a pump authorization registry. The device applications 96-97 can register message types and publish messages to the gateway device 99. Any medical device of the medical devices 101, including sensors that may plug into a medical device (see other 37 in FIG. 2) of the medical devices 101 (e.g. respiratory monitor into PCA) can be used to publish data via the gateway device 99. The device applications 96-97 may act as "information refineries." Each of the device applications 96-97 subscribes to messages from a particular type of bed-side device of the medical devices 101 via the gateway device 99. Each of the device applications 96-97 can synthesize CQI, clinical, and biomed information from an event stream received from one or more of the medical devices 101 through the device gateway 99. In some embodiments, each of the device applications 96-97 re-publishes these higher level events to the device gateway 99 or to other subscribers, such as the CQI listener 93.

In some embodiments, some of the CQI messages may be used for auto-documentation, auto-programming and billing functions. In yet some additional embodiments, the CQI messages may be used for auto-documentation from the medical device 101 into the EMR 85 and/or for auto-programming of the medical device 101 from an eMAR system (e.g., part of HIS 84). The CQI messages may include drug safety events and latency information.

The CQI listener 93 subscribes to events related to continuous quality improvement of drug safety and ensures their reliable delivery to the hosted environment. The CQI listener 93 may store the events in the database 98 for periodic transmission to the CQI receiver 108 (through the firewall 103).

The CQI receiver 108, the CQI server 109, and the CQI UI 110 may be provided in a hosted environment 83 (i.e., cloud services). A master-slave database replication (database 105 as master and 106 as slave) may be used in the hosted environment 83 in order to reduce conflicts between user queries and CQI data updates. The CQI server 109 may post-process CQI events into summary (reportable) form prior to storing them in the database 105 in order to reduce response time for top-level queries and presentation requests. The CQI UI 110 may provide a series of standard reports (compliance, limit violations, titration safety, events by stage, and events by priority). The CQI sever 109 may support a query API, to be used by the DERS editor 112 and the CQI UI 110 to drill down to more detailed summaries and into details of particular CQI messages.

The CQI server 109 provides analysis and query services for a user using the CQI UI 110. The CQI server 109 may provide the user of the CQI UI 110 summary totals for CQI messages and update summary tables (on a configurable interval). The purpose of these summary tables is to reduce response time for top-level CQI queries. These summaries may cover the following statistical measures: (1) programming modes used, such as infusions using DERS limits vs. wildcard; (2) soft and hard limit violations; (3) titration safety information, such as titration increase/decrease settings and dose limit violations; (4) reportable clinical events (e.g., RCEs 149 of FIG. 5, described below) by priority level; and/or (5) reportable clinical events (e.g., RCE 149 of FIG. 5, described below) by infusion stage. Each of these summaries may compute subtotals for the following data views: (1) organization name; (2) institution name (e.g., facility name); (3) care area; (4) hour of day; and/or (5) week.

A web service query API may be used to enable the CQI UI 110 and/or the DERS editor 112 to select: (1) summary totals for each data view described above, filtered by the specified selectors; (2) RCE detail by infusion; and/or (3) actual programming, limits and infusion statistics by patient (i.e. infusion stories). In some specific embodiments, the DERS editor 112 and/or any system of the hosted services 83 may be based upon a J2EE-compliant application server. The databases 104, 105, 106, and 113 may use a database management server.

Once the J2EE and database management servers are installed and configured, the following shared database tables may be imported to perform a DERS database 113 initialization: (1) reference tables, such as units of measure, dose modes, etc.; (2) access control tables for administrative users, roles, privileges and permissions; (3) DERS medication list; (4) National Database of Nursing Quality Indicators (NDNQI) care area list; (5) institution attributes; and/or (6) database tables required by the DERS editor 112. The DERS editor 112 may be used to add or edit organizations, add or edit regions, and/or add or edit access control (each with or without attributes).

In one embodiment, the DERS Editor 112 and/or the DERS database 113 may run in a single application server and database environment for multiple facilities 82. In yet another embodiment, each institution 82 may be hosted in its own virtual environment (e.g., cloud services 2).

The CQI UI 110 and/or DERS editor 112 may support an HTTP/Javascript interface for producing CQI reports and interactive drill-down operations to users who are running a web browser, in some specific embodiments.

The CQI messages are received by the CQI receiver 108 which stores them in the database 105. If the CQI receiver 108 cannot process all of the incoming CQI messages at a predetermined rate and/or the CQI receiver's 108 buffer is full, the CQI messages are temporarily stored in the database 104, which may be accessed by the CQI receiver 108 for storage within the database 105 when the CQI receiver is unloaded. The database 105 may be replicated by the database 106. The database 106 is user accessible via the CQI server 109 using either the CQI user interface 110 and/or the DERS editor 112.

The CQI databases' 105, 106 records depend on the DERS editor 112. The records include: (1) reference tables, such as units of measure, dose modes, etc.; (2) access control tables for administrative users, roles, privileges and permissions; (3) DERS Medication List; (4) NDNQI care area list; and/or (5) institution attributes.

Since these references are dependent on the DERS editor database's 113 version, consistency is preferable. One option is to share the tables between the databases 113, 105, 106. While this option is convenient, it increases deployment coupling between the two databases 113 and 105, 106. Alternatively, coupling can be reduced by maintaining read-only copies of these tables inside the CQI databases 105, 106, with a procedure to update them whenever they are changed in the DERS Editor 112.

Access control for the CQI databases 105, 106 may be similar in structure but different in content versus the DERS database 113. Some users may be defined for the CQI server 109 but not for the DERS editor 112. Even for those users which appear in both, permissions may differ (e.g. some CQI data is read-only). In some embodiments, users and their permissions and access credentials may be stored in a user database 7000 which may be in the hosted environment.

Certain database tables (e.g. reportable clinical events and statistical summaries) may be required by the CQI databases 105, 106 and may be setup when the CQI databases are 105, 106 created.

The CQI UI 110 and/or the DERS editor 112 may each utilize data from the CQI server 109 (and thus data from the database 106) and data from the DERS editor 112 (and thus with the database 113) to generate a DAL file 114.

The clinical state manager 91 is an intermediary between the device gateway 99 the integration engine 89 which orchestrates asynchronous workflows involving several actors and components.

Pharmacists and select clinicians 111 use the DERS editor 112 to define drug limits for an institution and create a DAL file 114 (which may be in an XML format). The drug limits may be defined using a well-defined, carefully controlled, fully documented process, with controlled release procedures. Drug limits may be specified using the DERS editor 112 of the DAL manager 5. The facility 82 may use common reference models for medications, care areas, dose modes, etc. to facilitate later cross-institutional comparison. The DERS editor 112 may run in the hosted environment 83 such that users access it using a web browser. In some embodiments, no client-side software is required to run the DERS editor 112 except for a sufficient browser. The DERS editor 112 may provide drug limits and defaults that are organized by care area, medication, clinical use, medication concentration, etc. The DERS editor 112 may support a query interface to the CQI server 109 to integrate the search and analysis of CQI insights to improve the next DAL version.

In some embodiments, a formulary database 7002 may also be included. The formulary database 7002 may include a master list of medications and drugs which may be included in various DAL files 114. The formulary database 7002 may interface with the DERS editor 112 and the CQI server. The DERS editor 112 may draw from the formulary database 7002 during the creation of DAL files 114. This may help to ensure consistency of data across various DAL files and facilitate comparison of a number of DAL files 114.

Figure 5:
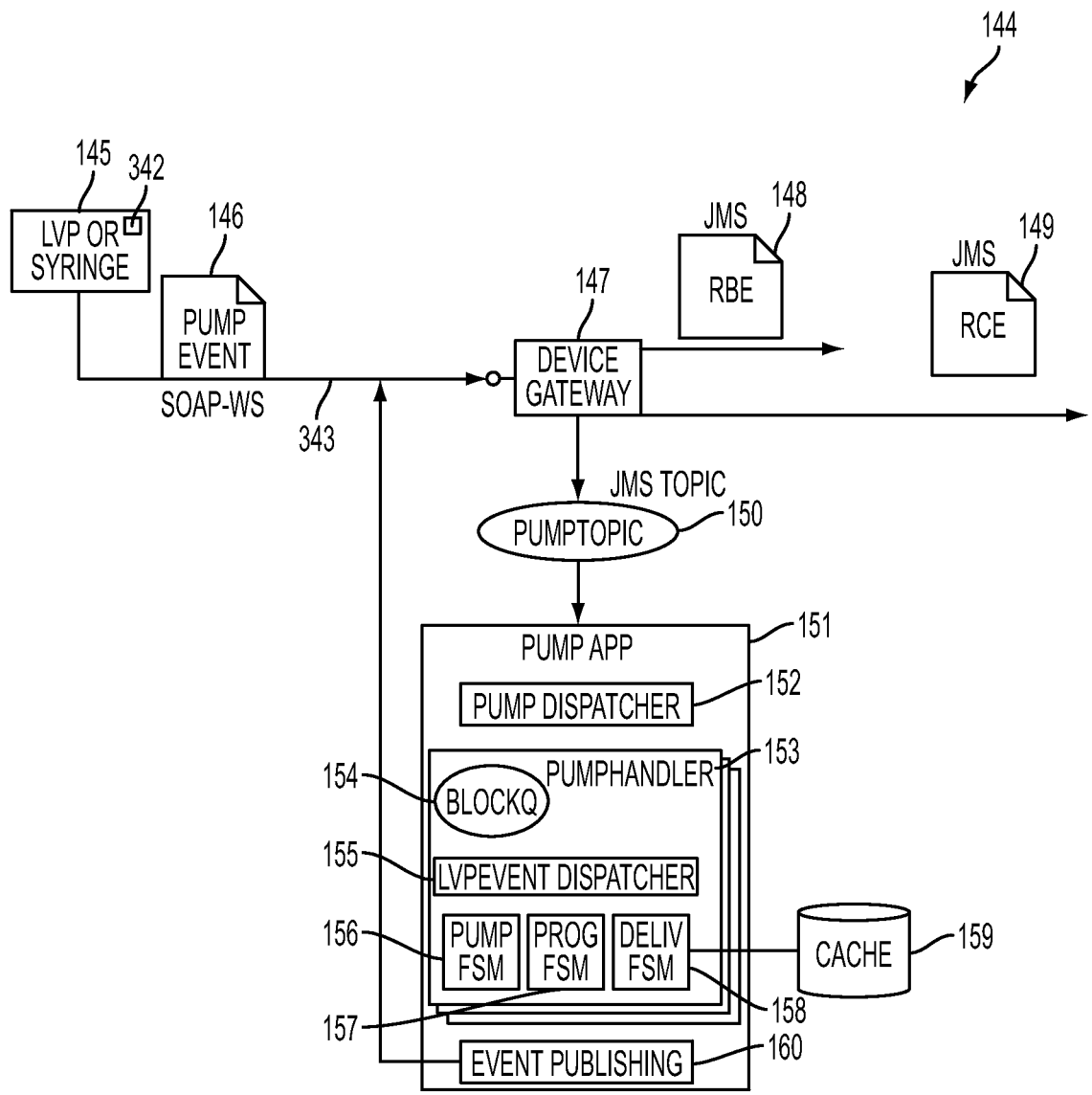
FIG. 5 is a block diagram to illustrate some aspects of an electronic communication between a medical device and a device application in accordance with an embodiment of the present disclosure.

FIG. 5 shows a block diagram 144 to illustrate some aspects of a communication between a medical device 145 (e.g., an infusion pump) and a device application 151 (e.g., a pump application) in accordance with an embodiment of the present disclosure. Although a pump 145 is described herein with reference to FIG. 5, it is contemplated to use any other medical device in place of or with the pump 145 to generate the event 146.

Shown in the block diagram 144 is a medical device 145 (e.g., an infusion pump) that communicates an event 146 (e.g., a pump event) to a device gateway 147. The pump event 146 may be a CQI-message, may be the basis for a CQI-message, or it may be other data, such as raw data, from the medical device 145. The pump event 146 may be an operating parameter, a delivery parameter, and/or other operating events. In some specific embodiments, the pump event 146 may use Simple Object Access Protocol ("SOAP") using Web Services ("WS") addressing. In some embodiments, the event 146 is communicated using Representational State Transfer ("REST") which may use the full HTTP (or HTTPS) protocol.

The event 146 may be an event as shown Table 1 as follows:

TABLE 1

| ID | Pump Event Name |
|---|---|
| 2 | Infusion Events (Alarms, Alerts, Notifications) |
| 2.1 | High priority technical Alarm signaled |
| 2.2 | High priority Operational Alarm signaled |
| 2.3 | Occlusion Alarm signaled |
| 2.4 | Side clamp not installed when loading administartion set |
| 2.5 | Peristaltic pump not sealed |
| 2.6 | Administration set removed during infusion |
| 2.7 | Under infusion Alarm |
| 2.8 | Air limit reached |
| 2.9 | Air single bubble exceeds allowable |
| 2.1 | Alarm condition cleared by operator |
| 2.11 | Internal Software Error |
| 2.12 | Medium priority Alert signaled |
| 2.13 | Medium priority Alert escalated signaled |
| 2.14 | Operator inactivity during programming |
| 2.15 | Low priority Alert signaled |
| 2.16 | Infusion near end Alert |
| 2.17 | Callback alert signaled |
| 2.18 | Notification signaled |
| 2.19 | Alarm silenced |

TABLE 1-continued

| ID | Pump Event Name |
|---|---|
| 3 | Infusion Events (infusing) |
| 3.1 | Pump status update |
| 3.2 | Pump switch to Bolus delivery |
| 3.3 | Pump switch to Loading Dose delivery |
| 3.4 | Pump switch to Multirate delivery |
| 3.5 | Pump switch to next Multirate step |
| 3.6 | Pump switch to primary delivery |
| 3.7 | Pump switch to KVO |
| 3.8 | Infusion end awaiting operator input |
| 3.9 | Infusion end revert to primary |
| 3.1 | Infusion end stop infusion |
| 3.11 | Infusion end switch to KVO |
| 4 | Infusion Events (programming) |
| 4.1 | Set programming context as primary |
| 4.2 | Set programming context as secondary |
| 4.3 | Set programming context as Bolus |
| 4.4 | Set programming context as Loading Dose |
| 4.5 | End programming mode |
| 4.6 | Cancel programming |
| 4.7 | Rate set |
| 4.8 | Dose rate set |
| 4.9 | Care Area set |
| 4.1 | Drug Name set via selection |
| 4.11 | Drug Name set via operator override |
| 4.12 | Clinical use set |
| 4.13 | Drug Concentration set |
| 4.14 | Volume to be infused set |
| 4.15 | Time remaining set |
| 4.16 | Pump mode set |
| 4.17 | Patient ID set |
| 4.18 | Patient name set |
| 4.19 | Patient weight set |
| 4.2 | Patient BSA set |
| 4.21 | Program Cleared |
| 4.22 | DERS soft limit exceeded |
| 4.23 | DERS soft limit attempted |
| 4.24 | DERS hard limit attempted |
| 4.25 | DERS not used for programming |
| 4.26 | Titrating program |
| 4.27 | Occlusion threshold set |
| 5 | Device Events (Communication) |
| 5.1 | WIFI Comm Status Change |
| 5.2 | Device Gateway Comm Status Change |
| 5.3 | Authentication Comm Status Change |
| 5.4 | Generic Device Log Message |
| 5.5 | Infusion Program Received from Device Gateway |
| 5.6 | Patient instructions received from Device Gateway |
| 6 | Device Events (Access requests) |
| 6.1 | Clinician login attempt |
| 6.2 | Biomed login attempt |
| 6.3 | Device access unlock attempt |
| 7 | Device Events (Configuration Updates) |
| 7.1 | DAL update available |
| 7.2 | DAL update received |
| 7.3 | DAL update installed |
| 7.4 | DAL update rejected |
| 7.5 | Software update available |
| 7.6 | Software update received |
| 7.7 | SW update installed |
| 7.8 | SW update rejected |
| 7.9 | Detected different Battery installed |
| 7.1 | Detected new security certificate |
| 7.11 | Detected new Device Gateway address |
| 8 | Device Events (Logging) |
| 8.1 | Device identification |
| 8.2 | Event Log Created |
| 8.3 | Infusion log entrys deleted without sending |
| 9 | Device Events (Other) |
| 9.1 | Battery Status |
| 9.2 | Power off request |
| 9.3 | Sleep request |
| 9.4 | Battery current at recharge |
| 9.5 | Battery current when recharge stops |
| 9.6 | Time to reach control point |
| 9.7 | Device Hardware Status Array (provide a set of hardware parameters, e.g., 20 hardware parameters specific to the internal functioning of the device) |

The items listed as 1, 2, 3, 4, 5, 6, 7, 8, and 9 in Table 1 are pump event classes. When the medical device 145 is not connected to the device gateway 147, these events are stored in a local memory buffer of the medical device 145. While connected (and once re-connected), these events are published to the device gateway 147 using a secure protocol, e.g., SSL, SSH, symmetrical-key encryption, and/or asymmetrical-key encryption. Alternatively, these events may be copied to a portable storage medium and manually published to a device gateway 147. As previously mentioned, the device gateway 147 may act as (or contain) a publish-subscribe engine that is configured to route pump events to interested subscribers.

Referring again to FIG. 1 the pump events may be sent to the CQI manager 4 that relates to the device events of the devices 26. These events may be used to monitor an entire fleet of the medical devices 26 across many facilities 10. For example, the Device Hardware Status Array 9.71 may be converted to a CQI message and is communicated to the CQI manager 4. A user may log into the CQI manager 4 to schedule maintenance events, order new parts based upon the data, to provide predictive or preventive maintenance, and/or to order new parts for preventative reasons or predictive reasons. The user may use deterministic heuristics to determine what to order, when to order it, and/or when to flag some of the devices 26 in various facilities 10 for maintenance. The CQI manager 4 may be used for supply chain management of parts for a fleet of devices 26, and may provide real-time information about the status of the fleet of devices 26. For example, the Device Hardware Status Array may include battery information such as the current at full charge, which indicates the health of an internal battery. For all of or a subset of the devices 26 among several facilities 10, the CQI manager 4 may automatically order new batteries when the health of the battery falls below a predetermined threshold. Additionally or alternatively, the CQI manager 4 may automatically schedule for the battery to be replaced in these identified devices of the devices 26.

Referring again to FIG. 5, a device application 151 (e.g., a pump application configured for operation with a pump) may be executed on the device gateway 147 (in some embodiments, they may be different hardware and/or software). The device application 151 subscribes to events published by the medical device 145.

The pump app 151 may process the stream of raw events and refine them into streams of higher-level clinical events, e.g., the reportable clinical event 149 which may be reported to a server of the hosted cloud services for storage therein (e.g., the database 30 of FIG. 2).

In some embodiments of the present disclosure, the device application 151 is deployed in a J2EE application server as a message driven bean ("MDB"). The MDB is a stateless component that subscribes to a Java Message Service (JMS) Topic, e.g., PumpTopic 150. An application server of the device gateway 147 may activate the device application 151 on a worker thread when a message is available.

The device application 151 is a stateful component and contains one pump handler 153 instance for each pump 145 deployed in the institution. The pump dispatcher 152 maintains a lookup table of pump handlers 153 using the pump's 145 serial number as a unique key.

The pump MDB uses the application server's naming service to access the pump application 151. It gets the pump's 145 serial number from the message header, and uses the pump dispatcher 152 to find the appropriate pump handler of the pump handlers 153. If the respective pump handler of the pump handlers 153 is busy (processing another message, on another thread, etc.), the pump MDB queues the message to the pump dispatcher 152 (to ensure messages are processed in sequence). If the respective pump handler of the pump handlers 153 is idle, the pump MDB asks the respective pump handler of the pump handlers 153 to process the event. Each pump handler of the pump handlers 153 maintains a set of finite state machines ("FSM"), each of which processes a relevant subset of the pump events (see Table 1 above), including a pump FSM 156, a program FSM 157, and a delivery FSM 158.

The pump FSM 156 is the top-level state machine that processes events which do not belong to any infusion. The program FSM 157 is a child state machine which is activated when an infusion programming context is started, and is responsible for processing infusion programming events. The delivery FSM 158 is a child state machine which is activated when infusion delivery is started, and is responsible for processing operational events during an infusion. A separate programming FSM 157 and delivery FSM 158 may be used because a secondary infusion (incl. loading, bolus, or titration) can be programmed while a primary infusion is in progress.

The medical device's 145 operating model, e.g., pump FSM 156, may be used to construct reportable clinical events (RCEs) 149 or to construct reportable biomed events (RBEs) 148. For example, the pump FSM 156 may: keep track of the pump 145 when it completes one infusion and reverts to another which was suspended; keep track of programming of one infusion while another is running; and/or keep track of more than one high-priority operational alarm that may occur at one time. That is, the pump FSM 156 may include nested state models.

Each pump handler of the pump handlers 153 may also maintain some context objects to hold programming and delivery context information. These context objects will be generated as Biomed Events (for tracking pump utilization) when complete, and will be persisted for recovery, in case the pump application 151 needs to be restarted. The context objects may include an infusion state, an infusion mode, and an infusion segment. The infusion state includes the programming/delivery state data for primary and secondary infusions. The infusion mode includes the programming/delivery state data for a particular dose/rate (e.g. loading, bolus, and/or titration). The infusion segment includes the delivery state for an operational period within an infusion mode (e.g. pumping, stopped, alarmed, etc.). Upon processing the pump event 146, a respective FSM 156, 157, or 158 may transition to a new state, create, update or delete a context object, and output a reportable event (a CQI-message), such as a reportable biomed event 148 or a reportable clinical event 149. In a specific embodiment of the present disclosure, a list of reportable clinical events is shown in Table 2 as follows:

TABLE 2

| RCE ID | Reportable Clinical Event Name |
|---|---|
| Unmapped | |
| 0.01 | Pump Failure |
| 0.02 | Clinical Advisory |
| 0.03 | (Un)Successful Self-Test |
| 0.04 | Temperature Excursions |
| 0.05 | Secondary Alert/Alarm |
| 0.06 | Second Clinician Check |
| 0.07 | KVO Alarm (Group, Drug) |

TABLE 2-continued

| RCE ID | Reportable Clinical Event Name |
|---|---|
| 0.08 | High Pressure Alert/Notification |
| 0.09 | Scheduled Service Notification |
| 0.10 | KVO Soft Limit Override (Group) |
| 0.11 | KVO Soft Limit Fullback (Group) |
| | Alarms |
| 1.01 | Air in Line (Group. Drug) |
| 1.02 | Up Stream Occlusion (Group) |
| 1.03 | Down Stream Occlusion (Group) |
| 1.04 | Tube Misload |
| 1.05 | Door Open |
| 1.06 | Syringe Misload |
| 1.07 | Syringe Incompatibility |
| 1.08 | Syringe Ajar |
| 1.09 | Inactivity Alarm |
| 1.10 | Alarm to Resolution to Start |
| 1.11 | Alarm to Silence Time |
| 1.12 | Silence to Resolution to Start |
| 1.13 | Battery Alerts/Alarms |
| | Alerts and Notifications |
| 2.01 | Standby Alert/Callback |
| 2.02 | Clinical Notification |
| 2.03 | (Near) End Infusion Notification |
| 2.04 | Upgrade Needed (at power down) |
| | Infusion Story |
| 3.01 | Begin Infusion Story |
| 3.02 | End Infusion Story |
| 3.03 | Link Infusion to Infusion Story |
| | Infusion Delivery Status |
| 4.01 | Start |
| 4.02 | Stop |
| 4.03 | Bag End |
| 4.04 | Infusion Complete |
| 4.05 | Bolus Dose |
| 4.06 | Standby |
| 4.07 | Loading Dose |
| 4.08 | Restarts Up Stream Occlusion (Group) |
| 4.09 | Restarts Down Stream Occlusion (Group) |
| | Soft Limit Overrides |
| 5.01 | Dose Soft Limit Override |
| 5.02 | Titration Limit Override |
| 5.03 | Bolus Dose Soft Limit Override |
| 5.04 | Bolus Time Soft Limit Override |
| 5.05 | Load Dose Soft Limit Override |
| 5.06 | Load Time Soft Limit Override |
| 5.07 | Rate Soft Limit Override |
| 5.08 | Time Soft Limit Override |
| 5.09 | Concentration Soft Limit Override |
| 5.10 | Weight Soft Limit Override (Group) |
| 5.11 | BSA Soft Limit Override (Group) |
| 5.12 | Rate Soft Limit Override (Group) |
| 5.13 | Volume Soft Limit Override (Group) |
| | Programming |
| 6.01 | End Infusion Programming |
| 6.02 | New Infusion |
| 6.03 | Titration |
| 6.04 | Program Changes prior to Start |
| 6.05 | Wildcard Use |
| | Pullbacks to Hard or Soft Limit Violations |
| 7.01 | Dose Soft Limit Pullback |
| 7.02 | Dose Hard Limit Pullback |
| 7.03 | Titration Limit Pullback |
| 7.04 | Bolus Dose Soft Limit Pullback |
| 7.05 | Bolus Time Soft Limit Pullback |
| 7.06 | Load Dose Soft Limit Pullback |
| 7.07 | Load Time Soft Limit Pullback |
| 7.08 | Rate Soft Limit Pullback |
| 7.09 | Time Soft Limit Pullback |
| 7.10 | Concentration Soft Limit Pullback |
| 7.11 | Weight Soft Limit Pullback (Group) |
| 7.12 | BSA Soft Limit Pullback (Group) |
| 7.13 | Rate Soft Limit Pullback (Group) |
| 7.14 | Time Soft Limit Pullback (Group) |

Referring to FIG. 4, the CQI Listener 93 of FIG. 4 may run inside each facility 82, can connect to the device gateway (99 in FIG. 4 or 147 of FIG. 5), and subscribe to CQI RCEs 149 or the CQI RBEs 148. The CQI Listener 93 of FIG. 4 may establish a secure private connection to the CQI receiver 108 in the hosted environment 83 (see FIG. 4). This connection may be physical (continuously connected) or logical (transient connection while transmitting messages).

The device gateway 147 may route the RCEs 149 or RBEs 148 to the CQI listener 93. The CQI listener 93 may ensure message durability (i.e. no messages are lost during transmission due to network congestion or disconnection). As a result, the CQI listener 93 may: (1) store each message to be transmitted to a local persistent queue (for buffering); (2) transmits each of the RCEs 149 and/or RBEs 148 from the head of the queue to the CQI Receiver 108; and/or (3) remove the message after receiving acknowledgement from the CQI receiver 108.

The CQI receiver 108 runs inside a hosted environment within the hosted environment 83. The CQI receiver 108 listens for and accepts secure network connection requests from one or more CQI listeners 93. The CQI receiver 108 receives RCEs 149 from each connected CQI listener 93. The CQI receiver 108 may ensure message durability, so upon receipt, it writes each RCE 149 into the database 105. The CQI receiver 108: (1) stores each message received (CQI messages) to a local persistent queue (for buffering); (2) appends each CQI message from the head of the queue to a table in a CQI event database; (3) acknowledges receipt of the message to the CQI listener 93 that sent the message; and (4) removes the CQI message from the local queue (as it is safely in the CQI event database 105).

As previously mentioned, the CQI Event Database 105 is implemented using a Master-Slave replication. That is, database 105 is the master while database 106 is the slave. With this approach, there are two copies of the CQI event database with identical schemas, in some specific embodiments. As insert, update, and delete transactions are applied to the master database 105, a database management system (DBMS) within the database 105 writes the changes to a journal, and is able to transmit unposted changes to the slave database 106.

Each CQI message (e.g., a RCE) may belong to a specific institution. This institution reference should match the institution which operates the medical device (e.g., a medical device of the medical devices 101 of FIG. 4 or the medical device 145 of FIG. 5) and which released the Drug Administration Library (DAL) which is deployed in that device. As a result, the CQI databases 105, 106 may require a list of institutions which are consistent with the DERS database 113.

Figure 6:
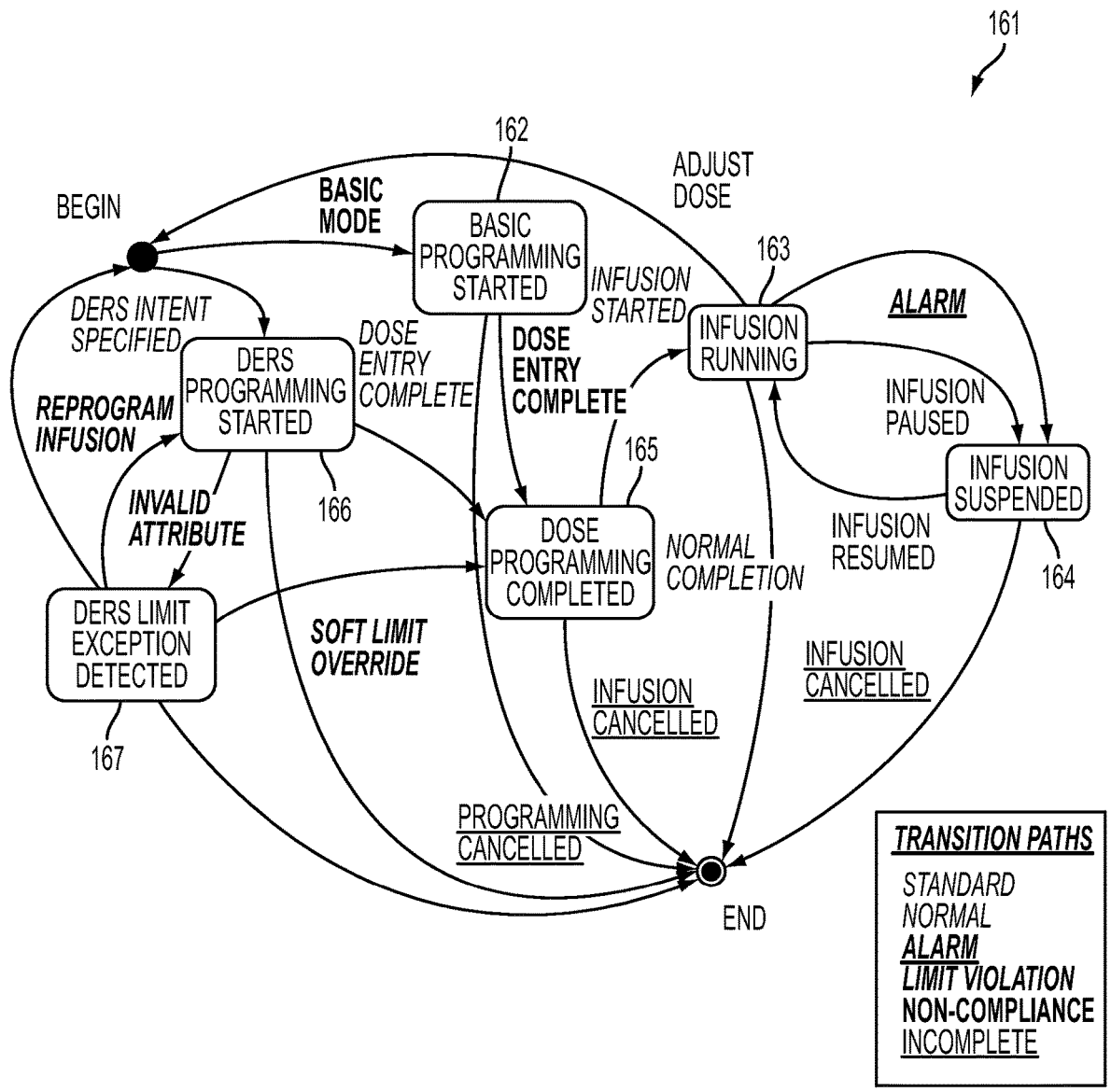
FIG. 6 shows a state diagram illustrating a method of programming an infusion device in accordance with an embodiment of the present disclosure.

FIG. 6 shows a state diagram illustrating a method 161 of programming an infusion device (e.g., of devices 16 of FIG. 1) in accordance with an embodiment of the present disclosure. The method 161 begins with the user capable of interfacing with a UI of the device.

The infusion programming starts in the state shown as the state labeled as "begin." State 162 is when the basic mode programming is used (e.g., when a DERS compliance exception device is used, for example). After programming using a DERS compliance exception device, the method transitions to state 165 in which the drug programming is complete.

State 166 is when the DERS-based protection is used and dose parameters are programmed into the device, which transitions to state 165 if no limit violation is detected. If there is a soft limit violation detected or a hard limit violation detected, the method 161 transitions to state 167. If it is a soft limit, the clinician may: (1) override the software limit which causes the method to continue to state 165; (2) program the infusion attributes with unchanged infusion intent, which either continues to state 165 if no new violation is found or to state 167 if a new violation is found; or (3) change the infusion intent (e.g. change the medication, care area, clinical use and/or concentration) which causes the method 161 to restart at state 166.

If a hard limit is detected, the method transitions from state 166 to state 167, which requires the state to re-transition back to state 166 and does not allow the clinician to override the DERS violation.

The infusion method 161 may be cancelled during many states. In the basic mode programming state 162, the clinician can cancel the infusion before programming is completed. In the DERS programming state 166, the clinician can cancel the infusion before the programming is completed. In state 167 when a DERS soft limit or hard limit violation has been detected, the clinician can cancel the infusion.

During state 165, the medical device will present an "infusion start" button in which the caregiver can press to transition a medical device to state 163, in which the infusion begins. A suspend button may be present on the user interface when in state 163, which causes the device to suspend when pressed thereby transitioning the device to state 164. A continue button may be present on the user interface when in state 164, which causes the device to return to state 163 when pressed to continue therapy. If a fatal error (a predetermined set of errors) is detected in states 163 and/or 164, the method 161 transitions to the end state.

Upon completion of the infusion, the pump sends an infusion complete message to the clinical server via the device gateway. The clinical server links the completion event to the prescription record. The clinical server may format an IHE auto-documentation message and sends it to one of the facility IT apps 11 (see FIG. 1), e.g., for recording in an Electronic Medical Administration Record ("eMar"), to update the patient's Electronic Medical Record (EMR) 17, and/or update the hospital's billing system to record successful infusion of the medication.

Figure 7:
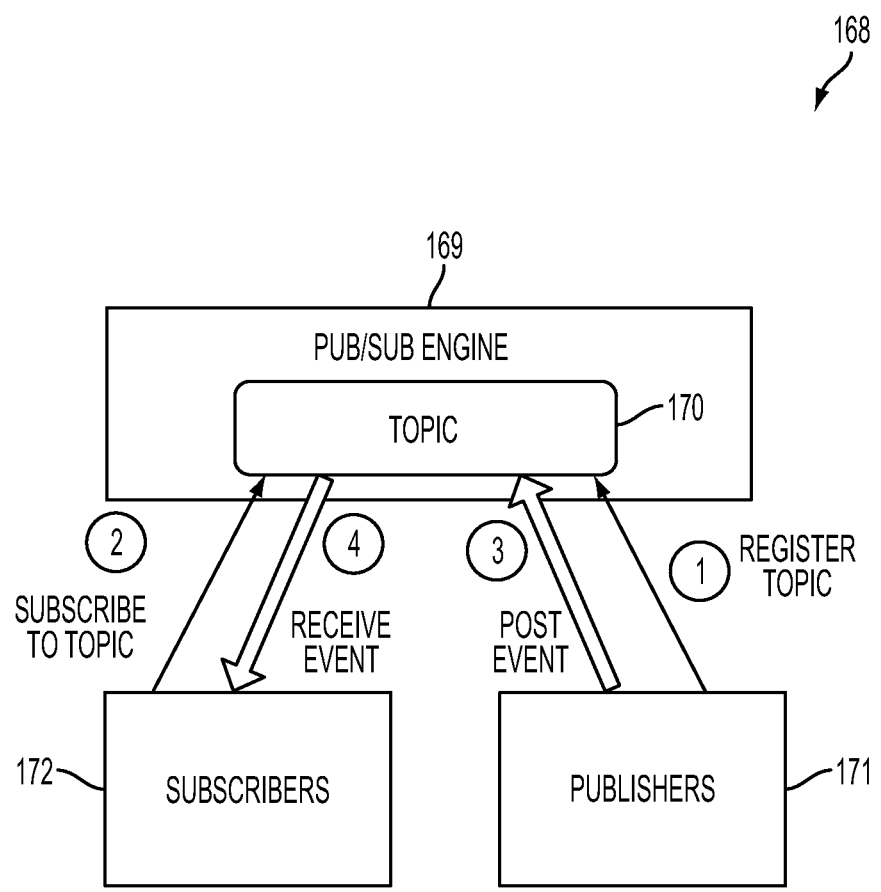
FIG. 7 illustrates a software program that is executable on a processor, the software program and processor are configured for implementing a publish-subscribe model for use by the facility gateway of FIG. 1, and by the applications and the device gateway shown in FIGS. 2 and 4 in accordance with an embodiment of the present disclosure.

FIG. 7 illustrates a publish-subscribe model 168 for use by the facility gateway 21 of FIG. 1, by the applications 41, 42, 43, 44 and device gateway 40 in FIG. 2 or FIG. 4 in accordance with an embodiment of the present disclosure.

The model uses a pub/sub engine 169 that allows publishers 171 to register one or more topics 170 with the pub-sub engine 169. Once the topic 170 is registered, one or more subscribers 172 can subscribe to the topic 170. The subscribers 172 may subscribe using a guaranteed subscription to the topic 170, in some specific embodiments. When a publisher of the publishers 171 posts an event related to the topic 170, all subscribers of the subscribers 172 that have subscribed to the topic 170 receive the data from the pub/sub engine 169.

A publisher (of the publishers 171) may register one or more topics 170. Each topic of the topics 170 may be a unique topic. One or more subscribers 172 may subscribe to one or more topics of the topics 170 to receive events therefrom. When a publisher 171 posts an event to a unique topic (e.g., a "first topic") of the topics 170, all subscribers to the first topic of the topics 170 will receive that event; nonsubscribers to the first topic of the topics 170 will not receive that event. Subscribers 172 subscribed to other topics (e.g., a second topic) of the topics 170 but not the first topic will not receive events sent that only corresponded to the first topic.

The topics 170 may provide a level of indirection enabling the publishers 171 and the subscribers 172 to be anonymous, in some embodiments. The pub/sub engine 169 may allow the communication to be one-way and asynchronous (e.g., a "fire and forget" communication). The pub/sub engine 169 may provide durable message delivery, on both sides. Durable topics of the topics 170 may ensure that messages will not be lost if the pub-sub engine 169 fails. Durable subscriptions used by the subscribers 172 may ensure that a subscriber 172 will not miss messages when it is not running.

The pub/sub engine 169 may be part of the device gateway 22, may be part of any other software within the facility gateway 21, or may be a stand-alone application of FIG. 1. The pub/sub engine 169 may be part of the device gateway 40, within an application 41-44, or may be a stand-alone application of FIG. 2. The pub/sub engine 169 may be part of the device gateway 99 of FIG. 4, may be part of the applications 94, 96, 97, or may be a stand-alone application of FIG. 4.

Figure 8:
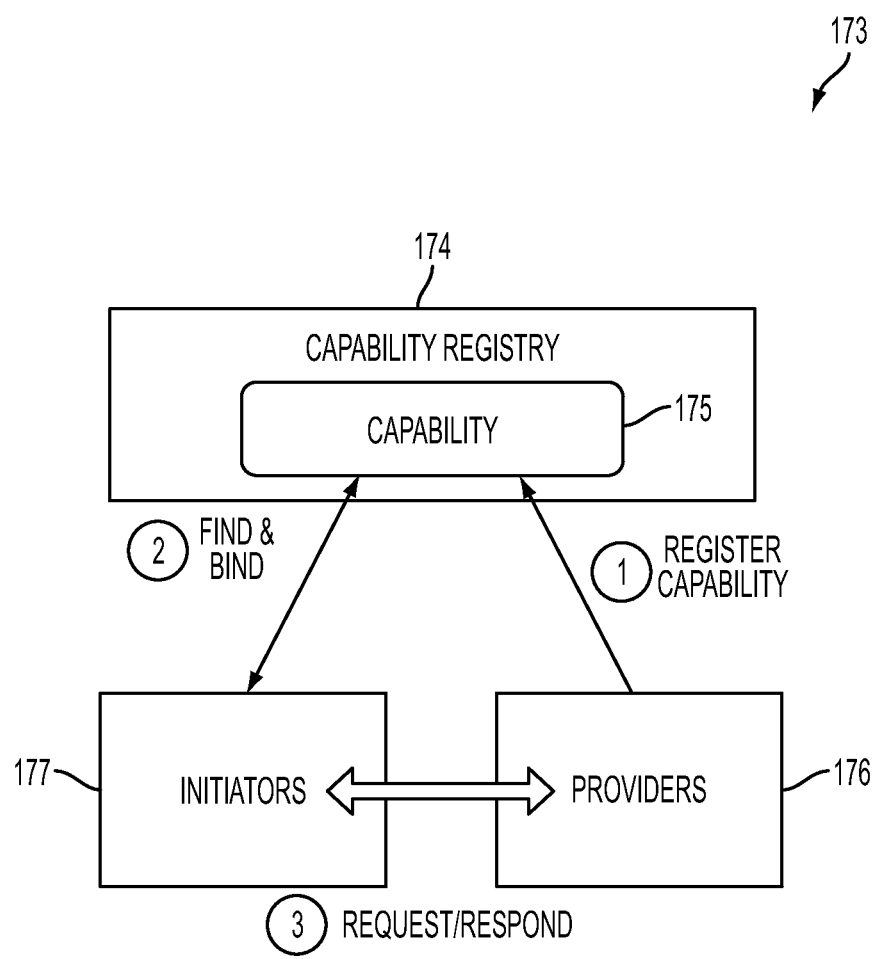
FIG. 8 illustrates a software program that is executable on a processor, the software program and processor are configured for implementing a capability-registry model in accordance with an embodiment of the present disclosure.

FIG. 8 illustrates a capability-registry model 173 in accordance with an embodiment of the present disclosure. A provider 176 registers its capability 175 with a capability registry 174. The capability 175 may include two aspects, including an interface and an attribute. The interface is the list of request/response pairs and notifications (in both directions). The attributes is the service level agreement parameters specifying limits on the quality of delivery (e.g. response times, error rates and recovery policies, costs, etc.).

An initiator 177 can communicate with the capability registry 174 to find and bind to the capability 175. Thereafter, the initiators 177 can request information from the providers 176 and receive a response. The capability registry 174 may be part of the device gateway 22, may be part of any other software within the facility gateway 21, or may be a stand-alone application of FIG. 1. The capability registry 174 may be part of the device gateway 40, within an application 41-44, or may be a stand-alone application of FIG. 2. The capability registry 174 may be part of the device gateway 99 of FIG. 4, may be part of the applications 94, 96, 97, or may be a stand-alone application of FIG. 4. The capability registry 174 may supplement or replace the pub/sub engine 169 in some specific embodiments.

Figure 9:
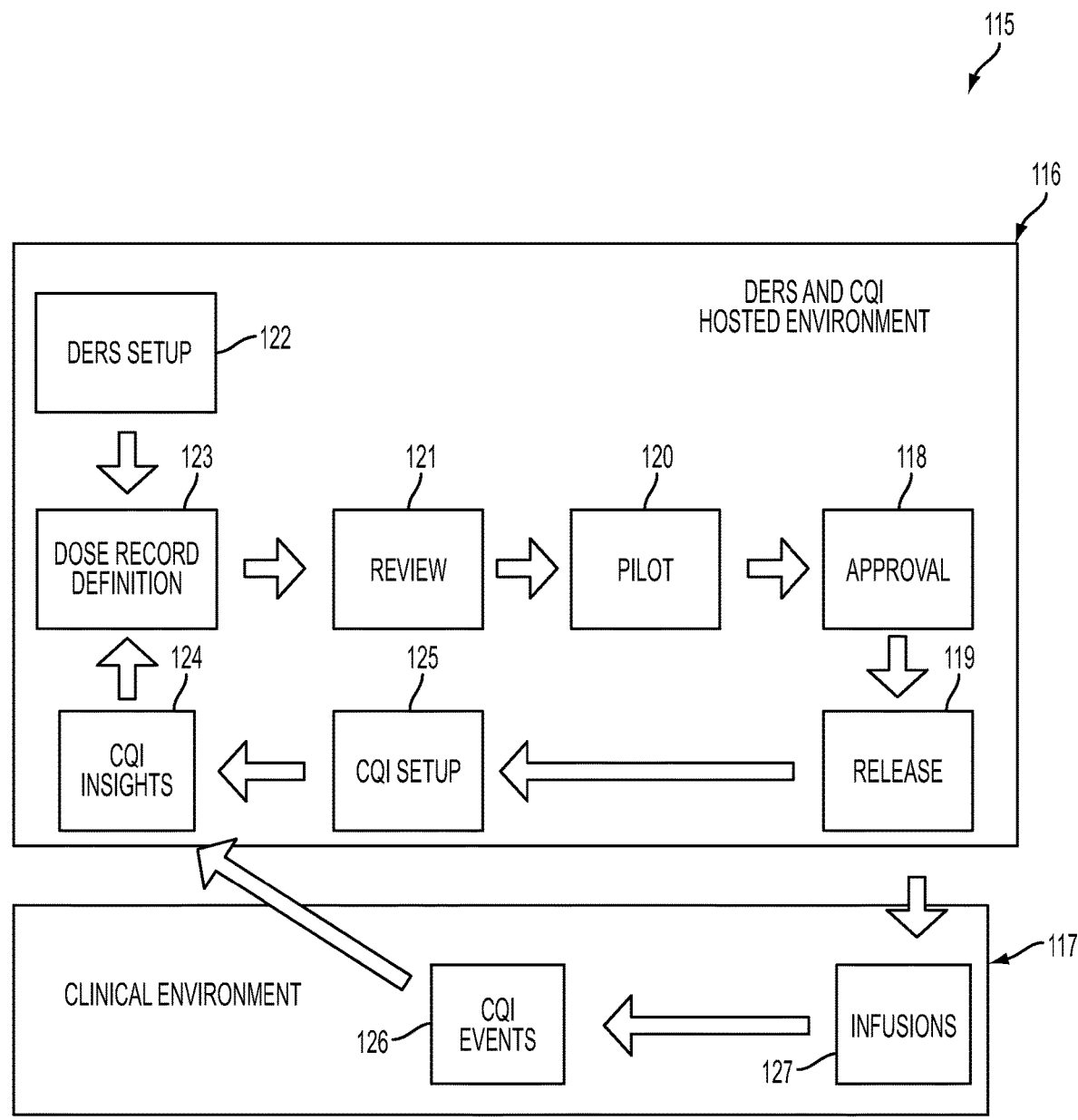
FIG. 9 illustrates a software program that is executable on a processor, the software program and processor are configured for implementing a drug safety method used to generate a drug administration library file in accordance with an embodiment of the present disclosure.

FIG. 9 shows a drug safety method 115 used to generate a DAL file in accordance with an embodiment of the present disclosure. The method 115 may be used with the system 1 of FIG. 1, the system 27 of FIG. 2, the system 81 of FIG. 4, or any other electronic patient care system. The method 115 is but one of many methods which may be used to generate a DAL file. Some embodiments may differ.

Participants from a pharmacy, clinical care area, etc. (e.g., selected users from 6, 7, 8, 9, 18, and 19 of FIG. 1 or 102, 107, and 111 of FIG. 4) may be selected to help generate and define a DAL File 35 (see FIG. 2) that contains safety rules for drug administration that may consider the type of medication, clinical care group, clinical care area, mode (e.g. amount-based, rate-based or weight-based, dose strategy (loading, bolus, ramp), etc.), concentration, etc.

Method 115 includes acts 116 and 117. Act 116 includes acts 118-125 as subacts and act 117 includes acts 126-127 as subacts. Act 116 generates a DAL file and act 117 monitors the use of the DAL file to help inform updates of the DAL file 35 (see FIG. 2).

Act 122 sets up a DAL file, e.g., an initial DAL file without field entries or a template DAL file. Act 123 receives modifications to the DAL file in accordance with an entry from one of the selected users (e.g. via the DERS editor 112 of FIG. 4). Act 121 reviews the DAL file, e.g., by running a medical device simulator via the DERS editor 112 of FIG. 4. After review during act 121, a pilot DAL file may be (electronically) released in act 120. Act 118 approves the pilot DAL file. However, after the pilot has completed, adjustments may be made to the DAL. Act 118 may be performed via clicking on a "approve" button on a web browser to approve the use of a referenced file (e.g., referenced by version number, creation date, etc.).

In act 119, the DAL file is released and is sent to the medical device. In Act 125, the CQI server imports reference data (i.e. medications, care areas, dose modes, etc.) from the DAL file. Upon DAL release, a file containing the drug records is released to both the hospital and to the CQI environment. A biomed technician may install the DAL file on each device after release in act 119. Act 126 is the medical device sending CQI events to the CQI receiver 108. The CQI events sent in act 126 may be generated in therapies performed by a device using the DAL file in act 127

During operation, medical devices generate CQI events (i.e., CQI messages). The CQI messages may include information about when a normal infusion occurs, when an infusion bypasses the DERS checks, when a soft limit is exceeded and overridden, and/or when a soft or hard limit is exceeded and the therapy is reprogrammed, among others.

The CQI events are transmitted to a CQI Server in act 126, which collects and stores them. Safety officers can run reports which summarize these events and provide drill-down capabilities to identify opportunities for procedural improvement in act 124. Similarly, pharmacists and clinicians can query the CQI database to identify opportunities to improve drug records in the next release of the DAL file in act 124. That is, in act 124, the CQI messages are analyzed or reviewed. Modifications to the DAL file may be made in act 123 to create a new version of the DAL file. The new DAL file may then be reviewed, piloted, and released as described above.

In some embodiments, usage of a DERS editor, such as the DERS editor 112 in FIG. 4, to create a DAL file is a collaborative process involving a number of individuals or parties. Every person or party involved in the creation of a DAL file may contribute to the creation of the DAL file by accessing the DERS editor and interacting with a DERS editor user interface. In some embodiments, no client-side software may be required to access the DERS editor except a sufficient web browser. In some embodiments, the DERS editor user interface may be accessed via an app on a tablet computer or the like. The individuals or parties involved in the creation of the DAL file may use an internet capable computer, tablet computer, smartphone, etc. to access the DERS editor and make contributions to the DAL file.

Each individual or party involved in building a DAL file may have specific assigned roles, responsibilities, and/or privileges. These roles may be assigned using an Access Control List (ACL) and/or Role Based Access Control (RBAC) model. The roles and responsibilities may be fulfilled as part of a method which may be used to generate a DAL file. The roles, responsibilities, privileges, etc. may be assigned to structure the collaborative process. They may also be assigned to encourage maximum input and oversight for DAL file generation. This may help to assure that the DAL file created by the collaborative process is well designed and mitigates drug errors to the greatest possible extent. Various roles and privileges for users may be stored in a user database (not shown) which is hosted in a hosted environment. In some embodiments, various roles and privileges may instead be stored in a DERS database.

A DERS editor may also allow users to provide unsolicited contributions, feedback, requests, comments, notes, questions, etc. which may be used to build a DAL file or better a DAL file. If during a DAL file pilot, simulation, or during everyday usage, a user finds an issue, concern, opportunity for improvement, etc. a user may submit a change request to address it. Such a request may be tied to CQI data or a specific CQI report to provide context to a reviewer.

CQI data may be readily accessible, perhaps to differing degrees depending on user or party, while contributing to a DAL file. This information may be presented on the DERS editor user interface in an easily comprehensible form. In some embodiments, at least some of this data may be presented in the form of a graph, chart, or other visual aid. Users may also use the DERS editor to filter out undesired CQI data so as to present a more concise data set which focuses more narrowly on data of interest to the user. The availability of this CQI data may be utilized by an individual or party to help inform decisions about modifications, etc. to various entries. The data may also be used to evaluate the appropriateness of various entries in a DAL file.

Additionally, the creation and modification of DAL files via the DERS editor may be an entirely traceable process. Each entry or modification made in the DERS editor may be tied to a unique user login or ID which is associated with a specific individual or party. Each modifiable item within a DERS editor may be associated with a stored historical record documenting all past comments, notes, modifications, requests, parameter values, etc. related to the item.

Figure 10:
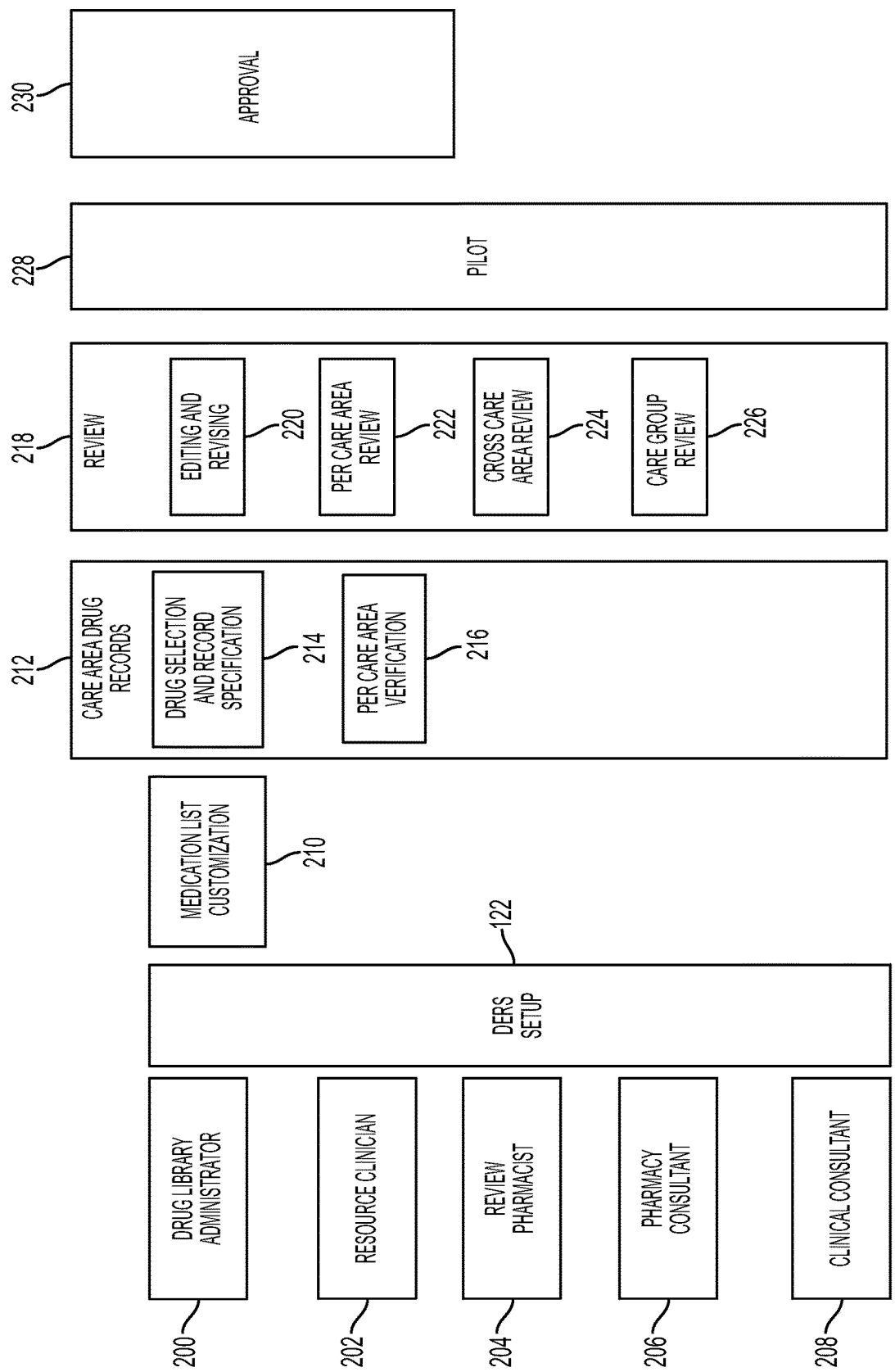
FIG. 10 depicts an example conceptual diagram detailing possible roles, responsibilities, and privileges of various users and parties which may be involved in the creation of a drug administration library file in accordance with an embodiment of the present disclosure.

An example conceptual diagram showing possible roles, responsibilities, and privileges of various users and parties involved in collaboratively creating a DAL file is shown in FIG. 10. The example conceptual diagram is one of many possible examples and in alternate embodiments, may be arranged differently. For example, some actors/parties may be combined or not included. Roles and responsibilities may also differ. As shown, the roles, responsibilities and privileges are allocated to promote creation of a well thought out DAL file which minimizes the possibility for potential drug errors. Multiple reviews of entries and a consensus of a number of individuals is required for a DAL file to be released in the example embodiment.

Each actor may make contributions to a DAL file with a DERS editor such as the DERS editor 112 shown in FIG. 4. In some embodiments, various actors may access the DERS editor via a DERS editor user interface which may be navigated to on a web browser. A number of actors are shown to the left of the diagram. Other embodiments may include additional actors or fewer actors than shown here. Some actors may be a single individual in some embodiments and at least one group of multiple individuals in others. In some embodiments, two different actors may, in fact, be the same individual or party performing different roles. The actors shown in the example in FIG. 10 include a drug library administrator 200, resource clinicians 202, a review pharmacist 204, a pharmacy consultant 206, and a clinical consultant 208. In the example embodiment, the actors fall into two broad categories; administrator or editing users (drug library administrator 200) and reviewing users (resource clinician 202, review pharmacist 204, pharmacy consultant 206, and clinical consultant 208).

The drug library administrator 200 may be an individual or individuals such as doctors, care givers, pharmacists, etc. In some embodiments, the drug library administrator 200 may for example be the pharmacist 8 shown in FIG. 1 or the safety staff 107 shown in FIG. 4. The drug library administrator 200 may be given administrator capabilities in the DERS editor. That is, the drug library administrator 200 may have editing permissions granting them the ability to alter most, if not all, modifiable entries and have final oversight over any proposed changes to a DAL file. The drug library administrator 200 may have privileges which allow them access to most if not all functionalities of the DERS editor. The drug library administrator 200 may also be required to sign off on a finalized DAL file before it is released for use on various medical devices.

The resource clinicians 202 may in some embodiments be an individual or individuals such as doctors, nurses, nurse managers, etc. In some embodiments the resource clinicians 202 may be the nurse manager 7 and/or nurses 9 of FIG. 1. In some embodiments, the resource clinicians 202 may be the pharmacy and clinicians of FIG. 4. The resource clinicians 202 may have the ability to review, comment, add notes, propose changes, etc. to a DAL file via the DERS editor. Resource clinicians 202 may be divided into a number of sub groupings. For example, resource clinicians 202 may be divided into care area groups in some embodiments.

The review pharmacist 204 may in some embodiments be an individual or individuals such as a pharmacist, etc. In some embodiments, the review pharmacist 204 may be the pharmacist 8 in FIG. 1. The review pharmacist 204 may review all entries in a DAL file via the DERS editor and check for any entries which may need to be revised. The review pharmacist 204 may also have the ability to comment, add notes, request changes, etc. to various entries in a DAL file.

The pharmacy consultant 206 may in some embodiments be an individual or individuals such as a pharmacist, etc. In some embodiments the pharmacy consultant 206 may be the pharmacist 8 in FIG. 1. A pharmacy consultant 206 may review one or more portion(s) of all of the entries in a DAL file via the DERS editor. The pharmacy consultant 206 may check for any entries which may need to be revised and may also have the ability to comment, add notes, request changes, etc. to various entries in a DAL file.

The clinical consultant 208 may in some embodiments be an individual or individuals such as doctors, nurses, nurse managers, risk officers, other suitable personnel, etc. In some embodiments, the clinical consultant 208 may be the nurse manager 7, nurses 9, biomed 19, and/or risk officer 6 of FIG. 1. The clinical consultant 208 may in some embodiments be the safety staff 107 of FIG. 4. The clinical consultant 208 may be involved in performing a pilot of a DAL file. The clinical consultant 208 may have the ability to review, comment, add notes, etc. to entries in a DAL file or a portion of entries in a DAL file.

As shown in FIG. 10, the DERS is first setup in the DERS SETUP act 122. In this act, various actors may be identified and assigned user IDs which allow the various actors differing degrees of DERS functionality. Additionally, in this act, the environment in which a DAL file is to be used in may be divided up into a number of different sub-environments or groupings. This may be done according to the environments organizational hierarchy. For example, a hospital may be divided into its constituent care groups (ICU, ER, NICU, Oncology, etc.).

In various embodiments, the roles, responsibilities, and privileges assigned to each actor may differ. For example, in some embodiments, a larger number of actors may be required to sign off on a DAL file before it is released for use in various medical devices. Various actors may be allocated a greater or less degree of software functionality.

The DERS medication list or lists may then be setup in the medication list customization step 210. As shown in the example conceptual diagram, the drug library administrator 200 may be the only actor with the privileges required to do this. In some embodiments, this step may be performed by a pharmacist for example. During the medication list customization list step 210, all of the medications which are available for use within a facility or number of facilities that will use a DAL may be compiled into a single list. Additionally, if a medication has a number of different names or aliases, these may be defined and linked to their respective medications. Other information may also be defined for each medication. The full list of medications created in the medication list customization step 210 may be used in subsequent steps to ensure uniformity and increase efficiency. In some embodiments, the full medication list may be created by selecting medications from a master list or medications provided by a DERS editor service. In some embodiment, the full medication list may be created by selecting various medications from a master list of medications stored on a formulary database in a hosted environment.

In the Care Area Drug Records step 212 in the example in FIG. 10, the Drug Library Administrator 200 may perform the Drug Selection and Record Specification sub-step 214. In this sub-step, various medications identified in step 210 may be selected for inclusion in specific sub-divisions or care areas/groups of an institution. For example, in a hospital, a sub-set of the drugs defined in step 210 may be selected as drugs which are used in intensive care units of the hospital. The various medications which are selected for each care group may then have their records modified to suit the needs of each care area within the care group. For example, in this step, a drug for a specific care area may have various clinical uses, concentrations, limits, etc. specified. In some embodiments, this step may be carried out by one or more pharmacist(s) in addition or in conjunction with the Drug Library Administrator 200.

After the Drug Selection and Record Specification sub-step 214 of the Care Area Drug Records step 212 is complete, the Per Care Area Verification sub-step 216 may be performed by at least one resource clinician 202. In this sub-step, the selected drugs and their records are reviewed and verified for each care area. In a hospital, one or more nurses or doctors who are assigned or work in a particular care area may be the resource clinicians 202 who perform this sub-step for that care area. During this sub-step, the resource clinicians 202 may provide feedback on the various drug selections and records for each care area.

In the Review step 218, the drug selections and records from the Care Area Drug Records step 212 are reviewed to ensure that they are appropriate and correct. In the example in FIG. 10, the Drug Library Administrator 200 edits and revises records which may need such action in the Editing and Revising sub-step 220. This may include addressing any feedback or requests produced by the resource clinicians 202 in the Care Area Drug Records step 212. It may also include addressing any feedback, concerns, requests, etc. from other actors involved in the Review step 218.

During the Review step 218, a Per Care Area Review 222 sub-step may be performed by at least one resource clinician 202. In this sub-step, the selected drugs and their records are reviewed for each care area. In a hospital, one or more nurses or doctors who are assigned or work in a particular care area may be the resource clinicians 202 who perform this sub-step for that care area. During this sub-step, the resource clinicians 202 may provide feedback or change requests on the various drug selections and records for each care area.

Additionally, a Cross Care Area Review sub-step 224 and Care Group Review 226 sub-step may be respectively performed by the review pharmacist 204 and the pharmacy consultant 206. In the Cross Care Area Review sub-step 224, the selected drugs and their records for each care area may be reviewed by the review pharmacist 204 and feedback denoting any concerns, suggestions, requests, etc. may be produced. In the Care Group Review 226 sub-step a pharmacy consultant 206 may review a care group's drug list, drug records, and feedback denoting any concerns, suggestions, requests, etc. There may be a number of pharmacy consultants 206, each having a specific care group assigned to one of the number of pharmacy consultants 206. In some examples, the pharmacy consultants 206 may additionally review other records as well. For example, in some examples, the pharmacy consultants 206 may also review the records for all drugs within an institution which are considered to be high risk if delivered in erroneous fashion.

In the Pilot step 228, all of the actors shown in FIG. 10 (and perhaps other actors not shown in FIG. 10) participate in a pilot of the new DAL file which has been produced through steps 210, 212, and 218. During the Pilot step 228, various actors may use a pump simulator on a DERS UI to test or review all of the entries for each care area. In some embodiments, a provisional DAL file may be created and sent to a test medical device. The DAL file may be tested and reviewed on the UI of the test medical device by various actors. Any feedback produced by various actors involved in the Pilot step 228 may be addressed and any necessary changes may be made to the DAL file.

To complete a DAL file, the DAL file may be required to go through the Approval step 230. In this step various actors may sign off on the DAL file and thus allow it to be released to medical devices in an institution. In the example in FIG. 10, the Drug Library Administrator 200 and the Resource Clinicians 202 are required to sign off on the DAL file. In some implementations, a larger number or a smaller number of actors may be required to sign off on the DAL file before it is released. After the Approval step 230, the DAL file may be released for use in the institution.

In various embodiments, a DAL file may be arranged in a hierarchical fashion. That is, a DAL file may include a number of superior and subordinate entries or parent and child entries which specify settings for a DAL file. These entries may be arranged in various strata. As one progresses farther down a hierarchy, entries for the DAL file may become more specific. Parent entries, for example, may broadly define parameters, limits, etc. and child entries may further narrow or refine these parameters, limits, etc.

Figure 11A:
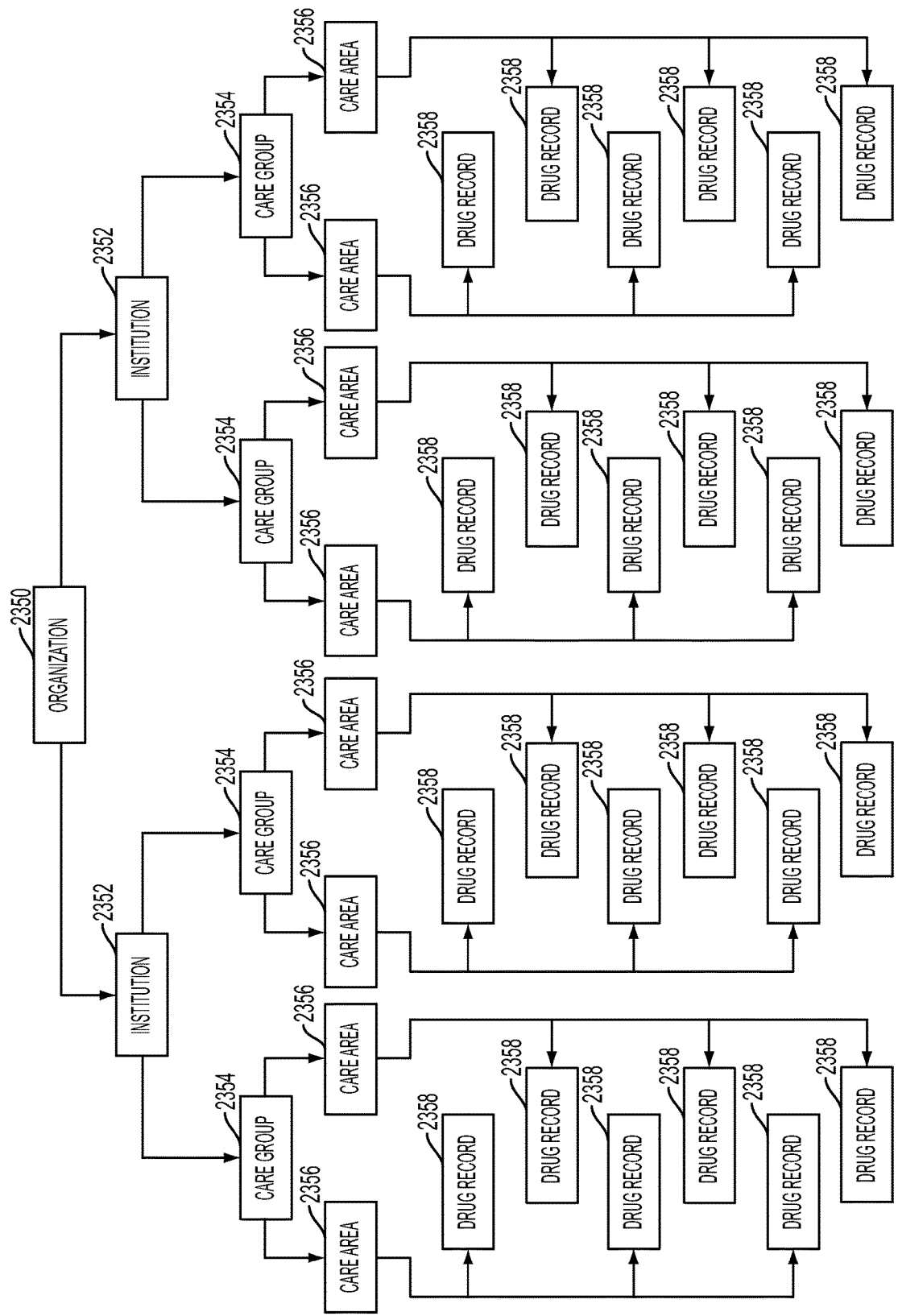
FIG. 11*a* depicts a diagram which outlines an example hierarchical organization structure of a drug administration library ("DAL") file in accordance with an embodiment of the present disclosure.

FIG. 11*a* depicts an example hierarchical arrangement of a DAL file. As shown, the example hierarchical arrangement shown in FIG. 11*a* is similar to an institution/organization's hierarchy. In some embodiments, the hierarchical arrangement of a DAL file may differ. For example, some DAL files may not include the care group and/or organization strata shown in FIG. 11*a*. This may be particularly true of DAL files used in a small, stand alone institution.

As shown, the hierarch of the example hierarchy for a DAL file may be the organization 2350 in which a DAL file is to be used. Below the organization 2350 may be the constituent institutions 2352 which make up the organization 2350. For some DAL files, an institution 2352 may be the hierarch of the DAL file hierarchy. This may, for example, be true in scenarios where a DAL file is being created for an institution 2352 which is not part of an organization 2350.

Each institution 2352 may be divided into a number of care groups 2354. The care groups 2354 may each include a number of care areas 2356. A care group 2354 may be an organizational category into which a number of care areas 2356 may belong. For example, a number of ICU type care areas 2356 (e.g. neonatal, pediatric, adult, medical, surgical, cardiac, neuro, trauma, burn, etc. ICU's) may be grouped into an ICU care group 2354. Each care area 2356 may include a number of specific drug or medication records 2358 which are associated with that care area 2356.

At the various levels of the hierarchy, a number of parameters may be defined. The defining of these parameters may be the process through which a DAL file is created. These parameters may include but are not limited to various operational settings, data formatting settings, acceptable input ranges or values for data on a medical device, guardrails or limits for therapies or medical devices, etc. A number of possible example settings which may be defined in a DAL file are described throughout the specification. Other settings may also be included in some embodiments. In some instances, values defined at higher levels of the hierarchy may act as parent values for other values defined at lower levels of the hierarchy.

In some embodiments, the same parameters may be defined at multiple levels of the hierarchy. In such embodiments, the child parameter value (value defined at the subordinate hierarchical level) may default to the value defined for the parent parameter (value defined at the superior hierarchical level) when a user is specifying parameter values for subordinate levels of the hierarchy. A user may alter these child values. In some embodiments a user may only be able to alter the value to a more restrictive value. For example, a user may define a patient weight high hard limit at the care group level. This value may act as the default setting for the same parameter in any care areas which are included in the care group. If the care group included a care area for pediatric patients, a user may desire to make the patient weight high hard limit more restrictive and may be allowed to do so. Such inheritance of parameter values may help to facilitate DAL file creation and improvement, as well as increase ease of use and efficiency.

For another example, a care group 2354 may have a number of drugs which are associated with it. Drug records 2358 for these drugs defined at the care areas 2356 level within that care group 2354 may specify the specific drug's clinical uses and concentrations that are appropriate for the specific care areas 2356. As an example, in a care group 2354 consisting of five care areas 2356 which use similar drugs, a user may only need to add the common drugs at the care group 2354 level instead of once for each care area 2356 in the care group 2354. Adding the drugs to the care group 2354 may cause the drug to consequentially be added to the care areas 2356 in the care group. Additionally, in some embodiments, a user may define some or all parameters for each common drug at the care group 2354 level. These parameters may then be inherited as the defaults for their respective child parameters in each care area 2356 in the care group 2356. Such an arrangement may facilitate DAL file creation and improvement, as well as increase ease of use and efficiency.

Additionally, in some embodiments, some levels of the example DAL file hierarchy may be divided into a number of sub levels. For example, drug records 2358 may be divided into general drug settings, clinical use settings, and settings for specific concentrations of the drug. These sub levels may furthermore have their own hierarchical arrangement.

Figure 11B:
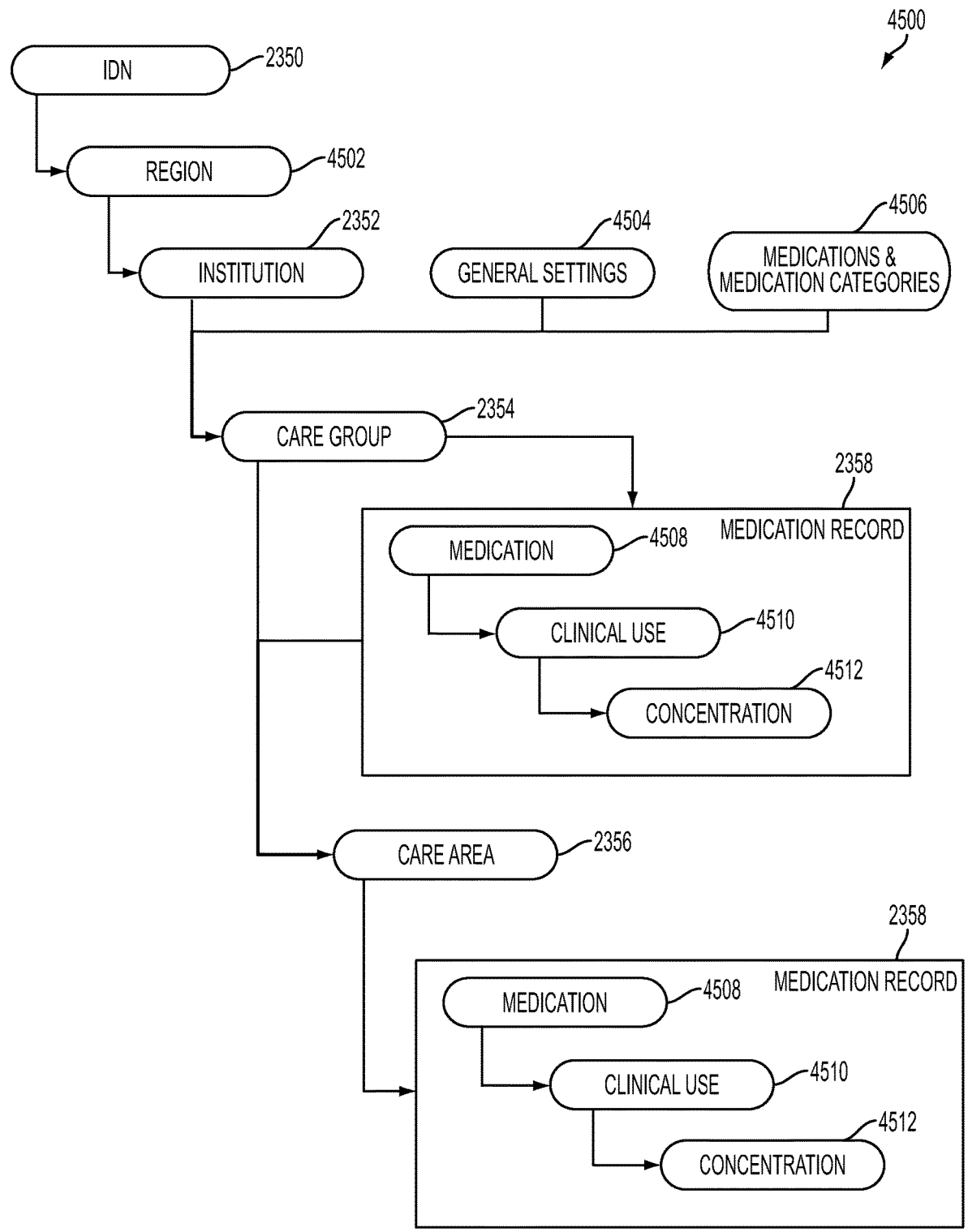
FIG. 11*b* depicts a diagram which outlines an example hierarchical organization structure of a drug administration library file in accordance with an embodiment of the present disclosure.

FIG. 11*b* depicts another example embodiment of a DAL file hierarchy 4500. As shown, the DAL file hierarchy 4500 shown in FIG. 11*b* includes a number of additional hierarchical strata than that shown in FIG. 11*a*. Other embodiments may include different or a different number of strata. A user may be able to define various parameter values to create the DAL file at each level shown. In some embodiments, the same or related parameter values may be defined at multiple levels of the hierarchy. In some such cases, a value defined at a higher level of a DAL file hierarchy 4500 may operate as a parent value for the same or related value at lower levels of a DAL file hierarchy 4500. It should also be noted that there may be multiple constituent parts at each level of a DAL file hierarchy which make up the higher levels of a DAL file hierarchy 4500. For example, referring back to FIG. 11*a*, multiple care groups 2354 may make up each institution 2352.

As shown in FIG. 11*b*, the hierarch of the DAL file hierarchy 4500 is an IDN or organization 2350. The next level down is the region 4502. This level may be included in instances where an IDN includes a number of institutions which are spread out of a large geographic area. In other embodiments, this level of the hierarchy may be used to create groups of similar institutions (e.g. urgent care centers, clinics, etc.)

The next level of the DAL file hierarchy 4500 is shared. A user may define various settings at an institution level 2352. A user may also define general settings 4504. A user may also define medications and medication categories 4506 at this level. In some embodiments this may be done at a higher level of a DAL file hierarchy 4500. These may be defined by creating a master medications list for an institution and then dividing it into a number of categories. A user may also define parameters for medications and categories 4506. Any values defined at this shared level of a DAL file hierarchy 4500 may act as parent settings for the care group 2354 level of a DAL file hierarchy 4500.

A user may define various parameters for the care group 2354 level of a DAL file hierarchy 4500. A user may define one or more medication records 2358 and parameters for those medication records 2358 for each care group 2354. Various parameters defined for a care group 2354 may function as parent settings for any medication records 2358 defined for the care group 2354. Care group 2354 parameter settings may also act as parent settings for entries in care areas 2356 within a care group 2354. Additionally, any medication records 2358 and parameters associated with them defined for a care group 2354 may be included automatically in care areas 2356 within a care group 2354.

A user may define various parameters at the care area 2356 level of a DAL file hierarchy 4500. A user may define one or more medication records 2358 and parameters for those medication records 2358 for each care area 2356. Various parameters defined for a care area 2356 may function as parent settings for any medication records 2358 defined for the care area 2356.

As shown, medication records 2358 are divided into a number of sub levels. Medication records 2358, in the example embodiment in FIG. 11*b* include a medication 4508 sub level which is at the top of their internal hierarchy. A user may choose the name of a medication from a master medication list to populate this sub level of the hierarchy. This may apply any parent values defined for that medication in the master medication list or medication categories list. A user may be able to define additional other parameters at the medication 4508 sub level. Any values defined for the medication 4508 sub level may act as parent values for the clinical use 4510 sub level. A user may define various parameters at a clinical use 4510 sub level. These values may act as parent values for the concentration 4512 sub level. A user may also be able to define various parameters at the concentration 4512 sub level.

Figure 12:
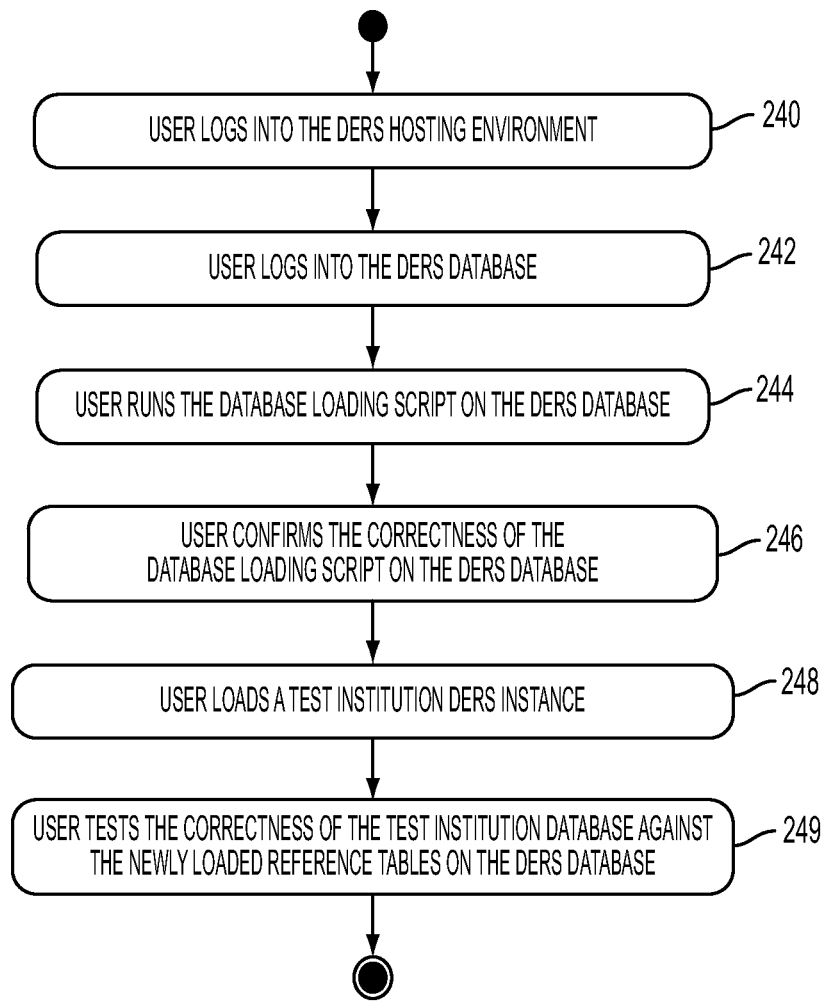
FIG. 12 depicts a flowchart detailing a number of example steps which may be part of a drug error reduction system setup phase of drug administration library file creation in accordance with an embodiment of the present disclosure.

FIGS. 12-71 depict a number of example flowcharts which detail a number of aspects of DERS editor usage. These flowcharts and the steps shown within these flowcharts are only exemplary. In other embodiments, usage of the DERS editor may differ from that shown and described in FIGS. 12-71. Some steps, for example, may not be performed or may not be performed in the same order as shown and described herein. Some embodiments may include different or additional steps. It should also be recognized that some of the flowcharts depicted detail only one example of many possible ways of accomplishing the same result. Many embodiments may include multiple alternative workflows which may be followed to realize the same end result. For the sake of brevity, not all alternative workflows considered within the scope of this disclosure are shown. The flowcharts shown and described in FIGS. 12-71 may be related to the various screens shown and described in FIGS. 72-181.

FIG. 12 depicts a flowchart detailing a number of exemplary steps which may be a part of the DERS SETUP 122 (see, for example, FIG. 9) phase of the creation of a DAL file. The steps detailed in the flowchart in FIG. 12 may be performed prior to any use of a DERS editor at a medical institution. A user may log into a DERS hosting environment in step 240. The user may be a part of the hosting IT for the hosted environment 83 in FIG. 4. In some embodiments, the user may be a DERS editor service administrator. In step 242, the user may login to the DERS database within the DERS hosted environment. The DERS database may, in some embodiments, be the DERS database 113 depicted in FIG. 4. In step 244 a user may run a database loading script on the DERS database. This loading script may load DERS reference tables onto the DERS database. The loading script may load DERS reference tables which will be used for all institution and organizations which use the DERS editor service. The reference tables may load drugs, drug aliases, substitute drugs, drug incompatibilities, care area types, roles, units of measure, comment types, approval/verification states, various attributes, etc. onto the database. In step 246, the correctness of the database loading script may be confirmed by the user. In step 248, a user may load a test institution DERS instance. This instance may be used by the user to test the correctness of the reference tables which were loaded onto the DERS database in step 249. The steps detailed in the flowchart in FIG. 12 may be performed by a user with direct or remote access to the DERS hosted environment.

Figure 13:
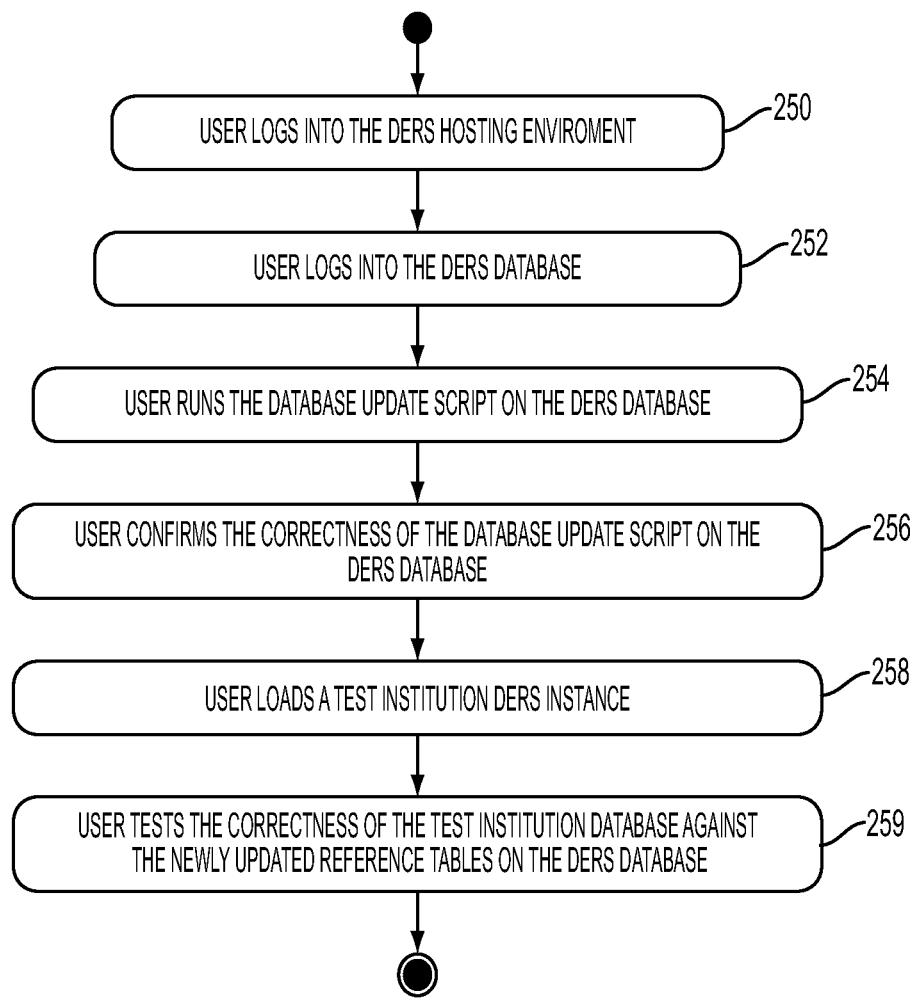
FIG. 13 depicts a flowchart detailing a number of example steps which may be used to update reference tables loaded on to a drug error reduction system database in accordance with an embodiment of the present disclosure.

FIG. 13 depicts a flowchart detailing a number of example steps which may be used to update reference tables loaded on to a DERS database. In some embodiments, the reference tables may be those described in relation to FIG. 12. In step 250, a user logs into a DERS hosting environment. The user may be a part of the hosting IT for the hosted environment 83 in FIG. 4. In some embodiments, the user may be a DERS editor service administrator. In step 252, the user may login to the DERS database within the DERS hosted environment. The DERS database may, in some embodiments, be the DERS database 113 depicted in FIG. 4. In step 254 a user may run a database update script on the DERS database. This update script may update DERS reference tables on the DERS database. This update script may update the DERS reference tables used by all institutions or organizations which use the DERS editor service. In step 256, the correctness of the database update script may be confirmed by the user. In step 258, a user may load a test institution DERS instance. This instance may be used by the user to test the correctness of the reference tables which were updated on the DERS database in step 259. The steps detailed in the flowchart in FIG. 13 may be performed by a user with direct or remote access to the DERS hosted environment.

Figure 14:
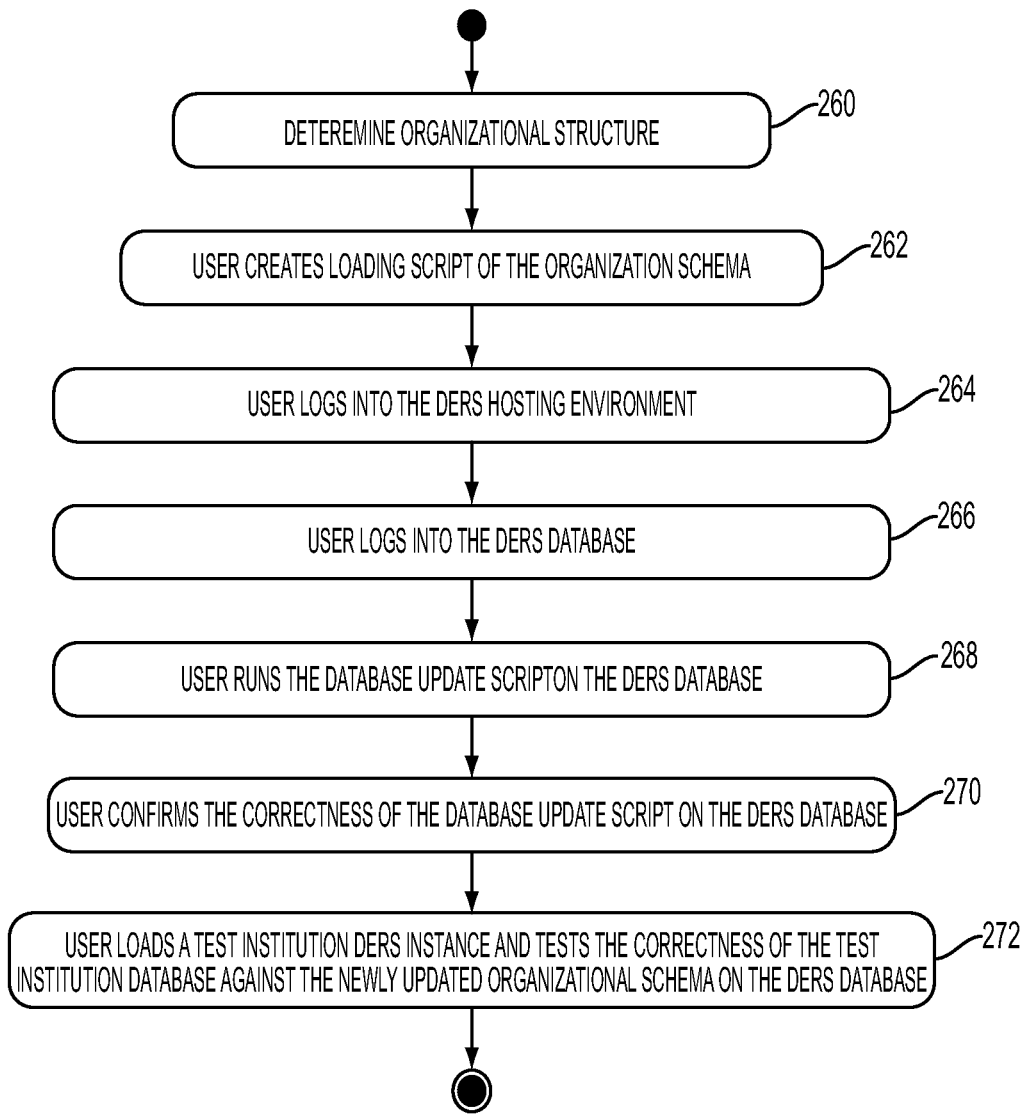
FIG. 14 depicts a flowchart showing a number of example steps which may be used to establish institution and organizational hierarchies in a drug error reduction system database in accordance with an embodiment of the present disclosure.

FIG. 14 depicts a flowchart showing a number of example steps which may be used to establish institution and organizational hierarchies in a DERS database. The various steps shown in the flowchart in FIG. 14 may be performed as part of the DERS SETUP 122 (see, for example, FIG. 9) phase of the creation of a DAL file. In step 260, the organizational structure of the institution or organization is determined. In the simplest cases, there may be only a single institution which uses its own DAL and has no parent organization. In other cases, an organization may include a number of different institutions all of which use the same DAL. In some cases, an organization may include a number of different institutions with at least 2 different DAL files. In cases where a DERS database is being used by an organization, a field for the institution name may be included. This name may be used for intra-organizational data comparison and may be included in CQI messages from institutions within the organization.

In step 262, the loading/update script for the organizational schema may be created. In step 264 a user logs into a DERS hosting environment. The user may be a part of the hosting IT for the hosted environment 83 in FIG. 4. In some embodiments, the user may be a DERS editor service administrator. In step 266, the user may login to the DERS database within the DERS hosted environment. The DERS database may, in some embodiments, be the DERS database 113 depicted in FIG. 4. In step 268, a user may run a database update script on the DERS database. This update script may create a new database or databases for the specified organizational schema. In step 270, the correctness of the database update script may be confirmed by the user. In step 272, a user may load a test institution DERS instance. This instance may be used by the user to test the correctness of the organizational schema which was updated onto the DERS database. The steps detailed in the flowchart in FIG. 14 may be performed by a user with direct or remote access to the DERS hosted environment.

Figure 15:
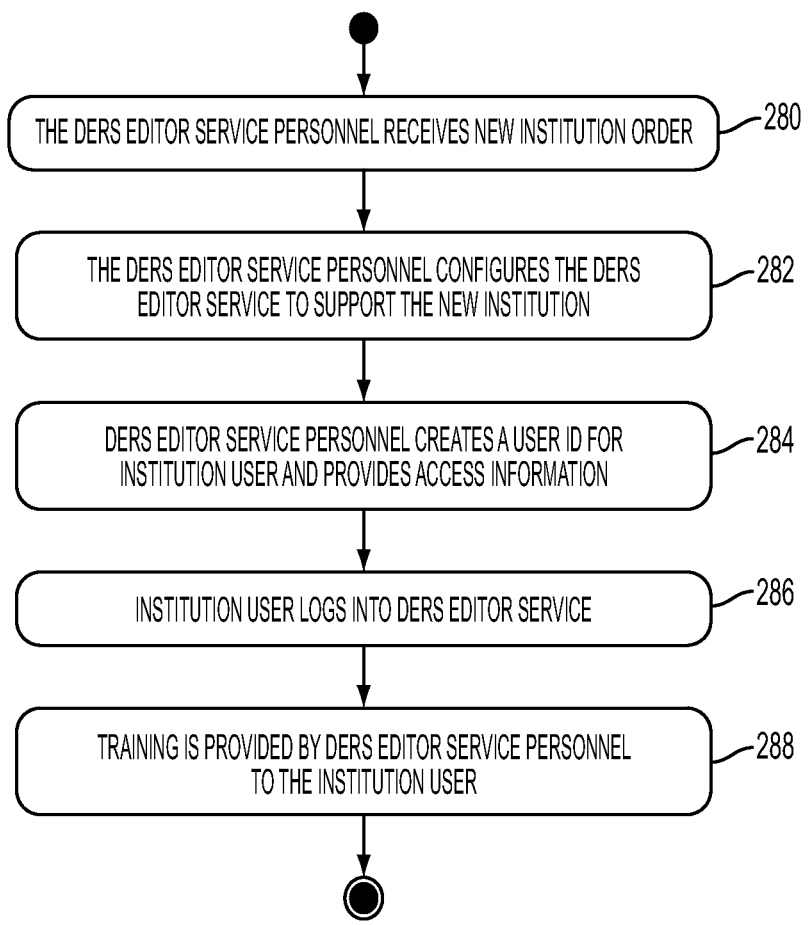
FIG. 15 shows a flowchart showing a number of exemplary steps which may be used when giving a subscribing party access to a drug error reduction system editor

FIG. 15 shows a flowchart showing a number of exemplary steps which may be used when giving a subscribing institution access to a DERS editor. In step 280, an institution or organization may sign a contract for enrollment in the DERS service with a DERS editor service provider. The DERS editor service may be configured to support the new institution or organization in step 282. In some embodiments, this may involve setting up a database and application server for the new institution or organization. In some other embodiments, a new dataset may be created within an existing database for the new institution or organization. This step may be performed by hosting IT for a hosted environment in which the DERS editor service databases, servers, etc. reside. In some embodiments, step 282 may involve performing the steps detailed and depicted in FIG. 14.

In step 284, DERS editor service personnel (e.g., the Hosting IT of the hosted environment 83 of FIG. 4) may set up a user account for a user at the institution or organization. In some embodiments, this user may be a drug library administrator such as the drug library administrator 200 shown in FIG. 10. The access information for the user account may also be provided to the user at the institution or organization in this step. In step 286, the user at the institution or organization may log in to the DERS editor. In some embodiments, the user at the institution may also be required to change their password in step 286. The user at the institution may then be provided training by DERS editor service personnel in step 288. The user at the institution may then have access to the DERS editor.

Figure 16A:
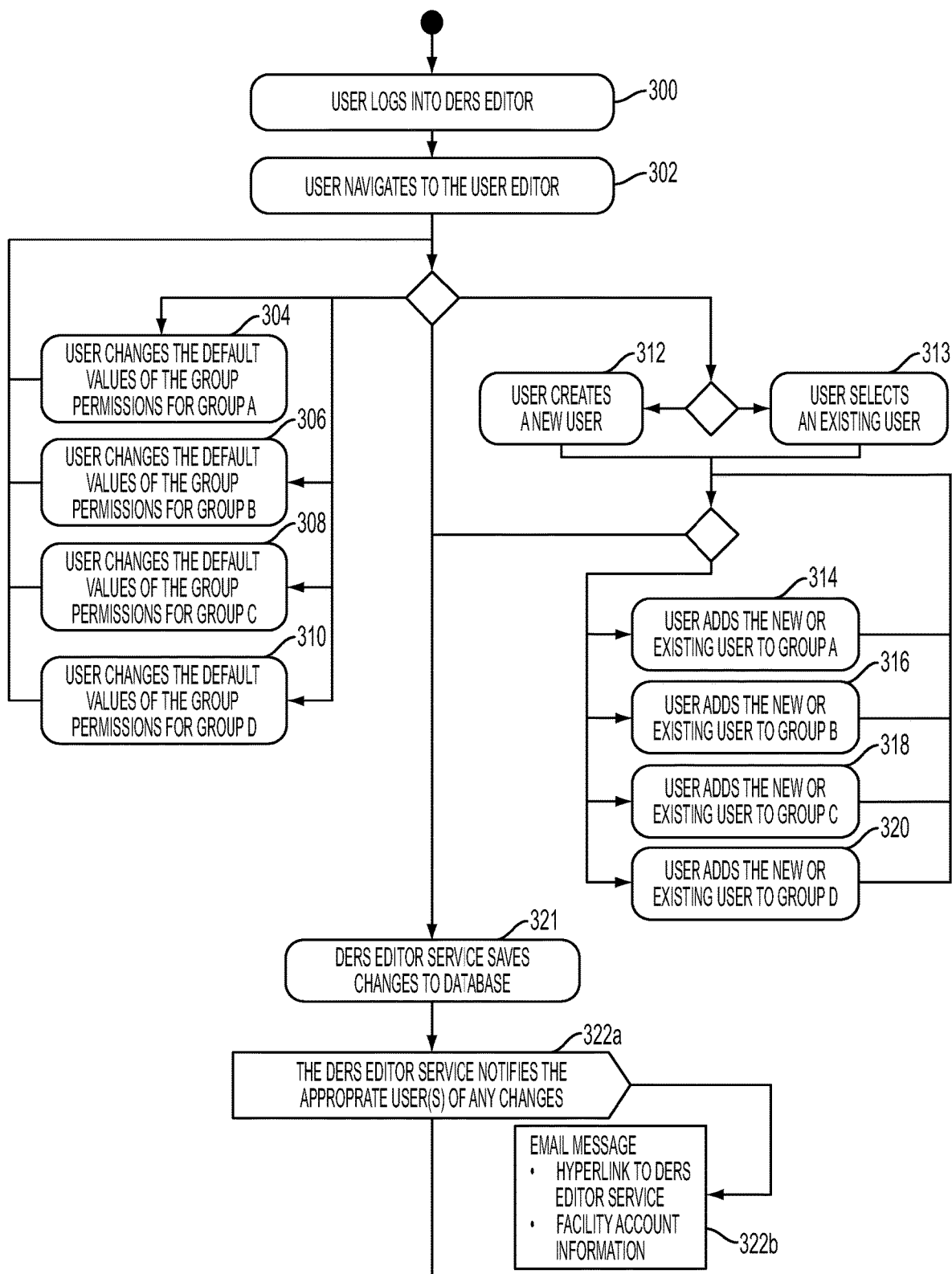
FIG. 16*a* depicts a flowchart detailing a number of example steps which may be used to setup various aspect of a drug error reduction system within an organization or institution in accordance with an embodiment of the present disclosure.

A flowchart detailing a number of example steps which may be used to setup various aspect of a DERS within an organization or institution is shown in FIG. 16a. Specifically, the example steps shown in the flowchart in FIG. 16a may be used to define users, the groups they belong to, and their various permissions and privileges. The steps shown in FIG. 16a may be part of a DERS SETUP 122 phase (see, for example, FIG. 9). In step 300, a user may log into the DERS editor. The user may, in some embodiments, be the drug library administrator 200 of FIG. 10. This may be done by accessing a DERS editor user interface. As mentioned above, this may be accessed via a suitable web browser with no client-side software needed. The user may then navigate to a user editor on a DERS editor user interface in step 302. The user may then perform any of steps 304, 306, 308, and 310.

Step 304 changes the values of the group permissions for Group A. Step 306 changes the values of the group permissions for Group B. Step 308 changes the values of the group permissions for Group C. Step 310 changes the values of the group permissions for Group D. Groups A-D may be various categories of possible institution employees. For example, one of Group A-D may be a pharmacist group, another may be a biomed group, another may be a nurse manager group, and the last may be a safety staff group. In various embodiments, there may be additional groups for other categories of institution or organization employees. The groups may be user defined in some embodiments. In some embodiments, the groups may be predefined and may have a set of default values of group permissions which are provided by the DERS editor service. Some embodiments may not include groups, but rather allocate permission based on specific user. Additionally, some groups may include sub-groups (not shown). The permissions which are available for allocation may allow a user to customize groups or subgroups to best fit the needs and/or current structuring of their institution/organization.

In a specific embodiment of the present disclosure, a list of possible permissions is shown in Table 3 as follows:

| | Permission Name |
|---|---|
| 0.01 | Create User |
| 0.02 | Update User |
| 0.03 | Delete User |
| 0.04 | Edit Institution/Organization Drug List |
| 0.05 | Change Group Permissions |

-continued

| Permission Name | |
|---|---|
| 0.06 | Create Group |
| 0.07 | Delete Group |
| 0.08 | Remote Login |
| 0.09 | Update Care Area |
| 0.10 | Delete Care Area |
| 0.11 | Read Care Area |
| 0.12 | Review Care Area |
| 0.13 | Approve Care Area |
| 0.14 | Add Comment or Note |
| 0.15 | Read Comment or Note |
| 0.16 | Create Change Request |
| 0.17 | Review Change Request |
| 0.18 | Approve/Deny Change Request |
| 0.19 | Access Medical Device Simulator |
| 0.20 | Add/Modify Drug Records for Care Area(s) |
| 0.21 | Release DAL |
| 0.22 | Download DAL |
| 0.23 | Modify General Settings |
| 0.24 | Modify Clinical Advisories |
| 0.25 | Change Permissions for Individual Users |
| 0.26 | Approve DAL for Release |
| 0.27 | Create DAL Report |
| 0.28 | Create Intra-Organization DAL Report |
| 0.29 | Create Inter-Organization DAL Report |
| 0.30 | Create CQI Report |
| 0.31 | Schedule Automated CQI Report |
| 0.32 | Read Only Access |
| 0.33 | Assign Review Task to User |
| 0.34 | Approve Change Request |
| 0.35 | Update Care Group |
| 0.36 | Delete Care Group |
| 0.37 | Read Care Group |
| 0.38 | Review Care Group |
| 0.39 | Approve Care Group |

Still referring to FIG. 16a, a user may also choose to create a new user in step 312. This may involve defining a user name and a temporary password for the new user. It may also involve providing the email address of the new user. A user may then proceed to any of steps 314, 316, 318, and 320. A user may also choose to proceed to any of steps 314, 316, 318, and 320 from step 313 in which the user selects an existing user. In step 314 a user may assign a newly created user, or existing user to Group A. In step 316 a user may assign a newly created user or existing user to Group B. In step 318 a user may assign a newly created user or existing user to Group C. In step 320 a user may assign a newly created user or existing user to Group D. In some embodiments, a user may assign a newly created user or existing user to more than one group. In some embodiments, additional steps (not shown) may be included where a user may assign a newly created user or existing user to further groups or sub-groups.

In step 321, the DERS editor service may save the changes to a database. In some embodiments, the database may be the DERS database 113 of FIG. 4. In other embodiments the database may, for example, be a user database in a hosted environment. In step 322a, the DERS editor service may notify the appropriate users that changes have been made. For example, if a new user account is created the new user may be notified. As shown in 322b, in some embodiments, this may involve an automatically generated email message which is sent to the new user. This message may provide the new user with a hyperlink to the DERS editor in embodiments where the DERS editor may be accessed via a suitable web browser. This message may include account information and instructions detailing how the new user should make use of the DERS editor. It may also include password and access information to the newly created user. Alternatively, this information may be manually provided to the new user.

Figure 16B:
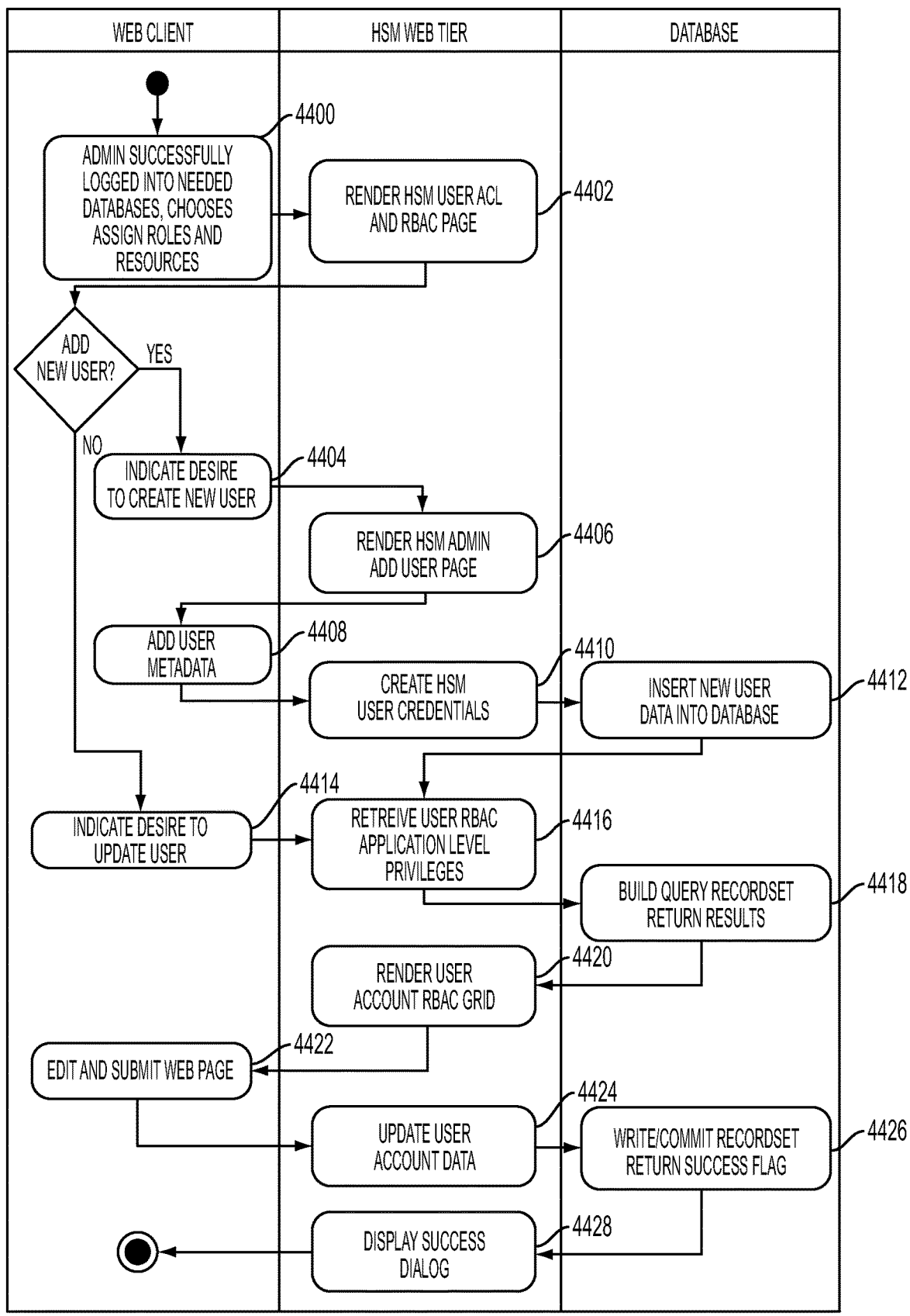
FIG. 16*b* depicts a flowchart detailing a number of example steps which may be used to define users, the groups they belong to, and their various permissions and privileges in relation to a drug error reduction system editor in accordance with an embodiment of the present disclosure.

FIG. 16b depicts a flowchart detailing a number of example steps which may be used to define users, the groups they belong to, and their various permissions and privileges. The example flowchart shown in FIG. 16b depicts a number of steps which may be used with a web browser based DERS editor service. In step 4400, a user may log into the DERS editor and indicate that they would like to use a user editor. A web tier for the DERS editor may then render the user editor page in step 4402. A user may then have the choice of adding a new user or updating/deleting an existing user.

A user may indicate, in step 4404, that they would like to add a new user. A web tier for the DERS editor may then render an add user page in step 4406. The user may then add various user metadata for the new user in step 4408. After the metadata is added for the new user, a web tier may create the user credentials for the new user in step 4410. In step 4412, the new user data may be inserted into a database. The database may, for example, be the DERS editor database 113 of FIG. 4 or a user database in a hosted environment.

After the new user data has been added to the database, or after a user has indicated that they would like to update an existing user in step 4414, a web tier may retrieve the user privileges and information in step 4416. A query record set for the requested user may be built and sent to the web tier in step 4418. The web tier may then render a user editor interface for the selected user in step 4420. In step 4422, a user may make desired edits to the user and submit any changes. Such edits may include, but are not limited to, modifying group assignments, modifying privileges, deletion of the user, assigning user responsibilities, etc. A web tier may update the user account data in step 4424. In step 4426, the data for the edited user may be written or committed to a database. Additionally, in step 4426, a success notification may be sent to the web tier to indicate a successful update of the database. A web tier may display a success dialog box in step 4428 to indicate that the user account information has been updated.

Figure 17:
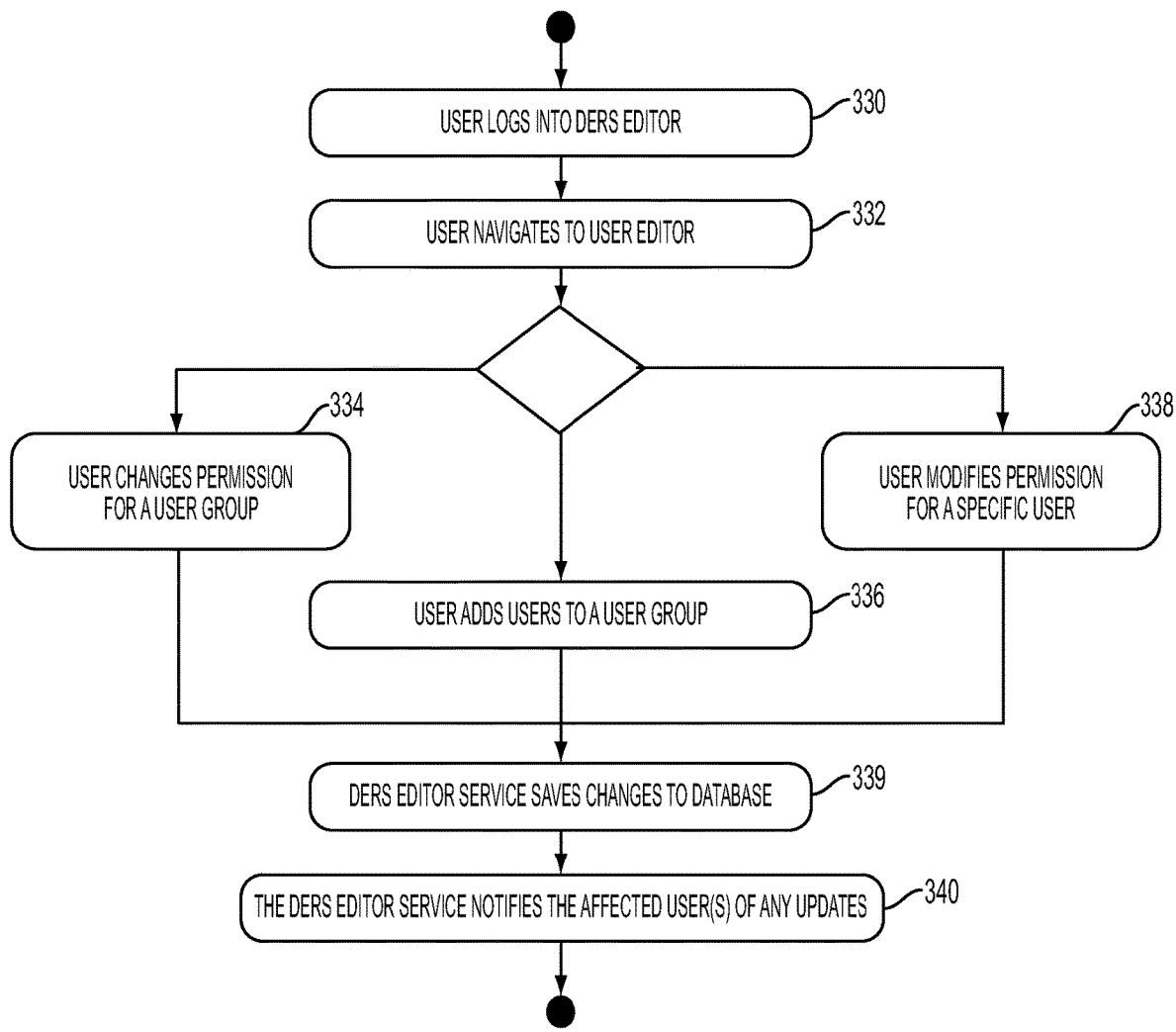
FIG. 17 shows a flowchart detailing a number of example steps which may be used to update various aspects of a drug error reduction system within an organization or institution in accordance with an embodiment of the present disclosure.

FIG. 17 shows a flowchart detailing a number of example steps which may be used to update various aspects of a DERS within an organization or institution. Specifically, the example steps shown in the flowchart in FIG. 17 may be used to update users, the groups they belong to, and their various permissions and privileges. In step 330, a user may login to the DERS editor. The user may, in some embodiments, be the drug library administrator 200 of FIG. 10. This may be done by accessing a DERS editor user interface. As mentioned above, this may be accessed via a suitable web browser with no client-side software needed. The user may then navigate to a user editor on a DERS editor user interface in step 332. The user may then perform any of steps 334, 336, and/or 338. Performing these steps may involve following steps similar to those shown and described in relation to FIGS. 16a and 16b. In step 334, a user may modify the various permissions for a group which may, for example, be one of Groups A-D shown in FIG. 16a. In step 336, the user may add a user to a group which has been previously created. This may be done, for example, to add a newly hired employee to a group. In step 338, the user may individually modify the permissions of users with access to the DERS editor. In some embodiments, this step may not be included. In some embodiments, this step may be included while steps 334 and 336 are not included. The former case may be well suited to institutions which are relatively large and/or complex. The latter case may be well suited to small institutions or medical settings where the DERS editor may only have a small number of total users. After a user has finished updating various aspects of the DERS editor, the DERS editor service may save any changes to a database in step 339. This database may be the database 113 of FIG. 4 or a user database in some embodiments. The DERS editor service may notify affected users of any updates in step 340. This may be accomplished by an automatically generated email which is sent to affected users.

Figure 18:
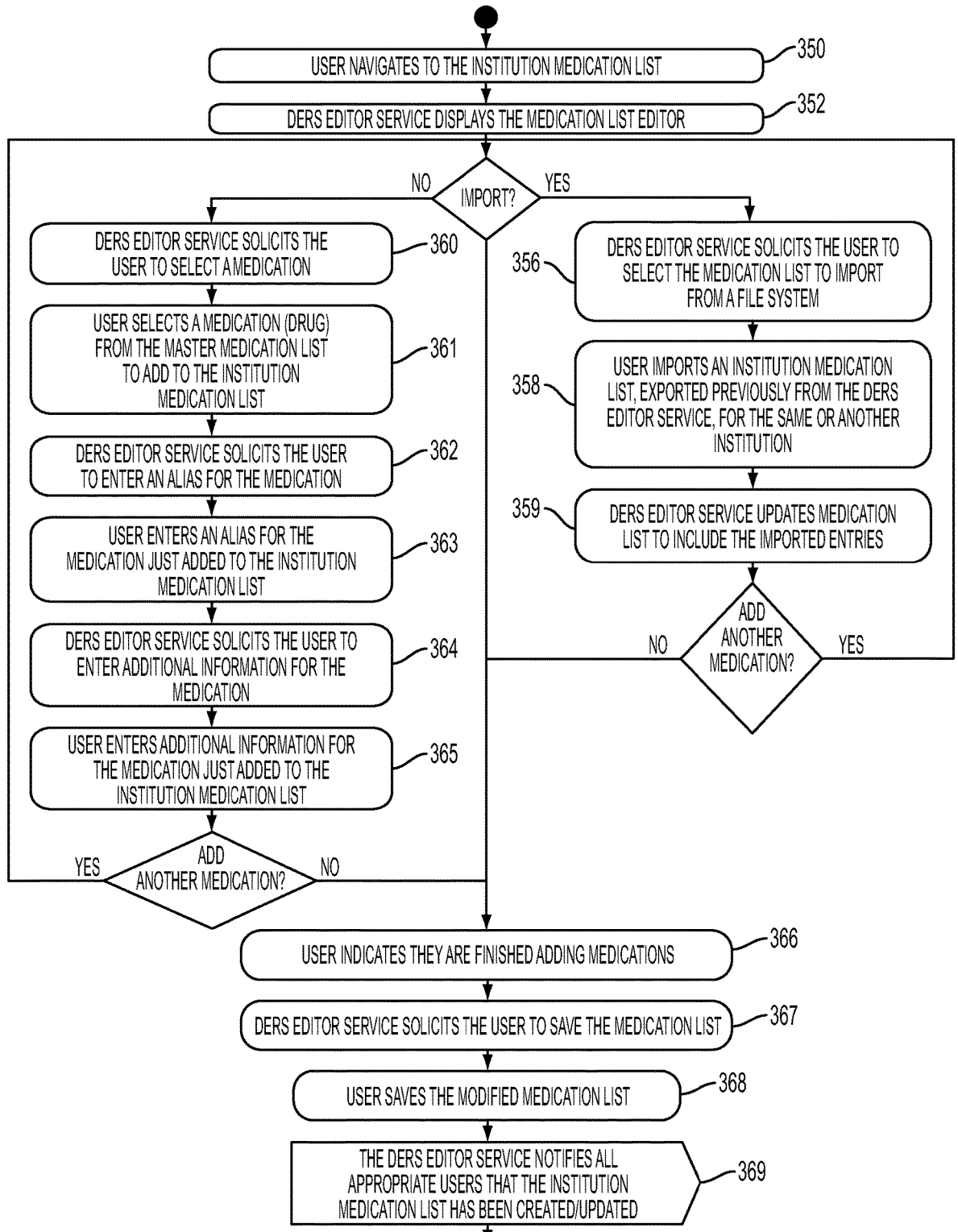
FIG. 18 depicts a flowchart detailing a number of example steps which may be used to create or update an institution/ organization master medication list in accordance with an embodiment of the present disclosure.

FIG. 18 depicts a flowchart detailing a number of example steps which may be used to create or update an institution/organization master medication list. In some embodiments, the steps shown in the flowchart in FIG. 18 may be a part of the medication list customization 210 described in relation to FIG. 10. In step 350, the user navigates to the medication list for the institution or organization on the DERS editor user interface. The DERS editor service may then display the medication list editor in step 352. The user may be a drug library administrator such as the drug library administrator 200 in FIG. 10. In other embodiments the user may be a pharmacist, or any user granted permission 0.04 of Table 3. After navigating to the medication list for the institution or organization, the user may either import a medication list from the DERS editor service or may select a medication or medications from a master list provided by the DERS editor service.

If a user elects to import a list from the DERS editor service, the user may be prompted by the DERS editor service to select a medication list to import in step 356. This step may involve displaying a list of importable lists stored by the DERS editor service or on a database associated with the DERS editor service. The user may then import the desired list in step 358. The DERS editor service may then update the medication list for the institution/organization so that it includes the imported entries in step 359. If a user desires to add more medications to the institution/organization medication list, the user may import another medication list or may select a medication from a master medication list accessed via the DERS editor service. If a user is finished updating or creating the institution/organization medication list, the user may proceed to step 366. Step 366 will be described later in the specification.

If a user does not import a medication list or if a user has imported a medication list and desires to add additional medications, the user may add desired medications to the institution/organization medication list by proceeding to step 360. In step 360, the DERS editor service may prompt the user to select a medication to add to the medication list as illustrated by step 361. These medications may be selected by a user from a master medication list provided by the DERS editor service in some embodiments. The DERS editor service may then prompt users to enter an alias or other name for the medication in step 362. The user may provide the alias in step 363. The DERS editor service may solicit the user to provide additional information for added medications in step 364. The user may provide any additional information in step 365. If a user wants to add other medications to the institution/organization medication list after completing step 365, the user may decide whether they would like to import a medication list or select a medication from a master list and proceed as described above.

When a user is finished adding medications to the medication list, the user may proceed to step 366. The user may indicate they are finished adding medication in step 366. The DERS editor service may then prompt the user to save the created or updated medication list for the institution or organization in step 367. The user may then save the created or updated medication list in step 368. This may cause the medication list to be saved on a database such as the DERS database. The DERS editor service may then notify appropriate users at the institution or organization that its medication list has been created or updated in step 369. For instance, the DERS editor service may notify all users responsible for creating or maintaining care area medication lists that the institution/organization medication list has been created or updated.

Referring now to FIG. 19, a flowchart detailing a number of example steps which may be used to add clinical advisory entries to a database is shown. A clinical advisory may provide information about a medication to a user of a medical device. This information may include administration guidelines, information from a pharmacy formulary, contraindications, etc. In various embodiments, a clinical advisory may include text, an image or graphic, and/or and electronic file such as a .pdf or the like. A clinical advisory may be a free text entry in which a user may enter anything they desire. Some embodiments may include a number of types of clinical advisories. For example, some embodiments may include a short text clinical advisory and a full clinical advisory. The short text clinical advisory may be limited to a predefined number of characters (e.g. 40) to allow it to be easily displayed on a graphic user interface of a medical device.

These steps may be performed as part of the medication list customization 210 described in relation to FIG. 10. In step 370, a user navigates to the clinical advisory list. The user may then decide to either import a clinical advisories list from the DERS editor service or may add his or her own clinical advisories to the clinical advisories list. If the user decides to import a list of clinical advisories from the DERS editor service, the user may import the list in step 372. If the user decides to add their own clinical advisories to the list, the user may proceed to step 374 and add these clinical advisories. The user may repeat step 374 as many times as desired until the user is finished adding clinical advisories to the clinical advisories list. In step 376, the user may log out and save changes to the clinical advisory list for the institution or organization. Changes may be saved on the DERS database. In step 378, the DERS editor service may notify all pertinent users that the clinical advisories list has been updated. Step 378, in some embodiments, may include automatically sending an email to relevant users informing them of the changes.

In some embodiments, additional steps may be included in which a user may upload files (e.g. images, documents, etc.) to a clinical advisory. In some embodiments, clinical advisories may not be added, modified, etc. at the clinical use level. Instead, these advisories may be added to medication records when such records are being defined by a user. In some embodiments, a user may define clinical uses for a drug as well as the various clinical uses and concentrations of the drug.

FIG. 20 shows a flowchart detailing a number of example steps which may be used to modify the general settings for an institution or organization. The steps may be performed as part of a DERS SETUP 122 (see, for example, FIG. 9) phase. In step 380, a user navigates to the general settings list on a DERS editor user interface. As mentioned above, this may be accessed via a suitable web browser with no client-side software needed. In some embodiments, the DERS editor service may prompt the user to enter values for various general settings in step 381. The user may then modify, enter, update, etc. any of the desired values in the general settings in step 382. In step 384, the user may log out and save any changes made to the general settings. Changes may be saved on the DERS database. The DERS editor service may then notify all the appropriate users that the general settings have been modified in step 386. In a specific embodiment of the present disclosure, a non-limiting list of possible General Settings is shown in Table 4 as follows:

| | General Settings |
|---|---|
| 0.01 | Drug Library Name |
| 0.02 | DAL Release Notes/Description |
| 0.03 | DAL Version Number |
| 0.04 | DAL Approval State |
| 0.05 | Time/Date DAL Version Created |
| 0.06 | Institution/Organization Name |
| 0.07 | Region |
| 0.08 | Facility |
| 0.09 | Language |
| 0.10 | Screen Lock Passcode |
| 0.11 | Date Format |
| 0.12 | Locale |
| 0.13 | Decimal Format |
| 0.14 | Syringe List |

FIG. 21 shows a flowchart detailing a number of example steps which may be used to add a care group to an institution or organization. As detailed above in relation to FIGS. 11a-11b, within a DAL file, an organization or institution may be broken into a number of sub-areas or groups which may, for example, reflect departments within the organization or institution. The steps shown in FIG. 21 may be part of a DERS SETUP 122 (see, for example, FIG. 9) phase. In step 2370, a user navigates to a care group list on the DERS editor user interface. The user chooses to add a new care group to the list in step 2372. When adding a new care group to a care group list, the user may have a number of options. In some embodiments, a user may start from a blank template or nearly blank template. In the flowchart for the embodiment depicted in FIG. 21, a user may also choose to copy the information for an existing care group to expedite the process. If a user elects to copy a pre-existing care group, the user proceeds to step 2374. In step 2374 a user specifies the pre-existing care group which the user would like to copy, and copies the care group. The user may then change the type of care group by modifying the care group type to that of the new care group in step 2376. In some embodiments, a user may also adjust care group settings in step 2376.

If a user chooses not to copy a pre-existing care group, or no pre-existing care group exists, the user may proceed to step 2378. In step 2378, a user specifies the type of new care group which will be added to this list. This step may include selecting a care group from a list of possible care group types. The care group type may be a broad category into which a number of care areas within an institution or organization may fit. Example care groups may include ICU, Emergency, Pediatric, Neonatal, Adult, Step Down, Surgery, Psychiatric, etc.

A user may proceed from step 2376 or step 2378 to step 2380. In step 2380, a user may modify the name of the care group so that it matches the name used for that care group within the institution or organization. A user may specify various users that are associated with the newly created care group in step 2382. For example, a user may specify a number of clinicians which work in or are assigned to the care group in step 2382. A user may also specify other individuals within an institution or organization which may have responsibilities for reviewing or contributing to the new care group.

In step 2384, a user may define various care group parameters for the new care group. This may involve modifying default values, filling in a blank template, modifying copied values, etc. In a specific embodiment of the present disclosure, a non-limiting list of possible care group parameters is shown in Table 5 as follows:

| | Care Group Parameters |
|---|---|
| 0.01 | Care Group Name |
| 0.02 | Care Group Type |
| 0.03 | Require Second Review |
| 0.04 | Require Second Review for High Risk Medications |
| 0.05 | Require Operator Identification |
| 0.06 | Can Speaker Volume be Changed by Operation |
| 0.07 | Default Speaker Volume |
| 0.08 | Default Screen Brightness |
| 0.09 | Automatically Adjust Screen Brightness |
| 0.10 | Auto-Lock UI After Predetermined Period of Inactivity |
| 0.11 | Option to Input Weight In Pounds |
| 0.12 | Allow Operator to Select a Syringe not on Facility Syringe List |
| 0.13 | Require Second Entry of Patient Weight |
| 0.14 | Require Second Entry of Patient BSA |
| 0.15 | Patient Weight High Hard Limit |
| 0.16 | Patient Weight High Soft Limit |
| 0.17 | Patient Weight Low Hard Limit |
| 0.18 | Patient Weight Low Soft Limit |
| 0.19 | Patient BSA High Hard Limit |
| 0.20 | Patient BSA High Soft Limit |
| 0.21 | Patient BSA Low Hard Limit |
| 0.22 | Patient BSA Low Soft Limit |
| 0.23 | Rate High Hard Limit |
| 0.24 | Rate High Soft Limit |
| 0.25 | Default KVO Value |
| 0.26 | Can KVO be Changed by Operator |
| 0.27 | Default Downstream Occlusion Sensitivity |
| 0.28 | Default Upstream Occlusion Sensitivity |
| 0.29 | Can Occlusion Sensitivity be Changed on Device |
| 0.30 | Default Air Infusion Limit |
| 0.31 | Can Air Infusion Limit be Changed on Device |

After specifying care group parameters, a user may save the new values in step 2386. The care group and the parameter values may be saved on the DERS editor database. The user may then indicate that the new care group is ready to be reviewed by those responsible for reviewing the care group in step 2388. The DERS editor service may then notify the appropriate users that the care group has been created and is ready for review in step 2390. This may be done by an automatically generated email.

Similar steps may, for example be followed to add a care area to a DAL file in some embodiments. Though the screens used on a DERS editor user interface may differ, a user may define similar information and parameters for a care area. In some embodiments, some of the care group parameters shown in Table 5 may instead or also be defined at the care area level. Parameters at the care group may act as parent parameters for a care area. For example, a care group parameter may be the default setting for the same parameter at the care area level. Additionally, a user may create a list of medications which may be used within the care group when defining a care group. This may be accomplished following steps similar to those shown and described in relation to FIG. 18.

FIG. 22 shows a flowchart detailing a number of example steps which may be used to add a care area to an institution or organization. As detailed above in relation to FIGS. 11a-11b, an organization or institution may be broken into a number of sub-areas or groups which may, for example, reflect departments with the organization or institution. The steps shown in FIG. 22 may be part of a DERS SETUP 122 (see, for example, FIG. 9) phase. In step 390, a user navigates to a care area list on the DERS editor user interface. The user chooses to add a new care area to the list in step 392. When adding a new care area to a care area list, the user may have a number of options. In some embodiments, a user may start from a blank template or nearly blank template. In the flowchart for the embodiment depicted in FIG. 22, a user may also choose to copy the information for an existing care area to expedite the process. If a user elects to copy a pre-existing care area, the user may proceed to step 394. In step 394 a user specifies the pre-existing care area which the user would like to copy and copies the care area. The user may then change the type of care area by modifying the care area type to that of the new care area in step 398. In some embodiments, a user may also adjust care area settings in step 398.

If a user chooses not to copy a pre-existing care area, or there are no pre-existing care areas, the user may proceed to step 396. In step 396, a user specifies the type of new care area which will be added to this list. This step may include selecting a care area from a list of possible care area types. In a specific embodiment of the present disclosure, a non-limiting list of possible care areas is shown in Table 6 as follows:

| Care Area Types | |
|---|---|
| 0.01 | Ambulatory Surgery |
| 0.02 | Birthing |
| 0.03 | Cardiac Catheterization |
| 0.04 | Cardiac Rehabilitation |
| 0.05 | Community Health Center |
| 0.06 | Complementary Medical Center |
| 0.07 | Emergency Department/Room |
| 0.08 | Preventative Medicine |
| 0.09 | General |
| 0.10 | Hemodialysis |
| 0.11 | Peritoneal Dialysis |
| 0.12 | Hospice |
| 0.13 | Infusion Center |
| 0.14 | Intensive Care Unit |
| 0.15 | Neonatal Intensive Care Unit |
| 0.16 | Step Down |
| 0.17 | Pediatric |
| 0.18 | Internal Medicine |
| 0.19 | Laboratory |
| 0.20 | Acute Care |
| 0.21 | Long Term Care |
| 0.22 | Microbiology |
| 0.23 | Nursing Home |
| 0.24 | Pre-Operation Unit |
| 0.25 | Operating Room |
| 0.26 | Patient Home/Residence |
| 0.27 | Anesthesia |
| 0.28 | Post Anesthesia Care Unit |
| 0.29 | Primary Care Clinic |
| 0.30 | Public Health Clinic |
| 0.31 | Radiology |
| 0.32 | Reproductive Health |
| 0.33 | Fertility |
| 0.34 | Surgical |
| 0.35 | Critical Care |
| 0.36 | Geriatric |
| 0.37 | Behavioral |
| 0.38 | Psychiatric |
| 0.39 | OB/GYN |
| 0.40 | Skilled Nursing |
| 0.41 | Peri-Operative |
| 0.42 | Diagnostic Imaging |
| 0.43 | Endoscopy |
| 0.44 | Gastroenterology |
| 0.45 | Hematology |
| 0.46 | Neurology |
| 0.47 | Nephrology |
| 0.48 | Oncology |
| 0.49 | Renal Unit |
| 0.50 | Urology |
| 0.51 | Rheumatology |
| 0.52 | Pain Management/Palliative |
| 0.53 | Ophthalmology |
| 0.54 | Dental |
| 0.55 | Nutrition |
| 0.56 | Other |
| 0.57 | User Defined Care Group |

A user may proceed from step 396 or step 398 to step 400. In step 400, a user may modify the name of the care area so that it matches the name used for that care area within the institution or organization. A user may specify a care group (if any) to which the new care area belongs in step 401. A user may specify various users that are associated with the newly created care area in step 402. For example, a user may specify a number of clinicians which work in or are assigned to the care area. A user may also specify other individuals within an institution or organization which may have responsibilities for reviewing or contributing to the new care area.

In step 404, a user may define various care area parameters for the new care area. This may involve modifying default values, filling in a blank template, modifying copied values, etc. In some embodiment, parent parameter values, i.e., values defined for the same parameter at the care group level, may be automatically used as default values for child parameters at the care area level. In a specific embodiment of the present disclosure, a non-limiting list of possible care area parameters is shown in Table 7 as follows:

| Care Area Parameters | |
|---|---|
| 0.01 | Sort Order On Medical Device User Interface |
| 0.02 | Second Review Required |
| 0.03 | Screen Lock Enabled |
| 0.04 | Default Speaker Volume |
| 0.05 | Default Screen Brightness |
| 0.06 | Automatically Adjust Brightness |
| 0.07 | Second Entry of Weight Required |
| 0.08 | Second Entry of Body Surface Area Required |
| 0.09 | Patient Weight High Hard Limit |
| 0.10 | Patient Weight High Soft Limit |
| 0.11 | Patient Weight Low Hard Limit |
| 0.12 | Patient Weight Low Soft Limit |
| 0.13 | Patient Body Surface Area High Hard Limit |
| 0.14 | Patient Body Surface Area High Soft Limit |
| 0.15 | Patient Body Surface Area Low Hard Limit |
| 0.16 | Patient Body Surface Area Low Soft Limit |
| 0.17 | Syringe Types Allowed |
| 0.18 | Default KVO Value |
| 0.19 | KVO Value Change by User Allowed |
| 0.20 | Rate High Hard Limit |
| 0.21 | Rate High Soft Limit |
| 0.22 | Rate Low Hard Limit |
| 0.23 | Rate Low Soft Limit |
| 0.24 | Volume To Be Infused High Hard Limit |
| 0.25 | Volume To Be Infused High Soft Limit |
| 0.26 | Volume To Be Infused Low Hard Limit |
| 0.27 | Volume To Be Infused Low Soft Limit |
| 0.28 | Default Air Sensitivity Limit |
| 0.29 | Air Sensitivity Limit Change by User Allowed |
| 0.30 | Air Sensitivity Hard Limit |
| 0.31 | Default Downstream Occlusion Sensitivity |
| 0.32 | Downstream Occlusion Sensitivity Change by User Allowed |
| 0.33 | Downstream Occlusion Sensitivity Hard Limit |
| 0.34 | Back-Pump to Relieve Occlusion Pressure |
| 0.35 | Care Group in which the Care Area Belongs |
| 0.36 | Care Area Name |

| | Care Area Parameters |
|---|---|
| 0.37 | Care Area Type |
| 0.38 | Require Second Review of High Risk Medication |
| 0.39 | Require Operator Identification |
| 0.40 | Can Speaker Volume Be Changed By Operator |
| 0.41 | Auto-Lock UI After Predetermined Period of Inactivity |
| 0.42 | Option to Input Weight in Pounds |
| 0.43 | Devices Supported in Care Area |
| 0.44 | Operator Allowed to Select Syringe not in Facility List |
| 0.45 | Rate High Hard Limit |
| 0.46 | Rate High Soft Limit |
| 0.47 | VTBI High Hard Limit |
| 0.48 | VTBI High Soft Limit |

After specifying care area parameters, a user may save the new values in step 406. The care area and the parameter values may be saved on the DERS editor database. The user may then indicate that the new care area is ready to be reviewed by those responsible for reviewing the care area in step 408. The DERS editor service may then notify the appropriate users that the care area has been created and is ready for review in step 410. This may be done by an automatically generated email.

Referring now to FIG. 23, a flowchart detailing a number of example steps which may be used in the verification of a care area is shown. Similar steps may also be well suited to the verification of a care group. The steps may need to be performed by all designated reviewers before a DAL file containing the care area may be released. In some embodiments, these steps may define one of many processes which need to be completed before a DAL file may be released. These steps may be performed as a part of the Review 121 phase of FIG. 9 or the Per Care Area Verification sub-step 216, Per Care Area Review sub-step 222, Cross Care Area Review sub-step 224, and/or Care Area Review sub-step 226 of FIG. 10 in some embodiments. The steps shown in FIG. 23 may be performed by one or more actors. For example, the steps may be performed by the nurse managers 7, pharmacist 8, risk officer, 6, and/or biomed 19 of FIG. 1. These steps may be performed by the resource clinician 202, review pharmacist 204, pharmacy consultant 206, and/or clinical consultant 208 of FIG. 10. The steps shown in FIG. 23 may be completed on a DERS editor user interface which may be accessible through a suitable internet browser.

In step 420, a reviewing user may navigate to the care areas list. In some embodiments, the DERS editor may then solicit the reviewing user to select a care area from the list in step 421. In step 422, a reviewing user may select the care area they would like to or are responsible for reviewing. In some embodiments, a reviewing user may be responsible for reviewing all items, elements, parameters, etc. in a care area. In some embodiments, a reviewing user may only be assigned a portion of the items, elements, parameters, etc. in a care area. The reviewing user may review an element of the care area in step 424.

In some embodiments, the reviewing user may be required to enter a comment for all items, elements, or parameters of a care area as the reviewing user is reviewing the care area. In the example flowchart depicted in FIG. 23, as the reviewing user is reviewing the various parameters for the care group, the reviewing user is required to either approve the item, element, parameter, etc. or enter a comment about the item, element, parameter, etc. If a reviewing user has no concern or question about the element, the user may indicate their verification of the element in step 425.

If a reviewing user does not approve of an item, element, parameter, etc. for the care area, or has other comments/feedback/questions, the user may proceed from step 424 to step 426. In step 426, the reviewing user may enter a comment, question, or provide feedback about a specific item, element, parameter, etc. for the care area. For a hypothetical example, if a parameter for Patient Weight High Hard Limit in a Neonatal Intensive Care Unit was specified as 70 kg, a reviewer may enter a comment saying, "this limit appears to be very high, perhaps a typo was made and a zero was added to the entry. Should this value be lower?" Additionally, some comments in some embodiments may include a change request which can be accepted or denied. Any comment, question, or feedback may be tied to the parameter such that other users or actors may view and in some cases act on the comment or feedback. In some embodiments, a reviewing user may include various attachments, links, pictures, CQI data, etc. in comments.

Once a reviewing user has verified or commented on an item, element, parameter, etc., the user may return to step 424 if there are further items, elements, parameters, etc. to review. If there is nothing left in the care area which requires review, a reviewing user may have the option of providing general feedback about the care area. In step 428, the user may provide general feedback or comments about the care area as a whole. Comments, questions, and/or feedback provided in step 428 may be tied to the care area such that other users may view and in some cases act on the comment or feedback. After a reviewing user has provided all of the general comments and feedback they desire to provide, the reviewing user may indicate they have completed their review in step 429. Various comments, questions, feedback, etc. may be saved on the DERS editor database.

After indication that a user is done reviewing a care area, a DERS editor service may send out a notification that the user has finished reviewing the care area in step 430. This notification may be sent out to other users or actors and may be in the form of an automatically generated email message. This message may, for example, be sent to a drug library administrator such as the drug library administrator 200 shown in FIG. 10. In some embodiments, it may be necessary for at least one actor or user to address all comments, questions, and feedback provided in steps 426 and 428 before a DAL file containing the care area may be released.

FIG. 24 shows a flowchart detailing a number of example steps which may be used to update a care area. Specifically, the example flowchart in FIG. 24 details a number of steps which may be used to update a care area after it has been reviewed. The review process may be that described and shown in relation to FIG. 23. The steps shown in the example flowchart in FIG. 24 may be a part of the Editing and Revising sub-step 220 shown in FIG. 10. The steps depicted in FIG. 24 may be performed by a user such as a drug library administrator. Steps similar to those in FIG. 24 may be used to update a care group.

In step 440, a user may navigate to a care area list on a DERS editor user interface. The DERS editor user interface, in some embodiments, may be accessed via a suitable web browser. In some embodiments, the DERS editor service may prompt the user to select a care area in step 441. A user may select the care area they would like to revise in step 442. In step 444, the user reviews a comment, question, or feedback regarding the new care area or a parameter within the new care area. A user may take a number of actions with each comment, question, or piece of provided feedback.

If a reviewing user asked a question about the care area or a parameter in the care area, a user may proceed to step 446. In step 446, a user may enter an answer to the question. This answer may then be made available for the initial reviewing user to see. In some embodiments, after a user provides an answer in step 446, a DERS editor service may notify the reviewing user who asked the question that an answer has been made available. This notification may be sent as part of step 448. In some embodiments, the reviewing user may be able to respond to the answer if necessary or may be required to acknowledge that a satisfactory answer was received.

If a reviewing user enters a comment, question, or feedback that is not readily understood, warrants further discussion, etc. a user may proceed to step 450. In step 450, a user may enter a question regarding the reviewing user's initial input. This question may then be made available for the initial reviewing user to see and respond to. In some embodiments, after a user enters a question in step 450 a DERS editor service may notify the reviewing user that a question has been entered about a comment, question, or feedback of theirs. This notification may be sent as part of step 452.

If a reviewing user enters a comment, question, or feedback which includes a request to change a parameter of the care area, a user may accept or deny the change request. If a user accepts a change, they may proceed to step 454 and change the parameter in the care area in response to the change request. If a user decides to deny the change request provided by the reviewing user, the user may deny the request in step 456. In some embodiments, a user may be able accept or deny a change request by interfacing with one or more virtual buttons which are included as part of the change request on a DERS editor user interface. In such embodiments, acceptance of a change request may automatically change the parameter for the care area.

If a reviewing user enters a comment or feedback which does not include a change request, give rise to a question, or require a response, a user may be required to mark the comment or feedback as read in step 458.

After addressing a comment, question, or feedback, the DERS editor service may update the DERS Review Status information in step 459. A user may then review other comments, questions, and, feedback until all comments, questions, and feedback from reviewing users have been addressed. When all comments, questions, and feedback have been addressed, a user may proceed to step 460. In step 460, a user may indicate that they have finished updating the care area. The updates may be saved and the user may then log out of the DERS editor in step 462.

In step 464, the DERS editor service may notify all of the relevant users that the care area has been updated and is ready for re-verification. This notification may consist, in some embodiments, of an automatically generated email message. The re-verification process may be similar to that described and shown in relation to FIG. 23.

Referring now to FIG. 25, a flowchart detailing a number of exemplary steps which may be used to add drug records or medication records to a specified care area. The terms "drug record" and "medication record" are herein used interchangeably. These drug records may define the medications available for use within a care area and various limitations, characteristics, etc. which may apply to those medications. The example steps shown in the flowchart in FIG. 25 may be performed as a part of the Drug Selection and Record Specification sub-step 214 shown in FIG. 10. In some embodiments, these steps may be performed by a drug library administrator such as the drug library administrator 200 shown in FIG. 10. In other embodiments a different individual such as a pharmacist or other actor may be responsible for adding drug records to a care area. In some embodiments, similar steps may be used to add a drug record to a care group.

In step 470, a user may navigate to a list of care areas on a DERS editor user interface. A user then may select a care area to add drug records to in step 471. In some embodiments, it may be required that parameters for the care area have been pervious defined and verified before drug records may be added to the care area. In such embodiments, the defining and verification of parameters may be accomplished by performing steps similar to those shown and described in relation to FIGS. 22-24.

When a user is ready to add drug records to a care area, the user may decide to add a specific drug or may elect to add a non-specified drug. If a user elects to add a specific drug, a user may copy a Medication Record from an existing group (step 474) or may define a medication to create a Medication Record for the care area (step 476). If a user elects to copy a Medication Record, the user may proceed to step 474. In step 474 a user may copy a Medication Record for a desired medication from an existing care area. In some embodiments, this may involve selecting a medication record from a list of medication records displayed on the DERS user interface. In some embodiments and situations, a user may be able to copy a medication record from a different institution. This may be especially true if an institution is part of an IDN, for example.

Copying of the Medication Record may copy all of the Rule Sets and Concentration Records for the medication. In some embodiments, a user may have the ability to opt out of copying some or all of the Rule Sets and/or Concentration Records when copying the Medication Record over to the new care area. After copying a Medication Record a user may repeat step 474 for as many records as desired or may perform step 476 to add additional Medication Records. If, after copying a Medication Record, there are no more medications to add to the care area, a user may proceed to step 486. Step 486 will be described later in the specification. In some embodiments, a step may be included to allow a user to make adjustments and modifications to a copied care area.

Step 476 may be performed if a user wants to create a Medication Record without copying the record from another care area. In this step a user may define the name of the medication for which the Medication Record will be created. In some embodiments, a user may select the name of the medication from a master list of medications. Such a list may be provided by a DERS editor service or may be compiled within an institution or organization. In a specific embodiment of the present disclosure, a non-limiting list of possible Medication Record parameters is shown in Table 8 as follows:

| | Medication Record Parameters |
|---|---|
| 0.01 | Medication Name |
| 0.02 | Aliases/Other Names for Medication |
| 0.03 | Medication Name Displayed on Medication Device |
| 0.04 | Medication Category |
| 0.05 | Drug Classification (e.g. AHFS Classification) |
| 0.06 | List of Incompatible Medications |
| 0.07 | Log Medication as CQI Compliant |
| 0.08 | High Risk Medication |
| 0.09 | Add Drug Family |

After defining a medication name and various medication parameters for the Medication Record, a user may then be required to define one or more Rule Sets for each Medication Record. Each Rule Set, in some embodiments, may be provided for a specific clinical usage of a drug or medication. Rule Set and clinical use are used herein interchangeably. A medication may, for example, have a Rule Set which governs how the medication may be delivered when it is delivered as a weight based infusion and another which governs how the medication may be delivered when delivered as an intermittent infusion. A non-limiting list of other possible clinical usages may include: non-weight based infusion, body surface area (BSA) based infusion, continuous infusion, etc.

In some embodiments, such as that shown in FIG. 25, the user may have a choice between copying a Rule Set for a medication from an existing Medication Record (step 478) or defining their own Rule Set for the drug (step 480). If a user elects to copy a Rule Set, the user may proceed to step 478. In step 478, a user may choose a Rule Set to copy from an existing Medication Record. This may involve selecting a desired Rule Set from a list displayed on a DERS editor user interface. In some embodiments and situations, a user may be able to copy a Rule Set from a different institution. This may be especially true if an institution is part of an IDN, for example.

Copying of the Rule Set may copy all of the Concentration Records for the Rule Set as well. In some embodiments, a user may have the ability to opt out of copying certain Concentration Records or all Concentration Records when copying the Rule Set. After copying a Rule Set, a user may repeat step 478 for as many Rule Sets as desired or may perform step 480 to add additional Rule Sets. If, after copying a Rule Set, there are no more Medication Records or Rule Sets to add to the care area, a user may proceed to step 486. Step 486 will be described later in the specification. Some embodiments may include a step where a user may edit or modify the copied Rule Set.

Step 480 may be performed by a user if a user desires to create a Rule Set for a Medication Record without copying a pre-existing Rule Set. In this step, a user may create the Rule Set and define parameters for the Rule Set. In some embodiments, depending on the type of Rule Set being created, a user may be required to define different parameters. In a specific embodiment of the present disclosure, a non-limiting list of possible Rule Set parameters is shown in Table 9 as follows:

| | Rule Set Parameters |
|---|---|
| 1 | General Parameters |
| 1.01 | Clinical Use Name |
| 1.02 | Order Displayed on Medical Device |
| 1.03 | Allowed Medical Device Type(s) |
| 1.04 | Notes for Display in DERS Editor |
| 1.05 | Clinical Advisory |
| 1.06 | Detailed Clinical Advisory |
| 1.07 | Second Review Required During Device Programming |
| 1.08 | Alert Near End of Infusion |
| 1.09 | Infusion Near End Notification Time(s) |
| 1.10 | Volume to be Infused Zero Handling |
| 1.11 | Volume to be Infused Zero Handling Changeable on Device |
| 1.15 | Infusion Type |
| 1.16 | Infusion Route |
| 1.17 | Allow Relay Infusion |
| 1.18 | General Notes |
| 1.19 | Confirm Before Starting In Relay |
| 2 | Therapy Based Risk Controls |

-continued

| | Rule Set Parameters |
|---|---|
| 2.01 | Keep Vein Open Value |
| 2.02 | Air Sensitivity |
| 2.03 | Occlusion Sensitivity |
| 3 | Primary Continuous Infusion |
| 3.01 | Dose Mode |
| 3.02 | Can Rate Be Changed By Operator |
| 3.03 | Dose Rate |
| 3.04 | Dose Rate High Hard Limit |
| 3.05 | Dose Rate High Soft Limit |
| 3.06 | Dose Rate Low Hard Limit |
| 3.07 | Does Rate Low Soft Limit |
| 3.08 | Total Dose Rate Limit |
| 3.09 | Dose Rate Titration Increase Soft Limit |
| 3.10 | Dose Rate Titration Decrease Soft Limit |
| 3.11 | Time Period Between Titrations Soft Limit |
| 4 | Intermittent Infusions |
| 4.01 | Dose High Hard Limit |
| 4.02 | Dose High Soft Limit |
| 4.03 | Dose Low Hard Limit |
| 4.04 | Dose Low Soft Limit |
| 4.05 | Total Dose Limit |
| 4.06 | Can Time Be Changed By Operator |
| 4.07 | Default Time |
| 4.08 | Time High Hard Limit |
| 4.09 | Time High Soft Limit |
| 4.10 | Time Low Hard Limit |
| 4.11 | Time Low Soft Limit |
| 5 | Multi-Rate Infusion |
| 5.01 | Step Change Behavior |
| 5.02 | Dose For Each Step |
| 5.03 | Time For Each Step |
| 5.04 | Time High Hard Limit for Each Step |
| 5.05 | Time High Soft Limit for Each Step |
| 5.06 | Time Low Hard Limit for Each Step |
| 5.07 | Time Low Soft Limit for Each Step |
| 5.08 | Dose High Hard Limit for Each Step |
| 5.09 | Dose High Soft Limit for Each Step |
| 5.10 | Dose Low Hard Limit for Each Step |
| 5.11 | Dose Low Soft Limit for Each Step |
| 6 | Bolus Parameters |
| 6.01 | Is Bolus Allowed |
| 6.02 | Allow Rapid Bolus |
| 6.03 | VTBI Zero Handling for Bolus |
| 6.04 | Can VTBI Zero Handling for Bolus be Changeable on Device |
| 6.05 | Bolus Dose Mode |
| 6.06 | Bolus Default Dose |
| 6.07 | Can Bolus Dose be Changed on Device |
| 6.08 | Bolus Dose High Hard Limit |
| 6.09 | Bolus Dose High Soft Limit |
| 6.10 | Bolus Dose Low Hard Limit |
| 6.11 | Bolus Dose Low Soft Limit |
| 6.12 | Total Bolus Dose Limit |
| 6.13 | Default Time for Time Based Bolus |
| 6.14 | Can Time for Time Based Bolus be Changed on Device |
| 6.15 | Time Based Bolus Time High Hard Limit |
| 6.16 | Time Based Bolus Time High Soft Limit |
| 6.17 | Time Based Bolus Time Low Hard Limit |
| 6.18 | Time Based Bolus Time Low Soft Limit |
| 7 | Loading Dose |
| 7.01 | Loading Dose Allowed |
| 7.02 | Allow Rapid Loading Dose |
| 7.03 | VTBI Zero Handling for Loading Dose |
| 7.04 | Can VTBI Zero Handling be Changed on Pump |
| 7.05 | Dose Mode |
| 7.06 | Can Dose be Change by Operator |
| 7.07 | Default Dose |
| 7.08 | Dose High Hard Limit |
| 7.09 | Dose High Soft Limit |
| 7.10 | Dose Low Hard Limit |
| 7.11 | Dose Low Soft Limit |
| 7.12 | Total Dose Limit |
| 7.13 | Can Time for Time Based Loading Dose be Changed on Device |
| 7.14 | Default Time |
| 7.15 | Time Based Loading Dose Time High Hard Limit |
| 7.16 | Time Based Loading Dose Time High Soft Limit |

-continued

| | Rule Set Parameters |
|---|---|
| 7.17 | Time Based Loading Dose Time Low Hard Limit |
| 7.18 | Time Based Loading Dose Time Low Soft Limit |

After defining a Rule Set and parameters for the Rule Set, a user may then be required to define one or more Concentration Records for each Rule Set. Each Concentration Record may be created for every concentration of the medication which is to be used with a particular Rule Set. In some embodiments, such as that shown in FIG. 25, the user may have a choice between copying a Concentration Record for a Rule Set of an existing Medication Record (step 482) or defining their own Concentration Record for the Rule Set (step 484).

If a user elects to copy a Concentration Record, the user may proceed to step 482. In step 482, a user may choose a Concentration Record to copy from an existing Rule Set. After copying a Concentration Record, a user may repeat step 482 for as many Concentration Records as desired or may perform step 484 to add additional Concentration Records. If, after copying a Concentration Record, there are no more Medication Records, Rule Sets, or Concentration Records to add to the care area, a user may proceed to step 486. Step 486 will be described later in the specification. In some embodiments, an additional step may be included in which a user may alter or adjust the copied Concentration Record.

Step 484 may be performed by a user if a user desires to create a Concentration Record for a Rule Set without copying a pre-existing Concentration Record. In this step, a user may create the Concentration Record and define parameters for the Concentration Record. In a specific embodiment of the present disclosure, a non-limiting list of possible Concentration Record parameters is shown in Table 10 as follows:

| | Concentration Parameters |
|---|---|
| 1 | General Concentration Parameters |
| 1.01 | Can Concentration be Changed On Device |
| 1.02 | Units of Measure for Drug Amount |
| 1.03 | Drug Amount in Container |
| 1.04 | Total Volume In Container |
| 1.05 | Default VTBI |
| 1.06 | Units of Measure for Concentration |
| 1.07 | Concentration |
| 1.08 | Concentration High Hard Limit |
| 1.09 | Concentration High Soft Limit |
| 1.10 | Concentration Low Hard Limit |
| 1.11 | Concentration Low Soft Limit |
| 1.12 | Display Format for Concentration |
| 1.13 | Syringe |
| 1.14 | Display Character String |
| 1.15 | Require Text Comment After Soft Limit Override |
| 2 | Primary Continuous Infusion |
| 2.01 | Dose Mode |
| 2.02 | Can Rate Be Changed By Operator |
| 2.03 | Dose Rate |
| 2.04 | Dose Rate High Hard Limit |
| 2.05 | Dose Rate High Soft Limit |
| 2.06 | Dose Rate Low Hard Limit |
| 2.07 | Does Rate Low Soft Limit |
| 2.08 | Total Dose Rate Limit |
| 2.09 | Dose Rate Titration Increase Soft Limit |
| 2.10 | Dose Rate Titration Decrease Soft Limit |
| 2.11 | Time Period Between Titrations Soft Limit |
| 3 | Intermittent Infusions |
| 3.01 | Dose High Hard Limit |

-continued

| | Concentration Parameters |
|---|---|
| 3.02 | Dose High Soft Limit |
| 3.03 | Dose Low Hard Limit |
| 3.04 | Dose Low Soft Limit |
| 3.05 | Total Dose Limit |
| 3.06 | Can Time Be Changed By Operator |
| 3.07 | Default Time |
| 3.08 | Time High Hard Limit |
| 3.09 | Time High Soft Limit |
| 3.10 | Time Low Hard Limit |
| 3.11 | Time Low Soft Limit |
| 4 | Multi-Rate Infusion |
| 4.01 | Step Change Behavior |
| 4.02 | Dose For Each Step |
| 4.03 | Time For Each Step |
| 4.04 | Time High Hard Limit for Each Step |
| 4.05 | Time High Soft Limit for Each Step |
| 4.06 | Time Low Hard Limit for Each Step |
| 4.07 | Time Low Soft Limit for Each Step |
| 4.08 | Dose High Hard Limit for Each Step |
| 4.09 | Dose High Soft Limit for Each Step |
| 4.10 | Dose Low Hard Limit for Each Step |
| 4.11 | Dose Low Soft Limit for Each Step |
| 5 | Bolus Parameters |
| 5.01 | Is Bolus Allowed |
| 5.02 | Allow Rapid Bolus |
| 5.03 | VTBI Zero Handling for Bolus |
| 5.04 | Can VTBI Zero Handling for Bolus be Changeable on Device |
| 5.05 | Bolus Dose Mode |
| 5.06 | Bolus Default Dose |
| 5.07 | Can Bolus Dose be Changed on Device |
| 5.08 | Bolus Dose High Hard Limit |
| 5.09 | Bolus Dose High Soft Limit |
| 5.10 | Bolus Dose Low Hard Limit |
| 5.11 | Bolus Dose Low Soft Limit |
| 5.12 | Total Bolus Dose Limit |
| 5.13 | Default Time for Time Based Bolus |
| 5.14 | Can Time for Time Based Bolus be Changed on Device |
| 5.15 | Time Based Bolus Time High Hard Limit |
| 5.16 | Time Based Bolus Time High Soft Limit |
| 5.17 | Time Based Bolus Time Low Hard Limit |
| 5.18 | Time Based Bolus Time Low Soft Limit |
| 6 | Loading Dose |
| 6.01 | Loading Dose Allowed |
| 6.02 | Allow Rapid Loading Dose |
| 6.03 | VTBI Zero Handling for Loading Dose |
| 6.04 | Can VTBI Zero Handling be Changed on Pump |
| 6.05 | Dose Mode |
| 6.06 | Can Dose be Change by Operator |
| 6.07 | Default Dose |
| 6.08 | Dose High Hard Limit |
| 6.09 | Dose High Soft Limit |
| 6.10 | Dose Low Hard Limit |
| 6.11 | Dose Low Soft Limit |
| 6.12 | Total Dose Limit |
| 6.13 | Can Time for Time Based Loading Dose be Changed on Device |
| 6.14 | Default Time |
| 6.15 | Time Based Loading Dose Time High Hard Limit |
| 6.16 | Time Based Loading Dose Time High Soft Limit |
| 6.17 | Time Based Loading Dose Time Low Hard Limit |
| 6.18 | Time Based Loading Dose Time Low Soft Limit |

After completing step 484, a user may add additional Concentration Records to a Rule Set, add additional Rule Sets to a Medication Record, or add additional Medication Records to a care area. If, after completing step 484, there are no more Medication Records, Rule Sets, or Concentration Records to add to the care area, a user may proceed to step 486. Step 486 will be described later in the specification. In some embodiments, various parameters defined in Tables 8-10 may be defined at different hierarchical levels of a DAL file than shown here. For example, some values defined at the Rule Set level may be defined at the Medication Record level in some embodiments.

As mentioned above, a user may, in some embodiments, also choose to add Medication Records for a non-specified medication. Such records may function as a wildcard or semi-wildcard. That is, such medication records may define broad parameters governing the use of any number of non-specified medications. These records may, for example, allow a user to run an infusion pump in a volume per duration of time mode unconstrained by any limits, etc. defined by users in a DERS editor. Medication Records for non-specified medications may allow a caregiver to more quickly start a therapy in an emergency situation. They may also be helpful if it is necessary to use a drug that is not in the medication list for a care area (e.g. when using an experimental or investigational drug). These Medication Records may also be useful in unusual cases where limits defined in a DERS may be inappropriate for a situation. For example, if a severely overweight patient weighing required an infusion, limits defined via the DERS editor may prohibit a clinically effective infusion from being administered. In this case, a user may bypass the limits using a Medication Record for a non-specified medication to administer an infusion which would have the desired effect.

As mentioned, these Medication Records may also be configured as semi-wildcards. For example, a Medication Record for an unspecified medication may be configured such that it is given parameters which may govern a category or sub-category of drugs. Categories of drugs may include, but are not limited to, blood products, investigational drugs, IV fluids, medications, and so on. This may be useful for providing greater flexibility when needed while at the same time imposing some of the protections which can be created in the DERS editor. In some embodiments, if a user selects a Medication Record for some or all non-specified medications, a user may be required to enter text which describes the medication being used and why it is being delivery using a Medication Record for a non-specified medication.

When adding a Medication Record for a non-specified medication, a user may copy a non-specified medication from another care area (step 472) or may create a new non-specified medication (step 473). If a user decides to copy a Medication Record for a non-specified medication, the user may choose and copy the desired record by performing step 472. If a user desires to create a Medication Record for a non-specified medication, the user may create the Medication Record and its various parameters in step 473. In some embodiments, a user may be able to define any desired parameters for the non-specified medication. These parameters may include some or all of the parameters included in Tables 7-9. This may allow a user to tailor the Medication Record for the non-specified medication such that it is as broad or narrow as is needed. If after completing step 472 or step 473, the user desires to add additional medications to the care area list, they may do so as described above.

When a user has finished adding to or creating the care area medication list, the user may proceed to step 486. In step 486, a user indicates that the care area medication list is ready to be reviewed by the appropriate reviewing users and logs out. The DERS editor service may notify the appropriate reviewing users that the care area medication list is ready for review in step 488. This notification may be in the form of an automatically generated email from the DERS editor service. The medication list may be saved on the DERS database.

FIG. 26 depicts a flowchart detailing a number of example steps which may be used to review a medication list for a particular care area. Similar steps may be used to review a medication list for a care group. The medication list may be created following steps similar to those described in FIG. 25. The example steps shown in the flowchart in FIG. 26 may be a part of the Review 121 phase shown and described in relation to FIG. 9. The steps shown in FIG. 26 may be a part of the Per Care Area Verification sub-step 216, Per Care Area Review sub-step 222, Cross Care Area Review sub-step 224, and/or Care Area Review sub-step 226 shown and described in relation to FIG. 10. The example steps depicted in the flowchart in FIG. 26 may be performed by at least one reviewing user. A reviewing user may be the nurse managers 7, pharmacist 8, risk officer, 6, and/or biomed 19 of FIG. 1. The reviewing user may be the resource clinician 202, review pharmacist 204, pharmacy consultant 206, and/or clinical consultant 208 of FIG. 10.

In step 490, a reviewing user may navigate to a care area list on a DERS editor user interface. A reviewing user may then select the care area with the medication list they are to review in step 492. In step 494, a reviewing user may review an item or parameter in the medication list. In some embodiments, items and parameters a user is required to review may be displayed to a user in a task list, window, widget, or the like on the DERS editor user interface. In some embodiments, a user may not need to navigate to a care areas list to review a medication list. In some embodiments, the reviewing user may review items in the medication list via a medical device simulator on the DERS editor user interface. Such a medical device simulator may simulate how the medication list will look when used on a specific medical device. A user may also navigate to a review screen or drugs screen to review a medication list in some embodiments.

After reviewing an item, a reviewing user may either enter a comment or verify that they believe the item to be proper and does not require any changes. If a reviewing user decides to comment on the item the reviewing user may proceed to step 495 and provide any comments they would like to provide. If a reviewing user decides to verify an item, the reviewing user may proceed to step 496 and indicate their verification of the item. After completing step 495 or step 496 for an item, the DERS editor service may update the review status of the care area and/or item on the DERS database in step 498. A reviewing user may then return to step 494 if there are further items requiring review. This may be repeated until all items and parameters in a medication list have been reviewed.

If there are no further items or parameters in a medication list which require review, a reviewing user may proceed to step 499. In step 499, the DERS editor service may display a list of comments made by the user during their review. In step 500, a reviewing user may review, expand upon, or refine their comments. If a reviewing user has any general comments about the medication list or elements of the medication list, the reviewing user may enter these comments in step 502. If the reviewing user does not have any general comments about the medication list or elements in the medication list or if a reviewing user has already entered all such comments, the reviewing user may indicate they have completed their review in step 504. The reviewing user may then log out of the DERS editor in step 506. In step 508, The DERS editor service may then notify another user, such as a drug library administrator, that a reviewing user has completed their review of the medication list.

Referring now to FIG. 27, a flowchart detailing a number of example steps which may be used to update a medication list. The steps shown in FIG. 27 may be performed after a medication list for a particular care area has been reviewed. Similar steps may be used to update a care group. The medication list review may be performed by utilizing the steps detailed and shown in FIG. 26. The steps shown in the example flowchart in FIG. 27 may be a part of the Editing and Revising sub-step 220 shown in FIG. 10. The steps depicted in FIG. 27 may be performed by a user such as a drug library administrator. In some embodiments, one or more users may collaborate to update a medication list. For example, a drug library administrator may work with a pharmacist to update a medication list.

In step 510, a user may navigate to a care area list on a DERS editor user interface. The DERS editor user interface, in some embodiments, may be accessed via a suitable web browser. A user may then select the care area with the medication list they would like to revise in step 512. In some embodiments, a user need not select a care area, but rather may update a medication list using a review screen, drug screen, or the like on a DERS editor user interface. In step 514, the user reviews a comment, question, or feedback regarding the medication list or an item or parameter within the medication list. A user may take a number of actions with each comment, question, or piece of provided feedback.

If a reviewing user asked a question about the medication list or a parameter in the medication list, a user may proceed to step 516. In step 516, a user may enter an answer to the question. This answer may then be made available for the initial reviewing user to see. In some embodiments, after a user provides an answer in step 516, a DERS editor service may notify the reviewing user who asked the question that an answer has been made available. This notification may be sent as part of step 518. In some embodiments, the reviewing user may be able to respond to the answer if necessary or may be required to acknowledge that a satisfactory answer was received.

If a reviewing user enters a comment, question, or feedback that is not readily understood, warrants further discussion, etc. a user may proceed to step 520. In step 520, a user may enter a question regarding the reviewing user's initial input. This question may then be made available for the initial reviewing user to see and respond to. In some embodiments, after a user enters a question in step 520 a DERS editor service may notify the reviewing user that a question has been entered about a comment, question, or feedback of theirs. This notification may be sent as part of step 522. In some embodiments, a user may enter an answer or question using the same field. In such embodiments, the notification sent in step 518 or step 522 may simply state that a response has been submitted.

If a reviewing user enters a comment, question, or feedback which includes a request to change an item or parameter of the medication list, a user may accept or deny the change request. If a user accepts a change, they may proceed to step 524 and change the item or parameter in the medication list in response to the change request. If a user decides to deny the change request provided by the reviewing user, the user may deny the request in step 526. In some embodiments, a user may be able accept or deny a change request by interfacing with one or more virtual buttons which are included as part of the change request on a DERS editor user interface. In such embodiments, acceptance of a change request may automatically change the item or parameter in the medication list.

If a reviewing user enters a comment or feedback which does not include a change request, give rise to a question, or require a response, a user may be required to mark the comment or feedback as read in step 528.

After addressing a comment, question, or feedback, a user may then review other comments, questions, and, feedback until all comments, questions, and feedback from reviewing users have been addressed. When all comments, questions, and feedback have been addressed, a user may proceed to step 530. In step 530, a user may indicate that they have finished updating the medication list. The updates may be saved in a DERS database and the user may then log out of the DERS editor in step 532.

In step 534, the DERS editor service may notify all of the relevant users that the medication list has been updated and is ready for re-verification. This notification may consist, in some embodiments, of an automatically generated email message. The notification may be sent to all reviewing users who originally reviewed the medication list. The re-verification process may be similar to the process described and shown in relation to FIG. 26. In some embodiments, the re-verification process may be similar to the process detailed and depicted in FIG. 28.

FIG. 28 shows a flowchart detailing a number of example steps which may be used to re-verify a medication list. The example steps depicted in the flowchart in FIG. 28 may be performed by at least one reviewing user. A reviewing user may be the nurse managers 7, pharmacist 8, risk officer, 6, and/or biomed 19 of FIG. 1. The reviewing user may be the resource clinician 202, review pharmacist 204, pharmacy consultant 206, and/or clinical consultant 208 of FIG. 10.

In step 540, a reviewing user may navigate to a care area list on a DERS editor user interface. A reviewing user may then select the care area with the medication list they are to review in step 542. In some embodiments, review need not be conducted by navigating to a care areas list. In some embodiments, a user may review entries from a DERS user interface review screen, task list widget, or drug list screen for example. In step 543, a list of items which require review may be displayed on DERS editor user interface by a DERS editor service. In some embodiments, a user may apply a filter on the DERS editor user interface to cause the DERS editor service to generate and display such a list. In step 544, a reviewing user may review an item or parameter which has been changed or commented on by selecting it from the list. In some embodiments, the reviewing user may review items in the medication list via a medical device simulator on the DERS editor user interface. Such a medical device simulator may simulate how the medication list will look when used on a specific medical device.

Some embodiments, including that shown in FIG. 28, may include a step 545 in which the DERS editor service displays a review history for the item. This review history may provide a user with context as to why a change was made to the item. For example, the review history may include a list of comments, questions, responses, accepted or denied change requests, etc. for the item. The review history may include the original setting or value for the item and any other historical settings or values for the item. Values, comments, questions, responses, accepted/denied change request for an item may be stored in a database such as a DERS database as they are created, generated, and submitted.

After reviewing an item, a reviewing user may either enter a comment or verify that they believe the item or parameter to be proper and does not require any changes. If a reviewing user decides to comment on the item the reviewing user may proceed to step 546 and provide any comments they would like to provide. If a reviewing user decides to verify an item, the reviewing user may proceed to step 547 and indicate their verification of the item. After completing step 546 or step 547 for an item, the DERS editor service may update the review status for the medication list in step 548. A reviewing user may then return to step 544 if there are further items or parameters requiring review. This may be repeated until all items and parameters in a medication list have been reviewed.

If there are no further items or parameters in a medication list which require review, a reviewing user may proceed to step 550. In step 550, the reviewing user may indicate they have completed their review. The reviewing user may then log out of the DERS editor in step 552. In step 554, The DERS editor service may notify another user, such as a drug library administrator, that a reviewing user has completed their review of the medication list. If there are still unresolved issues, questions, feedback, and/or comments, a user may re-update the medication list in question and the medication list may then be re-verified. This may be done until all users agree on and have no questions about a medication list. The list may be re-updated following steps similar to those shown and described in relation to FIG. 27

FIG. 29 depicts a flowchart which details a number of example steps which may be used to submit a DAL file for approval. These steps may be performed after a DAL file has been created/updated and subjected to various review and verification processes as described above. In some embodiments, these steps may be performed after a pilot of the DAL file has been conducted. The example steps shown in the flowchart in FIG. 29 may be performed by a user or actor such as a drug library administrator or other actor.

In step 560, a user checks that all care areas, drug records, other items, etc. which have been created/updated in the DERS editor have been verified by the users who are responsible for verifying and reviewing them. Once a user has confirmed that all care areas, drug records, items, etc. have been verified, the user may indicate that the DAL file which has been created/updated is ready to be approved by those responsible for approval of DAL file releases in step 562. These may, in some embodiments, be institution or organization officials. After a user completes step 562, the DERS editor service may notify individuals responsible for approval of the DAL file release that the DAL file is ready to be approved in step 564. The user may then log out of the DERS editor service in step 566.

Based on various institutional or organization defined procedures, the various individuals responsible for approving a DAL file for release may review and approve the created/updated DAL file. In some embodiments, such procedures may include procedures similar to the review and verification process described above. Once the DAL file has been approved, the DAL file may be placed into condition for release by following a number of steps such as those depicted in the example flowchart in FIG. 30. As shown in FIG. 30, a user such as a drug library administrator may receive a notification from the DERS editor service that a created/updated DAL file has been approved (step 580). Once a user receives notification that the DAL file has been approved, the user may proceed to step 582 and login to the DERS editor service. The user may then verify that all individuals responsible for approving the DAL file have in fact approved the DAL file in step 584. In step 586, the user may indicate that the DAL file is ready to be released to various medical devices within an institution or organization.

Referring now to FIG. 31*a*, a flowchart detailing a number of exemplary steps which may be used to deploy a DAL file onto various system components is shown. The steps shown in FIG. 31*a* may be performed after a DAL file has been approved and indicated as ready for release through a process which may be similar to that described in relation to FIGS. 29-30. Various components may include, among others, the CQI server 109 of FIG. 4, device gateway 99 of FIG. 4, and any number of medical devices such as the devices 26 of FIG. 1. The steps depicted in FIG. 31*a* may be performed by any number of users or actors. In some specific embodiments, the steps depicted in FIG. 31*a* may be conducted by users such as the facility IT 18, biomed 19 of FIG. 1, or biomeds 102 of FIG. 4. Transmission of a DAL file may occur over a secure connection. Some embodiments may specifically utilize Secure Socket Layer (SSL) connection to transmit a DAL file.

The example flowchart shown in FIG. 31*a* begins with step 590 where the DERS editor service notifies a CQI user that a DAL file has been released and is ready to be deployed. In step 592, a CQI user receives the notification generated in step 590. The CQI user may then log onto the CQI application in step 594. The CQI application may be accessed by a user with no client-side software required. This may, for example, be accomplished via a suitable web browser. The CQI user may then use the CQI application to deploy the DAL file on the CQI service in step 596. In some instances the CQI user may be a biomed.

In step 598, the CQI application may notify a DERS editor service that the DAL file has been successfully deployed on the CQI service. The DERS editor service may then notify users that the DAL file is available to be deployed to the Device Gateway in step 600. In step 602 a user receives notification that the DAL is available to be deployed on the Device Gateway. In some embodiments, the user receiving this notification may be a biomed. The user may then log into a Device Gateway application in step 604. In step 606, the user may instruct the Device Gateway application to download the DAL onto the Device Gateway. The Device Gateway application may request the DAL file from the DERS editor service in step 608. In step 610, the DERS editor service may provide the DAL to the Device Gateway.

A user may choose to deploy the DAL onto various medical devices in a number of ways. In the example embodiment shown in FIG. 31*a*, the user may either deploy the DAL using the Device Gateway or do so manually. If a user decides to use the Device Gateway to deploy the DAL file, the DAL file may be deployed to medical devices remotely in step 612. A user may manually deploy the DAL file by proceeding to step 614. Manual deployment may be desirable or necessary in a number of scenarios. For example, manual deployment may be necessary in a non-connected environment. In step 614, a user may log into the DERS editor service. The user may then use the DERS editor service to load the DAL onto a local storage device for manual deployment to medical devices in step 616. The local storage device may be a USB memory stick, external or portable hard drive, or the like. In step 618, the user may manually deploy the DAL file onto medical devices by connecting the local storage device to the medical devices and downloading the DAL file onto the medical devices from the local storage device.

FIG. 31*b* depicts an example flowchart detailing a number of steps which may be used to package and stage a resource for release to a facility gateway. Such a resource may be a DAL in some embodiments. In step 4700, a user may select the resource they would like to release. The resource may then be signed with a cryptographic algorithm in step 4702. The file may then be hashed in step 4704. In some embodiments, additional packing steps may be included. For example, in some embodiments, a compression step may also be included. In some embodiments, an encryption step may be included. The packing steps used may depend on the type of file which is to be released.

A staging location for the hash may be determined in step 4706. This staging location may, in some embodiments, be a location on a database. The signed hash may then be copied to the staging location in step 4708. The original signed hash file may then be saved in an archive location in step 4710. The archive location, in some embodiments, may be a database or other file system. In step 4712, a notification message may be generated for a facility data exchange to send to each facility gateway which is to be notified of the availability of the resource. The notification may include information such as the type of file, the hash of the file, a unique identifier for the file, and an identifier for the facility gateway. The notification message may be posted to the facility data exchange in step 4714. This notification message may then be sent to the intended recipient facility gateway(s).

FIG. 31c depicts a flowchart detailing a number of example steps which may be used to track the deployment of various resources. Such a resource may include a DAL file or any number of other resources. These steps may be performed on a user interface which may, in some embodiments, be a DERS editor user interface. In step 4730, a user selects a specific resource whose deployment they desire to track. This resource may be selected from a list of trackable resources stored in memory associated with a device manager. In step 4732, a device manager in a hosted environment may then query a database for the version of the selected resource at each institution. In some embodiments, the database may only be queried for information about institutions which the user is associated with. The device manager may then display a list of institutions which details the latest downloaded version of the resource at each institution in step 4734. If a user would like detailed information about resource version deployment within an institution, the user may, in step 4736, select a desired institution from the list. In step 4738, the device manager may query a database to determine how many of each resource version are deployed at the selected institution. A list of the versions and quantities of versions deployed at the selected institution may be displayed in step 4740.

It may be necessary or desirable to update a DAL file once it has been created and deployed. During usage, it may become apparent, among other things, that some of the limits in the DAL file which govern delivery of certain medications are too restrictive. If, for example, nurses in a certain care area find that they must frequently choose a Medication Record for a non-specified drug to deliver a specific medication in a therapeutically effective manner, one or more of the nurse may be able to request a change to the specific medication's, or care area's limits. Additionally, changes may need to be made to a DAL file in the event of a change in hospital policy, when new drugs come on the market, etc. FIG. 32 depicts a flowchart which details a number of example steps which may be used to update an existing DAL file.

In step 620, a reviewing user may log onto the DERS editor service and indicate that they would like to input an update or change request for the current DAL. The reviewing user may then choose the type of request they would like to submit. A reviewing user may, for example, enter a general comment in step 622. A reviewing user may also choose to enter a more specific comment. In some embodiments, a user may be able to enter comments relating to any of the various hierarchical levels of the DAL file. In step 624, the reviewing user may select a specific care area which they would like to make an update request in regards to. In some embodiments, additional steps (not shown) may be included to create an update request for a care group. The reviewing user may enter a general comment about the care area in step 626 or the reviewing user may proceed to step 628 if they would like to make a more specific request. A user may also enter an update request for any parameter values defined for the care area in step 626.

In step 628, a reviewing user may select a specific Medication Record within a care area for which they would like to input an update request. If the reviewing user desires to input a general update request about the Medication Record the user may do so in step 630. The user may also place an update request for any parameter values defined for the Medication Record in this step. If a reviewing user would like their update request to be more specific, a reviewing user may proceed to step 632. In step 632, a user may select a Rule Set for the Medication Record to submit an update request for. If the reviewing user desires to place an update request for the Rule Set in general, the reviewing user may enter the update request in step 634. A user may also submit an update request for any of the parameters defined at the Rule Set level in step 634. If the reviewing user desires to enter a more specific update request, the reviewing user may proceed to step 636. In step 636, a reviewing user may select a specific Concentration Record from the Rule Set to create and update request for. The reviewing user may enter the update request for the Concentration Record in step 638. The update request may be input into an update request field which is displayed on the user interface of a DERS editor.

Once a reviewing user has completed any of steps 622, 626, 630, 634, or 638, the reviewing user may proceed to step 640. In step 640, the reviewing user may submit the update request they have entered. A submitted update request may be saved on the DERS database. The DERS editor service may then notify at least one other user that an update request has been submitted in step 642. The DERS editor service may for example notify a drug library administrator that an update request has been submitted. A reviewing user may then add additional update requests for the current DAL file by returning to step 620 if desired.

In some embodiments, a reviewing user may choose an element, item, parameter, etc. in the DAL file (e.g. care area) before performing step 620. This may be done by navigating to the desired DAL entry using a DERS editor user interface. After a user has navigated to the desired entry, the user may indicate they would like to input an update request in step 620. This may cause an update request field to be displayed into which the user may input the update request. The user may then enter an update request for that item and submit it in step 640.

FIG. 33 depicts a flowchart detailing a number of example steps which may be used to update an institution/organization's medication list. This may be necessary as new drugs come on the market or as generics for existing drugs become available. It may also be necessary if an institution/organization expands and adds care areas which use drugs which would have otherwise not been needed by an institution. Experimental or investigational drugs may also be added to an institution/organization's medication list in this way. The steps depicted in FIG. 33 may be performed by a drug library administrator and/or pharmacist. In some embodiments, additional users may be able to perform these steps.

In step 650 a user navigates to the institution/organization medication list on the DERS editor. The DERS editor service may then display the institution/organization medication list to the user in step 652. A user may then choose to add a drug to the medication list by creating an entry for the new medication (step 656) or selecting a medication from a Master medication list provided by a DERS editor service (step 654). This choice may be made by clicking a virtual button or the like on the user interface. If a user decides to select a medication from the master medication list, the user may proceed to step 654. In step 654, the user may select the medication from the master medication list. A search functionality may be included for this step to allow a user to more quickly find the medication they desire to add to the institution/organization's medication list. If a user decides to enter a medication without using the master medication list or cannot find the desired medication on the master medication list, a user may perform step 656. In step 656, the user may enter a new medication into the institution/organization's medication list. A user may also define any parameters which may be associated with the new medication in this step. The DERS editor service may then add the new medication for the institution/organization to the DERS database in step 657. After a new medication has been added to the institution/organization's medication list, in step 658, the DERS editor service may notify all users responsible for creating the care group and care area medication lists that the institution/organization's medication list has been updated.

FIG. 34 depicts a flowchart detailing a number of example steps which may be used to update the clinical advisories list. The example steps shown in FIG. 34 may be performed by a drug library administrator, pharmacist or other user. In step 660, a user navigates to a clinical advisories list on a DERS editor. The DERS editor service may then display the institution/organization's clinical advisories list in step 662. In the example embodiment depicted in FIG. 34, a user may update the existing list by adding clinical advisories to the list or by modifying clinical advisories which are currently on the list. In step 664 the user may add a clinical advisory to the list. In step 666 a user may update a clinical advisory on the list.

After an update to the clinical advisories list has been created, the user may make further updates to the list if necessary by returning to the clinical advisories list displayed in step 662. When the user is finished updating the institution/organization's clinical advisories list, the user may proceed to step 672. In step 672, the user may indicate that the clinical advisories list should be saved and log out of the DERS editor. The DERS editor service may then save the updates to a database in step 674. The database may be a DERS editor database. In step 676, the DERS editor service may notify users responsible for creating care area medication lists that the institution/organization's clinical advisory list have been updated.

In some embodiments, a user may not update clinical advisories by selecting or adding to a displayed list of clinical advisories. Instead a user may navigate to a specific entry within a DAL file (e.g. a clinical use) and add a clinical advisory for the specific entry. This may be done by modifying a clinical advisory parameter for the desired entry.

Referring now to FIG. 35, a flowchart detailing a number of example steps which may be used to update the general settings for an institution/organization is shown. The steps may, in some embodiments, be performed by a drug library administrator. In step 680, a user may navigate to the general setting on a DERS editor. The DERS editor service may then display the general settings in step 682. In step 684 the user may update general settings as desired. The user may indicate that they have finished updating the general settings and they would like them to be saved in step 686. The DERS editor service may then save the general settings for the institution/organization in a DERS editor database in step 687. The DERS editor service may then notify appropriate users that the general settings have been changed in step 688.

FIG. 36 depicts a flowchart detailing a number of example steps which may be used to update a care area. Steps similar to those shown in FIG. 36 may be used to update a care group in some embodiments. In step 690, a user may navigate to the care area list. In step 692, the user selects the care area that they would like to update. The user may then have the option of updating a number of aspects of the care area. A user may update the list or group of users who have administrative permissions for a particular care area. This may be done in step 694. Among other things, administrative permissions for a care area may allow a user to have editing capabilities for entries and parameters in the care area. A user may also have the option of updating the list or group of users who are reviewing users for the care area. This may be done in step 696. The user may also modify care area entries or parameters in step 698.

After making an update, a user may return to step 692 to make additional updates if a user would like to make additional updates. If a user is finished making updates, the user may save the updated care area on the DERS database in step 700. The DERS editor service may then notify the appropriate users that the care area has been updated in step 702. If necessary the DERS editor service may notify the appropriate users that the care area is ready to be reviewed. In some embodiments, the review and verification process for care area updates may be the same or similar to that described above in relation to FIGS. 23 and 24.

FIG. 37 shows a flowchart detailing a number of example steps which may be used to update Medication Records for a care area. Similar steps may be used to update a medication record for a care group. Such updates may occur in response to various update requests which may be submitted by reviewing users. Update requests may, for example, be submitted by following steps similar to those depicted and described in relation to FIG. 32. Additionally, such updates may occur if new medications need to be added to a care areas medication list. Medication Records for a Care Area may also be updated if analysis of CQI data for medical devices using a DAL file indicates that certain values in one or more Medication Record(s) in the DAL file may not be appropriate.

In step 710 a user may navigate to a care area list on a DERS editor. The DERS editor service, in some embodiments, may then prompt the user to select a care area from a list of displayed care areas in step 712. The user may then select the care area they would like to update in step 714. In some embodiments, a user need not navigate to a care areas list to update Medication Records. For example, a user may navigate to a drug list on the DERS user interface or to a review screen or the like to update entries.

The user may be able to update the Medication Records for a care area in a number of ways. In FIG. 37, the user may add Medication Records to the care area by performing step 716. Step 716 may be completed by following a number of steps such as those depicted and described in relation to FIG. 25. A user may also update a Medication Record for a care area. To do so, a user may select an existing Medication Record for a care area in step 718. A user may then modify the Medication Record, Rule Sets for the Medication Record, and/or Concentration Records for the Medication Record in step 720.

A user may also update Medication Records for a care area by addressing any update requests which have been submitted. To address a submitted update request, a user may select a submitted update request from a list of update requests in step 722. Such a list may, for example, be a part of a task list, window, widget, etc. which details any update requests, comments, questions, etc. a user is responsible for reviewing. In other embodiments an update request may be selected without being chosen from a list. After selecting an update request the user may have a number of options. If a user agrees with the request, the user may accept the request. In this instance, the user may proceed to step 724. In step 724 the user makes changes in the DERS editor based on the accepted update request. In some embodiments, a user may do so by manually updating the record by following steps similar to step 718 and 720 shown in FIG. 37. Preferably, a user may be able to click a virtual button on the DERS editor user interface to accept or decline the update request. Accepting the request may automatically update the entry in the DERS editor and DERS database.

If a user does not agree with the update request selected in step 722 or views the update request as unnecessary, etc. the user may deny or decline the update request. To deny the update request the user may proceed to step 726. In step 726 the user may indicate that they would like to deny the request. Preferably, a user may be able to click a virtual button on the DERS editor user interface to deny the update request. In some embodiments, a user may be required to enter a rationale for denying the request. In such embodiments, the rationale may be saved and conveyed to the user who submitted the request.

A user may also ask a question about an update request if it warrants further discussion. To do so, a user may perform step 728. In step 728, the user may enter a question about the update request. In some embodiments, the user may enter text into a text field on the DERS editor user interface which is associated with the update request to input their question. In some preferred embodiments, a text field, and virtual accept and deny buttons may appear in a window after a user selects an update request in step 722. After a user has submitted a question, in step 730, the DERS editor service may notify the user who submitted the update request that a question about their request has been submitted. This notification may also solicit the user for an answer. The question may be saved on the DERS database.

In some embodiments, once a user has opened an update request, the user may have the option of clicking a virtual button or the like on the DERS editor user interface to view additional information. This additional information may in some embodiments include a history of all update requests, comments, changes, etc. associated with the item in an update request. In some embodiments, the additional information may include CQI data associated with the item in an update request. For instance, a user may access such additional information to see if the item in the update request has been generating large numbers of non-compliant infusions (infusions which violate, for example, limits defined in a DAL file). Other additional information may also be accessible after selecting an update request. This additional information may help a user to gather context and decide if the update request is requesting an update which is proper and desirable and/or necessary. This additional information may be stored, for example, on a DERS database.

After a user has updated a Medication Record for a care area or reviewed an update request, the DERS editor service may update the DAL Review Status information on the DERS editor database in step 732. The user may then make additional updates or review additional update requests if desired. If there are no further updates to make or update requests to review, the user may indicate they have finished updating Medication Records in step 734. In step 736, the DERS editor service may notify various users that Medication Records have been updated and are ready for review. Before being used in a DAL file for medical devices, updates may be reviewed, verified, and approved by following steps similar to those shown and described in relation to FIGS. 26-30. The updated DAL file may be deployed to various medical devices by following steps similar to those shown and described in relation to FIGS. 31a-c.

Referring now to FIG. 38, a flowchart detailing a number of example steps which may be used to create and save a DAL report is shown. A DAL report may be a detailed report which includes all entries, items, elements, parameters, etc. defined in the DAL file. This report may provide a user with a spreadsheet or the like. Such a report may also, if desired, be printed out in hard copy. A DAL report may be useful for documentation purposes. The information included in a DAL report may be user selectable. DAL reports may also be generated based on DAL file version so a user can generate reports for past versions of the DAL file. A user may, for example, generate a DAL report for a care group or care area of an institution. Such a report may include only the entries, parameters, items, elements, etc. defined for the specified care group or care area. This data may be displayed on the user interface of a DERS editor. Though a user is solicited to select a care area for the DAL report in FIG. 38, in some embodiments, a user may instead select their own filtering criteria. Such criteria may include, but is not limited to drug name, care group, care area, clinical use, etc.

In step 740, a user may indicate on a DERS editor user interface that they would like to create a DAL Report. The DERS editor service may then prompt a user to choose what they would like to include in the report (e.g. a care area or number of care areas) in step 742. In step 744, the user may select the data they would like to include in the report. In other embodiments, a user may not necessarily choose the data for which to generate the DAL report, but rather create a DAL report for the entire DAL file.

In step 746, the user may select further configuration features for the report. The user may submit the request to create the report in step 748. The DERS editor service may create and display the report to the requesting user in step 750. This may involve querying a database, such as a DERS database for the requested info and rendering a report for display on the DERS editor user interface.

After the report has been created and displayed, a user may view the report in step 752. A user may be able to download a copy of the DAL report. If a user desires to download the DAL report, a user may indicate this in step 754. In step 756, the DERS editor service may then prompt the user to provide a file format and location to save the file to. The user may then provide the location and format in step 758. In step 760, the DERS editor service may save the report. In some embodiments, a user may be able to copy a hyperlink which links to the report.

FIG. 39 shows a flowchart detailing a number of example steps which may be used to create a DAL differences report. A DAL differences report may be used to view differences between two DAL versions. For example, a DAL differences report may display differences between the original DAL file released by an institution and a current, updated DAL file in use by the institution. The records may be displayed in a side by side format on a DERS editor user interface to allow for easy comparison by a user. In some embodiments, only differences between the two DAL files may be shown.

In step 770, a user may indicate on a DERS editor user interface that they would like to create a DAL Differences Report. The DERS editor service may then prompt a user to choose a care area or number of care areas for which to generate the report in step 772. Some embodiments may default on a care area the user is associated with. In step 774, the user may select the care areas they would like to include in the report. As mentioned above in relation to FIG. 38, a user may choose their own filtering criteria instead of choosing a care area in some embodiments. In step 776, the DERS editor service may prompt the user to select which DAL versions they would like to compare. The user may select the desired DAL versions in step 778. The user may then select further features for the report in step 780. The user may submit the request to create the report in step 782. The DERS editor service may create and display the report to the requesting user in step 784. This may involve querying a database where the requested information is stored and rending the DAL difference report for display on the DERS editor user interface.

After the report has been created and displayed, a user may view the report in step 786. A user may be able to download a copy of the DAL report. If a user desires to download the DAL report a user may indicate this in step 788. In step 790, the DERS editor service may then prompt the user to provide a file format and location to save the file to. The user may then provide the location and format in step 792. In step 794, the DERS editor service may save the report. In some embodiments, a user may be able to copy a hyperlink which links to the report.

FIG. 40 depicts a flowchart detailing a number of example steps which may be used to create an intra-organization DAL Comparison Report. Such a report may be useful for comparing DAL files from a number of institutions within an organization. Such a report may, for example, be useful when updating various items in a DAL file. In some embodiments, such a report may only detail or be made to only detail the differences between the selected DAL files.

In step 800, a user may indicate on a DERS editor user interface that they would like to create a DAL Comparison Report. The DERS editor service may then prompt a user to choose an institution within the organization for which to generate the report in step 802. In step 804, the user may select the institutions they would like to include in the report. In step 803, the DERS editor service may prompt the user to select which care groups they would like to compare. The user may select the desired care groups in step 805. In step 806, the DERS editor service may prompt the user to select which care areas they would like to compare. The user may select the desired care areas in step 808. In some embodiments, a user may choose their own filtering criteria within an institution and not necessarily a care area or areas. In step 810, the DERS editor service may prompt the user to select which DAL versions they would like to compare. The user may select the desired DAL versions in step 812. The user may repeat steps 802, 804, 806, 808, 810, and 812 until all of the desired DAL files have been selected. A user may be required to select at least two DAL files to compare.

The user may submit the request to create the report in step 814. The DERS editor service may create and display the report to the requesting user in step 816. This may involve querying a DERS database for the requested information and rendering the report comparison for display. After the report has been created and displayed, a user may view the report in step 818. A user may be able to download a copy of the DAL report. If a user desires to download the DAL report a user may indicate this in step 820. In step 822, the DERS editor service may then prompt the user to provide a file format and location to save the file to. The user may then provide the location and format in step 824. In step 826, the DERS editor service may save the report. In some embodiments, a user may be able to copy a hyperlink which links to the report.

FIG. 41 depicts a flowchart detailing a number of example steps which may be used to create an inter-organization DAL Comparison Report. Such a report may be useful in comparing DAL files between a number of organizations or institutions within different organizations. Such a report may, for example, be useful when updating various items in a DAL file. In some embodiments, such a report may only detail or be made to only detail the differences between the selected DAL files.

In step 830, a user may indicate on a DERS editor user interface that they would like to create a DAL Comparison Report. The DERS editor service may then prompt a user to choose an organization for which to generate the report in step 832. In step 834, the user may select the organization they would like to include in the report. In step 836, the DERS editor service may prompt the user to select which institution within the organization they would like to compare. The user may select the desired institution in step 838. In step 840, the DERS editor service may prompt the user to select which care groups and areas they would like to compare. The user may select the desired care groups and areas in step 842. In some embodiments, a user may choose their own filtering criteria within an institution and not necessarily care groups and area(s). In step 844, the DERS editor service may prompt the user to select which DAL versions they would like to compare. The user may select the desired DAL versions in step 846. The user may repeat steps 832, 834, 836, 838, 840, 842, 844, 846 until all of the desired DAL files have been selected. A user may be required to select at least two DAL files to compare.

The user may submit the request to create the report in step 848. The DERS editor service may create and display the report to the requesting user in step 850. This may involve querying a DERS database for the requested information and rendering a report for display on the DERS editor user interface. After the report has been created and displayed, a user may view the report in step 852. A user may be able to download a copy of the DAL report. If a user desires to download the DAL report a user may indicate this in step 854. In step 856, the DERS editor service may then prompt the user to provide a file format and location to save the file to. The user may then provide the location and format in step 858. In step 860, the DERS editor service may save the report. In some embodiments, a user may be able to copy a hyperlink which links to the report.

FIG. 42 depicts a flowchart detailing a number of example steps which may be followed to create a DAL History Report. Such a report may detail the change history for specified items or group(s) of items in a DAL file. This may be useful in determining why various changes were made and by whom. In step 950, the user may indicate that they want to create a DAL History Report. This may be done by navigating to an option on the DERS editor user interface which allows a user to create DAL history report. After indication that a user would like to create a DAL History Report, the DERS editor service may prompt a user to select a care area for which to create the report in step 952. The user may then select the desired care area in step 954. In other embodiments, a user may select their own filter criteria for the DAL History Report which need not necessarily include a care area. The DERS editor service may then solicit the user to select a range of DAL file versions or dates for which to create the report in step 956. In step 958, the user may select the range of versions or dates which they would like to create a DAL History Report for. In step 960, the DERS editor service may ask the user to specify any further constraints around which they would like the DAL History Report to be based. The user may select these various constraints in step 962. In step 964, the user may submit a request to create the report. In step 966, the DERS editor service may create and display the DAL History Report requested by the user. This may involve querying a DERS database for the requested information and rendering the report for display on the DERS editor user interface.

The user may view the DAL History Report in step 968. A user may be able to download a copy of the DAL report. If a user desires to download the DAL report a user may indicate this in step 970. In step 972, the DERS editor service may then prompt the user to provide a file format and location to save the file to. The user may then provide the location and format in step 974. In step 976, the DERS editor service may save the report. In some embodiments, a user may be able to copy a hyperlink which links to the report.

Referring now to FIG. 43, a flowchart detailing a number of example steps which may be used to log into a DERS editor is shown. In step 870 the user may initiate a login action. In some embodiments, this may be accomplished by attempting to open the DERS editor on a web browser. The DERS editor service may then prompt the user to provide their login information in step 872. In the example embodiment depicted in FIG. 43, the login information includes a user ID and password. In step 874, the user may enter their login information. The DERS editor service may then authenticate the user ID and password in step 876. This may involve checking a user database for a user ID and password pair matching that provided by the user. If the password and user ID are correct, the user may be allowed to access the DERS editor in step 878. The DERS editing session will also be associated with the user ID such that any contributions made to the system are tied to and can be traced back to the specific individual assigned the user ID. If the user ID and password are not authenticated (e.g. typo in password, forgotten password, CAPS LOCK mistakenly left on, attempted unauthorized access, etc.) the DERS editor service may display an authentication failed notification or message in step 880. A user may acknowledge this notification in step 882. After acknowledging the notification, steps 872, 874, and 876 may be repeated if the user desires to retry logging in to the DERS editor service.

A flowchart detailing a number of example steps which may be used to change a password for a DERS editor service is shown in FIG. 44. In step 890, a user may initiate a change password action. There may be a number of ways of initiating a change password action. In some embodiments, the user may be required to change their password after a predetermined period of time, e.g. 6 months. After the expiration of the predetermined period of time the user may automatically initiate a change password action upon their next attempted login. A change password action may also be initiated, in some embodiments, if a user repeatedly types in an incorrect password for a user ID. This may help to prevent unauthorized access. A change password action may also be initiated by navigating to a change password option on a DERS editor user interface.

The DERS editor service may then display a change password prompt in step 892. In step 894, a user may enter their current password and desired new password. In some embodiments, the user may need to type in one or both their current and desired new password a number of times as a confirmation. The DERS editor service may authenticate the current password and user ID in step 896. If the current password is incorrect, the DERS editor service may display a message to this effect on the DERS editor user interface in step 898. A user may acknowledge this in step 899. Steps 892, 894, and 896 may be repeated if the user desires to retry changing their password. If the current password entered is correct, the DERS editor service may validate the desired new password in step 900. A password may, for example, be required to be at least a certain number of characters long, include a number, include a letter, include a capital letter, not be longer than a certain number of characters, etc. If the new desired password is invalid against the set of requirements, an invalid password message may be displayed in step 902. The user may acknowledge this in step 899 and return to step 892 to pick a different new password. A user may be notified or reminded of the password requirements before returning to step 892 in some embodiments. If the desired new password is valid in light of the password requirements, the new password may be associated with the user ID in step 904. The new user ID and password pair may also be committed to a user database for example. The DERS editor service may then display a message indicating that the password change was successful in step 906.

Referring now to FIG. 45, a flowchart detailing a number of example steps which may be used to recover a password is depicted. In step 910, a user may initiate a password recover action. This action may be initiated by navigating to a recover password option on a DERS editor user interface in some embodiments. The DERS editor service may then display a password recovery prompt in step 912. In step 914, a user may enter their user ID.

If the user ID is invalid the DERS editor service may display a message to this effect in step 916. The user may acknowledge this in step 917 and then be required to start over at step 912. If the user ID is valid, the DERS editor service may send a password recovery email to the user in step 918. The user may then open the email and follow instructions specified in the email to recover the password. In the example embodiment shown in FIG. 45, the user is required to create a new password. In the example embodiment, a user may click on a link in the email to create the new password in step 921. The DERS editor service may display a prompt to enter a desired new password in step 923. The user may enter the desired new password in step 922. The DERS editor service may validate the desired new password. A password may, for example, be required to be at least a certain number of characters long, include a number, include a letter, include a capital letter, not be longer than a certain number of characters, etc. If the new desired password is invalid against the set of requirements, an invalid password message may be displayed in step 924. The user may acknowledge this in step 925 and return to step 923 to pick a different new password. A user may be notified or reminded of the password requirements before returning to step 923 in some embodiments. If the desired new password is valid in light of the password requirements, the new password may be associated with the user ID in step 926. The new user ID and password pair may also be committed to a user database for example. The DERS editor service may then display a message indicating that the password change was successful in step 928.

Referring now to FIG. 46, a flowchart detailing a number of example steps which may be used to review drug library entry such as a Medication Record using a medical device programming simulator is shown. The device programming simulator may be accessible by navigating to a device programming simulator option on a DERS editor user interface. The device programming simulator may mimic the graphic user interface for a specific medical device. In some embodiments, the simulated medical device may be an infusion pump such as a peristaltic pump, syringe pump, patient controlled analgesia machine, etc. In some other embodiments, the simulated medical device may be any other type of medical device. For purposes of example, the flowchart in FIG. 46 details steps which may be used on a device programming simulator for an infusion pump. The steps shown in the example flowchart in FIG. 46 may be a part of a pilot phase of DAL file creation. For example, the example steps shown in the flowchart in FIG. 46 may be a part of the pilot phase 228 shown and described in relation to FIG. 10. A device programming simulator may also be useful in employee training, for example.

In step 980, a user may navigate to a device programming simulator option on a DERS editor user interface. In step 982, a user may select a care group and/or care area for which they would like to review Medication Records. The DERS editor service may then display a work list dashboard to the user in step 984. The work list dashboard may include summary information about review progress made with the device programming simulator. The work list dashboard is not limited to, but may include one or more of the following: total number of Medication Records in the care area, number of Medication Records the user has reviewed, list of Medication Records the user has reviewed, the number of Medication Records which have not been reviewed, etc. The work list dashboard may also include a virtual button or the like which allows a user to select a Medication Record from the care area's medication list to review. In some embodiments, the work list dashboard may differ. Some embodiments may not include a work list dashboard.

In step 986, the device programming simulator may prompt a user to choose a Medication Record from the care area's medication list. The user may then select a Medication Record to review using the device programming simulator. The user may select a specific Medication Record in step 988 or may select a Medication Record for a non-specified medication in step 998. If a user selects a specific Medication Record, the device programming simulator may prompt a user to select a Rule Set for the Medication Record in step 990. The user may select the Rule Set for the Medication Record in step 992. The device programming simulator may then prompt the user to choose a Concentration Record in step 994. The user may select the Concentration Record in step 996.

If a user chooses a Medication Record for a non-specified medication in step 998, the user may be required to enter a description of what the medication is and why it is being delivered using a Medication Record for a non-specified medication. If a user is required to do so, a user may satisfy this requirement by entering text information in step 1000. In some embodiments, where there is a requirement to enter a description a keypad and associated text entry field may automatically be displayed on the device programming simulator.

After the user has completed step 996, 998, or 1000 (if necessary), the device programming simulator may prompt a user to enter patient weight information in step 1002 if the medication is delivered as a weight based dosage. The user may enter patient weight in step 1004. If the medication is delivered as a body surface area (BSA) based dosage, the device programming simulator may prompt a user to enter a patient's BSA in step 1006. The user may enter the patients BSA in step 1008. Other embodiments may include steps to define other patient based parameters if necessary.

The device programming simulator may then, in some embodiments, prompt a user to enter keep vein open (KVO) values in step 1010. Such values may define a reduced delivery rate which is sufficient to keep an infusion site patent and may be used, in some instances, when an infusion has finished. A user may enter KVO values in step 1012. The user may then set the infusion parameters for the infusion in step 1014. These infusion parameters may include, but are not limited to, dose, rate, volume to be infused, and time. In step 1016, the device programming simulator may display a summary of the programmed infusion to the user. The reviewing user may then confirm the programmed infusion in step 1018. The device programming simulator may then display a virtual start button or the like in step 1020. The user may use the virtual start button or the like to start the infusion in step 1022. The DERS editor service may then note that the Medication Record has been reviewed using the device programming simulator in step 1024. If there are further Medication Records to review, the user may return to step 984 and repeat the process until all Medication Records have been reviewed. The work list dashboard may be updated reflecting reviewed Medication Records as the user finishes reviewing the various Medication Records in the care area.

In some embodiments, users who are responsible for reviewing care area Medication Records via the device programming simulator may be required to review all Medication Records for a particular care area. In some embodiments, users responsible for reviewing care area Medication Records may be required to review each Rule Set and each Concentration Record for each Rule Set for a given Medication Record. If the device programming simulator is being used in a pilot phase for a DAL file, it may be required that at least one reviewing user has reviewed each medication in the DAL file before the DAL file can be submitted for approval.

In some alternate embodiments, a medical device programming simulator may not make use of a medical device programming simulator work list dashboard. Instead the medical device programming simulator may function in a context sensitive manner. This may allow a user to more efficiently make use of the programming simulator by quickly bringing a user to an entry of interest on the simulator. When a user navigates to the medical device programming simulator from another DERS editor screen, the medical device programming simulator may automatically open to a specific simulated medical device screen which is relevant to that DERS editor screen. For example, if a user is viewing a drug library entry for a clinical use of a specific drug on a DERS editor screen and navigates from that entry to the medical device programming simulator, the medical device programming simulator may open to the screen which would be presented after a user had programmed the medical device to use that clinical use for that specific drug. That is, the medical device programming simulator may behave as if a user had just completed step 992 of FIG. 46. As mentioned above, this may allow a user to more quickly review entries which they want to review via the simulator. Otherwise a user may be required to define a care group, care area, drug, clinical use, etc. before being able to view the desired programming screens on the simulator.

FIG. 47 depicts a flowchart detailing a number of exemplary steps which may be used to compare records in a DAL file. Such a comparison may be done by a DERS editor user to compare two Rule Sets defining two clinical usages of the same Medication Record, for example. In step 1030 a user may navigate to a list of records in the DERS editor. These records may for example be Medication Records. The user may then indicate the specific records that they would like to compare in step 1032. The DERS editor service may enable a functionality to compare when more than one record has been selected. This functionality may be enabled in step 1034. The user may then use the compare functionality to compare the indicated items in step 1036. In step 1038, the DERS editor may display all data, parameters, etc. associated with the selected items on the DERS editor user interface. This data may be retrieved by querying a DERS database for the selected information. The data, parameters, etc. for each compared item may be shown side by side for ease of understanding.

A user may also have the ability to filter the result of the comparison. In the example flowchart shown in FIG. 47, the user may have the option of filtering the result such that only differences between the compared items are shown. If a user desires to filter the comparison to display only differences between the items, a user may proceed to step 1040. In step 1040 a user may indicate that they would like to view only the differences between the compared items. The DERS editor service may then display the differences between the compared items on the DERS editor user interface in step 1042.

FIG. 48 depicts a flowchart detailing a number of example steps which may be used to update a DAL file on a medical device. The steps shown in FIG. 48 may be used in a connected medical environment. In step 1050, a user may indicate that an updated DAL file has been approved and is ready to be distributed. This may "publish" the DAL file for distribution. In step 1052, the hosting environment may make the DAL available to the facility gateway at the proper institution or organization.

In step 1054, the facility gateway checks for and requests any DAL updates. The facility gateway may periodically check for and request DAL updates from the hosted environment. The hosted environment may receive these requests in step 1056. If, as in the example flowchart in FIG. 48, an updated DAL file has been made available, the hosted environment may send the DAL file update via a WAN connection with the facility gateway in step 1058. In step 1060, the facility gateway may receive the DAL file update via its WAN connection with the hosted environment. In some embodiments, the hosted environment may push the DAL file update to a facility gateway instead of waiting for the facility gateway to check for DAL updates. After the facility gateway has received the DAL file update, the facility gateway may indicate to at least one user that a DAL file update is available in step 1062. The user may, for example be a biomed user.

In step 1064, a user may indicate they would like to deploy the DAL file update to various medical devices. The user may select various medical devices to deploy the DAL file update on or may deploy the DAL file update to a full fleet of medical devices or a subset thereof. The facility gateway may then make the DAL file update available to the selected medical devices in step 1066. In step 1068, a medical device of the selected medical devices checks for and requests any DAL updates. Medical devices may periodically check for and request DAL updates from the hosted environment. In some alternate embodiments, DAL file updates may be pushed to medical devices from the facility gateway. The facility gateway may receive these requests in step 1070. If, as in the example flowchart in FIG. 48, an updated DAL file has been made available, the DAL file update may be sent to the medical device over a WiFi connection. The DAL file may be sent to the medical device in step 1072. The medical device may receive the DAL file in step 1074. The medical device may then validate the DAL file update in step 1076. In step 1078 the medical device may update its copy of the DAL file.

After the medical device successfully updates its DAL file, the medical device may send a confirmation message in step 1080. This message may be sent to the facility gateway over WiFi. The facility gateway may receive the message in step 1082. After receiving the confirmation message from the medical device, the facility gateway may then update a record of medical devices to reflect the change in DAL version on the updated medical device in step 1084.

FIG. 49 depicts a flowchart detailing a number of example steps which may be used to update a DAL file on a medical device. The steps shown in FIG. 49 may be used in a medical environment where various medical devices are not on a connected network. In step 1090, a user may indicate that an updated DAL file has been approved and is ready to be distributed. This may "publish" the DAL file for distribution. In step 1092, the hosting environment may make the DAL available to the facility gateway at the proper institution or organization.

In step 1094, the facility gateway checks for and requests any DAL updates. The facility gateway may periodically check for and request DAL updates from the hosted environment. In some alternate embodiments, DAL file updates may be pushed to a facility gateway. The hosted environment may receive these requests in step 1096. If, as in the example flowchart in FIG. 49, an updated DAL file has been made available, the hosted environment may send the DAL file update via a WAN connection with the facility gateway in step 1098. In step 1100, the facility gateway may receive the DAL file update via its WAN connection with the hosted environment. After the facility gateway has received the DAL file update, the facility gateway may indicate to at least one user that a DAL file update is available in step 1102. The facility gateway may also make the update available to a biomed P.C. tool in step 1104.

In step 1106, a biomed P.C. tool checks for and requests any DAL updates. A biomed P.C. tool may periodically check for and request DAL updates from the hosted environment. In some embodiments, a biomed P.C. tool user may be required to manually check for an updated DAL file using the biomed P.C. tool. In some embodiments, the biomed P.C. tool may automatically check for updates. The hosted environment may receive these requests in step 1108. In some alternate embodiments, DAL file updates may be pushed to a biomed P.C. tool from the facility gateway.

If, as in the example flowchart in FIG. 49, an updated DAL file has been made available, the facility gateway may send the DAL file to the biomed P.C. tool in step 1110. This may be done over a WAN connection. The biomed P.C. tool may receive the update in step 1112. A biomed P.C. tool user may then be able to deploy the DAL file update onto desired medical devices. In FIG. 49, a biomed P.C. tool user deploys the DAL file update using a programming medical device rack. In other embodiments, the programming rack need not be used. For example, a user may plug a USB drive into a USB port on the medical device to transfer the DAL file update to the medical device. The programming rack may be similar to one of those shown and described in U.S. Provisional Application Ser. No. 61/843,574 and entitled "System, Method, and Apparatus for Clamping" which is incorporated herein by reference in its entirety.

The biomed P.C. tool user may connect to a medical device programming rack in step 1114. In some embodiments, including that shown in FIG. 49, the user may connect to the programming rack via a USB connection. The biomed P.C. tool user may then attach a medical device or number of medical devices to the programming rack in step 1116. The biomed P.C. tool user may then command a DAL file update using the biomed P.C. tool in step 1118. After receiving an update command from the biomed P.C. tool user, the biomed P.C. tool may send the DAL file update, in step 1120, to the medical device or medical devices connected to the programming rack. As mentioned above, the DAL file update may be sent over a USB connection. In step 1122, the medical device or medical devices may receive the DAL file update. The medical device (s) may then validate the updated DAL file in step 1124. In step 1126 the medical device may update its copy of the DAL file.

After a medical device successfully updates its DAL file, the medical device may send a confirmation message in step 1128. This message may be sent to the biomed P.C. tool over a USB connection, for example. The biomed P.C. tool may receive the message in step 1130. The biomed P.C. may then send a message to the facility gateway that the medical device's DAL file has been updated in step 1132. The facility gateway may receive the message in step 1134. This message may be sent over a WAN connection. After receiving the message from the biomed P.C. tool, the facility gateway may then update a record of medical devices to reflect the change in DAL version on the updated medical device in step 1136.

FIG. 50 depicts a flowchart detailing a number of example steps which may be used to configure a user interface for a DERS editor service or CQI service. Some embodiments of the present disclosure may include a dashboard based, or at least partially dashboard based, DERS editor user interface. Additionally, a CQI user interface may be dashboard based or partially dashboard based. The steps shown in FIG. 50 are specifically for configuring a dashboard-based DERS editor user interface.

In some embodiments, when a user accesses the DERS editor service or CQI service, the user interface for the respective service may open up to a dashboard view. In embodiments where the DERS editor service or CQI service is web browser based, the dashboard view may be the first page displayed after a user has logged into the service. In some embodiments, a user may navigate to a dashboard view on a user interface by clicking on a dashboard tab, link, or the like. A dashboard user interface may display important information at a glance. It may include charts, graphs, tables, gauges, other visual aids, quick links, etc.

In step 1320, a user accesses the dashboard on the user interface. A user may then decide to configure the dashboard to suit their needs. If a user would like to configure the dashboard, the user may indicate this by selecting a configure dashboard utility on the user interface in step 1322. The user may then have the choice of loading a dashboard configuration (step 1342). If a user does not want to load a dashboard configuration, they may indicate this in step 1324. The user may then customize the dashboard as desired in step 1326. The user interface may then display a preview of the customized dashboard configuration in step 1328. Customization options may allow a user to display information most important or relevant to the user. A user may, for example, define various charts or graphs to display on a dashboard. A user may also choose to include frequently used DERS editor functionalities on their dashboard. A user may include certain CQI data on a dashboard or may include a tasks list on their dashboard. A user may also customize their dashboard in any number of other desired ways.

If a user desires to save the custom configuration, the user may indicate this in step 1330. The user may then be prompted to provide a save configuration name or identifier and visibility settings for the customized configuration in step 1332. Visibility settings may allow a user to make the dashboard configuration available as a loadable dashboard for other users or a subset of other users. The user may specify the saved configuration name or identifier and visibility settings in step 1334. In step 1336, the custom configuration may be saved and associated with the name or identifier and the visibility settings. The dashboard settings for a user may be stored on a database such as a user database or DERS database.

If, after a preview of the customized dashboard configuration is displayed on the user interface, a user does not desire to save the configuration, a user may indicate this in step 1338. In some embodiments, this may cause the dashboard configuration utility to be exited. In such embodiments, the dashboard configuration utility may be exited in step 1340. In some embodiments, a user may instead be returned to step 1326 to make adjustments to the configuration.

If a user would like to load a dashboard configuration instead of create a custom configuration, the user may proceed to step 1342 instead of step 1324. In step 1342, the user may indicate they would like to load a dashboard configuration. A list of loadable dashboard configurations may then be displayed on the user interface in step 1344. In some embodiments, an institution or organization may create specific dashboard configurations for specific user groups. An institution may, for example, configure a dashboard for users who are care givers in the ICU to display information which is associated with the ICU. Users in specific user groups may then load their dashboard configuration without needing to spend time customizing and learning how to customize their dashboard. This may increase overall efficiency. Institution/organization personnel may accomplish this by performing the steps described above for customization of a dashboard.

In step 1346 a user may select the configuration that they would like to load. The system may then solicit the user to choose whether they would like to use the selected configuration or refine the selected configuration in step 1348. In some embodiments, a preview may also be displayed. If a user would like to refine the selected dashboard configuration, a user may indicate this in step 1350. This may involve making adjustments to the data and information displayed on the dashboard. For example, an institution created dashboard for a care area may present summary information for a care area. A user within the care area may also want to include summary information (e.g. compliance data, review progress, task lists, etc.) for themselves and may do so when refining. The user may then be solicited for refinement criteria in step 1352. In step 1354, the user may specify the refinement criteria. After completing step 1354, a user may be returned to step 1348. If a user would not like to refine the selected configuration, the user may indicate this in step 1356. The user interface may then display the dashboard configuration in step 1358.

In some embodiments, additional steps may be included for the configuration of the user interface of a DERS editor service or CQI service. Steps may be included to allow a user to create multiple configurations. For example, a user may choose to create a configuration which is used when the user accesses the DERS editor service or CQI service via a mobile device. A user may specify a second configuration which is used when the user accesses the DERS editor service or CQI service via a PC or laptop.

FIG. 51 depicts a flowchart detailing a number of example steps which may be used to view and make use of Continuous Quality Improvement (CQI) data. As mentioned in detail above, CQI data may be data corresponding to any number of clinical events. This data may be useful, among other things, in the continuous improvement of an institution or organization's DAL file. This data may be helpful in determining where there is room for improvement of a DAL file. The data may also be useful in determining if changes to a DAL file have had a desired effect or have caused an unforeseen or unexpected result. CQI data may also be useful for linking to change or update requests, for example, to provide context for an update request. Such data may also be useful for a number of other applications, purposes, and/or usages, some of which are described herein.

In step 1140, a user may indicate they would like to view CQI data. In some embodiments, a user may be able to do this by navigating to a CQI tab or the like on a DERS editor user interface. In some embodiments, a user may be able to access CQI data by logging into a CQI service in a hosted environment. In such embodiments, the CQI service need not be accessed through a DERS editor user interface. In some embodiments, a user may be able to view CQI data through a DERS editor user interface as well as a CQI user interface for a CQI service in a hosted environment. In some embodiments, CQI data may be viewable over a suitable web browser.

After completion of step 1140, a CQI user interface may be displayed in step 1142. A CQI user interface may provide a user with a number of options. A user may, for example, be able to generate a CQI report by selecting at least one filtering criteria for CQI data in step 1144. Such filtering criteria may include, but is not limited to, a specific dataset or datasets within an institution/organization (e.g. care area, care giver, medication, etc.), a time frame or range of dates, DAL version, medical device type, medical event type, a user customized filter, etc. By performing step 1144, the user may generate a specific report or summary of clinical data based on the selected filters. For example, a user may generate a summary of soft limit violations over the preceding month for infusion pumps in the emergency department of an institution/organization.

A CQI user interface may also allow a user to modify how data, reports, CQI summaries, etc. are presented to the user. In the example flowchart shown in FIG. 51, a user may modify how data, reports, CQI summaries, etc. are presented by performing step 1146. In step 1146, a user may modify various presentation criteria for CQI data including, but not limited to, selecting how data will be displayed (e.g. pie chart, bar chart, graph, list, tables, etc.), changing time units for displayed data, showing/hiding various panels of data, toggling whether data will be displayed in a summary or detailed view, toggling counts/dates, sorting data (e.g. alphabetically, chronologically, by medication, etc.), etc. A user may also be able to compare a report to other reports. In some embodiments, a user may have a drill-down capability which allows a user to view more detailed information about CQI data of interest.

A CQI user interface may also include a number of utilities which allow a user to perform various other functions. A user may make use of a CQI utility by performing step 1148. In embodiments where the CQI user interface is a user configurable dashboard type user interface, the CQI user interface may include a save or load dashboard configuration utility. A number of other utilities may also be included. Such utilities may include, but are not limited to, a report configuring utility, a print report utility, a download report utility, a save report utility, an email report utility, an export report data utility, a link to report utility, a schedule automated generation of report utility, etc.

FIG. 52 depicts a flowchart detailing a number of exemplary steps which may be used to display a desired CQI report on a user interface. In step 1200, a number of available report types may be displayed on a user interface. The user interface may, for example, be a DERS editor user interface or a CQI user interface. The user may then choose a report from the different report types available or in some embodiments, the user may choose to create a custom report. The example flowchart in FIG. 52 shows only four report types: a compliance report, a medication report, an infusion report, an infusion story report. Other report types may also be available.

If a user desires to view a compliance report, the user may indicate that they would like to view a compliance report in step 1202. In some embodiments, the user may be able to define various filtering criteria for the compliance report. In step 1204, the compliance report may be generated and displayed on the user interface. If a user desires to view a medication report, the user may indicate that they would like to view a medication report in step 1206. In some embodiments, the user may be able to define various filtering criteria for the medication report. In step 1208, the medication report may be generated and displayed on the user interface. If a user desires to view an infusions report, the user may indicate that they would like to view an infusions report in step 1210. In some embodiments, the user may be able to define various filtering criteria for the infusions report. In step 1212, the infusions report may be generated and displayed on the user interface. If a user desires to view an infusion story report, the user may indicate that they would like to view an infusion story report in step 1213. The user may be able to define various filtering criteria for the infusion story report. In step 1214, the infusion story report may be generated and displayed on the user interface. Generation of a CQI report may include querying a CQI database for the requested information and rendering it for display on the user interface of the device.

After a report has been generated and displayed, a user may define further filtering criteria for the report. The user may also drill-down on various aspects of the report to create a more detailed view of a select portion or portions of the report. A user may also save, link to, extract data from, print, download, etc. the report. If so inclined, a user may return to step 1200 to generate and view additional reports.

FIG. 53 depicts a flowchart detailing a number of example steps which may be used to configure a CQI report. In some embodiments, a user may be able to configure a CQI report using a DERS editor user interface and/or a CQI user interface. In some embodiments, a user interface may include a configure CQI report utility to allow a user to configure CQI reports. In some embodiments, the steps performed in FIG. 53 may be performed after a user selects a report type following steps similar to those shown and described in FIG. 52.

In step 1360, a user accesses the user interface. A user may then decide to configure a CQI report. If a user would like to configure a CQI report, the user may indicate this by selecting a configure CQI report utility on the user interface in step 1362. The user may then have the choice of loading a CQI report (step 1382). If a user does not want to load a CQI report, they may indicate this in step 1364. The user may then configure a CQI report as desired in step 1366. The user interface may then display a preview of the customized CQI report in step 1368.

If a user desires to save the custom CQI report, the user may indicate this in step 1370. The user may then be prompted to provide a name or identifier and visibility settings for the customized report in step 1372. Visibility setting may allow a user to make a CQI report available as a loadable report for other users or a subset of other users. The user may then specify the name or identifier and visibility settings in step 1374. In step 1376, the custom CQI report may be saved and associated with the name or identify and the visibility settings.

If, after a preview of the customized CQI report is displayed on the user interface, a user does not desire to save the CQI report, a user may indicate this in step 1378. In some embodiments, this may cause the system to exit the CQI report configuration utility. In such embodiments, the CQI report configuration utility may be exited in step 1380.

If a user would like to load a CQI report instead of creating a custom CQI report, the user may proceed to step 1382 instead of step 1364. In step 1382, the user may indicate they would like to load a CQI report. A list of loadable CQI reports may then be displayed on the user interface in step 1384. The list may be arranged such that commonly used reports are prominently displayed (e.g. displayed at the top of the list). The list may also be arranged such that reports more relevant to the user are more prominently displayed than others. For example, if a user is a care giver in an oncology care area of an institution, reports using data from the emergency department of the institution may be displayed less prominently than those using data from the oncology care area.

In step 1386, a user may select the report that they would like to load. The user may then be solicited to choose whether they would like to display the selected report or modify the selected report in step 1388. If a user would like to modify the selected CQI report, a user may indicate this in step 1390. The user may then be solicited for modifying criteria in step 1392. In step 1394, the user may specify the modifying criteria. For example, a user may select a report which spans data over the preceding month and modify the data range criteria such that it includes data from the current month. After completing step 1394, a user may be returned to step 1388. If a user would not like to modify the selected CQI report, the user may indicate this in step 1396. The system may then display the CQI report in step 1398. This may involve querying a CQI database such as database 106 of FIG. 4 for the requested information and rendering the CQI report to be displayed on the user interface.

FIG. 54 depicts a flowchart detailing a number of example steps which may be used to configure a CQI report. A user may configure a report by applying various filters to CQI data which separate out sets of data that do not meet the filtering criteria. This filtering may allow a user to display only data of interest to the user. Filtering may also allow a user to tailor a CQI report to their needs. In step 1400, a user indicates that they would like to configure a report. This step may, for example, be completed by performing step 1364 or step 1390 shown and described in FIG. 53.

A user may then choose to apply filters in one of a number of categories. The example flowchart shown in FIG. 54 includes six filtering data categories: institution/organization hierarchy, date range, report type, DAL version, device type, and a custom or user defined filter. In other embodiments, the number of filter categories and type of filter categories may differ. To filter CQI data to be included in a CQI report based on are based criteria such as institution/organization hierarchy, a user may proceed to step 1402. In this step a user may apply various filters based on, for example, geographic region, institution, care area, device, care-giver, and/or patient. To filter CQI data to be included in a CQI report based on date, a user may proceed to step 1404. In this step a user may modify a time frame of reported CQI data to include in a CQI report. To filter CQI data based on a specific report type, a user may proceed to step 1406. In step 1406, a user may choose one or more specific report types to include in a CQI report. In this step, a user may filter based on therapy based criteria, for example, choose to include non-compliant infusion events in the CQI report. To filter CQI data to be included in a CQI report based on DAL version, a user may proceed to step 1407 and indicate that they would like to do so. In step 1408, a list of DAL versions may be displayed on the user interface. A user may then, in step 1410, choose a DAL version or DAL versions for which to include CQI data for in a CQI report. To filter CQI data to be included in a CQI report based on device type a user may proceed to step 1412. In step 1412, a list of device types may be displayed on the user interface. A user may then, in step 1414, select a device type to include CQI data for in a CQI report. To filter CQI data based on a custom selection, a user may proceed to step 1416 and define the custom filter for the CQI data. After applying a filter, a user may apply additional filters to create a more narrowly defined CQI report.

FIG. 55 depicts a flowchart detailing a number of example steps which may be used to apply a filter to CQI data using organization/institutional hierarchy. In step 1420, a user may select a configure CQI report utility on a user interface. A user may then indicate their desire to filter by institution/organization hierarchy. If a user would like to filter by region, a user may indicate that they would like to filter by region in step 1422. The user interface may then display a list of regions in step 1424. In step 1426, the user may select a desired region or regions from the list. The regions may, for example, be geographic regions in which the various institutions of an organization such as an IDN are located. The regions need not be geographic. In some embodiments, filtering by region may not be available to users who are not a part of an organization.

If desired, a user may filter by institution by indicating they would like to filter by institution in step 1428. The user interface may then display a list of institutions in step 1430. The list presented in step 1430 may differ depending upon previously applied filtering criteria. For example, the list may only include institutions within the region or regions selected in step 1426. The user may select an institution or number of institutions from the list in step 1432. In some embodiments and in some instances, filtering by institution may not be available to users who are not a part of an organization.

If desired, a user may filter by care group and/or care area by indicating that they would like to filter by care group and/or care area in step 1434. The user interface may then display a list of care groups and/or areas in step 1436. This list may differ depending upon previously applied filtering criteria. For example, the list may only include care groups and/or areas which exist in an institution or institutions selected in step 1432. In step 1438, a user may select a care group and/or area from the list of care groups and/or areas. In some embodiments, a user may be required to select an institution or institutions before filtering by care group and/or area. In other embodiments, a user may be able to filter for CQI data from all care groups and/or areas of the same type or name within an organization or region.

A user may also be able to filter CQI data at the clinician, patient, or device level. If a user desires to filter CQI data by clinician or care giver, the user may indicate this in step 1440. The user may then be able to apply a filter using a care giver identifier. The user interface may display a list of clinicians in step 1442. This list may differ depending on previously applied filtering criteria. For example, if a user has selected a care area or care areas in step 1438, the list of clinicians may only include clinicians associated with the selected care area or areas. The user may select a clinician or number of clinicians from the list in step 1444.

If a user desires to filter CQI data by patient, the user may indicate their desire to do so in step 1446. The user interface may then display a list of patients in step 1448. In some embodiments, this list may not be a list of names. This list may be a list of patient IDs or a list of otherwise unique entries which correspond to specific patients. The list displayed in step 1448 may differ depending on previously applied filtering criteria. For example, if a care area or areas have been selected in step 1438, the list of patients displayed may exclude patients who have not produced CQI data in the selected care area or areas.

If a user desires to filter by device a user may indicate that they desire to filter by device in step 1452. The user interface may then display a list of devices in step 1454. In some embodiments the list displayed in step 1454 may be a list of unique device identifiers such as device ID numbers or the like. A user may then apply a filter using a medical device identifier. In some embodiments, the list may be a list of medical device types. The device types displayed may differ depending on previously applied filter criteria. For example, device types shown may only be those supported by the care area selected. In such embodiments, a user may select a medical device type and then have the option of choosing a specific medical device of that type by selecting the desired unique device identifier. The medical devices displayed in step 1454 may differ depending on previously applied filtering criteria. For example, if a medical device has not produced CQI data for a care area selected in step 1438, the device may not be included in the list. A user may select the desired device from the list in step 1456. The CQI database may be queried based on the selected filter criteria to produce the requested report. The report may be rendered and displayed on the user interface.

FIG. 56 depicts a flowchart detailing a number of example steps which may be used to apply a filter to CQI data using a date range or time frame. In step 1460, a user selects a configure CQI report utility on a user interface. A user may then indicate that they would like to apply filtering criteria based on a date range in step 1462. The user may then have the option of creating a custom date range or using a predefined date range. If a user would like to use a custom date range, the user may indicate this in step 1464. The user interface may then display a date range selection interface. This date range selection interface may be any suitable date selection interface. For example, the date range selection interface may include a field or fields in which a user types in a date range. The selection interface may also be a virtual calendar which a user may select dates off of. A user may select the custom date range in step 1468.

A user may also choose to use a predefined date range. In some embodiments, the predefined date ranges may be commonly used date ranges (e.g. last 7 days, last 30 days, last quarter, etc.). If a user would like to use a predefined date range to filter CQI data, the user may indicate this in step 1470. The user interface may then display a number of predefined date ranges in step 1472. The user may select a date range from the number of predefined date ranges in step 1474.

FIG. 57 depicts a flowchart detailing a number of example steps which may be used to apply a filter to CQI data based on user defined, custom filtering criteria. For purposes of illustration, the example flowchart depicts various example categories of user customizable filters. In some embodiments, a user may select from various categories to more efficiently create custom filters for CQI data. These filter categories may allow a user to specify filtering criteria which is related to a parent CQI report category. In some embodiments, categories may not be included. In other embodiments, such as that shown in FIG. 57, a user may either create custom filter without using a category or may have the option of selecting a category.

In step 1480 a user may select a configure CQI report utility on a user interface. The user may then indicate that they would like to define a custom filter for CQI data included in the report in step 1482. A user may then have the option of selecting from a category of customizable filtering options or create a filter without using a custom filter category. In the example embodiment, four example categories are included: DERS compliance, Medication, Infusion, and Infusion Story. Other embodiments may include a differing number or differing types of categories.

If a user desires to create a custom filter using the DERS compliance category, the user may proceed to step 1484. In step 1484 a user may indicate that they would like to create a custom filter using the DERS compliance category. A list of customizable related filtering criteria may then be display on the user interface in step 1486. A user may customize the desired filtering criteria in step 1488. In a specific embodiment of the present disclosure, a list of possible filtering criteria for the DERS compliance category is shown in Table 11 as follows:

| | Customizable Filtering Criteria for DERS Compliance |
|---|---|
| 0.01 | Non-specified medication or "wildcard" Medication Record usage |
| 0.02 | Compliant Infusions |
| 0.03 | Non-Complaint Infusions |
| 0.04 | Soft Limit Pull Backs |
| 0.05 | Soft Limit Overrides |
| 0.06 | Hard Limit Pull Backs |
| 0.07 | Hard Limit Reached Followed by Programming using Non-specified medication or "wildcard" Medication Record |

If a user desires to create a custom filter using the Medication category, the user may proceed to step 1490. In step 1490 a user may indicate that they would like to create a custom filter using the Medication category. A list of customizable related drug filtering criteria may then be displayed on the user interface in step 1492. A user may customize the desired filtering criteria in step 1494. Among others, possible drug criteria may include a drug name or drug type. In a specific embodiment of the present disclosure, a list of possible filtering criteria for the Medication category is shown in Table 12 as follows:

| Customizable Filtering Criteria for Medication | |
|---|---|
| 0.01 | Medication Record |
| 0.02 | Rule Set |
| 0.03 | Concentration |
| 0.04 | Delivery Route |
| 0.05 | Drug Family |
| 0.06 | Infusion Type |
| 0.07 | Medication Site |
| 0.08 | Delivery Method |

If a user desires to create a custom filter using the Infusions category, the user may proceed to step 1496. In step 1496 a user may indicate that they would like to create a custom filter using the Infusions category. A list of customizable related filtering criteria may then be display on the user interface in step 1498. This list may include some or all of the event types listed in Table 1. A user may customize the desired filtering criteria in step 4770. In a specific embodiment of the present disclosure, a list of possible filtering criteria for the Infusions category is shown in Table 13 as follows:

| Customizable Filtering Criteria for Infusion | |
|---|---|
| 0.01 | Primary Infusion |
| 0.02 | Secondary Infusion |
| 0.03 | Bolus |
| 0.04 | Loading Dose |
| 0.05 | Dose Rate |
| 0.06 | Dose |
| 0.07 | Titrated Infusion |
| 0.08 | Improperly Loaded Syringe or Tubing |
| 0.09 | Downstream Occlusion |
| 0.10 | Upstream Occlusion |
| 0.11 | Air in Line |
| 0.12 | KVO Rate |
| 0.13 | Delivered at KVO Rate |
| 0.14 | Battery Power Used |
| 0.15 | Infusion Complete |
| 0.16 | Infusion Paused |
| 0.17 | Infusion Stopped |
| 0.18 | Programming of Infusion Cancelled |
| 0.19 | Weight |
| 0.20 | Notification Issued |
| 0.21 | Call Back Issued |
| 0.22 | Patient Weight |
| 0.23 | Patient BSA |
| 0.24 | VTBI |
| 0.25 | Rate |
| 0.27 | Time |
| 0.28 | Alert Issued |
| 0.29 | Alarm Issued |

If a user desires to create a custom filter using the Infusion Story category, the user may proceed to step 4772. In step 4772 a user may indicate that they would like to create a custom filter using the Infusion Story category. A list of customizable related filtering criteria may then be display on the user interface in step 4774. A user may customize the desired filtering criteria in step 4776. In a specific embodiment of the present disclosure, a list of possible filtering criteria for the infusion story category is shown in Table 14 as follows:

| Customizable Filtering Criteria for Infusion Story | |
|---|---|
| 0.01 | Infusion Number |
| 0.02 | Patient |
| 0.03 | Medical Device |
| 0.04 | Clinician or Care Giver |

If a user desires to create a custom filter without using a category, the user may proceed to step 4778. In step 4778 a user may indicate that they would like to create a custom filter without using a category. A list of customizable filtering criteria may then be displayed on the user interface in step 4780. This list may include all possible filtering criteria that may be customized by the user. Such filtering criteria may include, but is not limited to any of the various filtering criteria described herein. A user may customize the desired filtering criteria in step 4782.

Once a user has selected various filtering criteria, a database such as the CQI database 106 of FIG. 4 may be queried for the requested information. The data may then be used to render a CQI report for display on the user interface. The data may be displayed in any number of suitable ways including, but not limited to charts, graphs, tables, gauges, lists, etc. A user may select the way in which data is displayed in some embodiments. A user may also then drill down on various aspects of the CQI report. For example, if a user generated a compliance report for soft limit overrides, a user may have the option to drill down on this information to display soft limit overrides for a specific drug or care area.

FIG. 58 depicts a flowchart detailing a number of example steps which may be used to modify the appearance of CQI data such as a CQI report on a user interface. In step 4750, a user may indicate on the user interface that the user would like to modify the presentation of CQI data. The CQI data may be a CQI report. The CQI report may be created by defining and applying various filters as described in FIGS. 54-57.

In various CQI reports, CQI data may be display as a summary over a period of time (e.g. 3 months). A user may, however, desire to view a month by month breakdown of the data. In some embodiments, various CQI reports may be displayed in graphical format or a user may select to present a CQI report in graphical format. For example, a CQI report on non-compliant infusions over a period of time may be displayed as a line graph to display trends. In some embodiments, a user may be able to specify the type of graph they would like to use if more than one type may be appropriate. It may be desirable to include a greater or lesser number of data points in such a graph. A user may modify the time units used in a CQI report in step 4752 in order to modify the report presentation to match their needs. A user may, for example, change the time unit from months to weeks.

In various CQI reports a number of different panels or widgets may be included or may be selected by a user for inclusion. For example, if a user chooses to drill-down on various report details of interest, the specific detailed information may open in a new panel. Additionally, some CQI reports may display the same CQI data or similar CQI data in a number of different formats (e.g. a chart and a table). The user interface may become cluttered or the report may become encumberingly long and large with an excessive number of panels in some instances. In such instances, a user may elect to toggle certain panels as shown or hidden to make the report more manageable. A user may toggle a panel between a shown condition and hidden condition by performing step 4754.

In some embodiments, CQI reports may have a summary view and a detailed view presentation style. When a report is generated, the report may default to one or the other presentation style. A detailed view of a report may also be created by a user as the user drills-down on various aspects of the CQI report. In some embodiments, a user may have the ability to toggle between various presentation styles (e.g. summary view, detailed view, drilled-down view, etc.) by performing step 4756.

A user may toggle counts or dates by performing step 4758. This may cause data to be displayed in a different fashion on a CQI user interface. For instance, performing step 4758 may change how a graph of CQI data may be displayed on a user interface. In such embodiments, toggling between counts and dates may change the type of units used for the axes of the graph.

CQI data may also be sorted by a user to better display or organize information of interest to a user. For example, a user may desire to sort the information in a CQI report such that it is presented in ascending or descending alphabetical, numeric, or chronological order. A user may also desire to sort information by another element or value. For example, in a CQI report detailing non-compliant infusions by drug name, it may be desirable to sort drugs in ascending or descending order based on compliance percentage or number of compliant infusions. If a CQI report is presented in a table format, a user may be able to sort data based on any column in the table. A user may sort data by performing step 4760.

In some instances it may be desirable to request a comparison between aspects of data in a CQI report or a comparison between one of more different CQI reports. Such a comparison may be helpful in creating an easily understood visual summary of a large quantity of information. For example, a user may request that a pie chart be created showing the percent of compliant v. non-compliant infusions in a report containing both compliant and non-compliant infusions. Such a comparison may also be helpful in trend recognition or tracking. A user may, for example, request a comparison between similar CQI reports for two different DAL versions to determine if changes in a DAL file had the desired effect or to what extend changes in a DAL file had a desired effect. A user may request a comparison be created by performing step 4762. In some embodiments, performing step 4762 may include performing steps similar to those shown in FIG. 47.

View perspective of a CQI report may also be toggled by performing step 4764. This may be used to change the way that a CQI report or portion of a CQI report is displayed on a user interface. For example, performing step 4764 may cause bars in a bar graph to change in appearance from 2D to 3D. In other embodiments, performing step 4 may change the display format of data on the user interface. Toggling the view perspective in step 4764 may for example toggle between whether data is displayed in graph or tabular format.

After modifying the report presentation, a user may have the option of further modifying the CQI data presentation if desired. The user may continue to modify the CQI data presentation until the data is presented in the fashion which suits best suits the user.

FIG. 59 depicts a flowchart detailing a number of example steps which may be used to modify the time units used in a report. The steps depicted in the example flowchart in FIG. 59 may, in some embodiments, be used to perform step 4752 of FIG. 58. In step 4550, a user indicates that they would like to modify the time units used in a CQI report. If multiple time units for the report are available for use, the user interface may display the possible valid time unit selections in step 4552. The user may then select a time unit (e.g., year, quarter, month, week, day, hour, minute, etc.) to use in the CQI report in step 4554. If only a single time unit is available for the report the user interface may display a notification to the user that only one valid time unit exists or is supported for the CQI report. This may be done in step 4556.

FIG. 60 depicts a flowchart detailing a number of example steps which may be used to hide a shown panel or show a hidden panel in a CQI report. If a panel is shown, the user interface may display a hide panel option for the panel in step 4560. The hide panel option may be a virtual button indicating that the panel may be hidden. In such embodiments, the virtual button may be included in a way which clearly associated the button with the panel to be hidden. A user may select the hide panel option in step 4562 if the user desires to hide the panel. The panel may then be hidden and the user interface may display a show panel option in step 4564.

If a panel is hidden, the user interface may provide a display panel option for the hidden panel in step 4566. The display panel option may be a virtual button indicating that a panel has been hidden. A user may select the display panel option in step 4568 if they would like to show the hidden panel. The user interface may then show the panel and display a hide panel option for the panel in step 4570.

FIG. 61 depicts a flowchart detailing a number of example steps which may be used to toggle between a summary view and a detailed view in a CQI report. If a CQI report is displayed in the detailed view, the user interface may display a summary view option for the CQI report in step 4580. If desired, a user may toggle to the summary view by selecting the summary view option in step 4582. The summary view of the CQI report may then be displayed on the user interface in step 4584. If the CQI report is displayed in the summary view, the user interface may display a detailed view option in step 4586. If desired, a user may toggle to the detailed view by selecting the detailed view option in step 4588. The user interface may then display the detailed view of the report in step 4590.

FIG. 62 depicts a flowchart detailing a number of example steps which may be used to sort CQI data in a CQI report. The example steps shown in the flowchart in FIG. 62 may, in some embodiments, be the steps used to perform step 4760 of FIG. 58. The steps depicted in FIG. 62 detail logic which may be used to sort CQI data in a table based CQI report. Some non-table based reports may also be sortable in various embodiments. Additionally, sorting need not be limited to sorting by ascending or descending order as shown in FIG. 62.

In step 4600 a user may select a column of the CQI report to use as sorting criteria. If the selected column has not been previously used to sort the CQI report, the column may be used to sort the CQI report based on the descending order of the column in step 4602. That is, the row with the highest value in the column will be the first row of the table and so on. If the column was previously used to sort the CQI report, the column may be used to sort the CQI report in the opposite order. For example, the column may be used to sort the CQI report in the descending order of the column in step 4602 if the column was last used to sort the CQI report based on its ascending order. If the column was previously used to sort the CQI report based on descending order of the column, the column be use to sort the CQI report based on the ascending order of the column in step 4604.

In some embodiments, the logic used to sort a CQI report may differ. For example, in some embodiments, after a user selects a column to use a sorting criteria, the user interface may prompt the user to choose if they would like to sort the CQI based on the ascending or descending order of the column or another sorting criteria based on the column.

FIG. 63 depicts a flowchart detailing a number of example steps which may be used to toggle between a counts view and a dates view in a CQI report. If a CQI report is displayed in the counts view, the user interface may display a dates view option for the CQI report in step 4610. If desired, a user may toggle to the dates view by selecting the dates view option in step 4612. The dates view of the CQI report may then be displayed on the user interface in step 4614. If the CQI report is displayed in the dates view, the user interface may display a counts view option in step 4616. If desired, a user may toggle to the counts view by selecting the counts view option in step 4618. The user interface may then display the counts view of the report in step 4620.

FIG. 64 depicts a flowchart detailing a number of example steps which may be used to select a utility on a user interface which may allow a user to perform a function or functions. In step 1220, a user views a report. A user may view a report by following steps similar to those shown and described in relation to FIG. 52-63. A user may then choose from a number of available utilities. The example flowchart shown in FIG. 64 includes six example utilities. Other utilities may be available.

If a user desires to print the selected report, the user may proceed to step 1222 and print the report. If a user desires to download the selected report the user may proceed to step 1224 and download the report. If a user desires to email the selected report, the user may proceed to step 1226 and email the report to one or more recipients. If a user desires to export data from the selected report, a user may do so by proceeding to step 1228 and using the export data utility. If a user desires to save the selected report or load another report, the user may proceed to step 1230 and save or load a report. If a user desires to create a link to the selected report, the user may proceed to step 1232 and create a link to the report using the link utility. After a user has finished using a utility, the user may perform further functions with other utilities if desired.

FIG. 65 depicts a flowchart detailing a number of example steps which may be used to print a CQI report. The steps shown in FIG. 65 may in some embodiments be a number of sub-steps for step 1222 in FIG. 64. In step 1240, a user specifies a report. This may be done, for example, by following steps shown in FIG. 52-63. The user may then select the print utility 1242. After a user selects the print utility, the user interface may display a preview of the report in step 1244. The user interface may for example be a DERS editor user interface or CQI user interface. After the preview has been displayed a user may then decide whether or not they would like to print the report. If a user does not want to print the report, the user may proceed to step 1246 and indicate that they would not like the report to be printed. This may exit the print utility in some embodiments. If a user would like to print the report, the user may proceed to step 1248 and indicate that they would like to print the report. The user may then be prompted to select a printer in step 1250.

After a user selects the desired printer, the user may cancel printing of the report or may print the report. To a cancel printing of a report, a user may proceed to step 1252 and indicate their desire to cancel printing of the report. If a user cancels printing of the report, the user may return to step 1244. If a user wants to print the report, a user may indicate that they would like to print the report in step 1254. The report may then be formatted and sent to the printer in step 1256.

FIG. 66 depicts a flowchart detailing a number of example steps which may be used to download a CQI report. The steps shown in FIG. 66 may in some embodiments be a number of sub-steps for step 1224 in FIG. 64. In step 1260, a user specifies a report. This may be done, for example, by following steps shown in FIG. 52-63. The user may then select the download utility 1262. After a user selects the download utility, the user interface may display a preview of the report in step 1264. The user interface may for example be a DERS editor user interface or CQI user interface. After the preview has been displayed a user may then decide whether or not they would like to download the report. If a user does not want to download the report, the user may proceed to step 1266 and indicate that they would not like the report to be downloaded. This may exit the download utility in some embodiments. If a user would like to download the report, the user may proceed to step 1268 and indicate that they would like to download the report. The user may then be prompted to select a format and destination for the report in step 1270. The report may be downloaded in any number of suitable formats which may, for example, include Portable Document Format (.pdf) or static html format.

After a user selects the desired format and destination, the user may cancel downloading of the report or may download the report. To a cancel downloading of a report, a user may proceed to step 1272 and indicate their desire to cancel downloading of the report. If a user cancels downloading of the report, the user may return to step 1264. If a user wants to download the report, a user may indicate that they would like to download the report in step 1274. The report may then be formatted and downloaded to the specified destination 1276.

FIG. 67 depicts a flowchart detailing a number of exemplary steps which may be used to email a CQI report. The steps shown in FIG. 67 may in some embodiments be a number of sub-steps for step 1226 in FIG. 64. In step 1280, a user specifies a report. This may be done, for example, by following steps shown in FIG. 52-63. The user may then select the email report utility 1282. After a user selects the email utility, the user interface may display a preview of the report to be emailed in step 1284. The user interface may for example be a DERS editor user interface or CQI user interface. After the preview has been displayed a user may then decide whether or not they would like to email the report. If a user does not want to email the report, the user may proceed to step 1286 and indicate that they would not like the report to be emailed. This may exit the email utility in some embodiments. If a user would like to email the report, the user may proceed to step 1288 and indicate that they would like to email the report. The user may then be prompted to provide at least one email address to email the report to in step 1290.

After a user selects the desired email address(es), the user may cancel emailing of the report or may email the report. To a cancel emailing of a report, a user may proceed to step 1292 and indicate their desire to cancel emailing of the report. If a user cancels emailing of the report, the user may return to step 1284. If a user wants to email the report, a user may indicate that they would like to email the report in step 1294. The report data may then be formatted for email and sent to the indicated email address(es) in step 1296.

FIG. 68 depicts a flowchart detailing a number of example steps which may be used to export data from a CQI report.

The steps shown in FIG. 68 may in some embodiments be a number of sub-steps for step 1228 in FIG. 64. In step 1300, a user specifies a report. This may be done, for example, by following steps shown in FIG. 52-63. The user may then select the export utility in step 1302. After a user selects the export utility, the user may select the data to be exported from the report in step 1304. The user interface may display a preview of the selected data in step 1306. The user interface may for example be a DERS editor user interface or CQI user interface. After the preview has been displayed a user may then decide whether or not they would like to export the data. If a user does not want to export the data, the user may proceed to step 1308 and indicate that they would not like the report data to be exported. This may exit the export utility. If a user would like to export the report data, the user may proceed to step 1310 and indicate that they would like to export the report. The user may then be prompted to select a format, destination directory, file name, etc. for the data in step 1312.

After a user completes step 1312, the user may cancel export of the report data or may export the report data. To a cancel export of report data, a user may proceed to step 1314 and indicate their desire to cancel exporting of the report data. If a user cancels exporting of the report data, the user may return to step 1306. If a user wants to export the report data, a user may indicate that they would like to export the report data in step 1316. The report data may then be formatted and downloaded to the selected destination with the provided file name in step 1318.

Referring now to FIG. 69 a flowchart detailing a number of example steps which may be used to schedule a report for automatic generation and distribution is shown. In step 1150, a user may choose from a list of saved reports or configure a report which they would like to schedule for automatic generation and distribution. A report using the same filtering criteria as the chosen report may be automatically generated and distributed on the prescribed schedule or on a prescribed date. In step 1152, a user may provide a name for the report. In step 1154, the user may define a schedule for when the report should be generated and distributed. A user may also define the distribution list for the report in step 1154. The distribution list may be a list of email addresses or an email address to which the report is automatically sent after generation. In step 1156, a user may save the scheduled report definition. When the report comes due to be generated, a CQI database may be queried for the selected data and the report may be created.

FIG. 70 depicts a flowchart showing a number of example steps which may be used to generate and distribute a scheduled CQI report such as those shown and described in relation to FIG. 69. In step 1160, a scheduled report may be triggered. That is, the point at which the report was schedule for generation is reached. The schedule for the report may be kept by a scheduling service in a hosted environment.

The filtering criteria for the triggered report may be retrieved in step 1162 by a CQI server after notification that the report has been triggered. A CQI reporting service may then retrieve the data for the triggered report in step 1164. This data may be returned to the CQI server and formatted into the report in step 1166. The report, or a link to the report, may be emailed to the distribution list in step 1168. After the report has been emailed to the distribution list, the scheduling service may be notified that it has been delivered. The scheduling service may log that the report was delivered in step 1170.

FIG. 71 depicts a flowchart showing a number of example steps which may be used to generate an automated CQI summary report. Such a report may, for instance, be generated on a daily basis or other regular interval. CQI summary reports may be configured to present a snapshot of a large number of detailed events. These reports may save time and mitigate the opportunity for confusion by presenting a large number of events in a pre-digested form.

In step 1180, a scheduled report may be triggered. As mentioned above, summary reports may be automatically generated on a daily basis. Such reports may be generated on any other time frame as well. In some embodiments, an automated summary report may be generated after a predetermined number of CQI events have been received. The schedule for the report may be kept by a scheduling service in a hosted environment.

Metadata for the triggered report may be retrieved in step 1182 by a CQI server after notification that the report has been triggered. A CQI reporting service may then retrieve the data for the triggered report in step 1184. The CQI reporting service may populate the summary tables for the report in step 1186. The CQI server may acknowledge the creation of the report in step 1188. After the creation of the report has been acknowledged a scheduling service may be notified that the report has been created. The scheduling service may log that the report was created in step 1190.

Referring now to FIGS. 72-180, a number of example user interface screens are shown. Such screens may be accessed and presented to a user on a DERS editor user interface or CQI user interface. For purposes of example, the screens shown are those of a DERS editor user interface. In some embodiments, similar or identical screens may be used in other interfaces for other services such as a user interface for a CQI service. Screens shown in FIGS. 72-180 may be related to the flowcharts shown in FIGS. 11-71. Such screens may follow similar workflows to what is shown and described in FIGS. 11-71. In various embodiments, these screens may be displayed to a user via a web browser user interface. A user may, for example, view such screens using a computer, tablet, smart phone, etc. As a user navigates from screen to screen, a database such as a DERS database may be queried for the information needed to display the screen. This information may then be rendered for display and displayed on the user interface. Any suitable client-server interaction scheme may be used.

Referring now specifically to FIGS. 72 and 73, an example graphical user interface login screen 1500 which may be presented to a user when a user attempts to access a DERS editor service or CQI service is shown. Such a screen may be rendered and presented to a user as a user tries to access a service via a web browser.

As shown, the login screen 1500 includes a banner 1502 with a service identifier 1504. The service identifier 1504 may be text identifying the service that a user is running (e.g. DERS editor service, CQI service, user editor service, etc.). In the example embodiment shown in FIGS. 72 and 73, the service identifier 1504 reads "DERS Editor". In other embodiments, the service identifier may be an icon, logo, or the like. In some embodiments, the banner 1502 may additionally include other information, for example, company information, version number information, institution/organization information, etc.

The example login screen 1500 additionally includes a login box 1506. The login box 1506 in the example embodiment includes text which instructs the user to enter their login details. The login box 1506 may include a User ID field 1508 in which the user may enter their user ID. The login box 1506 may include a Password field 1510 in which the user may enter their password. These fields are shown filled out in FIG. 73. Other embodiments may include a differing number of fields or different fields.

The login box 1506 may, in some embodiments, include a forgotten password link 1512 which may be used by a user to retrieve a forgotten password. In some embodiments, the forgotten password link 1512 may have expanded functionalities. For example, the forgotten password link 1512 may additionally allow a user to change their password or retrieve their user ID.

The login box 1506 on the example login screen 1500 may also include a login option 1514. The login option 1514 may be a virtual button or the like. The login option 1514 may include text indicating its function or may include an icon which indicates its function. In some embodiments, the login option 1514 may be disabled until a user has filled out the User ID field 1508 and Password field 1510. In some embodiments, disabled buttons may be grayed out or otherwise visually altered to indicate that they are disabled. Once a user has entered their login details in the correct fields a user may click, press, touch, etc. the login option 1514 to login to the service.

FIG. 74 depicts an example initialization screen 1520. Such a screen may be presented to a user such as a drug library administrator during their first login to a DERS editor service. The initialization screen 1520 may be used by a user to set up the DERS editor service for an institution or organization. In the example embodiment, the initialization screen 1520 includes a number of utilities. The initialization screen 1520 may include a create new library utility 1522, an import library utility 1524, and help utility 1526. These utilities may be displayed as virtual buttons on the user interface.

A user may use the help utility 1526 to open a help or informational page. In some embodiments, clicking on the help utility 1526 may cause a tutorial to begin. A user may use the import library utility 1524 to import a pre-existing library. Such a library may, for example, be a library from another institution within the same organization. In some embodiments, such a library may be prepared by a service provider. A user may use the create new library utility 1522 to create a new library.

In some embodiments, if a user clicks a virtual button or option on an initialization screen 1520, an initialization wizard may be displayed on the user interface. Various initialization wizard screens 1530 are depicted in FIGS. 75-77. The example initialization wizard screens 1530 may be used to define an institution/organization's organizational schema. The example initialization screens may also be used to define various users of the DERS editor service.

FIG. 75 depicts an example initialization wizard screen 1530 which may be used to provide various information about an institution or organization that will be using the DERS editor. The initialization wizard screen 1530 in FIG. 75 includes a number of user definable fields. The example embodiment in FIG. 75 includes an institution/organization name field 1532. This field may be used to define the name of the institution or organization for which the library is being created. In some embodiments, if a user indicates the name given is that of an organization, a user may be prompted to fill out an institution name field (not shown) identifying one or more institutions within the organization that will be using the new library. An upload logo link 1534 may also be included in some embodiments. A user may use the upload logo link 1534 to upload the institution's logo to the DERS editor. This logo may be displayed on various screens on the DERS editor user interface.

The example initialization wizard screen 1530 in FIG. 75 also includes language selection field 1536. The language selection field 1536 may be used to specify the default language which will be used on the library and DERS editor service. In some embodiments, the language selection field 1536 may be populated using a drop box which when expanded displays a selection of all supported languages. The example embodiment in FIG. 75 includes a date format field 1538 as well. A user may use this field to select how dates will be formatted (e.g., mm/dd/yy, dd/mm/yy, dd/mm/yyyy, etc.). Once a user has populated the fields shown on FIG. 75, a user may click a next option 1540 to proceed to the next initialization wizard screen 1530. In various embodiments, the next option 1540 may be disabled until a user fills out all required fields on the current screen.

FIG. 76 depicts another example initialization wizard screen 1530. The example initialization wizard screen 1530 shown in FIG. 76 may be used to define an institution's DERS editor users and their privileges. The example embodiment shown in FIG. 76 includes a user field 1550. A user may input a user in the user field 1550. In some embodiments, this may be accomplished by providing an e-mail address for the user. In such embodiments, the DERS editor service may send an email to the given email address with a user ID and password. The newly created user may then use the credentials provided in the email to access the DERS editor service. In some embodiments, a newly created user may be required to, for example, change their password upon their first login.

Additionally, the example initialization wizard screen 1530, depicted in FIG. 76, includes a role selector 1552 functionality. In some embodiments, the role selector 1552 functionality may be a user populated field which may include a drop down box. In the example embodiment depicted in FIG. 76, the role selector 1552 functionality provides a number of selectable options which a user may check off if desired. The selectable options are shown as radio buttons in FIG. 76, but need not be radio buttons in all embodiments. In the example embodiment in FIG. 76, a review, editor, and administrator role are shown. Other embodiments may include additional roles. In some embodiments, a user may be required to define additional information about new users. This additional information may include care areas in which they work or are responsible for. An add another user option 1554 is also included in the example initialization wizard screen 1530 shown in FIG. 76. This may be used if a user wishes to define multiple DERS editor users and their privileges. Clicking the add another user option 1554 may cause the DERS editor user interface to display additional fields which may be used to define additional users and their privileges. In some embodiments, a user may assign a customized role to a user by choosing from amongst a number of privileges such as but not limited to any of those shown in Table 3.

The example embodiment shown in FIG. 76 also includes a back option 1555 and a next option 1540. The back option 1555 may be used to return to the previous initialization wizard screen 1530. The next option 1540 may be used to proceed to the next initialization wizard screen 1530. The next option 1540 may be disabled until the user has filled out all of the required fields on the current screen.

FIG. 77 depicts an example initialization wizard screen 1530 which may be used to define the various care areas which exist within an institution. The example embodiment shown in FIG. 77 includes a care area selector 1560. The care area selector 1560 may include a list of care areas which may be checked off by the user. In some embodiments, the list of care areas may be organized into like care groups of care areas for ease of user. For example, a number of psychiatric care areas may be grouped together under a psychiatric heading or column. In some embodiments, a care group selector screen may be included as well. A user may use such a screen to define a number of care groups which are present at the institution. The user may then specify care areas that are included in each defined care group.

In some embodiments, the care area selector 1560 may include at least one care area selector field (not shown). In such embodiments a user may populate the care area selector field by selecting the desired care area from a drop down list or the like. Such embodiments may also include an add additional care area option (not shown) which may be used to add additional fields which may be populated with care areas.

The example embodiment shown in FIG. 77 also includes a back option 1562 and a finish option 1564. The back option 1562 may be used to return to the previous initialization wizard screen 1530. The finish option 1564 may be used to proceed to the next initialization wizard screen 1530. The finish option 1564 may be disabled until the user has filled out all of the required fields on the current screen. In some embodiments, a user may be required to select at least one care area in the care area selector 1560 before the finish option 1564 becomes enabled.

Some embodiments may include additional screens which may be included in an initialization wizard. For example, some embodiments may include a general settings screen or a number of general settings screens. In some embodiments, a user groups or roles screen may be included in which a user may define the groups and/or roles which will be displayed in the role selector 1552 of FIG. 76. In such embodiments, the user may customize the DERS editor service privileges for each group and/or role on a user groups or roles screen. Other screens may also be included as part of an initialization wizard. In such embodiments, the finish option 1564 shown on FIG. 77 may instead be a next option which allows a user to proceed to any additional screens.

FIG. 78 depicts an example embodiment of a "welcome" screen 1570. The example welcome screen 1570 may be the screen displayed to a user after first initializing the DERS editor service for the institution. The welcome screen 1570 shown in FIG. 78 may, in some embodiments, be the screen displayed to a user upon logging into a DERS editor service. In some embodiments, the welcome screen 1570 may be displayed upon login until sufficient content has been added to the drug library in the DERS editor. Some embodiments may not include a welcome screen 1570.

As shown the welcome screen 1570 includes a title bar 1572. The title bar 1572 may include a service identifier 1574. The service identifier 1574 may include the name, logo, icon, etc. of the service. The title bar 1572 may also include a number of selectable links/menu options 1576. In the example embodiment, the title bar 1572 includes selectable links/menu options 1576 including a home option, hospital setting option, account settings option, help option, and a sign out option.

If a user has uploaded the logo for the institution, the institution logo 1578 may be displayed on the DERS editor user interface. In the example embodiment, the institution logo 1578 is display in the top left corner of the DERS editor user interface, but may be displayed elsewhere in other embodiments. In some embodiments, the institution logo 1578 may not be displayed on all screens of the DERS editor user interface.

The welcome screen 1570 shown in FIG. 78 additionally includes a side bar 1580. The side bar 1580 may include various information of interest, links to DERS editor items, action items the user is responsible for, etc. In the example embodiment shown in FIG. 78, the side bar 1580 includes links to a list of the care areas in the institution.

The welcome screen may also include an informational box 1582. The informational box 1582 may display information or notifications which may be of interest to a user. The informational box 1582 may in some embodiments provide instructional information to a user. Some embodiments of a welcome screen 1570 may also include a quick links box 1584. This box may include links to a number of editing functionalities in the DERS editor service. In the example embodiment, the quick links box 1584 includes an add drug link, import drug link, add care area link, and a tutorial link. Other embodiments may include different links or a differing number of links.

Some DERS editor screens may also include a search bar 1586. In the example embodiment, a search bar 1586 is included on the welcome screen 1570. The search bar 1586 may allow a user to search the drug library for various items or elements. For example, a user may use the search bar 1586 to search for a specific medication record or a care area.

FIG. 79 depicts an example of a DERS editor dashboard screen 1590. In some embodiments, a DERS editor dashboard screen 1590 may function as a home screen and/or be the screen which is displayed upon login to the DERS editor service. The DERS editor dashboard screen 1590 may provide a user with a quick "snapshot" of important drug library information. The DERS editor dashboard screen 1590 may differ from user to user depending on the privileges or groups the user belongs to. The DERS editor dashboard screen 1590 may also differ due to users configuring the DERS editor dashboard screen 1590 to suit their individual needs. Additionally, the DERS editor dashboard screen 1590 may differ depending on the stage of development of a drug library. For example, the DERS editor dashboard screen 1590 may differ when a drug library is in the creation phase (has not yet been released) and after the drug library has been released.

As shown, the DERS editor dashboard screen 1590 shown in FIG. 79 includes a title bar 1572. The title bar 1572 includes a service identifier 1574. The title bar 1572 may include other important information. In the example embodiment shown in FIG. 79, the title bar 1572 includes a drug library version number 1592. In some embodiments, the title bar 1572 may also indicate if the drug library version is in progress or has been released. The title bar 1572 in the example embodiment also includes the DERS editor user name 1594 of the user. In some embodiments, a user may click on the user name 1594 to view or modify account settings, change password, log out, etc.

The DERS editor dashboard screen 1590 may include a number of widgets which provide information, links, action items, etc. to a user. In some embodiments, the widgets displayed on the dashboard screen 1590 may be selected and/or modified by the user. In some embodiments, a user may only be able to choose from a sub-set of widgets depending on a role or permissions assigned the user. A user may thus be able to arrange their DERS editor dashboard screen 1590 in a manner which best fits their needs. In some embodiments, various DERS editor dashboards may be arranged by an institution for particular groups of DERS editor users (drug library administrator, reviewer, pharmacist, etc.). In some embodiments, the DERS editor dashboard screen 1590 may differ for an in progress drug library and a released/active drug library. The specific dashboard settings for each user may be stored in a database, for example a DERS database or a user database.

The DERS editor dashboard screen 1590 shown in FIG. 79 includes an overview widget 1596a. An overview widget 1596a may show the drug library version number, its review status or release status, the number of facilities, care areas, and/or drugs in the library, etc. The DERS editor dashboard screen 1590 in FIG. 79 includes a quick links widget 1596b. A quick links widget 1596b may allow a user to click various links to navigate to commonly used or important DERS editor functionalities. In some embodiments, a user may choose which links are displayed on a quick links widget 1596b. A progress widget 1596c is also shown in FIG. 79. A progress widget 1596c may include various information about the review progress or creation progress made for a library. In some embodiments, at least a portion of the information displayed in the progress widget 1596c may be presented in a graphical format. Information displayed in a progress widget 1596c may include, but is not limited to, changes reviewed or needing review, feedback, review progress by care area, review progress by DERS editor user, etc. Some embodiments of a progress widget 1596c may include a link to any action items for the DERS editor user and acts as a task list. A feedback and requests widget 1596d is also shown in FIG. 79. A feedback and requests widget 1956d may show a user feedback and update requests for a library. This information may be displayed in, for example, a table. The table may include the drug name, care area, clinical use, concentration, date of the feedback or request, name or user ID of the user who submitted the request, etc. A user may be able to click on desired items shown in the feedback and requests widget 1596d to address the items. Other embodiments may include different or additional widgets. Some widgets, for example, the feedback and requests widget 1596d may be separated into one or more different widgets in alternate embodiments.

Also shown in FIG. 79 are a number of tabs 1598. A user may click these tabs 1598 to navigate to different portions of the DERS editor. In the example embodiment in FIG. 79, the DERS editor dashboard screen 1590 includes tabs 1598 to navigate to a drug editor, a care area screen, a library review screen, and a pump simulator. The open tab 1598 of the DERS editor may be highlighted or otherwise visually indicate that it is open in some embodiments. These various screens may be used to create or modify various aspects of a drug library. A care area screen may for example be used to edit care area entries in a drug library. Various embodiments may include different or a different number of tabs 1598.

Referring now to FIG. 80, an example care area screen 1600 is shown. A user may, in some embodiments, navigate to the care area screen 1600 by clicking the proper tab 1598. The care area screen 1600 may display a list of care areas in the drug library to a user. Only four care areas are shown in FIG. 80. Other information about the care areas may also be displayed. For example, the number of drugs for each care area, review progress, etc. for each care area may also be shown. Some embodiments may display the care areas and related information in a care area table 1602. A user may be able to click or select care areas from the list to view more detailed information about the care area or edit the care area settings.

The care area screen 1600 additionally includes an add care area option 1604 and a copy option 1606 which are shown as virtual buttons in FIG. 80. A user may select one of these options if they would like to add a new care area to the drug library. A user may select the copy option 1606 if they would like add a new care area by copying an existing care area. This may save time if there will be few differences in the settings for the care areas. In some embodiments, using the copy option 1606 to create a new care area may copy over all of the medication records, rule sets, concentrations, etc. from the copied care area to the new care area. In some embodiments, a user may indicate that they would not like to copy various entries associated with a care area when using the copy option 1606 to create a new care area. If a user would like to create a new care area without copying an existing care area, a user may click the add a care area option 1604.

The progression of FIGS. 81-86 depict a number of examples of an add a care area screen 1610. In other embodiments, the screens or steps used to add a care area may differ. In some embodiments, these screens may be displayed on the DERS editor user interface after a user clicks the add a care area option 1604 shown in FIG. 80. The add a care area screen 1610 shown in FIG. 81 may be one of many screens which are part of an add a care area wizard in some embodiments. In some embodiments, the add a care area screen 1610 may be a part of the care area screen 1600. In some embodiments, the add a care area screen 1610 may be displayed as a modal window over top of the care area screen 1600.

Adding a care area may involve specifying a number of different parameters, elements, items, etc. When adding a care area, a user may specify a care area type or name as well as other DERS editor service users who are associated with the care area. A user may also specify drugs and types of medical devices used or supported in a care area. A user may also be required to specify a number of parameters for the care area which may relate to drug administration within the care area (e.g. patient weight limits, B.S.A. limits, etc.). In some embodiments, a user may also specify a care group (if any) to which the care area belongs. In other embodiments, adding a care area may differ and may involve specifying different or additional parameters, elements, items, etc. Once the care area is added, the care area and all specified information for the care area may be saved in the DERS database. A similar process may be used to add care groups to a drug library.

As shown, a care area types list 1612 is depicted in the add a care area screen 1610 shown in FIG. 81. The care area types list 1612 shown in FIG. 81 is separated into a number of care area categories to allow a user to quickly locate the desired care area type. In the example embodiment shown in FIG. 81, a user may select the desired care area using a check box. In other embodiments, a user may select the desired care area type by toggling a radio button on or off, by clicking the desire care area, or in any other suitable manner. A user may be required to select a care area type before proceeding to any additional steps in the process of adding a care area. In some embodiments, an asterisk or other indicia may be used to indicate if a field, parameter, or other element is required to be defined on a DERS editor screen. Fields, parameters, or other elements indicated as required herein need not be required in all embodiment of the present disclosure.

If a user desires to cancel their adding of a new care area, the user may use a cancel option 1614 on the add a care area screen 1610. If a user would like to proceed to define additional care area settings, a user may use a next option 1616.

FIG. 82 depicts another add a care area screen 1610. The add a care area screen 1610 shown in FIG. 82 includes a number of parameter fields which may be used to define setting for the care area. In other embodiments, an add a care area screen 1610 for various care area settings may include different parameter fields or a different number of parameter fields than that shown in FIG. 82.

In the example embodiment shown in FIG. 82, a name parameter field 1620 is included. This field may be used to specify the name of a care area within the institution. In FIG. 82, a user has entered "4 West" in the name parameter field 1620.

A care area type parameter field 1622 is also included in the example embodiment. This field may be automatically populated with the care area a user selects on a previous add a care area screen 1610 such as that shown in FIG. 81. In some embodiments, an add a care area screen 1610, such as the one shown in FIG. 81, may not be included. The care area type may instead be defined by populating a care area type parameter field 1622 such as the one shown in FIG. 82. A care area type parameter field 1622 may be useful to create uniformity and allow for easy comparison between institutions.

A sort order parameter field 1624 may also be included in some embodiments. This field may be used to define in what order the added care area is to be displayed on the user interface of a medical device during programming of the medical device. For example, if a medical device is used in a number of care areas, as it is programmed it may ask a user to select which care area the device is in from a list. The sort order parameter field 1624 may be used to define where in the list the care area will appear.

A require second review parameter field 1626 is also included in FIG. 82. This field may be used to define whether infusions, therapies, etc. programmed in the care area require a second review before they are administered. This second review may in some embodiments be done by the same user that programmed the original infusion or may be conducted by another user. In some embodiments, a user may have the option of specifying that a second review is only required if a soft limit is being overridden, for example.

The example embodiment in FIG. 82 additionally includes a screen lock parameter field 1628. This field may be used to define whether or not a user may lock the user interface screen of a medical device in the care area. In some embodiments, the screen lock parameter field may be used to select a type of screen lock from a number of possible screen locks. For example, a user may be able to choose between a screen lock which may be locked or unlocked with a virtual button, a slider, a keypad, etc. A user may also define if a passcode or password is required to unlock the screen. In some embodiments a screen lock parameter field 1628 may be used to set a time-out duration for a medical device user interface. For example, a user may specify that if a device's user interface is not touched for two minutes, the device may automatically lock its user interface.

A default speaker volume parameter field 1630 and a default screen brightness parameter field 1632 are also included in the example add a care area screen 1610 shown in FIG. 82. The default speaker volume parameter filed 1630 may be used to define the default speaker volume for devices in the care area. The default screen brightness parameter field 1632 may be used to define the default screen brightness of device in the care area. Some embodiments, including that depicted in FIG. 82 may include an automatically adjust screen brightness parameter field 1634. This field may be used to define whether or not screens of medical devices in a care area will automatically adjust their brightness in response to ambient lighting conditions or time of day.

Once a user has finished defining parameters for the care area settings, a user may click a next option 1616. Clicking the next option 1616 on the add a care area screen 1610 shown in FIG. 82 may progress a user to another add a care area screen 1610 with additional parameter fields to be defined. In some embodiments, clicking the next option 1616 on FIG. 82 may progress a user to the add a care area screen 1610 shown in FIG. 83. The add a care area screen 1610 shown in FIG. 83 includes a number of parameter fields which may be used to define patient settings for the care area. In other embodiments, an add a care area screen 1610 for various patient settings may include different parameter fields or a different number of parameter fields than that shown in FIG. 83.

As shown, a second weight/BSA entry parameter field 1640 is included. This field may be used to define whether or not a user is required to enter a patient's weight or body surface area twice to confirm that the information is correct. This may, for example, be desirable in a NICU where small errors in these values can cause severe adverse events to occur. Other parameters may also be included as safeguards against incorrect weight or BSA value entry.

A number of patient weight limit parameter fields may also be included. In the example embodiment shown on FIG. 83, the add a care area screen 1610 includes a weight high hard limit parameter field 1642, weight high soft limit parameter field 1644, weight low soft limit parameter field 1646, weight low hard limit parameter field 1648. Hard limits may not be overridden during programming and soft limits may be overridden with a manual override in some embodiments. The weight high hard limit parameter field 1642 and weight high soft limit parameter field 1644 may be used to define the high limits for weights which may be entered during programming of a medical device. The weight low soft limit parameter field 1646 and the weight low hard limit parameter field 1648 may be used to define the low limits for weights which may be entered during programming of a medical device. These hard and soft limits may help to ensure that correct information is entered when programming a patient's weight. Among other benefits, these limits may help to protect against order of magnitude errors which may occur if a user mistakenly types in an extra zero when programming weight. For example, if a user types in "2500 lbs" in a patient weight field instead of "250 lbs" when programming a medical device, the hard limit may prevent a user from delivering the therapy.

Once a user has finished defining parameters in the add a care area screen 1610 in FIG. 83, a user may use a next option 1616. The next option 1616 on the add a care area screen 1610 shown in FIG. 83 may progress a user to another add a care area screen 1610 with additional parameter fields to be defined. In some embodiments, clicking the next option 1616 on FIG. 83 may progress a user to the add a care area screen 1610 shown in FIG. 84. The add a care area screen 1610 shown in FIG. 84 includes a number of parameter fields which may be used to define patient settings for the care area. In some embodiments, the add a care area screens 1610 shown in FIGS. 83-84 may be combined into a single screen. In other embodiments, an add a care area screen 1610 for various patient settings may include different parameter fields or a different number of parameter fields than those shown in FIG. 84.

A number of patient body surface area parameter fields are shown in FIG. 84. In the example embodiment shown on FIG. 84, the add a care area screen 1610 includes a BSA high hard limit parameter field 1650, BSA high soft limit parameter field 1652, BSA low soft limit parameter field 1654, and a BSA low hard limit parameter field 1656. The BSA high hard limit parameter field 1650 and BSA high soft limit parameter field 1652 may be used to define the high limits for BSA which may be entered during programming of a medical device. The BSA low soft limit parameter field 1654 and the BSA low hard limit parameter field 1656 may be used to define the low limits for BSA which may be entered during programming of a medical device. As indicated above in reference to hard and soft limits for weights in the discussion of FIG. 83, these hard and soft limits may help to ensure that correct information is entered when programming a patient's BSA.

FIG. 84 also includes a parameter field for syringe settings in the event the medical device being used in the care area is a syringe pump. In some embodiments, syringe pump settings parameters may be included on another add a care area screen 1610. In the example embodiment shown in FIG. 84, a syringe parameter field 1658 is included. This field may be used to define syringes that may be used or may not be used in the care area. Again, using the example of a NICU, it may be desirable to disallow usage of larger volume syringes such as 60 cc syringes. If, for example, during pump programming, the user enters a syringe size or the pump determines a syringe is in place that is too large, the user may be prevented from delivering a therapy.

Once a user has finished defining parameters in the add a care area screen 1610 in FIG. 84, a user may click a next button 1616. Clicking the next button 1616 on the add a care area screen 1610 shown in FIG. 84 may progress a user to another add a care area screen 1610 with additional parameter fields to be defined. In some embodiments, clicking the next button 1616 on FIG. 84 may progress a user to the add a care area screen 1610 shown in FIG. 85. The add a care area screen 1610 shown in FIG. 85 includes a number of groups of parameter fields which may be used to define KVO setting, rate limits, and VTBI limits for the care area. In other embodiments, an add a care area screen 1610 for these settings may include different parameter fields or a different number of parameter fields than those shown in FIG. 85. In some embodiments, there may be a separate add a care area screen 1610 for each group of parameter fields shown in FIG. 85.

In the example embodiment shown in FIG. 85, there are a number of parameter fields which may be used to define KVO settings for a care area. A default KVO value parameter field 1660 is included in the example embodiment. This field may be used to define the default KVO rate for the care area. A KVO can be changed by user parameter field 1662 is also included in the example embodiment shown in FIG. 85. This field may be used to define whether or not a user in the care area is able to change the KVO rate from that defined in field 1660 or that defined in a drug record.

The example add a care area screen 1610 shown in FIG. 85 also includes parameter fields which may be used to define infusion rate limits for the care area. In the example embodiment shown in FIG. 85, a rate high hard limit parameter field 1664 and a rate high soft limit parameter field 1666 are shown. Other embodiments may include a rate low hard limit parameter field (not shown) and a rate low soft limit parameter field (not shown). The rate high hard limit parameter field 1664 and the rate high soft limit parameter field 1666 may be used to define limits for infusion rates which may be entered during programming of an infusion pump. These rates may help to ensure that a dangerous amount of a drug is not delivered over a specific time window. In some embodiments, various drug records for drugs used in the care area may include rate limits as well. Such rate limits may supersede any rate limits defined for the care area. Some other limits which may be defined at the care area level may also be superseded by limits defined in drug records for those drugs used in the care area (e.g. VTBI, alarm sensitivities, etc.).

The example embodiment shown in FIG. 85 also includes parameter fields which may be used to define VTBI limits for the care area. As shown, a VTBI high hard limit parameter field 1668 and a VTBI high soft limit parameter field 1670 are included. In some embodiments, a VTBI low hard limit parameter field (not shown) and a VTBI low soft limit parameter field (not shown) may be included as well. The VTBI high hard limit parameter field 1668 and the VTBI high soft limit parameter field 1670 may be used to define limits for the VTBI which may be entered during programming of a medical device. These limits may be beneficial for a number of reasons. For example, these limits may help to prevent over delivery of medication to a patient.

Once a user has finished defining parameters in the add a care area screen 1610 in FIG. 85, a user may use a next option 1616. The next option 1616 on the add a care area screen 1610 shown in FIG. 85 may progress a user to another add a care area screen 1610 with additional parameter fields to be defined. In some embodiments, the next option 1616 on FIG. 85 may progress a user to the add a care area screen 1610 shown in FIG. 86. The add a care area screen 1610 shown in FIG. 86 includes a number of groups of parameter fields which may be used to define an air infusion limit and occlusion sensitivity limits for the care area. In other embodiments, an add a care area screen 1610 for these settings may include different parameter fields or a different number of parameter fields than those shown in FIG. 86. In some embodiments, there may be a separate add a care area screen 1610 for each group of parameter fields shown in FIG. 86.

In the example embodiment shown in FIG. 86, a number of parameter fields which may be used to define air infusion limits are included. A default air infusion limit parameter field 1680, user can change air infusion limit parameter field 1682, and an air infusion hard limit parameter field 1684 are included in the example add a care area screen 1610 in FIG. 86. The default air infusion limit parameter field 1680 may be used to define the default air-in-line alarm sensitivity for the care area. The user can change air infusion limit parameter field 1682 may be used to define whether or not a user can change the air infusion limit defined in field 1680 or within a drug record for the care area. The air infusion hard limit field 1684 may be used to define an air-in-line alarm sensitivity level which the user cannot modify air infusion limits beyond. These parameter fields may help to prevent adverse events such as air embolisms.

A number of parameter fields which may be used to define occlusion sensitivity are also included in FIG. 86. In the example embodiment depicted in FIG. 86, a default occlusion sensitivity parameter field 1686, user can change occlusion sensitivity parameter field 1688, occlusion sensitivity hard limit parameter field 1690, and back-pump to relieve occlusion pressure field 1692 are included. Some embodiments may include separate occlusion parameter field groups for upstream occlusion sensitivity and downstream occlusion sensitivity. The default occlusion sensitivity parameter field 1686 may be used to define the default occlusion sensitivity for medical devices in a care area. The user can change occlusion sensitivity parameter field 1688 may be used to define whether or not a user may be able to change the occlusion sensitivity specified in field 1686 or a drug record for a care area. The occlusion sensitivity hard limit parameter field 1690 may be used to define an occlusion sensitivity level which the user cannot modify the occlusion sensitivity below. The back-pump to relieve occlusion pressure field 1692 may be used to define whether a medical device will back-pump to relieve occlusion pressure if an occlusion is sensed by the device. This back-pumping may be desirable to ensure that a large over delivery does not occur if the occlusion source is removed (e.g. a nurse removes an IV line clamp from an infusion line). These parameters may help to ensure that a patient safely receives the prescribed therapy.

Once a user has finished defining parameters in the add a care area screen 1610 in FIG. 86, a user may use a next option similar to the next option 1616 show in FIGS. 81-85. Such an option may progress a user to another add a care area screen 1610 with additional parameter fields to be defined. In some embodiments, after progressing through the defining of parameters in FIGS. 81-86 a user may have completed defining the items, parameters, elements, etc. necessary to add the care area. In such embodiments, and as shown in FIG. 86, a finish option 1694 may be included. A user may use the finish option 1694 to add the care area to the drug library. In various other embodiments, a user may be required to define additional or different parameters, items, elements, etc. before a care area may be added to a drug library. For example, care areas which use patient controlled analgesia machines (PCAs) may include parameter fields for minimum dose intervals and the like.

FIG. 87 depicts an example care area screen 1600. After defining the required parameters, items, elements, etc. to add a care area and clicking a finish option such as the finish option 1694 shown in FIG. 86, a user may be returned to the care area screen 1600. As shown, the care area "4 West" added in the example progression of add a care area screens 1610 in FIGS. 80-86 is included in the care area list on the care area screen 1600 in FIG. 87. As shown, the newly added care area is shown with zero added drugs and concentrations. The newly added care area is also shown with a zero percent review progress value.

Referring now specifically to FIG. 88, an example drug screen 1700 is shown. A user may, in some embodiments, navigate to the drug screen 1700 by selecting the proper tab 1598. Drug screens 1700 may display a list of drugs in the drug library or a care area, an entry for a specific drug in a drug library, a comparison of a number of different drug library entries, etc. A list of ten drugs is shown in FIG. 88. Other information about the drugs may also be displayed. The care areas in which the drugs are used, number of defined clinical uses for each drug, review progress, number of defined concentration records for each drug, number of requests or comments associated with each drug, etc. are also shown in FIG. 88. Some embodiments may display a list of the drugs and related information in a drug table 1702. A user may be able to click or select drugs from the list to view more detailed information about the drug or edit the drug record settings.

As shown, some of the drugs in the drug table 1702 employ tall man lettering. Tall man lettering may help ensure that a user does not mistake drugs with similar names for one another. Tall man lettering may be used on various screens of a DERS editor user interface in order to minimize any possible opportunity for such confusion to occur.

The drug screen 1700 additionally may include a compare drug option 1704, a copy drug option 1706, and an add drug option 1708. A user may select the compare drug option 1704 if they would like to compare settings for two or more drugs the drug library. The comparing of various drug records will be described later in the specification. A user may select the copy drug option 1706 if they would like add a new drug by copying an existing drug. This may save time if there will be few differences in the settings for the drugs. In some embodiments, using the copy option 1706 to create a new drug may copy over all of the rule sets, concentrations, etc. from the copied drug to the new drug. In some embodiments, a user may indicate that they would not like to copy various items or parameter associated with a drug when using the copy drug option 1706 to create a new drug. If a user would like to create a new drug without copying an existing drug, a user may click the add a drug option 1708.

The progression of FIGS. 89-98 depicts a number of example screens which may be used to add a drug record to a care area using the DERS editor user interface. In other embodiments, the screens or process of adding a drug record to a care area may differ. In some embodiments, the items, parameters, elements, etc. which may need to be defined when adding a drug may differ. In some embodiments, the example screens may be included as part of an add a drug wizard.

Adding a drug to a care area may involve specifying a number of different parameters, elements, items, etc. When adding a drug, a user may specify a drug name for the drug. This name may be chosen from a master list provided by a DERS editor service. A user may also specify a drug type or category for the drug. A user may also specify care areas or care groups to which the drug will be added. A user may also be required to specify a number of parameters for the drug which may relate to its administration (e.g. administration route, whether the drug may administered with a secondary infusion, etc.). A user may also specify various Rule Sets and Concentration Records for the drug. In other embodiments, adding a drug may differ and may involve specifying different or additional parameters, elements, items, etc. Once the drug is added, the drug and all specified information for the drug may be saved in the DERS database.

FIG. 89 depicts an example add a drug screen 1710 which may be one of many add a drug screens 1710 which may need to be filled out when adding a drug to the drug library. The example add a drug screen 1710 shown in FIG. 89 includes a drug name parameter field 1712. The drug name parameter field 1712 may be used to define the name of the new drug which is to be added to the drug library. In some embodiments, including that shown in FIG. 89, a user may type a drug name into the drug name parameter field 1712. The drug name parameter field 1712 may suggest a list of drug names to the user based on the text typed in. As shown in FIG. 89, a user has typed in the letter "D" which has caused a list of drugs beginning with the letter "D" to be displayed on the user interface. In some embodiments, if a drug already in the drug library is displayed in the list, the drug may be displayed with an indicia 1714 to that effect. In the example embodiment shown in FIG. 89, the indicia 1714 includes the words "in library" to indicate that the drug "Dobutamine" is already in the drug library.

FIG. 90 shows another view of the add a drug screen 1710 shown in FIG. 89. As shown, the user has typed the letters "DOP" into the drug name parameter field 1712. In the example embodiment, these letters are sufficient to narrow the number of drug possibilities to a single drug, "Dopamine." In some embodiments, a user may select the drug by clicking on the desired drug in the list of drugs. The user may also finish typing out the full drug name into the drug name parameter field 1712 if desired.

Once a user has finished defining parameters in the add a drug screen 1710 shown in FIGS. 89 and 90, a user may use a next option 1716. The next option 1716 on the add a drug screen 1710 shown in FIGS. 89 and 90 may progress a user to another add a drug screen 1710 with additional parameter fields to be defined. In some embodiments, the next option 1716 on FIGS. 89 and 90 may progress a user to the add a drug screen 1710 shown in FIG. 91. The add a drug screen 1710 shown in FIG. 91 includes a number of parameter fields which may be used to define various drug details/settings for the drug. In other embodiments, an add a drug screen 1710 for these settings may include different parameter fields or a different number of parameter fields than those shown in FIG. 91.

As shown, FIG. 91 includes a drug name parameter field 1720. The drug name parameter field 1720 may be automatically populated with the drug name specified on a previous add a drug screen such as the add a drug screen 1710 shown in FIGS. 89 and 90. In some embodiments, an add a drug screen 1710 such as the one shown in FIGS. 89 and 90 may not be included. The drug name may instead be defined by populating a drug name parameter field 1720 such as the one shown in FIG. 91.

An other names parameter field 1722 may also be included in some embodiments. In some embodiments, this field may be automatically populated with other names or aliases for the drug defined in the drug name parameter field 1720. In some embodiments, the other names parameter field 1722 may not be automatically populated and the user may define any other names for the drug. In embodiments where the other names parameter field 1722 is automatically populated, a user may be able to add additional other names. For example, a user may want to add Oxytyramine and Revivan in addition to the name Intropin which has already been added in FIG. 91. A user may be able to search for the drug when programming the pump using either the name defined in field 1720 or any of the other names defined in the other name parameter field 1722.

A drug name to be displayed on device parameter field 1724 is also included in the example embodiment depicted in FIG. 91. In this field a user may define the name for the drug that they would like displayed on a medical device which is administering the drug. In some embodiments, the drug name to be displayed on device parameter field 1724 may be automatically populated with the drug name defined in field 1720. If a user would like to use a different name they may enter the desired name in field 1724. In some embodiments, a user may not be able to enter a name which is not defined in either field 1720 or 1722.

A drug category parameter field 1726 is also included on the add a drug screen 1710 shown in FIG. 91. A user may define a category which the drug belongs to in this field. In some embodiments the user may choose a category from list of drug categories. The list of drug categories may be a drop down list which is displayed when a user clicks on the drug category parameter field 1726. Such a list may help to ensure consistency if multiple users are able to add drugs to a drug library.

An AHFS classification parameter field 1728 may also be included in some embodiments. In other embodiments, a classification parameter field need not use the AHFS classification scheme. A user may define the AHFS classification for the drug in the AHFS classification parameter field 1728. In some embodiments, this field may be automatically populated based on the drug name defined in field 1720.

The add a drug screen 1710 shown in FIG. 91 also includes an incompatible medications parameter field 1730. In some embodiments, this field may be automatically populated based on the drug name defined in field 1720. In some embodiments a user may type in any medications which are incompatible with the drug being added to the drug library. In some embodiments, the user interface may display a list of drug names based on the letters which a user has typed. This may be similar to the description of how a user may populate the drug name parameter field 1712 shown in FIGS. 89 and 90.

In some embodiments, a high alert or high risk medication parameter field 1732 may also be included. The high risk medication parameter field 1732 may be used to define whether or not a drug should be categorized as a high risk drug in the drug library. It may be desirable to categorize a drug as such if the potential for an adverse effect is high when the drug is administered in an inappropriate fashion. If a drug is defined as high risk, the drug may, in some embodiments, be subject to stricter limits, a second review of medical device programming before the drug can be administered, and/or may be displayed on a medical device user interface with an indicia marking the drug as high risk.

Once a user has finished defining parameters in the add a drug screen 1710 shown in FIG. 91, a user may use a next option 1716. The next option 1716 on the add a drug screen 1710 shown in FIG. 91 may progress a user to another add a drug screen 1710 with additional parameter fields to be defined. In some embodiments, the next option 1716 on FIG. 91 may progress a user to the add a drug screen 1710 shown in FIG. 92. The add a drug screen 1710 shown in FIG. 92 includes a list of care areas which the drug may be made available to.

As shown, the add a drug screen 1710 shown in FIG. 92 includes a care area list 1740. A user may select any number of desired care areas from the care areas list 1740 for which the drug will be added to. In some embodiments, a user may also have the option to add the drug to a care group. In the example embodiment shown in FIG. 92, a user has indicated that the drug is to be added to the care area "4 West". In some embodiments, including that shown in FIG. 92, a user may select care areas from the care areas list 1740 by toggling radio buttons on or off, checking or unchecking checkboxes, clicking care area names, etc.

Once a user has finished choosing care areas in the add a drug screen 1710 shown in FIG. 92, a user may use a next option 1716. The next option 1716 on the add a care area screen 1710 shown in FIG. 92 may progress a user to another add a drug screen 1710 with additional parameter fields to be defined. In some embodiments, the next option 1716 on FIG. 92 may progress a user to a confirmation screen (not shown) which asks the user to confirm the drug should be added to the drug library. In the example embodiment, the next option 1716 on FIG. 92 may progress a user to a drug added screen such as the drug added screen 1750 shown in FIG. 93. The drug added screen 1750 shown in FIG. 93 includes a confirmation message 1752 indicating that the drug was successfully added to the drug library and selected care areas. The drug added screen may include a number of links 1754 which may allow a user to define additional parameters for the drug such as clinical uses and concentrations. In some embodiments, a drug added screen 1750 may include a back option 1756. A user may use the back option 1756 to correct any errors made when defining any of the parameters, items, elements, etc. in FIGS. 89-92. An "OK" option 1758 may also be included. A user may use the "OK" option 1758 to acknowledge that the drug has been added to the drug library and the selected care areas.

In some embodiments, a user may also enter in at least one rule set (e.g. clinical use record) and/or concentration for a drug when adding a new drug. In some embodiments, clicking the "OK" option 1758 in FIG. 93 may cause the user interface to display an add clinical use screen similar to the add clinical use screen 1760 shown in FIG. 94. In other embodiments, a drug added screen such as the drug added screen 1750 shown in FIG. 93 may not be included. FIGS. 94-98 depict an example progression of screens which may be displayed to add a clinical use and concentration to a drug.

FIG. 94 depicts an example embodiment of an add clinical use screen 1760. As shown, the add clinical use screen 1760 in FIG. 94 includes a number of parameter fields which may be used to define general settings for the clinical use. A clinical use name parameter field 1762 is included in FIG. 94. This field may be used to define a clinical use for the drug. Clinical uses may include, among others, weight based, BSA based, non-weight based, central line, peripheral line, etc. A display order parameter field 1764 is also shown in FIG. 94. The display order parameter field 1764 may be used to define in what order the clinical use will appear on the user interface of a medical device when a user is programming a therapy. The add clinical use screen 1760 in FIG. 94 also includes an infusion type parameter field 1766. This field may be used to define the type of the infusion which will be delivered by the medical device. Infusion types may include, but are not limited to, loading dose, primary, secondary, relay, continuous, bolus, etc. Some embodiments may also include a device parameter field 1768. This field may be used to define the types of medical devices to which the clinical use being added is available.

Some embodiments may include a general notes parameter field 1770, clinical advisory summary parameter field 1772, and detailed clinical advisory parameter field 1774. The general notes parameter field 1770 may be used to type in general notes about the clinical use. In some embodiments, anything entered in this field may not appear on a medical device or a user may have to use an option on a medical device user interface to view what is entered in this field. This field may be viewable by DERS editor users when reviewing the drug library. The field may, for example be used to post links, documents, studies, etc. providing information on the clinical usage being defined.

An advisory summary parameter field 1772 may be used to display a clinical advisory summary. The clinical advisory summary may be a short text version of the detailed clinical advisory which is entered into the detailed clinical advisory parameter field 1774. These fields may be displayed on a medical device during programming of a therapy. In some embodiments, a user may not define clinical advisories when adding a clinical use to a drug. Clinical advisories may instead be added by navigating to a clinical advisories list on a DERS editor user interface. In some embodiments, a user may include images, links, documents etc. as part of a clinical advisory.

One or more parameters which may be defined on the add clinical use screen 1760 shown in FIG. 94 may determine which parameters will be displayed in subsequent screens. For example, if a user defines the clinical use is for a drug which is delivered as a secondary infusion, it may require the definition of parameters which may only relate to and are only appropriate for secondary infusions. Subsequent add clinical use screens 1760 may then include these parameter fields.

Once a user has finished defining parameters in the add clinical use screen 1760 shown in FIG. 94, a user may user a next option 1716. The next option 1716 on the add clinical use screen 1760 shown in FIG. 94 may progress a user to another add a clinical use screen 1760 with additional parameter fields to be defined. In some embodiments, the next option 1716 on FIG. 94 may progress a user to the add clinical use screen 1760 shown in FIG. 95. The add clinical use screen 1760 shown in FIG. 95 includes a number of groups of parameter fields which may be used to further define information about the clinical use. The groups of parameter fields may include a general settings group, and therapy settings group, and a group of settings for the infusion type specified in the infusion type parameter field 1766 in FIG. 94. In some embodiments, each group of parameter fields may be displayed on a different add clinical use screen 1760. Some embodiments may include different parameter fields or a different number of parameter fields than those shown in FIG. 95.

The group of general settings parameter fields shown in FIG. 95 includes a can be run with secondary parameter field 1780, second review required parameter filed 1782, and VTBI zero handling for primary infusions parameter field 1784. The can be run with secondary parameter field 1780 may be used to define if the clinical use allows the drug to be delivered with a secondary infusion. The second review required parameter field 1782 may be used to define if the clinical use requires a second review before a drug may be administered. In some embodiments, a user may be able to further define if the second review can be performed by the same user or if it is required that a second individual review the programmed therapy before it may be administered.

The VTBI zero handling for primary infusions parameter field 1784 may be used to define how a medical device should behave when the programmed VTBI has been fully delivered. This field may, in some embodiments, default to KVO. In some embodiments, a user may be able to define if an alert is issued and if so what type of alert is issued when the VTBI has reached zero. A number of other possible behaviors may also be specified.

The example add clinical use screen 1760 shown in FIG. 95 includes an alert near end of therapy parameter field 1786 and alert proximity to end of therapy parameter field 1788 in the group of therapy settings parameters. The alert near end of therapy parameter field 1786 may be used to define if a medical device will issue an alert when the therapy is nearing its end. The alert proximity to end of therapy parameter field 1788 may be used to define the proximity of an issued alert to the end of the therapy. In some embodiments this field may not be defined if a user has specified an alert is not be generated in the alert near end of therapy parameter field 1786. A user may define the alert proximity in time or volume remaining in various embodiments. In some embodiments a user may additionally define a schedule on which the alert will reoccur if it has not been addressed (e.g. every 10 minutes).

The group of settings for the infusion type may differ depending upon the infusion type defined for the clinical use. In the example embodiment, the infusion type is defined as a primary continuous infusion. One parameter field for the infusion type, a dose mode parameter field 1790, is shown on FIG. 95. The dose mode parameter field 1790 may be used to define the units of measure which will be used when programming the dosage of an infusion. These units may be English or metric in some embodiments. Additionally, in some embodiments the units defined may be volume/time, volume/weight/time, volume/BSA/time, etc.

Once a user has finished defining parameters in the add clinical use screen 1760 shown in FIG. 95, a user may use a next option 1716. The next option 1716 on the add clinical use screen 1760 shown in FIG. 95 may progress a user to another add a clinical use screen 1760 with additional parameter fields to be defined. In some embodiments, clicking the next option 1716 on FIG. 95 may progress a user to the add clinical use screen 1760 shown in FIG. 96. The add clinical use screen 1760 shown in FIG. 96 includes a number of groups of parameter fields which may be used to further define information about the clinical use. The groups of parameter fields may include additional parameter fields which are conditional on the type of infusion defined for the clinical use. In some embodiments, each group of parameter fields may be displayed on a different add clinical use screen 1760. Some embodiments may include different parameter fields or a different number of parameter fields than those shown in FIG. 96.

In some embodiments, a default dose rate parameter field 1800 may be included on the add clinical use screen 1760 shown in FIG. 96. This field may be used to define a default does rate for the clinical use. In some embodiments, this field may not be included for certain drugs. This field may automatically update to reflect the units of measure defined in the dose rate parameter field 1790 shown in FIG. 95.

The example add clinical use screen 1760 shown in FIG. 96 also includes a number of parameter fields which may be used to define dose rate limits. In the example embodiment, a dose rate high hard limit parameter field 1802, a dose rate high soft limit parameter field 1804, a dose rate low soft limit parameter field 1806, and a dose rate low hard limit parameter field 1808 are shown. The dose rate high hard limit parameter field 1802 and dose rate high soft limit parameter field 1804 may be used to define the high limits for dose rates which may be entered during programming of a medical device. The dose rate low soft limit parameter field 1806 and the dose rate low hard limit parameter field 1808 may be used to define the low limits for dose rates which may be entered during programming of a medical device. These limits may help to ensure that correct and safe information is programmed into a medical device.

The add clinical use screen 1760 shown in FIG. 96 also includes a dose titration increase hard limit parameter field 1810. In some embodiments, additional dose titration limit parameter fields may be included. For example some embodiments may include a dose titration increase soft limit parameter field (not shown). Dose titration interval limit parameter fields may also be included to define a minimum time limit between titrations. A user may use the dose titration increase hard limit parameter field 1810 to define a maximum amount that a user may titrate a dose of medication. In some embodiments, this limit may be defined as a percentage of the original dose.

Once a user has finished defining parameters in the add clinical use screen 1760 shown in FIG. 96, a user may use a next option 1716. The next option 1716 on the add clinical use screen 1760 shown in FIG. 96 may progress a user to another add a clinical use screen 1760 with additional parameter fields to be defined. In some embodiments, clicking the next option 1716 on FIG. 96 may progress a user to the add clinical use screen 1760 shown in FIG. 97. The add clinical use screen 1760 shown in FIG. 97 includes a number of groups of parameter fields which may be used to further define information about the clinical use. The groups of parameter fields may include a bolus settings parameter group and a loading dose parameter group. In some embodiments, each group of parameter fields may be displayed on a different add clinical use screen 1760. Some embodiments may include different parameter fields or a different number of parameter fields than those shown in FIG. 97.

In the example embodiment shown in FIG. 97 the bolus settings parameter group includes an is bolus allowed parameter field 1820. This field may be used to determine if a user may deliver a bolus when administering a therapy using the clinical use. In some embodiments, there may be additional bolus settings parameters. For example, parameter fields may be included for bolus hard and soft limits in some embodiments.

In the example add clinical use screen 1760 shown in FIG. 97, the loading dose parameters group includes a loading dose allowed parameter field 1822 and a loading dose settings parameter field 1824. The loading dose allowed parameter field 1822 may be used to define whether or not a loading dose may be administered when using the clinical use. The loading dose settings parameter field 1824 may be used to define various settings for loading doses if a loading dose is allowed. In some embodiments, the loading dose settings parameter field 1824 may instead be a number of parameter fields. Such fields may, for example, include parameter fields for parameters 7.01-7.18 of Table 9.

Once a user has finished defining parameters in the add clinical use screen 1760 shown in FIG. 97, a user may use a next option 1716. The next option 1716 on the add clinical use screen 1760 shown in FIG. 97 may progress a user to another add a clinical use screen 1760 with additional parameter fields to be defined. In some embodiments, clicking the next option 1716 on FIG. 97 may progress a user to a confirmation screen (not shown) which prompts the user to confirm that the clinical use should be added. In some embodiments, clicking the next option 1716 on FIG. 97 may progress a user to an add concentration screen such as the add concentration screen 1830 shown in FIG. 98. The add concentration screen 1830 shown in FIG. 98 includes a number of groups of parameter fields which may be used to define information about a drug concentration. Some embodiments may include different parameter fields or a different number of parameter fields than those shown in FIG. 98.

In the example embodiment shown in FIG. 98, a group of general concentration parameters are included. As shown, this group of parameters includes an allow operator change parameter field 1832 and a display format parameter field 1834. The allow operate change parameter field 1832 may allow an operator to change the concentration defined in the concentration record when programming the medical device. The display format parameter field 1834 may be used to define how the concentration will be displayed on the user interface of a medical device. A user may for example choose to display the concentration as an amount/diluent volume, or as a concentration (e.g. percentage of drug in diluents).

A group of parameter fields which may be used to define the concentration are also shown in FIG. 98. As shown, a drug amount in container parameter field 1836 is included. This field may be used to define the amount of a drug in a container. In some embodiments a user may define a numeric value and a unit of measure to define this parameter field. A container volume parameter field 1838 is also included in the example embodiment. This field may be used to define the volume of the container in which the drug will be held. In some embodiments, the user may define both a numeric value and unit of measure for this parameter field. Some embodiments may include a default VTBI parameter field 1840. This field may be used to define a default VTBI which may be used when a user programs a medical device using the concentration record. Some embodiments may not include this field. FIG. 98 also includes a concentration parameter field 1842. In some embodiments this field may be automatically populated when sufficient information has been entered in other fields. This field may be used to define the concentration of the drug for the concentration record which is to be added.

Once a user has finished defining parameters in the add concentration screen 1830 shown in FIG. 98, a user may use a next option. Clicking the next option may progress a user to another add concentration screen 1830 with additional parameter fields to be defined. In some embodiments, such as the embodiment in FIG. 98, a next option may not be included on the add concentration screen 1830. In such embodiments, a finish option 1844 may be included on the add concentration 1830 screen. Clicking the finish option in FIG. 98 may add the concentration to the drug library.

FIG. 99 depicts an example embodiment of a drug screen 1700. The drug, clinical use, and concentration added to the drug library in the example progression of FIGS. 89-98 are included in the drug list 1702 shown in FIG. 99. In some embodiments, a user may be returned to a drug screen 1700 after a user has finished adding or modifying a drug, clinical use, or a concentration to the drug library. In such embodiments, when the user is returned to the drug screen 1700 the drug record which was added or modified may be highlighted and shown with a detailed view.

FIGS. 100-104 depict a number of alternate examples of add clinical use screens 1760 which may be displayed on a DERS editor user interface. The alternate examples of add clinical use screens 1760 shown in FIGS. 100-104 are similar to those shown in FIGS. 94-97. The add clinical use screens 1760 shown in FIGS. 100-104 are organized similarly to and include many of the same parameter fields as those displayed in FIGS. 94-97. The example add clinical use screens 1760 shown in FIGS. 100-104 include a number of additional example parameter fields which may be used to define a clinical use.

FIG. 100 includes a medication route parameter field 1850. This field may be used to define the medication route to be used for a specific clinical use. Possible medication routes may include, but are not limited to intravenous, subcutaneous, enteral, gastro-intestinal, intrathecal, epidural, arterial, intramuscular, intraperitoneal, intraosseous, etc. A medication site parameter field 1850 is also included in the example embodiment in FIG. 100. This field may be used to define, for example, the infusion site which is to be used with the clinical use. A delivery method parameter field 1854 is also shown in FIG. 100. This field may be used to define the delivery method for the clinical use. Delivery methods may include, but are not limited to, infusion, patient controlled infusion, oral administration, etc.

FIGS. 100-103, also include a finish later option 1858. A user may be able to use this option to finish adding the clinical use at a later time. This may be desirable, if for example, a user has a question or would like to research what an appropriated value for a parameter may be. Additionally, this option may be useful if a user does not have enough time to finish defining all of the parameters for a clinical use at the current time. If a user uses the finish later option any progress made up to that point may be saved. Other DERS editor screens, for example add a care areas screens, may also include such an option as well.

The add clinical use screen 1760 shown in FIG. 101 includes a VTBI handling for secondary infusion parameter field 1860. This field may be used to define how medical devices behave when the full programmed volume of a secondary infusion being administered by a medical device has been delivered. For example, a user may specify that the medical device delivering the primary infusion resumes the primary infusion and issues a notification to this effect.

The add clinical use screen 1760 shown in FIG. 103 includes a dose titration increase soft limit parameter field 1870. This field may be used to define a soft limit for dose titration increases. This field may be defined as a percentage of the original dose in some embodiments.

The example embodiment shown in FIG. 104 includes a loading dose secondary parameter field 1880. This field may be used to define various parameters for a loading dose which is administered as part of the clinical use. In some embodiments, there may be a number of parameters fields instead of a single secondary loading dose parameter field 1880. These fields may be used to define various parameters such as parameters 7.01-7.18 of Table 9.

A group of other parameter fields is also included in FIG. 104. A KVO value parameter field 1884 is included in this group in the example embodiment. This field may be used to define a KVO value for the clinical use. An air infusion limit parameter field 1886 is also included in FIG. 104. This field may be used to define the sensitivity for an air-in-line alert or alarm. In some embodiments, a user may define a volume/time when defining the air infusion limit parameter field 1886. A number of occlusion re-starts parameter field 1888 is also shown in FIG. 104. This field may be used to define the number of re-starts a medical device will attempt before issuing an occlusion alert or alarm.

FIG. 105 depicts an example view of a drug screen 1700. As mentioned above, in reference to FIG. 88, a user may be able to click a drug in a drug list 1702 on the drug screen 1700 to view more detailed information about the drug. Drugs in a drug list 1702 may, for example, be expandable. If a drug is clicked, a detailed sub-list 1890 for the specific drug may be displayed on the DERS editor user interface. In some embodiments, this detailed sub list 1890 may appear in a modal window as shown in FIG. 105. In other embodiments, drugs in the drug list may be expandable. Clicking a drug may cause the drug to expand and a number of rows containing the detailed sub list 1890 for the drug may be displayed beneath the specific drug in the drug table 1702 (see, for example, FIG. 109). In such embodiments, the detailed sub list 1890 may be displayed on the DERS user interface in a manner which makes it clear that the detailed sub list 1890 is associated with the specific drug selected by the user. In some embodiments, a user may have a number of detailed sub lists 1890 for different drugs open or in expanded state at the same time.

A detailed sub list 1890 for a drug may in some embodiments at least include a row for each care area the drug has been added to. A row may also be included for each clinical use and concentration of the drug in each care area. In some embodiments a row may be added in the detailed sub list 1890 which provides quick links for a user to add the drug to a care area, add a clinical use for the drug, or add a concentration for the drug. In other embodiments, the detailed sub list 1890 may differ.

If desired a user may be able to click a row in the detailed sub list 1890 in order to display and/or edit the various parameters defined for the drug, clinical use, or concentration selected. This may, in some embodiments, cause a detailed drug library entry screen, such as the detailed drug library entry screen 1900 shown in FIG. 106, to be displayed on the DERS editor user interface. In some embodiments, a user may be able to copy a drug, clinical use, or concentration entry in the drug library by selecting a row in the detailed sub list 1890 and clicking a copy option (not shown in FIG. 105). In some embodiments, a user may be able to select multiple entries in a detailed sub list 1890 or may be able to select multiple entries in a number of detailed sub lists 1890 and compare the defined parameters of the selected entries. The DERS editor user interface may display the comparison in a side-by-side manner.

FIG. 106 depicts an example drug library entry screen 1900. Such a screen may display a list of defined items, elements, parameters, etc. associated with a selected drug library entry. A drug library entry screen 1900 may include a drug library entry identifier 1902. The drug library entry identifier 1902 may identify the drug library entry being displayed. The drug library entry identifier 1902 may, for example, be a care area name, or drug name. In some embodiments, the drug library entry identifier 1902 may identify a hierarchy to which the drug library entry belongs. For instance, a drug library entry for a clinical use may be identified by a drug library identifier including the drug name, care area, and clinical use name. In the example embodiment, the drug library entry identifier 1902 identifies the drug name, "Acyclovir", the care area, "Surgery", and the clinical use name "Non-Weight Based".

A progress summary 1904 may also be included on the detailed drug library entry screen 1900 for a drug library entry. The progress summary 1904 may in some embodiments, indicate how many parameter fields have been completed, how many parameter fields remain to be completed, how many fields are associated with an update request or other feedback, how many fields require a user's review, etc.

A drug library entry screen 1900 may also show an entry parameters list 1906. An entry parameters list 1906 may show a list of all defined parameters, elements, items, etc. associated with the drug library entry. The entry parameters list 1906 may be divided into a number of expandable groups to limit the amount of information shown on the user interface at one time. The groups may be expanded to show related parameter values which fall into that group. For example, a general settings group has been expanded in the example embodiment shown in FIG. 106. Groups may be expanded by a click, double click, or any other suitable action. In some embodiments, a user may be able to edit various parameters, items, or elements, by clicking a parameter in the entry parameters list 1906. In some embodiments, a notification 1908 may be included in association with each group or parameter in the entry parameters list 1906. In the example embodiment shown in FIG. 106, a notification 1908 indicating the number of empty parameter fields in each group is displayed. In other embodiments, a notification 1908 may indicate the number of parameters in a group needing review or the number of parameters in a group which are associated with an update or change request. If the entry parameters list 1906 is too large to be displayed on a user interface for the DERS editor, only a portion of the list may be displayed on the user interface and a scroll bar or the like may be included to allow a user to view the other information when and if desired.

A number of buttons, links, options, or the like may also be included on a drug library entry screen 1900. The example drug library entry screen 1900 shown in FIG. 106 includes a save changes option 1910, a copy option 1912, and a delete option 1914. These options are depicted as virtual buttons in the example embodiment in FIG. 106, but need not be buttons in all embodiments. If a user makes changes to any parameters, items, elements, etc. in a entry parameters list 1906, a user may use the save changes option 1910 to save the changes. In some embodiments, a save changes option 1910 may be disabled until a user has changed the drug library entry in some way. The copy option 1912 may be used to copy the drug library entry and create a new drug library entry using the defined, parameters, items, elements, etc. of the old drug library entry. The delete drug library option 1914 may be used to delete the drug library entry in some embodiments. A back option 1916 or button may also be included in some embodiments. This option may return a user to a drug screen such as the drug screen 1700 shown in FIG. 105.

In some embodiments, a drug library entry screen 1900 may include subordinate or child tabs 1918 which may be used to view child drug library entries. For example, if the drug library entry screen 1900 is displaying information for a clinical use of a drug in a particular care area, child tabs 1918 for any concentration records defined for the clinical use may be included. The example embodiment shown in FIG. 106 includes one child tab 1918 for a concentration record.

FIG. 107 depicts an example of a drug screen 1700 where a detailed sub list 1890 for a drug is displayed. The drug screen 1700 and detailed sub list 1890 shown in FIG. 107 are the same as those shown in FIG. 105. As shown, a number of rows in the detailed sub list 1890 have been selected. A user may select these various rows by, for example, checking or unchecking checkboxes for each row. Once at least two rows have been selected, a compare function may be enabled. In the example embodiment, a compare option 1920 becomes enabled on the user interface after at least two rows have been selected. A user may use the compare option 1920 to compare the selected drug library entries.

FIG. 108 depicts a drug library entry comparison screen 1930 in which two drug library entries are being compared. The drug library entries being compared in FIG. 108 are those selected in FIG. 107. In the example embodiment shown in FIG. 108, the two drug library entries are displayed on the user interface in a side-by-side manner. In other embodiments, the user interface may display the compared drug entries in any other suitable way. As shown, the compared drug library entries may be displayed using entry parameter lists 1932 for the compared drug library entries which are similar to the entry parameter list 1906 shown and described in FIG. 106.

Some embodiments may allow a user to edit one of the compared drug library entries. In the example embodiment, an edit option 1934 is included and may be used if it desired to edit an item, parameter, element, etc. associated with one of the compared drug library entries. In some embodiments, using an edit option 1934 may cause a drug library entry screen similar to the drug library entry screen 1900 shown in FIG. 106 to be generated for the selected drug library entry. In some embodiments, the drug library entry may be edited while the drug library entry comparison screen 1930 is still displayed on the user interface. A back option 1916 or back button may also be included on a drug library entry comparison screen 1930 in some embodiments. The back option 1916 or button may be used by a user to return to the drug screen 1700.

FIG. 109 depicts another example drug screen 1700 in which a detailed sub list 1890 for a drug is displayed. The detailed sub list 1890 shown in FIG. 109 is different from that depicted in FIG. 105 or FIG. 107. As shown, the detailed sub list 1890 shown in FIG. 109 is shown as a list, but also is connected together as a hierarchical tree. Additionally, the detailed sub list 1890 includes a column which identifies the device type for each row. In the example embodiment this column uses skeuomorphic indicia 1940 to indicate the device type. Where suitable, skeuomorphic indicia may be used on the DERS editor user interface to display information while conserving screen space. The skeuomorphic indicia used in FIG. 109 include a syringe icon to indicate a syringe pump and a solution bag to indicate an LVP pump. As shown in FIG. 109, three rows of the detailed sub list 1890 have been selected. The compare option 1920 on the drug screen 1700 is consequentially enabled.

FIG. 110 depicts a drug library entry comparison screen 1930 in which three drug library entries are compared. The drug library entry comparison screen 1930 shown in FIG. 110 differs from that shown in FIG. 108. As shown, the compared drug library entries are shown in a side-by-side manner. In the example embodiment, the parameters for the drug library entries are displayed in a comparison table 1950. As shown, the rows of the comparison table 1950 may be identified by parameter field names. The columns of the comparison table 1950 may be identified by the drug library entries being compared. The comparison table 1950 may be populated with the parameter field values for the parameter fields of each drug library entry. In some embodiments, rows of the comparison table 1950 in which differences between the defined parameter values for the compared drug library entries exist may be highlighted or otherwise visually marked or indicated.

In embodiments of drug library entry comparison screens 1930 which display a comparison of drug entries using a comparison table 1950, a user may be able to hide or expand various portions of the comparison table 1950. In some embodiments, the comparison table 1950 displayed may display child drug library entries or parent drug library entries as hidden content of the table which may be expanded if desired. As shown in the example comparison table in FIG. 110, the clinical use drug library entries (parent drug library entries) are shown as hidden content. A user may use an expand/hide option 1952 associated with the shown or hidden content to toggle the content between a shown or hidden state on the DERS editor user interface.

In some embodiments, the drug library entry comparison screen 1930 shown in FIG. 110 may include a differences only option 1954. The difference only option 1954 may used to hide parameters in a drug entry comparison for which there are no differences between the compared drugs entries. A back option 1916 or button may also be included. The back option 1916 or button may be used by a user to return to the drug screen 1700.

FIG. 111 depicts an example embodiment of a drug library entry comparison screen 1930 in which only parameters where there are different defined values between the compared drug library entries are shown in the comparison. FIG. 111 depicts an example of how the drug comparison table 1950 in FIG. 110 would look if a user were to use the differences only option 1954 shown in FIG. 110. As shown, the drug comparison table 1950 in FIG. 111 only includes rows of the drug comparison table 1950 in FIG. 110 where all of the parameter values are not the same.

In some embodiments, when the drug library entry comparison screen 1930 is displaying a differences only comparison, a differences only option 1954 (see FIG. 110) may not be displayed. In some embodiments, the differences only option 1954 may be replaced with, for example, view full comparison option (not shown) which, when used, causes the full comparison to be displayed on the DERS editor user interface.

In some embodiments, the DERS editor may include a medical device programming simulator. This simulator may provide a user with a virtual simulation of a medical device user interface. In some embodiments, a user may be able to choose between a number of possible medical device user interfaces they would like to simulate. For example, a user may choose to simulate the user interface of a type of syringe pump or a type of large volume pump. The simulator may allow a user to simulate manual button presses, finger input on a touch screen, switch toggling, etc. using a mouse.

The medical device programming simulator may allow DERS editor users to view how a drug library entry would look on a medical device if the entry were to be included in a DAL file released to the device. This may be desirable in situations where the user editing the drug library does not commonly use a medical device which they are designing a drug library for. Additionally, the medical device programming simulator may allow a user to dry run the drug library on a virtual device before releasing a DAL file for the drug library to that device. The medical device programming simulator may also be used during the review of drug library entries. This may be helpful in cases where a reviewing user is a nurse, for example, and frequently uses the device being simulated.

FIGS. 112-114 depict a number of example medical device programming simulator screens 1960. A user may navigate to a medical device programming simulator screen 1960 by clicking the proper tab 1598 on the DERS editor user interface. In some embodiments, the user may then select a device type to simulate. The DERS editor may then display a medical device programming simulator screen 1960 with the home screen, main menu, etc. of the simulated device. The example medical device programming simulator screen 1960 shown in FIG. 112 depicts a user programming a clinical use for a therapy using the drug acyclovir. The example medical device programming simulator screen 1960 shown in FIG. 113 depicts a user programming a dose, rate, VTBI, and time for a dopamine infusion on a simulated infusion pump user interface. FIG. 114 shows another example of a medical device programming simulator screen 1960 in which a user is searching for a drug in a drug list on a simulated medical device user interface.

As mentioned above in relation to FIG. 46, the medical device programming simulator may be context sensitive. When a user navigates to the medical device programming simulator from another DERS editor screen, the medical device programming simulator may automatically open to a specific medical device programming simulator screen 1960 which is relevant to that DERS editor screen. For example, if a user were to open the medical device programming simulator from the drug screen 1700 shown in FIG. 109, the medical device programming simulator may open to the medical device programming simulator screen 1960 depicted in FIG. 113.

FIGS. 115-131 depict a number of example CQI screens 1970. A user may navigate to a CQI screen 1970 by clicking the proper tab 1598 on the DERS editor user interface. CQI screens 1970 may allow a user to view various CQI data that may be useful or of interest. This data may, for example, be used when revising a DAL file. The data may help to identify where room for improvement exists and bring attention to items, parameters, elements, etc. that may need to be changed. Additionally, access to CQI data through the DERS editor user interface provides a wealth of other benefits. For instance, a user may link to specific CQI data to provide context for an update or change request. The data may also be used to determine why and how an adverse event may have occurred and what may be done to prevent similar events in the future.

CQI screens 1970 may display CQI data and information to a user in any of a various number of CQI reports. The reports may be user selectable and modifiable. In some embodiments, CQI reports may be displayed in summary report form. A user may be able to drill down and/or filter data to view more detailed CQI reports. In some embodiments, users may be able to view data as specific as individual therapy data. Graphs, charts, and other visual aids may be used on various CQI screens 1970. In some embodiments, a user may be able to toggle how data is presented (e.g. trend data over a time period v. totals for the time period). In some embodiments, various CQI reports may include a visual which is accompanied by additional textual report details. In such embodiments, the visual may serve as a "snapshot" which quickly conveys important aspects of a report in an easily comprehensible way. In some embodiments, a user may be able to click, double click, etc. elements in a CQI report chart, graph, table, etc. to drill down on various aspects of the CQI report. Based on the report type selected, filters applied, drill downs requested, etc., the DERS editor service may query a CQI database such as database 106 in FIG. 4 for the appropriate information. This information may then be rendered by a web tier into the proper/requested report format. The report may then be displayed on the DERS editor user interface. CQI screens 1970 may also include links, buttons, options, utilities, or the like which may allow a user to save, print, export, link to, load, etc. desired CQI reports.

As shown in FIG. 115, a CQI screen 1970 may include a report type indicator 1974. The report type indicator 1974 may specify the type of report (e.g. compliance report, drug report, infusion report, etc.) which is being displayed. In FIG. 115, the report type indicator 1974 reads "Compliance Report". In some embodiments, a user may be able to click the report type indicator 1974 to display a different type of report on the CQI screen 1970.

In some embodiments and/or for some CQI reports, a filter utility 1976 may be displayed on the CQI screen 1970. In the example embodiment shown in FIG. 115, a filter utility 1976 is included on the CQI screen 1970. The filter utility 1976 may be used to refine or drill down on what data is displayed in the CQI report. A filter utility 1976 may provide a user with a number of predefined filtering categories of filters which may be applied to CQI data. In some embodiments, various filtering categories shown in a filter utility 1976 may be expandable. In an expanded state, the filtering categories include the category name and a number of possible individual filters within that category that a user may apply. A care area filter category, for example, may be expanded to show a list of care areas for which CQI data is available. A user may then indicate which care areas they would like the CQI report to include data from to apply a care area based data filter to the CQI report. Filter categories may be caused to be displayed in the expanded state by any suitable user input. In the example embodiment clickable expand icons 1980 may be clicked to cause the category to be displayed in an expanded state.

A user may be able to filter based on data produced by specific levels of an institution/organization's organizational hierarchy. In the example embodiment shown in FIG. 115, a user may use the filter utility 1976 to filter CQI data displayed in the report by region, facility/institution, care area, etc. A user may be able to filter based on data produced by specific groups of medical devices. In the example embodiment shown in FIG. 115, a user may be able to filter report data based on the device type (e.g. syringe pump, LVP, PCA, etc.). A user may also use the filter utility 1976 in FIG. 115 to filter report data by DAL version running on a medical device. In some embodiments, a user may be able to filter report data based on date. In the example embodiment shown in FIG. 115, a user may filter CQI report data using the filter utility 1976 based on a date range which may be defined by the user.

In some embodiments, a user may also have the option of defining and applying customized filters to CQI report data. In various embodiments, a user may want to apply a custom filter based on a specific drug, specific medical device, or a specific care giver or clinician. In some embodiments, a user may apply a custom filter based on other criteria. For example, a user may apply a custom filter to filter CQI data for infusions where a soft limit override occurred during programming. In the example embodiment shown in FIG. 115, a custom filter may be defined and applied using a search bar 1978 in the filter utility 1976. In some embodiments, if a user enters a search query into the search bar 1978, a results list (not shown) of possible filtering options may be displayed on the CQI screen 1970. In some embodiments, the results list may appear in a modal window displayed over the CQI screen 1970. In such embodiments, a user may select one or a number of filtering criteria from the results list to apply the filter. A filter identifier (not shown) identifying the applied filter may be displayed in the filter utility 1976 to indicate that the filter has been applied to CQI data displayed in the CQI report.

In some embodiments and/or for some CQI reports a number of links, buttons, options, or utilities may be displayed on the CQI screen 1970. In the example shown in FIG. 115, a print utility 1982, a link utility 1984, an export utility 1986, and a save utility 1988 are included. The print utility 1982 may be used to print a hard copy of the displayed CQI report. The link utility 1984 may be used to generate a link to the CQI report. The export utility 1986 may be used to export CQI data from a CQI report for use in another program or analysis tool. The save utility 1988 may be used to save a copy of the displayed CQI report for later viewing.

FIG. 115 depicts an example CQI screen 1970 in which a compliance report 1972 is displayed. A compliance report 1972 may provide a user with CQI data and information which relates to compliance of therapies to entries, limits, etc. defined in a DAL file. A compliance report 1972 may display CQI data in any suitable fashion or number of different fashions (e.g. chart, graph, table, diagram, etc.). The compliance report 1972, shown in FIG. 115, shows an overall summary of compliance for a number of institutions. Such a compliance report 1972 may be generated for an IDN for example.

As shown, the specific compliance report depicted in FIG. 115 includes a compliance chart 1990 which shows compliance totals for a time period selected in the filter utility 1972. The compliance chart 1990 is a pie chart in the example embodiment. The compliance chart 1990 includes a title 1992 which identifies what is being displayed by the chart. In FIG. 115, the chart title 1992 reads "Compliance Overall: All Facilities, All Care Groups, Jan. 1, 2013-Feb. 1, 2013. The chart may be color coded. As shown, various segments, bars, data points, etc. of a chart or graph on a CQI report may be labeled or captioned with additional details. In the example embodiment, the compliance chart 1990 includes labels for each segment of the chart that detail the data set, percentage, and number of infusions for each segment. A total number of infusions is also shown.

A data presentation adjuster 1994 is also shown in FIG. 115. A user may use the data presentation adjuster 1994 to toggle between a number of different ways data may be displayed on the CQI screen. In the example embodiment in FIG. 115, a user may toggle between the shown "Totals" view and a "Trends" view. Other view types may also be available in other embodiments. If a user were to select the "Trends" view, the compliance chart 1990 may be replaced with a compliance trend graph (not shown). This graph may, for example, be a line graph which graphs non-compliance and/or compliance over time.

In some embodiments a user may be able to scroll down on the user interface to view additional information. FIG. 116 depicts an example CQI screen 1970 which includes a portion of a CQI report. The CQI report data shown in FIG. 116 is shown in a tabular format. The CQI screen 1970 shown in FIG. 116 is a scrolled down view of the CQI report in FIG. 115. In some embodiments, scrolling down on a CQI report may display data shown in a chart or graph portion of a CQI report in tabular format. In some embodiments, scrolling down on a CQI report may show a more detailed breakdown of data shown in a CQI "snapshot" displayed at the top of the CQI report. This more detailed breakdown need not be shown in a tabular format.

In the example embodiment shown in FIG. 116, a number of compliance tables 2000 are shown. The compliance tables 2000 give a more nuanced breakdown of the compliance data shown in the compliance chart 1990 in FIG. 115. In the example in FIG. 116, as indicated by the compliance table 2000 titles, the compliance tables 2000 detail compliance totals per institution and per clinicians. Other embodiments may, for example, give a breakdown by care area, drug, device type, etc. In some embodiments, a user may be able to show or hide various tables such as compliance tables 2000 by using an expand icon similar to the expand icons 1980 shown and described in relation the filter utility 1976 in FIG. 115.

In some embodiments, a user may be able to click, double click, etc. elements in a CQI report chart, graph, table, etc. to "drill down" on various aspects of the CQI report. For example, if a user were to click the title of the compliance table 2000 for facilities in FIG. 116, a user may cause a Non-Compliance by Institution CQI report such as that shown in FIG. 117 to be generated and displayed on the CQI screen 1970. If a user were to click on the Non-Compliant segment of the compliance chart 1990 shown in FIG. 115, a user may cause a Non-Compliant Infusions CQI report such as that shown in FIG. 118 to be generated and displayed on the CQI screen 1970.

Referring specifically to FIG. 117, a CQI compliance report for non-compliant infusions by institution is shown. The portion of the compliance report shown in FIG. 117 includes a compliance chart 1990. The compliance chart 1990 shown in FIG. 117 is a pie chart illustrating the breakdown of non-compliant infusions in various institutions. As shown, the CQI report may also include a back option 2010 or button if the report being displayed is a drilled down version of a previous report. The back option 2010 or button may be used to return to the previous report which was displayed on the CQI screen 1970.

FIG. 118 depicts a non-compliance report. As may be true of various embodiments, the CQI screen 1970 shown in FIG. 118 is slightly different from those shown in FIG. 115-117. The portion of the non-compliance report shown in FIG. 118 includes a compliance chart 1990. The compliance chart 1990 is a pie chart which gives a breakdown of non-compliant infusions by category of non-compliance.

Also shown in FIG. 118 is a favorite reports list 2020. Various embodiments may include a favorite reports list 2020 on CQI screens 1970. A favorite reports list 2020 may include a list of commonly viewed CQI reports. In some embodiments, a user may add desired reports to a favorite reports list 2020. Clicking a report on a favorite reports list 2020 may cause the report to be generated and displayed on the CQI screen 1970.

FIG. 119 depicts an example embodiment of a CQI screen 1970. As shown in FIG. 119, a user may click a save utility 1988 to add the report to a favorite reports list such as the favorite reports list 2020 shown in FIG. 118. In some embodiments, using the save utility 1988 may prompt a user to select from a number of different options. In the example embodiment, the user is prompted to choose between saving the report so that it appears on their dashboard screen and adding it to a favorite reports list. Other embodiments may include other options.

FIG. 120 depicts an example embodiment of a CQI screen 1970. A save window 2030 is shown in FIG. 120. As shown, the save window 2030 is a modal window prompting a user to specify a name for the report before saving it. Save windows 2030 may differ in other embodiments. Such a window may, for example, be generated if a user uses a save utility, such as the save utility 1988 in FIG. 119, to save a report. In some embodiments, a user may be able to modify the report before saving. For example, a user may adjust the time frame for the report. In the example embodiment, a user has adjusted the time range such that filtering data used in the report being saved will be used to filter CQI data generated over the previous month when the saved report is opened.

FIG. 121 depicts an example embodiment of a CQI screen 1970. In the example embodiment, a link window 2040 is displayed. A link window 2040 may provide a link to the current CQI report. This link may be copied by a user. The link may then be saved to allow a user to later follow the link to view the CQI report. The link may also, for example, be placed in an update or change request for a drug library entry to provide context for the request. A user may, in some embodiments, cause a link window 2040 to be displayed by clicking a link utility 1984 on a CQI screen 1970.

FIG. 122 depicts an example embodiment of a CQI screen 1970. The example CQI screen 1970 includes a CQI report for compliance by care area. As show, the CQI report includes a compliance chart 1990. In the example embodiment, the compliance chart 1990 is a bar graph. The compliance chart 1990 shows the percentage of complaint infusions by care area. Additionally, the CQI report in FIG. 122 includes two compliance tables 2000. One of the compliance tables 2000 displays compliance by care area while the other displays compliance by clinicians.

FIG. 123 depicts an example embodiment of a CQI screen 1970. As shown, the example CQI screen 1970 in FIG. 123 depicts a CQI report for compliance in the care area "4 West". Such a report may, for example be generated and displayed by clicking on the "4 West" bar in the compliance chart 1990 shown in FIG. 122. Such a report may also be generated and displayed by using the filtering utility 1976 in FIG. 122 to filter the CQI report by the care area "4 West". The CQI report includes a compliance chart 1990. The compliance chart 1990 is a pie chart illustrating the percentage of compliant and non-compliant infusions in FIG. 123. The CQI report shown in FIG. 123 also includes a compliance table 2000. The compliance table 2000 depicted in FIG. 123 provides a breakdown of the percentage of compliant infusions for each clinician working in the care area "4 West".

FIG. 124 depicts an example embodiment of a CQI screen 1970. As shown, the example CQI screen 1970 shown in FIG. 124 depicts a CQI report for non-compliance in the care area "4 West". Such a CQI report may be generated and displayed, for example, by clicking the non-compliant infusion segment of the compliance chart 1990 shown in FIG. 123. As shown, the compliance report includes a compliance table 2000 which details each non-compliant infusion that occurred in the care area for the time range specified in the filter utility 1976. The compliance table 2000 may include data such as the date of the infusion, time the infusion was initiated, clinician name, drug, and a pump ID. In some embodiments, a user may be able to click, double click, etc. a specific infusion in the compliance table 2000 in FIG. 124 to view the infusion story for that infusion.

FIG. 125 depicts an example embodiment of a CQI screen 1970. As mentioned above in relation to FIG. 115, a user may, in some embodiments, click a report type indicator 1974 to display a different type of report on a CQI screen 1970. In the example embodiment shown in FIG. 125 a dropdown list 2050 is displayed below the report type indicator 1974. A dropdown list 2050 may be displayed if a user clicks the report type indicator 1974. In the example embodiment, the dropdown list 2050 includes an infusion report selection and a drug report selection. In various embodiments, the report type selections or number of report type selections may differ. In some embodiments, a dropdown list 2050 may not be included. Report type selections may instead be displayed in another suitable manner (e.g. a window) in other embodiments.

FIG. 126 depicts an example embodiment of a CQI screen 1970 in which an infusion report 2060 is displayed. An infusion report 2060 may provide a user with CQI data and information which relates to events and infusions administered by medical devices. An infusion report 2060 may display CQI data in any suitable fashion or number of different fashions (e.g. chart, graph, table, diagram, etc.). The infusion report 2060 shown in FIG. 126 shows an overall summary of compliance for a number of institutions. Such an infusion report 2060 may be generated for an IDN, for example.

As shown, the specific infusion report 2060 depicted in FIG. 126 includes an infusions chart 2062 which shows infusion summary data for a time period selected in the filter utility 1972. The infusions chart 2062 is a bar graph in the example embodiment. The infusions chart 2062 includes a title 2064 which identifies what is being displayed by the chart. In FIG. 126, the chart title 2064 reads "Infusions by Institution: All Institutions, All Care Groups, Jan. 1, 2013-Feb. 1, 2013. The chart may be color coded. As shown, various segments, bars, data points, etc. of a chart or graph on a CQI report may be labeled or captioned with additional details. In the example embodiment the infusions chart 2062 includes labels for each bar of the chart that detail the data set, number of infusions, and number of events for each bar. A total number of infusions is also shown.

In some embodiments, a user may be able to scroll down on the user interface to view additional information. FIG. 127 depicts an example CQI screen 1970 which includes a portion of a CQI report. The CQI report data shown in FIG. 127 is shown in a tabular format. The CQI screen 1970 shown in FIG. 127 is a scrolled down view of the CQI report in FIG. 126. In some embodiments, scrolling down on a CQI report may display data shown in a chart or graph portion of a CQI report in tabular format. In some embodiments, scrolling down on a CQI report may show a more detailed breakdown of data shown in a CQI "snapshot". This more detailed breakdown need not be shown in a tabular format.

In the example embodiment shown in FIG. 127, a number of infusion tables 2070 are shown. The infusion tables 2070 give a more nuanced breakdown of the infusion data shown in the infusions chart 2062 in FIG. 126. In the example in FIG. 127, as indicated by the infusion table 2070 titles, the infusion tables 2070 detail infusions for each institution. Other embodiments may, for example, give a breakdown by care area, drug, clinician device type, etc. In some embodiments, the CQI report may only display a portion of an infusion table 2070. This may, for example, be desirable because it efficiently uses user interface screen real estate when there is a very large amount of information to be displayed. As shown, only ten infusions of 66,000 are shown in the infusion table 2070 for "Uni. Hospital—Oakland". If desired a user may select a view all infusions option 2072 to view a full infusion table 2070. In other embodiments, a user may use a table scroll bar 2078 which is associated with a table to scroll through data in the table.

Some embodiments of CQI reports or CQI screens 1970 may also include a table filter utility 2074. A user may use the table filter utility to filter the data displayed in a table (e.g. compliance table 2000, infusions table 2070, etc.). This may be particularly useful in situations where the amount of data in the table is very large. In the example embodiment in FIG. 127, a user may use the table filter utility 2074 to filter infusions in the infusions table 2070 by event category. Specifically, the user may filter by alert type or alarm type.

Some embodiments of CQI reports or CQI screens 1970 may also include a compare button 2076. In such embodiments, the compare option 2076 may be used to compare a number of elements of a CQI report or may be used to compare a number of CQI reports. For example, a user may select two or more infusions in an infusion table 2070 to compare using the compare option 2076.

FIGS. 128 and 129 depicts example embodiments of CQI screens 1970 in which a filter options window 2080 is displayed on the CQI screen 1970. The filter options window 2080 may allow a user to pick a specific filter option from a category of filter options. A filter options window may, for example, be displayed if a user clicks a filtering category in a filter utility 1976 (see FIG. 115 for example) or a table filter utility 2074. FIG. 128 specifically depicts a filter options window 2080 for an alerts event category of a table filter utility 2074. FIG. 129 specifically depicts a filter options window 2080 for an alarms event category of a table filter utility 1074. In some embodiments, selecting a filter from a table filter utility 2074 may only apply the filter to a designated table. In some embodiments, selecting a filter from a table filter utility 2074 may apply the filter to all tables in the CQI report. In some embodiments, selecting a filter from a table filter utility 2074 may apply the filter to any chart, graph, etc. included with the CQI report. In some embodiments, a user may be prompted to choose which parts of a CQI report a filter selected from a table filter utility 2074 will be applied to.

FIG. 130 depicts an example embodiment of a CQI screen 1970 which includes an infusions table 2070. As is true in various embodiments, the CQI screen 1970 has a different appearance than other CQI screens 1970 depicted herein. As shown in FIG. 130, in some tables where individual infusions are listed, a user may be able to select an infusion from the table for which to show infusion story information. In the example embodiment shown in FIG. 130, a user may click a desired infusion to show an infusion graph 2090 of the infusion.

FIG. 131 depicts an example embodiment of a CQI screen 1970. An infusion story report 2100 is shown in the example CQI screen 1970 shown in FIG. 131. An infusion story report 2100 may include detailed information about a specific infusion. An infusion story report 2100 may include an infusion summary table 2102. Such a table may include information such a date of the infusion, time started, time ended, duration, if the infusion was aborted, if the infusion was completed, patient ID, Clinician, Pump ID, DAL version, whether the infusion was DERS compliant, drug, clinical use, concentration, medication route, etc.

An infusion story report 2100 may also include an infusion chart or graph 2104. The infusion chart or graph 2104 may illustrate the course of the infusion to a user. In the example embodiment depicted in FIG. 131, the infusion chart or graph 2104 depicts the dose rate delivered over time. In some embodiments, a user may be able to select specific data points or portions of an infusion chart or graph 2104 to view more detailed information (e.g. a list of relevant pump events).

A data presentation adjuster 1994 is also shown in FIG. 131. A user may use the data presentation adjuster 1994 to toggle between a number of different ways data may be displayed on the CQI screen 1970. In the example embodiment in FIG. 131, a user may toggle between the shown "Chart" view and a "Table" view. Other view types may also be available in other embodiments. If a user were to select the "Table" view, the infusion chart or graph 2104 may be replaced with a table of infusion events (not shown) in some embodiments.

FIGS. 132-159 depict a number of exemplary DERS editor user interface screens from various DERS editor embodiments which may be displayed when a user is reviewing and/or verifying a drug library for release as a DAL file. Many of the screens shown in FIGS. 132-159 display information about items which require review or have been reviewed. Additionally, many of the screens shown display information about feedback that has been submitted. Many of these screens may be used to edit or request an edit for various items, elements, parameters, etc. in a drug library. In other embodiments, the screens used to edit, review, and/or verify a drug library may differ. In some embodiments, the screens which are presented to a reviewing user and a drug library administrator may differ. The screens shown in FIGS. 132-159 may relate to the flowcharts depicted in FIGS. 23, 24, 26-28, 32, 36, and 37.

FIG. 132 depicts an example embodiment of a dashboard screen 1590. The dashboard screen shown in FIG. 132 is similar to that depicted in FIG. 79. As shown, the example dashboard screen 1590 includes an overview widget 1596a, a quick links widget 1596b, a progress widget 1596c, and a feedback widget 1596e. The feedback widget 1596e includes feedback from a number of DERS editor reviewer users in the example embodiment in FIG. 132. In some embodiments, the feedback may be displayed in a tabular format. The feedback widget 1596e may include information for each feedback item which may include, drug name, care group, reviewer name, when the feedback was submitted, the change requested (if any), and/or a comment.

The title bar 1572 of the DERS editor user interface may include a task notification 2130. In some embodiments, a task notification 2130 may only be displayed during certain phases of DAL file creation, for example, when the DAL file is being reviewed or verified. A task notification 2130 is included in the title bar 1572 shown in FIG. 132. As shown, the task notification 2130 is for new tasks (i.e. tasks since last login). In some embodiments, the task notification 2130 may list all tasks which must be performed by a DERS editor user instead of only new tasks. In some embodiments, a task notification 2130 may only provide notifications for a specific type of task (e.g. update/change requests, feedback items, changes needing review, etc.) A user may click the tasks notification 2130 to view and select a task to perform.

FIG. 133 depicts an example embodiment of a dashboard screen 1590. The dashboard screen 1590 shown in FIG. 133 is the same as that shown in FIG. 132, however, a user has accessed a feedback item in FIG. 133. This may, for example, be accomplished by clicking a feedback item in a feedback widget 1596e. In the example embodiment, when a feedback item has been clicked, a review feedback window 2140 may be displayed on the DERS editor user interface. This window may include non-summarized information about the feedback item. In the example embodiment, the feedback window 2140 includes the full reviewer comment which is shown abbreviated in the feedback widget 1596e. The feedback window 2140 may also include a respond option 2142, a decline or ignore option 2144, and a revise option 2146. Other embodiments may include different options or a different number of options. In some embodiments, a feedback widget 1596e may only be available to users with editing permissions. In some embodiments a feedback widget 1596e may be available to all users. The options available to an individual user from a particular widget may depend on the privileges assigned to the individual user. For example, a reviewing user may only have a comment option for feedback items in a feedback widget 1596e.

The respond option 2142 may be used to submit a response to the feedback item. The response may be a comment in the form of a text response. Submitting a response, may, in some embodiments, automatically generate an email to the user indicating that their feedback item has been responded to. The decline or ignore option 2144 may mark the feedback as an addressed task without making any changes to the drug library. The revise option 2146 may be used to revise the drug library using the feedback provided by a user. In some embodiments, clicking the revise option 2146 may cause the entry in the drug library for the parameter, item, element, etc. to be opened so that the user may revise the entry. The entry may, for example, be opened in a drug library entry screen similar to the drug library entry screen 1900 shown in FIG. 106.

FIG. 134 depicts another example embodiment of a dashboard screen 1590. As shown the dashboard screen 1590 includes an overview widget 1596a, quick links widget 1596b, progress widget 1596c, and a feedback and requests widget 1596d. As shown, the feedback and requests widget 1596d includes a section for feedback and for change requests. In some embodiments, the feedback and requests widget 1596d may only show a portion of the feedback items and/or change requests which have been submitted. The feedback and requests widget 1596d may include a view all option 2150. In the example embodiment, the feedback and requests widget 1596d includes two view all options. One of the view all options 2150 is for viewing all feedback items and the other is for viewing all change requests. Other widgets may be similarly configured with a view all option 2150.

FIG. 135 shows a portion of an example dashboard screen 1590. The portion of the dashboard screen 1590 shown in FIG. 135 is a portion of the dashboard screen 1590 shown in FIG. 134. A change request has been accessed using the feedback and requests widget 1596d in FIG. 135. This may be accomplished by, for example, clicking on a change request shown in the feedback and requests widget 1596d. Clicking a change request may cause a change request window 2160 to be displayed on the DERS editor user interface. The change request window 2160 may identify the specific entry in the drug library for which the request has been submitted. In the example change request window 2160, the entry is identified as hydrocortisone in the neonate care area for a continuous infusion clinical use at a concentration of 50 mg/250 ml. Additionally, a change request window 2160 may provide details about the request. The change request window 2160 may also include the submitting user's name or user ID and the date of submission for the request.

As shown, the example change request window 2160 includes a decline option 2144 and a view record option 2162. In some embodiments, only a drug library administrator or user with editing permissions may have these options. Options for reviewing users may differ. For example, reviewing users may only be able to comment by using a comment option.

The decline option 2144 may be used to mark the request as addressed without making a change to the drug library. The view record option 2162 may be used to view the specific entry in the drug library for which the request is being submitted. In some embodiments, clicking such a view record option 2162 may cause the entry to be displayed on the DERS editor user interface on a drug library entry screen 1900 similar to the drug library entry screen 1900 in FIG. 106. In some embodiments, clicking a view record option 2162 may cause a historical record of any changes or modifications to the entry to be displayed. Some embodiments may include different options or a different number of options. For example, some embodiments may include a respond option similar to the respond option 2142 shown in FIG. 133. Some embodiments may include an accept option (not shown in FIG. 135) which may be clicked to automatically update the drug library in accordance with the change request.

FIG. 136 depicts another example embodiment of a dashboard screen 1590. The example dashboard screen 1590 shown in FIG. 136 includes an overview widget 1596*a*, a CQI widget 1596*f*, and a change request widget 1596*g*. A CQI widget 1596*f* may be a medical data widget which may, for example, include CQI information which may be of interest to the user. For example, a user may be able to choose a CQI report or a portion of a CQI report that they would like to be displayed in a CQI widget 1596*f*. In the example embodiment shown in FIG. 136, the CQI widget 1596*f* includes a compliance chart 1990. In some embodiments a report selector 2170 may also be included in a CQI widget 1596*f*. A report selector may be used to select a different CQI report or portion of a CQI report for display in a CQI widget 1596*f*. A CQI link 2172 is also included in the CQI widget 1596*f* shown in FIG. 136. The CQI link 2172 may be used to open a CQI screen similar to CQI screens 1970 shown in FIGS. 115-131 on the DERS editor user interface.

A change request widget 1596*g* may include change requests submitted by DERS editor users. In some embodiments, changes requests may be presented to a user in a tabular format. In the example embodiment, the change request widget 1596*g* includes a change requests section and a completed requests section. The change request section may display information related to change requests which have not yet been addressed or are in progress. The completed requests section may display information related to change requests which have already been addressed. The change request information shown in each section may differ. In the example embodiment, the information shown for change requests in each section includes the drug name and an abbreviated description of the change request.

The change request widget 1596*g* also includes summary information 2174. In the example embodiment, the summary information 2174 details the total amount of requests for the change request section and completed request section of the change request widget 1596. A view all option 2150 may also be included in a change request widget 1596*g*. In the example embodiment, two view all options 2150 are included. One of the view all options 2150 may be used to view all change requests which have not been addressed and the other may be used to view all completed change requests.

FIG. 137 depicts another example embodiment of a dashboard screen 1590. As shown, the example dashboard screen 1590 shown in FIG. 137 includes an overview widget 1596*a*, a quick links widget 1596*b*, a CQI widget 1596*f*, a change request widget 1596*g*, and a trends widget 1596*h*. A trends widget 1596*h* may be useful when in the process of reviewing a drug library and in identifying where it may be possible to improve the library. A trends widget 1596*h* may also help in identifying if previous changes have had a desired effect.

A trends widget 1596*h* may include information such as a trend description, number of occurrences and an indicator which conveys whether or not occurrences have increased or decreased. One of the trends shown in the example trends widget 1596*h* is a dose high soft limit override. The trends widget 1596*h* shows there were 1257 occurrences of dose high soft limit overrides. The number of occurrences may be over a predetermined period of time (e.g. since last DAL file version release). The indicator shown in the example trends widget is a downward facing arrow. This arrow may convey that the rate of occurrence has fallen when compared to a period of time preceding the predetermined period of time. In some embodiments, the arrow may be color coded. For example, a decrease in the rate of limit overrides may have a downward facing arrow which is green. An increase in occurrence rate for a limit override may have an upward facing red arrow. A view all option 2150 is also included in the example trends widget 1596*h*. This option may be used to display all of the available trends.

In some embodiments a user may be able to click trends in a trends widget 1596*h* to display detailed information related to the trend. For example, if a user were to click the dose high soft limit override trend, a user may be shown a breakdown of soft limit overrides by care area or drug name, or the like. In some embodiments, clicking a trend in the trends widget 1596*h* may open a CQI screen with a CQI report of the selected trend.

FIG. 138 depicts an example embodiment of a dashboard screen 1590. As shown, the example dashboard screen 1590 depicted in FIG. 138 includes an overview widget 1596*a*, a quick links widget 1596*b*, a progress widget 1596*c*, a CQI widget 1596*f*, and a change request widget 1596*g*. As shown, the CQI widget 1596*f* includes a trends section which is similar to the trends widget 1596*h* shown in FIG. 137. The change request widget 1596*g* includes a view all option 2150. The change request widget 1596*g* in the example embodiment also includes a change page option 2180. This may allow a user to navigate between a number of pages of change requests. This may be used if a user would prefer not to use the view all option 2150. Some change requests widgets 1596*g* may only include one of a view all option 2150 or a change page option 2180. Various other widgets may include a change page option 2180 and/or a view all option 2150.

FIG. 139 depicts an example embodiment of a dashboard screen 1590. The example dashboard screen 1590 shown in FIG. 139 is a portion of the dashboard screen 1590 depicted in FIG. 138. As shown, a change request has been accessed and a change request window 2160 is shown in the example embodiment in FIG. 139. The change request window 2160 shown is similar to that shown in FIG. 135.

FIG. 140 depicts another example embodiment of a dashboard screen 1590. The example dashboard screen 1590, shown in FIG. 140, is the same as that shown in FIG. 139. The change request window 2160 includes a rationale field 2190. In the example embodiment, the rationale field 2190 is a reason for declining field. Such a field may be displayed if a user selects the decline option on a change request window 2160. In some embodiments, a user may be required to enter a comment after declining or editing a change request, feedback request, or the like. This may be useful for traceability purposes. Once a user has filled out a rationale field 2190, a user may use an OK option 2192, finish option, accept option or the like to mark the request as addressed and save the text entered in the field. A user may also use a cancel option 2194 if desired.

FIG. 141 depicts another example embodiment of a dashboard screen 1590. The dashboard screen 1590 show in FIG. 141 may be well suited to a reviewing user. As shown, the dashboard screen 1590 includes an overview widget 1596a, a progress widget 1596c, a changes to review widget 1596i, and a administrator comments widget 1596j. The changes to review widget 1596i may include a list, table, or the like for all changes which a user is responsible for reviewing. An administrator comments widget 1596j may include comments from an administrator such as a drug library administrator. These comments may include responses to feedback items, explanations from reason for action fields, questions about change requests, or other comments. In some embodiments, an administrator comments widget 1596j may only include comments on feedback items, change requests, etc. submitted by the user.

FIG. 142 depicts an example embodiment of a dashboard screen 1590. The example dashboard screen 1590 shown is the same as the dashboard screen 1590 shown in FIG. 141. As shown, a changes to review window 2200 is shown in FIG. 142. A changes to review window 2200 may include information identifying what drug library entry the change is being made for. In the example embodiment, the changes to review window 2200 is displaying changes for Lidocaine in an ICU for a weight based clinical use at a concentration of 2 mg/250 ml. The changes to review window 2200 may include more than one change as it does in FIG. 142. This may be desirable if more than one change has been made for the same entry. In some embodiments, other windows such as feedback window or change request window may include more than one feedback item or change request.

A user may use the changes to review window 2200 to indicate whether or not they agree that the change should be made. In the example embodiment, a user may check a checkbox next to the proposed change to indicate that they agree that the change should be made. If a user disagrees with a proposed change or believes further discussion is warranted a user may click an add comment option 2202 to submit a comment about the proposed change. In some embodiments, an add a comment option 2202 may be displayed on the DERS editor user interface when a user moves their cursor over a proposed change in a changes to review window 2200. A changes to review window 2200 may also include a view record option 2204. The view record option 2004 may be used to view the specific entry in the drug library for which the change is being proposed. In some embodiments, the specific entry may be viewed on a drug library entry screen 1900 (see FIG. 106 for example). In some embodiments, clicking such a view record option 2204 may cause the entry to be displayed on the DERS editor user interface. In some embodiments, clicking a view record option 2204 may cause a historical record of any changes or modifications to the entry to be displayed.

FIG. 143 depicts an example embodiment of a dashboard screen 1590. The example dashboard screen 1590 shown in FIG. 143 is the same as the dashboard screen 1590 shown in FIG. 142. As shown, the changes to review window 2200 includes a comment field 2210 in FIG. 143. Such a field may, for example, be displayed if a user clicks a comment option such as the comment option 2202 shown in FIG. 142. A user may enter a comment into the comment field 2210 about the change. In the comment, a user may explain why they disagree with or feel a change needs further discussion before approving the change. Once a comment has been entered a user may use the save option 2212 to save the comment. This may also mark the change as reviewed. If desired, a user may also use the cancel option 2214 to cancel their addition of a comment.

If more than one change is shown in a window, such as the changes to review window 2200 shown in FIG. 143, an undo option 2216 may be displayed in association with each change after it has been addressed. An undo option 2216 may be used to undo any action taken in relation to the change. It may also unmark the change as addressed or reviewed.

FIG. 144 depicts an example dashboard screen 1590. The example dashboard screen 1590 in FIG. 144 includes a progress widget 1596c and a changes to review widget 1596i. As shown, the changes to review widget 1596i include a list of changes which is displayed in a tabular format. Each drug library entry displayed in the changes to review widget 1596i is expandable. In such embodiments, a window such as the changes to review window 2200 shown in FIG. 143 may not be necessary. In some embodiments, a user may click the entry to expand and review the entry. The entry for Lidocaine in the ICU for a weight based clinical use at a concentration of 2 g/250 ml is shown in an expanded state in FIG. 144. In an expanded state, any changes needing review may be shown in the table. A user may review the changes for each entry by checking boxes and entering text in the expanded portion of the table. In some embodiments, other windows, such as the feedback window 2140 of FIG. 133 or the change request window 2160 of FIG. 135 may be replaced by using an expandable table in their respective widgets.

FIG. 145 depicts another example embodiment of a dashboard screen 1590. The example dashboard screen 1590 depicted in FIG. 145 includes an overview widget 1596a, a progress widget 1596b, a recent changes widget 1596k, and a changes in progress widget 1596l. Such a dashboard screen 1590 may be well suited for a reviewing user of a drug library. A recent changes widget 1596k may display changes which are new or have been recently proposed (e.g. since last login, in the last week, in the last few days, etc.). A changes in progress widget 1596l may display changes which have been initiated, but not yet been through an entire review, verification, and approval process. Changes displayed in the changes in progress widget 1596k may, for example, be changes which have already been reviewed by the reviewing user but are awaiting review from other users or waiting for an administrator action.

As shown, a change to review window 2200 is also displayed in the example embodiment shown in FIG. 145. The change to review window 2200 in FIG. 145 differs from that shown in FIG. 142 for example. In the example embodiment in FIG. 145, the change to review window 2200 includes the proposed new parameter value for the entry in question. The current parameter value is also shown in the change to review window 2200 in FIG. 145. The name or user ID of the user who made the change and date on which the change was made may also be shown in some embodiments.

The change to review window 2200 in FIG. 145 includes a comment option 2220, a dispute option 2222, and an accept option 2224. The comment option 2220 may be used to make a comment on the change being reviewed. The dispute option 2222 may be used if a user feels that a change is improper or needs further discussion. The accept option 2224 may be used if a user feels the change is appropriate and should be made. In some embodiments, a user may be required to enter a comment after using the dispute option 2222.

FIG. 146 depicts another embodiment of a dashboard screen 1590. The dashboard screen 1590 shown in FIG. 146 is the same as that shown in FIG. 145. As shown, a user may use a search bar 1568 on the DERS editor user interface to search for a drug, change, comment, etc. As shown, a user need not type in a full word for a search. In the example embodiment, the user has typed in the letters "Acycl" and a list of possible entries with these letters is displayed on the DERS editor user interface. A user may then select a desired entry from the list to view it. This may be useful during review of a drug library if, for example, a user desired to view records to similar drug entries in other care areas and any comments or changes associated with those entries. This may help provide context to a user when reviewing drug library entries.

FIG. 147 depicts an example embodiment of a review screen 2230 which may be displayed on a DERS editor user interface. A review screen 2230 may provide a user with a centralized user interface for reviewing a drug library. A review screen 2230 may be similar to a number of the widgets which may, in some embodiments, be included on a dashboard screen. A review screen 2230 may allow a user to drill down on or filter for certain aspects of the review process. For example, an administrator may be able to view review progress by a desired care area or reviewing user.

A progress indicator 2232 may be included on some review screens 2230. In the example embodiment in FIG. 147, a progress indicator 2232 is included. The progress indicator 2232 shown consists of a numerical percentage of the changes which have been reviewed and a progress bar. Other progress indicators 2232 may differ. Some embodiments may also include a progress breakdown display 2234. A progress breakdown display 2234 may for example include at least one of a progress bar or numerical percentage of review progress in association with care area names or reviewing users. In some embodiments, the progress breakdown display 2234 may be different depending on the review screen 2230 being displayed. For example, a review screen 2230 detailing review progress in a specific care area may include a progress breakdown display 2234 which displays the review progress of reviewing users assigned to that care area.

A review screen 2230 may also include various feedback items, change requests, changes needing review, etc. In some embodiments, various feedback items, change requests, changes needing review, etc. may be displayed in a review table 2236. In other embodiments, this information may be displayed by another suitable means and not necessarily a review table 2236. In embodiments including a review table 2236, the review table 2236 may include information such as drug name, care area, clinical use, concentration, name of user submitting the change or feedback, when the feedback was submitted, etc. If a sufficient number of feedback items, change requests, changes needing review, etc. exist, not all of these may be displayed on the same review screen 2230. In some embodiments a change page option 2238 may be included to allow a user to view additional feedback items, change requests, changes needing review, etc.

In some embodiments a review type filter 2240 may also be included on a review screen 2230. In the example embodiment shown in FIG. 147, the review type indicator is included as a part of the review table 2236. A user may select a review type from the review type filter 2240 in order to filter the type of information displayed on the review screen 2230. In the example embodiment, the user may filter such that only feedback items are shown, such that only change requests are shown, or may show both feedback items and change requests. In the example embodiment only feedback items are shown as is indicated at the top of the review table 2236.

FIG. 148 depicts an example embodiment of another review screen 2230. The example review screen 2230 shown in FIG. 148 is a drilled down view of the review screen 2230 shown in FIG. 147. As shown, the review screen 2230 shown in FIG. 148 displays review information related to a specific reviewing user. In some embodiments, a user may navigate to such a screen by clicking on the proper care areas and reviewing users in a progress breakdown display 2234 (see FIG. 147 for example) or a number of progress breakdown displays 2234 on different review screens 2230.

As shown, the example review screen 2230 in FIG. 148 includes a progress indicator 2232. The progress indicator 2232 in FIG. 148 details the progress of a reviewing user with the user name Jane Doe. An example review screen 2230 detailing the progress of a reviewing user may include a review table 2236 which displays feedback items, change requests, etc. which have been generated by the user. In some embodiments, this information may be displayed on a review screen 2230 in a fashion other than a table.

FIG. 149 depicts an example embodiment of a review screen 2230. As shown, the example review screen 2230 in FIG. 149 is similar to the example review screen shown in FIG. 147. A progress breakdown display 2234 (see FIG. 147 for example) is not included in FIG. 149. The review type filter 2240 for the review table 2236 in FIG. 149 is set so that both feedback items and change requests are displayed. A progress indicator 2232 is also included in FIG. 149.

As shown, the entries for various feedback items and change requests in the example review table 2236 shown in FIG. 149 are expandable. A user has expanded the entry for "Abciximab ICU Non-weight based 50 mg/500 ml." In the example embodiment in FIG. 149, when a user expands an entry, a details window 2250 is displayed for that entry. The details window 2250 may include specific information about the entry which was expanded. In the example embodiment in FIG. 149, the details window 2250 is for a feedback item and includes information identifying the original change and the feedback from the user about the change. Other details windows 2250, for example those for a change request, may include different information. A details window 2250 for a change request may include information such as the original value, the proposed change, and any rationale given by the user proposing the change.

The details window 2250 shown in FIG. 149 includes a decline option 2252 and a view record option 2254. A user may use the decline option 2252 to decline to make a change based on the feedback item. In some embodiments, if the decline option 2252 is used, a user may be required to enter a rationale for declining to make any changes. A user may use the view record option 2254 to display the record on the DERS editor user interface. The user may then view the record and make a change if appropriate.

FIG. 150 depicts another example embodiment of a review screen 2230. The review screen 2230 is the same as that shown in FIG. 149. As shown, a details window 2250 is displayed in FIG. 149. The details window 2250 may be an example of a details window 2250 which would be displayed if the decline option 2252 in FIG. 149 was used. As shown, the details window 2250 includes a comment field 2260. The user may use the comment field 2260 to enter a rationale for declining to make a change based on the feedback item. After entering a comment in the comment field 2260, a user may use the save option 2262 to save the comment. This may also cause the feedback item to be marked as having been addressed by the user. A user may also use the cancel option 2264 if desired.

FIG. 151 depicts an example embodiment of a review screen 2230. The example review screen 2330 shown in FIG. 151 is similar to the review screens 2230 shown in FIGS. 147-150. The review screen 2230 shown in FIG. 151, however, is more suited for a reviewing user while those shown in FIG. 147-150 are more suited for a user with editing permissions such as a drug library administrator.

As shown, the example review screen 2230 includes a progress indicator 2232. The progress indicator 2232 is similar to that shown in FIG. 147-150. A review table 2236 is also shown in FIG. 151. The review table 2236 may include information about changes needing a user's review, administrator comments on user feedback items, etc. In some embodiments, this information may be displayed in a non-tabular format. In embodiments with a review table 2236, the review table 2236 may include columns for status, care area, drug name, clinical use, concentration, date submitted, admin comment, etc. A review type filter 2240 may also be included. In the example embodiment, the review type filter 2240 includes filtering options for changes to review, admin comments, and an option to show both changes to review and admin comments. The review type filter 2240 has been set to changes to review in FIG. 151.

A user may address changes needing review, administrator comments, etc. by clicking on the entry for them in a review table 2236 in some embodiments. This may cause a details window similar to the details window 2250 shown in FIG. 150 to be displayed on the DERS editor user interface. A reviewing user may then use the details window 2250 to take the appropriate action on the change needing review, administrator comment, etc.

FIG. 152 depicts an example embodiment of a drug library entry screen 1900 in which a user is in the process of submitting a change request. A user may in some embodiments, review a drug library using drug library entry screens 1900. A user may also submit change requests, feedback items, and change drug entry parameters, items, elements, etc. using drug library entry screens 1900. In some embodiments, the drug library entry screen 1900 for an entry may be displayed if a user selects, for example, a view record option such as the view record option 2254 shown in FIG. 149. In various embodiments, a user may review a drug library by looking at a drug list 1702 on a drug screen 1700 (see FIG. 88 for examples). The drug list 1702 may include indications for each drug as to whether an update/change or task exists for the drug. A user may then click on a drug in the drug list 1702 to display the drug library entry screen 1900 for the drug library entry.

As shown, the drug library entry for dopamine in the care area "4 West" for the peripheral line clinical use at a concentration of 400 mg/250 ml is being displayed on the drug library entry screen 1900. The drug library entry screen 1900 shown in FIG. 152 includes a compare option 1704, an agree with all option 2270, and a submit change request option 2272. In some embodiments, different options or a different number of options may be included on a drug library entry screen 1900. The options shown on a drug library entry screen 1900 may differ depending on the specific drug library entry screen 1900 being displayed, the status of the entry, etc.

The compare option 1704 may be used to compare the drug library entry to another drug library entry. Such a comparison may be similar to the description provided above in relation to FIG. 108. In some embodiments, the compare option 1704 may also be used to compare two versions of the same drug entry. For example, a user may compare the drug entry from the current drug library version with the same drug entry including any proposed changes to be included in a future version.

The agree with all option 2270 may be used to agree with all changes which have been proposed for a drug entry. In some embodiments, this option may not be displayed and a user may be required to individually agree with each change to the entry. Additionally, this option may not be displayed if only a single change has been made to the drug library entry.

A submit change request option 2272 may be used to submit a change request for a parameter, item, element, etc. in a drug entry. In the example embodiment shown in FIG. 152 use of the submit change request option 2272 may cause a details window 2250 to be displayed on the DERS editor user interface. The details window 2250 may be used to enter the desired change to the drug entry. In some embodiments a user may need to select a parameter, item, element, etc. for which to open a details window 2250. In the example embodiment shown in FIG. 152, a details window 2250 in which a user may change the drug amount in container parameter for the drug entry is shown. In a details window 2250 for a change request a user may enter a new parameter value and a rationale for the change in some embodiments.

The details window 2250 for a change request may include a submit option 2274 and a cancel option 2276. The submit option 2274 may be used to submit the change request for the drug entry. The cancel option 2276 may be used to cancel the creation of a change request for the drug entry. In some embodiments, using the submit option 2274 may cause a notification to be sent to a user with drug library editing permissions which informs the user that a change request has been submitted.

FIG. 153 depicts an example embodiment of a drug library entry screen 1900 in which a user is in the process of submitting a feedback item. The example drug library entry screen 1900 shown in FIG. 153 includes a compare option 1704 and an agree with all option 2270 which may function similarly to those described in relation to FIG. 152. The example drug library entry screen 1900 in FIG. 153 also includes a provide feedback option 2280. In some embodiments, a provide feedback option 2280 and a submit change request option may both be included on a drug library entry screen 1900.

A provide feedback option 2280 may be used to provide a feedback item for a parameter, item, element, etc. in a drug entry. In the example embodiment shown in FIG. 153 use of the provide feedback option 2280 may cause a details window 2250 to be displayed on the DERS editor user interface. The details window 2250 may be used to enter the desired feedback for the drug entry. In some embodiments a user may need to select a parameter, item, element, etc. for which to open a details window 2250. In the example embodiment shown in FIG. 153, a details window 2250 in which a user may provide feedback for the drug amount in container parameter of the drug entry is shown. In a details window 2250 for a feedback item a user may enter a comment or question. In some embodiments, a user may also be able to suggest a different parameter value.

The details window 2250 for a feedback item may include a submit option 2274 and a cancel option 2276. The submit option 2274 may be used to submit the feedback item for the drug entry. The cancel option 2276 may be used to cancel the creation of a feedback item for the drug entry. In some embodiments, using the submit option 2274 may cause a notification to be sent to a user with drug library editing permissions which informs the user that a feedback item has been submitted.

FIG. 154 depicts another example embodiment of a drug library entry screen 1900. The example embodiment shown in FIG. 154 depicts a view of a user with editing permissions viewing the change request which was entered in FIG. 152. As shown, a details window 2250 for the change request is displayed on the DERS editor user interface in FIG. 154. In some embodiments, such a window may be displayed after a user clicks on the parameter value for which the change request has been submitted. In some embodiments, an indicator 2290 which notifies a user a change request, feedback item, etc. has been submitted for an entry may be displayed in association with the entry. A user may click the indicator 2290 to display a details window 2250 for the change request, feedback item, etc. As shown, the details window 2250 displays the suggested parameter value change and the rationale for the change. In the example embodiment shown in FIG. 154, the details window includes a decline option 2292 and an accept option 2294. If the user disagrees with the change, they may use the decline option 2292. If a user agrees that the change should be made, the user may use the accept option 2294. The accept option may automatically change the parameter to conform to the value suggested in the change request. In some embodiments, after a change has been made to a drug entry on a drug library entry screen 1900 a user may be required to use a save option 2296 on the drug library entry screen 1900 to save to the change.

FIG. 155 depicts another example embodiment of a drug library entry screen 1900. The layout of the example drug screen 1900 shown in FIG. 155 is different than that shown in FIGS. 152-154. A details window 2250 is shown in FIG. 155. The details window 2250 displays information similar to the details window 2250 shown in FIG. 154. The details window 2250 also includes a decline option 2292 and an accept option 2294 which may function similarly to those described in relation to FIG. 154.

FIG. 156 depicts an example embodiment of a drug library entry screen 1900. As shown, the example drug library entry screen 1900 shown in FIG. 156 is the same as that shown in FIG. 155. However, the parameter identified in the details window 2250 for the change request in FIG. 155 has been changed. The example drug library entry screen 1900 shown in FIG. 156 may be the drug library entry screen 1900 which would be displayed if a user selected the accept option 2294 on the details window 2250 in FIG. 154.

As shown, the parameter field for the changed parameter may be outlined in a heavy weight line 2300 to draw attention to the change in parameter value. In some embodiments, the heavy weight line 2300 may be colored to draw additional attention. In some embodiments, a previous value message 2302 may be associated with any changed parameter values on a drug library entry screen 1900. Such a previous value message 2302 may identify the previous parameter value and identify the drug library version number in which the previous value was used. After changing the desired value or values on a drug library entry screen 1900 a user may use a save option 2296 on a drug library entry screen 1900 to save the changes to the drug library.

FIG. 157 depicts another example embodiment of a drug library entry screen 1900 in which a note is being added to a drug library entry. A note may, for example, be added to a drug library entry by right clicking a parameter in a drug library entry and selecting an add note option (not shown). A note may be viewable by all DERS editor users. A note may be used to provide a link to a CQI report, peer reviewed literature which the setting for the parameter value was drawn from, drug manufacturer information for the drug, etc. Notes may also be used to attach a file such as an image file or .pdf to a drug entry. Notes may be helpful during the review process because they may help to convey a rationale for a specific parameter value setting. Notes may also help to suggest guidelines for what a proper parameter value may be.

When a user indicates that they would like to add a note to a drug entry, a details window 2250 for the note may be displayed on the user interface. Such a details window 2250 may include a note entry field 2310. A user may use the note entry field 2310 to add a desired note. Some details windows 2250 for notes may include an upload option 2312 which may be used to upload various files to the note. In some embodiments, a details window 2250 for a note may include text formatting options 2314 to allow a user to format text entered into the note entry field 2310. The example embodiment shown in FIG. 157 also includes a save note option 2316 which may be used to save the note. In some embodiments, multiple notes may be added for a single drug entry or parameter value.

FIG. 158 depicts an example embodiment of a drug library entry screen 1900 in which a note for a drug entry has been opened. As shown, the note window 2320 includes the note which was entered in FIG. 157. Additionally a second note is displayed in the note window 2320 in FIG. 158. Both of the notes in the note window 2320 are resources which may be helpful in determining a proper parameter value. As shown, a note window 2320 may include an add new note option 2324. This option may be used to add an additional note to an entry in a drug library if desired. As shown once a note has been added to an entry, the entry may be depicted with a note indicator. In the example embodiment, the note indicator is an icon which looks like a piece of paper with a folded down corner.

FIG. 159 depicts an example embodiment of a drug library entry screen 1900 in which a reviewing user is reviewing a change to a drug library entry. As shown, a details window 2250 for the change is displayed on the DERS editor user interface in FIG. 159. A reviewing user may cause a details window 2250 for the change to be displayed by clicking on the changed parameter on the drug library entry screen 1900 in some embodiments. In some embodiments, a user may click an indicator 2290 associated with the drug library entry to cause a details window 2250 to be displayed.

A details window 2250 for reviewing a change may display the current value for the parameter and the proposed change value for the parameter to a user. The details window 2250 may also display the user name or ID of the user who submitted the change and the date on which the change was submitted. A details window 2250 for reviewing a change may also include a comment option 2330, a dispute option 2332, and an accept option 2334. A user may use the comment option 2330 to enter a comment about the change. A user may use the dispute option 2332 to disagree with the change. In some embodiments, a user may be required to enter a comment if they use the dispute option. A user may use the accept option 2334 to accept the change.

FIGS. 160-180 depict a number of screens detailing aspects of another example embodiment of a user interface. Such screens may be accessed and presented to a user on a DERS editor user interface or CQI user interface. For purposes of example, the screens shown are those of a DERS editor user interface. In some embodiments, similar or identical screens may be used in other interfaces for other services such as a user interface for a CQI service. Screens shown in FIGS. 160-180 may be related to the flowcharts shown in FIGS. 11-71. Such screens may follow similar workflows to what is shown and described in FIGS. 11-71. In various embodiments, these screens may be displayed to a user via a web browser user interface. A user may, for example, view such screens using a computer, tablet, smart phone, etc. As a user navigates from screen to screen, a database such as a DERS database may be queried for the information needed to display the screen. This information may then be rendered for display and displayed on the user interface. The DERS editor service may function using any suitable client-server interaction scheme.

Referring now specifically to FIG. 160, an example drug library screen 4100 which may be shown on a DERS editor user interface is depicted. A drug library screen 4100 may be used to access, view, add, modify, review, etc. drug library entries. A user may navigate to a drug library screen 4100 by opening the appropriate tab 1598 on the DERS editor. Such drug library screens 4100 may allow a user to navigate through and modify a DAL file by drilling down through the hierarchy of the DAL file.

As shown, the example drug library screen 4100 shown in FIG. 160 includes high level hierarchy field 4102 and a lower level hierarchy field 4104. A user may use the high level hierarchy field 4102 to select high level portions of the hierarchy in which a drug record of interest is located. In the example embodiment shown in FIG. 160, user may select a various care groups and care areas in the high level hierarchy field 4102. In some embodiments, or for some users, additional levels of hierarchy may be included. For example, a user who is part of an IDN may have the additional option of selecting an institution or region from the high level hierarchy field 4102.

The lower level hierarchy field 4104 may include various DAL file entries which have been defined for a selected higher level hierarchy from the higher level hierarchy field 4102. In the example embodiments, the lower level hierarchy field 4104 displays drugs defined for the selected care group in the higher level hierarchy field 4102. The lower level hierarchy field 4102 may also display various other information. In FIG. 160, information related to the medications defined for the selected care group is shown in the lower level hierarchy field 4102. Additionally, a user may be able to select (e.g. by clicking or double clicking on) various medication records shown in the lower level hierarchy field 4102 to cause a "drilled down" view to be displayed. Such a view may allow a user to review and modify clinical uses, concentrations, etc. for a selected medication.

Also shown in FIG. 160 are a number of filter options 4106. Such filter options 4106 may be used to help a user navigate through drug library screens 4100 in an efficient manner. Such filter options 4106 may be used to limit the number of possible selections a user may be presented with in various fields of a drug library screen 4100. The example filter options 4106 may be toggled on or off via user interaction with a number of radio buttons. In other embodiments, filter options 4106 may be chosen from a drop down menu, through, checkboxes, etc.

In the example embodiment shown in FIG. 160, the filter options 4106 are specifically device type filter options 4106. A user may use a device type filter option 4106 to filter what is shown in the higher level hierarchy field 4102 and lower level hierarchy field 4104. In the example embodiment, a user has elected to filter so that DAL file entries associated with or specified for use with "Device Type A" are displayed. In the higher level hierarchy field 4102, this may cause care groups, care areas, etc. to be displayed only if they include an entry which is associated with or specified for use with "Device Type A". In the lower level hierarchy field 4104, only DAL file entries associated with or specified for use with "Device Type A" may be displayed. In various embodiments, additional filter options 4106 may be available to a user.

A user may add drugs (as well as clinical uses, concentrations, etc. for those drugs) to the care group. When a drug record is added to a care group, the drug record may be propagated into all care areas within the care group as a common drug record. If a user would like to add a drug to the care group shown in FIG. 160, a user may use an add drug option 4108. In the example embodiment in FIG. 160, the use may click the add drug option 4108 to add a drug to the care group. The user may then enter the name of the drug which they would like to add. This may be done on a screen similar to that shown in FIG. 89. In some embodiments, a user may then be required to enter in various parameters for the drug on a screen similar to that shown in FIG. 91. Preferably, a user may instead define at least some of the required information when the drug is added to the master medication list for the DAL file. In such an instance, this information may be automatically carried into the drug entry in the care group when a drug is added using the add drug option 4108. This may increase overall efficiency of the building of a DAL file. If desired, after adding the drug, the user may specify clinical uses, concentrations, etc. for that drug.

If a user adds a drug to a care group, the drug (along with any clinical uses, concentrations, etc. for that drug) may be automatically be propagated down to any care areas within that care group. In other embodiments, such as that shown in FIG. 160, a user may be required to use an update care area option 4110 to indicate that they would like the drug record to be propagated to care areas within the care group. The DERS editor service may propagate the drug record into all appropriate care areas in response to usage of an update care area option 4110.

FIG. 161 shows another example embodiment of a drug library screen 4100 which may be displayed on a user interface of a DERS editor service. In FIG. 161, a user has selected a care area from the higher level hierarchy field 4102. This has caused the lower level hierarchy field 4104 to display drug records which exist for that care area.

In some embodiments, the background color of the lower level hierarchy field 4104 may change to visually indicate the level of hierarchy selected from the higher level hierarchy field 4102. This may be helpful to minimize any confusion and possibility for a user to mistakenly add or modify drug records at the wrong level of the hierarchy. A record level identifier 4120 may also be associated with the lower level hierarchy field 4104. A record level identifier 4120 may specify the hierarchical relationship for the set of information displayed in the lower level hierarchy field 4104. In the example embodiment, the record level identifier 4120 indicates that the drug records shown are those belonging to Care Area 1 of Care Group 2. Again, this may help to minimize any confusion or possibility for mistakenly altering drug records at the wrong level of the hierarchy.

The care area selected in FIG. 161 is assigned to the care group which was selected in FIG. 160. As shown in the lower level hierarchy field 4104 in FIG. 161, the care area includes the medications which are shown as defined for the care group in FIG. 160. A user may have the option of adding drug records to the care area using the add drug option 4108. This may useful if it is desirable to create a unique (not shared or common) drug record for the care area. For example, not all care areas in the care group may use a particular drug and it may therefore be more appropriate to individually add the drug record to proper care areas within the care group. Alternatively, a user may also delete or remove a drug record from a care area. If a majority of care areas within a care group use a particular drug, it may be more efficient to create a common record for the drug at the care group level. The user may then delete the drug record from various care areas that do not use that drug.

FIG. 162 depicts an example embodiment of a drug library screen 4100 which may be displayed on a user interface such as a DERS editor user interface. As indicated by the record level indicator 4120, a user has selected to "drill down" on a specific drug record to view detailed information associated with the drug record. In the example embodiment in FIG. 162, a user has chosen to view details for the drug record of "Drug 2" in Care Area 1 of Care Group 2. A user may be able to progress from FIG. 161 to FIG. 162 by, for example, clicking on "Drug 2" in the lower level hierarchy field 4104 of FIG. 161.

As shown, the lower level hierarchy field 4104 includes all of the clinical uses and concentrations defined for "Drug 2". In the example drug library screen 4100 shown in FIG. 162, there are three clinical uses each of which having 3 defined concentrations. The clinical uses and/or concentrations defined for a select drug record may also be associated with an indicia 4130. The indicia 4130 may indicate to a user if the associated part of the drug record is common or unique. In the example embodiment, the triangle shaped indicia 4130 indicates that the associated part of the drug record is common and was propagated from the care group level. The star shaped indicia 4130 indicates the associated part of the drug record is unique and was not propagated from the care group level.

An example drug record parameters field 4132 is also displayed on the drug library screen 4100 shown in FIG. 162. Such a field may allow a user to view, modify, etc. various aspects of the drug record. This may be done by entering in or modifying various parameters in their associated parameter fields 4134. In the example embodiment in FIG. 162, the drug record parameters field 4134 shown is for the clinical use entitled "Clinical Use F. Other drug record parameter fields 4134 may be displayed in response to a user selecting a different portion (e.g. a concentration or other clinical use) of the drug record from the lower level hierarchy field 4104. The drug record parameters field 4132 may be displayed on the user interface such that it does not block or cover other information displayed on the screen. Any changes made to parameters in the drug record parameters field 4132 may be saved using a save option 4134 or cancelled using a cancel option 4132.

The example drug library screen 4100 also includes options to add additional clinical uses and concentrations to a drug record. If a user would like to add a clinical use to the drug record, a user may use the add clinical use option 4142. This may cause the DERS editor service to create a new clinical use for the selected drug record. The user may then modify various parameter values for the clinical use via the drug record parameters field 4132 for that clinical use. To add a concentration in the example embodiment, a user may click on a clinical use to open the drug record parameters field 4132 for that clinical use. The user may then select the add concentration option on the drug record parameters field 4132. This may cause the DERS editor service to create a new concentration for the indicated clinical use. A user may then modify various parameter values for the new concentration via the drug record parameters field 4132 for that concentration.

The example progression of FIGS. 163-164 depicts how a user may edit a drug record at the care group level. This may be necessary in the event that a user needs to change a parameter value for a clinical use or concentration within the drug record. It may also be necessary if a user did not finish defining all parameter values for the drug record during their last DERS editor session.

FIG. 163 depicts example embodiment of a drug library screen 4100 which may be displayed on a user interface such as a DERS editor user interface. A user may alter values defined in the parameter fields 4134 in a desired drug record parameters field 4132 to edit a drug record. As shown by the record level indicator 4120, the user has opened the drug record for "Drug 2" in Care Group 2. The drug record parameters field 4132 for "Clinical Use 3" is open for editing. This specific portion of the drug record for "Drug 2" in Care Group 2 may be edited if a user alters the various parameters defined in the drug record parameters field 4132.

If a user alters parameters in the drug record parameters field 4132, the user may save changes using a save option 4136. In some embodiments a user may also use an update care area option 4150 to save changes. Some embodiments may only include one of a save option 4136 or update care area option 4150. If a user would like to cancel any edits made to the portion of the drug record, the user may use a cancel option.

In response to an indication that the user would like to save the edits to a particular drug record for a care group, the DERS editor may prompt the user to specify which care areas within the care group the changes should be applied to. The form of this prompt may, in some embodiments, be similar to the prompt 4160 depicted in FIG. 164. Such a prompt may be displayed as a modal window covering portions of a drug library screen 4100 similar to that shown in FIG. 163.

The example prompt 4160 shown in FIG. 164 includes instructions 4162. The instructions 4162 shown in FIG. 164 explain that a user should select desired care areas in the care group for which they would like their changes applied to. The example prompt 4160 also includes a change(s) summary 4164. A change(s) summary 4164 may convey a summary of changes made to the user. This may allow the user to review the change(s) before they are saved. The change(s) summary 4164 may be displayed in the form of a bulleted list showing the previous parameter value and the new parameter value for any changed parameters. The example prompt 4160 also includes a care area selector 4166. The care area selector 4166 may be used to select which care areas within the care group to apply the changes to. Once a user has selected the desired care areas, the user may use a save option 4168 on the prompt 4160 to cause the DERS editor to save the changes and propagate them down to the selected care areas. A cancel option 4169 may also be included to cancel the changes if desired.

The example progression of FIGS. 165-166 depicts how a user may edit a drug record at the care area level. This may be necessary in the event that a user needs to change a parameter value for a clinical use or concentration within the drug record. It may also be necessary if a user did not finish defining all parameter values for the drug record during their last DERS editor session.

FIG. 165 depicts example embodiment of a drug library screen 4100 which may be displayed on a user interface such as a DERS editor user interface. A user may alter values defined in the parameter fields 4134 in a desired drug record parameters field 4132 to edit a drug record. As shown by the record level indicator 4120, the user has opened the drug record for "Drug 2" in Care Area 1 of Care Group 2. The drug record parameters field 4132 for "Clinical Use 2" is open for editing. This specific portion of the drug record for "Drug 2" in Care Area 1 of Care Group 2 may be edited if a user alters the various parameters defined in the drug record parameters field 4132. If a user alters parameters in the drug record parameters field 4132, the user may save changes using a save option 4136. If a user would like to cancel any edits made to the portion of the drug record, the user may use a cancel option 4138.

In response to an indication that the user would like to save the edits to a particular drug record for a care area, the DERS editor may prompt the user to affirm that they would like to make the changes. If the edits are being made to a common drug record which was propagated to the care area from a care group, the DERS editor may prompt the user to affirm that they would like to make the drug record unique and no longer tied to the care group record. The form of these prompts may, in some embodiments, be similar to the prompt 4170 depicted in FIG. 166. Such a prompt may be displayed as a modal window covering portions of a drug library screen 4100 similar to that shown in FIG. 165.

The example prompt 4170 shown in FIG. 166 includes a warning 4172. The warning 4172 shown in FIG. 166 includes text explaining that if a user saves the changes, the drug record will become unique and will be no longer tied to the care group drug record. The example prompt 4170 also includes a change(s) summary 4174. A change(s) summary 4174 may convey a summary of changes made to the user. This may allow the user to review the change(s) before they are saved. The change(s) summary 4174 may be displayed in the form of a bulleted list showing the previous parameter value and the new parameter value for any changed parameters. Once a user would like to make the change(s) the user may use a save option 4176 on the prompt 4160 to cause the DERS editor to save the changes. If a user would like to cancel any edits made to the portion of the drug record, the user may use a cancel option 4178.

The example progression of FIGS. 167-168 depicts how a user may copy a drug record or portion of a drug record to another desired portion of the DAL file hierarchy. Copying drug records may help to speed up the process of building a DAL file as well as make the process more efficient. Copying may, for example, be useful in the event that a user will be creating a number of drug records with the same defined parameter values for a number of different care groups or areas. Copying drug records may also be useful in the event that two drug records will share a number of common parameter values. Instead of starting with a blank slate for the drug record, it may, in such a case, be faster and more efficient to copy the drug record and edit it as needed.

FIG. 167 depicts an example embodiment of a drug library screen 4100 which may be displayed on a user interface such as the user interface of a DERS editor service. As shown by the record level indicator 4120, a user is viewing the detailed information for "Drug 2" in Care Group 2. Various clinical uses and concentrations for "Drug 2" are shown in the lower level hierarchy field 4104. A user has selected "Clinical Use 3" and is viewing the drug record parameters field 4132 for that use in FIG. 167.

In some embodiments, when a user selects a drug record or a portion of a drug record in the lower level hierarchy field 4104, the DERS editor service may cause a number of options to be displayed in association with the drug record or portion of the drug record. These options may allow a use to perform a number of actions on the portion of the drug record selected. In the example embodiment in FIG. 167, three options are displayed next to "Clinical Use 3". From right to left, the options shown include a delete option 4180, a copy option 4182, and a compare option 4184. Other embodiments may include different or a different number of options. The delete option 4180 may be used to delete the selected drug record or portion of the drug record. The delete option 4180 will be described further later in the specification. The compare option 4184 may be used to compare the selected drug record or portion of the drug record with another drug record or portion thereof. After a user uses a compare option 4184 and selects a drug record portion of a drug record they would like to make a comparison with, the DERS editor service may cause a comparison similar to that shown in FIG. 108 to be display on the DERS editor user interface. The copy option 4182 may be used to copy the drug record or portion of the drug record to a different portion of the DAL file hierarchy.

In response to an indication that the user would like to copy a drug record or portion of a drug record, the DERS editor may prompt the user to affirm that they would like to copy the drug record. The DERS editor service may also prompt the user to specify where the user would like to copy the drug record or portion of the drug record to. The form of these prompts, may in some embodiments be similar to the example prompt 4190 depicted in FIG. 168. Such a prompt may be displayed as a modal window covering portions of a drug library screen 4100 similar to that shown in FIG. 167.

The example prompt 4190 depicted in FIG. 168 includes a copy summary 4192. The copy summary 4192 may indicate which drug record or portions of a drug record have been selected for copying. The example prompt 4190 also includes a copy destination selector 4194. The copy destination selector 4194 may be used to select which care groups and care areas to copy the changes to. Selecting a care group may automatically select every care area in that care group. Once a user has selected the desired care groups and care areas, the user may use a save option 4196 on the prompt 4190 to cause the DERS editor to save the changes and propagate them down to the selected care areas. If a user would like to cancel copying of the drug record or portion of the drug record a user may use a cancel option 4198 on the prompt 4190.

FIGS. 169 and 170 depicts two example embodiments of drug library screens 4100 which may be displayed on a user interface such as a DERS editor user interface. The drug library screens 4100 shown in FIGS. 169 and 170 include a copied portion of a drug record in their lower level hierarchy field 4104. A copy indicia 4200 may be included in association with the copied portion of the drug record in some embodiments. The copy indicia 4200 may indicate that a drug record or portion of a drug record has been copied from somewhere else in the DAL file. A copy indicia 4200 may be an icon, symbol, text, shape, etc. The copy indicia 4200 in the example embodiment includes the text "COPY" on a colored background.

Referring now to FIG. 171, an example embodiment of a master medication list screen 4300 which may be displayed on a user interface such as a DERS editor user interface is depicted. In the example embodiment, a user may navigate to a master medication list screen 4300 on a DERS editor user interface by selecting the proper tab 1598 on the user interface. The master medication list screen 4300 may be used to modify the master medication list 4302 from which a DAL file may be built. A user may use various master medication list screens 4300 to add the drugs used within an institution or organization in order to create a master medication list 4302. A user may then search through and pick drugs from the created master medication list 4302 when adding drug records to various care groups or care areas of an institution for example.

A user may use various master medication list screens 4300 to add various drug categories to be used within the DAL file. In some embodiments, these drug categories may be used to help filter the number of possible drug choices when adding drug records to a care group, care area, etc. For example, if a user knows that they would like to add a number of blood products to a care group, they may choose to search through only drugs which have been categorized as blood products in the master medication list 4302. Additionally, in some embodiments, drug categories may also be useful on a medical device which is using the selected DAL file. This may help to make programming of a therapy more efficient. When searching for the drug to be used for the therapy, a user may select a drug category to filter out all drugs which are not categorized as being in that category. If a user, for example, is going to infuse a nutrition product into a patient, the user may filter possible drug choices by selecting a nutrition drug category. This may allow a user to more quickly find the desired drug on the medical device.

The master medication list screen 4300 shown in FIG. 171 includes a search utility 4312. The search utility 4312 may be used to search for a desired drug in a master medication list 4302. This may be useful if a user needs to edit or delete the drug from the master medication list 4302 for example. As a user types in characters in the drug name, the master medication list 4302 may automatically filter such that only drugs beginning with the entered characters are shown. If a user types a drug into the search utility 4312 that is not already included in the master medication list 4302 a user may prompted by the DERS editor service as to whether or not they would like to add the drug to the master medication list 4302.

The master medication list screen 4300 in FIG. 171 includes a number of options which may be selected by a user. These options may allow a user to modify the master medication list 4302 in a variety of ways. From right to left, the options shown in FIG. 171 include a delete option 4304, an edit option 4306, an add option 4308, and an edit medication categories option 4310.

If a user selects a drug from the master medication list 4302, the user may use the delete option 4304 to delete the selected drug form the master medication list 4302. The edit option 4306 may be used to edit the details for a selected drug from the master medication list 4302. In some embodiments, the delete option 4304 and the edit option 4306 may be disabled (e.g. grayed out) if a drug in the master medication list 4302 has not been selected.

A user may use the add option 4308 to add any desired drugs to the master medication list 4302. If a user uses the add option 4308 a user may be required to specify the name of the drug as well as a number of other details related to the drug. This information may be entered in on a screen similar to that shown in FIG. 91 in some embodiments.

A user may use the edit medication categories option 4310 to edit the medication categories which may be assigned to drugs included in the master medication list 4302. In some embodiments and referring now also to FIG. 172, when a user selects the edit medication categories option 4310, the DERS editor user interface may display an edit medication categories prompt 4320. Such a prompt may be displayed over or covering a portion of a master medication list screen 4300 as a modal window. A user may edit the available medication categories via an edit medication categories prompt 4320.

The example edit medication categories prompt 4320 shown in FIG. 172 includes text instructions 4322. The instructions in the example prompt 4320 explain to a user how to add or delete various medication categories. Also included in the example prompt 4320 is a categories list 4324. A user may use the categories list to view, edit, and add to the various categories available. A number of options are also included in the example prompt 4320. In the example embodiment, an add option 4326, a delete option 4328, a cancel option 4330, and a save option 4332 are included.

If a user uses the add option 4326, the DERS editor user interface may add a category to the categories list 4324 which reads "New Drug Category", as shown in FIG. 172 for example. The user may then change the name of the newly added category to the desired category name. The delete option 4328 will be described later in the specification. Any changes made to the categories list 4324 may be saved using the save option 4332 if a user desired to save the changes. If a user does not desire to save the changes, the user may cancel the changes using the cancel option 4330.

In some embodiments a user may be able to use a DERS editor service define a number of parameters which may apply to all medications in those categories. Any defined parameters at the drug category level may be used as defaults or parent settings when medications in that category are added to the DAL file as medication records for various care groups and care areas. This may increase overall efficiency of DAL file creation. For example, in some embodiments, a user may define a drug classification parameter for the category. This may then be automatically populated into the drug classification parameter field when a user adds medications from this category as medication records. Any suitable parameters from Tables 4-10 may be defined at the category level in various embodiments. In some embodiments, it may be optional for a user to define various parameters at this level. This may allow for increased flexibility.

FIG. 173 depicts an example edit medication categories prompt 4320 which may be displayed on the user interface of a DERS editor service. A user may select (e.g. by clicking or double clicking) a medication category from the categories list 4324 and perform a number of actions. In the example embodiment, a user has selected the medication category "Code Blue". This may highlight the name of the medication category and cause the medication category name to become editable.

If desired, a user may change the name of the medication category by typing in a new name. In FIG. 174 the user has changed the name of the medication category "Code Blue" to "Heart Attack Meds". After a user has finished making changes to the medication categories list, a user may select the save option 4332 on the edit medication categories prompt 4320 to save changes to the list on a DERS editor database or the like. In some embodiments, a user may be prompted to confirm the category name change before the DERS editor service will allow the name change to be saved. A user may cancel the name change by using the cancel option 4330.

Referring again to FIG. 173 once a user has selected a medication category from the medication categories list 4324, a user may delete the medication category from the list. This may be done through use of a delete option 4328. Use of a delete option 4328 may cause the DERS editor to remove the medication category from the medication categories list 4324 as shown in FIG. 175. A user may then save the medication categories list 4324 by using a save option 4332. A user may also cancel deletion of the medication category by using a cancel option 4330. In some embodiments, a user may be prompted to confirm that they would like to delete the medication category before the DERS editor service will allow a user to save the medication categories list 4324. In some embodiments, a user may also be notified which drugs are currently in the category before the DERS editor service will allow a user to delete a category.

The progression of FIGS. 176-177 depicts an example process which may be used to delete a drug from a master medication list 4302. Deleting a medication from a master medication list 4302 may also delete the drug from any care groups and areas that the medication is used in. Additionally, deleting a drug may cause all clinical uses and concentrations defined in the DAL file for that drug to be deleted as well. FIG. 176 depicts an example master medication list screen 4300 which may be displayed on a user interface such as a DERS editor user interface. As shown, the master medication list screen 4300 includes a master medication list with a number of example drugs. In the example embodiment, the drug "DOPamine" is shown as selected. A user may select a medication from the master medication list 4302 by, for example, clicking on the desired medication in the master medication list 4302. A user may use a delete option 4034 to indicate to the DERS editor service that they would like to delete the medication from the master medication list 4302. In some embodiments, the user may be required to confirm deletion of a medication from the master medication list 4302 via a prompt.

FIG. 177 depicts an example embodiment of a delete medication prompt 4340 which may be displayed on a user interface such as a DERS editor user interface. Referring now also to FIG. 176, such a prompt may be displayed by the DERS editor service in response to a user indicating that they would like to delete a drug from the master medication list 4302. The delete medication prompt 4340 may be displayed as modal window over a master medication list screen 4300 in some embodiments. As shown, the delete medication prompt 4340, includes summary information 4342. The summary information 4342 may include information about the drug being deleted. In the example embodiment, the summary information 4342 indicates which care groups and care areas the drug is used in.

The example delete medication prompt 4340 also includes a cancel option 4344 and a save option 4346. If after reviewing the summary information 4342 displayed in the delete medication prompt 4340 a user desires to cancel deletion of the medication from the master medication list 4302, a user may use the cancel option 4344. If a user would like to proceed with deleting the medication, a user may use the save option 4346. This may cause the DERS editor service to delete the medication from the master medication list 4302 as well as delete any DAL file entries using that medication.

The progression of FIGS. 178-179 depicts an example process which may be used to delete a medication record or portion of a medication record from a care group. FIG. 178 depicts an example embodiment of a drug library screen 4100 which may be displayed on a user interface such as a DERS editor user interface. As called out by the record level indicator 4120, the lower level hierarchy field 4104 is displaying details defined for "Drug 2" in Care Group 2 . . . . A user has selected "Clinical Use 3" and is viewing the drug record parameters field 4132 for that use in FIG. 178. As mentioned above, when a user selects a medication record or portion of a medication record, a number of options may become available on the user interface. One such option may be a delete option 4180. A user may use a delete option 4180 to delete a medication record or portion of a medication record from the DAL file.

If a user indicates to the DERS editor service that they would like to delete a medication record or portion of a medication record from the DAL file via the delete option 4180, a user may be required to confirm deletion through a prompt. In some embodiments, a user may also be required to specify additional information through the prompt. For example, a user may indicate which care areas they would like to delete the medication record or portion of the medication record from. Such a prompt may be displayed as a modal window over and/or covering portions of a drug library screen 4100.

FIG. 179 depicts an example of a delete medication record prompt 4350. As shown, the example delete medication record prompt 4350 includes instructions 4352. The instruction 4352 in FIG. 179 ask a user to select which care areas within the care group they would like to delete the medication record portion from. The instructions 4352 may also warn the user that deleting medication record or portion of a medication record will also delete any child medication record portions. The example delete medication record prompt 4350 also includes summary information 4354. The summary information 4354 may convey a summary of changes made by the user. This may allow the user to review the change(s) before they are saved. The summary information 4354 may be displayed in the form of a bulleted list, text description, etc. The example delete medication record prompt 4350 also includes a care area selector 4356. The care area selector 4356 may be used to select which care areas within the care group to delete the medication record or portion of the medication record from. Once a user has selected the desired care areas, the user may use a save option 4360 on the prompt 4350 to cause the DERS editor to delete the medication record or portion of the medication record and save. If a user wishes to cancel deletion of the medication record or portion of the medication record, a user may use a cancel option 4358.

Depending on where the medication record or portion of the medication record is deleted from, the delete medication record prompt 4350 may differ. For example, if a user deletes a medication record from a care area, instead of a care group, the care area selector 4356 may not be included. FIG. 180 depicts another example embodiment of delete medication record prompt 4350 which may be displayed on a user interface such as a DERS editor user interface. The delete medication record prompt 4350 shown in FIG. 180 may be displayed by a DERS editor service when a user deletes a portion of a medication record from a care area. As shown, the delete medication record prompt 4350 does not include a care area selector 4356 or instructions 4352 (see FIG. 180). Instead the delete medication record prompt 4350 only includes summary information which describes the change so that the user may review it. The user may use a save option 4360 on the prompt 4350 to cause the DERS editor to delete the medication record or portion of the medication record and save. If a user wishes to cancel deletion of the medication record or portion of the medication record, a user may use a cancel option 4358.

Once a DAL file has been created, reviewed, and approved, the DAL file may be released to any of a variety of target medical devices. Any suitable medical device may use a DAL file. In some embodiments, a DAL file may be created to support various infusion devices and/or physiological monitors. An example software architecture of an example medical device is shown schematically in FIG. 181. The example software architecture described in FIG. 181 is given solely for purposes of example. Not all medical devices included in the scope of the present disclosure may employ such software architecture. The software architecture shown and described in FIG. 181 is, however, equally applicable to any number of medical device types and embodiments.

The example software architecture divides the software into cooperating subsystems that interact to carry out required actions. Each subsystem may be composed of one or more execution streams controlled by the underlying operating system. Useful terms used in the art include operating system, subsystem, process, thread and task.

Asynchronous messages 4000 are used to 'push' information to the destination task or process. The sender process or task does not get confirmation of message delivery. Data delivered in this manner is typically repetitive in nature. If messages are expected on a consistent schedule, the receiver process or task can detect a failure if a message does not arrive on time.

Synchronous messages 4002 may be used to send a command to a task or process, or to request ('pull') information from a process or task. After sending the command (or request), the originating task or process suspends execution while awaiting a response. The response may contain the requested information, or may acknowledge the receipt of the sent message. If a response is not received in a timely manner, the sending process or task may time out. In such an event, the sending process or task may resume execution and/or may signal an error condition.

An operating system (OS) may be a collection of software that manages computer hardware resources and provides common services for computer programs. The operating system may act as an intermediary between programs and the computer hardware. Although some application code may be executed directly by the hardware, the application code may frequently make a system call to an OS function or be interrupted by it.

The RTP 4004 may run on a Real Time Operating System (RTOS) that has been certified to a safety level for medical devices. An RTOS may be a multitasking operating system that aims at executing real-time applications. Real-time operating systems often use specialized scheduling algorithms so that they can achieve a deterministic nature of behavior. The UIP 4006 may run on a Linux operating system. In the example embodiment described in relation to FIG. 181, the UIP runs on a Linux operating system. Other embodiments need not run on a Linux operating system. The Linux operating system is a Unix-like computer operating system.

A subsystem may be a collection of software (and perhaps hardware) assigned a specific set of (related) system functionality or functionalities. A subsystem may have clearly defined responsibilities and a clearly defined interface to other subsystems. A subsystem may be an architectural division of the software that uses one or more processes, threads or tasks.

A process may be an independent executable running on a Linux operating system, for example, which runs in its own virtual address space. The memory management hardware on the CPU is used to enforce the integrity and isolation of this memory, by write protecting code-space, and disallowing data access outside of the process' memory region. Processes may only be able to pass data to other processes using inter-process communication facilities.

In Linux, a thread is a separately scheduled, concurrent path of program execution. On Linux, a thread is always associated with a process (which must have at least one thread and can have multiple threads). Threads share the same memory space as its 'parent' process. Data can be directly shared among all of the threads belonging to a process but care should be taken to properly synchronize access to shared items. Each thread has an assigned execution priority.

A Task on an RTOS (Real Time Operating System) may be a separately scheduled, concurrent path of program execution, analogous to a Linux 'thread'. All tasks share the same memory address space which consists of the entire CPU memory map. When using an RTOS that provides memory protection, each task's effective memory map may be restricted by the Memory Protection Unit (MPU) hardware to the common code space and the task's private data and stack space.

Tasks running on the RTP 4004 may be required to communicate with each other as well as to tasks that are executing on the UIP 4006. The processes on the UIP 4006, communicate via IPC calls as shown by the one-way arrows in FIG. 181. Each solid-lined arrow represents a synchronous message 4000 call and response, and dotted-line arrows are asynchronous messages 4002. The tasks on the RTP 4004 similarly communicate with each other. The RTP 4004 and UIP 4006 may be bridged by an asynchronous serial line 4008, with one of an InterComm Process 4010 or InterComm Task 4012 on each side. The same communications API (Application Programming Interface) may be present on both sides of the bridge, so all processes and tasks can use the same method calls to interact.

The RTP 4004 messaging system may use a unified global addressing scheme to allow messages to be passed to any task in the system. Local messages may be passed in memory utilizing the facilities of the RTOS' message passing, with off-chip messages routed over the asynchronous serial link 4008 by the InterComm Task 4012.

The InterComm Task 4012 may manage the RTP 4004 side of the serial link 4008 between the two processors. The InterComm Task 4012 is the RTP 4004 equivalent of the InterComm Process 4010 on the UIP 4006. Messages received from the UIP 4006 may be relayed to their destination on the RTP 4004. Outbound messages may be forwarded to InterComm Process 4010 on the UIP 4006.

All messages between the RTP 4004 and the UIP 4006 may be checked for data corruption using an error-detecting code (e.g. 32 bit CRC). Messages sent over the serial link 4008 may be re-sent if corruption is detected. This may help to provide a communications system that is more tolerant to ESD. Corrupted messages within the processor between processes may be handled as a hard system failure. All of the message payloads used with the messaging system may be data classes derived from a common baseclass (MessageBase) to assure consistency across all possible message destinations.

In the example embodiment, the Executive Process 4014 may be invoked by the Linux system startup scripts after all of the operating system services have started. The Executive Process 4014 may then start the various executable files that comprise the software on the UIP 4006. If any of the software components should exit or fail unexpectedly, the Executive Process 4014 may be notified, and may generate the appropriate alarm.

While the system is running, the Executive Process 4014 may act as a software 'watchdog' for various system components. After registering with the Executive Process 4014, a process is required to 'check in' or send a signal periodically to the Executive Process 4014. Failure to 'check in' at the required interval may be detected by the Executive Process 4014. Upon detection of a failed subsystem, the Executive Process 4014 may take remedial action of either: do nothing, declaring an alarm, or restarting the failed process. The remedial action taken may be predetermined by a table entry compiled into the Executive Process 4014. The 'check-in' interval may vary from process to process. The amount of variance between 'check-in' times for different processes may be based in part on the importance of the process. The check-in interval may also vary during medical device operation to optimize the device controller response by minimizing computer processes. In one specific example embodiment where the medical device is a syringe pump, during syringe loading, the device controller may check-in less frequently than during active pumping.

In response to the required check-in message, the Executive Process 4014 may return various system status items to processes that checked-in. The system status items may be the status of one or more components of the medical device and/or errors. The system status items may include, but are not limited to: battery status, WiFi connection status, device gateway connection status, device status (Idle, Infusion Running, Diagnostic Mode, Error, etc.), technical error indications, and engineering log levels.

A thread running in the Executive Process 4014 may be used to read the state of the battery 4016 from an internal monitor chip in the battery 4016, for example. This may be done at a relatively infrequent interval such as every 10 seconds.

The UI View 4018 may implement the graphical user interface (also referred to herein as GUI, see 3420 of FIG. 210 for example), rendering the display graphics for a display, and responding to inputs (e.g. received via a touch screen, buttons, or other data input scheme). The UI View 4018 design may be stateless. The graphic being displayed may be commanded by a UI Model Process 4020, along with any variable data, user input dialogues, etc. to be displayed. The commanded graphic may be refreshed periodically regardless of data changes.

The style and appearance of user input dialogues (virtual keyboard, drop down selection list, check box, parameter entry fields etc.) may be specified by the screen design, and implemented entirely by the UI View 4018. User input may be collected by the UI View 4018, and sent to the UI Model 4020 for interpretation. The UI View 4018 may provide for multi-region, multi-lingual support with facilities for the following list including but not limited to: virtual keyboards, unicode strings, loadable fonts, right to left entry, translation facility (loadable translation files), and configurable numbers and date formats.

The UI Model 4020 may implement the screen flows, and so controls the user experience. The UI Model 4020 may interact with the UI View 4018, specifying the screen to display, and may supply any transient values to be displayed on the screen. Here "screen" refers to the image displayed on the physical display and the defined interactive areas or user dialogues i.e. buttons, sliders, keypads etc, on a physical touch screen display. The UI Model 4020 may interpret any user inputs sent from the UI View 4018, and may either update the values on the current screen, command a new screen, or pass the request to the appropriate system service (e.g. 'start pumping' may be passed to the RTP 4004).

When selecting a medication to infuse from the Drug Administration Library, the UI Model 4020 may interact with the DAL file stored in the local data base which is part of a Database System 4022. The user's selections may setup the run time configurations for programming and administration of the desired medication.

While the operator is entering an infusion program, the UI Model 4020 may relay the user's input values to the Infusion Manager 4024 for validation and interpretation. Therapeutic decisions may not be made by the UI Model 4020. The treatment values may be passed from the Infusion Manager 4024 to the UI Model 4020 to the UI View 4018 to be displayed for the user.

The UI Model 4020 may continuously monitor the device status gathered from the Infusion Manager 4024 (current infusion progress, alerts, etc.) for possible display by the UI View 4018. Alerts/alarms and other changes in system state may provoke a screen change by the UI Model 4020.

The Infusion Manager Process (1M) 4024 may validate and control the therapy delivered by the device. To start a therapy, the user may interact with the UI View/Model 4018/4020 to select a specific medication, clinical use, concentration, etc. This selects one specific DAL file entry for use. The IM 4024 loads this DAL file entry from the database 4022, for use in validating and running the infusion.

Once a DAL file entry is selected, the IM 4024 may pass the dose mode, limits for all user enterable parameters, and the default values (if set) up to the UI Model 4020. Using this data, the UI Model 4020 may guide the user in entering the infusion program.

As each parameter is entered by the user, the value may be sent from the UI View/Model 4018/4020 to the IM 4024 for verification. The IM 4024 may echo the parameters back to the UI View/Model 4018/4020, along with an indication of the parameter's conformance to any applicable DAL file limits. This allows the UI View/Model 4018/4020 to notify the user of any values that are not allowed or unacceptable. When a complete set of valid parameters has been entered, the IM 4024 also may return a valid infusion indicator, allowing the UI View/Model 4018/4020 to present a 'Start' control to the user.

The IM 4024 may simultaneously make the therapy/device status available to the UI View/Model 4018/4020 upon request. If the UI View/Model 4018/4020 is displaying a 'status' screen, it may request this data to populate it. The data for the status screen may be a composite of the infusion state, and the pump state.

When requested to run the (valid) infusion, the IM 4024 may pass a 'Therapy Worksheet' containing user specified data and a 'Therapy Template' containing the read-only limits from the DAL file as a CRC'd binary block to the Infusion Control Task 4026 running on the RTP 4004. The Infusion Control Task 4026 on the RTP 4004 may take the same user inputs, conversions and DAL file inputs and recalculates the Therapy Worksheet. The Infusion Control Task 4026 calculated results may be stored in a second CRC'd binary block and compared to the first binary block from the UIP 4006. The therapy calculations performed on the UIP 4006 may be recalculated and double checked on the RTP 4004 before the therapy may be run.

Coefficients to convert the input values (i.e., μl, grams, %, etc.) to a standard unit (e.g., ml) may be stored in the UIP 4006 memory or database system 4022. The coefficients may be stored in a lookup table or at specific memory locations. The lookup table may contain 10's of conversion values. In a specific example embodiment, in order to reduce the chance that flipping a single bit will result in the wrong conversion factor being used, the addresses for the conversion values may be distributed among values from zero to 4294967296 or $2^{32}$. The addresses may be selected so that the binary form of one address is never just one bit different from a second address.

While a therapy is running, the IM 4024 may monitor its progress, sequences, pauses, restarts, secondary infusions, boluses, and KVO (keep vein open) scenarios, etc. as needed. Any user alerts requested during the therapy (Infusion near complete, KVO callback, Secondary complete callback, generic callbacks, etc.) may be tracked and triggered by the IM 4024.

Processes on the UIP 4006 may communicate with each other via a proprietary messaging scheme based on a message queue library that is available with Linux. The system provides for both acknowledged (synchronous message 4000) and unacknowledged (asynchronous message 4002) message passing.

Messages destined for the Real-time Processor (RTP) 4004 may be passed to the InterComm Process 4010 which forwards the messages to the RTP 4004 over a serial link 4008. A similar InterComm Task 4012 on the RTP 4004 may relay the message to its intended destination via the RTP 4004 messaging system.

The messaging scheme used on this serial link 4008 may provide for error detection and retransmission of flawed messages. This may help make the system less susceptible to electrical disturbances that may occasionally 'garble' interprocessor communications.

To maintain a consistent interface across all tasks, the message payloads used with the messaging system may be data classes derived from a common baseclass (MessageBase). Such a class may add both data identity (message type) and data integrity (CRC) to messages.

The Audio Server Process 4028 may be used to render sounds for a medical device. All user feedback sounds (key press beeps) and alarm or alert tones may be produced by playing pre-recorded sound files. The sound system may also be used to play music or speech if desired. Sound requests may be symbolic (such as "Play High Priority Alarm Sound"), with the actual sound file selection built into the Audio Server process 4028. The ability to switch to an alternative soundscape may be provided. This ability may be used to customize the sounds for regional or linguistic differences.

The Device Gateway Communication Manager Process (DGCM) 4030 may manage communications with the Device Gateway Server over a Wi-Fi network 4032. The DGCM 4030 may be started and monitored by the Executive Process 4014. If the DGCM 4030 exits unexpectedly, it may be restarted by the Executive Process 4014. If the failures are persistent the system may continue to function without the gateway running.

It may be the function of the DGCM 4030 to establish and maintain the Wi-Fi connection and to then establish a connection to the Device Gateway. All interactions between the DGCM 4030 and the Device Gateway may use a system such as the system described in the cross referenced non-provisional application for System, Method, and Apparatus for Electronic Patient Care.

If the connection to the gateway is unavailable or becomes unavailable, the DGCM 4030 may discontinue any transfers in progress, and attempt to reconnect the link. Transfers may be resumed when the link is reestablished. Network and Gateway operational states may be reported periodically to the Executive Process 4014. The Executive Process 4014 may distribute this information for display to the user.

The DGCM 4030 may function as an autonomous subsystem, polling the Device Gateway Server for updates, and downloading newer items when available. In addition the DGCM 4030 may monitor the logging tables in the database, uploading new events as soon as they are available. Events that are successfully uploaded may be flagged as such in the database. After a reconnection to the Device Gateway Server, the DGCM 4030 may 'catch up' with the uploads, sending all items that were entered during the communications disruption. Firmware and DAL file updates received from the Gateway may be staged in the UIP's 4006 file system for subsequent installation. Infusion programs, clinical advisories, patient identification and other data items destined for the device may be staged in the database.

The DGCM 4030 may report connection status and date/time updates to the Executive Process 4014. There may not be other direct connections between the DGCM 4030 and any of the other operational software. Such a design decouples the operational software from the potentially transient availability of the Device Gateway and Wi-Fi network.

The Motor Check Process 4034 may read a hardware counter or encoder that reports motor rotation. The Motor Check Process 4034 may independently estimate the motor's movements, and compare them to the expected motion based on the user inputs for rate of infusion. This may be an independent check for proper motor control. The primary motor control software may be executed on the RTP 4004.

Event information may be written to a log via the Logging Process 4036 during normal operation. These events may consist of internal device status and measurements, as well as therapy history events. Due to the volume and frequency of event data, these logging operations may be buffered in a queue, such as a FIFO queue, while waiting to be written to the database.

A SQL database or the like may be used to store the DAL file, Local Machine Settings, Therapy History and Device Log data. Stored procedures executed by the database server may be used to insulate the application from the internal database structures. The database system 4022 may be used as a buffer for event data destined for the Device Gateway server, as well as a staging area for therapy settings and warnings sent to the device from the Device Gateway.

Upon requesting the start of a therapy, the DAL file entry and all user selected parameters may be sent to the Infusion Control Task 4026. All of the DAL file validations and a cross check of programmed parameters against one another (e.g. rate, volume, and dose) may be performed. The result may be checked against the results calculated by the IM 4024 on the UIP 4006. These results may be required to match to continue.

When running an infusion, the Infusion Control Task 4026 may control the delivery of each therapy 'segment'; e.g. one part of an infusion consisting of a volume and a rate. Examples of segments are: a primary infusion, KVO, bolus, remainder of primary after bolus, primary after titration, etc. The therapy segments may be sequenced by the IM Process 4024 on the UIP 4006.

The Device Control Task 4038 may incorporate the controllers that drive a pumping mechanism, for example. In such embodiments, the desired infusion rate and amount (VTBI) may to be administered may be specified in commands sent from the Infusion Control Task 4026.

The Device Control Task 4038 may receive periodic sensor readings from the Sensor Task 4040. In a specific embodiment, the new sensor 4046 readings may be used to determine motor speed and position, as well as to calculate the desired command to send to the Brushless Motor Control IRQ 4042. The receipt of a sensor message may trigger a recalculation of the controller output.

Brushless Motor Control IRQ 4042 may not run as a task; it may be implemented as a strict foreground (interrupt context) process. Interrupts may be generated from the commutator or Hall Effect sensors associated with a motor, and the commutation algorithm may be run entirely in the interrupt service routine.

While delivering fluid, the Device Control Task 4038 may perform at least one of, but is not limited to, the following tasks: controlling pumping speed, measuring volume delivered, measuring air detected (over a rolling time window), measuring fluid pressure or other indications of occlusions, and detecting upstream occlusions.

Relevant measurements may be reported to the RTP Status Task 4044 periodically. The Device Control Task 4038 may execute one infusion segment at a time, stopping when the commanded delivery volume has been reached. The Sensor Task 4040 may read and aggregate the sensor 4046 data used for the dynamic control of a pumping system.

In a specific embodiment, the Sensor Task 4040 may be scheduled to run at a consistent 1 kHz rate (every 1.0 ms) via a dedicated counter/timer. After all of the relevant sensors 4046 are read, the data may be passed to the Device Control Task 4038 via an asynchronous message 4002. The periodic receipt of this message may be used as the master time base to synchronize the medical device's control loops.

The RTP Status Task 4044 may be the central repository for both the state and the status of the various tasks running on the RTP 4004. The RTP Status Task 4044 may distribute this information to both the IM 4024 running on the UIP 4006, as well as to tasks on the RTP 4004 itself. The RTP Status Task 4044 may also be charged with fluid accounting for the ongoing therapy. Device starts and stops, as well as therapy progress may be reported to RTP Status Task 4044 by the Device Control Task 4038. The RTP Status Task 4044 may account for at least one of the following: total volume delivered, primary volume delivered, primary VTBI (counted down) volume delivered, VTBI volume delivered for a bolus while the bolus is in progress, and VTBI volume delivered for a secondary infusion while the secondary infusion is in progress.

All alerts or alarms originating on the RTP 4004 may be funneled through the RTP Status Task 4044, and subsequently passed up to the UIP 4006.

While the unit is in operation, the program flash, and RAM memory may be continually tested by the Memory Checker Task 4048. This test may be non-destructive. This test may be scheduled so that the entire memory space on the RTP 4006 is tested every few hours. Additional periodic checks may be scheduled under this task if needed.

FIG. 182 depicts a flowchart detailing a number of example steps which may be used to install a syringe on a medical device when preparing to administer an infusion with the medical device. As shown, the device may determine if a user has installed a syringe on the medical device in step 2500. The device may make the determination that a syringe is not present in any number of suitable ways. This determination may be made based data generated by one or more sensor on the device. For example, the determination may be based upon on a position signal from a syringe barrel clamp, a position signal from a plunger flange retainer, a signal from a sensor on a clip for a syringe barrel flange, a combination thereof, etc. In some embodiments, this determination may only be made when a user has reached a predefined point when in the process of programming the device for a therapy. For example, the determination may be made after a user has chosen the clinical use for a drug. In alternative embodiments, this decision may not be made by the device. A user may instead install the syringe at any convenient time during programming of the medical device.

If a user has not already installed a syringe on the device, the user interface of the device may prompt the user to install the syringe on the device in step 2502. This may include a graphical animation of a syringe being installed on the medical device. In some embodiments it may also include an annotated illustration which informs the user how to install a syringe on the device. In other embodiments the prompt may be any other suitable type of prompt. The user may then install the syringe in step 2504. In some embodiments, step 2502 may also be caused to occur if the medical device determines (e.g. via sensor data from any of the sensors mentioned above) that a user is attempting to install a syringe on the medical device.

If the medical device determines that a user had already installed a syringe in step 2500 or after a user installs a syringe in step 2504 the device may check to see if the syringe was correctly installed in step 2506. This determination may be based upon data generated by one or more sensor on the device. For example, the determination may be based upon a position signal from a syringe barrel clamp, a position signal from a plunger flange retainer, a signal from a sensor on a clip for a syringe barrel flange, a combination thereof, etc.

If the syringe is not properly installed, the device may prompt a user to fix any issues with how the syringe is loaded. This may include a graphic animation, annotated illustration, text instruction, etc. on the user interface which shows a user how to resolve the issue with how the syringe is installed. For example, if it is determined that the syringe barrel flange is not clipped into place, the user interface of the device may notify a user of this. The user interface may also display an illustration which shows how the issue may be resolved. The user may then resolve any issues in step 2510.

If the device determines that a syringe was properly installed in step 2506 or after a user has resolved any issue with the syringe installation in step 2510 the device may attempt to identify the installed syringe in step 2512. This may be done by measuring the dimensions of the syringe with one or more sensors on the device. For example, possible syringes may be identified using a position signal from a syringe barrel clamp, a position signal from a plunger flange retainer, a signal from a sensor on a clip for a syringe barrel flange, a combination thereof, etc. The dimensions may be compared to a lookup table or the like stored in memory of the device to determine which possible syringes may be installed on the device.

In step 2514, a list of possible syringes may be displayed on the device user interface. The user may then select the syringe they installed on the medical device from the list in step 2516. In some embodiments, the device may then check the syringe against any restrictions which have been defined in the DAL file in step 2518. If the syringe is determined to be acceptable, the device may allow a user to continue programming or start an infusion if one has already been programmed.

If the syringe is determined to break a restriction defined in the DAL file, the device may indicate this on its user interface in step 2520. The user may then remove the syringe and get an appropriate syringe for the infusion in step 2522. The syringe installation process may then return to step 2502 in some embodiments. A user may also cancel the infusion in step 2524 if desired.

In some embodiments, the syringe list displayed in step 2514 may not include syringes which break restrictions in the DAL file. In some embodiments, a user may have the option of accessing a larger list of syringes if the installed syringe is not included in the list displayed in step 2514. After accessing the larger list, the user may select the installed syringe from that larger list. As a specific example, the list displayed in 2514 may be a list of syringes used in a care area, while the larger list may be a list of syringes used in a care group or institution. In some embodiments, a DAL file may be used to define syringes which a medical device will not allow to be used in a care area, for a particular medication, for a particular clinical use, etc. Such syringes may appear as grayed out in the syringe list displayed in step 2514 or a larger syringe list if such as list is accessed by a user. Alternatively, a notification that the syringes is disallowed and cannot be used with the programmed therapy may be displayed upon attempted selection of a disallowed syringe.

FIG. 183 depicts a flowchart detailing a number of example steps which may be used to prime an IV line of a medical device. As shown, in step 2530 a user may install a syringe or administration set on the device. This may be done following steps similar to those shown in FIG. 182 or FIG. 184. A user may then select the prime function on a medical device user interface to prime the line in step 2534. The device may then prime the line in step 2536. In some embodiments, the medical device may prime the line using a predefined volume delivered at a predefined rate. In such embodiments, this may be defined in the DAL file stored in the memory of the medical device. If necessary, the user may then return to step 2534 to prime the line again. In some embodiments, and for some devices, a user may not be able to deliver a therapy if the device has not been primed.

FIG. 184 depicts a flowchart detailing a number of example steps which may be used to load an administration set into a medical device such as a large volume pump. As shown, in step 2540, a user may open the door of the medical device. In step 2542, the user interface of the device may display a graphical animation of an administration set being installed in the medical device. In some embodiments it may also or instead include an annotated illustration, text instructions, etc. which informs the user how to install an administration set in the device. The user may then load the administration set and close the door of the device in steps 2544 and 2546 respectively. If a user does not want to load an administration set, but rather opened the door in step 2540 for another reason they may skip step 2544 and only perform step 2546.

The device may then check for the presence of the administration set in step 2548. If the device determines that a set has been loaded, the device may then check to see that a slide clamp is present in step 2550. If the device determines that a slide clamp has not been installed, the device may alert and display instructions on the user interface which show how to install the slide clamp in step 2552. This may include a graphic animation, annotated illustration, text instructions, etc.

If the device determines that the slide clamp has been installed, the device may then check for air in the IV line in step 2554. If the device determines that there is air in the IV line, the device may, for example, alert and display instructions on the user interface which show a user how to prime the administration set in step 2556. These instructions may include a graphic animation, annotated illustration, text instructions, etc.

If the device determines that the IV line is free of air in step 2554, then the device may check for leaks and determine if the set has been correctly installed in step 2558. If the device determines that there is an issue with the installed set, the device may alert and display instructions on the user interface which show how to reinstall the administration set in step 2560. These instructions may include a graphic animation, annotated illustration, text instructions, etc.

A user may proceed from any of steps 2552, 2556, or 2560 to step 2562 in which the user opens the door of the device. The user may then attempt to resolve the issue in step 2564. In step 2566, the user may then close the door. Once the door has been closed, the device may clear the alert in step 2568. The device may then return to step 2548 and check for the presence of the administration set. The process may then proceed as described above.

FIG. 185 depicts a flowchart detailing a number of example steps which may be used to select a care area, medication, clinical use, and a concentration for a drug when programming an infusion on a medical device. In step 2570, a user may select a care area on the user interface of a device. In some embodiments, an additional step in which a user selects a care group may precede step 2570. The device user interface may then display a medication selection screen in step 2572. The medication selection screen may allow a user to select the drug which will be infused from a list of drugs for the specific care area. The user may then select the medication in step 2574. In some embodiments, the user may select the medication from a list of medications displayed on the user interface. In some embodiments, the user may navigate through a number of lists to find the desired drug. For example, a user may select a drug category from a list of drug categories and then select the desired drug from a list of drugs assigned to that category. Such lists and categories may be defined in the DAL file stored in the memory of the device. These lists may be retrieved and rendered for display as necessitated by workflow progression. In some embodiments a user may also find the desired drug by entering a search query for the drug on the user interface of the device. The search query may be used to find the drug in the DAL file if the drug exists in the DAL file.

If the medication selected requires a text descriptor, the user may be prompted to provide one in step 2575. Whether or not a medication requires a text descriptor may be specified in the DAL file entry for the medication. If a user selects a Medication Record for a non-specified medication, for example, it may require a text descriptor which is entered by the user. In such a scenario, this descriptor may provide some information about what drug was infused and why it was infused using a Medication Record for a non-specified medication. A user may enter text for the descriptor in step 2576. The user may enter this descriptor using a virtual keyboard which is displayed on the user interface of the medical device.

If multiple clinical use records for the selected drug exist, the device may display the possible clinical uses on its user interface in step 2578. In some embodiments, this may involve displaying, in list or other format, the clinical uses defined for the drug in the DAL file. The user may then select the desired clinical use in step 2580. In some embodiments, the device may then display a clinical advisory or notes for the clinical use on the user interface in step 2582. In some embodiments, only the short text version of a clinical advisory may be displayed in this step. In some embodiments, the short text version may be displayed with an option which may be used to view the full clinical advisory. In embodiments where a clinical advisory is shown, the user may indicate acknowledgment of the clinical advisory in step 2584.

If the clinical use record selected has multiple concentration records defined, the medical device may display the possible concentration records on its user interface in step 2586. This may involve displaying, in list or other format, concentration records defined for the clinical use in the DAL file. The user may then select the desired concentration record in step 2588. If the concentration record allows the user to change the concentration of the drug (e.g. user selects a concentration record for a custom concentration) the user may then specify the concentration which will be used. A user may specify the concentration by defining a concentration (e.g. mg/ml) on the user interface of the device in step 2590. A user may also or instead define the total volume of the container and the amount of drug in the container in step 2592. After a user specifies the concentration, the device may check the concentration against any limits defined in the DAL file stored in the memory of the device in step 2594. If the parameters are outside of the limits defined in the DAL file a user a may override the limit if the limit exceeded is a soft limit. If the user desires to override a soft limit the user may do so in step 2596. If a user does not desire to override the limit or the limit exceed is a hard limit, the user may return to step 2590 or 2592 and redefine the concentration.

FIG. 186 depicts a flowchart detailing a number of example steps which may be used to program an infusion on a medical device. As shown, in step 2600 a user may specify a desired medication, clinical use, and a concentration for the infusion. This may in some embodiments, be done by following steps similar to those shown and described in FIG. 185. A user may then program how the medical device will deliver the drug by defining infusion parameters in one of steps 2602, 2604, 2606, or 2608. The infusion parameters defined for the infusion may depend on the type of infusion being administered. In some embodiments, the parameters which are defined may be different depending on the clinical use selected. For example, a weight based clinical use may require a user to define a patient's weight while a non-weight based infusion may not require a user to define a patient's weight. Similarly, a continuous infusion may require different parameters to be defined than an intermittent infusion. The steps 2602, 2604, 2606, and 2608 shown are only examples. In some embodiments, a user may proceed from step 2600 to different steps or a different number of steps depending on the type of infusion selected in step 2600.

The medical device may then check the parameters defined for the infusion against any limits defined in the DAL file stored in the memory of the medical device. If a parameter defined exceeds any of the limits defined in the DAL file, a notification to this effect may be displayed on the user interface of the medical device. If a parameter exceeds a hard limit, the user interface of the device may display a message that a hard limit has been exceeded in step 2612. A user may not be allowed to proceed with the infusion and may instead be required to re-define the infusion parameters when a hard limit is exceeded. If a parameter exceeds a soft limit the user interface of the device may display a message that a soft limit has been exceed in step 2614. A user may have the option of overriding the soft limit. If a user declines to override the soft limit the user may be required to re-define the infusion parameters. If a user decides to override the soft limit they may do so in step 2616.

If a user overrides a soft limit in step 2616 or the medical device determines that the entered parameter values are within the limits specified in the DAL file, the medical device may display an infusion summary in step 2618. The infusion summary may, in some embodiments, be displayed on an infusion summary screen on the device's user interface. Such a screen may include information about the infusion and list the parameters for the infusion defined by the user. Any parameters which required a soft limit override may be highlighted or otherwise marked on the user interface. A user may review the infusion summary screen. If needed a user may modify the infusion program in step 2620. If a user modifies the infusion program the device may return to step 2610 and proceed as described above.

In some embodiments or for some medications, clinical uses, concentrations, etc. a second review may be required before an infusion can be delivered to a patient. Whether a second review is required may be defined in the DAL file stored in the memory of a medical device. If a second review is required for the infusion, the second reviewer may review the programmed infusion in step 2622. The second operator may then enter their name, user ID, etc. to approve of the programmed infusion in step 2624. In step 2626, the medical device may enable a start infusion option on the medical device user interface.

FIG. 187 depicts a flowchart detailing a number of example steps which may be used to determine if a parameter entered on a medical device falls outside the limits defined for that parameter. As shown, a user may enter a parameter or a number of parameters in step 2630. These parameters may, for example, be entered on the user interface of the device. The device may then, in step 2632, check the parameter or parameters entered in step 2630 against limits defined for those parameters in the DAL file stored in the memory of the device. In some embodiments, in step 2632, the device may additionally check to see if the parameter or parameters entered will force other parameters to exceed limits defined in the DAL file. For example, the device may check to see if an entered time parameter and entered dose parameter may cause a rate parameter to exceed its defined limit. If the parameters entered are found to be valid, the parameters may be marked as valid in step 2633 and a user may be allowed to continue programming the medical device. The parameters may be marked as valid for CQI compliance tracking purposes.

If a parameter or parameters entered are determined to be outside of the hard limits defined in the DAL file, the device may display a notification to this effect on its user interface in step 2634. These parameters may be marked as invalid and the user interface may prompt a user to change them in step 2636. The parameters may be marked as invalid for CQI compliance tracking purposes. A user may then return to step 2630 and re-define the parameter or parameters.

If a parameter or parameters entered are determined to be outside of a soft limit, but not a hard limit in step 2632, the device may display a notification that a parameter exceeds a soft limit on its user interface in step 2638. A user may have the option of overriding the soft limit. If a user does not override the soft limit, the device may mark the parameters as invalid and the user interface may prompt a user to change the parameter or parameters in step 2636. The user may then return to step 2630 and re-define the parameters. If a user decides to override the soft limit, a user may indicate this in step 2640. In some embodiments, or for some drugs, clinical uses, concentrations, etc, a user may be required to enter a text descriptor if a soft limit is overridden. If required, a user may be prompted to do so in step 2641 and do so in step 2642. The device may then mark the parameters as a soft limit violation in step 2644. This may be done for CQI compliance tracking purposes. In some embodiments, or for some drugs, clinical uses, concentrations, etc. a soft limit override may require the review of a second user. If a second review is required the device may display the information needing review in step 2646. The second user may review this information in step 2648. The second user may enter their name, user ID, etc. in step 2650 to approve the override. The user may then be allowed to use the entered parameters and continue to program the medical device. Whether a parameter is marked as valid or invalid will be included in the infusion story for the infusion which is eventually sent to the CQI database.

FIG. 188 depicts a flowchart which details a number of example steps which may be used to deliver a primary continuous infusion. As shown, in step 2660, a user may enter various infusion parameters. This step may be completed by performing steps similar to those shown in FIGS. 185 and 186 for example. The device may then check to see that the parameters entered in step 2660 fall within any limits which are defined in the DAL file stored in the memory of the device in step 2662. This may be done following steps similar to those shown and described in FIG. 187. If the parameters are not valid, the user may be returned to step 2660 where they may re-enter the parameters. If the parameters are valid, the medical device may display an infusion summary screen in step 2664. The user may then indicate that they would like to start the infusion in step 2666. The device may then begin administering the programmed infusion in step 2668.

While the device is administering the programmed infusion, a user may use the user interface of the device to titrate the infusion in step 2670 if necessary. A user may also use the user interface of the device to stop the infusion in step 2672 if needed. If a user stops the infusion, a user may use the user interface of the device to restart the infusion in step 2674. A user may also cancel the infusion using the user interface in step 2676.

The device may complete the programmed infusion in step 2678. After completing the infusion, the device may check for the defined VTBI zero behavior in step 2680. There may be a number of possible options for what a medical device may do when it has delivered the entire infusion volume. The behavior for a specific drug, clinical use, concentration, etc. may be defined in the DAL file stored in the memory of a medical device. In the flowchart depicted in FIG. 188, only three behaviors are shown. In other embodiments, different behaviors or a different number of behaviors may be included. If the defined VTBI zero behavior is to notify the user and continue infusing at the programmed rate the device may do so in step 2682. This notification may be conveyed to the user via the user interface of the medical device. The user may acknowledge the notification and take any desired actions in step 2684. If the defined VTBI zero behavior is for the device to alert and switch to a KVO rate, the device may do so in step 2686. The alert may be conveyed to the user via the user interface of the device. The user may acknowledge the alert and take any desired actions in step 2688. If the defined VTBI zero behavior is for the device to stop the infusion and alert, the device may do so in step 2690. The alert may be conveyed to the user via the user interface of the device. The user may acknowledge the alert and take any desired actions in step 2692.

FIG. 189 depicts a flowchart detailing a number of example steps which may be used to deliver a bolus of a medication (during an ongoing infusion or as a loading dose) with a medical device. As shown, in step 2700, a user may enter a volume and a time for the bolus. A user may also instead enter a dose and a time for the bolus in step 2702. This may be done when another infusion (e.g. primary continuous infusion) is running. The device may check the parameters entered to define the bolus against limits defined in the DAL file stored in the memory of the device in step 2704. This may be done by following steps similar to those shown and described in relation to FIG. 187. If the parameters are invalid in view of the DAL file, the user may re-enter the parameters for the bolus by returning to one of step 2700 or 2702. If the parameters are valid the medical device may display a bolus summary in step 2705. In step 2706, the user may indicate that they would like to deliver the programmed bolus. The device may then begin delivering the bolus in step 2708.

In some embodiments a user may also have the option of programming a rapid bolus. Such a bolus may only require a user to define a volume of medication to deliver. The rate of delivery for the bolus may be automatically populated by the device. This rate may, in some embodiments, be the maximum rate the device is capable of delivering at. In some embodiments, this rate may be the maximum rate allowed for the drug in the DAL file. If the bolus being programmed is for a loading dose, a user may also program the rest of the infusion before administering the loading dose with the device.

If needed, a user may stop the delivery of the bolus in step 2710. If a user stops the delivery of the bolus, a user may proceed to step 2716 or 2718. In step 2716, a user may cancel the bolus. In step 2718, a user may cancel the bolus and any infusion that was scheduled to resume after completion of the bolus delivery. A user may also proceed to step 2714 and restart delivery of the bolus.

The medical device may complete delivery of the bolus in step 2720. The device may check for the defined bolus VTBI zero behavior in step 2720. There may be a number of possible options for what a medical device may do when it has delivered the entire bolus volume. The behavior for a specific drug, clinical use, concentration, etc. may be defined in the DAL file stored in the memory of a medical device. In the flowchart depicted in FIG. 189, only three behaviors are shown. In other embodiments, different behaviors or a different number of behaviors may be included.

If the defined bolus VTBI zero behavior is to notify the user and revert to the parent infusion (e.g. a primary continuous infusion) the device may do so in step 2724. This notification may be conveyed to the user via the user interface of the medical device. The parent infusion may then resume in step 2740. If the defined bolus VTBI zero behavior is for the device to alert and switch to a KVO rate, the device may do so in step 2726. The alert may be conveyed to the user via the user interface of the device. The user may acknowledge the alert in step 2728. If the defined bolus VTBI zero behavior is for the device to stop the infusion and alarm the device may do so in step 2730. The alarm may be conveyed to the user via the user interface of the device. The user may acknowledge the alarm in step 2732.

After a user has completed one of step 2728 or 2732, the user may proceed to one of step 2736 or 2738. In step 2736, a user may indicate on the user interface of the device that they would like to discontinue the parent infusion. The device may then cancel the parent infusion in step 2742. In some embodiments, the device may display a confirm message to ensure that the user does not accidentally cancel the parent infusion.

In step 2738, a user may indicate on the user interface of the device that they would like to start or resume administration of the parent infusion. The device may then begin administering the parent infusion in step 2740. In some embodiments, the device may display a confirm message which requires user interaction before the parent infusion may begin.

FIG. 190 depicts a flowchart detailing a number of example steps which may be used to deliver a secondary infusion. As shown, in step 2750, a user may indicate that they would like to administer a secondary infusion on the user interface of the medical device. In step 2752 a user may specify a medication, clinical use, and concentration for the drug which will be administered as the secondary infusion. In some embodiments, step 2752 may be accomplished by using steps similar to those shown and described in relation to FIG. 185. A user may then define infusion parameters for the secondary infusion in step 2754. In some embodiments, step 2754 may be accomplished using steps similar to those shown and described in relation to FIG. 186. The device may then check the infusion parameters entered against any limits defined in the DAL file stored in the memory of the medical device in step 2755. This may be accomplished by performing steps similar to those shown and described in relation to FIG. 187. If the parameters are found to be invalid, a user may be required to redefine the parameters before proceeding.

The device may then display a set-up help screen on its user interface in step 2756. The set-up help screen may also prompt a user to start the secondary infusion once the secondary infusion is set up. In some embodiments, the set-up help screen may include an animation, annotated illustration, text instructions, etc. which explain to a user how to set up a secondary infusion. In step 2758, a user may set up the secondary infusion. The user may then indicate on the user interface of the device that they would like to start the secondary infusion in step 2760. The device may start administration of the secondary infusion in step 2762.

While the device is administering the programmed secondary infusion, a user may use the user interface of the device to titrate the infusion in step 2764 if necessary. A user may also use the user interface of the device to stop the infusion in step 2766 if needed. If a user stops the infusion, a user may use the user interface of the device to restart the infusion in step 2768. A user may also cancel the infusion using the user interface in step 2770. If the user cancels the infusion in step 2770, the device may, in step 2772 display a message on its user interface that the user should clamp off the secondary line before resuming the primary infusion. In some embodiments, a user may be required to confirm they have clamped off the secondary line before they are allowed to continue.

The programmed secondary infusion may be completed by the device in step 2774. The device may then check for the defined VTBI zero behavior in step 2775. There may be a number of possible options for what a medical device may do when it has delivered the entire infusion volume. The behavior for a specific drug, clinical use, concentration, etc. may be defined in the DAL file stored in the memory of a medical device. In the flowchart depicted in FIG. 190, only three behaviors are shown.

If the defined VTBI zero behavior is to notify the user and resume the primary infusion device, the device may do so in step 2776. This notification may be conveyed to the user via the user interface of the medical device. The primary infusion may then resume in step 2794. If the defined VTBI zero behavior is for the device to alert and switch to a KVO rate, the device may do so in step 2778. The alert may be conveyed to the user via the user interface of the device. The user may acknowledge the alert in step 2780. If the defined VTBI zero behavior is for the device to stop the infusion and alarm the device may do so in step 2782. The alarm may be conveyed to the user via the user interface of the device. The user may acknowledge the alarm in step 2784.

In some instances, a user may proceed from step 2780 or 2784 to step 2786 in which the user increases the VTBI for the secondary infusion to compensate for overfill of a bag. If done, the user may then re-start the infusion in step 2768 and continue as described above.

A user may also proceed from any of steps 2780, 2784, or 2772 to one of steps 2788 or 2790. In step 2790, a user may indicate on the user interface of the device that they would like to discontinue the primary infusion. The device may then cancel the primary infusion in step 2792. In some embodiments, the device may display a confirm message to ensure that the user does not accidentally cancel the primary infusion.

In step 2788, a user may indicate on the user interface of the device that they would like to resume administration of the primary infusion. The device may then resume administering the primary infusion in step 2794. In some embodiments, the device may display a confirm message which requires user interaction before the primary infusion may resume.

FIG. 191 depicts an example flowchart which details a number of steps which may be used to deliver a multi-step infusion with a medical device. As shown, in step 2800, a user may specify a medication, clinical use, and concentration for the drug which will be administered via the multi-step infusion. In some embodiments, step 2800 may be accomplished by using steps similar to those shown and described in relation to FIG. 185. A user may then define infusion parameters for each step of the infusion in step 2802. In some embodiments, step 2802 may be accomplished using steps similar to those shown and described in relation to FIG. 186. The device may then check the infusion parameters entered against any limits defined in the DAL file stored in the memory of the medical device in step 2804. This may be accomplished by performing steps similar to those shown and described in relation to FIG. 187. If the parameters are found to be invalid, the user may be required to redefine the parameters before proceeding. If the parameters are valid, the device may display an infusion summary in step 2808. The user may then indicate that they would like to begin administration of the infusion in step 2810. In step 2812, the device may begin delivering the infusion.

After the device has started administering the infusion, the user may use the user interface of the device to stop the infusion in step 2814 if needed. A user may then indicate they would like to cancel the infusion using the user interface in step 2818. The device may then cancel the infusion in step 2820. If a user stops the infusion, a user may also use the user interface of the device to restart the infusion in step 2816.

The device may complete a step of the infusion in step 2822. The device may then check for the defined step complete behavior in step 2824. There may be a number of possible options for what a medical device may do when it has completed a step of a multi-step infusion. The step complete behavior for a specific drug, clinical use, concentration, etc. may be defined in the DAL file stored in the memory of a medical device. In the flowchart depicted in FIG. 191, only three behaviors are shown. Other embodiments may include different or a different number of possible behaviors.

If the defined step complete behavior is to notify the user and begin administering the next step of the infusion (if additional steps are programmed), the device may do so by proceeding to step 2826. The infusion may then advance to the next step in step 2838 if there are additional steps in the infusion program. If the defined step complete behavior is for the device to alert and switch to a KVO rate, the device may do so in step 2828. The alert may be conveyed to the user via the user interface of the device. The user may acknowledge the alert in step 2830. If the defined step complete behavior is for the device to stop the infusion and alarm the device may do so in step 2832. The alarm may be conveyed to the user via the user interface of the device. The user may acknowledge the alarm in step 2834.

If additional steps exist after a user has completed step 2830 or 2834, the user be required to confirm that they would like to advance to the next step of the infusion. In the example embodiment, if a user desires to advance to the next step of the infusion the user may proceed to step 2836. In step 2836, the user may confirm that the device should begin the next step of the infusion. The device may then advance to the next step of the infusion in step 2838. If a user does not wish to proceed to the next step of the infusion, a user may indicate they would like to cancel the infusion using the user interface in step 2818 and the device may then cancel the infusion in step 2820.

FIG. 192 depicts a flowchart detailing a number of example steps which may be used to titrate an infusion being administered by a medical device. As shown, in step 3030 a user may indicate their desire to titrate an infusion. A user may do so using the user interface of the medical device. After a user indicates their desire to titrate an infusion, the device may proceed to step 3032. In step 3032, the device may check the DAL file stored in the memory of the device to see if a time elapsed between titrations restriction exists. If such a restriction exists and insufficient time has elapsed since the infusion was last titrated, the device may notify the user in step 3034. This notification may be conveyed to the user via the user interface of the medical device. The user may acknowledge this notification in step 3036. If no such restriction exists or sufficient time has passed since the infusion was last titrated, the user may then titrate the infusion as desired. In some embodiments, the time limit between titrations may only be a soft limit which may be overridden by a user if needed.

To titrate an intermittent infusion being administered by the medical device, the user may perform step 3038. In step 3038, a user may titrate the infusion by changing the infusion parameter for infusion rate, infusion duration, and/or total volume in container. To titrate a continuous volume based infusion, a user may perform step 3040. In step 3040, a user may change the infusion parameter for infusion rate and/or VTBI. To titrate a continuous dose based infusion, a user may perform step 3042. In step 3042, a user may change the infusion parameter for dose, infusion rate, and/or VTBI. In some embodiments, different types of infusions or a different number of types of infusions may be titrated by a user. Various embodiments may include additional or different steps which may allow a user to titrate other types of infusions.

Once a user has titrated the infusion parameters as desired, the device may check the defined parameters against any limits defined in the DAL file stored in the memory of the device in step 3044. This step may be performed by following steps similar to those shown and described in relation to FIG. 187. If the infusion parameters are invalid, the user may be required to re-define the infusion parameters for the titration. If the parameters are found to be valid, the device may display an infusion or titration summary on its user interface in step 3046.

If a second review is required, a second user may review the titration in step 3048. The second user may then enter their name, user ID, etc. in step 3050. A user may then confirm titration of the infusion in step 3052. After the infusion titration has been confirmed, the device may begin delivering the titrated infusion in step 3054.

FIG. 193 depicts a flowchart detailing a number of exemplary steps which may be used at and near the end of an infusion administered by a medical device. As shown, a user may program and begin an infusion in step 2840. The device may deliver the infusion in step 2842. In step 2844, the device may alert to indicate that the infusion is near end. This alert may be conveyed to the user via the user interface of the device. The point at which an infusion near end alert is triggered may be defined in the DAL file stored in the memory of the medical device. In some embodiments, the infusion near end alert may be triggered when predetermined amount of time is remaining for the infusion. In some embodiments, the infusion near end alert may be triggered when a defined volume remains for the infusion. A user may acknowledge this alert in step 2846. The alert may then be cleared by the device in step 2848. The device may complete administration of the infusion in step 2850.

The device may check for the defined VTBI zero behavior in step 2852. There may be a number of possible options for what a medical device may do when it has delivered the entire infusion volume. The behavior for a specific drug, clinical use, concentration, etc. may be defined in the DAL file stored in the memory of a medical device. In the flowchart depicted in FIG. 193, only three behaviors are shown. In other embodiments, different behaviors or a different number of behaviors may be included.

If the defined VTBI zero behavior is to alert and continue infusing at the programmed rate, the device may do so in step 2854. The alert may be conveyed to the user via the user interface of the medical device. If the defined VTBI zero behavior is for the device to alert and switch to a KVO rate, the device may do so in step 2856. The alert may be conveyed to the user via the user interface of the device. The user may acknowledge an alert in step 2860. The device may then de-escalate the alert to a lower priority level alert in step 2862. If no action is taken by a user for a predetermined period of time after the alert is de-escalated, the device may re-alert in step 2864. A user may then have to repeat step 2860 to acknowledge the alert before proceeding.

If the defined VTBI zero behavior is for the device to stop the infusion and alarm the device may do so in step 2858. The alarm may be conveyed to the user via the user interface of the device. A user may acknowledge the alarm in step 2866.

After a user acknowledges the alert or alarm, a user may have a number of options. If the infusion is not going to be restarted or administered again, the user may indicate this in step 2868. This may cause the device to resolve the alert or alarm, and display an infusion summary in step 2870. In some embodiments, the device may transition to an idle state if no further actions are taken by the user for a predetermined period of time after the device performs step 2870.

If the device administering the infusion is a syringe pump, the user may take additional actions depending on the type of infusion being administered. If the pump was delivering an intermittent infusion a user may indicate that they would like to flush the IV line in step 2872. The user may set up pump for the flush and the pump may then flush the IV line in step 2874. The pump may then progress to step 2870 which is described above. In some embodiments, a user may also manually flush the IV line. If the pump was delivering a continuous infusion and the user would like to continue infusing the same parameters, the user may replace the syringe in step 2876. The device may resolve the alert or alarm and restart the infusion in step 2878.

If the device administering the infusion is a large volume pump, the user may have the option of hanging a new bag in step 2880. The user may then increase the VTBI for the infusion in step 2881. In some embodiments, an increase in VTBI over a certain percent of the originally programmed value may cause the medical device to register that a new bag has been hung. The device may then proceed to step 2878 and restart infusion.

FIG. 194 depicts a flowchart detailing a number of steps which may be used to resolve an air-in-line alarm on a medical device. As shown, in step 2890 a medical device may detect air in an IV line. This may, for example, be done using any known or obvious method. In step 2892, the device may advance air out of a pumping chamber. This may be done so that the detected air is downstream of the device and visible to the user. Depending on the device, this step may be skipped. In step 2894, the device may alarm indicating there is air in the line. This alarm may be conveyed to a user via the user interface of the device. The alarm may also instruct a user on how to resolve this issue. In some embodiments, the alarm may include an animation, annotated illustration, text instruction, etc. on how to resolve the air in line issue. The alarm may also, for example, include a reminder to clamp the line before opening the door of the device. The user may then silence the alarm using the user interface in step 2896.

The user may then clamp the line and open the door of the device in step 2898. Once the device registers that the door is open, the device may display a help screen on its user interface in step 2900. The help screen may indicate that the door is open, and may instruct a user how to resolve the air in line issue. The user may cancel the infusion in step 2904 if necessary. The user may attempt to resolve the issue in step 2902. This may involve occluding the IV line below a y-site, opening a slide clamp on the device and purging air out of the line. It may also, for example, involve replacing an empty infusate bag.

In step 2906, a user may restart the infusion by indicating they would like to do so on the user interface of the device. In some embodiments, this may also clear the alarm. The device may reset the air accumulation counter in step 2908. The device may then check whether or not air exists in the pumping segment of the line in step 2910. If there is, the device may return to step 2890 and proceed as described above. If there is no air in the pumping segment the infusion may resume as programmed in step 2912.

FIG. 195 depicts a flowchart detailing a number of example steps which may be used to detect and resolve an occlusion in an infusion line associated with a medical device. As shown, a medical device may detect an infusion in step 2930. This may be done with any known or obvious sensor and/or method. The medical device may then stop pumping in step 2932. The device may check to see how much time has elapsed since the infusion began in step 2934. If the infusion was started within a predetermined duration of time from the detection of the occlusion, the device may proceed to step 2944. In step 2944, the device may back pump to relieve any pressure in the line caused by the occlusion. If the infusion was started outside of the predetermined duration of time from the detection of the occlusion, the device may proceed to step 2936. In step 2936, the device may check an occlusion restart counter to see if the number of occlusion restarts has been exceeded. The number of occlusion restarts may be defined in the DAL file stored in the memory of the device. A user may, for example, define a different number of occlusion restarts are allowed for a short half life drug as opposed to a long half life drug. If the number of occlusion restarts has been exceeded, the device may proceed to step 2944.

If the number of occlusion restarts has not been exceeded, the device may proceed to step 2938. In step 2938, the device may decrement the occlusion restart counter. In step 2940, the device may then wait for a predetermined period of time. The device may then attempt to deliver the therapy. If the occlusion does not resolve itself the device may return to step 2930 and proceed as described above. In an alternative embodiment, the device may also alarm or alert in step 2938.

After the device back pumps to relieve built up occlusion pressure in step 2944, the device may generate an alarm indicating the occlusion exists in step 2946. This alarm may be displayed to the user on the user interface of the device. The alarm may include instructions on how to resolve the occlusion. These instructions may include an animation, annotated illustration, text instructions, or the like. In step 2948, a user may silence the alarm. A user may use the user interface of the device to silence the alarm. The user may then resolve the occlusion in step 2950. In step 2952, the device may clear the occlusion alarm. The user may then restart administration of the infusion in step 2954.

FIG. 196 depicts a flowchart detailing a number of steps which may be used to change the care area for a medical device during an on-going therapy. This may be necessary if the care area is incorrectly selected during initial programming of the medical device. Additionally, this may be necessary if a patient is moved around an institution during the therapy. Steps similar to those shown in the example embodiment in FIG. 196 may also be used to change the care group for a medical device.

As shown, in step 2960, a user may indicate that they would like to change the care area of the device. This indication may be input to the device via the device's user interface. In step 2962, the device may display possible care areas on its user interface. The user may then choose a care area on the user interface of the device in step 2964. The medical device may then check the DAL file stored in its memory in step 2966 to ensure that the change of care area is compatible with the on-going infusion. The device may check the DAL file to see if the medication exists in the new care area. The device may also check to see if a clinical use for the medication including the same dose mode, compatible limits, and compatible concentration is defined in the DAL file for the new care area. Further, the device may check that limits for the concentration record are compatible. In some embodiments, the device may check for compatibilities by looking at different or a different number of parameters, items, elements, defined in the DAL file.

If the check performed by the device in step 2966 indicates that the care area change is incompatible with the on-going infusion, the device may notify the user in step 2968. This notification may be conveyed to the user via the user interface of the device. The notification may also inform the user that they cannot change care areas. The user may then acknowledge the notification in step 2970. In some embodiments, the user may then need to wait until the infusion completes and switch care areas. In some embodiments, the device may prompt the user to define whether the device should change care areas after completion of the infusion.

If the check performed by the device in step 2966 indicates that the care area change is compatible the device may proceed to one of step 2972 or 2974. If there is only a single compatible clinical use record defined in the DAL file on the device, the device may automatically select that clinical use record in step 2972. In some embodiments, the user may be required to confirm this selection. If there are multiple compatible clinical use records, the device may display the compatible clinical use record options on its user interface in step 2974. In step 2976, the user may select a clinical use from the compatible clinical uses on the user interface of the device. In some embodiments, the device may then display a clinical advisory for the clinical use on the user interface in step 2978.

The device may proceed from step 2972 or 2978 to step 2980. In step 2980, the device may automatically select the compatible concentration record for the clinical use. This may be a predefined concentration record or a variable or user customizable concentration record. If the concentration record selected is a customizable concentration record, the concentration defined for the on-going infusion may be used to automatically define the customizable concentration. In some embodiments, a user may be required to confirm the concentration record selected by the medical device.

If any of the parameters for the on-going infusion are outside of the limits defined for the new care area, clinical use, concentration record, etc. the device may proceed to step 2982. In step 2982, the device may notify the user that a parameter or parameters are outside of the defined soft limits. Such a notification may be conveyed to the user via the user interface of the medical device. If the user desires to override the soft limit violation, the user may do so in step 2984. If a user does not desire to override the soft limit the user may cancel the care area change in step 2986. In some embodiments, the device may then prompt the user to define whether the device should change care areas after completion of the infusion.

A user may also modify the infusion program in step 2988. If a user modifies the infusion program in step 2988, the medical device may then check to make sure that the modifications to the infusion program do not exceed the limits defined in the DAL file. If these modifications exceed soft limits defined in the DAL file the device may proceed as described above. If the modifications place a parameter or parameters outside of the hard limits, the device may proceed to step 2990. In step 2990 the device may notify the user that a parameter or parameters are outside of the defined hard limits. The user may then cancel the care area change by performing step 2986. If desired, the user may also proceed to step 2988 and modify the infusion program again.

Once it is determined the on-going infusion is within the limits defined in the DAL file for the new care area or after a user has overridden any soft limits, the device may display an infusion summary in step 2992. After reviewing the infusion summary, the user may make any necessary modifications in step 2994. The device may then return to step 2992 and display an infusion summary reflecting the modifications made in step 2994. If no modifications or no further modifications are needed the user may confirm the change to the new care area in step 2996. The device may then switch to the new care area in step 2998.

FIG. 197 depicts a flowchart detailing a number of example steps which may be used to stop an on-going infusion on a medical device. As shown, in step 3000 a user may indicate that they would like to stop an infusion. This may be done by pressing a button, virtual button, or other input means on the user interface of the device. If the user interface of the device is locked, the device may proceed to step 3002 and continue infusing. This may help ensure inadvertent stopping of an infusion does not occur. In some embodiments, the device may behave differently. For example, the device may display a message instructing the user to unlock the user interface of the device before the user may be allowed to stop the infusion. In some embodiments, this behavior may be defined in the DAL file stored in the memory of the medical device.

If the user interface of the device is not locked, the device may prompt a user to confirm that they would like to stop the infusion in step 3004. If the user does not confirm stopping of the infusion, the device may proceed to step 3002 and continue infusing. If the user confirms stopping of the infusion, the medical device may stop the infusion in step 3006. The user interface of the device may also indicate that the infusion has been stopped. A user may then have number of possible options. A number of options are shown in the flowchart in FIG. 197. In other embodiments, different options or a different number of options may be available.

If desired, a user may titrate the infusion in step 3008. A user may titrate the infusion by following steps similar to those shown and described in relation to FIG. 192. A user may program and begin delivery of a secondary infusion in step 3010. A user may program and begin delivery of a secondary infusion by following steps similar to those shown and described in relation to FIG. 190. A user may also program and begin delivery of a bolus in step 3012. A user may program and begin delivery of a bolus by performing steps similar to those shown and described in relation to FIG. 189. If a user would like to restart the stopped infusion, the user may do so in step 3014. If a user restarts the infusion in step 3014, the device may display an infusion summary in step 3016. The user may be required to confirm such an infusion summary in step 3018. The device may then resume delivery of the infusion in step 3020. A user may be able to place the device in a standby mode by proceeding to step 3022. If a user takes no action for a predetermined period of time, the device may issue an inactivity alert in step 3024. Such an alert may be conveyed to the user via the user interface of the device.

FIG. 198 depicts a flowchart detailing a number of exemplary steps which may be used in the event that the batteries of a medical device become drawn down to a predetermined level. In the flowchart depicted in FIG. 198, various times, time durations, battery capacities, etc. at which the device may alert, alarm, or take another action are specifically given. In other embodiments, these times, time durations, battery capacities, etc. may differ. Additionally, the priority levels of various alerts shown in the flowchart may differ from embodiment to embodiment.

As shown, when 120 minutes of battery capacity remain, the device may alert at a low priority in step 3060. This alert may be conveyed to the user via the user interface of the device. The user may acknowledge the alert in step 3062. The device may then clear the alert in step 3064. If a user does not proceed to step 3066 and plug in the device, the device may alert again in step 3068 when 60 minutes of battery capacity remain. The alert generated by the device in step 3068 may be a low priority alert. This alert may be conveyed to a user via the user interface of the device. The user may acknowledge the alert in step 3070. The device may then clear the alert in step 3072.

If a user does not proceed to step 3066 and plug in the device, the device may alert again in step 3074 as the battery capacity remaining continues to fall. The alert generated by the medical device in step 3074 may be a medium priority alert. This alert may instruct the user to plug in the medical device. This alert may also prominently display the amount of battery time remaining. This alert may be conveyed to the user via the user interface of the medical device. The alert may be generated when the amount of battery capacity remaining drops to 30 minutes, 15 minutes, and 10 minutes. In step 3076, a user may acknowledge the alert generated in step 3074. The device may de-escalate the alert to a low priority alert in step 3078. The alert may include a constantly lit alert indicator light, audible reminder signals, graphic indication on the user interface of the device, etc.

If a user proceeds to step 3066 from step 3078 and plugs in the medical device, the device may then clear the alert in step 3080. If the user does not plug in the device, the device may return to step 3074 and alert at medium priority if more than 10 minutes of battery power remain. If a user has not plugged in the device and the battery capacity is drawn down to 5 minutes, the device may proceed to step 3082. In step 3082, the device may alert at medium priority. This alert may instruct the user to plug in the medical device. The alert may also prominently display the amount of battery time remaining. The alert may be conveyed to the user via the user interface of the device. This alert may not be de-escalated. In some embodiments, a user may be able to silence the alert audio in step 3084. If a user proceeds to step 3066 and plugs in the device, the device may then clear the alert in step 3080. If a user does not plug in the device the device may proceed to step 3086 and re-alert every 2 minutes. If a user still does not plug in the device, the device may proceed to step 3088 and alarm. The alarm may be conveyed to the user via the user interface of the device. The alarm may include instructions to plug in the medical device which are displayed on the user interface of the device. The alarm may cause the device to stop delivering the therapy. In such embodiments, the user interface of the device may indicate that device has stopped administering the therapy. This alarm may not be de-escalated or dismissed.

The user may proceed from step 3088 to 3092. In step 3092, the user may plug in the device and restart the therapy. This may cause the device to clear the alarm. The user may also proceed from step 3088 to step 3094. In step 3094, a user may power down the device. If no action is taken by the user, the device may proceed to step 3090 and the device may power down. If the device is powered down in either step 3090 or step 3094, the user may plug in the device in step 3096 and push the power button to turn the device back on. After completion of step 3096, the device may ask the user, in step 3098 if they would like to resume the therapy which was being administered prior to the device powering down. The user may choose not to resume the therapy by proceeding to step 3100. This may be done with a user providing input to the user interface of the device. If a user would like to resume the therapy, the user may indicate they would like to do so in step 3102. This may be done with a user providing input to the user interface of the device. If a user indicates they would like to resume the therapy in step 3102, the device may resume delivering the therapy in step 3104.

FIG. 199 depicts a flowchart detailing a number of steps which may be used to lock or unlock the user interface of a medical device. The flowchart shown in FIG. 199 also depicts a number of example steps which may be used to associate a device with a particular user or caregiver. In the flowchart depicted in FIG. 199, there are two different types of user interface locks: a screen lock and a programming lock. The screen lock may be used to prevent inadvertent input from being given to the user interface of the device. For example, the screen lock may ensure that a user brushing up against a touch screen display of a medical device may not register as user input to the device. A programming lock may be used to prevent an unauthorized individual from changing or tampering with an infusion program. A programming lock may for example require a user to enter a passcode/word, user ID, or both to unlock the device. A screen lock may be unlocked without requiring such an entry.

As shown, a user may indicate that they would like to lock the user interface of a device in step 3110. This may be done in any number of ways in various embodiments. For example, a user may select an option to lock the user interface on the user interface of the device. In some embodiments, this may be done by using a lock icon, button, or the like. In other embodiments, a lock option may be found by navigating to an options menu or the like on the user interface of the device. In some embodiments, if a user uses a lock option, the user may be prompted to select whether or not they would like to lock the device with a screen lock or programming lock. In some embodiments, the device may automatically lock to one or the other variety of lock based on a parameter defined in the DAL file stored in the memory of the device. The device may lock the user interface in step 3112. In some embodiments, the device may also lock the user interface in step 3112 if a predetermined amount of time elapses with no user actions. In some embodiments, the device may lock with a screen lock after the amount of time has elapsed. In some embodiments, the amount of time before the user interface is locked may be defined in the DAL file stored in the memory of the device.

If the device user interface is locked with a screen lock, the device user interface may display a visual cue on how to unlock the device in step 3114. If the user would like to unlock the user interface screen lock the user may perform an unlocking action in step 3116. Such an unlocking action may include swiping an unlock bar, tapping an unlock button, etc. on the user interface of the device. After the unlocking action has been performed, the device may unlock in step 3118.

If the user interface of the device is locked with a programming lock, the user may need to indicate that they would like to unlock the user interface in step 3120. After the device receives the indication that the user would like to unlock the user interface, the device may display a passcode entry field on the user interface in step 3122. A user may enter the passcode in step 3124. In some embodiments, the passcode may be a generic passcode which is used to unlock a programming lock. This passcode may be defined and be the same for everyone within a care area, care group, institution, organization, etc. In some embodiments, the user may need to enter a user ID and passcode in the passcode entry field. If the passcode entered in step 3124 is found to be valid, the device may unlock the user interface in step 3126. If the passcode entered in step 3124 is found to be invalid, the user may need to re-enter the passcode and be returned to step 3124. In some embodiments, the device may not require a user to input a passcode. Instead the device may be unlocked with an authorized user identifier. Such an identifier may be an RFID badge, swipe card with a magnetic strip, scanned fingerprint, etc.

If after being unlocked the device requires association with a user, the device may proceed to step 3128 and prompt a user to enter a user ID. In some embodiments, a user may be required to enter both a user ID and password. The user may enter the required information in step 3130 to associate the device with the user. If the information entered is invalid, the user may be required to re-enter the information and be returned to step 3130.

FIG. 200 depicts a flowchart detailing a number of exemplary steps which may be used to power down a medical device or put a medical device into a sleep state. As shown, the steps followed to power down a medical device or place a medical device into a sleep state may depend on the current status of the medical device. Additionally, different types of user input may cause the device to behave differently. For example, different durations of depression for the same button (e.g., momentary v. a few seconds) may either put the device to sleep or power off the device. To a user, the sleep state and powered off state may appear to be the same. In the sleep state, the device may appear as if it has been powered off, but have a comparatively quick start up. The device may use some power in the sleep state.

An idle state may be reached if the device is on, but a period of inactivity has elapsed. A stopped state may be reached if a user stops a therapy in progress. A standby state may be reached after a user programs a therapy, does not start it, and a period of inactivity elapses. A standby state may also be reached if a user stops a therapy in progress and a period of inactivity then elapses.

As shown, if the medical device is in an idle, stopped, or standby state, a user may have a number of options. If a user would like to shut off the device, a user may perform one of steps 3140 or 3142. In step 3140, a user may select a power off option on the display of the device. In step 3142, a user may hold down the power button of the device for a predetermined period of time (e.g. three seconds). If a user would like to put the medical device to sleep, a user may momentarily press the power button on the device in step 3144.

If a user performs step 3140 or 3142, the device may display a powering down notification on the user interface of the device in step 3146. This notification may include a countdown which counts down the seconds until the device powers down. The device may then power down in step 3148.

If a user momentarily presses the power button on the device, the device may transition into a sleep state in step 3150 if no active callbacks exist. If an active callback does exist, the user interface of the device may prompt a user to confirm they would like to put the device to sleep in step 3152. In some embodiments, such a prompt may also inform a user of any active callback(s) and that they will be cancelled if the device is put to sleep. The user may then have the option of cancelling putting the device to sleep in step 3154 or confirming that they would like the device to be put to sleep in step 3156. The user may confirm or cancel putting the medical device to sleep using the device's user interface. If a user cancels putting the device to sleep the device may remain powered on. If the user confirms that they would like to put the device to sleep, the device may proceed to step 3150 and transition to a sleep state.

In FIG. 200, if the medical device is being programmed and an infusion is not currently being delivered by the medical device, the device may behave differently. If a user momentarily presses the power button in step 3158 device may proceed to step 3160. In step 3160, the user interface of the device may ask a user to confirm they would like to cancel programming and transition the device to a sleep state. A user may cancel putting the device to sleep by proceeding to step 3154. If a user would like to put the device to sleep, the user may confirm this by proceeding to step 3156. The user may confirm or cancel putting the medical device to sleep using the device's user interface. If a user cancels putting the device to sleep the device may remain powered on. If the user confirms that they would like to put the device to sleep, the device may proceed to step 3150 and transition to a sleep state. If a user performs step 3142 when the device is being programmed and not administering an infusion, the device may behave as described above when the device is in an idle, stopped, or standby state.

If the medical device is currently delivering an infusion, the device may also behave differently. If the user momentarily pressed the stop button in step 3164, the device may proceed to step 3166. In step 3166, the user interface of the device may display an indication that the user should stop the infusion before powering off the device or putting the device to sleep. The device may remain powered on. If a user holds the power button down for a predetermined period of time in step 3162, the device may proceed to step 3168. In step 3168, the device may display a notification that the user should stop the infusion before powering down. The device may also generate an audible sound. If the user desires to power down the device, the user may again hold down the power button for a predetermined period of time 3170. In some embodiments, the user interface of the device may display a countdown clock which indicates how many seconds the user must hold down the power button before the device shuts down. If a user holds down the power button for the predetermined period of time identified in step 3170, the device may power down in step 3172.

In various embodiments, any of the steps performed with a button pressing in FIG. 200 could also or instead be performed via user interaction with a graphical user interface display on a device. In some embodiments, a medical device may also allow for a hard shutdown of the device. This may be accomplished by depressing a power button for a prolonged duration of time (e.g. 15 seconds).

FIG. 201 depicts a flowchart detailing a number of steps which may be used to flush an IV line associated with a medical device. Specifically, the flowchart shown in FIG. 201 depicts a number of steps which may be used to flush an IV line from a medical device which is a syringe pump. As shown, in step 3180, a user may indicate to the device that they would like to flush the IV line from the device. This may be done by selecting a flush line option or the like on the user interface of the medical device. The device may then display instructions for flushing the IV line on the user interface of the device in step 3182. These instructions may include an animation, annotated illustration, text instructions, etc. The user may then occlude the line in step 3184. In step 3186, a user may install the flush syringe. The flush syringe may be installed following steps similar to those shown and described in relation to FIG. 182. Installation of the flush syringe may also involve moving the occluded line to the flush syringe and then un-occluding the line. Once the syringe is installed on the medical device, the device may check the DAL file stored in the memory of the medical device in step 3188 to see if the flush parameters have been defined. In some embodiments, a rate, volume to be delivered and time parameter may be defined as flush parameters in the DAL file. In some embodiments, flush parameters may not be defined as part of the DAL file.

If flush parameters have been defined in the DAL file stored in the memory of the medical device, the device may use these parameters as default values for the flush in step 3190. If flush parameters have not been defined in the DAL file, the device may set the VTBI to the full volume of the flush syringe installed on the medical device in step 3192. In step 3194, the device may display a flush programming screen on its user interface. This screen may be at least partially populated with the values from steps 3190 or 3192. In step 3196, the user may edit the flush parameters and confirm that they would like the medical device to flush the line per those parameters. In step 3198, the device may check the syringe and plunger position against the programmed VTBI for the flush. These positions may, in some embodiments, be gathered and stored by the device in step 3186. These positions may be determined by any number of various sensors included as part of a medical device. Some such sensors are described above in the discussion of FIG. 182. Other sensors may also be used. This check may be done to ensure that the parameters programmed are compatible with the syringe installed on the medical device.

If the device determines that the syringe and/or plunger position are incompatible with the programmed flush, the device may proceed to step 3200. The device may notify a user that the syringe and/or plunger position are incompatible with the programmed VTBI in step 3200. A user may then choose to cancel the flush, modify the flush parameters, or get a compatible syringe for the flush. If a user desires to cancel the flush, the user may proceed to step 3202. In step 3202, the user may indicate that they would like to cancel the flush on the user interface of the device. The device may then cancel programming of the flush in step 3204. If a user desires to modify the programmed flush parameters, a user may return to step 3196 to do so. If a user desires to get a syringe compatible with the programmed flush, the user may proceed to step 3206. In step 3206, the user may remove the syringe and get a compatible syringe. The user may then return to step 3186 and install the compatible flush syringe on the medical device.

If the medical device determines that the syringe and plunger position are compatible with the flush parameters, the device may check the parameters entered for the flush against any parameters defined for the flush in the DAL file of the medical device in step 3208. This step may involve following steps similar to those shown and described in relation to FIG. 187. If the parameters are found to be invalid, the user may be returned to step 3196 to reenter the parameters. If the parameters are found to be valid, the device may begin flushing the line per the programmed parameters in step 3210. In some embodiments, the device may display a summary for the flush on its user interface before the flush begins. In such embodiments, the user may be required confirm that they would like to flush the line using the parameters shown in the flush summary. The device may complete delivering the programmed VTBI for the flush in step 3212. In some embodiments, in step 3212, the device may generate an alert to the user that the flush has completed. This alert may be conveyed to a user via the user interface of the device. A user may acknowledge such an alert in step 3214.

FIG. 202 depicts a flowchart detailing a number of example steps which may be used to install a replacement syringe on a medical device during the course of an infusion. Such action may be necessary, for example, in the event that the medical device is delivering a primary continuous infusion which will require more than one syringe worth of infusate. As shown, in step 3220, a user may indicate that they would like to install a replacement syringe on the medical device. The device may then display instructions for installing the replacement syringe in step 3222. Such instructions may include an animation, annotated illustration, text instructions, etc. which are displayed on the user interface of the device.

The user may then occlude the line associated with the syringe to be replaced in step 3224. The user may then install the replacement syringe in step 3226. The replacement syringe may be installed following steps similar to those shown and described in relation to FIG. 182. Installation of a replacement syringe may also involve moving the occluded line to the replacement syringe and then un-occluding the line. The device may then, in step 3228, populate parameters to be used to deliver infusate from the replacement syringe with those used for the previous syringe. These parameters may be displayed to the user in an infusion summary displayed on the user interface of the medical device. The user may then confirm the parameters and indicate that they would like to restart the infusion in step 3230.

The medical device may then check to see, in step 3232, whether the replacement syringe installed on the device is compatible with any restrictions defined in the DAL file stored in the memory of the medical device. If the replacement syringe installed is found to be compatible with any restrictions defined in the DAL file in step 3232, the device may proceed to step 3244 and begin delivering the infusion from the replacement syringe.

If the replacement syringe is found to be incompatible, the device may notify the user in step 3234. This notification may be conveyed to the user via the user interface of the medical device. The user may acknowledge the notification in step 3236. The user may then choose to either cancel the infusion or get a compatible syringe for the infusion. If the user desires to cancel the infusion, the user may proceed to step 3238 and indicate that they would like to cancel the infusion. The device may then cancel the infusion in step 3240. If the user would like to get a compatible syringe for the infusion, the user may proceed to step 3242 and do so. After getting a compatible syringe, the user may return to step 3226 and install the compatible replacement syringe.

FIG. 203 depicts a flowchart detailing a number of example steps which may be used to set up a relay infusion with a number of medical devices. Specifically, the flowchart depicted in FIG. 203 details a number of steps which may be used to set up a relay infusion with a number of medical devices installed on a medical device rack. In other embodiments, the relay may be established between a number of medical devices which communicate wirelessly, through a connector such as a cable, or in any other suitable manner. In embodiments where the medical devices communicate through a medical device rack, the medical devices may be connected into the rack and may communicate using a CAN bus for example. In other embodiments, the medical devices may communicate over the rack using other message passing schemes.

As shown, in step 3250, a user may install a first medical device on a medical device rack and begin administration of an infusion with the medical device. A user may then indicate to the first device that they would like to set up a relay infusion in step 3252. A user may place a second medical device on the medical device rack (if not already done) in step 3254.

After a user indicates that they would like to step up a relay infusion, the first medical device may send out a relay request in step 3256. The second medical device may receive the relay request sent from the first medical device in step 3258. The second medical device may then display a confirm relay prompt on its user interface in step 3260. A user may then confirm they would like to establish the relay in step 3262. If a user does not desire to establish the relay, the user may indicate that they would like to cancel establishment of the relay in step 3266. This may be done via the user interface on either of the first medical device or the second medical device. The first medical device may then display a relay cancelled notification on its user interface in step 3268. The confirm relay prompt on the user interface of the second medical device may also be dismissed in step 3268.

In some embodiments, the relay request sent in step 3256 may be sent to all medical devices installed on the rack. In such embodiments, any compatible device which is not currently delivering a therapy or is otherwise unavailable may display a confirm relay prompt on its user interface. A user may then confirm they would like to establish the relay with any one of the available compatible devices. This device may then become the second medical device. Confirming establishment of the relay on the desired device may cause the confirm relay prompt on all other available compatible devices to be dismissed.

The infusion may be set up on the second medical device in step 3264. The user may be required to define the medication, clinical use, and concentration for the medication which will be delivered in the relay infusion. In some embodiments the infusion program may be sent to the second medical device through the medical device rack. In some embodiments, a user may be required to enter in or confirm the desired relay infusion program on the second medical device. Setting up the infusion may also involve installing a syringe on the second device, identifying the type of syringe installed on the second device, priming the IV line associated with the second device, etc.

The second medical device may send a confirmation to the first medical device in step 3270. This confirmation may be sent after a user completes step 3262 in some embodiments. The first medical device may receive the confirmation from the second medical device in step 3272. After receiving the confirmation, in step 3274, the user interface of the first medical device may display an indication that the first medical device is part of a relay infusion. The second medical device may also be caused to display an indication on its user interface that the device is part of a relay infusion in step 3276.

The first medical device may continue to deliver its infusion as the first portion of the relay. If the user desires to titrate the infusion being delivered from the first medical device, the user may do so in step 3278. Step 3278 may involve following steps similar to those shown and described in relation to FIG. 192. In the event that a user titrates the infusion, the titrated infusion parameters may in some embodiments be transferred to the staged device. The titrated infusion parameters may replace any infusion parameters received by the staged device in step 3264.

A user may also stop the infusion being administered by the first medical device in step 3280 if desired. If a user stops the infusion being delivered by the first medical device by performing step 3280, the user may have a number of options. A user may cancel the infusion being administered by the first medical device in step 3282. The first medical device may then indicate that it has cancelled its part of the relay and may prompt a user to specify whether they would like to cancel the second part of the relay in step 3284. A user may cancel the relay by performing step 3266 which may cause the first medical device to indicate that the relay has been cancelled in step 3268. If a user does not desire to cancel the second part of the infusion, the user may indicate that they would like to begin the second part of the relay in step 3286. A user may also restart the infusion being administered by the first medical device in step 3288.

The infusion being delivered by the first medical device (the first part of the relay) may be completed in step 3290. The first device may then behave following the defined VTBI zero behavior in the DAL file stored in the memory of the device in step 3292. If required by the defined VTBI zero behavior in the DAL file, the user may confirm via the user interface of the first medical device or second medical device that the second part of the relay should begin. In the flowchart depicted in FIG. 203, the user may indicate that the second part of the relay should begin via the user interface of the first medical device in step 3294.

The first medical device may send a start command to the second medical device in step 3296. In step 3298, the second medical device may receive the start command. The second medical device may then send a confirmation that it has received the start command in step 3300 and start administering the second part of the relay in step 3302. The second medical device may also display a notification on its user interface that the device has started delivery of the second part of the relay in step 3302. In step 3304, the first medical device may receive the confirmation sent in step 3300. In some embodiments, if the first medical device does not receive the notification sent from the second medical device in step 3300, the first medical device may proceed to step 3306 and generate an alarm. This alarm may be conveyed to the user via the user interface of the first medical device.

FIG. 204 depicts a flowchart detailing a number of example steps which may be used if a medical device which is part of an established relay infusion is removed from a medical device rack. The device removed from the rack in the flowchart depicted in FIG. 204 is the first medical device. As shown, in step 3310, the user may remove the first medical device from the medical device rack. This may cause the first medical device to alert in step 3312. The staged device may also indicate that the relay has been broken in step 3314. In some embodiments, the user may be required to acknowledge relay broken indication displayed on the second device. The first device may continue to deliver the infusion once removed from the rack.

If a user does not desire to establish the relay, the user may cancel the relay in step 3316. This may cause the first medical device to cancel the relay in step 3318. If a user does not desire to cancel the relay, the user may place the first medical device back on the medical device rack in step 3320. Once the first medical device is placed back on the medical device rack, the first medical device may send out a confirmation request in step 3322 to see if the staged second device is still available. The second medical device may receive the confirmation request in step 3324. The second medical device may respond to the confirmation request in step 3326. The first medical device may receive the response to the confirmation request in step 3328.

If the response indicates that the second medical device is not available, the first medical device may notify the user in step 3330. The user may then perform step 3316 and indicate that they would like to cancel the relay. The first medical device may then cancel the relay in step 3318. If the response sent in step 3326 is a confirmation that the second medical device is still available, the first medical device may prompt a user to specify whether they would like to re-establish the relay in step 3332. This prompt may be displayed to the user via the user interface of the first medical device. If the user does not desire to re-establish the relay, the user may indicate they would like to cancel the relay by performing step 3316. The first medical device may then cancel the relay in step 3318. If the user would like to re-establish the relay, they may indicate that they would like to do so by performing step 3334.

If a user indicates that they would like to re-establish the relay in step 3334, the first medical device may send a re-establish relay request to the second medical device in step 3336. The second medical device may receive this request in step 3338. The second medical device may send a confirmation of re-establishment of the relay in step 3340. The first medical device may receive the confirmation in step 3342. The first medical device may then indicate on its user interface that the relay has been re-established in step 3344.

FIG. 205 depicts a flowchart detailing a number of exemplary steps which may be used in the event that a medical device which is part of an established relay infusion is removed from a medical device rack. The device removed from the rack in the flowchart depicted in FIG. 205 is the second medical device. As shown, in step 3350, the staged, second medical device is removed from the medical device rack. Removing the staged, second medical device from the rack may cause the first medical device to generate an alert in step 3352. The first medical device may continue to deliver the first portion of the relay infusion. Removing the staged, second medical device from the rack may also cause the second device to indicate that the relay has been broken in step 3354.

A user may then have a number of options. A user may, for example, indicate on the user interface of the first device that they would like to cancel the relay infusion in step 3356. The first medical device may then cancel the relay infusion in step 3358. A user may also have the option of proceeding to step 3360 and putting the second medical device back on the rack. If a second device is placed back on the rack in step 3360, the second device may send a re-establish relay request to the first medical device in step 3362. The first device may receive the re-establish relay request in step 3364. The first device may then prompt the user to specify whether they would like to re-establish the relay in step 3366. This prompt may be conveyed to the user via the user interface of the first medical device.

A user may then either cancel the relay or re-establish the relay. This may be done using the user interface of the device. If the user desires to cancel the relay the user may indicate this in step 3368. The first medical device may then cancel the relay and send a notification to the second medical device that the relay is to be cancelled in step 3370. The second medical device may receive the notification and cancel the relay in step 3372. The second medical device may then indicate that the relay has been cancelled in step 3374.

If a user desires to re-establish the relay, the use may indicate this on the first medical device in step 3376. The first medical device may then send a re-establish relay request to the second medical device in step 3378. The second medical device may receive the re-establish relay request in step 3380. In some embodiments, the user may be required to confirm re-establishment of the relay using the user interface of the second device in step 3382. The second medical device may then indicate that it is staged as part of a relay infusion in step 3384.

FIGS. 206-208 depict a number of example start-up screens 3390. These screens may be displayed on the user interface of a medical device while the device is powering on. Such screens may indicate that the device is powering on and may indicate time remaining before the device has fully powered on. Other features may also be included. The start-up screens 3390 shown in FIGS. 206-208 are example start-up screens 3390. In other embodiments, start-up screens 3390 may differ.

FIG. 206 depicts an example start-up screen 3390 which may be displayed on a medical device user interface. Such a screen may be displayed on the user interface of the medical device after a user has commanded the medical device to power on. This may be accomplished by pressing a power on button on the device. As shown, the start-up screen 3390 may include a start up indicator 3392. The start-up indicator may indicate to the user that the device is in the process of powering on. In the example embodiment shown in FIG. 206, the start-up indicator 3392 includes text that reads "Starting . . . ." The start-up indicator 3392 also includes a progress indicator 3394. The progress indicator 3394 may be used to indicate start up progress to the user. Progress may be indicated to a user by a change in color. In some embodiments, there may be a countdown clock which counts down the amount of time remaining before the device will be fully powered. Any other type of suitable progress indicator 3394 may also be used.

As shown in the example embodiment in FIG. 206, a start-up screen 3390 may include a logo 3396. Such a logo 3396 may be a company logo or a product logo. Additionally, as shown in the example embodiment, a tagline 3398 may also be included on a start-up screen 3390.

FIG. 207 depicts another example embodiment of a start-up screen 3390 which may be displayed on the user interface of the medical device. As shown, the example start-up screen 3390 shown in FIG. 207 includes a start-up indicator 3392. The start-up indicator 3392 includes text that reads "Starting . . . ." The example start-up screen 3390 in FIG. 207 also includes a progress indicator 3394. The progress indicator 3394 in FIG. 207 includes a countdown clock which counts down the amount of time before the device will be fully powered on. The example start-up screen 3390 shown in FIG. 207 also includes a logo 3396 and tagline 3398.

The start-up screen 3390 may also include a navigation guidance indicator 3400. The navigation guidance indicator 3400 may indicate to a user how the user may navigate between various screens, menus, options, etc. on the user interface of the medical device. The navigation guidance indicator 3400 may in some embodiments include an animation which shows a user how to navigate between various screens, menus, options, etc. on the user interface of the medical device. In other embodiments the navigation guidance indicator 3400 may include text instructions, an illustration, etc. In the example embodiment shown in FIG. 207 the navigation guidance indicator is an illustration which indicates that a use may navigate by swiping or flicking horizontally across the user interface screen.

FIG. 208 depicts an example embodiment of a start-up screen 3390 which may be displayed on the user interface of a medical device. As shown, the example start-up screen 3390 in FIG. 208 includes a start-up indicator 3392. The start-up indicator 3392 includes text which reads "Starting up". The example start-up screen 3390 also includes a progress indicator 3394. As shown, the progress indicator 3394 is a progress bar, which fills as the device approaches a fully powered on state. A logo 3396 and a product name 3402 are also shown on the example start-up screen 3390 in FIG. 208.

As shown in FIG. 208 the user interface display 3404 is surrounded by a bezel 3406. The user interface display may be any of a variety of suitable displays. In the example embodiments shown and described herein, the user interface display 3404 is a color touch screen display. As shown, a number of buttons 3408 may also be included as part of the user interface of a medical device. Each button 3408 may have an assigned function. The buttons 3408 may also have a number of functions assigned to each button which are activated by different user behaviors (e.g. momentary depression v. held down for a period of time). In a specific embodiment one button 3408 may be a power button, one button 3408 may be a stop button, and another button 3408 may be a silence alert/alarm button. Various embodiments may include different buttons 3408 or a different number of buttons 3408. The buttons 3408 may be able to light up and in some embodiments may light up in a variety of different colors. In some embodiments the buttons 3408 may be backlit by one or more LEDs. In the example embodiment, the topmost button 3408 is shown lit up. In some embodiments, the buttons 3408 may include text, a graphic, a symbol, etc. which indicates the function of the respective button 3408. In the example embodiment shown in FIG. 208, the buttons 3408 each include a symbol which may be backlit.

In some embodiments, the bezel may also have an icon 3410 or various icons 3410 which may light up. Such icons 3410 may also be backlit by one or more LEDs and may be able to light up in a variety of different colors. In the example embodiment, an icon 3410 is included which may light up when the device is plugged into an outlet and receiving power from the outlet. In some embodiments, such an icon 3410 may also light up, flash, etc. (perhaps in a different color) if the battery is running low. Other embodiments may include different icons 3410 or a different number of icons 3410.

FIGS. 209-211 depict a number of example login screens 3420. These screens may be displayed on the user interface of the device after the device has been powered on. Such screens may allow for a user to login and associate a device with their user ID. This may be useful for a number of purposes including prevention of usage by unauthorized individuals and CQI purposes. The login screens 3420 shown in FIGS. 209-211 are example screens. In other embodiments, login screens 3420 may differ.

FIG. 209 depicts an example embodiment of a login screen 3420 which may be displayed on the user interface of a medical device. In various embodiments, the login screen 3420 may differ. A user may use a login screen 3420 to logon to a medical device. Any programming or administration of a therapy on or by the device may be tied to the user logged onto the device.

As shown, the example login screen 3420 includes login instructions 3422. The example login instructions 3422 are text instruction which inform a user how to login to the device. In other embodiments, the login instructions may include an animation, illustration, or the like. The example login screen 3420 additionally includes a user ID input field 3424. Such a field may be used to type in a user ID. A login option 3430 may also be included on a login screen 3420. As shown, a login option 3430 may be a virtual button in some embodiments. In the example embodiment shown in FIG. 209, the login option 3430 is a virtual button which reads "Go". Some embodiments may also include a password input field (not shown in FIG. 209).

In the example embodiment, a login pass target 3426 is also included. This target 3426 may be used to indicate where a user should tap, swipe, place, etc. a login badge, card, pass, fob, etc. to login to the device. A login pass target 3426 may not be included in embodiments which are not RFID capable for example. If a user logs in with a login badge, pass, card, fob, etc., the user may not be required to type in a user ID and/or password. Likewise, if a user enters a user ID and/or password, the user may not be required to also login with a login badge, pass, card, fob, etc.

The example login screen 3420 in FIG. 209 additionally includes a virtual keyboard 3428. The virtual keyboard 3428 shown may be used to enter in a user ID and password. The virtual keyboard 3428 shown does not include any numbers. Instead the virtual keyboard 3428 includes an option which may be used to cause the virtual keyboard 3428 displayed on the screen to display numbers and punctuation.

Also included in the example login screen 3420 in FIG. 209 is a header 3432. In various embodiments and on various screens of the device user interface, a header 3432 may include menu options, various information icons, text, etc. The header 3432 on the example login screen 3420 includes a WiFi connectivity icon 3434, a battery charging icon 3436, and a battery remaining icon 3438. The battery remaining icon 3438 may provide an estimated time amount of battery life remaining. The battery remaining icon 3438 may also include a colored bar or bars which are displayed or partially displayed to reflect the amount of battery life remaining. The heading 3432 in the example embodiment also include a drop down menu option 3440 which may be used to open a drop down menu (not shown).

FIG. 210 depicts an example embodiment of a login screen 3420 which may be displayed on the user interface of a medical device. As shown, the login screen 3420 shown in FIG. 210 does not include a login pass target 3426 like that shown in FIG. 209. The example login screen 3420 includes both a user ID input field 3424 and a password input field 3450. Also shown in the example login screen 3420 is a virtual keyboard 3428. The virtual keyboard 3428 shown is only numeric. A user may use the virtual keyboard 3428 to fill in the user ID input field 3424 and the password input field 3450. A back option 3452 and a login option 3454 are also shown in FIG. 210. Both are grayed out.

FIG. 211 depicts an example embodiment of a login screen 3420 which may be displayed on the user interface of a medical device. As shown, the example login screen 3420 in FIG. 211 is the same screen as that shown in FIG. 210. The user ID input field 3426 and the password input field 3450 have been populated in FIG. 211. Once these fields have been populated, the login option 3454 may become enabled. A user may use the login option 3454 to login to the device. The back option 3452 remains grayed out. This may be true if there are no previous screens to go back to.

FIGS. 212-238 depict a number of screens which may be displayed to aid in setup and allow programming of a therapy which is to be performed by a medical device. A user may use such screens to program parameters and the like which are necessary for a device to administer a therapy. Additionally, such screens may provide a user instruction while setting up a therapy. The screens shown are shown only for exemplary purposes. In other embodiments, different screens, or a different number of screens may be displayed to a user during setup or programming. Additionally, the screens may differ depending on the type of therapy being administered, the device administering the therapy, etc. It should also be noted that these screens do not necessarily need to be displayed on the user interface in the progression presented or suggested herein.

FIG. 212 depicts an example select care group screen 3460 which may be displayed on the user interface of a medical device. Various select care group screens 3460 may differ from embodiment to embodiment. A select care group screen 3460 may allow a user to select the care group in which the medical device is being used. This may be necessary if a user is assigned to a number of different care groups. If user is only assigned to a single care group, a select a care group screen 3460 may not be displayed. Instead, the device may automatically associate the login session with the care group. In some embodiments, a user may not need to select a care group 3420. Instead a user may only select a care area for the device. Such embodiments may not include a select a care group screen 3460.

As shown, the example select a care group screen 3460 shown in FIG. 212 includes a list of a number of selectable care groups 3462 that the user is assigned to. A user may tap, double tap, or otherwise indicate the desired care group. In some embodiments, after a user has indicated the desired care group, the medical device may display another screen on the medical device user interface. In some embodiments, the user may be required to confirm the selection in a confirm dialogue box or the like. In other embodiments, indicating the desired care group may cause the indicated care group to be highlighted on the user interface. The user may then use a next option to use the highlighted care group and proceed to subsequent screens on the user interface. In other embodiments, the process of selecting a care group may differ.

FIG. 213 depicts an example embodiment of a select care area screen 3470. Various select care area screens 3470 may differ from embodiment to embodiment. A select a care area screen 3470 may allow a user to select the care area that the device is being used in. This may be necessary if a user is assigned to a number of different care areas. In some embodiments, if a user is assigned to only a single care area a select care area screen 3470 may not be displayed. Instead, the device may automatically associate the login session with the care area.

As shown, the example select a care area screen 3470 includes a list of a number of selectable care areas 3472. The selectable care areas 3472 displayed may depend on the care group selected on a select a care group screen 3470 such as the select care group screen 3460 shown in FIG. 212. If a user is assigned to a large number of care areas, not all of the care areas may be displayed on a select a care area screen 3472 at once. A scroll bar 3474 or the like may be displayed on the user interface of the medical device for a user to view additional selectable care areas 3472. In some embodiments, an indicator 3476 may be included in association with certain selectable care areas 3472. Such an indicator 3476 may indicate that this is a commonly used care area or the care area used during the last login session for example. Various other screens on a medical device user interface may include indicators which serve a similar end.

The example select a care area screen 3470 as well as various other user interface screens may include a number of option buttons 3478. In the example embodiment shown in FIG. 213, the option buttons 3478 are shown in a sidebar on the medical device user interface display 3404. In the example embodiment, a back option button 3478, a cancel option button 3478, and a menu option button 3478 are included.

FIG. 214 depicts an example embodiment of a select patient screen 3480. Some embodiments may not include a select patient screen 3480. In other embodiments, a select patient screen 3480 may differ. The select patient screen 3480 may be used to associate a therapy with a particular patient who is in the selected care area of an institution.

In the example embodiment, the select patient screen 3480 includes two input fields: a last name input field 3482 and a first name input field 3484. In some embodiments, the input fields may differ, for example, there may only be a single input field for a patient ID number. A user may use a virtual keyboard 3428 to populate these fields. As shown, as a user begins to populate a field, each letter typed in may cause the list of selectable patient IDs 3486 to be filtered accordingly. In the example embodiment, a user has entered "And" into the last name input field 3482. This has caused the user interface to display only selectable patient IDs 3486 which include a last name beginning with "And" in the list of selectable patient IDs 3486. A scroll bar 3474 may also be included if there are more selectable patient IDs 3486 than can be displayed on the user interface at once.

FIGS. 215-219 depict a number of example select a drug screens 3490. These screens may be used to select a drug to be used for a therapy to be delivered by a medical device. In various embodiments, these screens may differ. A select drug screen 3490 may be used to select a drug for a therapy to be administered by the medical device. In some embodiments, a select a drug screen 3490 may allow a user to select a category of drugs and then select a drug within that category. In some embodiments a user may be able to select a specific drug using a select a drug screen 3490.

FIG. 215 depicts an example embodiment of a select drug screen 3490 which may be displayed on the user interface of a medical device. In the example embodiment shown in FIG. 215, the select drug screen 3490 includes a list of a number of selectable drug categories 3492. A user may select one of the selectable drug categories 3492 to view a list of drugs in that category. A user may then choose the desired drug from that list. In other embodiments, a list of selectable drugs may be displayed on the user interface instead of a list of selectable drug categories 3492. Additionally, in the example embodiment, the select drug screen 3490 includes a search utility 3494. A user may use the search utility 3494 to search for a desired drug or drug category. In some embodiments, if a user taps, double taps, or otherwise indicates they would like to use the search utility 3494, a virtual keyboard may be displayed on the user interface. A user may then type in a search query using the virtual keyboard.

FIG. 216 depicts another example embodiment of a select drug screen 3490 which may be displayed on the user interface of a medical device. The select a drug screen 3490 in FIG. 216 may be navigated to by selecting a selectable drug category 3492 on a screen such as that shown in FIG. 215. Specifically, the screen shown in FIG. 216 may be similar to a screen which may be displayed if a user selected an IV fluids drug category. In the example embodiment in FIG. 216, the select a drug screen 3490 includes a number of selectable drugs 3495. The selectable drugs 3495 displayed are all example IV fluids. A user may use a search utility 3494 to search for a specific drug within a category. This may be particularly useful for categories with large quantities of drugs.

FIG. 217 depicts an example embodiment of a select drug screen 3490. As shown, a virtual keyboard 3428 is displayed on the select drug screen 3490 in FIG. 217. The virtual keyboard 3428 may be used to enter a search query into the search utility 3494. As mentioned above, the virtual keyboard 3428 may be displayed in response to a user inputting an indication on the user interface that they would like to input a search query. A hide keyboard option 3498 may also be included and used if a user would like to cancel input of the search query. As shown, the virtual keyboard 3428, search utility 3494, and hide keyboard option 3498 may be displayed in a modal window type arrangement over the rest of the select drug screen 3490 which may be grayed out and unusable.

FIG. 218 depicts an example embodiment of a select drug screen 3490. As shown, a user has used the virtual keyboard 3428 to type the letters "do" into the search utility 3494. As a user begins to populate the search utility 3494, each letter typed in may cause the list of selectable drug names 3500 to be filtered accordingly. The drug names displayed may be drawn from the list of drugs defined for the care area in the DAL file stored in the memory of the device. In some embodiments, the selectable drug names 3500 may employ tallman lettering to minimize any possible confusion between different drugs with similar spellings. As shown the selectable drug names 3500 shown in the list all begin with "do", the two letters typed into the search utility 3494.

FIG. 219 depicts an example embodiment of a select drug screen 3490 which may be displayed on the user interface of a medical device. As shown, a user has used the virtual keyboard 3428 to type the letters "dop" into the search utility 3494. This has narrowed the list of selectable drug names 3500 to a single drug, Dopamine. A user may select the desired drug from the list of selectable drug names 3500 by tapping, double tapping, or otherwise indicating that they would like to select one of the selectable drug names.

FIG. 220 depicts an example embodiment of a select clinical use screen 3510 which may be displayed on the user interface of a medical device. In various embodiments, a select clinical use screen 3510 may differ. A select clinical use screen 3510 may be used to specify what clinical use of a drug is going to be used for the therapy which the medical device will be administering. If only a single clinical use is defined for a drug in the DAL file stored in the memory of the medical device, a select clinical use screen 3510 may not be displayed. Instead, the clinical use may be automatically selected by the medical device. A select clinical use screen 3510 may also be used to view any advisory information associated with various clinical uses of a drug.

As shown in FIG. 220, the clinical use screen 3510 includes a drug name indicator 3512. In the example embodiment, the drug name indicator 3512 is prominently displayed and reads "DOPamine." An example list of selectable clinical uses 3514 is also displayed on the user interface of the medical device. A user may select a desired clinical use from the list by tapping, double tapping, or otherwise indicating that they would like to use one of the selectable clinical uses 3514.

Additionally, a view advisory option 3516 may also be displayed on the user interface of the medical device when the medical device is displaying a select clinical use screen 3510. A view advisory option 3516 may be associated with the clinical advisory for which the advisory is defined. This option may be used to display any clinical advisory that is defined in the DAL file for the clinical use. In some embodiments, a short text clinical advisory may also be shown in association with the clinical use for which it is defined.

If a user were to use the clinical advisory option 3516 in FIG. 220, a clinical advisory 3520 may be displayed on the user interface. The clinical advisory 3520 may be displayed as shown in FIG. 221. The clinical advisory 3520 may be displayed in a modal window over the select clinical use screen 3510. A clinical advisory 3520 may include text, images, documents, etc. In the example embodiment shown in FIG. 221 the clinical advisory 3520 shown only includes text. A clinical advisory may also include the drug name and clinical use name, for example. Once a user has finished reviewing the clinical advisory 3520 for the drug, the user may use a close option 3522 to close the clinical advisory 3520 and return to the select clinical use screen 3510.

FIG. 222 depicts an example embodiment of a select concentration screen 3530. In various embodiments, a select concentration screen 3530 may differ. A select concentration screen 3530 may be used to select the proper concentration for a drug to be administered by a medical device. If only a single concentration is defined for a drug in the DAL filed stored in the memory of the medical device, a select concentration screen 3530 may not be displayed. Instead, the device may automatically select the concentration.

As shown in FIG. 222, a select concentration screen 3530 may include a drug name indicator 3512. The drug name indicator 3512 may prominently display the name of the drug for which a user is selecting a concentration. A clinical use name indicator 3532 may also be included. The clinical use name indicator 3532 may display the name of the clinical use for which the user is selecting a concentration.

A select concentration screen 3530 may also include a list of selectable concentrations 3534. As shown, the selectable concentrations 3534 may display the concentration information in more than one fashion. In the example embodiment, the selectable concentrations 3534 depict a drug amount per container volume and a concentration value. In some embodiments, at least one of the selectable concentrations 3534 may be customizable. In the example embodiment, the bottom most selectable concentration 3534 is user definable.

In some embodiments, only a certain number of concentrations may be defined for each clinical use. The number of concentrations which may be defined for each clinical use may be the number of clinical uses which may be comfortably displayed on the user interface of the device at a single time. The number of selectable concentrations may be limited to four, for example. This may help to ensure that a user does not select an incorrect concentration because the proper concentration is not currently shown on the user interface.

In some embodiments, the selectable concentrations 3534 may also include a container type indicator 3536 which is associated with each selectable concentration 3534. The container type indicator 3536 may indicate, for example, if the container is a syringe or a medication bag. Additionally, the container type indicator 3536 may also indicate the relative size of the container. In the example embodiments, the container type indicators 3536 shown are skeuomorphic and resemble medication bags of various sizes.

FIGS. 223-225 depict a number of example screens which include patient information entry fields. Such fields may be used to gather information about a patient. This information may, for example, be necessary for various therapies depending upon the clinical use selected. This information may also be useful for CQI purposes. Patient information entry screens may include one or a number of parameter field(s) which may be populated by a user. In suitable situations a user may be required to confirm the entered information on a subsequent (e.g. by re-entering the information). Whether or not this is required may be defined in the DAL file stored in the memory of the medical device. A user may additionally have the option of entering the information in a number of different formats (e.g. English or metric units) when appropriate. The example patient information entry screens shown in FIGS. 223-225 are specifically enter patient weight screens 3540.

FIG. 223 depicts an example embodiment of an enter patient weight screen 3540 that may be displayed on the user interface of medical device. An enter patient weight screen 3540 may differ in various embodiments. An enter patient weight screen 3540 may be displayed if the user selects a weight based clinical use for the therapy. Similar screens (not shown) may be used to define a patient's BSA or other patient information, for example. Some clinical uses may not require such a screen to be displayed.

As shown, the enter patient weight screen 3540 shown in FIG. 223 may include a drug name indicator 3512. An enter patient weight screen 3540 may also include a concentration indicator 3542. A user may be able to define the patient weight by entering the patient's weight into a patient weight input field 3544. The weight may be entered by means of a virtual keyboard 3428 in some embodiments. As shown, two patient weight input fields 3544 may be included. One field is for metric units and the other field is for English units. A user may be able to type the patient information into either patient weight input field 3544 as desired.

FIG. 224 depicts an example embodiment of an enter patient weight screen 3540 which may be displayed on the user interface of a medical device. As shown, a user has populated one of the patient weight input fields 3544 using the virtual keyboard 3428. If a user fills out one of the patient weight input fields 3544, the other of the two fields may be automatically calculated and populated by the device.

In some embodiments, a user may be required to enter the patient weight twice to confirm its correctness. A user may also be required to enter various other parameters multiple times to confirm correctness. For example, a user may also be required to enter BSA twice for BSA based clinical uses. A user may also, for example, be required to input/confirm various programming parameters for high risk drugs more than once. FIG. 225 depicts an example embodiment of an enter patient weight screen 3540 which may be used to confirm a previously entered patient weight. As shown, the enter patient weight screen 3540 includes two confirm patient weight input fields 3550. A user may re-enter the patient weight as described above using the virtual keyboard 3428 on the user interface of the medical device. In some embodiments, a user may not need to re-enter the patient weight. Instead, a user may confirm the entered patient weight in a confirm dialogue box or the like. If the patient information entered is not the same as the original entry, a user may be required to re-enter and confirm the information again.

FIGS. 226-228 display a number of example instructional screens which may be displayed to a user at suitable times during programming of a medical device. Such instructional screens may explain or depict how a user should set up a therapy or part of a therapy. In some embodiments, such screens may also be used to convey troubleshooting information to a user. Depending on the device and/or therapy, the screens shown or which may be shown may differ. Additionally, from embodiment to embodiment, the screens which may be shown by a particular device or for a particular therapy may differ.

FIG. 226 depicts an example embodiment of a load set screen 3560 which may be displayed on the user interface of a medical device. A load set screen 3560 may prompt and provide instruction to a user on how to load an administration set into a medical device. A load set screen 3560 may include an animation, text instructions, annotated illustration, etc. Such a screen 3560 may for example be displayed on a medical device such as a large volume pump. Other medical devices may display different screens in place of a load set screen 3560. For example, a syringe pump may display a load syringe screen.

As shown, the example load set screen 3560 in FIG. 226 includes an illustration of a medical device 3562 which in the example embodiment is a large volume pump. The example load set screen 3560 also includes illustrated steps 3564 which may be used to install the administration set in the device. The illustrated steps 3564 are numbered so as to let a user know in which order they should be performed.

FIG. 227 depicts an example embodiment of a troubleshooting screen. Specifically FIG. 227 depicts a loading error screen 3570 which may be displayed on the user interface of a medical device. The example loading error screen 3570 shown in FIG. 227 is for an incorrectly loaded administration set. Other loading error screens 3570 may be displayed, for example, for an incorrectly loaded syringe on a medical device. Such a screen may be displayed on the user interface of a medical device in the event that the device detects a loading error. The loading error screen displayed 3570 may also differ depending on the specific loading error detected. For example, an IV line improperly seated loading error screen 3570 may differ from a door not fully closed loading error screen 3570.

In the example loading error screen 3570 an error message 3572 is included. In the example embodiment, the error message 3572 reads "SET LOADED INCORRECTLY". The loading error screen 3570 also includes an illustration of a medical device 3562 which in the example embodiment is a large volume pump. If an error is detected on a different device, the depicted device may reflect this. For example, if an error is detected on a syringe pump, the illustrated medical device 3562 may instead be a syringe pump.

The illustration of the medical device 3562 may include an indication of what the error may be. For example, the illustration of the medical device 3562 may highlight a problem on the illustration. In the example embodiment, the illustration of the medical device 3562 includes a number of arrows which point to the infusion line. Also shown on the loading error screen 3570 in FIG. 227 are troubleshooting instructions 3574. These instructions may explain to a user how the error or issue may be addressed.

In some embodiments, a user may indicate on the user interface of the medical device that they have resolved or attempted to resolve the problem. The medical device may then check to see if the problem has been resolved. In some embodiments, a troubleshooting screen such as a loading error screen 3570 may be cleared by the medical device automatically when the device detects that the error or issue has been resolved.

FIG. 228 depicts an example load syringe screen 3580 which may be displayed on the user interface of the medical device. A load syringe screen 3580 may prompt and provide instruction to a user on how to load syringe onto a medical device. A load syringe screen 3580 may include an animation, text instructions, annotated illustration, etc. Such a screen 3580 may, for example, be displayed on a medical device such as a syringe pump. Such a screen may be shown when a user is setting up an infusion, installing a flush syringe, installing a replacement syringe for a primary infusion, etc.

As shown, the example load syringe screen 3580 in FIG. 228 includes an illustration of a medical device 3562 which in the example embodiment is a syringe pump. The example load syringe screen 3580 also includes illustrated steps 3564 which may be used to install the syringe on the device. The illustrated steps 3564 are numbered so as to let a user know in which order they should be performed.

FIG. 229 depicts an example embodiment of a select syringe screen 3590 which may be displayed on the user interface of a medical device. A user may use such a screen to indicate the type of syringe installed on a medical device. The medical device may display a number of choices of syringes. As shown, in the example embodiment choices are shown in a list of selectable syringe types 3592. The choices displayed may be chosen based on data garnered from a number of sensors included on the medical device. Such sensor may include, but are not limited to, a syringe barrel size sensor, a syringe plunger flange size sensor, a syringe barrel flange size sensor, syringe plunger length sensor, or any other suitable sensor. Data from these sensors may be compared to a look-up table stored in the memory of the medical device. Matching syringe(s) from the look-up table may then be displayed on the user interface so the user may indicate which syringe is correct. If the syringe cannot be identified, the user may be required to choose the syringe from a full list of possible syringes which are used within an institution, for example.

In some embodiments, the syringes may be limited based on a care area, drug, clinical use, concentration, etc. In such embodiments, only syringes allowed for the care area, drug, clinical use, concentration etc. which a user has defined for the therapy may be displayed after comparison is made with the look-up table.

FIGS. 230-234 depict a number of example embodiments of infusion programming screens 3600. Such screens may be used to program in an infusion for a medical device to deliver. Such screens may include a number of user definable parameter fields which a user may populate to program an infusion. In some embodiments, such fields may at least in some instances be automatically populated or partially automatically populated. Infusion programming screens 3600 may vary depending on the type of infusion to be delivered. Screens may also differ from embodiment to embodiment. Programming screens may also include a number of other features and options.

FIG. 230 depicts an example embodiment of an infusion programming screen 3600 which may be displayed on the user interface of a medical device. Such a screen may be used by a user to program a number of delivery parameters for a therapy to be administered by a medical device. The device may then use the defined parameters to control administration of a therapy to a user.

As shown, the example infusion programming screen 3600 shown in FIG. 230 includes a drug name indicator 3512, a concentration indicator 3542, and a clinical use name indicator 3532. Various indicators may include additional relevant information. For example, the clinical use name indicator 3532 in FIG. 230 shows that the infusion is a continuous weight based infusion and the weight of the patient is also given.

The example infusion programming screen 3600 also includes a number of infusion parameter entry fields 3602. In the example embodiment, the infusion parameter entry fields 3602 include a dose entry field, a rate entry field, a VTBI entry field, and a time entry field. The infusion parameter entry fields 3602 shown may be different depending on the type of therapy to be administered by the medical device. Depending on the clinical use selected, for example, the infusion parameter entry fields 3602 may differ. A user may enter a value into a desired infusion parameter entry field 3602 by tapping, double tapping, or the like on the desired infusion parameter entry field 3602. After a user has populated a sufficient number of infusion parameter entry fields 3602, the device may automatically calculate and populate other, not yet populated, infusion parameter fields 3602.

An infusion programming screen 3600 may also include a number of option buttons 3478. In infusion programming screens 3600 including option buttons 3478, one or more of the option buttons 3478 may be disabled until some or all of the infusion parameter entry fields 3602 have been populated. In the example embodiment shown in FIG. 230, the options button 3478 include a menu button, a cancel button, a back button, a standby button, and a start infusion button. The option button 3478 entitled start infusion is disabled in the example embodiment because no parameters have been entered into the infusion parameter entry fields 3602.

FIG. 231 depicts an example embodiment of an infusion programming screen 3600 which may be displayed on the user interface of a medical device. As shown, the infusion parameter entry field 3602 for the dose has been opened for editing in FIG. 231. When an infusion parameter entry field 3602 is open for editing, the infusion parameter entry field 3602 may enlarge. A cursor may also be displayed in an infusion parameter entry field 3602 open for editing. A user may enter a value into an infusion parameter entry field 3602 using a virtual keyboard 3428 displayed on the user interface of the medical device.

FIG. 232 depicts another example embodiment of an infusion programming screen 3600 which may be displayed on the user interface of a medical device. As shown in FIG. 232, all of the infusion parameter entry fields 3602 have been populated and the screen is displaying an infusion summary. If a user would like to edit an entered value, the value may be tapped, double tapped, or the like and edited as described above. The option button 3478 for starting an infusion is enabled because the device has all of the information necessary to deliver an infusion. A user may use the option button 3478 for starting an infusion to cause the device to begin delivery of the programmed therapy to a target patient.

FIG. 233 depicts another example embodiment of an infusion programming screen 3600 which may be displayed on the user interface of a medical device. As shown, all of the infusion parameter entry fields 3602 have been populated. The infusion parameter entry field 3602 for dose is open for editing. In some embodiments, the text typed into an infusion parameter entry field 3602 may change in size when the value entered becomes large. Compared to FIG. 231 for example, the text of the value entered in FIG. 233 for the infusion parameter entry field 3602 for dose is smaller. This may help to fit the full value on the user interface. It may also help to visually reflect order of magnitude changes to help ensure a typo which results in an order of magnitude error is more easily recognized by a user. In some embodiments, the size of the text in an infusion parameter entry field may change with every order of magnitude.

FIG. 234 depicts an example embodiment of an infusion programming screen 3600 which may be displayed on the user interface of a device. As shown in FIG. 234, the text size for an infusion parameter entry field may also change on the infusion summary displayed on an infusion programming screen 3600. This may help to fit the entire value on the screen. Additionally, this may help to increase safety by visually signaling an erroneous order of magnitude change in an infusion parameter. In some embodiments, such changes may be signaled to a user in other ways. In some embodiments, for example, these changes may be reflected by a change in color.

FIGS. 235-238 depict a number of example screens which may be displayed on the user interface of a device in the event that a limit defined in a DAL file for a parameter is violated. When a user enters a parameter, the device may check the entered parameter value against any limits defined for that parameter in the DAL file stored in the memory of the device. In some embodiments, the device may also check to see if a value entered in a parameter field forces other parameters to exceed limits defined in the DAL file. This may for example occur if a user enters a VTBI value and time value which are within the DAL file limits, but the time value is sufficiently small as to force a rate value to exceed a DAL file limit. If an infusion parameter entered is found to be in violation of a defined limit, the device may display a screen indicating the limit has been violated. Such screens may provide a user with a number of options on how to resolve the limit violation. Such screens may differ in various embodiments or for different types of violations.

FIG. 235 depicts an example embodiment of an infusion programming screen 3600 in which a limit for an infusion parameter has been exceeded. Specifically, in the example embodiment shown in FIG. 235, the dose high soft limit has been exceeded. The user interface of the device may behave similarly for other limit violations as well (e.g. concentration, patient weight, etc.).

As mentioned above, as a user enters parameter values, they are checked against any applicable limits defined in the DAL file. If the value does not violate any of the limits defined in the DAL file, the user may be allowed to use the entered value. If the value entered does violate a limit defined in the DAL file, the value may be flagged on the user interface of the device. A notification may also be displayed on the user interface. The user may be required to override the limit or re-enter the value. Some limits (e.g. hard limits) may not be overridden.

In the example embodiment depicted in FIG. 235, the value entered by the user in the infusion parameter entry field 3602 for dose has exceeded the soft limit for that parameter defined in the DAL file. The infusion parameter entry field 3602 for the dose is enlarged. The field may also be shown in a different color (e.g. yellow or red). A warning indicator 3610 may also be included. A limit violation notification 3612 is also shown in the example embodiment in FIG. 235. In some example embodiments, the limit violation notification 3612 may display the limit value. As shown, the limit violation notification 3612 in FIG. 235 includes a re-enter option 3614 and an override limit option 3616. A user may use the re-enter option 3614 to re-enter the parameter. A user may use the override limit option 3616 to override the limit and use the limit violating value. In some embodiments, if a user overrides a limit, the user may be required to enter a rationale describing why the override was necessary. Furthermore, in some embodiments a second review for the override by a second user may be required.

FIG. 236 depicts an example embodiment of a limit override screen 3620 which may be displayed on the user interface of a medical device. Such a screen may be displayed if a user indicates that they would like to override a DAL file limit for a parameter. In some embodiments, including the example embodiment shown in FIG. 236, the user may be required to enter a rationale for the override.

As shown in FIG. 236, the limit override screen 3620 includes a text entry field 3622. A user may user a virtual keyboard 3428 to enter a rationale into the text entry field 3622. A cancel option 3624 is included on the example limit override screen 3620 and may be used to cancel overriding of the limit. A confirm or OK option 3626 is also included and may be used to confirm that a user would like to override the limit. In embodiments including a text entry field 3622, the confirm or OK option 3626 may not be enabled until a rationale has been entered.

FIG. 237 depicts an example embodiment of a second user approval screen 3630 which may be displayed on the user interface of a medical device. A second user approval screen 3630 may be displayed if the DAL file requires a second review for a parameter or a programmed infusion before the infusion may be administered. For example, it may be specified that all drugs require a second review, or that high risk drugs require a second review before they may be delivered to a patient. Such approval may help to increase safety. The example second user approval screen 3630 shown in FIG. 237 is for review of a limit override for a parameter of an infusion being programmed.

As shown, the second user approval screen 3630 includes summary information 3632 about what the user is being asked to approve. In the example shown in FIG. 237, this information includes the dose parameter soft limit value and the entered value for the dose parameter. Other information may be included in other embodiments. For example, any rationale entered by a user may also be included. A user ID entry field 3634 is also included. In the example embodiment, the second user may enter their user ID and password into the user ID entry field 3634 using a virtual keyboard 3428 to approve of the limit override.

FIG. 238 depicts an example embodiment of an infusion programming screen 3600 in which an infusion parameter value has exceeded a hard limit. Specifically, in the example embodiment shown in FIG. 238, the dose high hard limit has been exceeded. The infusion parameter entry field 3602 for the dose is enlarged. The field may also be shown in a different color (e.g. yellow or red). A warning indicator 3610 may be included. A limit violation notification 3612 is also shown in the example embodiment in FIG. 235. In some embodiments, the limit violation notification 3612 may display the hard and soft limit values. As shown, the limit notification 3612 includes a re-enter option 3614. A user may use the re-enter option 3614 to re-enter the parameter. An override option is not included.

FIGS. 239-253 depict a number of example screens which may be displayed on the user interface of a device while the device is administering an infusion. Such screens may display various information of interest to a user. Such information may include status information, infusion information, notifications, alerts, alarms, etc. Such screens may also include a number of options which may be used by a user while a programmed infusion is being delivered or is in a stopped state. The screens depicted and described in relation to FIGS. 239-253 are only exemplary. In various embodiments, screens displayed while an infusion is in progress may differ. Such screens may include different information, features, options, etc. than shown herein. Additionally, some such screens may include various elements from other screens shown in FIGS. 239-253.

FIG. 239 depicts an example embodiment of an infusion in progress screen 3640 which may be displayed on the user interface of a medical device. Such a screen may be displayed on the user interface of a device when the device is administering a therapy to a patient. In some embodiments, an infusion in progress screen 3640 may differ. An infusion in progress screen 3640 may provide various information about the infusion being administered. Additionally such a screen may display data from various sensors which are a part of the medical device. An infusion in progress screen 3640 may display different information or graphics depending on the type of device delivering the infusion.

As shown, the example embodiment of the infusion in progress screen 3640 shown in FIG. 239 includes a drug name indicator 3512, a clinical use name indicator 3532, and a concentration indicator 3542. The screen also includes a pressure indicator 3642. The pressure indicator may display pressure in the IV line of an LVP, for example. This pressure may be measured via a sensor associated with the medical device. The pressure indicator 3642 may provide a visual cue that there may be an occlusion. In some embodiments, the pressure indicator 3642 may provide a pressure trend indication over a period of time. In some embodiments, this may be a pressure graph depict pressure at various points in time, for example. The period of time may in, some embodiments, be 4 hours. In some embodiments, tapping, double tapping, or otherwise selecting the pressure indicator 3642 may open an enlarged view of the pressure indicator 3642 on the user interface. As shown, the pressure indicator 3642 is a segmented bar. The segmented bar fills to varying degrees to indicate different pressures.

An infusion summary 3644 is also shown on the example infusion in progress screen 3640. The infusion summary 3644 may detail the infusion parameters which were programmed in for the infusion being administered. In some embodiments, various information in the infusion summary 3644 may be updated as the infusion progresses. For example, the device may use data from various sensors to update the VTBI as infusate is delivered to the patient.

The example infusion in progress screen 3640 may also include a number of option buttons 3478. As shown, a bolus option, secondary infusion option, lock option, and a menu option are included as option buttons 3478 on the user interface. A user may use the option button 3478 for a bolus to program and deliver a bolus using the medical device. A user may use the option button 3478 for a secondary infusion to program and deliver a secondary infusion using the medical device. A user may use the lock option button 3478 to lock the user interface of the medical device. A user may use the option button 3478 for more to bring up a menu of additional options to choose from.

As shown, when an infusion is in progress, the buttons 3408 on the bezel 3406 of the medical device may indicate an infusion is in progress. As shown, the bottommost button 3408 is lit to indicate that an infusion is in progress.

FIG. 240 depicts an example embodiment of an infusion in progress screen 3640 which may be displayed on the user interface of a medical device. As shown, the specific infusion in progress screen 3640 shown in FIG. 240 may be shown on a syringe pump. The infusion in progress screen 3640 includes an infusion summary 3644 and a pressure indicator 3642 similar to the infusion in progress screen 3640 shown and described in relation to FIG. 239. The infusion in progress screen 3640 shown in FIG. 240 also includes a reservoir volume remaining indicator 3650. The reservoir volume remaining indicator 3650, in the example embodiment, is a virtual representation of a syringe and its contents. This may act analogous to a gas gauge. In the example embodiment in FIG. 240, as the infusion progresses, the plunger on the virtual syringe may progress in the syringe barrel in kind with the plunger on the physical syringe installed on the infusion pump. The syringe shown on a reservoir volume remaining indicator 3650 may also be displayed such that it looks like the syringe which is in place on the medical device. In other embodiments or for other medical devices, infusion reservoir volume remaining indicators 3650 may differ. For example, an LVP may display a reservoir volume remaining indicator 3650 which resembles a medication bag on its user interface while an infusion is in progress.

FIG. 241 depicts another example embodiment of an infusion in progress screen 3640. As shown, the infusion in progress screen 3640 shown in FIG. 241 includes an infusion summary 3644 and a number of option buttons 3478. The infusion in progress screen 3460 shown in FIG. 241 also includes an infusion progress indicator 3651. The infusion progress indicator 3651 is a progress bar which fills as the infusion is administered. Other suitable infusion in progress indicators may also be used in other embodiments. The infusion in progress screen 3640 is laid out differently than those shown in FIGS. 239 and 240.

FIG. 242 depicts an example embodiment of an infusion in progress screen 3460 in which an alert message 3660 is being displayed. Alert messages 3660 may be displayed for a number of reasons. In the example embodiment, the alert message 3660 displayed is indicating that the batteries for the device are running low. Alert messages 3660 may be displayed on the user interface of the device in a modal window. This may ensure that a user cannot ignore or fail to notice the alert message 3660 if they are actively using the medical device user interface. The user may be required to interact with or address the alert message 3660 before they can use any other functionalities of the user interface. In the example embodiment, a dismiss option 3662 is included on the alert message 3660. Additionally, an alert message 3660 may be prominently displayed on the user interface of the medical device so that a user may determine which from a number of medical devices the alert is issuing from. In some embodiments, and/or for some alerts, a dismiss option 3662 may not be included or may be disabled. A user may instead be required to resolve the cause of the alert before the alert message 3660 may be removed from the user interface.

As shown, one or more of the buttons 3408 in the bezel 3406 of the medical device may also indicate the alert condition. Such a condition may for example be indicated by one of the buttons lighting up and/or blinking. In the example embodiment the center button 3408 on the bezel 3406 is lit up to indicate the alert.

FIG. 243 depicts an example embodiment of an infusion in progress screen 3640 which may be displayed on a medical device user interface. As shown a details window 3670 is open on the user interface of the device. A user may open a details window 3670 by tapping, double tapping, pressing and holding, etc. an area of interest on the user interface. In the example embodiment, the details window 3670 is displaying detailed information about the various icons in the header 3432. As shown, the details window 3670 provides more detailed information about the battery remaining, WiFi connection and dismissed alerts. Other details windows 3670 (not shown) may also be opened. For example, a user may be able to open a details window 3670 which displays more detailed pressure information.

FIG. 244 depicts an example embodiment of an infusion in progress screen 3640 in which a notification message 3680 is being displayed on the user interface. Notification messages 3680 may be displayed for a number of reasons. In the example embodiment, the alert message 3680 displayed is indicating that a secondary infusion has completed and a primary infusion has resumed. Notification messages 3680 may be displayed on the user interface of the device in a modal window. This may ensure that a user cannot ignore or fail to notice the notification message 3680 if they are actively using the medical device user interface. The user may be required to interact with or address the notification message 3680 before they can use any other functionalities of the user interface. In the example embodiment, a dismiss option 3662 is included on the notification message 3680.

FIG. 245 depicts an example embodiment of an infusion in progress screen 3640 in which a notification message 3680 is displayed. In the example embodiment in FIG. 245 the notification message 3680 is not displayed in a modal window. This may be done because a notification message 3680 may not include critical information or may include relatively non-critical information. It may not be imperative that a user interact with or address the notification message 3680 before they can use any other functionalities of the user interface. In the example embodiment, an OK option 3682 is included on the notification message 3680. Such an option may be used to dismiss the notification message 3680.

FIG. 246 depicts an example embodiment of an infusion in progress screen 3640 which may be displayed on the user interface of a medical device. As shown, the drug name indicator 3512 shows that the drug being delivered is "High Alert Drug XYZ". Various drugs may be indicated as high risk or high alert when the DAL file for the device is created. A user may indicate a drug as high risk in a DAL file if the severity of consequences of improper use is high. If a drug is marked as high risk in the DAL file, the user interface of the device may convey this to the user on various screens displayed on the user interface. In some embodiments, this may be accomplished in part via a non-text indicator. In the example embodiment shown in FIG. 246, a non text warning indicator 3610 is included next to the drug name indicator 3512. Additionally, high risk or high alert drugs may be identified using a color coding scheme. In the example embodiment, the drug name indicator 3512 is highlighted or displayed on a colored background to further draw attention to the fact that the drug has been designated as high risk. This may help to increase safety for a number of reasons. For example, in an emergency situation a user may quickly determine which medical devices of a number of medical devices delivering to a patient require the most urgent attention.

In some embodiments, a drug name indicator 3512 may be color coded in a variety of other ways. Color coding may be used to identify the drug or class of the drug being delivered by the device. Additionally, the drug name indicator 3512 may be color coded to match existing color based drug identification schemes. For a specific example, if the medical device is an anesthesia pump, the drug name indicator 3512 may be displayed on a colored background which corresponds to the proper color in the standard ASTM colors set for anesthesia drugs.

FIG. 247 depicts an example embodiment of an infusion in progress screen 3640 which may be displayed on the user interface of a medical device. As shown, a stop infusion message 3690 is display on the example infusion in progress screen 3640. Such a message may be displayed if a user presses a stop button on the user interface of a medical device. In some embodiments, one of the buttons 3408 in the bezel 3406 of the device may function as a stop button. In some embodiments, a virtual stop button may be included on an infusion in progress screen 3640 or may be navigated to from an infusion in progress screen 3640. In some embodiments, such a message may not be displayed and pressing of a stop button may cause the infusion to stop without requiring a confirmation.

The example stop infusion message 3690 includes text which asks a user if they would like to stop infusing the drug to the patient. The stop infusion message 3690 includes a no option 3692 and a yes option 3694. The no option 3692 may be used to continue infusing the drug to the patient. The yes option 3694 may be used to stop the infusion. The stop infusion message 3690 may be displayed as a modal window in some embodiments.

FIG. 248 depicts an example embodiment of an infusion stopped screen 3700. As shown, the header 3432 may indicate that infusion has stopped. Additionally, the header 3432 may change to a different color (e.g. red, yellow, orange, etc.) to help visually indicate that the device has stopped delivering an infusion. Additionally, the option buttons 3478 on the user interface may also change when an infusion is stopped. In the example embodiment, the option buttons 3478 include an end infusion option and a resume infusion option. These option buttons 3478 may be used to end and cancel the infusion or resume delivery of the infusion respectively.

FIG. 249 depicts an example embodiment of an alarm screen 3710 which may be displayed on the user interface of a medical device. An alarm screen 3710 may be displayed in the event that one of a number of issues exists. Various alarms may include an occlusion alarm, an air in line alarm, a low battery alarm, etc. As shown by the alarm message 3712 in the example embodiment in FIG. 249, the alarm screen 3710 shown is for an occlusion alarm. In some embodiments or, for some alarms, a medical device may stop administering a therapy in the event that an alarm condition exists. An alarm screen 3710 may be sufficiently different from other user interface screens (e.g. infusion in progress screens) so as to be readily recognized as such. This may be helpful in the event that a user needs to quickly address an alarm on one of a number of medical devices all associated with the same patient.

An alarm screen 3710 may include various information about the therapy interrupted by the alarm. In the example embodiment, the alarm screen 3710 includes a drug name indicator 3512 and a concentration indicator 3542. The various information in FIG. 249 also includes infusion summary information 3714. Other embodiments may include different or a different amount of information about the interrupted infusion on alarm screens 3710.

An alarm screen 3710 may include a brief description 3716 of the alarm. Troubleshooting information 3718 may also be included on an alarm screen 3710. An alarm graphic 3720 may also be displayed as part of an alarm screen 3710. In the example embodiment, the alarm graphic 3720 indicates that there may be a problem with the IV line associated with the medical device. In some embodiments, the alarm graphic 3720 may, for example be animated and/or provide instruction on how a user may fix, resolve, or troubleshoot the alarm.

A button 3408 in the bezel 3406 of the medical device may also indicate that an alarm condition exists. In the example embodiment, the center button 3408 in the bezel 3406 of the medical device is lit up to indicate that the alarm condition exists. In some embodiments, a button 3408 in the bezel 3406 may light up or blink a specific color or colors (e.g. red, yellow, orange, etc.) to indicate and alarm condition exists.

FIG. 250 depicts an example embodiment of an infusion in progress screen 3640 in which a power off message 3730 is displayed. A user may power down a device by depressing a button 3408 on the bezel 3406 of the device. In some embodiments, a power off message 3730 may be displayed when a user depresses a button 3408. The button 3048 may then need to be held down for a predetermined period of time before the device shuts off. In some embodiments, the device may behave differently depending on its current status (e.g. idle, standby, infusing, programming, etc.). The steps shown and described in relation to FIG. 200 detail some possible example behaviors depending on the current status of the device.

In the example embodiment in FIG. 250, the power off message 3730 instructs the user to hold a button 3408 down for five seconds to power down the device. In other embodiments, the time duration may be shorter or longer. The power off message 3730 may also include a timer which decrements down as the user holds down the button 3408 which has been designated the power button. In some embodiments, or in some device statuses, a power off message 3730 may not be displayed in response to a button 3408. The device may, for example, power off without a power off message 3730 when a button 3408 is depressed.

FIG. 251 depicts an example embodiment of an infusion in progress screen 3640 which may be displayed on the user interface of a medical device. The example infusion in progress screen 3640 is arranged differently than those described above but includes similar information and indicators. As shown, the example infusion in progress screen 3640 includes a more option 3742. The more option 3742 will be described in greater detail later in the specification. The example infusion in progress screen 3640 also includes a lock option 3740.

A user may use a lock option associated with the user interface of the device to lock the user interface of the device. This may be desirable in situations where it is possible that unintended button or user interface input may occur. As mentioned above in respect to FIG. 199, there may be a variety of types of locks. Such locks may, for example, lock the user interface to different degrees, may require different amounts of user interaction to unlock, may require entry of a passcode of the like to unlock, etc.

In the example embodiment, the lock option 3740 includes a slider which may be dragged across the display of the user interface by a user dragging their finger across the user interface. When the slider is dragged across the user interface a sufficient amount, the device may lock its user interface or may prompt a user to indicate what type of lock they would like to lock the user interface with. In other embodiments, lock options may not require a slider to be dragged across a display. For example, a user interface may be locked by a user depressing one or more virtual buttons (e.g. the option buttons 3478 shown in FIG. 239) displayed on the user interface. A user may also lock the user interface of a device by navigating to a lock option 3740 on the menu of a device.

FIG. 252 depicts an example embodiment of an infusion in progress screen 3640 which may be displayed on the user interface of a medical device. Specifically, FIG. 252 depicts an example embodiment of an infusion in progress screen 3640 which has been locked. As described in relation to FIG. 251, a user may lock the user interface of a medical device. Additionally, in some embodiments, the user interface of a medical device may lock automatically after a predetermined period (e.g. 90 seconds) of time has passed without any user interaction.

As shown in FIG. 252, when the user interface of a medical device is locked, an unlock option 3750 may be displayed on the user interface of the medical device. Additionally, the rest of the user interface may be grayed out or dimmed to indicate that the user interface of the medical device has been locked. In the example embodiment shown, the unlock option 3750 may be used by a user dragging a slider across the user interface of the device. In other embodiments, unlock options 3750 may differ. For example, a user may unlock the user interface of a device by using one or more virtual buttons or navigating to an unlock option 3750 on a menu.

In some embodiments, when a user uses an unlock option 3750 the user interface may unlock. As mentioned above in regards to FIG. 199, in some embodiments or for some types of user interface locks, the user may be required to provide authentication to unlock the device. For example, a user may be required to enter a password or otherwise authenticate (e.g. using an RFID badge, card, fob, etc.) that they are authorized to use the medical device before the user interface of the medical device will unlock. In such embodiments, when a user uses an unlock option 3750, a user ID entry field similar to the user ID entry field 3634 shown in FIG. 237 may be displayed on the user interface. A user may use such a field to enter their user ID and password to provide authentication. In other embodiments, the user interface may display a screen similar to the login screens 3420 shown in FIGS. 209 and 210, for example. This may help to prevent use by unauthorized or untrained users, tampering with a therapy, etc.

FIG. 253 depicts an example embodiment of an infusion in progress screen 3640 which may be displayed on the user interface of a medical device. Specifically, FIG. 253 depicts an example infusion in progress screen 3640 in which an options menu 3760 is being displayed. A user may cause an options menu 3760 to be displayed on the user interface by using a more option 3742 on the user interface. An option menu 3760 may include various option buttons 3478. The example option menu 3760 includes option buttons 3478 to titrate an infusion, program a bolus, program a secondary infusion, view an infusion summary, view a clinical advisory, view various infusion settings, and hand off the medical device to another care giver (e.g. at shift change).

If a user uses the option button 3478 to hand off the device at shift change, for example, the device may allow the currently associated user to log out and may allow the new user, whose shift is starting, to login. In some embodiments, the device may, for example, display a user ID entry field similar to the user ID entry field 3634 in FIG. 237 for each of the currently associated user and the new user whose shift is beginning. In other embodiments, using the option button 3478 for handing off the device may log out the currently associated user and display a screen similar to the login screens 3420 shown in FIGS. 209 and 210 for the new user. After the new user logs onto the medical device, the user interface of the device may display a summary of important therapy events which have happened prior to the start of the new user's shift.

FIG. 254 depicts an example embodiment of a therapy complete screen 3770 which may be displayed on the user interface of the device. A therapy complete screen 3770 may be displayed after a programmed therapy has been administered by a medical device. Additionally, a therapy complete screen 3770 may also be displayed if a therapy is cancelled or otherwise aborted on the medical device. Such a screen may provide various information about the therapy and may, for example, allow a user to start a new therapy if desired.

As shown, the various information about the completed therapy includes a drug name indicator 3512 and a concentration indicator 3542. Various other information such as a clinical use indicator may also be included in some embodiments. In the example embodiment, the therapy complete screen 3770 includes a summary tab 3772 (which is open) and a history tab 3774. The summary tab 3772 may display an infusion summary 3644. The history tab 3774 may be used to display various other information about the therapy. For example, the history tab 3774 may display a delivery rate over time, a list of alerts and/or alarms which occurred during the therapy, a summary of any modification to the therapy which occurred while the therapy was in progress, etc.

A therapy complete screen 3770 may include a start new therapy option 3774 and an end option 3776. The start new therapy option 3774 may be used to begin a new therapy using the medical device. If the user does not desire to begin a new therapy 3776 the user may use the end option 3776.

FIG. 255 depicts an embodiment of an example therapy complete screen 3770 which may be displayed on the user interface of the medical device. Specifically, FIG. 255 depicts an example embodiment of a therapy complete screen 3770 in which a new therapy message 3780 is being displayed. A new therapy message 3780 may be displayed if a user uses a start new therapy option 3774 on the user interface of a medical device. In the example embodiment, the new therapy message 3780 includes a new option 3782 and a repeat option 3784. If a user would like to repeat the same therapy using the same drug, clinical use, concentration, and infusion parameters the user may use the repeat option 3784. If a user would like to program a new therapy on the medical device that is different from the just completed therapy, the user may use the new option 3782.

FIG. 256 depicts an example embodiment of a notification settings screen 3790 which may be displayed on the user interface of a medical device. Other notification settings screens 3790 may differ. In some embodiments, such a screen may be displayed during the device programming process. In some embodiments, a notifications settings screen 3790 may be accessed via a menu or the like from an infusion in progress screen. A notification setting screen 3790 may be used to set times or points during a therapy at which a medical device may generate a notification. Such notifications may serve as reminders and/or provide a user with information. In some embodiments, a user may also be able to set how the medical device will deliver the notification. For example, a user may be able to specify whether or not the notification should include an audible noise or the like.

As shown, the notifications settings screen 3790 in FIG. 256 includes a number of example notifications. Specifically, the notifications settings screen 3790 includes an infusion near end setting 3792, a reorder medication setting 3794, an infusion near end callback 3796, and a reorder medication callback 3798. The infusion near end setting 3792 may be used to set a notification which may indicate that the infusion is close to being finished. The reorder medication setting 3794 may be used to set a reminder to reorder medication for the patient associated with the medical device. The infusion near end callback 3796 may be used to set a time when the device may re-notify a user that the infusion is near end. Likewise, the reorder medication callback 3798 may be used to set a time at which the device may re-notify a user to reorder medication. In other embodiment, different settings or a different number of settings may be set on a notifications settings screen 3790. In some embodiments, a user may create and set times at which custom notifications may be generated by the device. For example, it may be desirable that a generic callback notification be set to occur every two hours for device in a NICU. This may be done to ensure that the devices are functioning properly.

As shown, in the example embodiment in FIG. 256 a user may set times at which the device may generate a notification for the user. This may be done by entering a value into an hour field 3800 and minute field 3802 using a virtual keyboard 3428. As user may need to select a notification that they would like to set in order for the display to show the hour field 3800 and minute field 3802 for that notification. In other embodiments, a user may specify criteria besides time which the device will use to generate a notification. For example, a user may be able to set notifications by defining a VTBI remaining value at which the device should generate the notification. When triggered, notifications may be displayed to a user in a manner similar to what is shown in FIGS. 244-245.

FIG. 257 depicts an example embodiment of a therapy parameters screen 3810 which may be displayed on the user interface of a medical device. Such a screen may allow a user to modify various medical device operating parameters which may be assigned default values in the DAL file stored in the memory of a medical device. Such a screen may be displayed as part of the programming process for a therapy. In other embodiments, a therapy parameters screen 3810 may be navigated to from an infusion in progress screen (e.g. through use of a menu option).

As shown, the therapy parameters screen 3810 includes a KVO rate setting 3812, an occlusion sensitivity setting 3814, an occlusion restarts setting 3816, and an air infusion limit setting 3818. A user may use the KVO rate setting 3812 to set the KVO rate which will be met by the medical device when the device is infusing at the KVO rate. A user may use the occlusion sensitivity setting 3814 to set the occlusion sensitivity for the device. A user may use the occlusion restarts setting 3816 to set the number of occlusion restarts the device may attempt before it issues and occlusion alarm. The air infusion limit setting 3818 may be used to set the amount of air which must be detected over a period of time before the device will issue an air in line alarm.

A user may select a therapy setting they would like to modify to enlarge the setting and display a setting parameter entry field 3820 for that setting. In the example embodiment a user has selected the KVO rate setting 3812. The user may enter a value in a setting parameter entry field 3820 using a virtual keyboard 3428. Also as shown, when a therapy setting has been selected, a reset to default option 3822 may be displayed for that therapy setting. A user may use this option to restore the setting to its default value as defined in the DAL file stored in the memory of the medical device.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in drawings are presented only to demonstrate certain examples of the disclosure. The drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context. It should also be noted that all therapies, drug library entries, etc. and their associated parameter values are simply hypothetical and given for example only.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present invention, the only relevant components of the device are A and B.

Furthermore, the terms "first", "second", "third" and the like, whether used in the description or in the claims, are provided for distinguishing between similar elements and other demonstrative purposes. These terms are not necessarily for describing a sequential or chronological order. It is to be understood that the terms so used are interchangeable under appropriate circumstances (unless clearly and unequivocally disclosed otherwise) and that the embodiments of the invention described herein are capable of operation in other sequences and/or arrangements than are described or illustrated herein.

What is claimed is:
1. A medical error reduction system comprising:
a medical error reduction software configured to:
create and revise at least one drug library, and provide one of a plurality of sets of privileges to each of a plurality of sets of users, each of the plurality of sets of privileges arranged to allocate a degree of software functionality to one of the plurality of sets of users, the degree of software functionality configured to define the ability of a user to alter the at least one drug library;
at least one server;
at least one editor computer, each of the at least one editor computer comprising a processor in communication with a display, the at least one editor computer and the at least one server are configured to communicate via a network in a client-server based model; and
a biomed personal computer ("PC") tool in operative communication with the at least one server,
wherein:
each of the at least one drug library configured to be in at least one medical device,
the at least one editor computer comprising a user interface on the display configured to access the medical error reduction software to edit an initial drug library of the at least one drug library to create an edited drug library, the at least one editor computer configured to access and display via the display the edited drug library and the initial drug library of the at least one drug library, and the at least one editor computer is configured to provide a review simulator configured to simulate a graphical user interface of a medical device of the at least one medical device using the edited drug library, the edited drug library not in the medical device of the at least one medical device, each of which is accessible via tab selections within the user interface,
the at least one editor computer is configured to notify at least one affected user of the edited drug library via an automatically generated email,
the review simulator is configured to simulate a plurality of medical device types in a plurality of care areas using the edited drug library, the plurality of medical device types includes at least two of a syringe pump, a large volume pump, a peristaltic pump, and a patient-controlled analgesia machine,
the at least one server is configured to indicate to the biomed PC tool that the edited drug library is available for loading into a plurality of medical devices only after each medication is simulated by the review simulator,
the biomed PC tool downloads the edited drug library over a network,
the biomed PC tool is configured to communicate the edited drug library over a serial bus to the plurality of medical devices,
each of the plurality of medical devices validates the edited drug library,
each of the plurality of medical devices installs the edited drug library therewithin,
each of the plurality of medical devices communicates a confirmation to the biomed PC tool confirming over the serial bus that the edited drug library was installed on the plurality of medical devices, and
the biomed PC tool communicates over the network the confirmation that the edited drug library was installed on the plurality of medical devices to the at least one server.

2. The system of claim 1, wherein each of the at least one drug library is organized in a hierarchy.

3. The system of claim 2, wherein the hierarchy includes a plurality of care areas which are subordinate to at least one care group.

4. The system of claim 2, wherein each level of the hierarchy includes a number of delivery parameters configured to program the at least one medical device.

5. The system of claim 1, wherein each of the at least one drug library includes a plurality of entries each corresponding to a specific medicament.

6. The system of claim 1, wherein the at least one drug library includes a number of parameters to inform operation of the at least one medical device.

7. The system of claim 1, wherein the drug library includes a plurality of programming limits configured to program the at least one medical device.

8. The system of claim 1, wherein the medical error reduction software is further configured to provide quality improvement information to a user.

9. The system of claim 1, wherein at least one of the plurality of sets of privileges allocates a drug library review privilege to one of the plurality of sets of users.

10. The system of claim 1, wherein at least one of the plurality of sets of privileges allocates a drug library editing privilege to one of the plurality of sets of users.

11. The system of claim 1, wherein at least one of the plurality of sets of privileges allocates a privilege set editing or creation privilege to one of the plurality of sets of users.

12. The system of claim 1, wherein at least one of the plurality of sets of privileges allocates an add user privilege to one of the plurality of sets of users.

13. The system of claim 1, wherein the plurality of sets of privileges allocated to each of the plurality of sets of users force a collaborative process between the plurality of sets of users to create and revise the at least one drug library.

14. The system of claim 1, wherein:
the medical error reduction software is configured to be executed by the at least one server, to be accessible via the at least one editor computer, and to display a simulated medical device graphical user interface, the simulated medical device graphical user interface mimicking behavior of the medical device graphical user interface for a medical device using a selected drug library of the at least one drug library;
the at least one medical device comprises a medical device processor and a medical device graphical user interface configured to display a user interface; and
each of the at least one drug library comprises a plurality of entries which guide user programming of the at least one medical device.

15. The system of claim 14, wherein the simulated medical device graphical user interface is context sensitive.

16. The system of claim 14, wherein the medical error reduction software includes a number of privilege sets each of which being assigned to one of a plurality of sets of users, the number of privilege sets each allocating a degree of software functionality to each of the plurality of sets of users.

17. The system of claim 16, wherein the simulated medical device graphical user interface is a software functionality configured to be toggled on or off by the number of sets of privileges.

18. The system of claim 14, wherein each of the at least one drug library is organized in a hierarchy.

19. The system of claim 18, wherein the hierarchy includes a plurality of care areas which are subordinate to at least one care group.

20. The system of claim 18, wherein each level of the hierarchy includes a number of delivery parameters for the at least one medical device.

21. The system of claim 14, wherein each of the at least one drug library includes a plurality of entries each corresponding to a specific medicament.

22. The system of claim 14, wherein the at least one drug library includes a number of parameters to inform operation of the at least one medical device.

23. The system of claim 14, wherein the drug library includes a plurality of programming limits configured to program the at least one medical device.

24. The system of claim 14, wherein the medical error reduction software is further configured to provide quality improvement information to a user.

25. The system of claim 1, further comprising a monitoring client configured to communicate with the at least one medical device.

26. A medical error reduction system comprising:
a drug library editing software configured to create and revise at least one drug library, the at least one drug library containing a plurality of entries, each of the at least one drug library configured to control at least one medical device, the software configured to provide one of a plurality of sets of privileges to each of a plurality of sets of users, each of the plurality of sets of privileges arranged to allocate a degree of software functionality to one of the plurality of sets of users;
at least one server;
at least one editor computer, each of the at least one editor computer comprising a processor in communication with a user interface, the at least one editor computer and at least one server configured to communicate via a network in a client-server based model; and
a biomed personal computer ("PC") tool in operative communication with the at least one server,
wherein:
at least one of the plurality of set of users instructs the software to send a request to change at least a portion of the at least one drug library,
the at least one editor computer having the user interface configured to edit an initial drug library of the at least one drug library to create an edited drug library, the at least one editor computer configured to access and display via the display the edited drug library and the initial drug library of the at least one drug library, and the at least one editor computer is configured to provide a review simulator configured to simulate a graphical user interface of the medical device using the edited drug library, each of which is accessible via tab selections within the user interface,
the at least one editor computer is configured to notify at least one affected user of the edited drug library via an automatically generated email,
the review simulator is configured to simulate a plurality of medical device types in a plurality of care areas using the edited drug library, the plurality of medical device types includes at least two of a syringe pump, a large volume pump, a peristaltic pump, and a patient-controlled analgesia machine,
the at least one server is configured to indicate to the biomed PC tool that the edited drug library is available for loading into a plurality of medical devices only after each medication is simulated in the review simulator, the biomed PC tool downloads the edited drug library over a network, the biomed PC tool is configured to communicate the edited drug library over a serial bus to the plurality of medical devices, each of the plurality of medical devices validates the edited drug library, each of the plurality of medical devices installs the edited drug library therewithin, each of the plurality of medical devices communicates a confirmation to the biomed PC tool confirming over the serial bus that the edited drug library was installed on the plurality of medical devices, and the biomed PC tool communicates over the network the confirmation that the edited drug library was installed on the plurality of medical devices to the at least one server.

27. The system of claim 26, wherein at least one of the plurality of sets of privileges is configured to decline implementation of the change in response to a user input.

28. The system of claim 26, wherein at least one of the plurality of sets of privileges is configured to accept implementation of the change in response to a user input.

29. The system of claim 26, wherein at least one of the plurality of sets of privileges is configured to submit a question to the change in response to a user input.

30. The system of claim 26, wherein at least one of the plurality of sets of privileges is configured to propose a revision to the change in response to a user input.

31. The system of claim 30, wherein the server is configured to execute the medical error reduction software.

32. The system of claim 26, wherein the degree of software functionality is configured to define the ability of a user to alter the at least one drug library.

33. The system of claim 26, wherein the at least one medical device is an infusion pump.

34. The system of claim 26, further comprising a monitoring client configured to communicate with the at least one medical device.

35. A medical error reduction system comprising:
a medical device comprising:
  a medical device processor; and
  a medical device graphical user interface configured to program the medical device;
at least one server;
at least one editor computer including a processor in communication with a display, wherein the at least one editor computer is configured to communicate to the at least one server via a network in a client-server based model;
a medical error reduction software configured to be executed by the at least one server and accessible via the at least one editor computer configured to create and revise at least one drug library, the at least one drug library configured to control the medical device and including a plurality of entries that guide user programming of the medical device, wherein the medical error reduction software is further configured to display a review simulator interface, the review simulator interface mimicking behavior of the medical device graphical user interface; and
a biomed personal computer ("PC") tool in operative communication with the at least one server,
wherein:
  the at least one editor computer comprising a user interface displayed on the display and configured to access the medical error reduction software to create an edited drug library from an initial drug library of the at least one drug library, the-at least one editor computer configured to access and display via the display the edited drug library and the initial drug library, and the user interface is configured to provide the review simulator interface using the edited drug library, each of which is accessible via tab selections within the user interface,
  the at least one editor computer is configured to notify at least one affected user of the edited drug library via an automatically generated email;
  the review simulator is configured to simulate a plurality of medical device types in a plurality of care areas using the edited drug library, the plurality of medical device types includes at least two of a syringe pump, a large volume pump, a peristaltic pump, and a patient-controlled analgesia machine,
  the at least one server is configured to indicate to the biomed PC tool that the edited drug library is available for loading into a plurality of medical devices only after each medication is simulated by the review simulator,
  the biomed PC tool downloads the edited drug library over a network,
  the biomed PC tool is configured to communicate the edited drug library over a serial bus to the plurality of medical devices,
  each of the plurality of medical devices validates the edited drug library,
  each of the plurality of medical devices installs the edited drug library therewithin,
  each of the plurality of medical devices communicates a confirmation to the biomed PC tool confirming over the serial bus that the edited drug library was installed on the plurality of medical devices, and
  the biomed PC tool communicates over the network the confirmation that the edited drug library was installed on the plurality of medical devices to the at least one server.

36. The system of claim 35, further comprising a monitoring client configured to communicate with the medical device.

* * * * *